US012358918B2

(12) United States Patent
Corsello et al.

(10) Patent No.: US 12,358,918 B2
(45) Date of Patent: Jul. 15, 2025

(54) ARYL HYDROCARBON RECEPTOR (AHR) ACTIVATOR COMPOUNDS AS CANCER THERAPEUTICS

(71) Applicants: THE BROAD INSTITUTE, INC., Cambridge, MA (US); DANA-FARBER CANCER INSTITUTE, INC.; INSTITUTO CARLOS SLIM DE LA SALUD, A.C., Mexico City (MX)

(72) Inventors: Steven Corsello, Boston, MA (US); Ryan Spangler, Cambridge, MA (US); Rohith Nagari, Cambridge, MA (US); Todd Golub, Cambridge, MA (US); Amael Madec, Cambridge, MA (US)

(73) Assignees: THE BROAD INSTITUTE, INC., Cambridge, MA (US); DANA-FARBER CANCER INSTITUTE, INC., Boston, MA (US); INSTITUTO CARLOS SLIM DE LA SALUD, A.C., Mexico City (MX)

( * ) Notice: Subject to any disclaimer, the term of this patent is extended or adjusted under 35 U.S.C. 154(b) by 962 days.

(21) Appl. No.: 17/293,255

(22) PCT Filed: Nov. 14, 2019

(86) PCT No.: PCT/US2019/061438
§ 371 (c)(1),
(2) Date: May 12, 2021

(87) PCT Pub. No.: WO2020/102506
PCT Pub. Date: May 22, 2020

(65) Prior Publication Data
US 2022/0017524 A1  Jan. 20, 2022

Related U.S. Application Data

(60) Provisional application No. 62/767,474, filed on Nov. 14, 2018.

(51) Int. Cl.
C07D 487/04 (2006.01)
A61K 45/06 (2006.01)
C07D 471/14 (2006.01)

(52) U.S. Cl.
CPC ............ C07D 487/04 (2013.01); A61K 45/06 (2013.01); C07D 471/14 (2013.01)

(58) Field of Classification Search
None
See application file for complete search history.

(56) References Cited

U.S. PATENT DOCUMENTS 4,713,383 A   12/1987 Francis et al.
6,358,964 B1   3/2002 Baraldi
2018/0222982 A1   8/2018 Dranoff et al.

FOREIGN PATENT DOCUMENTS

WO   2009/055506 A2   4/2009
WO   2018081625 A2   5/2018

OTHER PUBLICATIONS

PubChem ([Internet]. Bethesda (MD): National Library of Medicine (US), National Center for Biotechnology Information; 2004-. PubChem Compound Summary for CID 14948770, 2-(Furan-2-yl)-[1,2,4]triazolo[1,5-c]quinazoline; [cited Feb. 23, 2024.]. (Year: 2024).*
Kim, et. al. ((1996), Derivatives of the Triazoloquinazoline Adenosine Antagonist (CGS15943) Are Selective for the Human A3 Receptor Subtype, J. Med. Chem., 39, 4142-4148 (Year: 1996).*
Kovalenko et. al. ((2012), Synthesis and Anticancer Activity of 2-(Alkyl-, Alkaryl-, Aryl-, Hetaryl-)-[1,2,4]triazolo[1,5-c]quinazolines, Sci Pharm, 81, 359-391 (Year: 2012).*
International Search Report dated Mar. 24, 2020 for related Application No. PCT/US2019/061438.
Pubchem. CID 14948770. Feb. 9, 2007, pp. 1-11. Retrieved from the Internet <URL: https://pubchem.ncbi.nlm.nih.gov/compound/14948770>; p. 2, formula.
Francis, J. et al. Structure-Activity Profile of a Series of Novel Triazoloquinazoline Adenosine Antagonists, Jan. 1, 1988.
Bilyi, A. et al. 2-Heteroaryl-[1,2,4]triazolo[1,5-c]quinazoline-5(6?H)-thiones and Their S-Substituted Derivatives: Synthesis, Spectroscopic Data, and Biological Activity. Jun. 1, 2015.
Edling, C. et al. Caffeine and the analog CGS 15943 inhibit cancer cell growth by targeting the phosphoinositide 3-kinase/Akt pathway. May 1, 2014.
Extended European Search Report in corresponding European application No. 19883458.2 dated Jul. 13, 2022.

* cited by examiner

Primary Examiner — Kortney L. Klinkel
Assistant Examiner — Dawanna Shar-Day White
(74) Attorney, Agent, or Firm — Day Pitney LLP; Richard B. Emmons; Christopher R. Cowles

(57) ABSTRACT

The present disclosure relates to compositions and methods for the diagnosis and treatment or prevention of cancers, particularly cancers that exhibit elevated expression of FOXA1 and/or FOXA1 gene targets, such as certain breast, liver and/or prostate cancers, including luminal and/or ER-positive forms of breast cancer. Three previously identified adenosine receptor antagonists, CGS-15943, MRS-1220 and SCH-58261, as well as furan ring moiety-possessing derivatives of CGS-15943 are specifically provided for killing cancer cells in a manner that appears to involve activation of the aryl hydrocarbon receptor (AHR) by such compounds. The instant disclosure therefore provides for selecting and/or administering CGS-15943, MRS-1220, SCH-58261 and/or a furan-possessing derivative of CGS-15943, MRS-1220 and/or SCH-58261 as a therapeutic agent to target a cancer cell and/or subject having or at risk of developing a cancer. Methods and compositions for therapies that include such compounds are also provided.

3 Claims, 237 Drawing Sheets
Specification includes a Sequence Listing.

| feature | dataset | Target | Pearson.corr | Global.Z |
|---|---|---|---|---|
| GE | 2.5uM | AGR2 | -0.4604 | -4.444 |
| GE | 2.5uM | AGR3 | -0.4268 | -4.130 |
| GE | 2.5uM | PRR15L | -0.3870 | -3.758 |
| GE | 2.5uM | TC2N | -0.3844 | -3.733 |
| GE | 2.5uM | SOWAHB | -0.3713 | -3.610 |
| GE | 2.5uM | MAP7 | -0.3680 | -3.579 |
| GE | 2.5uM | EMP3 | 0.3967 | 3.579 |
| GE | 2.5uM | FOXA1 | -0.3666 | -3.567 |
| GE | 2.5uM | TJP3 | -0.3648 | -3.549 |
| GE | 2.5uM | C9orf152 | -0.3606 | -3.510 |

FIG. 2A

NH₂ not required, removal should abrogate A2a receptor binding

Furan required

Multiple substituents tolerated

FIG. 7A

Studies with reported in-vivo administration of CGS15943 in mice, rats, and non-human primates and its effects

| Year | Author | Journal | Species | Dose | Administration Route | Results |
|---|---|---|---|---|---|---|
| 2016 | Birnbaum et al | Cardiovasc Drug Ther | Rats | 10mg/kg | i.p. | |
| 2016 | Labay et al | Oncotarget | Mice | 3mg/kg | p.o. | Slowed tumor growth in a B16.SIY subcutaneous tumor model injected into C57BL/6 mice. |
| 2014 | Yamada et al | Psycho-pharmacology | Rats | 5 and 20 mg/kg | p.o. | Significantly improved escape response in comparison to control in Parkinson's rat model |
| 2005 | Triflieff et al | Br J Pharmacology | Mice | 10 mg/kg | local inj(lungs) and p.o. | |
| 2003 | Weerts and Griffith | Psycho-pharmacology | Baboons | 0.032-0.320 mg/kg 0.001-0.032 mg/kg | i.v. | |
| 1996 | Cox and Smitz | J Pharmaco Exp Ther | Rats | 1mg/kg | i.v. | |
| 1996 | Holtzman | J Pharmaco Exp Ther | Squirrel Monkeys | 1.0 mg/kg | i.m. | |
| 1994 | Imaizumi | Methods Find Exp Clin Pharmacol | Mice | 50 mg/kg | ? | |
| 1993 | Merkel et al | J Pharmaco Exp Ther | Rats | 0.1-10 mg/kg | i.p. | |
| 1993 | Howell and Byrd | J Pharmaco Exp Ther | Squirrel Monkeys | 0.1-3.0 mg/kg | i.m. and i.v. | Need to get PDF for dosing |
| 1991 | Griebel et al | Psycho-pharmacology | Mice | | | |
| 1991 | Holtzman | Life Sci | Rats | 0.1-10 mg/kg | i.p. | |

FIG. 19

| Compound | Route | Dose (mg/kg) | Matrix | $T_{max}$ (hr) | $C_{max}$ (ng/mL) | $AUC_{last}$ (ng/mL*hr) | $AUC_{inf}$ (ng/mL*hr) | $T_{1/2}$ (hr) |
|---|---|---|---|---|---|---|---|---|
| BRD-K49049886-001-12-9 | IP | 3 | Plasma | 0.08 | 145.25 | 144.31 | 169.11 | 0.72 |
| | | 15 | | 0.50 | 529.55 | 708.58 | 727.33 | 1.62 |

FIG. 21

| Structure | Name | SMILES string |
|---|---|---|
| (structure of paclitaxel) | paclitaxel | CC(=O)O[C@@H]1C2=C(C)[C@H](C[C@@](O)([C@@H](OC(=O)c3ccccc3)[C@@H]4[C@@]5(CO[C@@H]5C[C@H](O)[C@@]4(C)C1=O)OC(=O)C2(C)C)OC(=O)[C@H](O)[C@@H](NC(=O)c6ccccc6)c7cccc c7 |
| (structure of BRO-026) | BRO-026 | Nc1nc2cc(Cl)ccc2c2nc(nn12)-c1ccco1 |
| (structure of Phortress) | Phortress | Cc1cc(ccc1NC(=O)[C@@H](N)CCCCN)-c1nc2cc(F)ccc2s1 |

FIG. 21 (Continued)

| MDA_MB_468_Breast 5 day CTG viability - SENSITIVE cell line | MDA_MB_468_Breast AhR sg3 5 day CTG viability - RESISTANT cell line with AHR CRISPR KO | MDA_MB_468_Breast AhR sg4 5day CTG viability - RESISTANT cell line with AHR CRISPR KO | 7255-01-X01-01-02-ZR51_Breast 5day CTG viability - SENSITIVE cell line | MDA_MB_231_Breast 5day CTG viability - RESISTANT cell line control |
|---|---|---|---|---|
| qAC50 [M] | qAC50 [M] | qAC50 [M] | qAC50 [M] | qAC50 [M] |
| 3.02E-09 | 3.16E-09 | 3.32E-09 | 1.53E-09 | 3.77E-09 |
| 4.70E-08 | 3.00E-05 | 3.00E-05 | 1.90E-06 | 3.00E-05 |
| 6.48E-08 | 2.77E-07 | 2.58E-07 | 1.04E-07 | 9.91E-06 |

FIG. 21 (Continued)
| | | |
|---|---|---|
| 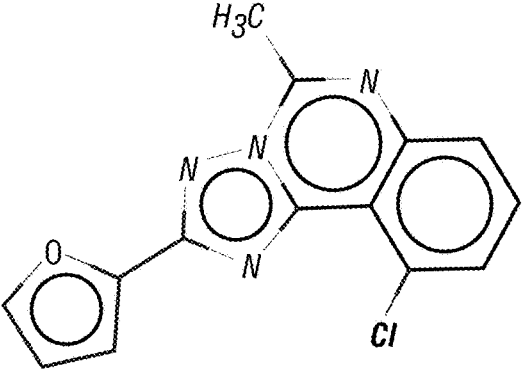 | BRO-027 | Nc1nc2cccc(Cl)c2c2nc(nn12)-c1ccco1 |
| 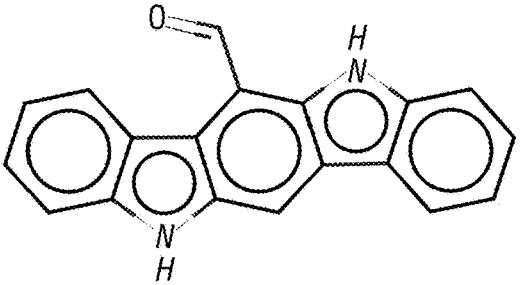 | FICZ | O=Cc1c2[nH]c3ccccc3c2cc4[nH]c5ccccc5c14 |
| 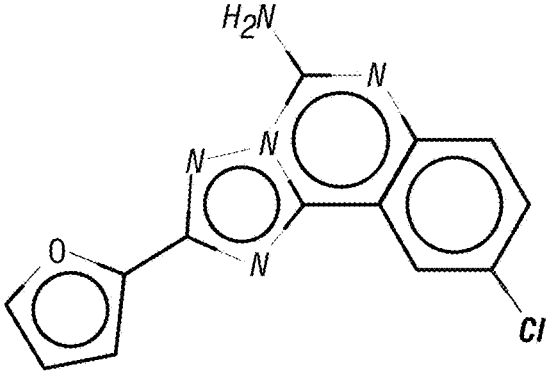 | CGS-15943 | Nc1nc2ccc(Cl)cc2c3nc(nn13)c4ccco4 |
| 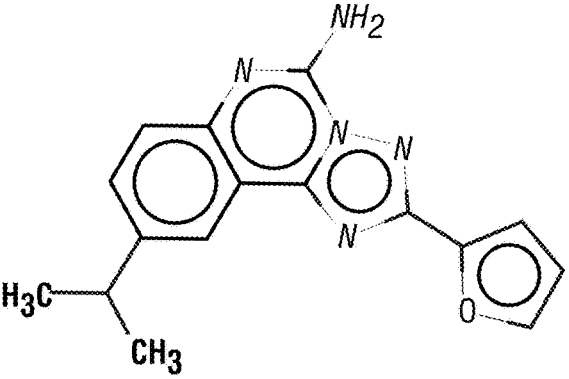 | BRO-025 | CC(C)c1ccc2nc(N)n3nc(nc3c2c1)-c1ccco1 |

FIG. 21 (Continued)

| | | | | |
|---|---|---|---|---|
| 1.65E-07 | 3.00E-05 | 3.00E-05 | 1.31E-07 | 3.00E-05 |
| 2.00E-07 | 3.00E-05 | 3.00E-05 | 1.19E-07 | 3.00E-05 |
| 2.54E-07 | 3.00E-05 | 3.00E-05 | 1.93E-07 | 3.00E-05 |
| 2.56E-07 | 3.00E-05 | 3.00E-05 | 5.72E-07 | 3.00E-05 |

FIG. 21 (Continued)

| Structure | Name | SMILES |
|---|---|---|
| (structure) | SCH-58261 | Nc1nc2n(CCc3ccccc3)ncc2c4nc(nn14)c5ccco5 |
| (structure) | 2-(2-furyl)-5-methylene-5,6-dihydro[1,2,4]triazolo[1,5-c]quinazoline | C=C1Nc2ccccc2-c2nc(nn12)-c1ccco1 |
| (structure) | | CN(C)c1nc2ccc(Cl)cc2c2nc(nn12)-c1ccco1 |
| (structure) | BRO-023 | Nc1nc2ccc(F)cc2c2nc(nn12)-c1ccco1 |

FIG. 21 (Continued)

| 2.57E-07 | 3.00E-05 | 3.00E-05 | 3.00E-05 | 3.00E-05 |
|---|---|---|---|---|
| 3.03E-07 | 3.00E-05 | 3.00E-05 | 2.38E-07 | 3.00E-05 |
| 3.99E-07 | 3.00E-05 | 3.00E-05 | 5.14E-07 | 3.00E-05 |
| 4.01E-07 | 2.61E-05 | 2.96E-05 | 4.28E-07 | 3.00E-05 |

FIG. 21 (Continued)
| Structure | Name | SMILES |
|---|---|---|
| 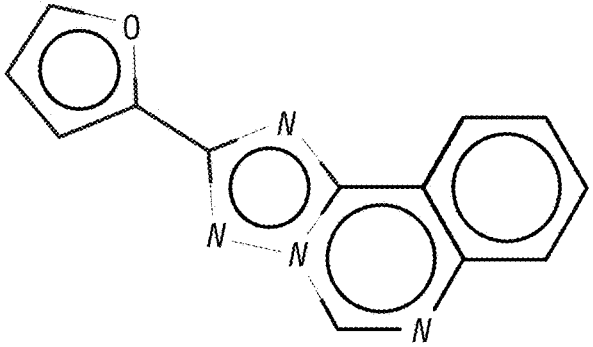 | 2-(2-furyl)[1,2,4]triazolo[1,5-c]quinazoline | c1coc(c1)-c1nc2c3ccccc3ncn2n1 |
| 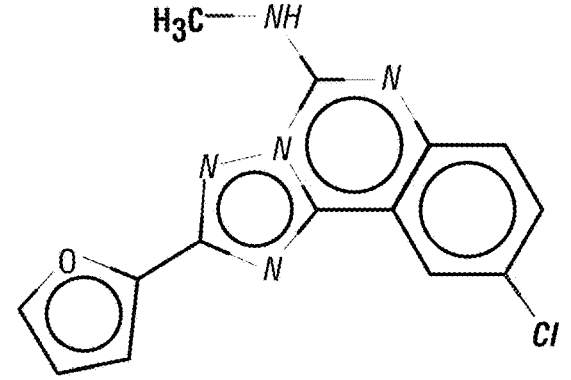 | | CNc1nc2ccc(Cl)cc2c2nc(nn12)-c1ccco1 |
| 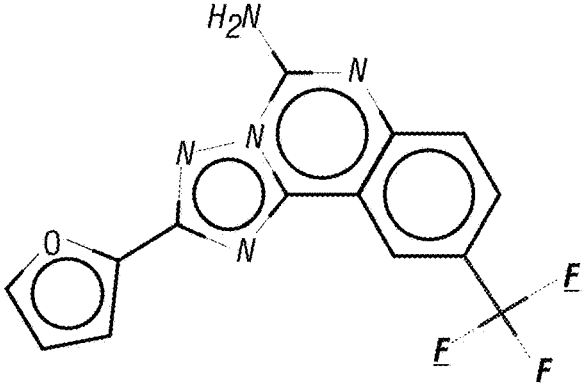 | BRO-024 | Nc1nc2ccc(cc2c2nc(nn12)-c1ccco1)C(F)(F)F |
| 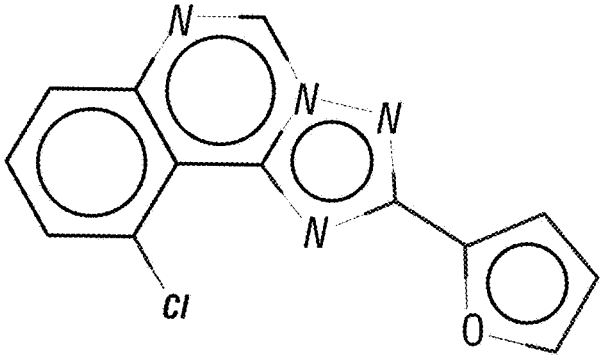 | 10-chloro-2-(2-furyl)[1,2,4]triazolo[1,5-c]quinazoline | Clc1cccc2ncn3nc(nc3c12)-c1ccco1 |

FIG. 21 (Continued)

| | | | | |
|---|---|---|---|---|
| 4.68E-07 | 3.00E-05 | 3.00E-05 | 4.86E-06 | 3.00E-05 |
| 4.90E-07 | 3.00E-05 | 3.00E-05 | 7.05E-07 | 3.00E-05 |
| 5.68E-07 | 3.00E-05 | 3.00E-05 | 1.00E-06 | 3.00E-05 |
| 5.96E-07 | 3.00E-05 | 3.00E-05 | 2.38E-07 | 3.00E-05 |

FIG. 21 (Continued)
| Structure | Name | SMILES |
|---|---|---|
| 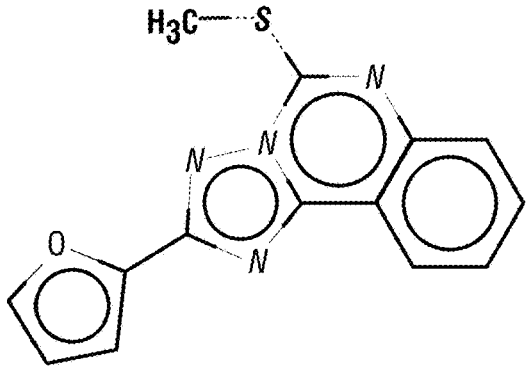 | 2-(2-furyl)-5-(methylsulfanyl)[1,2,4]triazolo[1,5-c]quinazoline | CSc1nc2ccccc2c2nc(nn12)-c1ccco1 |
| 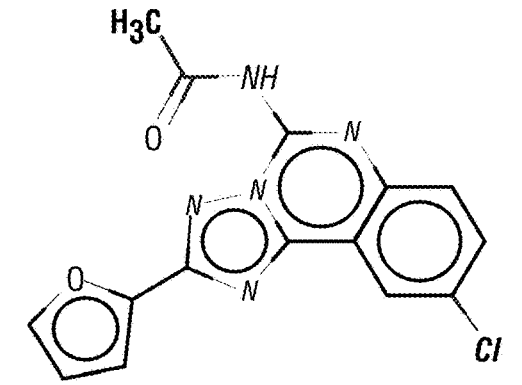 | BIMH-20171221_Cpd2 | CC(=O)Nc1nc2ccc(Cl)cc2c2nc(nn12)-c1ccco1 |
| 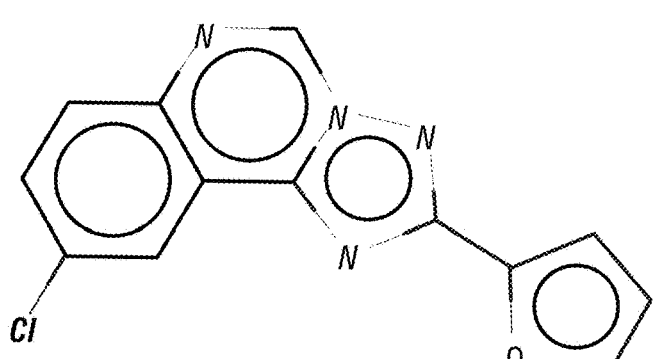 | | Clc1ccc2ncn3nc(nc3c2c1)-c1ccco1 |
| 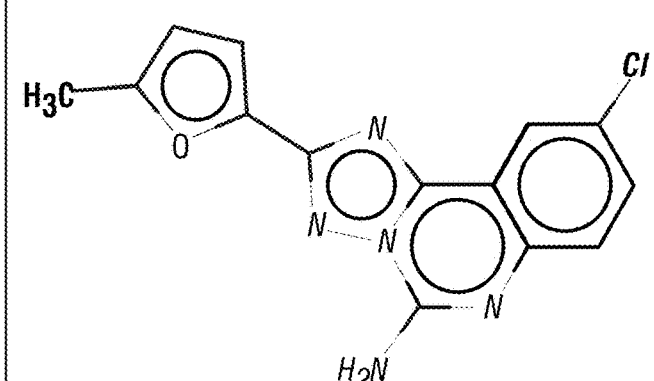 | BRO-013 | Cc1ccc(o1)-c1nc2c3cc(Cl)ccc3nc(N)n2n1 |

FIG. 21 (Continued)

| 6.17E-07 | 3.00E-05 | 3.00E-05 | 5.34E-07 | 3.00E-05 |
| --- | --- | --- | --- | --- |
| 6.50E-07 | 3.00E-05 | 3.00E-05 | 5.25E-07 | 3.00E-05 |
| 8.75E-07 | 3.00E-05 | 3.00E-05 | 6.79E-07 | 3.00E-05 |
| 2.13E-06 | 3.00E-05 | 3.00E-05 | 6.68E-07 | 3.00E-05 |

FIG. 21 (Continued)

| Structure | Name | SMILES |
|---|---|---|
| 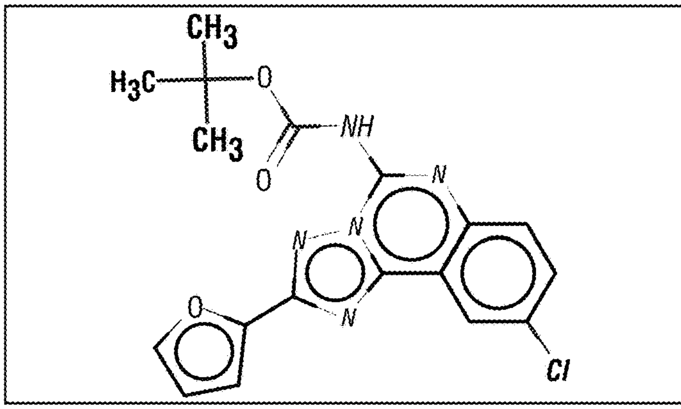 | BIMH-20171221_Cpd7 | CC(C)(C)OC(=O)Nc1nc2ccc(Cl)cc2c2nc(nn12)-c1ccco1 |
| 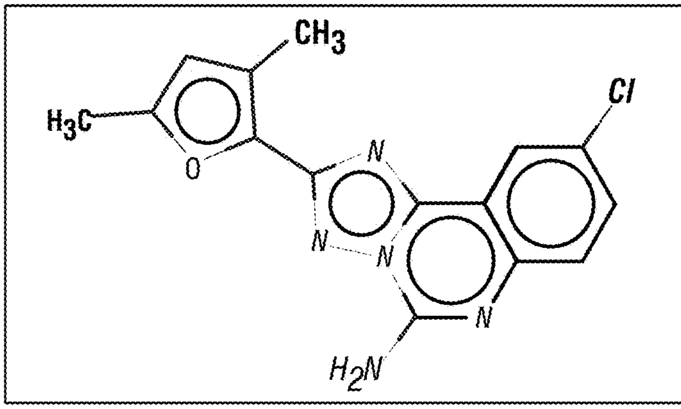 | BRO-014 | Cc1cc(C)c(o1)-c1nc2c3cc(Cl)ccc3nc(N)n2n1 |
| 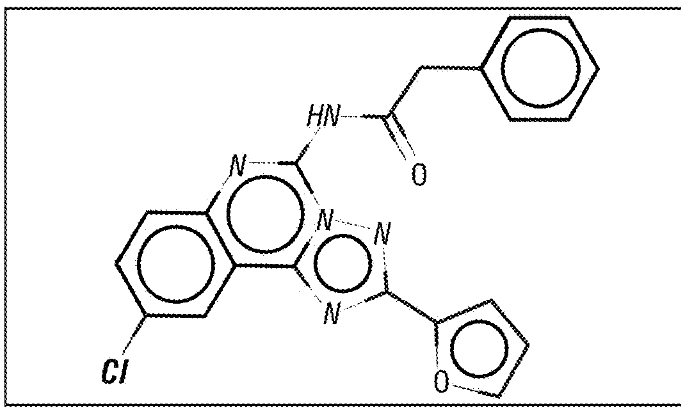 | MRS-1220 | Clc1ccc2nc(NC(=O)Cc3ccccc3)n4nc(nc4c2c1)c5ccco5 |
| 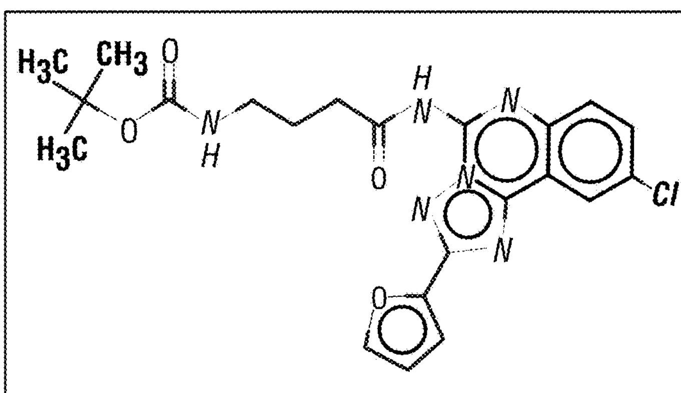 | BIMH-20171221_Cpd8 | CC(C)(C)OC(=O)NCCCC(=O)Nc1nc2ccc(Cl)cc2c2nc(nn12)-c1ccco1 |

FIG. 21 (Continued)

| 2.78E-06 | 3.00E-05 | 3.00E-05 | 2.64E-06 | 3.00E-05 |
|---|---|---|---|---|
| 2.00E-05 | 3.00E-05 | 3.00E-05 | 2.02E-05 | 3.00E-05 |
| 2.21E-05 | 3.00E-05 | 3.00E-05 | 1.69E-05 | 3.00E-05 |
| 2.89E-05 | 3.00E-05 | 3.00E-05 | 2.44E-05 | 3.00E-05 |

| | | |
|---|---|---|
| | BRO-017 | Nc1nc2ccc(Cl)cc2c2nc(nn12)-c1cc2ccccc2o1 |
| | L-Kynurenin | N[C@@H](CC(=O)c1ccccc1N)C(O)=O |
| | CH223191 | Cc1cc(ccc1NC(=O)c1ccnn1C)\N=N\c1ccccc1C |

FIG. 21 (Continued)

| 3.00E-05 | 3.00E-05 | 3.00E-05 | 3.00E-05 | 3.00E-05 |
|---|---|---|---|---|
| 3.00E-05 | 3.00E-05 | 3.00E-05 | 3.00E-05 | 3.00E-05 |
| 3.00E-05 | 3.00E-05 | 3.00E-05 | 3.00E-05 | 3.00E-05 |

FIG. 21 (Continued)

| | | |
|---|---|---|
| | BRO-021 | Clc1ccc2nc(Nc3ccccc3)n3nc(nc3c2c1)-c1ccco1 |
| | 6,2,4-Trimethoxyflavone | COc1ccc(c(OC)c1)-c1cc(=O)c2cc(OC)ccc2o1 |
| | ITE | COC(=O)c1csc(n1)C(=O)c2c[nH]c3ccccc23 |
| | BRO-018 | Cn1cccc1-c1nc2c3cc(Cl)ccc3nc(N)n2n1 |

FIG. 21 (Continued)

| 3.00E-05 | 3.00E-05 | 3.00E-05 | 3.00E-05 | 3.00E-05 |
|---|---|---|---|---|
| | | | | |

| 3.00E-05 | 3.00E-05 | 3.00E-05 | 3.00E-05 | 3.00E-05 |
|---|---|---|---|---|
| | | | | |

| 3.00E-05 | 3.00E-05 | 3.00E-05 | 3.00E-05 | 3.00E-05 |
|---|---|---|---|---|
| | | | | |

| 3.00E-05 | 3.00E-05 | 3.00E-05 | 3.00E-05 | 3.00E-05 |
|---|---|---|---|---|
| | | | | |

| Name | Structure | SMILES string | Solubility (μM) |
|---|---|---|---|
| Aminoflavone (NSC 686288) | 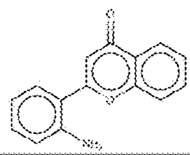 | Nc1ccccc1-c1cc(=O)c2ccccc2o1 | |
| B2 | 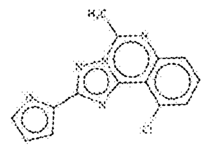 | Cc1nc2cccc(Cl)c2c2nc(nn12)-c1ccco1 | 2.1966 |
| B1 | 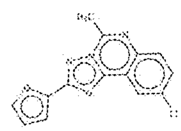 | Cc1nc2ccc(Cl)cc2c2nc(nn12)-c1ccco1 | 2.2169 |
| A14 | 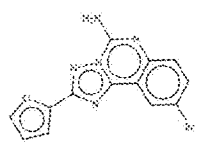 | Nc1nc2ccc(Br)cc2c2nc(nn12)-c1ccco1 | 0.6835 |
| 10-chloro-2-(2-furyl)[1,2,4]triazolo[1,5-c]quinazoline | 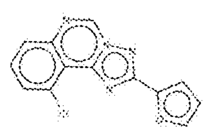 | 10-chloro-2-(2-furyl)[1,2,4]triazolo[1,5-c]quinazoline | 8.7058 |
| CGS 15943 | 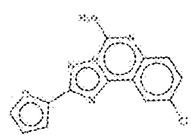 | Nc1nc2ccc(Cl)cc2c3nc(nn13)c4cccco4 | 3.2044 |
| CGS-15943 | 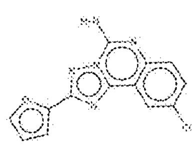 | Nc1nc2ccc(Cl)cc2c3nc(nn13)c4cccco4 | 2.6000 |
| Phortress | 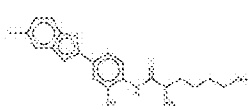 | Cc1cc(ccc1NC(=O)[C@@H](N)CCCCN)-c1nc2cc(F)ccc2s1 | |

FIG. 23

| Name | Structure | SMILES string | Solubility (μM) |
|---|---|---|---|
| BRO-023 | 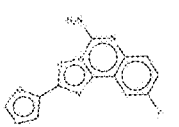 | Nc1nc2ccc(F)cc2c2nc(nn12)-c1ccco1 | 8.8036 |
| 2-(2-furyl)-5-(methylsulfanyl)[1,2,4]triazolo[1,5-c]quinazoline | 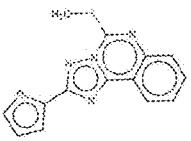 | CSc1nc2ccccc2c2nc(nn12)-c1ccco1 | 1.7863 |
| 2-(2-furyl)-5-methylene-5,6-dihydro[1,2,4]triazolo[1,5-c]quinazoline | 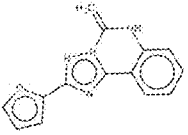 | C=C1Nc2ccccc2-c2nc(nn12)-c1ccco1 | 75.7552 |
| Z1222312995 | 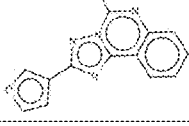 | Cc1nc2ccccc2c2nc(nn12)-c1ccoc1 | 29.7937 |
| BRD-K58390791-001-01-2 | 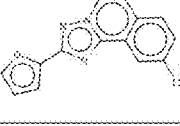 | CNc1nc2ccc(Cl)cc2c2nc(nn12)-c1ccco1 | 4.9304 |
| A17 | 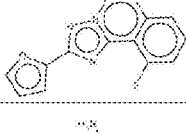 | Nc1nc2cccc(F)c2c2nc(nn12)-c1ccco1 | 7.0150 |
| BRO-027 | 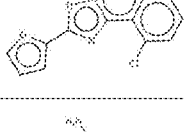 | Nc1nc2cccc(Cl)c2c2nc(nn12)-c1ccco1 | 3.3713 |
| BRO-024 | 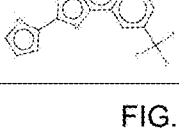 | Nc1nc2ccc(cc2c2nc(nn12)-c1ccco1)C(F)(F)F | 0.8463 |

FIG. 23 (Continued)

| Name | Structure | SMILES string | Solubility (μM) |
|---|---|---|---|

| Name | Structure | SMILES | Value |
|---|---|---|---|
| BIMH-20171221_Cpd4 | 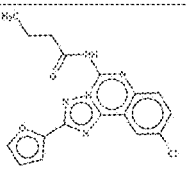 | CCCC(=O)Nc1nc2ccc(Cl)cc2c2nc(nn12)-c1ccco1 | 1.1070 |
| BRD-K85258437-001-01-8 | 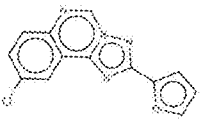 | Clc1ccc2ncn3nc(nc3c2c1)-c1ccco1 | 5.1651 |
| BRO-025 | 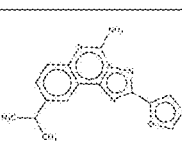 | CC(C)c1ccc2nc(N)n3nc(nc3c2c1)-c1ccco1 | 1.0547 |
| B7 | 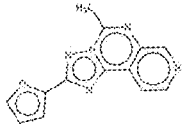 | Cc1nc2cnccc2c2nc(nn12)-c1ccco1 | 96.8134 |
| BIMH-20171221_Cpd7 | 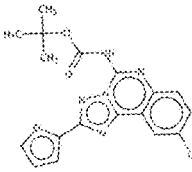 | CC(C)(C)OC(=O)Nc1nc2ccc(Cl)cc2c2nc(nn12)-c1ccco1 | 4.7147 |
| 3-Methylcholanthrene | 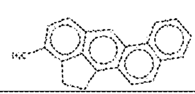 | Cc1ccc2cc3c(ccc4ccccc43)c5CCc1c52 | |
| A16 | 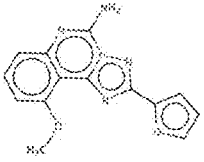 | COc1cccc2nc(N)n3nc(nc3c12)-c1ccco1 | 28.7773 |
| BIMH-20171221_Cpd2 | 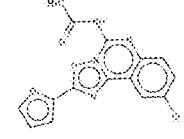 | CC(=O)Nc1nc2ccc(Cl)cc2c2nc(nn12)-c1ccco1 | 4.3324 |
FIG. 23 (Continued)

| Name | Structure | SMILES string | Solubility (μM) |
|---|---|---|---|
| BIMH-20171221_Cpd10 | 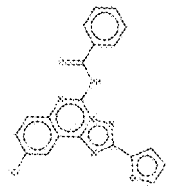 | Clc1ccc2nc(NC(=O)c3ccccc3)n3nc(nc3c2c1)-c1ccco1 | 0.8367 |
| 2-(2-furyl)[1,2,4]triazolo[1,5-c]quinazoline | 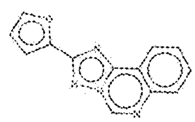 | c1coc(c1)-c1nc2c3ccccc3ncn2n1 | 92.8516 |
| BRO-026 | 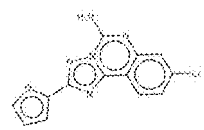 | Nc1nc2cc(Cl)ccc2c2nc(nn12)-c1ccco1 | 1.3113 |
| BRD-K10462076-001-01-2 | 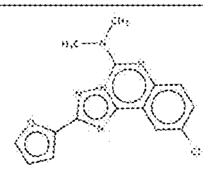 | CN(C)c1nc2ccc(Cl)cc2c2nc(nn12)-c1ccco1 | 0.3406 |
| BRO-017 | 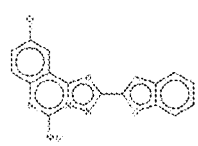 | Nc1nc2ccc(Cl)cc2c2nc(nn12)-c1cc2ccccc2o1 | 0.0178 |
| 5-(4-methyl-1-piperidinyl)-2-phenyl[1,2,4]triazolo[1,5-c]quinazoline | 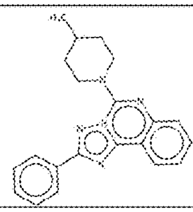 | CC1CCN(CC1)c1nc2ccccc2c2nc(nn12)-c1ccccc1 | 0.1043 |
| B5 | 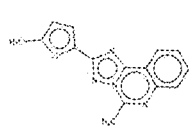 | Cc1ccc(o1)-c1nc2c3ccccc3nc(C)n2n1 | 5.5407 |
| Arcyriaflavin A | 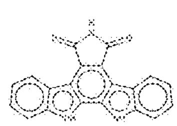 | O=C1NC(=O)c2c1c3c4ccccc4[nH]c3c5[nH]c6ccccc6c25 | |

FIG. 23 (Continued)

| Name | Structure | SMILES string | Solubility (μM) |
|---|---|---|---|
| MRS-1220 | 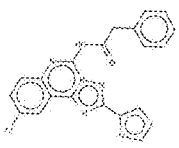 | Clc1ccc2nc(NC(=O)Cc3ccccc3)n4nc(nc4c2c1)c5ccco5 | 0.6872 |
| A2 | 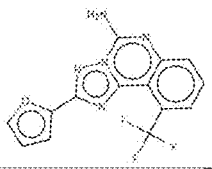 | Nc1nc2cccc(c2c2nc(nn12)-c1ccco1)C(F)(F)F | 0.4548 |
| SCH-58261 | 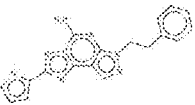 | Nc1nc2n(CCc3ccccc3)ncc2c4nc(nn14)c5ccco5 | 1.8987 |
| GTP 14564 | 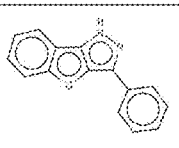 | c1ccc(cc1)c2n[nH]c3c2oc4ccccc34 | |
| B3 | 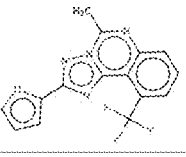 | Cc1nc2cccc(c2c2nc(nn12)-c1ccco1)C(F)(F)F | 0.2783 |
| A15 | 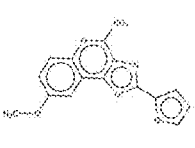 | COc1ccc2nc(N)n3nc(nc3c2c1)-c1ccco1 | 0.9263 |
| SCH 442416 | 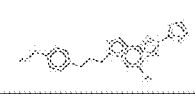 | COc1ccc(CCCn2ncc3c4nc(nn4c(N)nc23)c5ccco5)cc1 | 1.1041 |
| 2-(2-furyl)[1,2,4]triazolo[1,5-c]quinazolin-5(6H)-one | 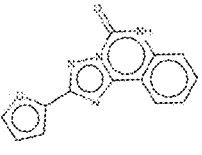 | O=c1[nH]c2ccccc2c2nc(nn12)-c1ccco1 | 54.4749 |
FIG. 23 (Continued)

| Name | Structure | SMILES string | Solubility (μM) |
|---|---|---|---|
| A1 | 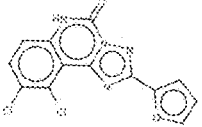 | Clc1ccc2[nH]c(=O)n3nc(nc3c2c1Cl)-c1ccco1 | 2.0180 |
| 2-(2-furyl)[1,2,4]triazolo[1,5-c]quinazolin-5-yl hydrosulfide | 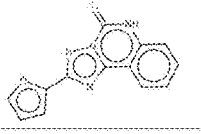 | S=c1[nH]c2cccccc2c2nc(nn12)-c1ccco1 | 141.5786 |
| BRO-018 | 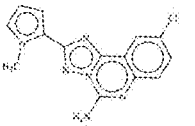 | Cn1cccc1-c1nc2c3cc(Cl)ccc3nc(N)n2n1 | 0.8214 |
| BRO-013 | 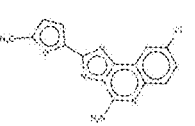 | Cc1ccc(o1)-c1nc2c3cc(Cl)ccc3nc(N)n2n1 | 0.4615 |
| FICZ | 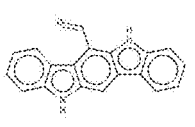 | O=Cc1c2[nH]c3cccc3c2cc4[nH]c5ccccc5c14 | |
| Indirubin-3'-oxime | 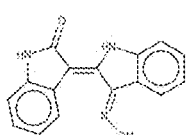 | O/N=C\1/C(=C\2/C(=O)Nc3ccccc23)/Nc4ccccc14 | |
| BRO-014 | 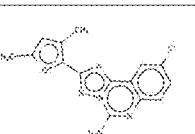 | Cc1cc(C)c(o1)-c1nc2c3cc(Cl)ccc3nc(N)n2n1 | 0.1375 |
| BRD-K17851208-001-01-0 | 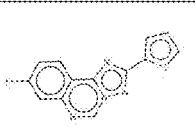 | Fc1ccc2c3nc(nn3cnc2c1)-c1cccs1 | 4.8869 |
FIG. 23 (Continued)

| Name | Structure | SMILES string | Solubility (μM) |
|---|---|---|---|
| MRS-1220 | 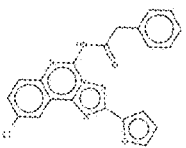 | Clc1ccc2nc(NC(=O)Cc3ccccc3)n4nc(nc4c2c1)c5ccco5 | 0.7679 |
| N-(2-phenyl[1,2,4]triazolo[1,5-c]quinazolin-5-yl)-N-(tetrahydro-2-furanylmethyl)amine | 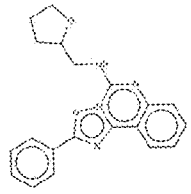 | C(Nc1nc2ccccc2c2nc(nn12)-c1ccccc1)C1CCCO1 | 2.6499 |
| 4-oxo-N'-(2-phenyl[1,2,4]triazolo[1,5-c]quinazolin-5-yl)-4-(1-pyrrolidinyl)butanohydrazide | 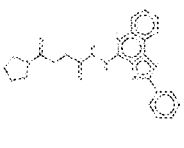 | O=C(CCC(=O)N1CCCC1)NNc1nc2ccccc2c2nc(nn12)-c1ccccc1 | 0.9686 |
| 2-methyl-7-phenyl-7H-pyrazolo[4,3-e][1,2,4]triazolo[1,5-c]pyrimidine | 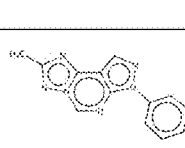 | Cc1nc2c3cnn(c4ccccc4)c3ncn2n1 | 104.8372 |
| 2-(3-methyl-2-thienyl)[1,2,4]triazolo[1,5-c]quinazoline | 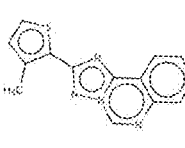 | Cc1ccsc1-c1nc2c3ccccc3ncn2n1 | 1.6916 |
| N-(2-furylmethyl)-2-phenyl[1,2,4]triazolo[1,5-c]quinazolin-5-amine | 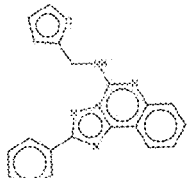 | C(Nc1nc2ccccc2c2nc(nn12)-c1ccccc1)c1ccco1 | 0.3711 |
| N-cyclopropyl-N-(2-phenyl[1,2,4]triazolo[1,5-c]quinazolin-5-yl)amine | 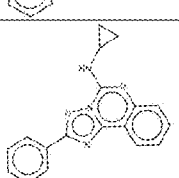 | C1CC1Nc1nc2ccccc2c2nc(nn12)-c1ccccc1 | 1.1321 |

FIG. 23 (Continued)

| Name | Structure | SMILES string | Solubility (µM) |
|---|---|---|---|
| L-Kynurenin | 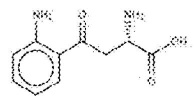 | N[C@@H](CC(=O)c1ccccc1N)C(O)=O | |
| CH223191 | 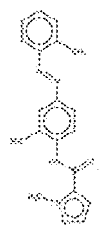 | Cc1cc(ccc1NC(=O)c1ccnn1C)\N=N\c1ccccc1C | |
| MeBIO | 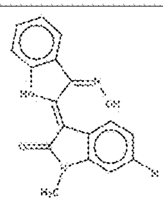 | CN1C(=O)/C(=C/2\Nc3ccccc3\C2=N\O)/c4ccc(Br)cc14 | |
| 2-(4-chlorobenzyl)-7H-pyrazolo[4,3-e][1,2,4]triazolo[1,5-c]pyrimidine | 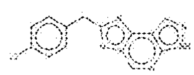 | Clc1ccc(Cc2nc3c4cn[nH]c4ncn3n2)cc1 | 7.3755 |
| BRO-021 | 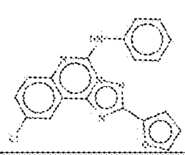 | Clc1ccc2nc(Nc3ccccc3)n3nc(nc3c2c1)-c1ccco1 | 0.0149 |
| N-(2-furylmethyl)-2-(3-pyridinyl)[1,2,4]triazolo[1,5-c]quinazolin-5-amine | 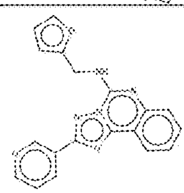 | C(Nc1nc2ccccc2c2nc(nn12)-c1cccnc1)c1ccco1 | |
| N-[2-(3-methylphenyl)ethyl]-2-(4-pyridinyl)[1,2,4]triazolo[1,5-c]quinazolin-5-amine | 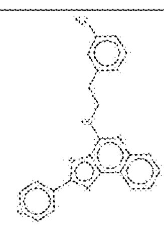 | Cc1cccc(CCNc2nc3ccccc3c3nc(nn23)-c2ccncc2)c1 | |

FIG. 23 (Continued)

| Name | Structure | SMILES string | Solubility (μM) |
|---|---|---|---|
| 6,2,4-Trimethoxyflavone | 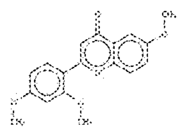 | COc1ccc(c(OC)c1)-c1cc(=O)c2cc(OC)ccc2o1 | |
| 2-(3-methoxyphenyl)-7H-pyrazolo[4,3-e][1,2,4]triazolo[1,5-c]pyrimidine | 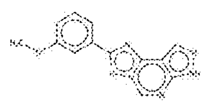 | COc1cccc(c1)-c1nc2c3cn[nH]c3ncn2n1 | |
| ITE | 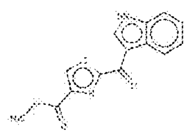 | COC(=O)c1csc(n1)C(=O)c2c[nH]c3ccccc23 | |
| Pifithrin-μ hydrobromide | | Cc1ccc(cc1)C(=O)Cn2c3CCCCc3sc2=N | |
| 2-(4-bromo-2-thienyl)[1,2,4]triazolo[1,5-c]quinazoline | 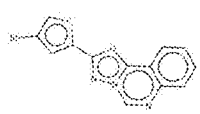 | Brc1csc(c1)-c1nc2c3ccccc3ncn2n1 | 0.8168 |
| N-(2-phenylethyl)-N-(2-phenyl[1,2,4]triazolo[1,5-c]quinazolin-5-yl)amine | 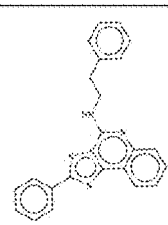 | C(Cc1ccccc1)Nc1nc2ccccc2c2nc(nn12)-c1ccccc1 | 0.0103 |
| BIMH-20171221_Cpd8 | 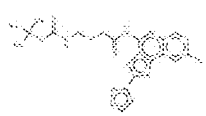 | CC(C)(C)OC(=O)NCCCC(=O)Nc1nc2ccc(Cl)cc2c2nc(nn12)-c1cccco1 | |

FIG. 23 (Continued)

| Name | Structure | SMILES string | Solubility (μM) |
|---|---|---|---|
| N-(2-furylmethyl)-2-(3-methylphenyl)[1,2,4]triazolo[1,5-c]quinazolin-5-amine | 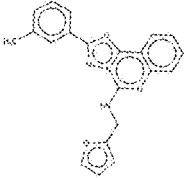 | Cc1cccc(c1)-c1nc2c3ccccc3nc(NCc3ccco3)n2n1 | 0.0851 |
| N-[2-(4-chlorophenyl)ethyl]-2-phenyl[1,2,4]triazolo[1,5-c]quinazolin-5-amine | 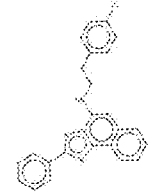 | Clc1ccc(CCNc2nc3ccccc3c3nc(nn23)-c2ccccc2)cc1 | |
| N-cyclopentyl-4-oxo-4-[2-(2-phenyl[1,2,4]triazolo[1,5-c]quinazolin-5-yl)hydrazino]butanamide | 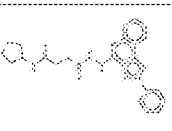 | O=C(CCC(=O)NC1CCCC1)NNc1nc2ccccc2c2nc(nn12)-c1ccccc1 | 0.2143 |
| 2,3,7,8-Tetrachloro-p-dioxin | 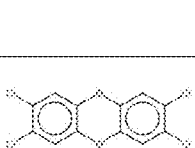 | Clc1cc2Oc3cc(Cl)c(Cl)cc3Oc2cc1Cl | |
| DiMNF | 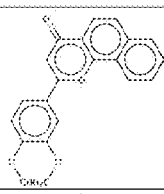 | COc1ccc(cc1OC)-c1cc(=O)c2ccc3ccccc3c2o1 | |
| paclitaxel | 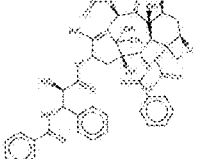 | CC(=O)O[C@@H]1C2=C(C)[C@H](C[C@@](O)([C@@H](OC(=O)c3ccccc3)[C@@H]4[C@@]5(CO[C@@H]5C[C@H](O)[C@@]4(C)C1=O)OC(=O)C)C2(C)C)OC(=O)[C@H](O)[C@@H](NC(=O)c6ccccc6)c7ccccc7 | |

| Name | Structure | SMILES string | Solubility (μM) |
|---|---|---|---|
| N-(4-methoxybenzyl)-2-(3-methylphenyl)[1,2,4]triazolo[1,5-c]quinazolin-5-amine | 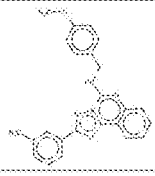 | COc1ccc(CNc2nc3ccccc3c3nc(nn23)-c2cccc(C)c2)cc1 | |
| N-(4-chlorobenzyl)-2-(3-methylphenyl)[1,2,4]triazolo[1,5-c]quinazolin-5-amine | 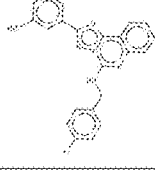 | Cc1cccc(c1)-c1nc2c3ccccc3nc(NCc3ccc(Cl)cc3)n2n1 | |
| N-butyl-2-(3-pyridinyl)[1,2,4]triazolo[1,5-c]quinazolin-5-amine | 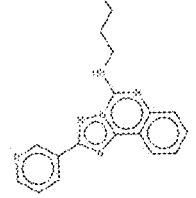 | CCCCNc1nc2ccccc2c2nc(nn12)-c1cccnc1 | |
| N-[2-(3-methylphenyl)ethyl]-2-phenyl[1,2,4]triazolo[1,5-c]quinazolin-5-amine | 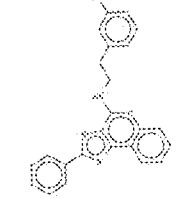 | Cc1cccc(CCNc2nc3ccccc3c3nc(nn23)-c2ccccc2)c1 | 0.0195 |
| Bortezomib | 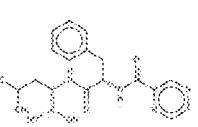 | CC(C)C[C@H](NC(=O)[C@H](Cc1ccccc1)NC(=O)c1cnccn1)B(O)O | |

FIG. 23 (Continued)

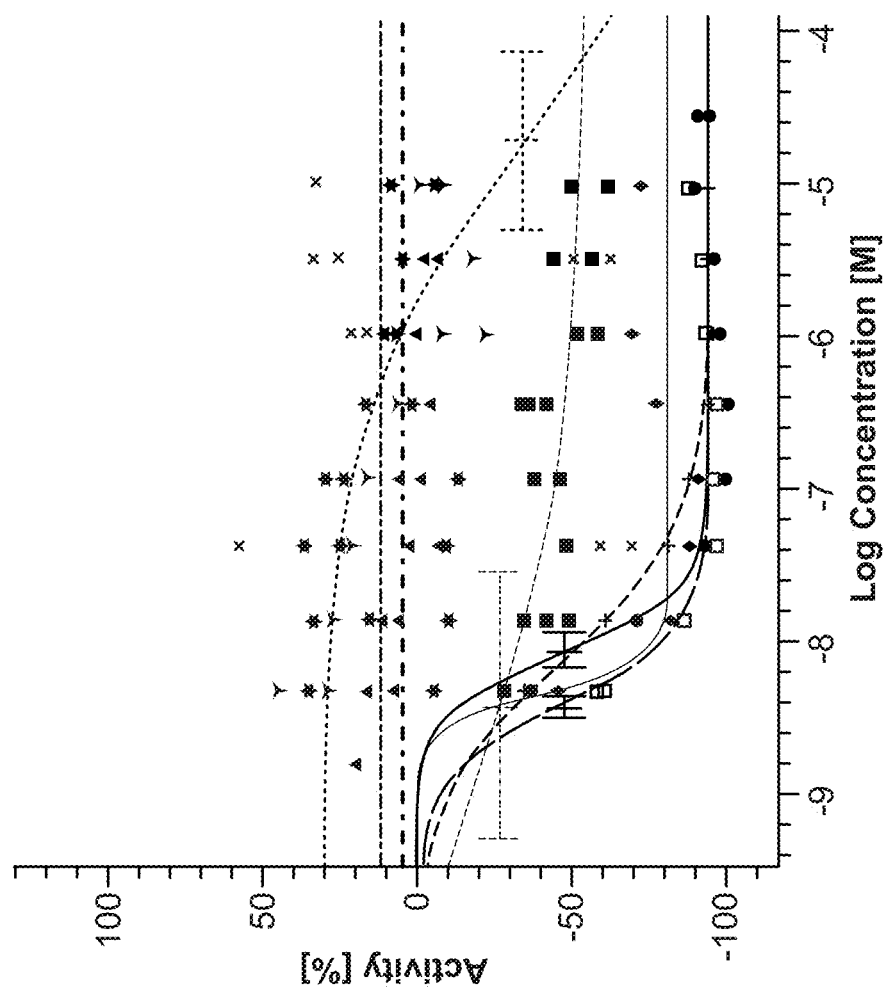
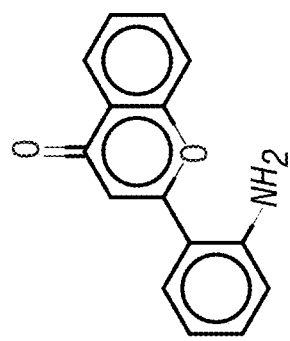
FIG. 24

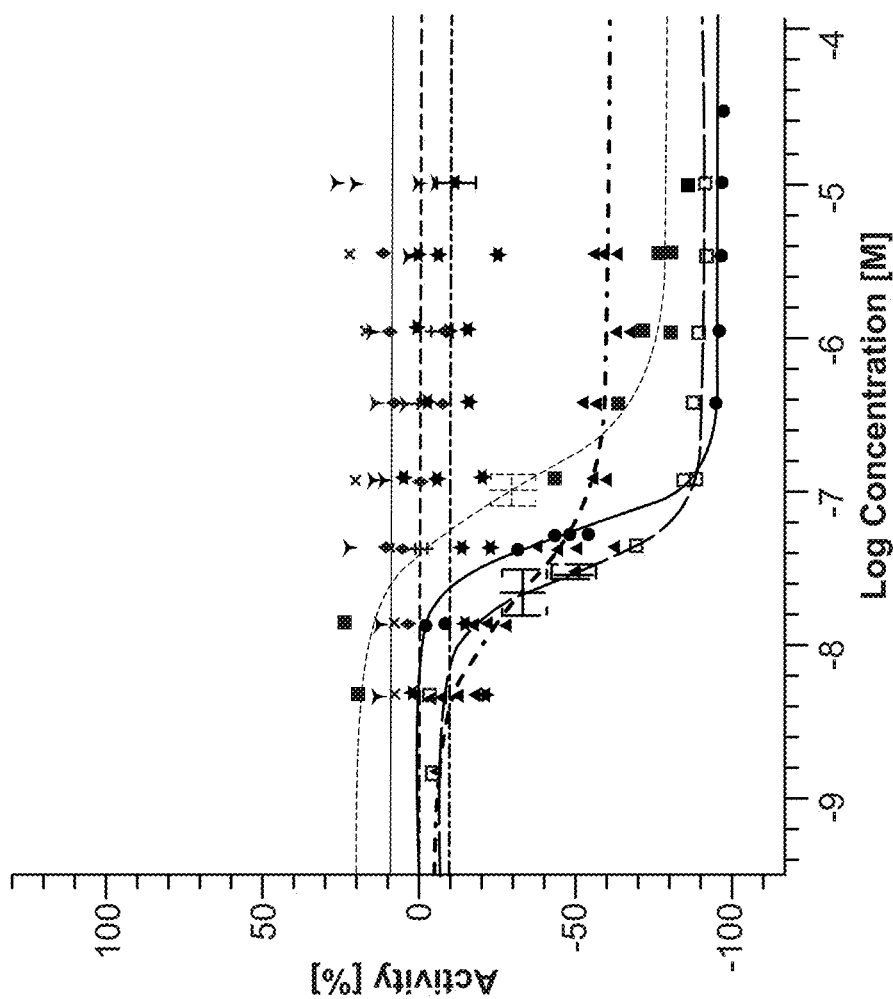
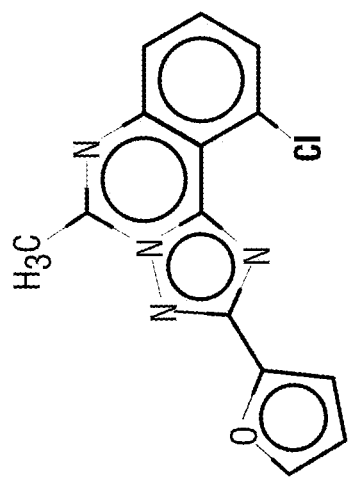
FIG. 24 (Continued)

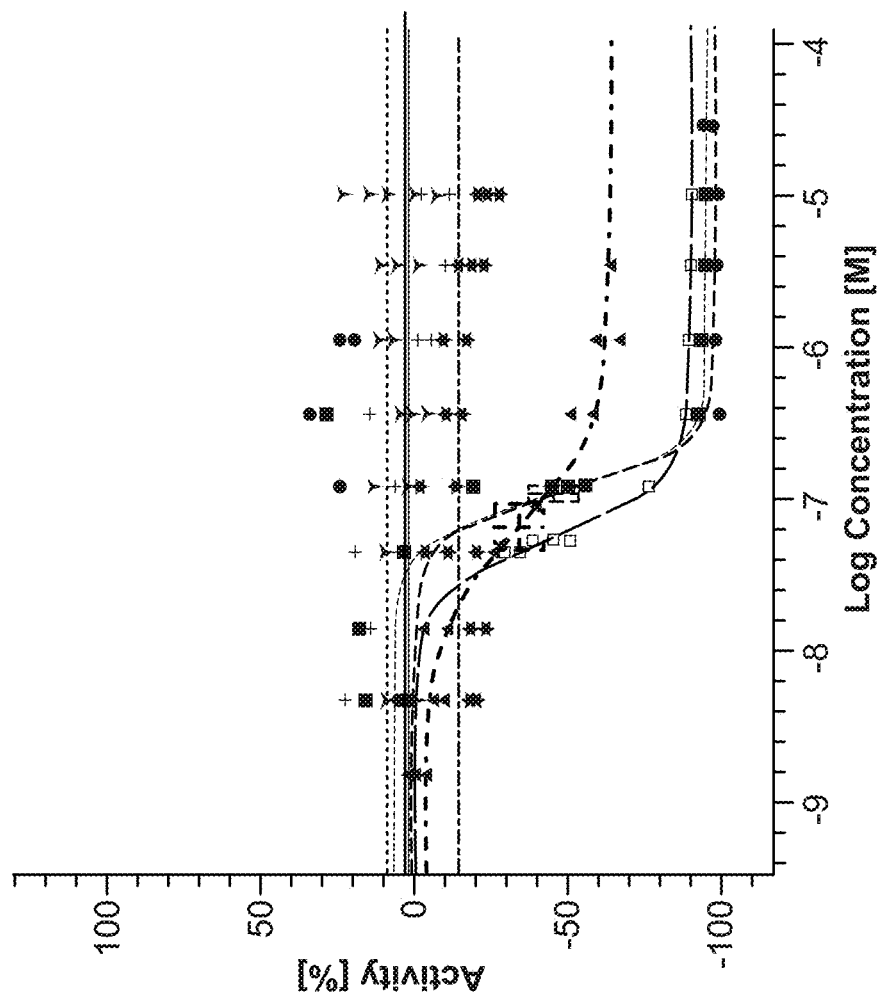
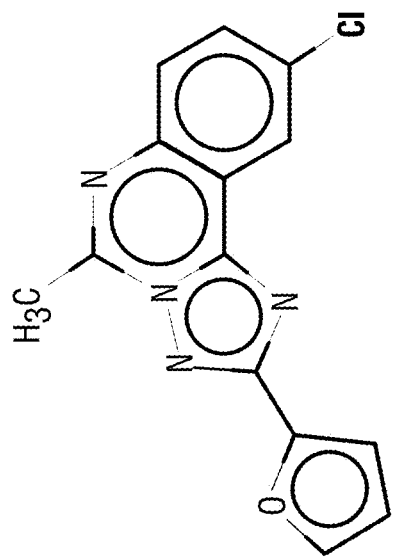
FIG. 24 (Continued)

FIG. 24 (Continued)
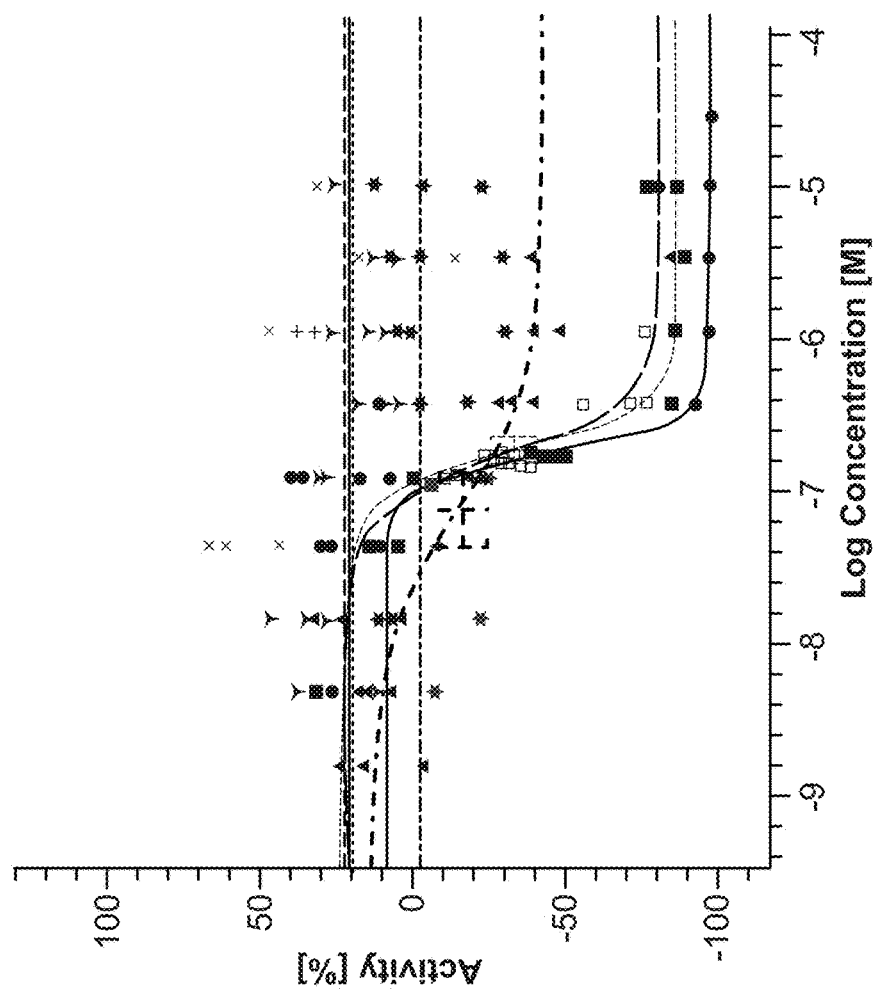
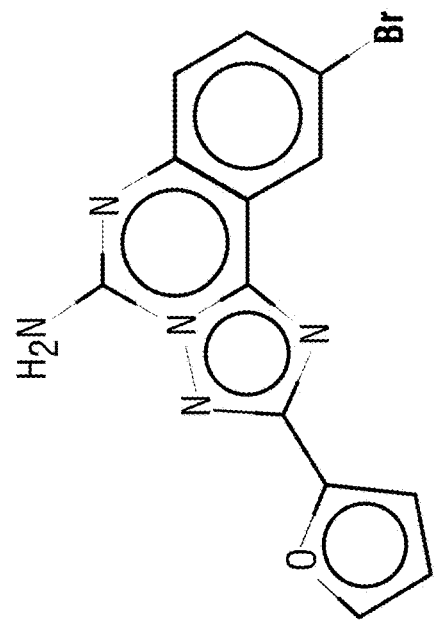

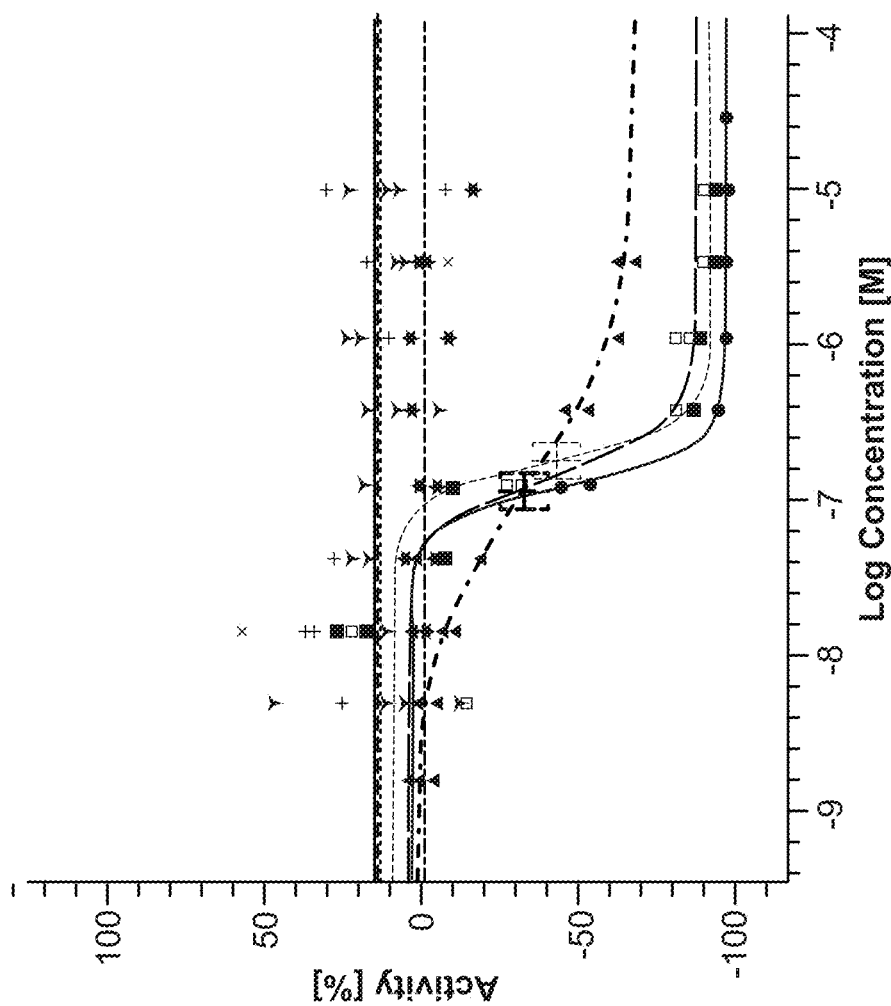
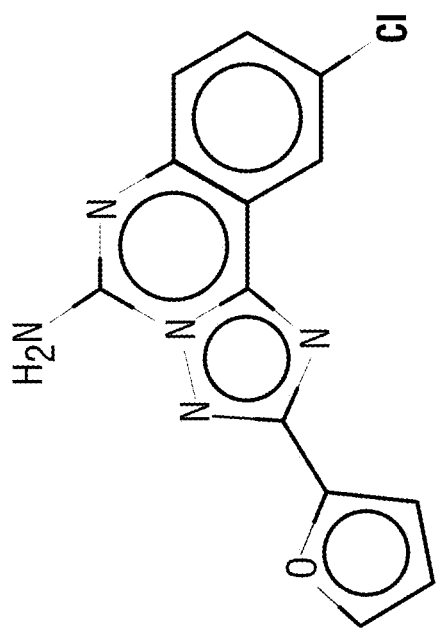
FIG. 24 (Continued)

FIG. 24 (Continued)
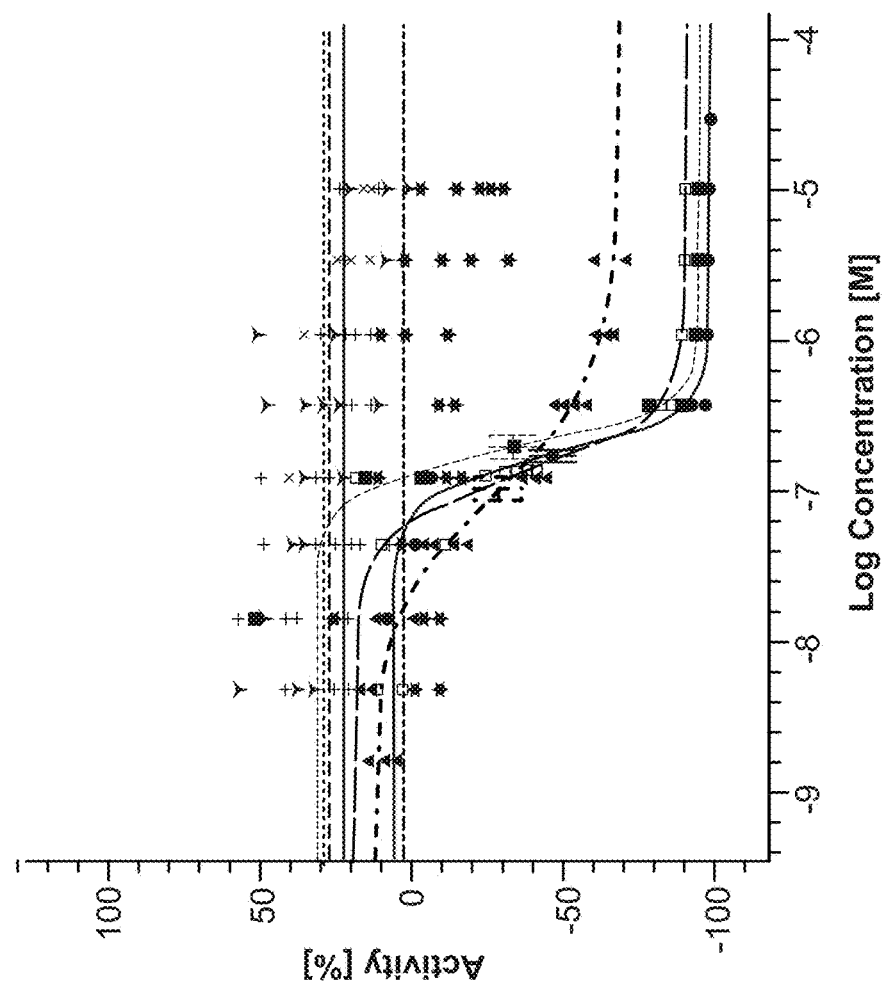
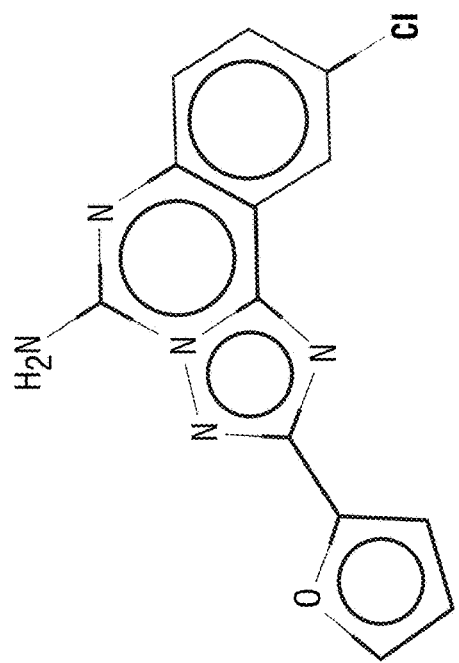

FIG. 24 (Continued)
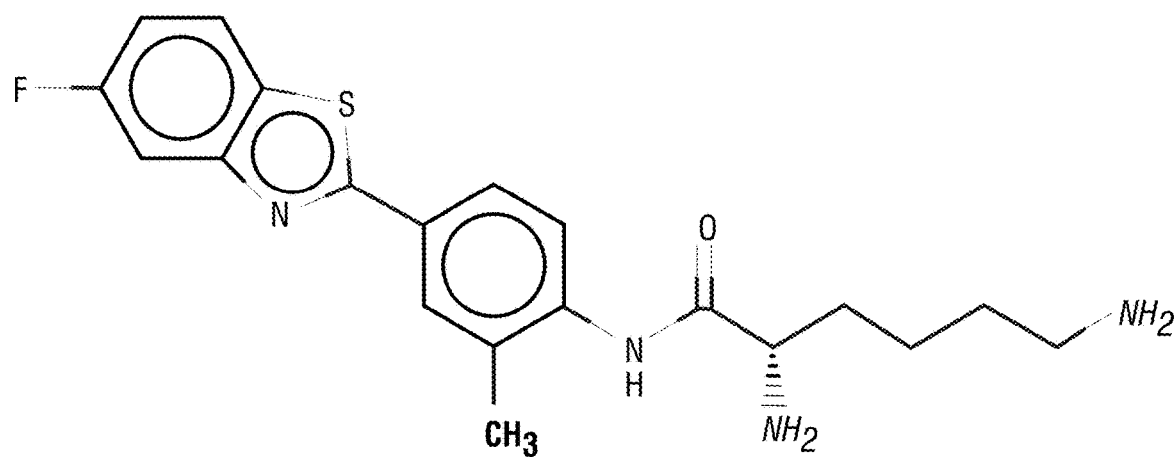
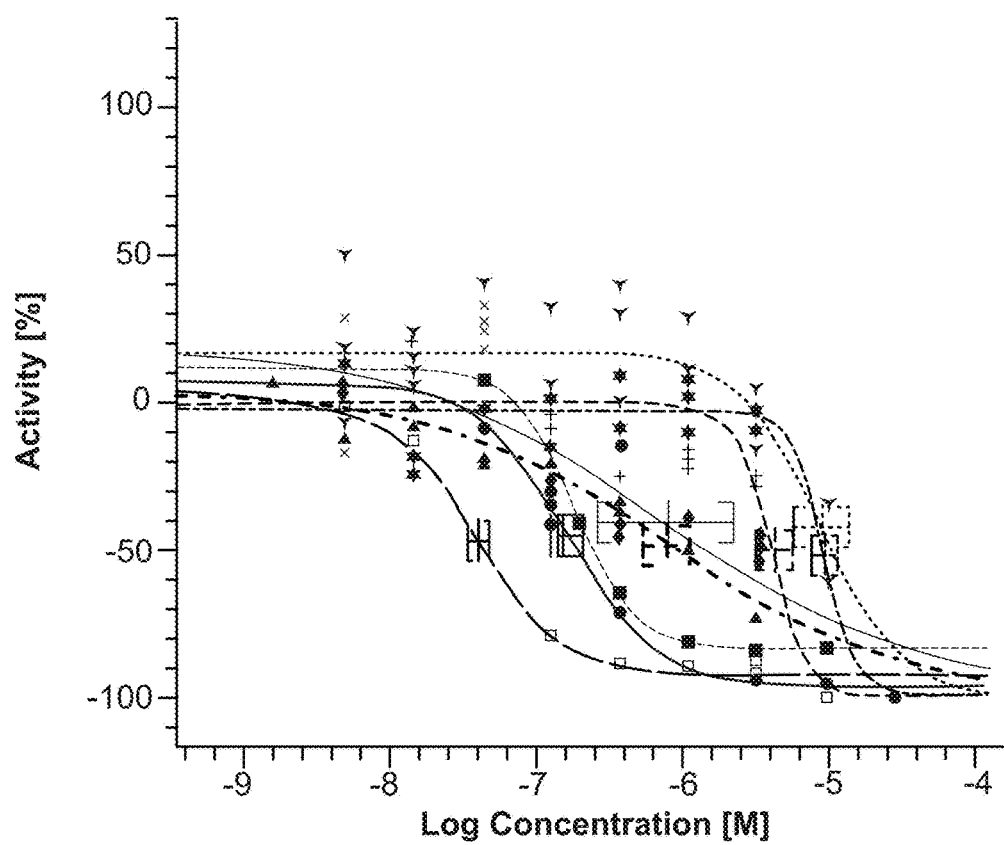

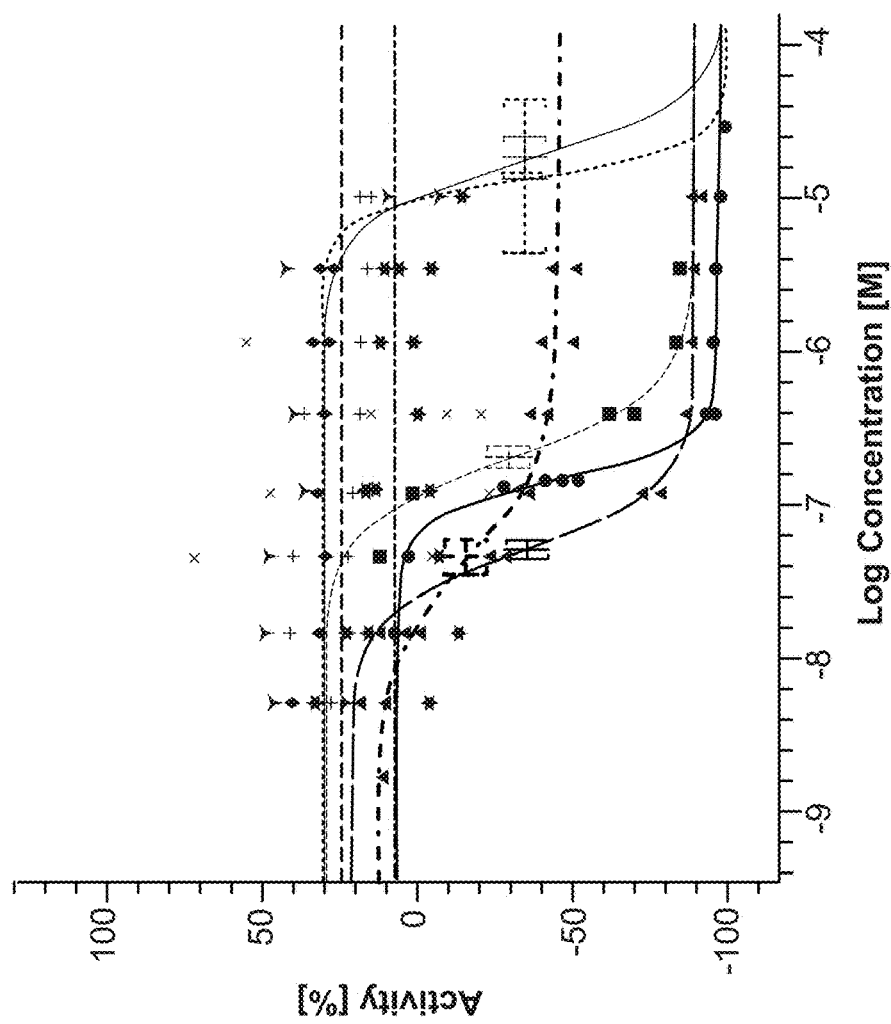
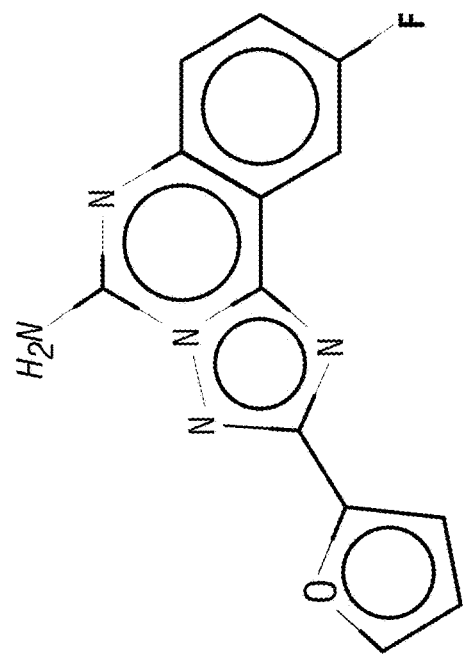
FIG. 24 (Continued)

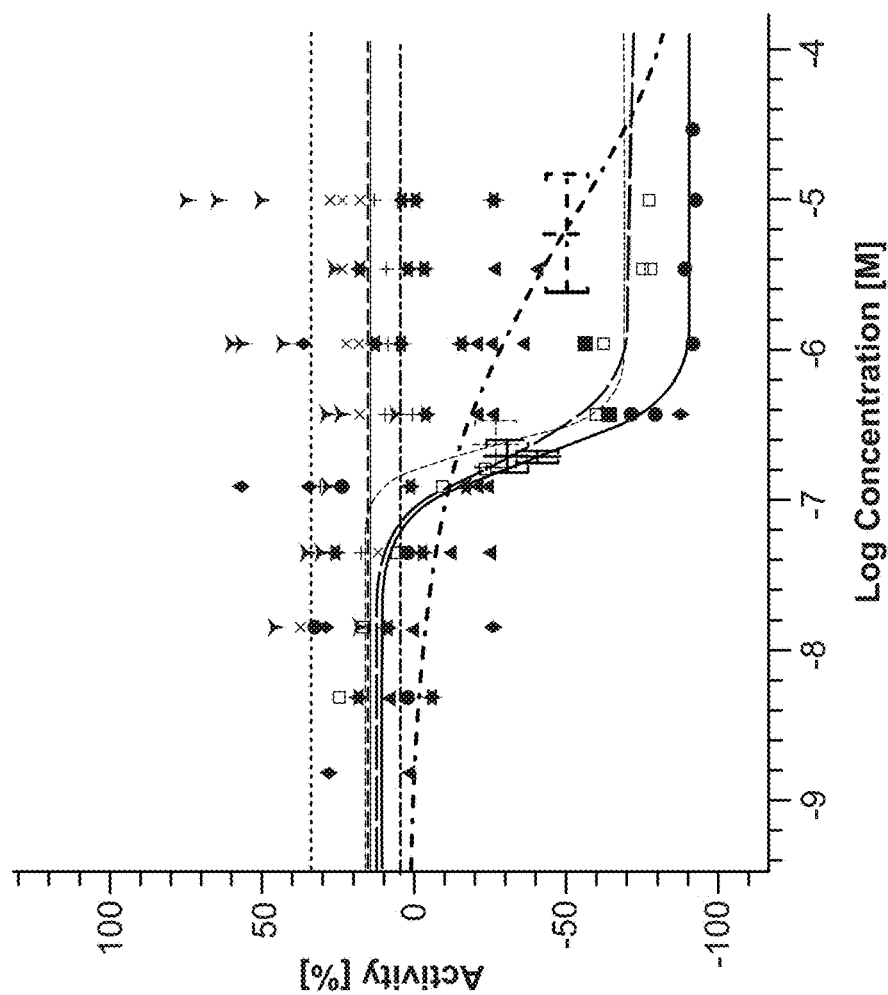
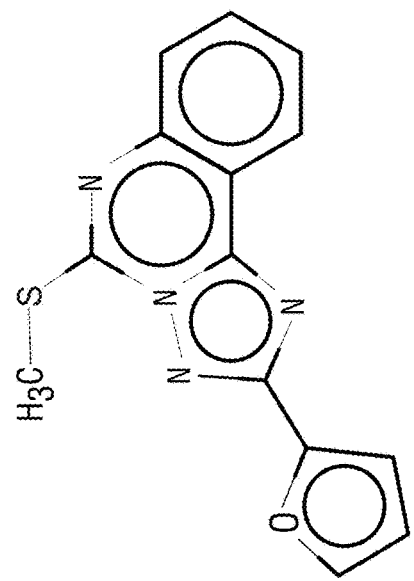
FIG. 24 (Continued)

FIG. 24 (Continued)
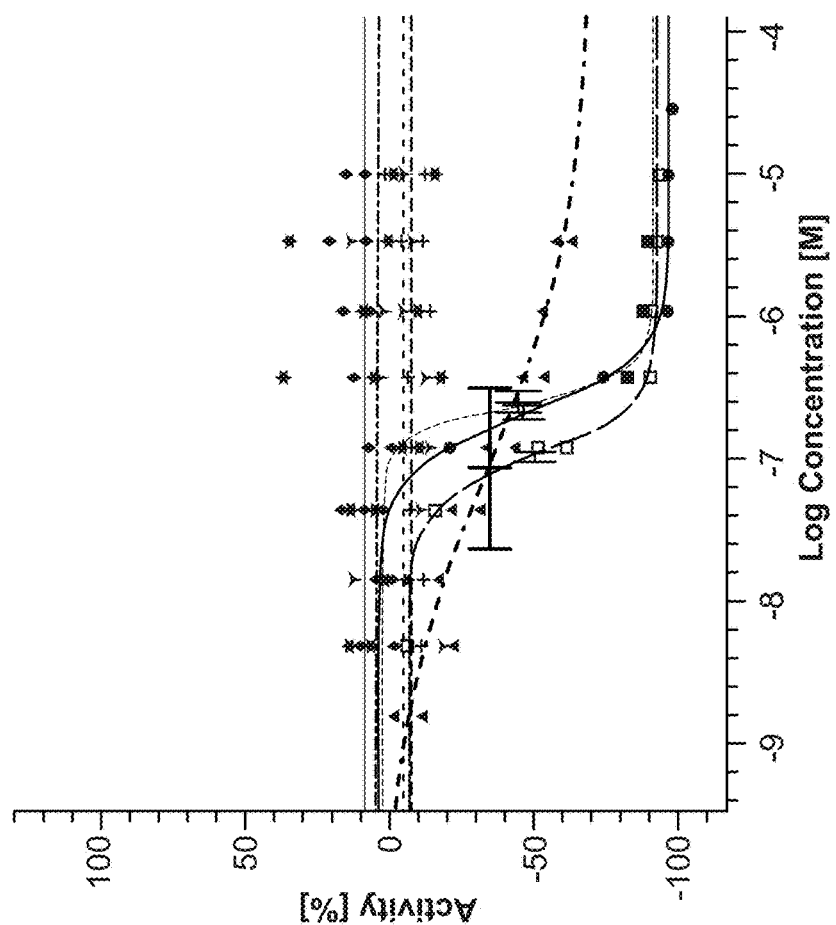
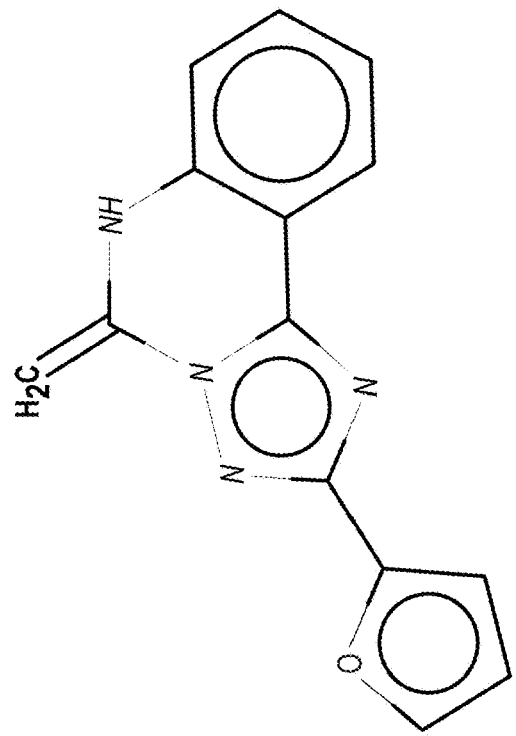

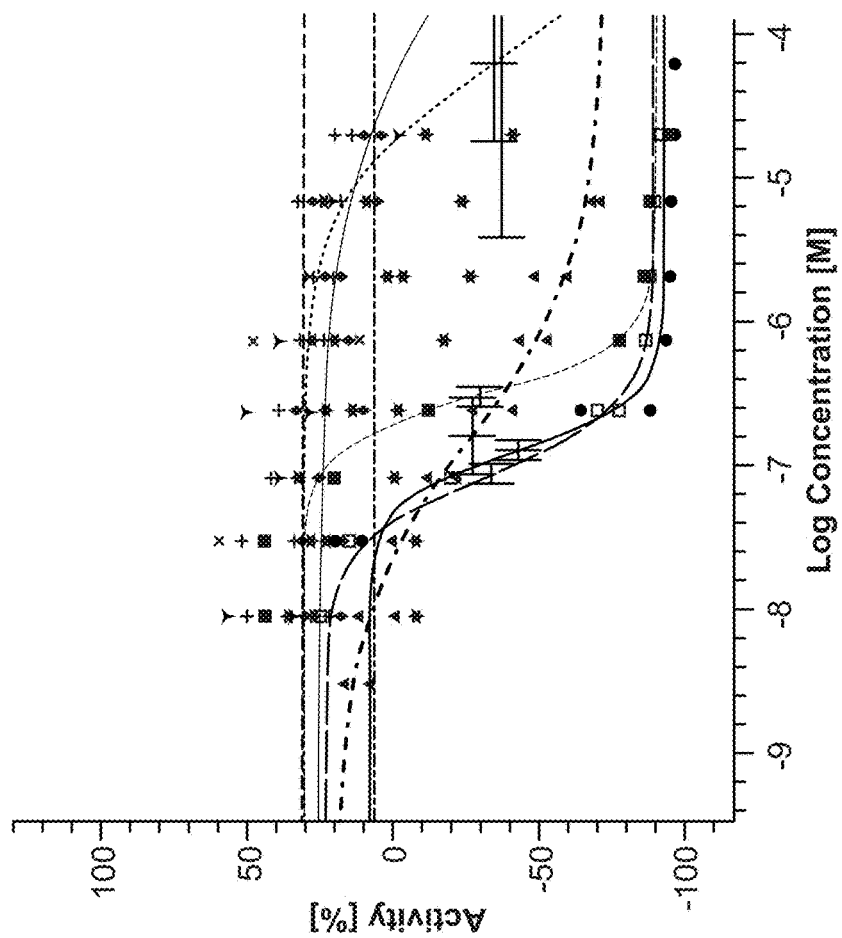
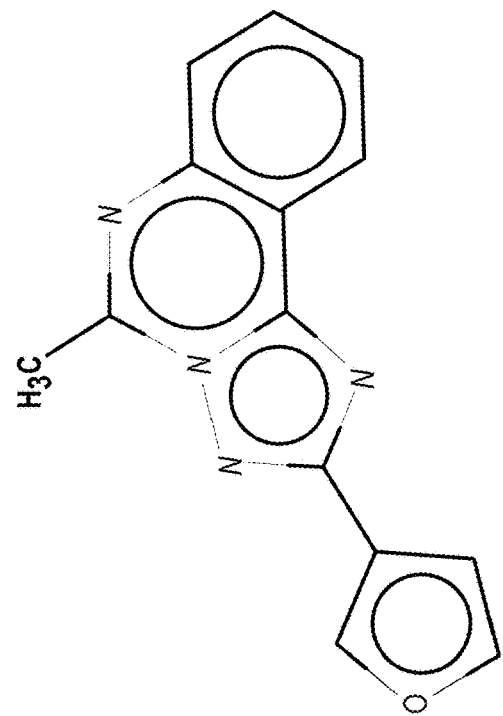
FIG. 24 (Continued)

FIG. 24 (Continued)
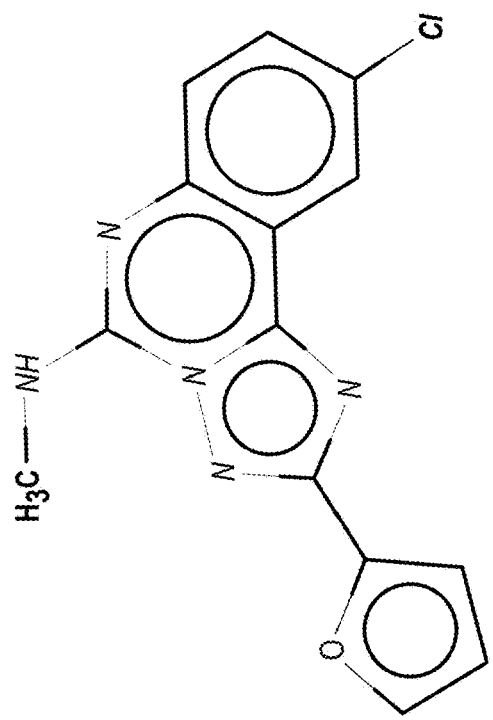
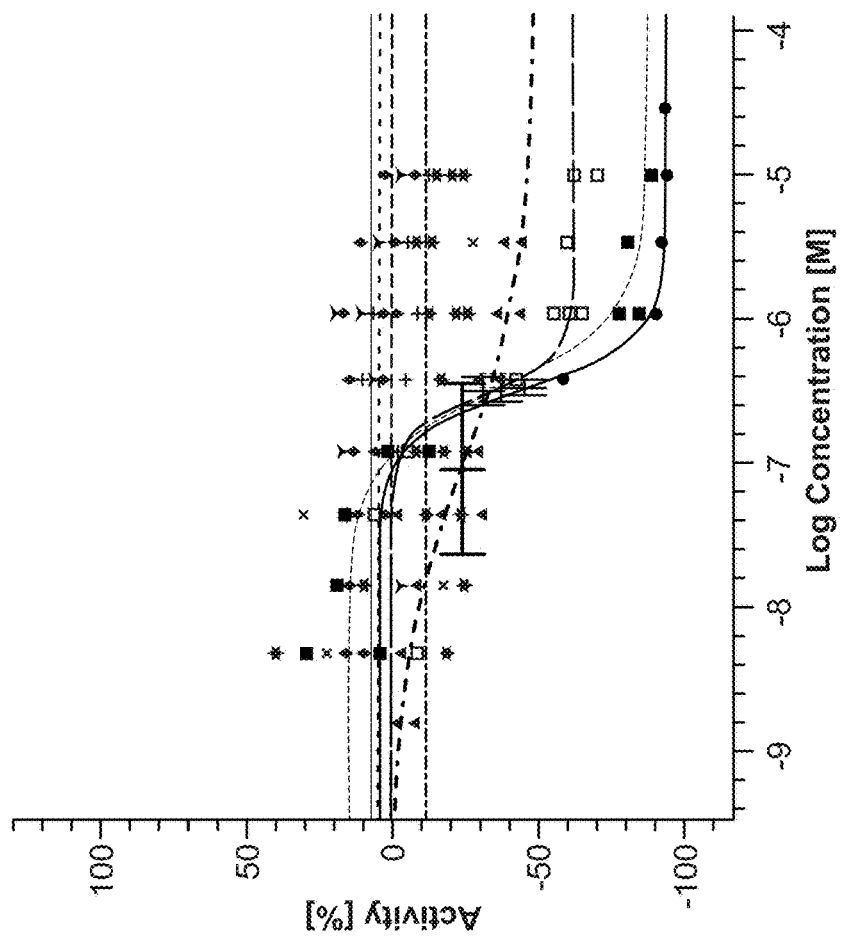

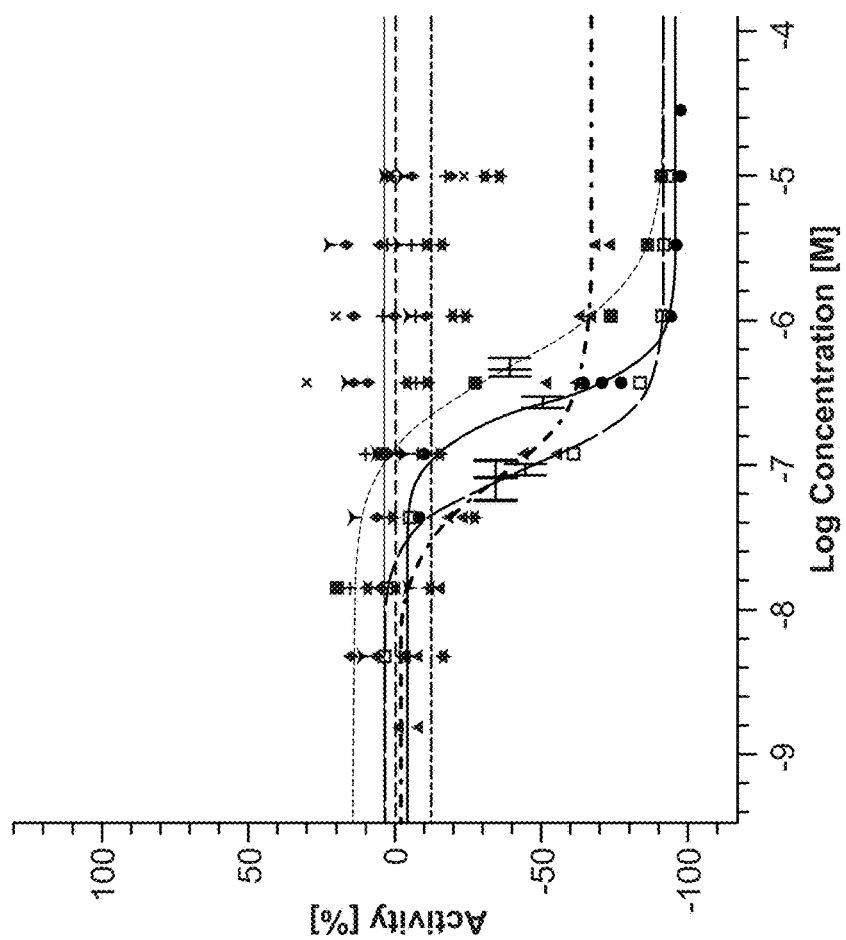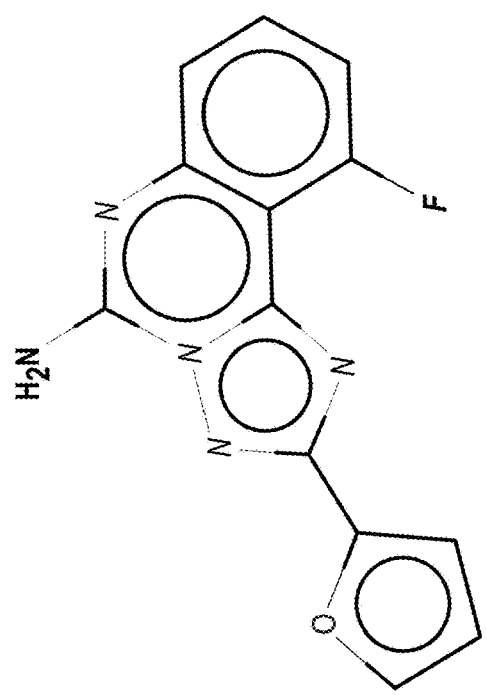
FIG. 24 (Continued)

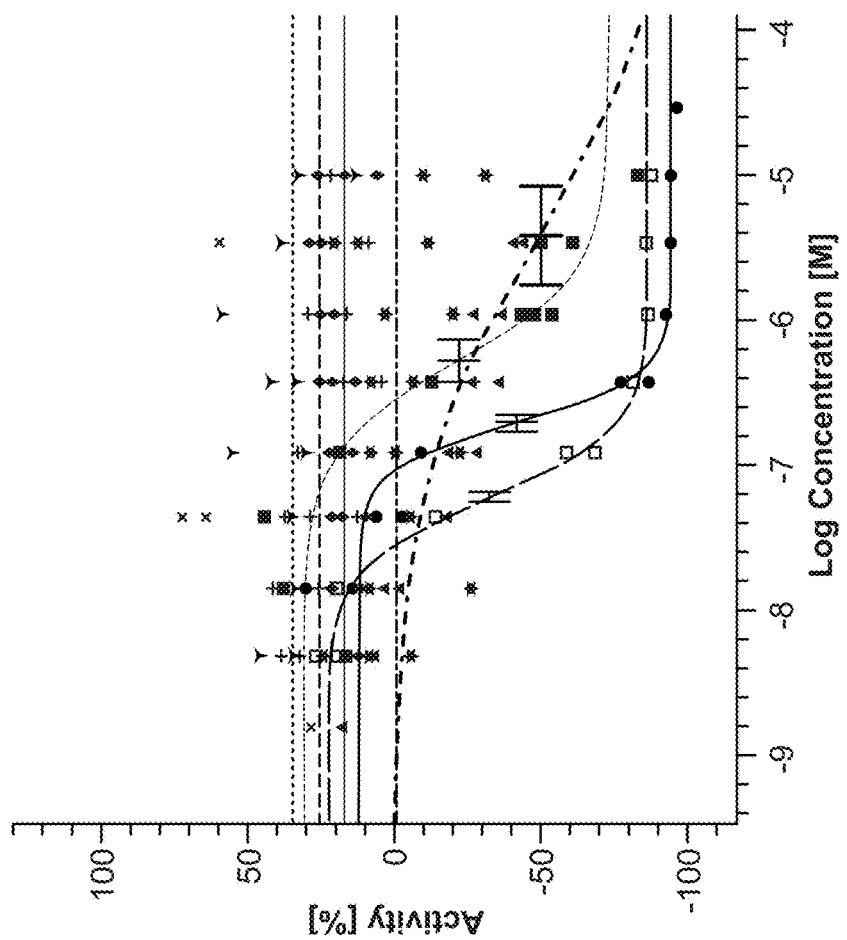
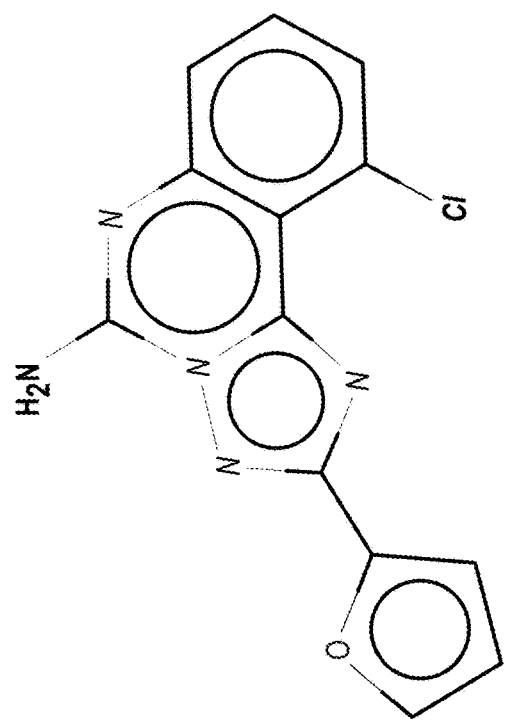
FIG. 24 (Continued)

FIG. 24 (Continued)
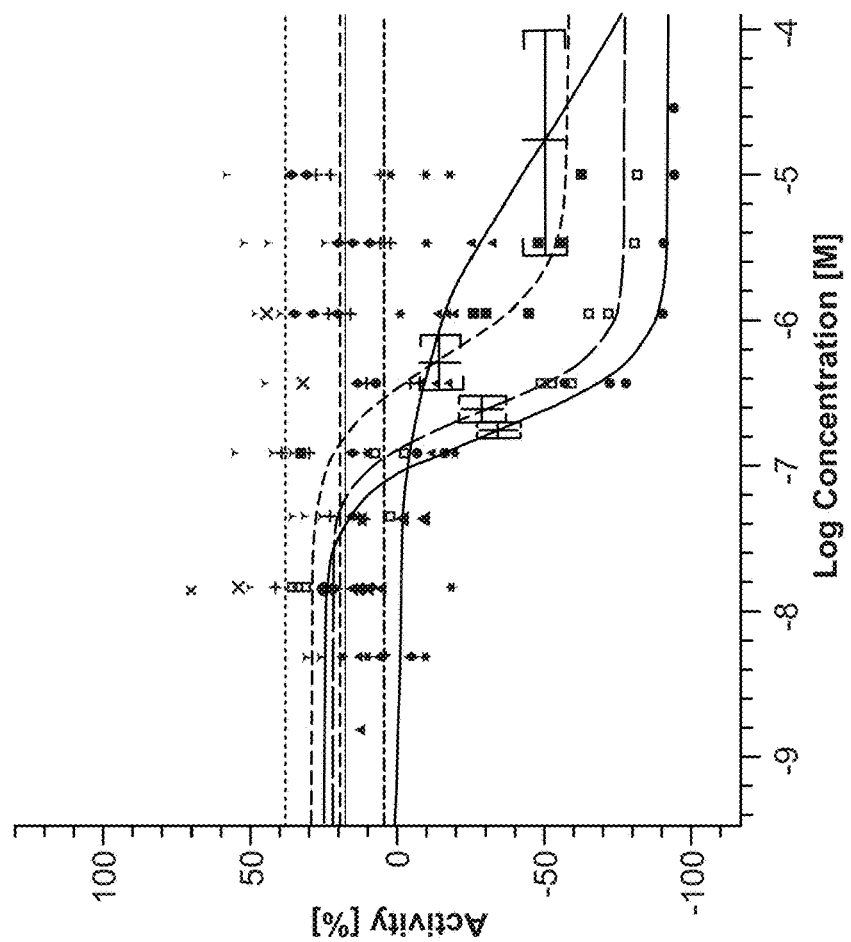
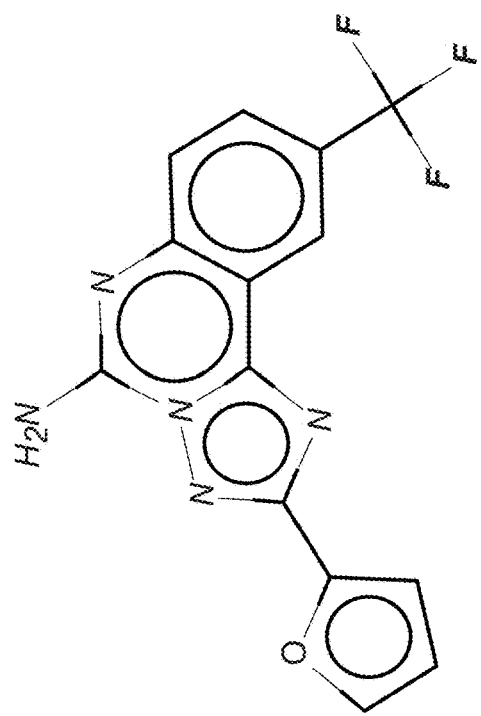

FIG. 24 (Continued)
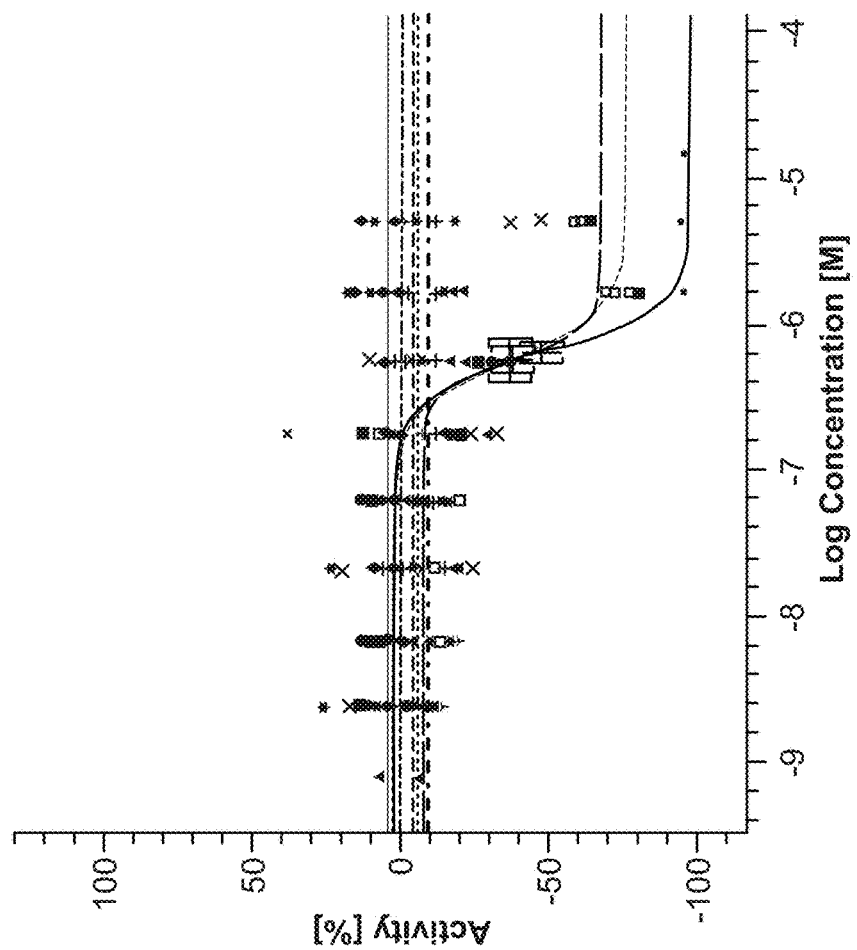
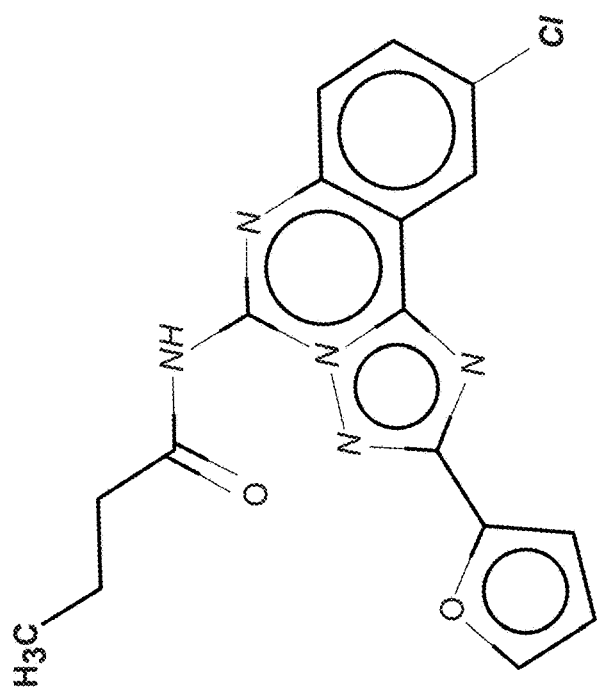

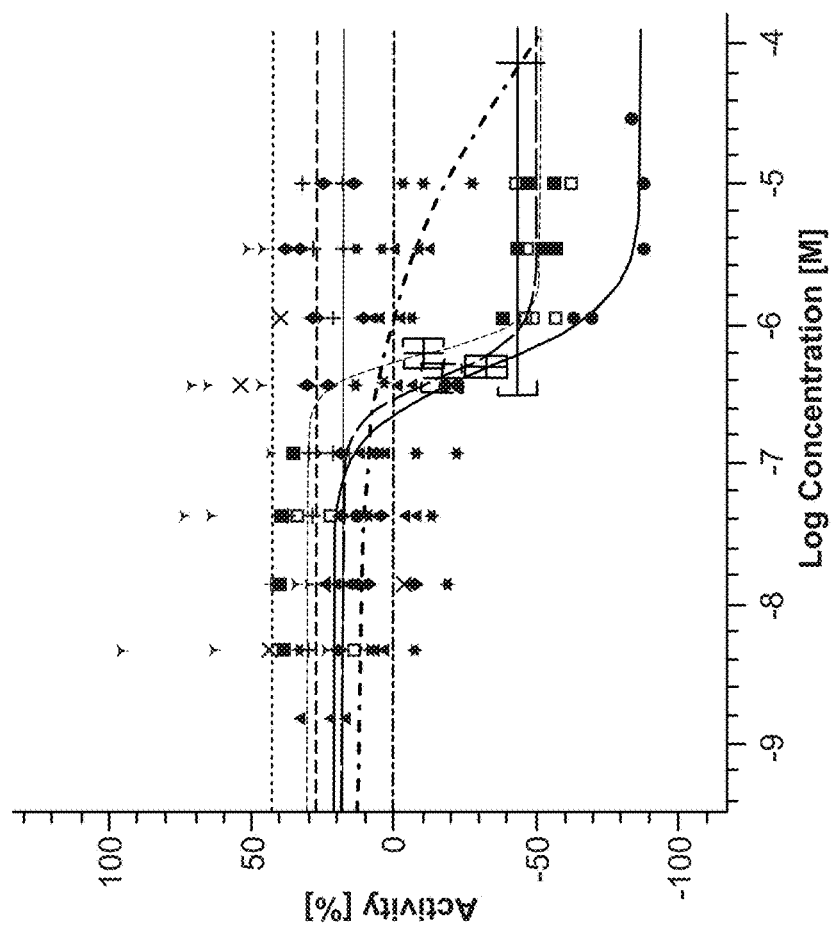
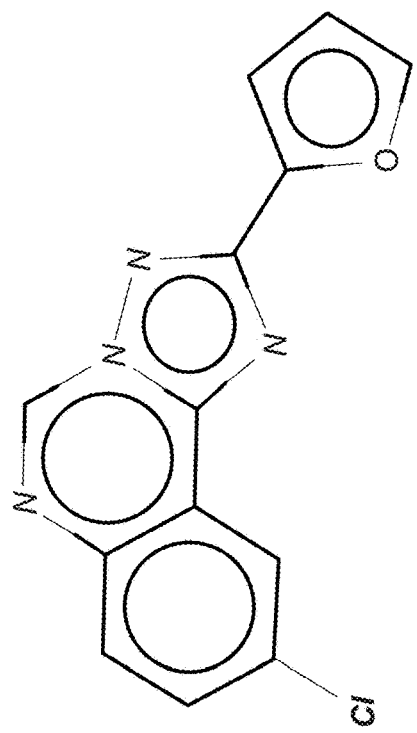
FIG. 24 (Continued)

FIG. 24 (Continued)
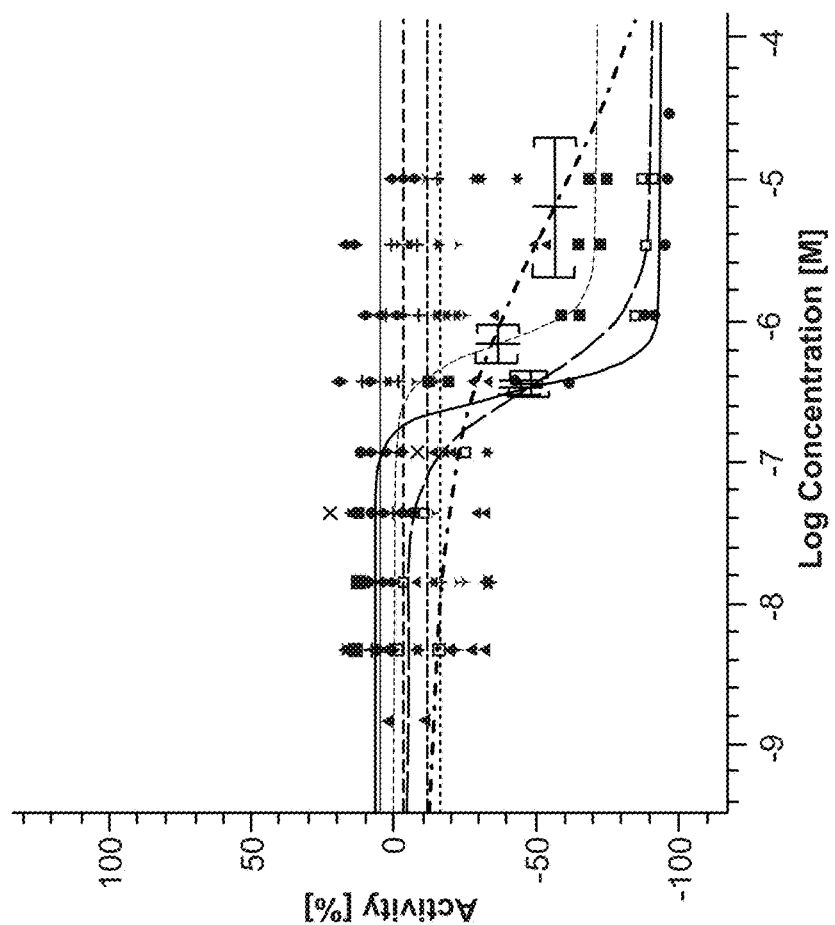
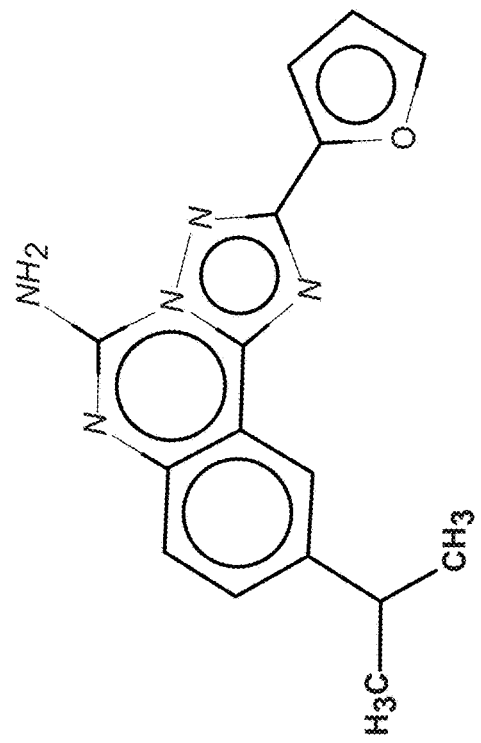

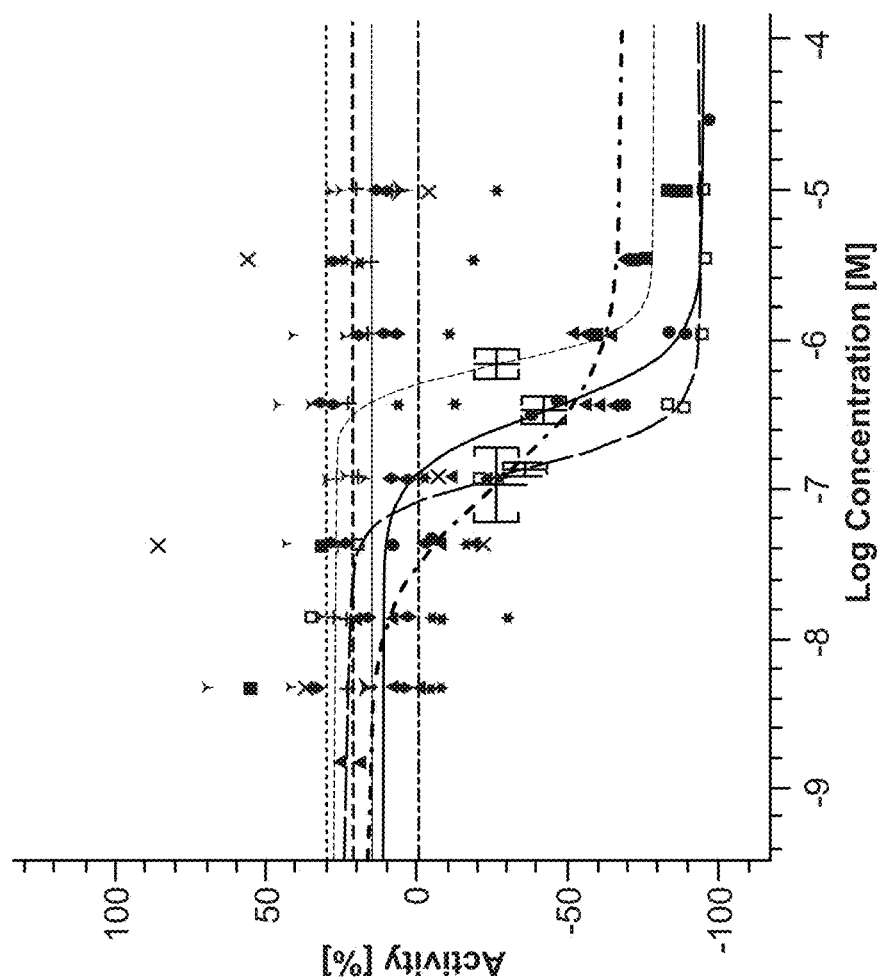
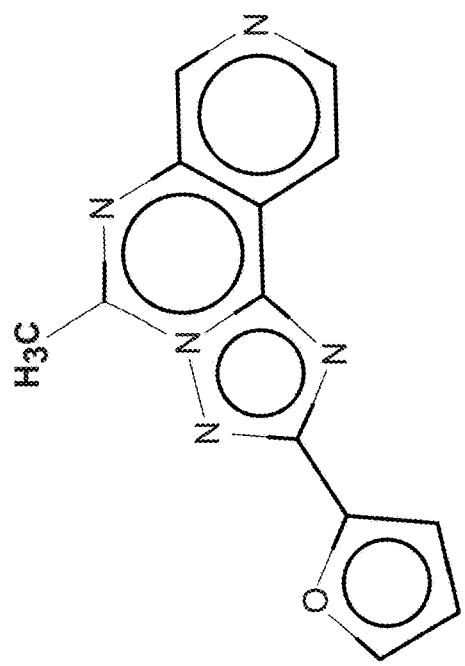
FIG. 24 (Continued)

FIG. 24 (Continued)
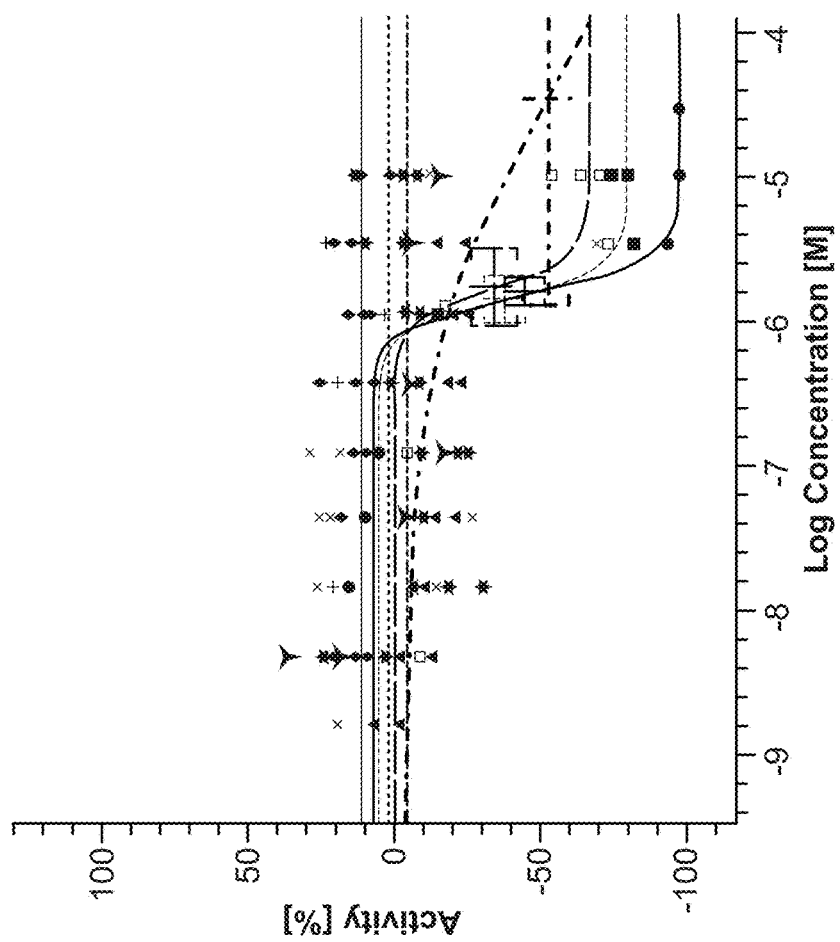
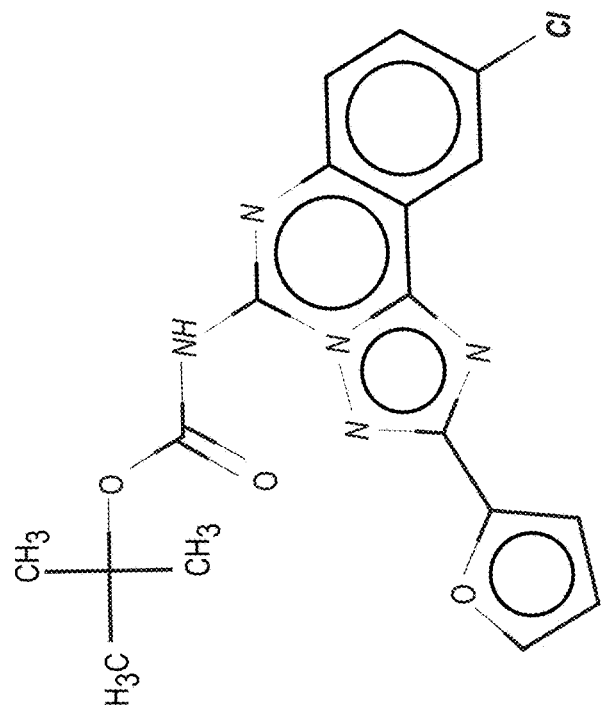

FIG. 24 (Continued)
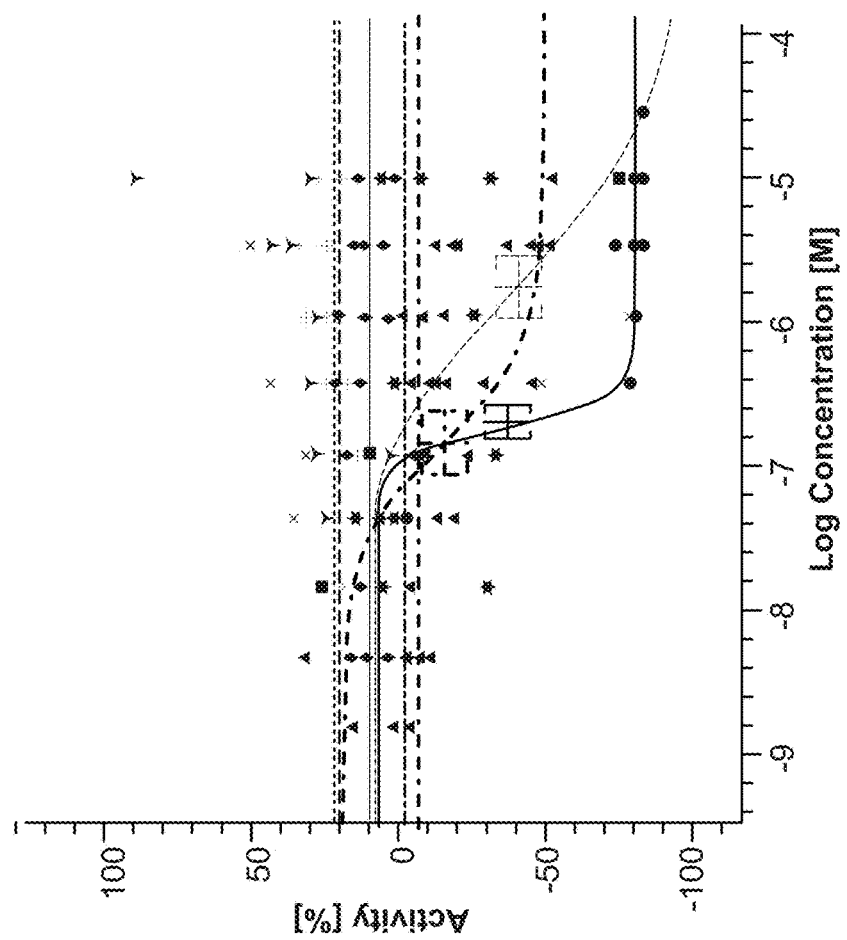
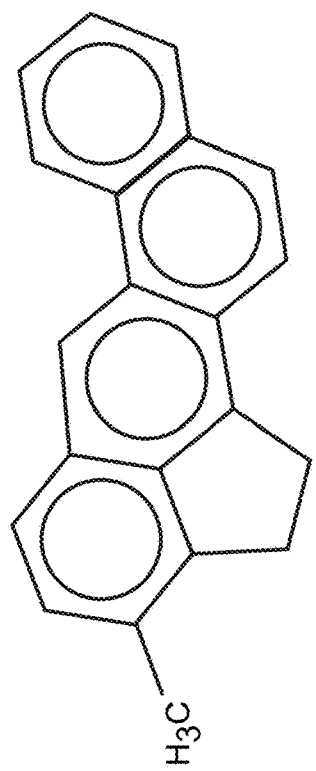

FIG. 24 (Continued)
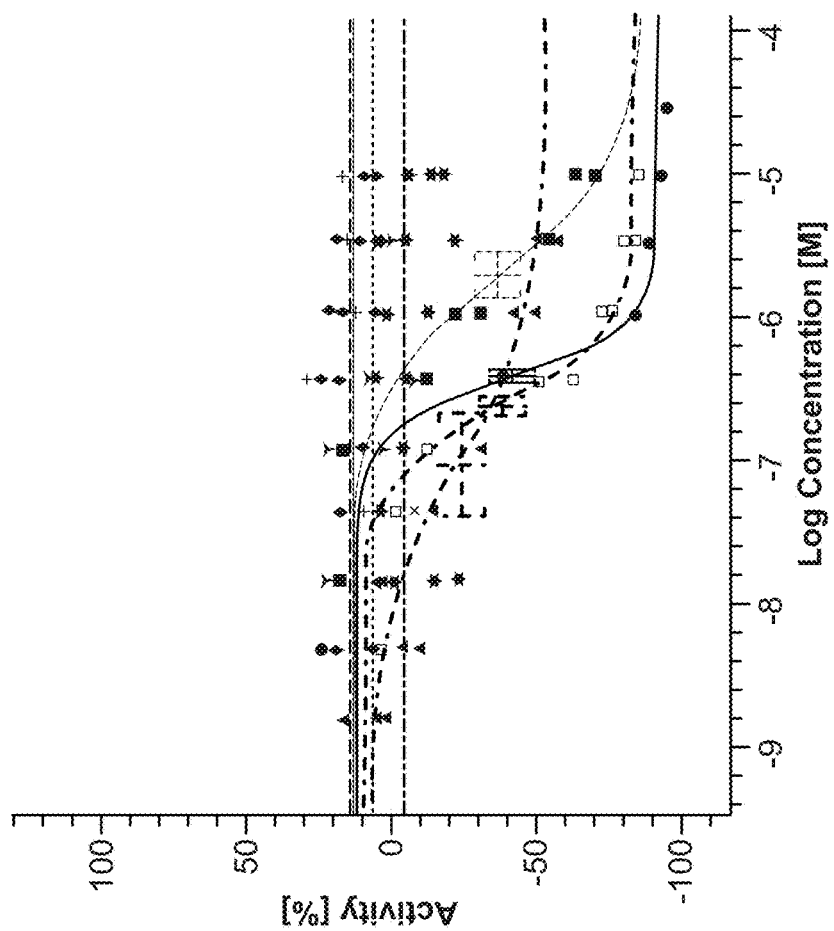
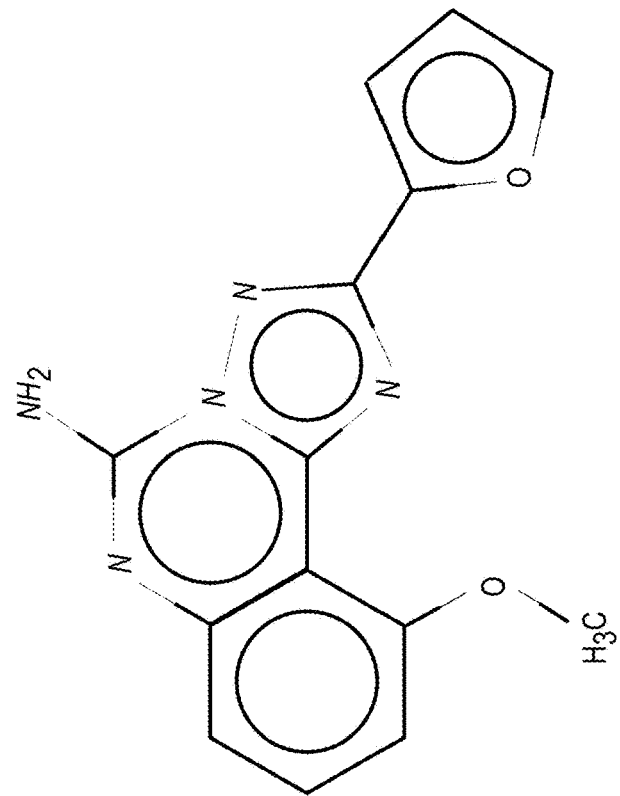

FIG. 24 (Continued)
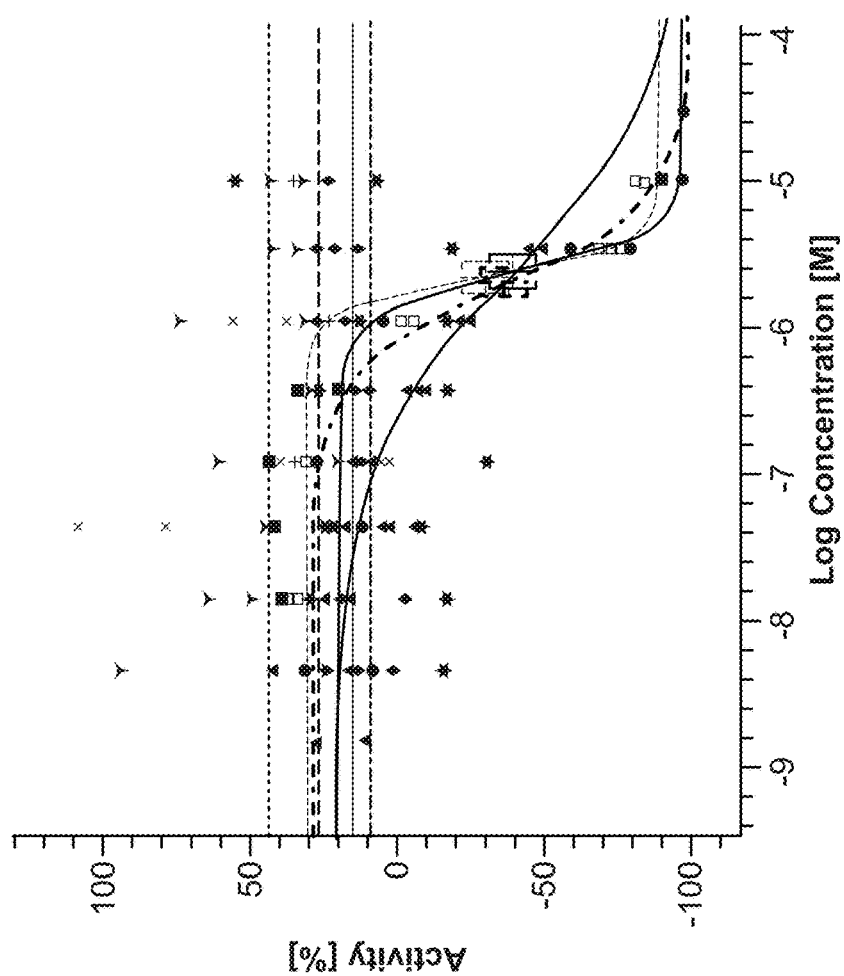
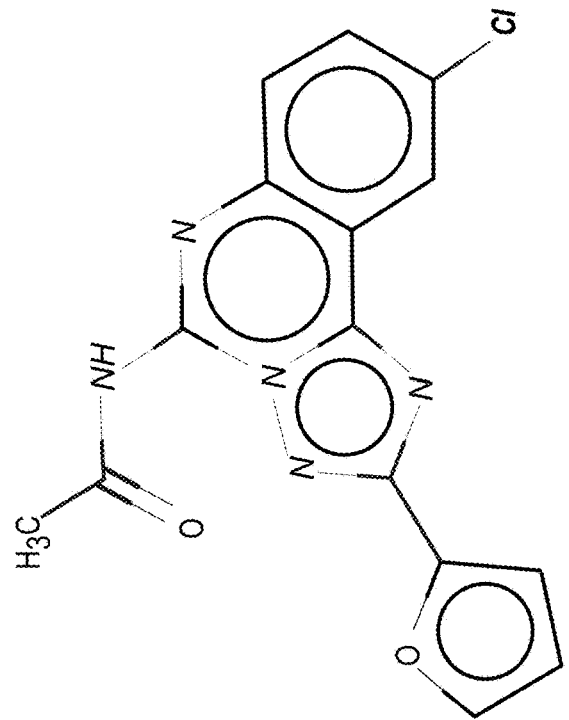

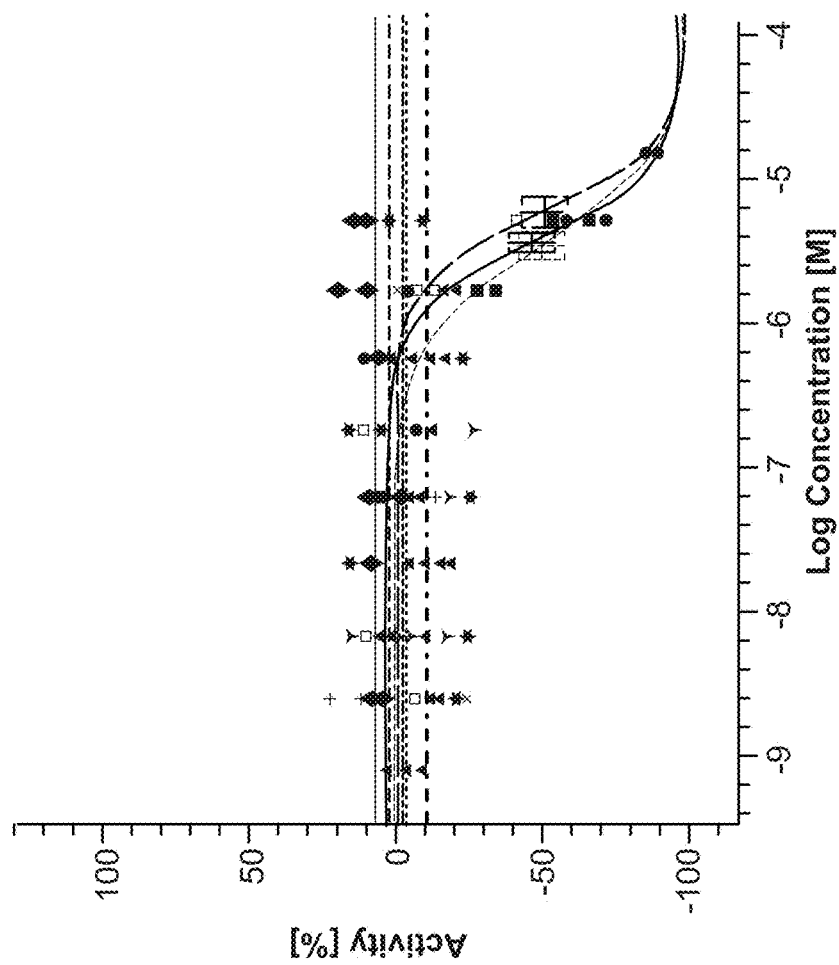
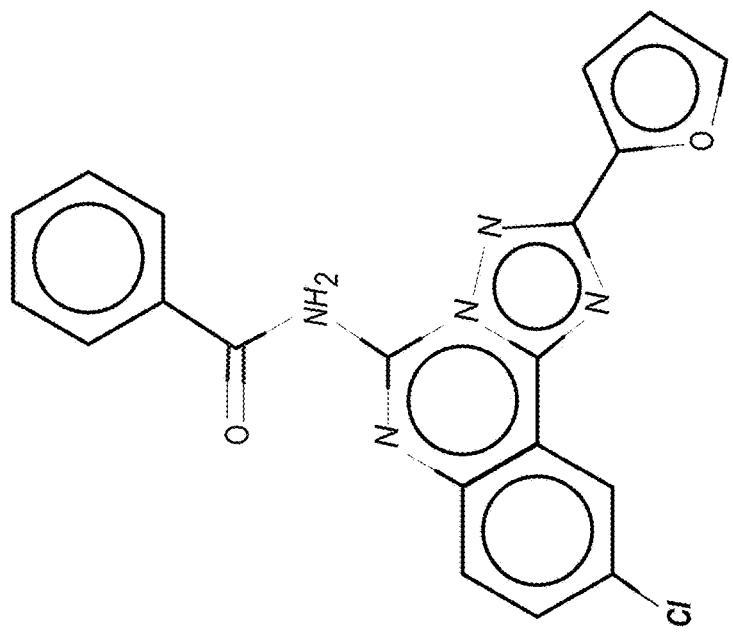
FIG. 24 (Continued)

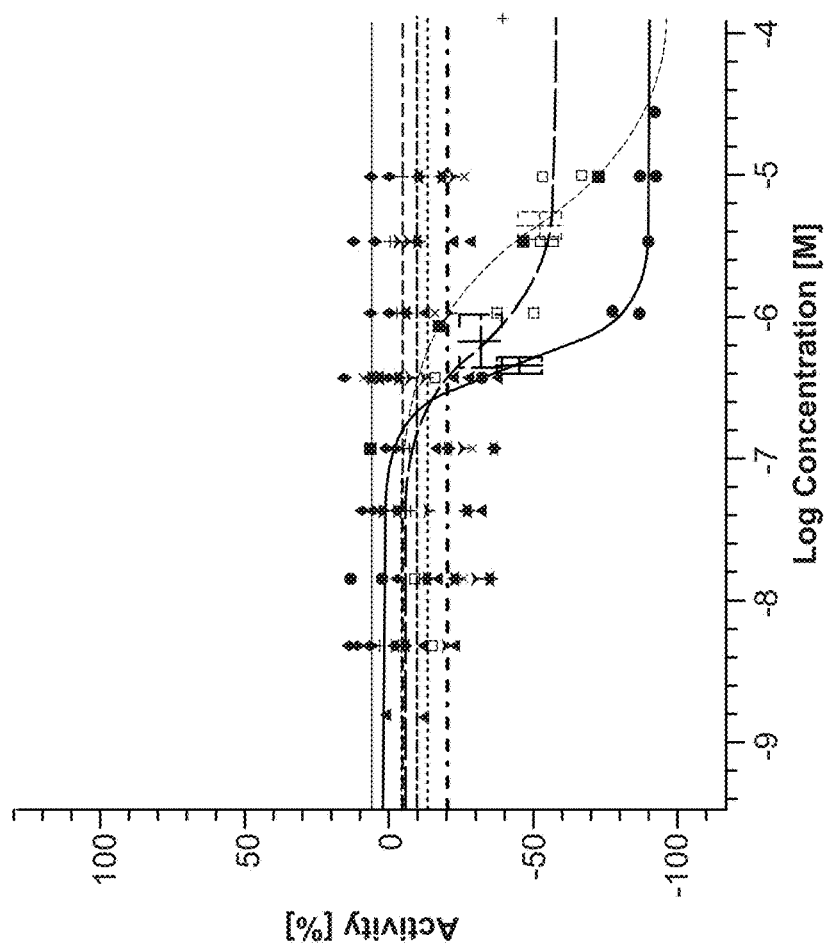
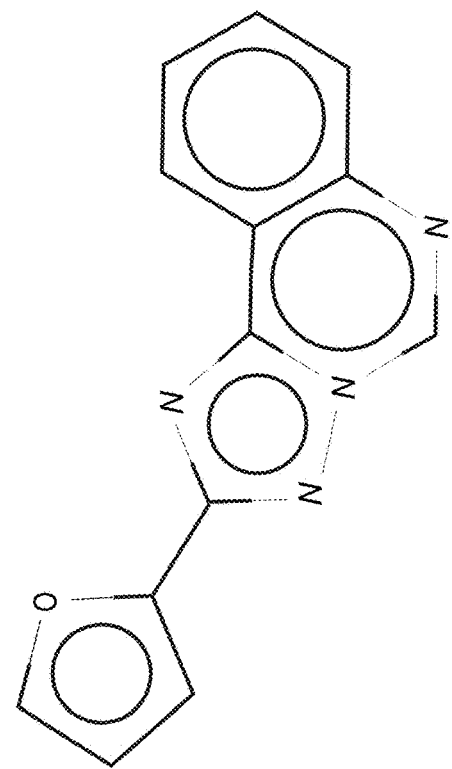
FIG. 24 (Continued)

FIG. 24 (Continued)
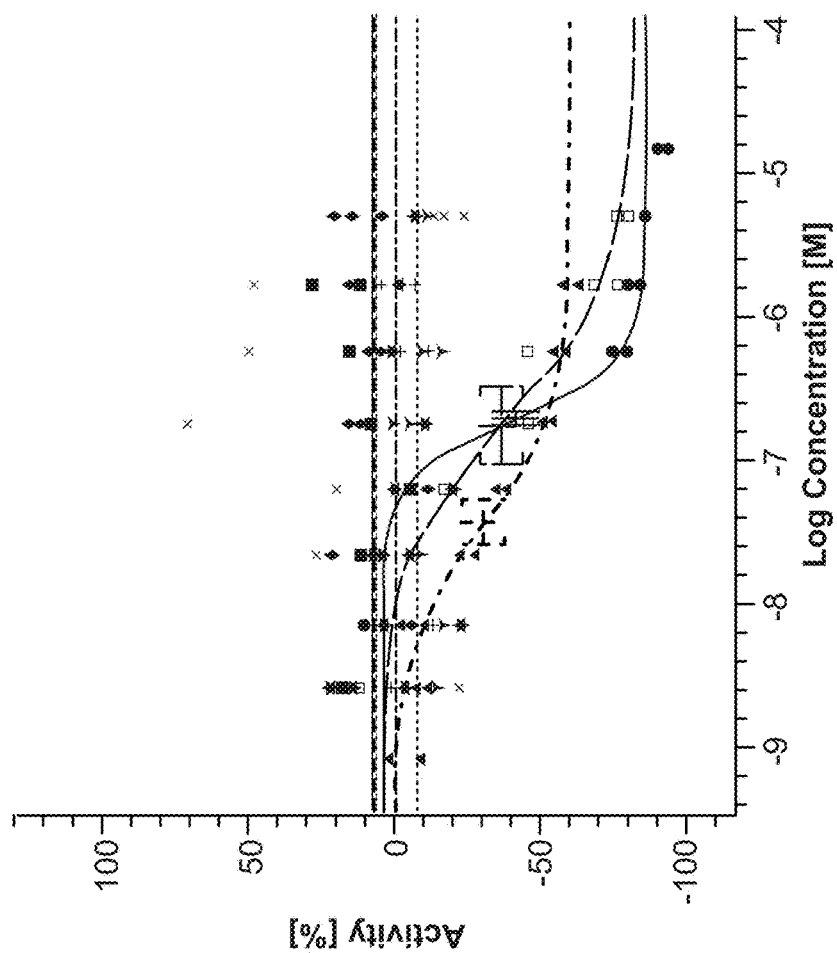
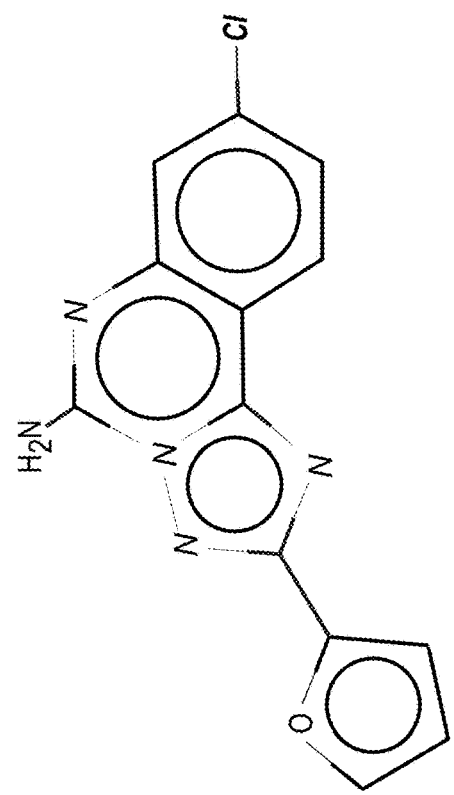

FIG. 24 (Continued)
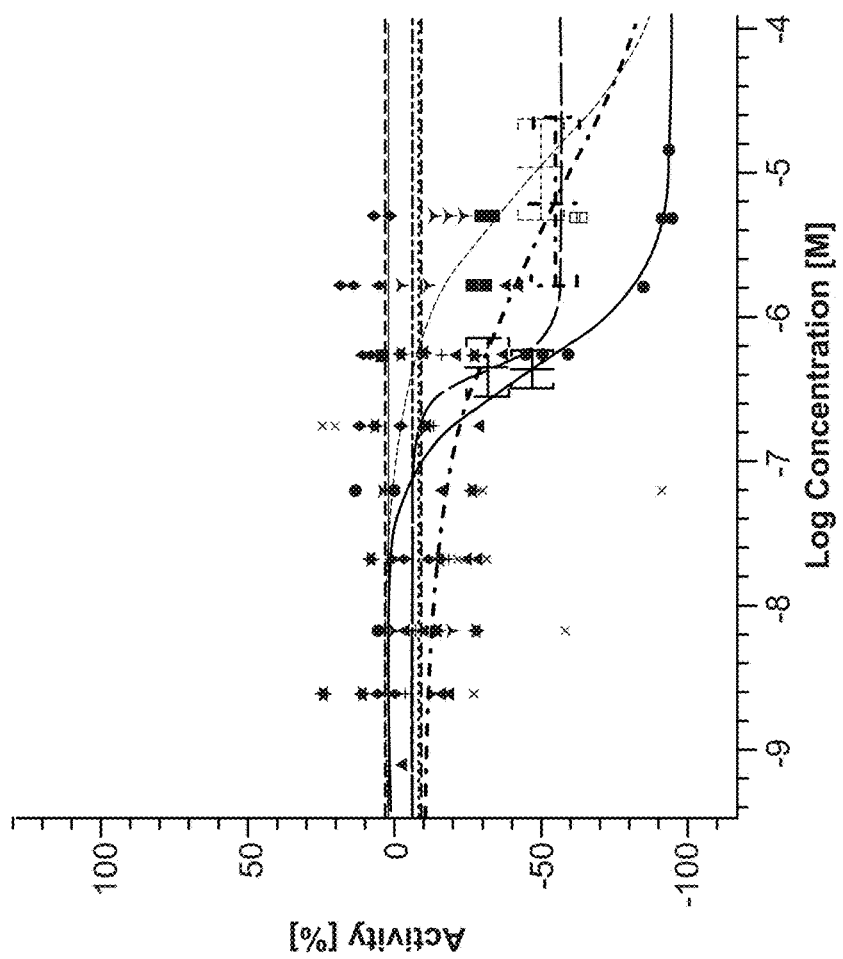
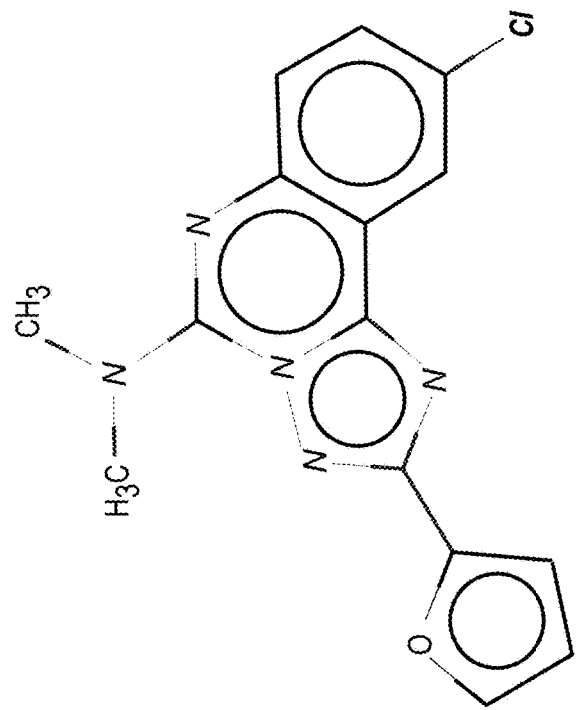

FIG. 24 (Continued)
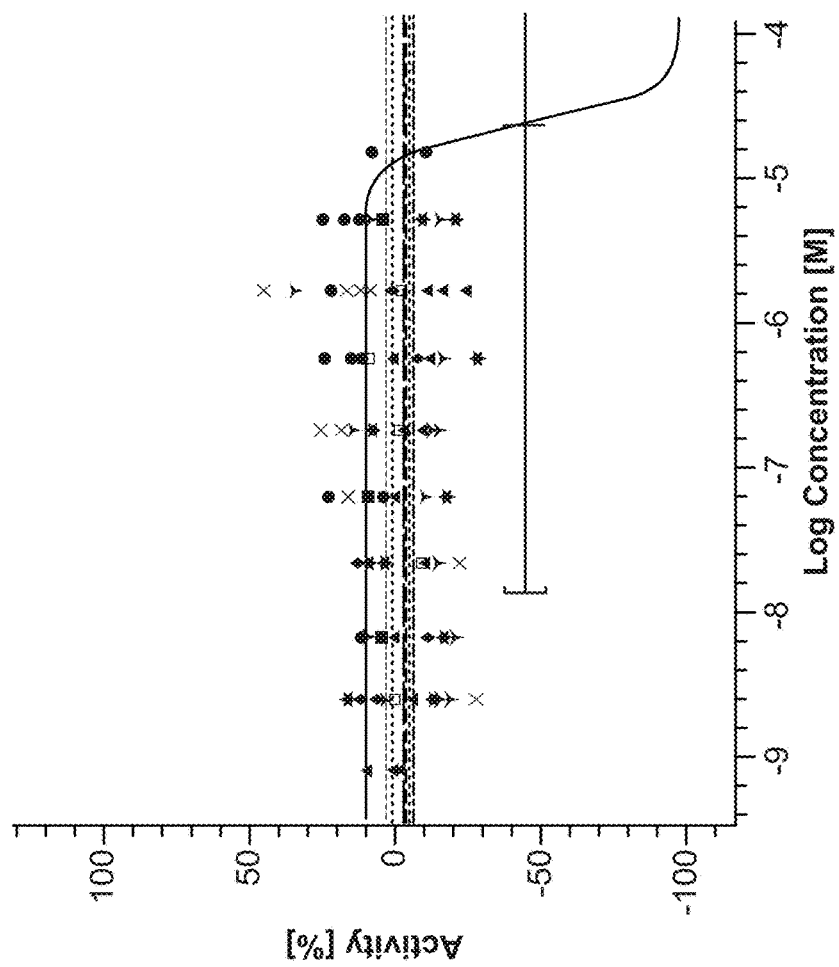
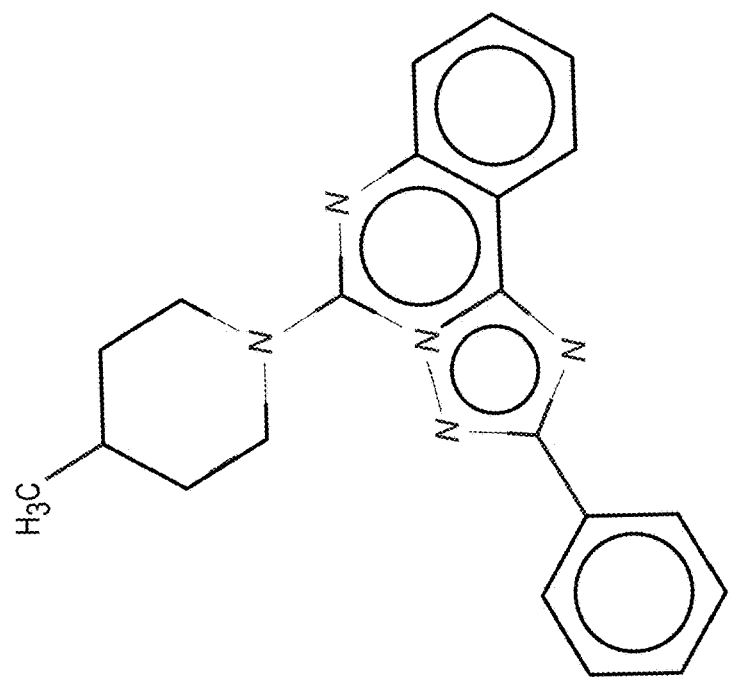

FIG. 24 (Continued)
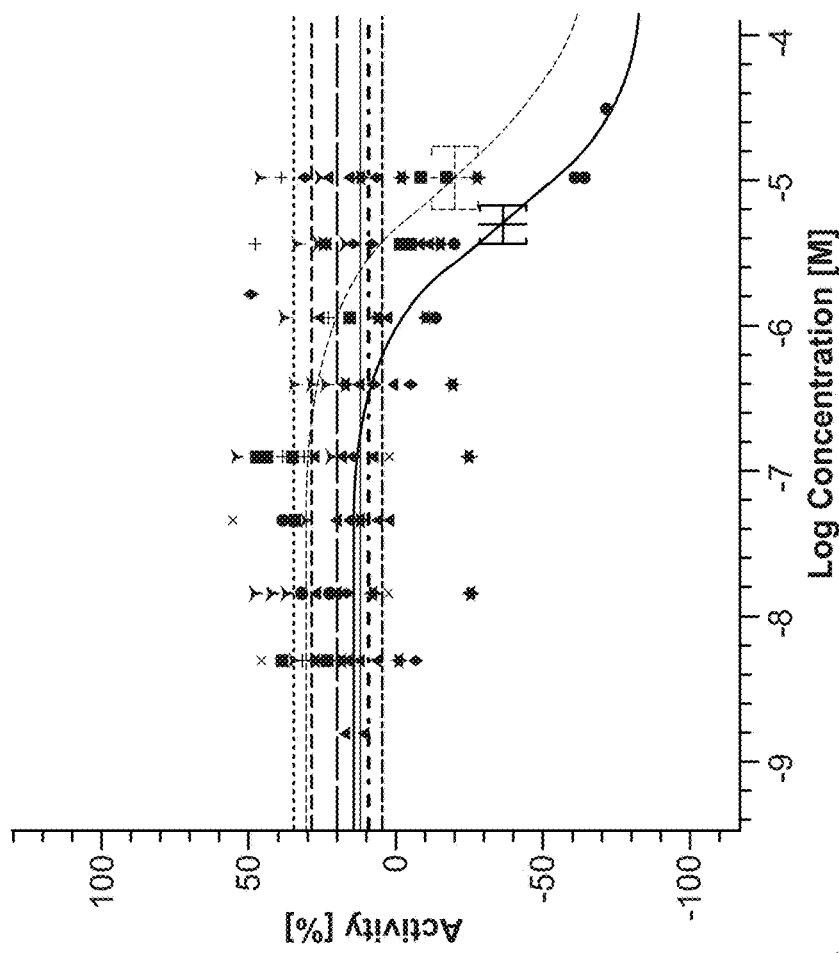
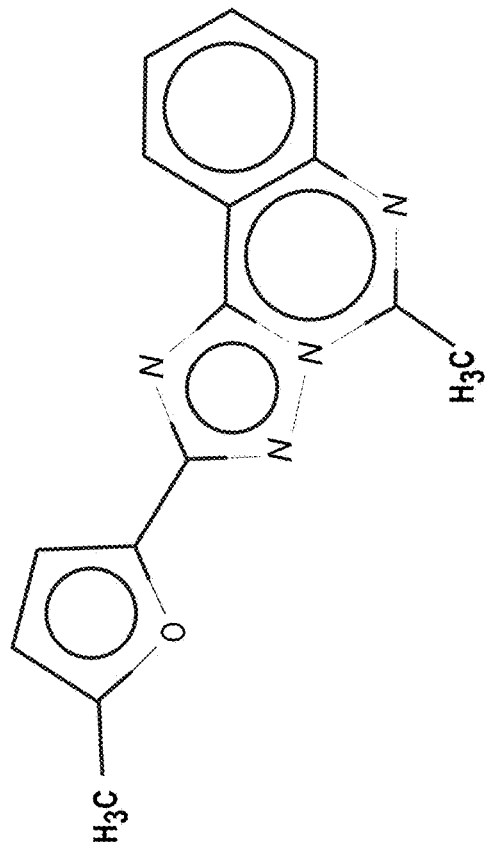

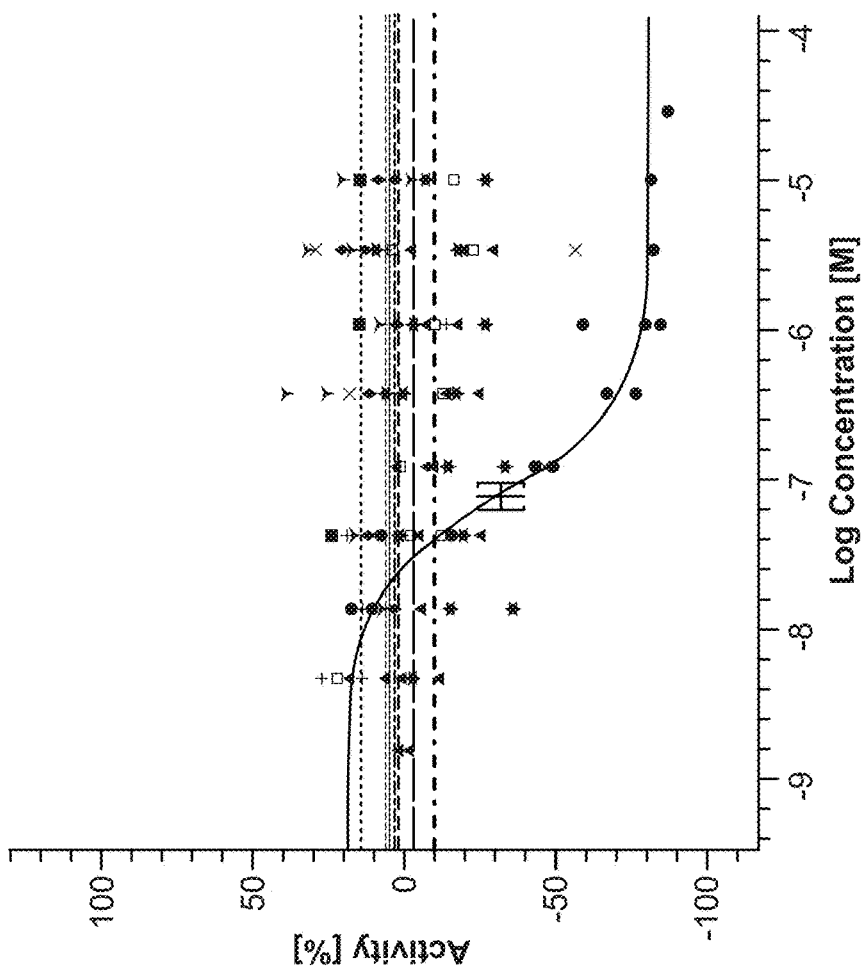
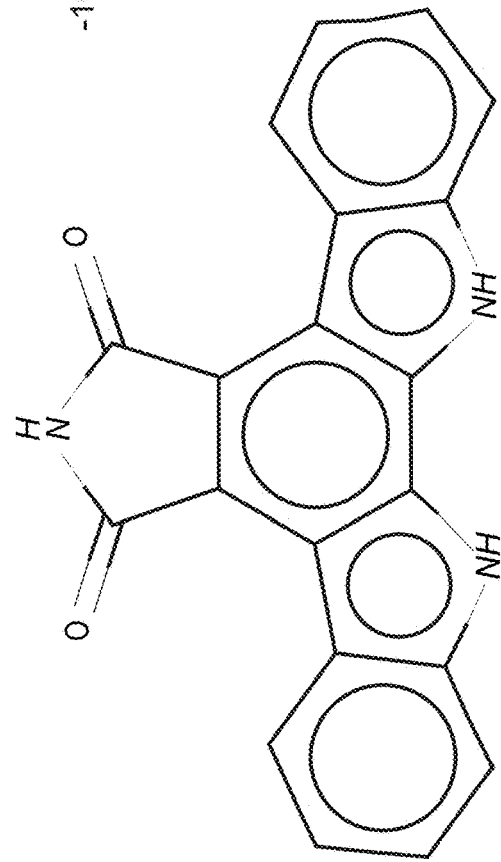
FIG. 24 (Continued)

FIG. 24 (Continued)
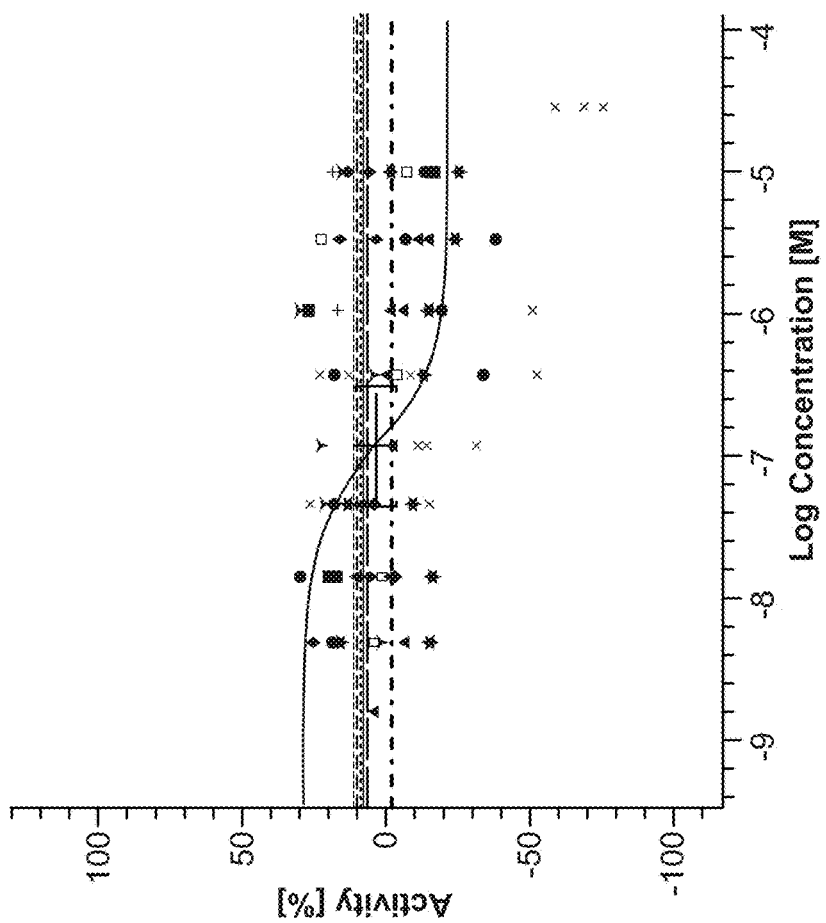
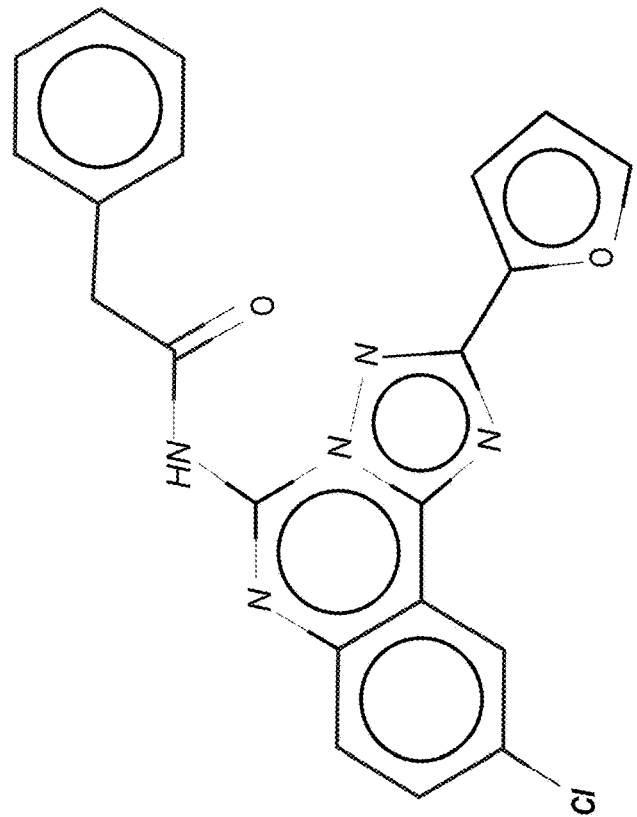

FIG. 24 (Continued)
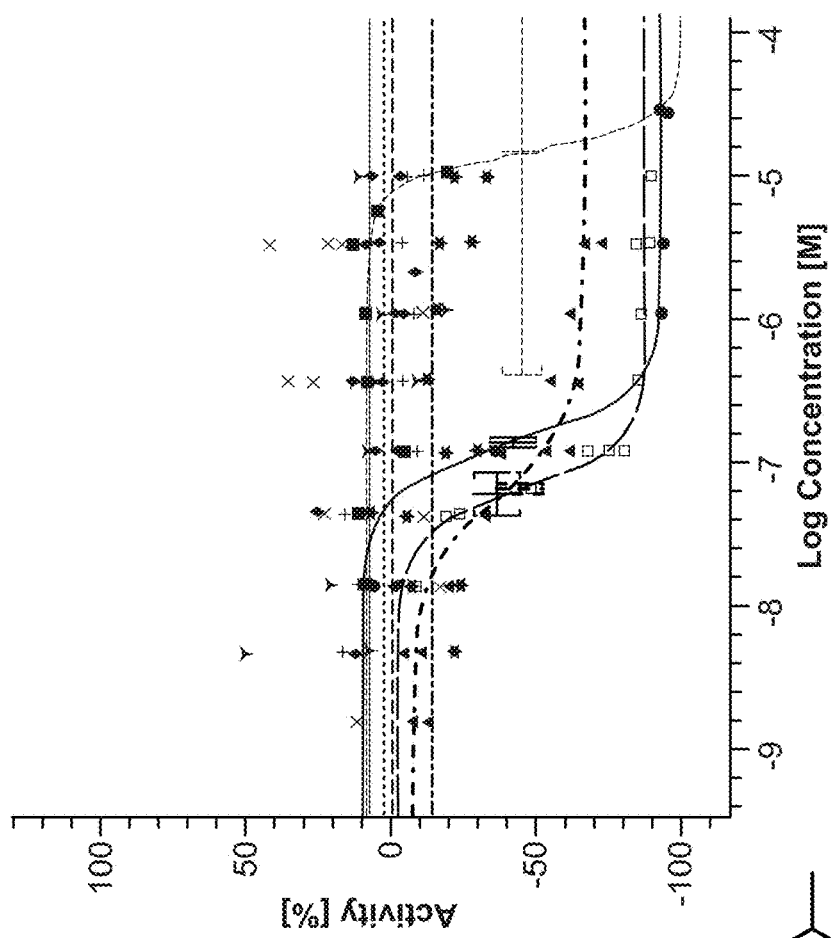
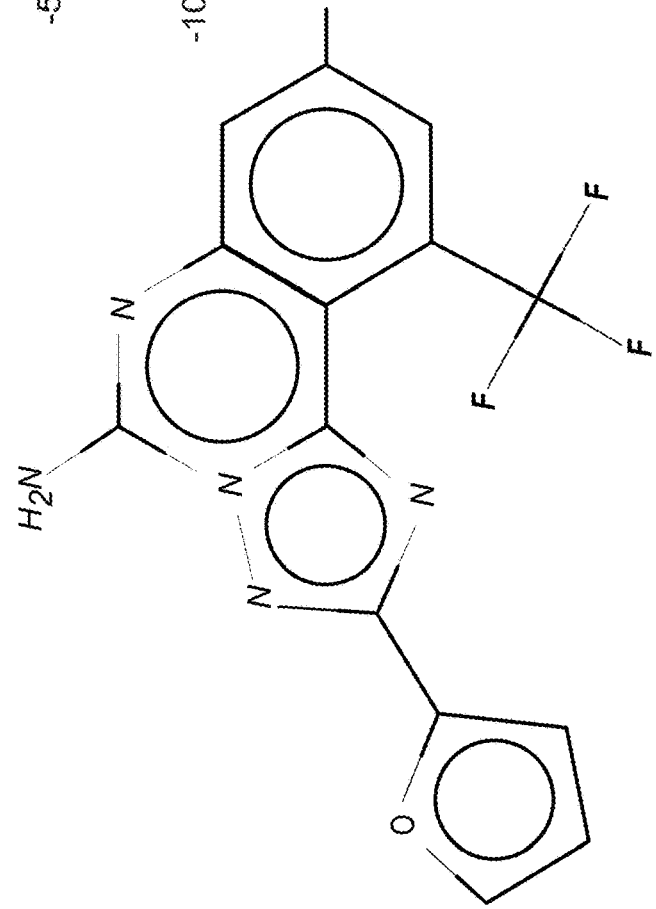

FIG. 24 (Continued)
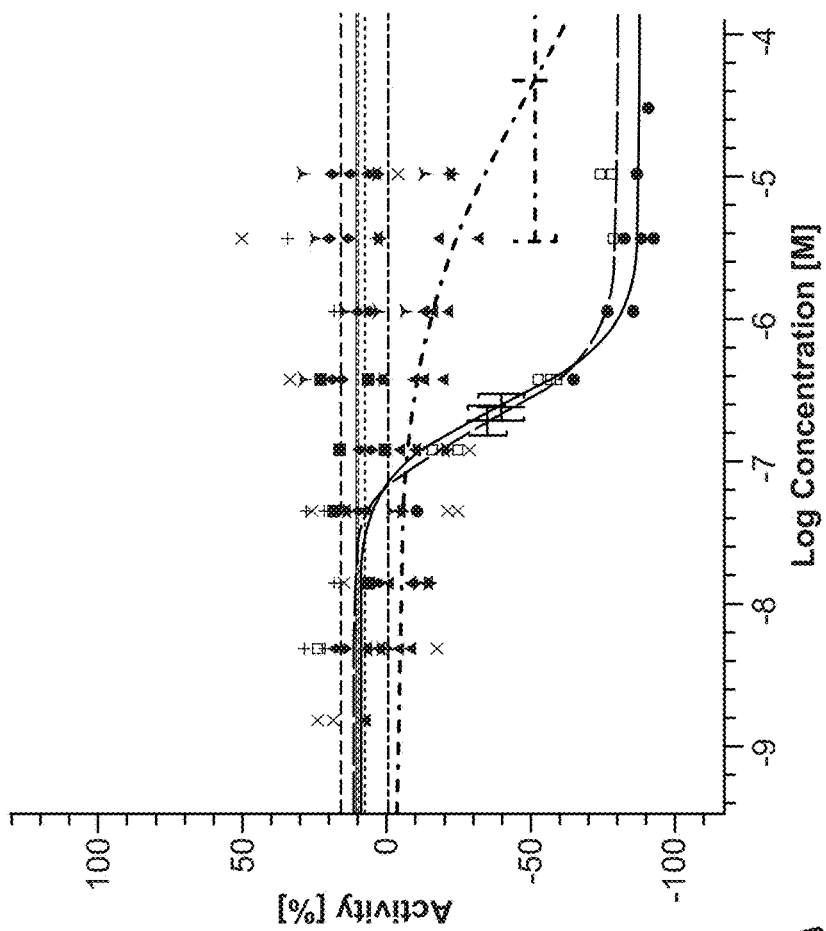
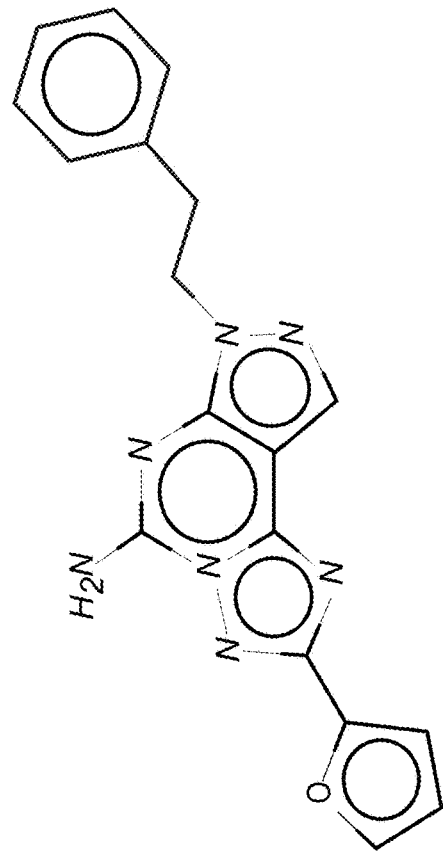

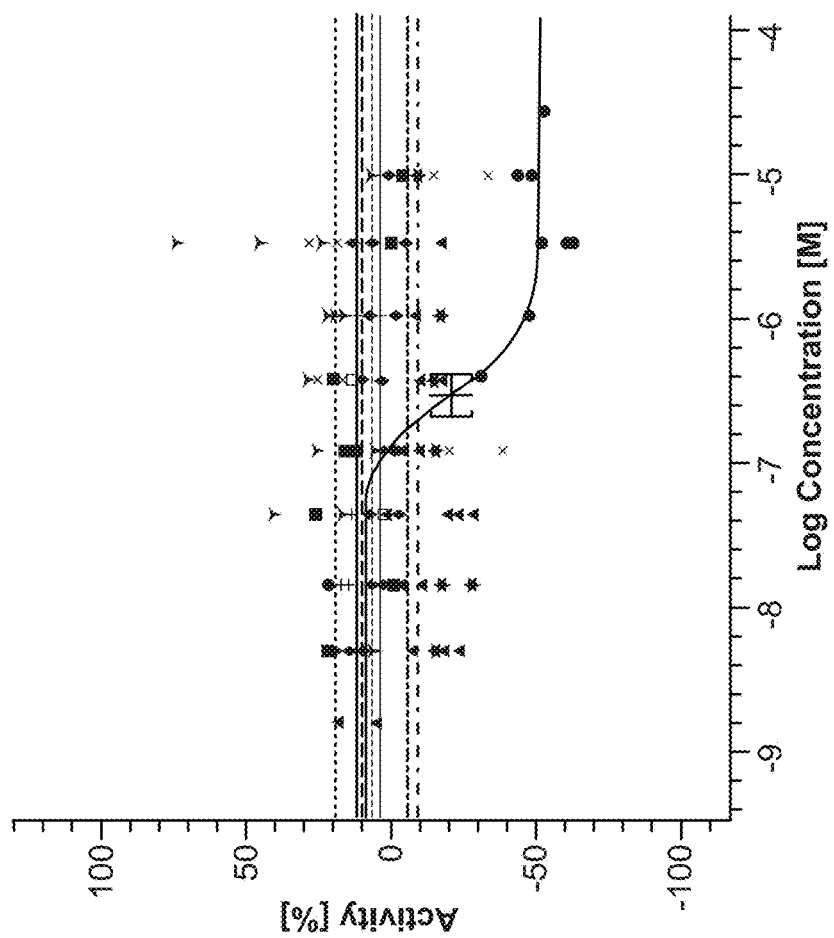
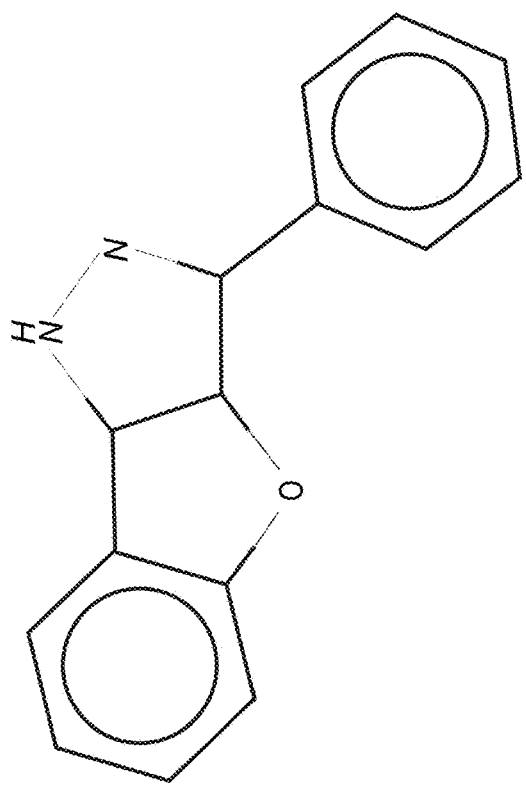
FIG. 24 (Continued)

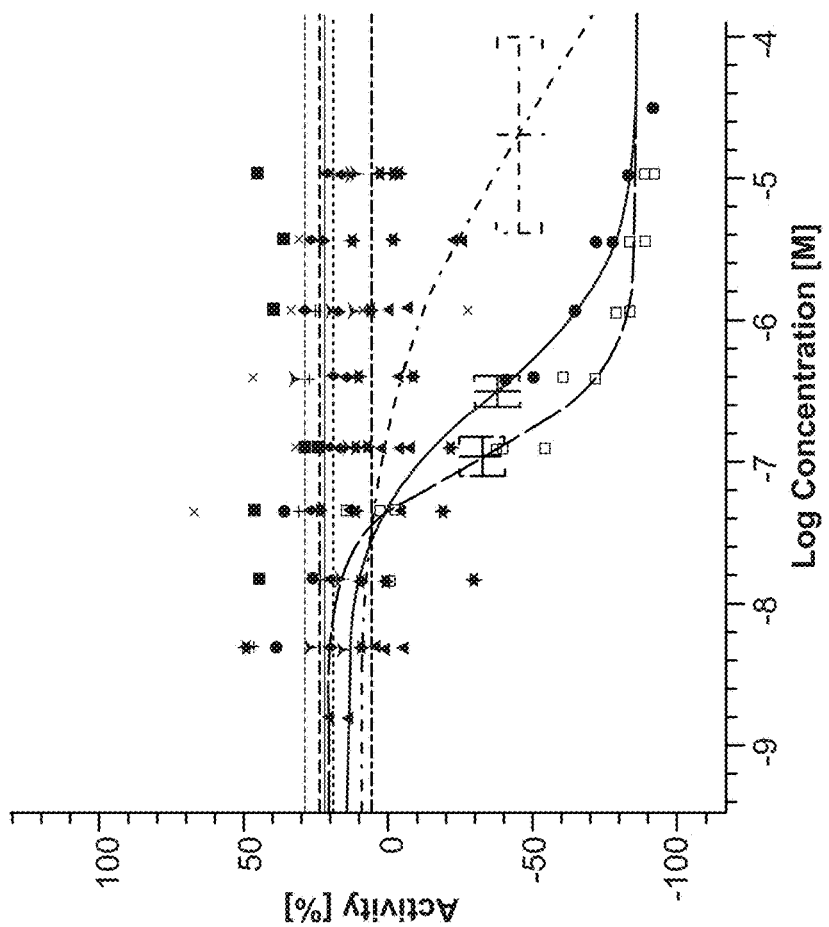
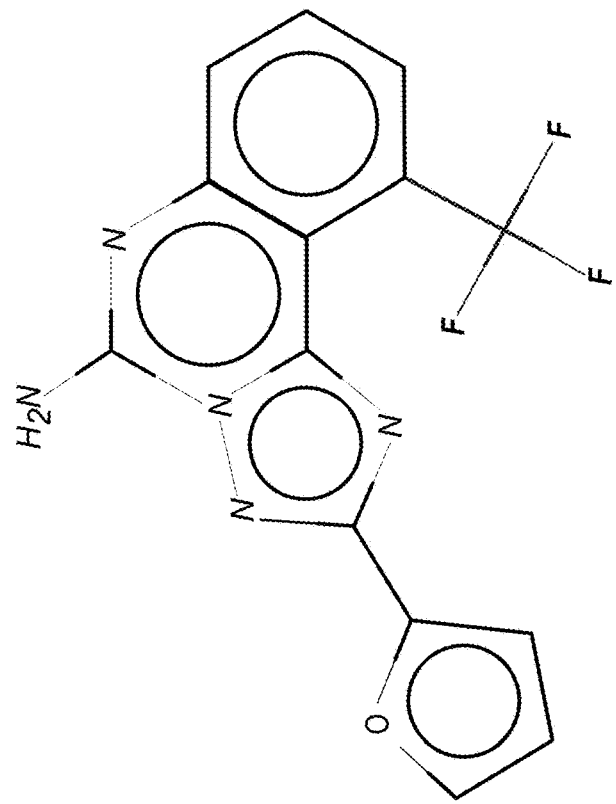
FIG. 24 (Continued)

FIG. 24 (Continued)
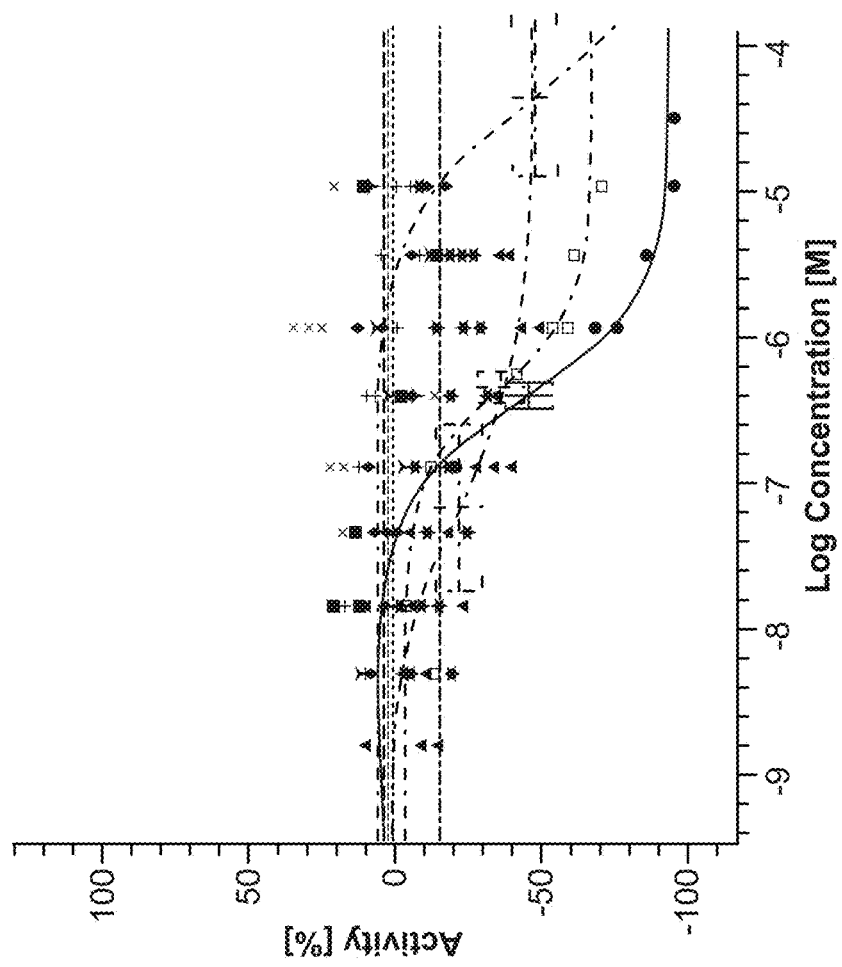
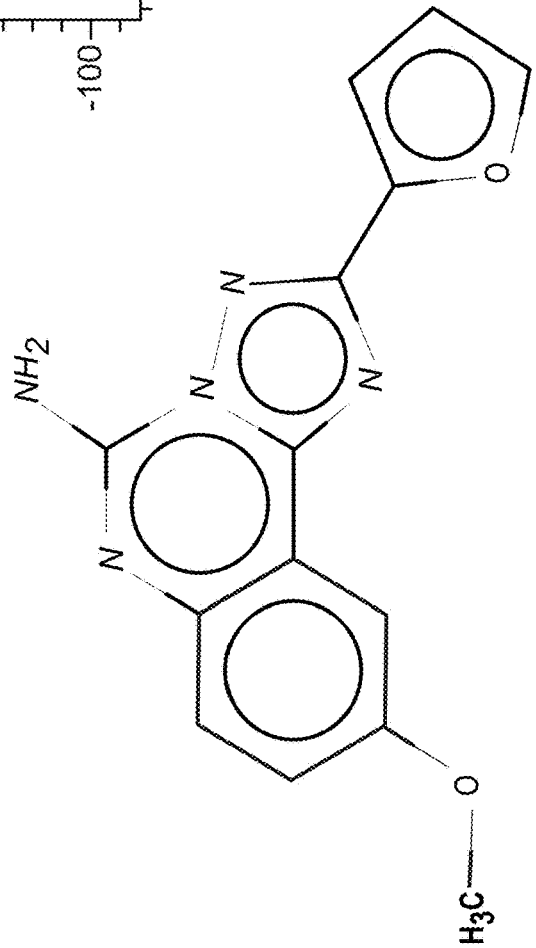

FIG. 24 (Continued)
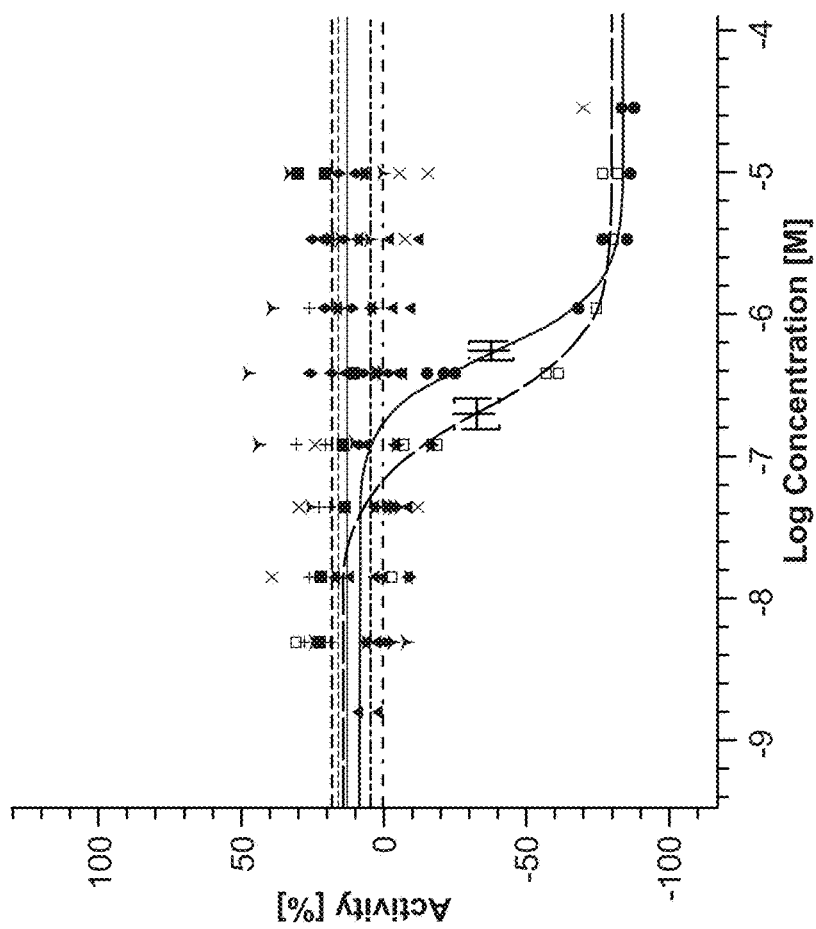
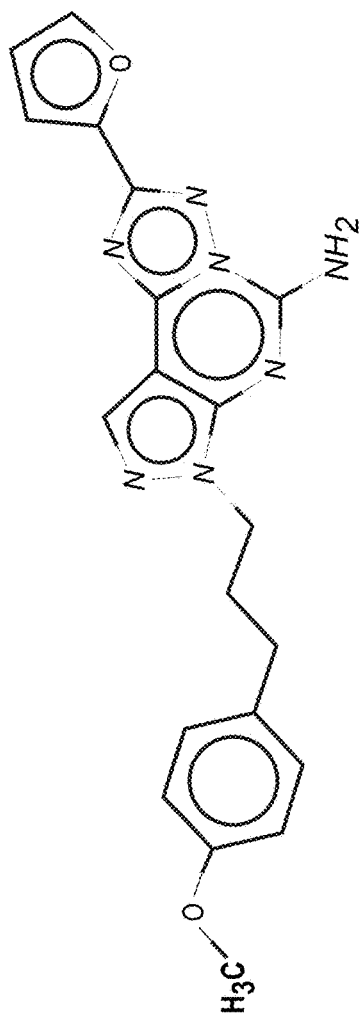

FIG. 24 (Continued)
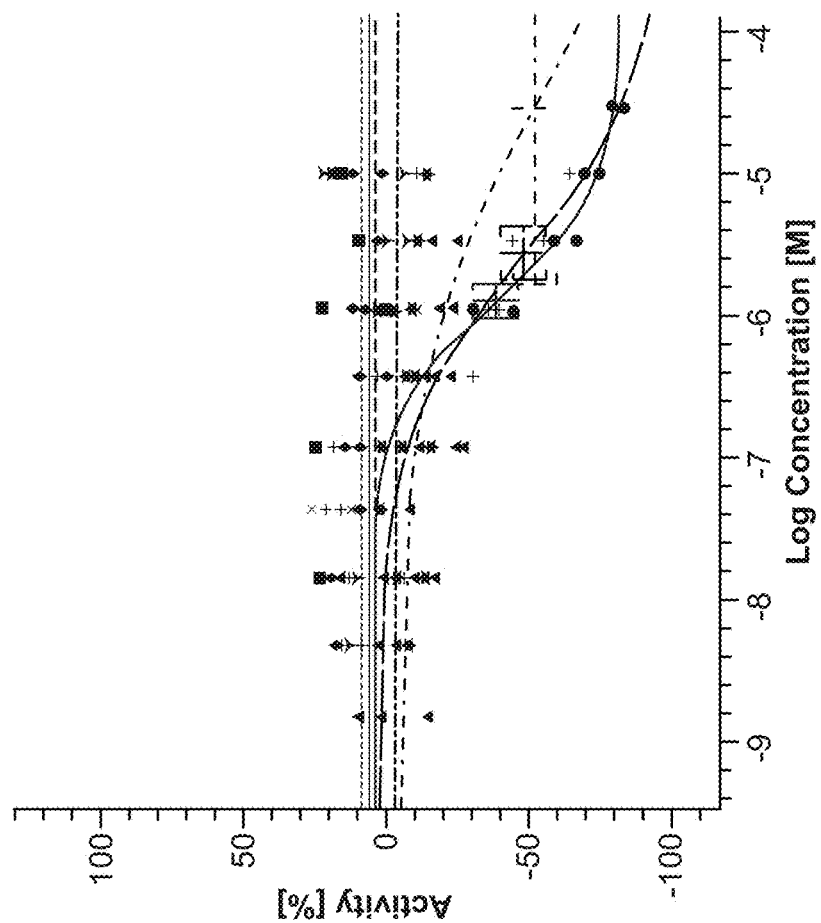
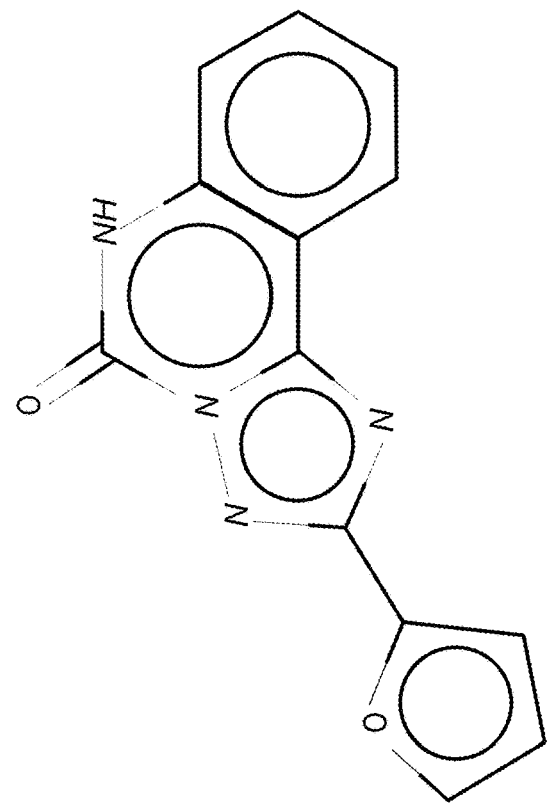

FIG. 24 (Continued)
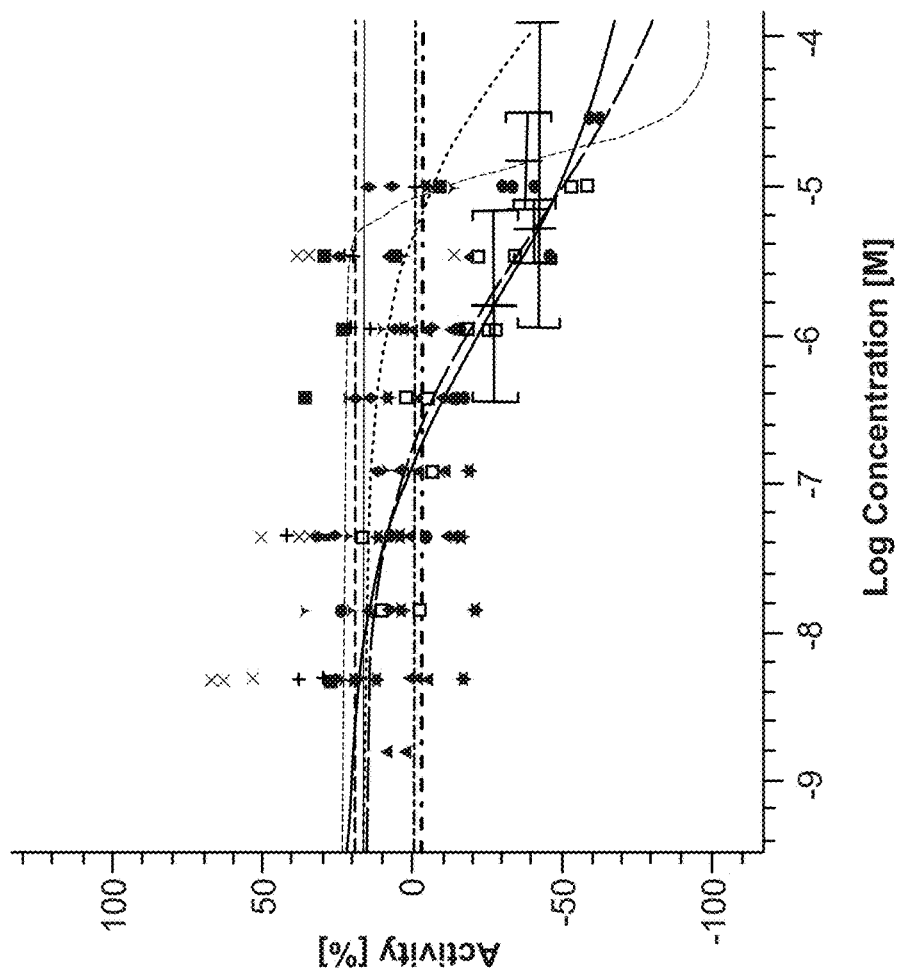
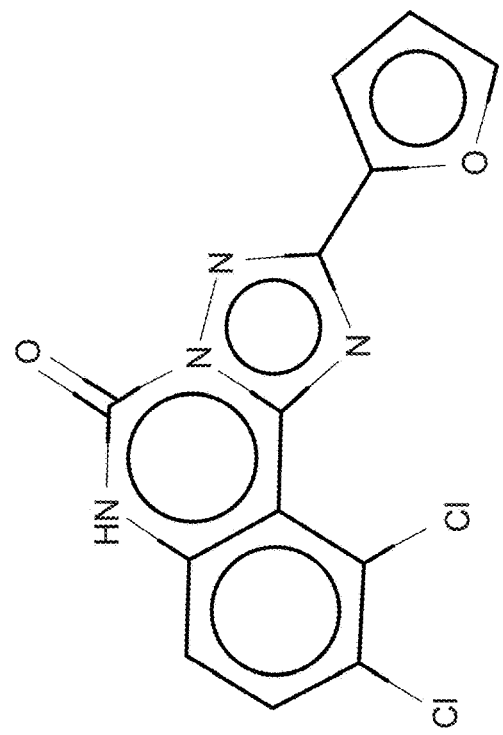

FIG. 24 (Continued)
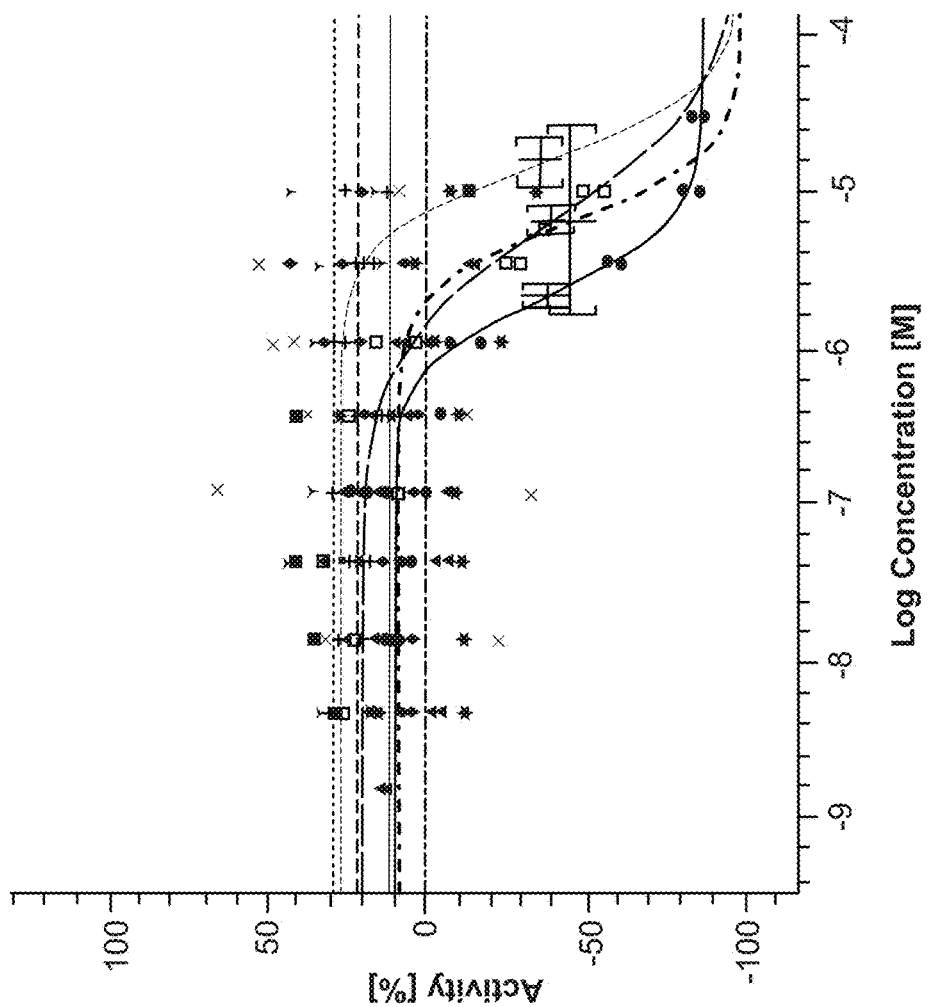
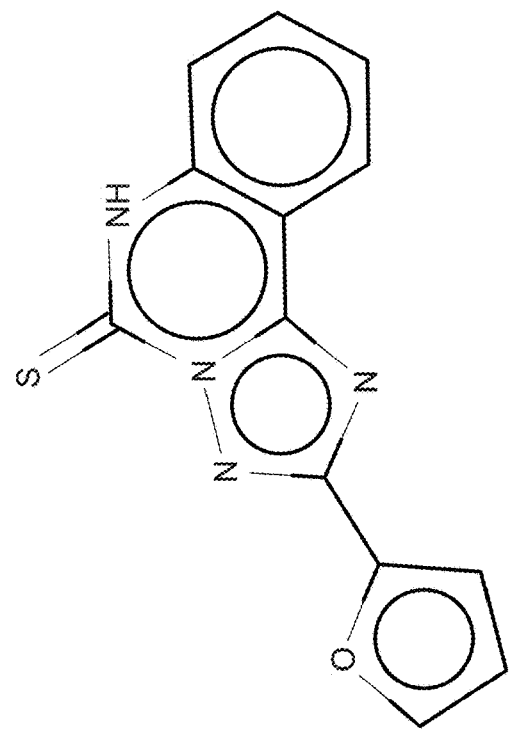

FIG. 24 (Continued)
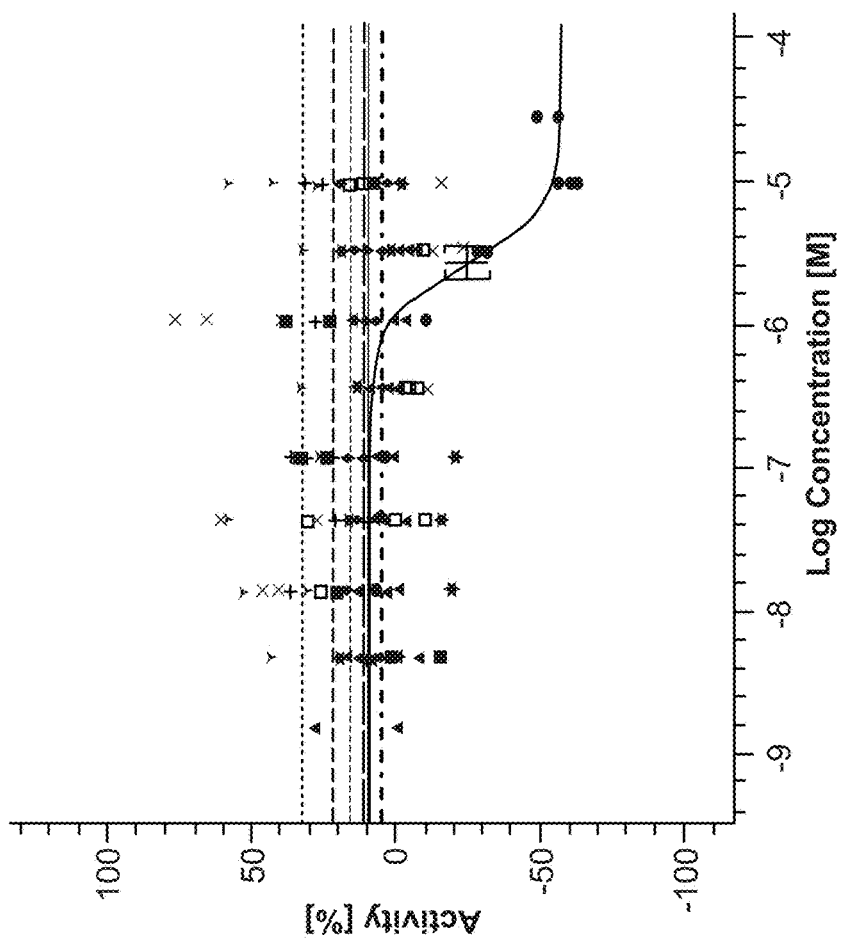
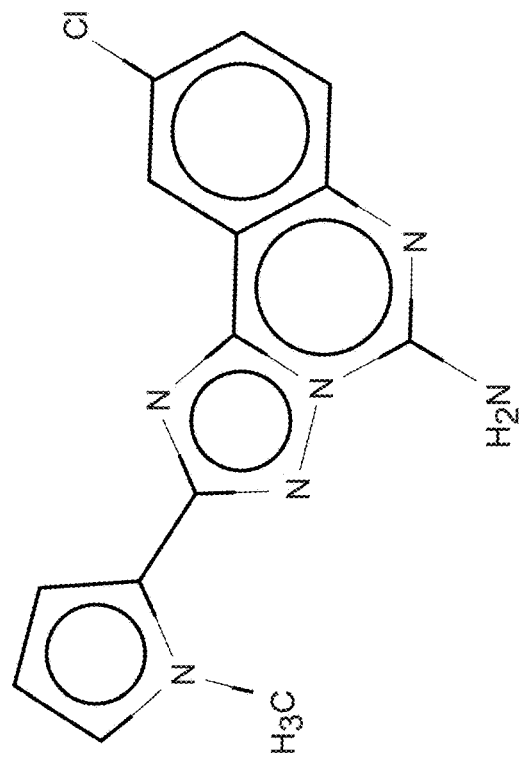

FIG. 24 (Continued)
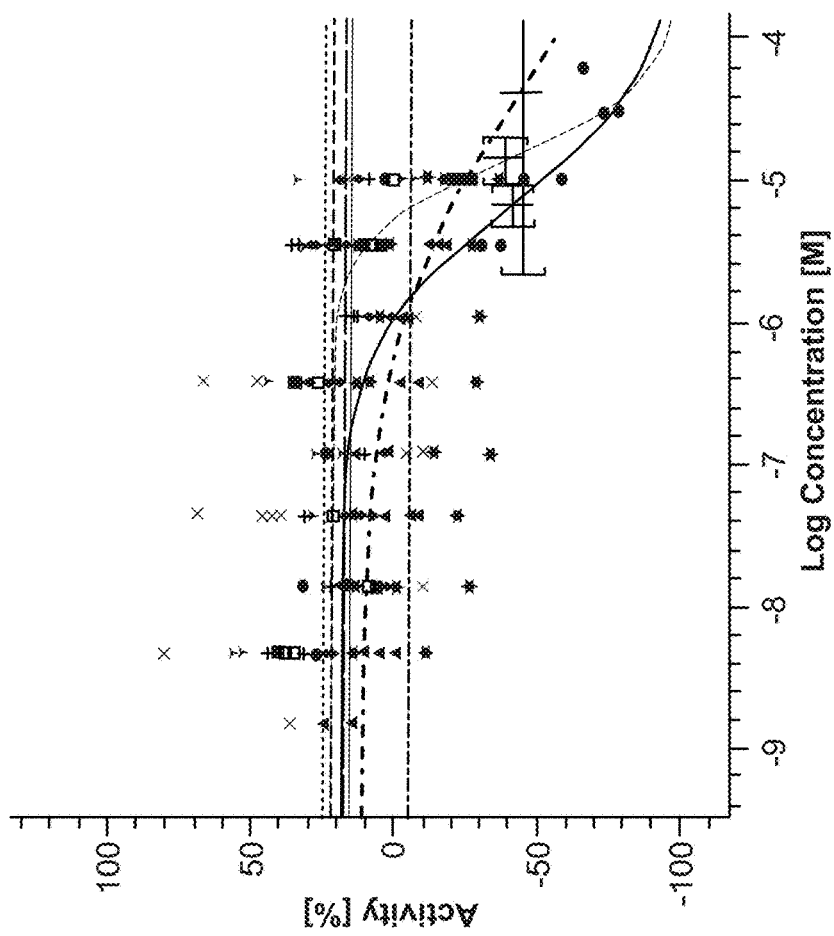
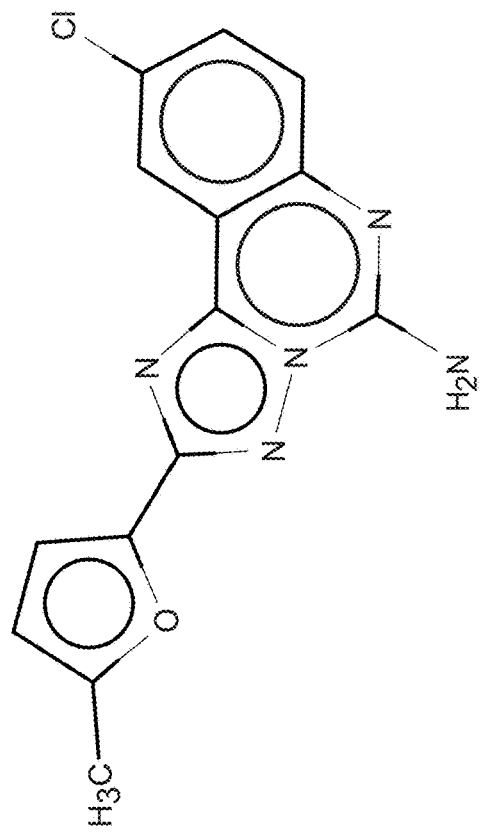

FIG. 24 (Continued)
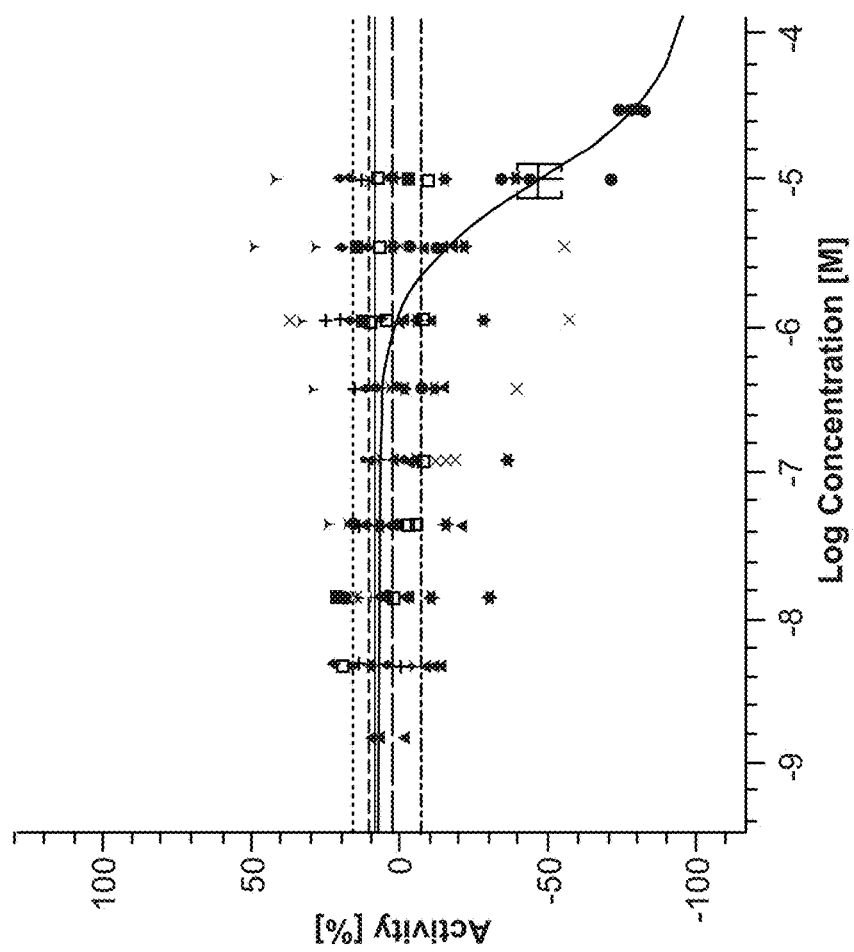
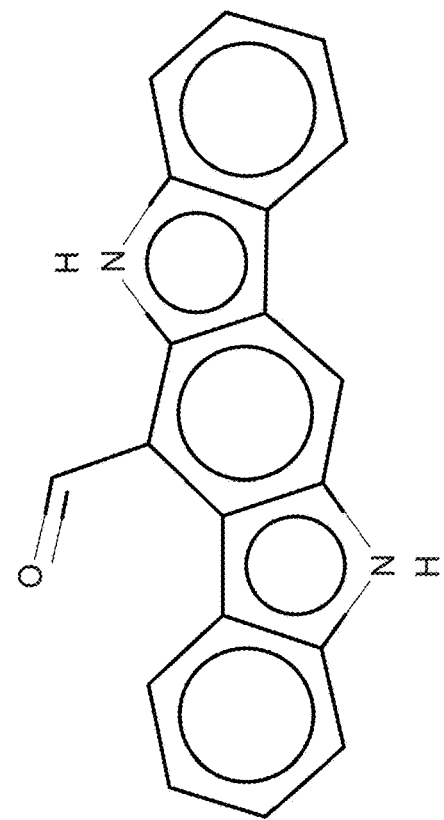

FIG. 24 (Continued)
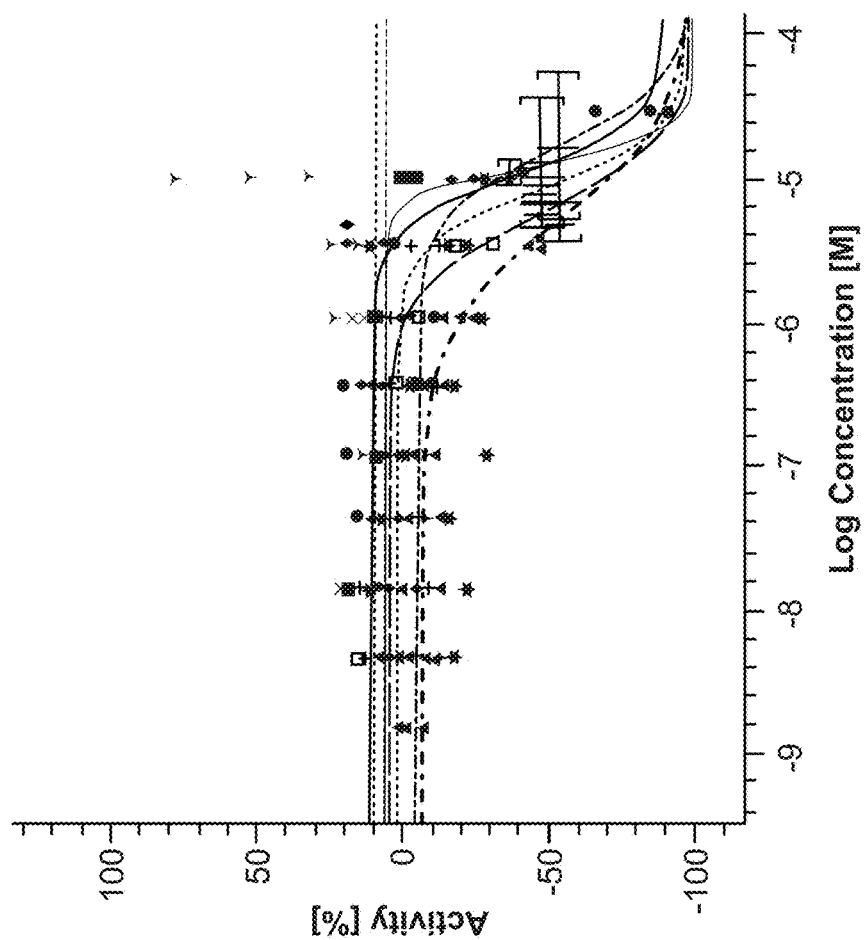
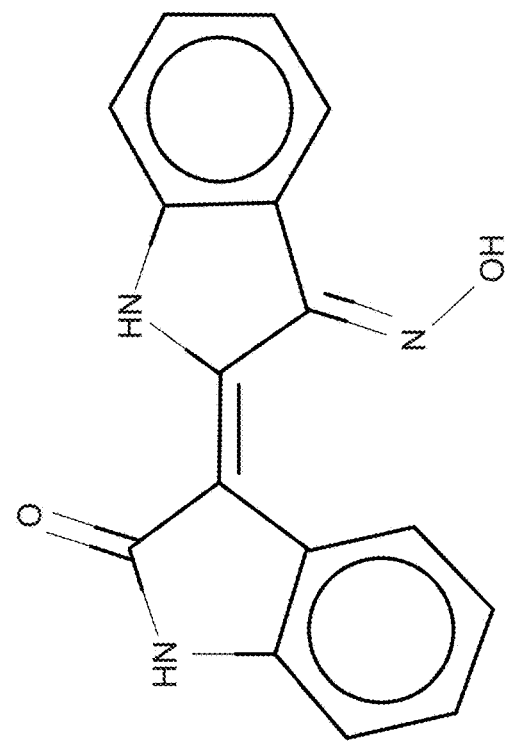

FIG. 24 (Continued)
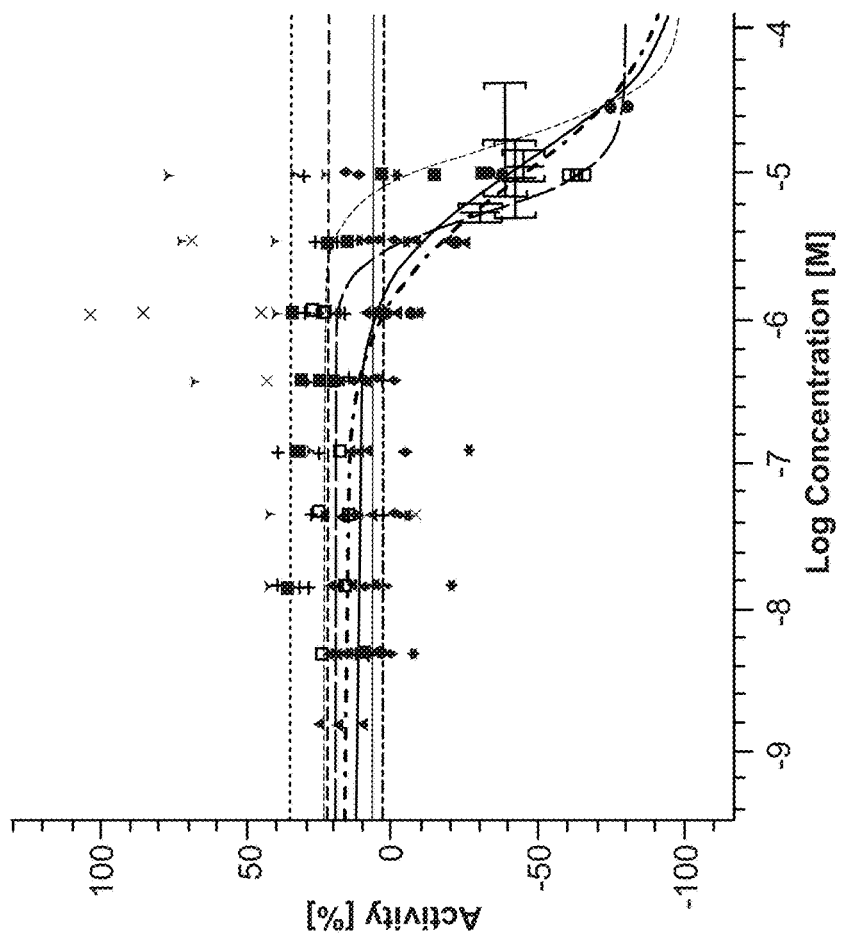
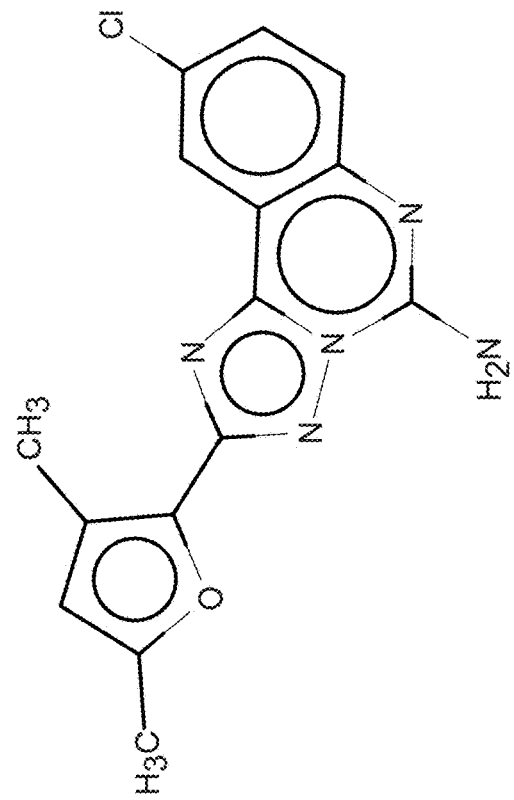

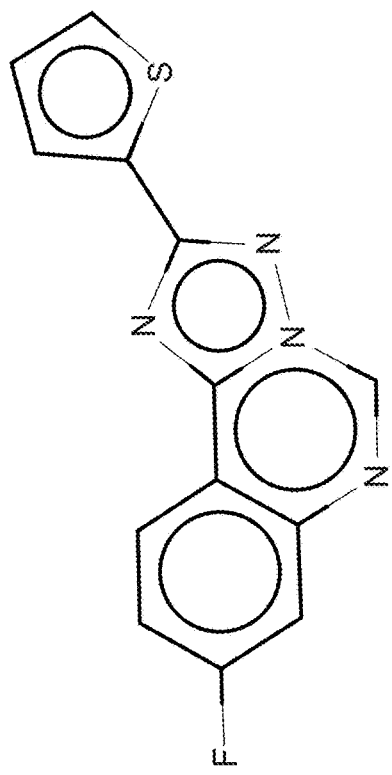
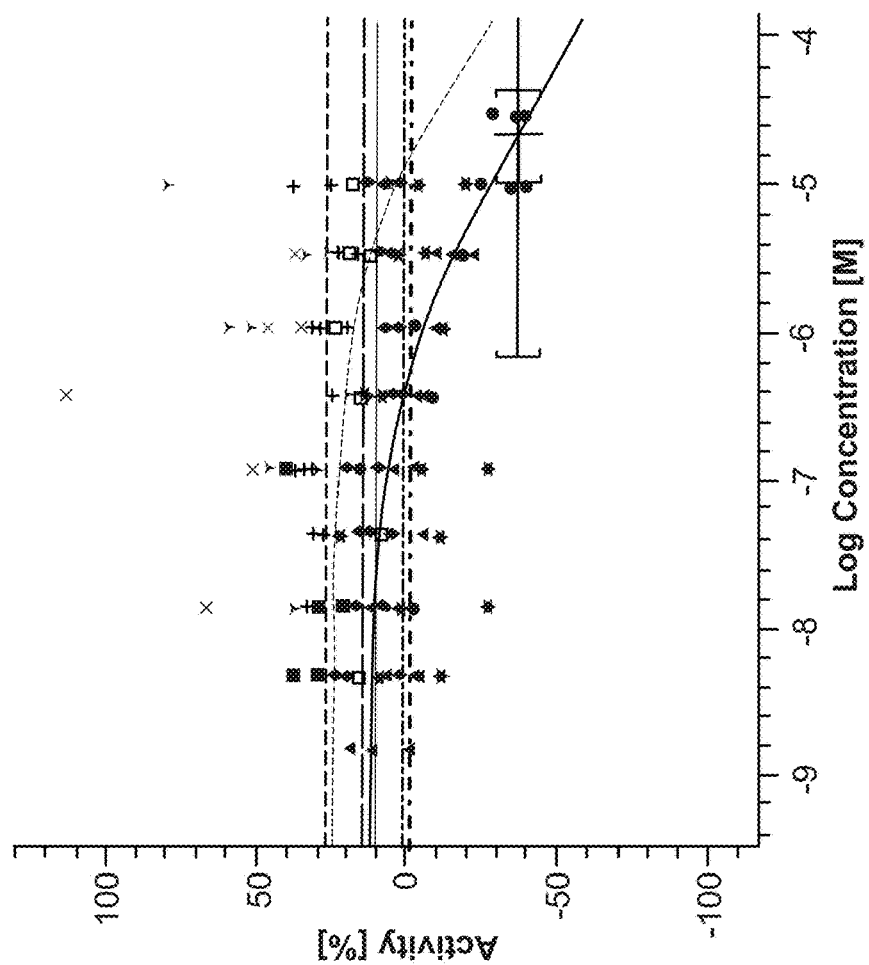
FIG. 24 (Continued)

FIG. 24 (Continued)
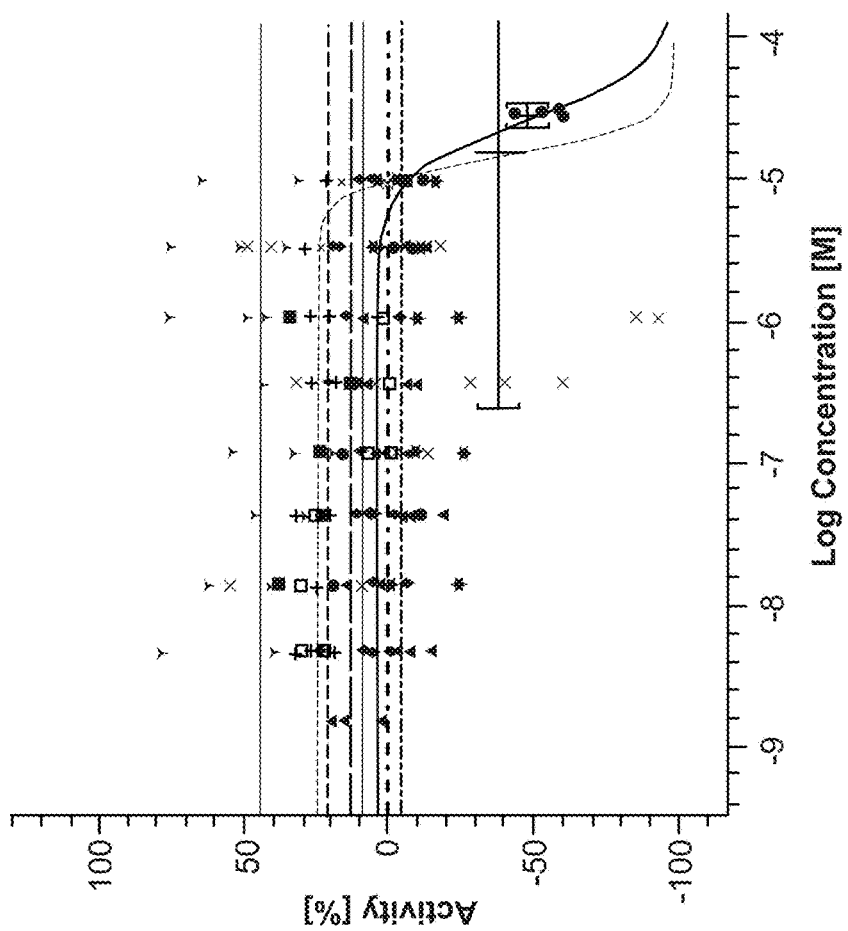
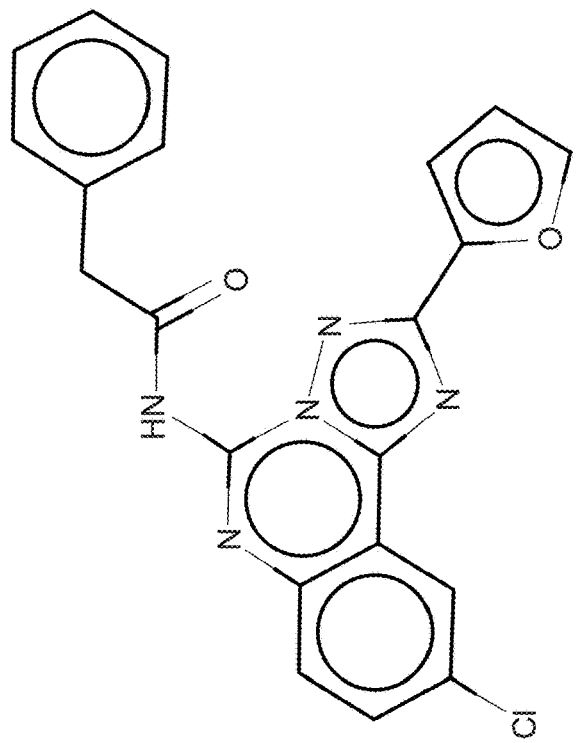

FIG. 24 (Continued)
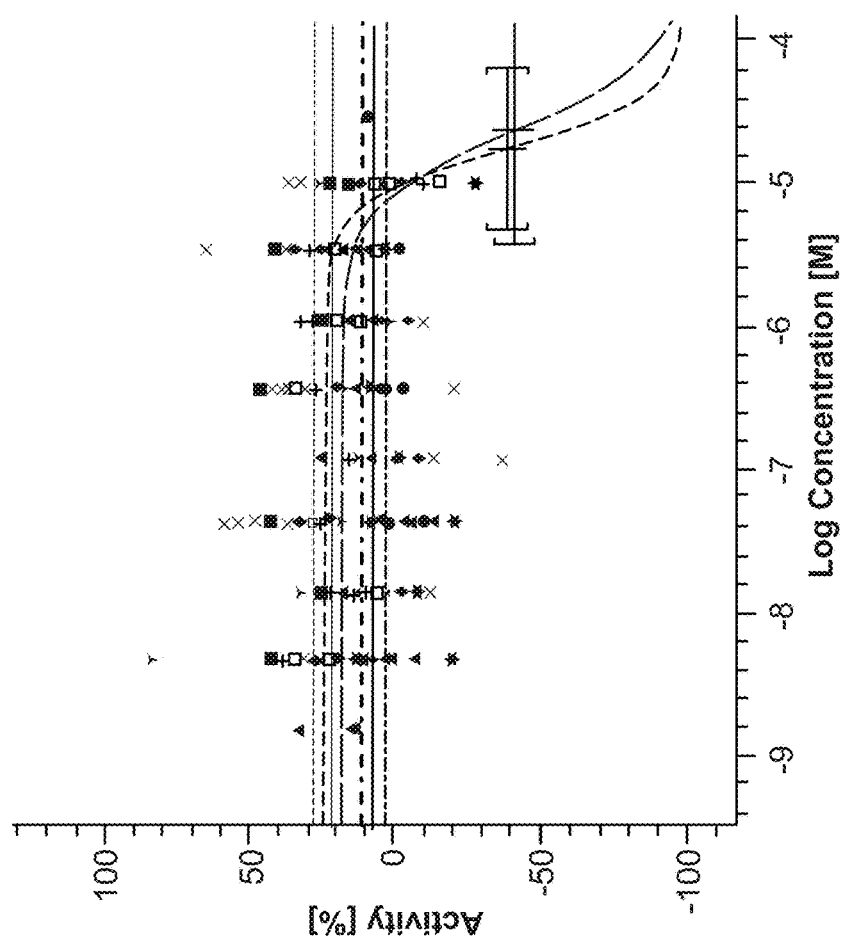
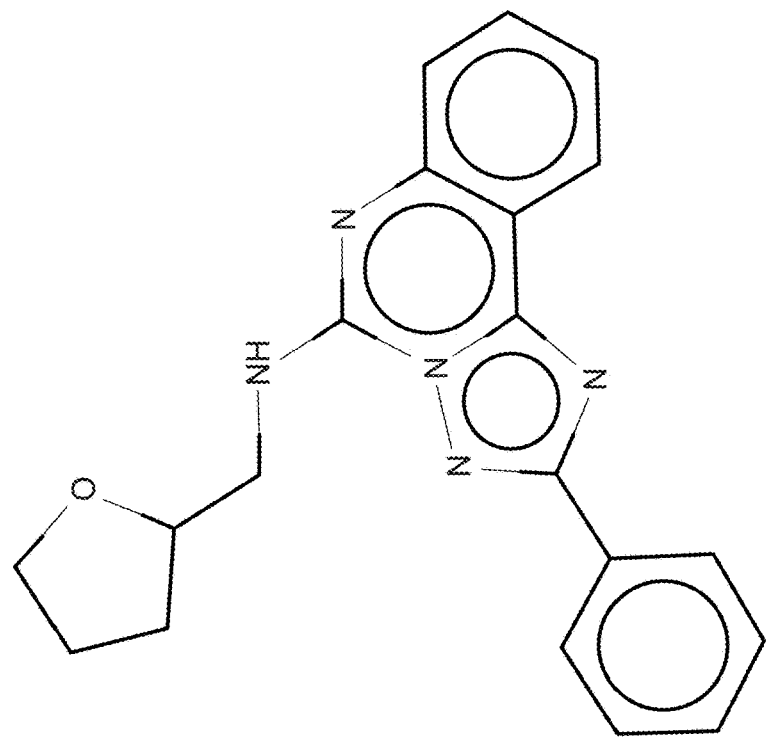

FIG. 24 (Continued)
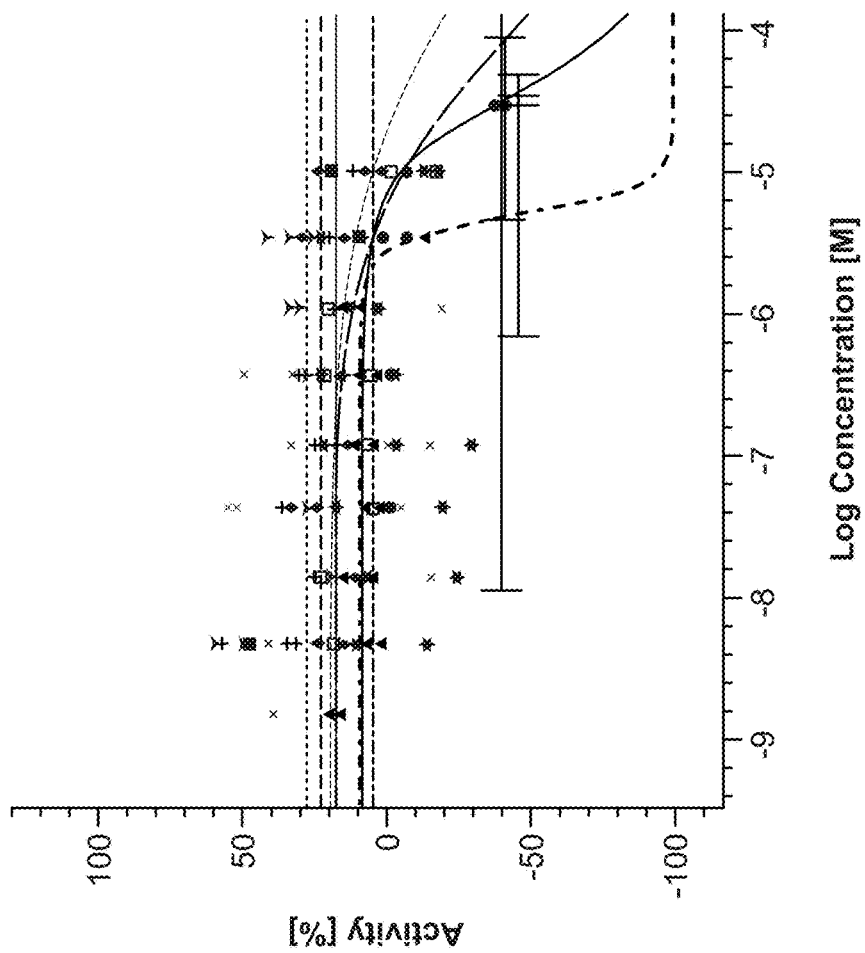
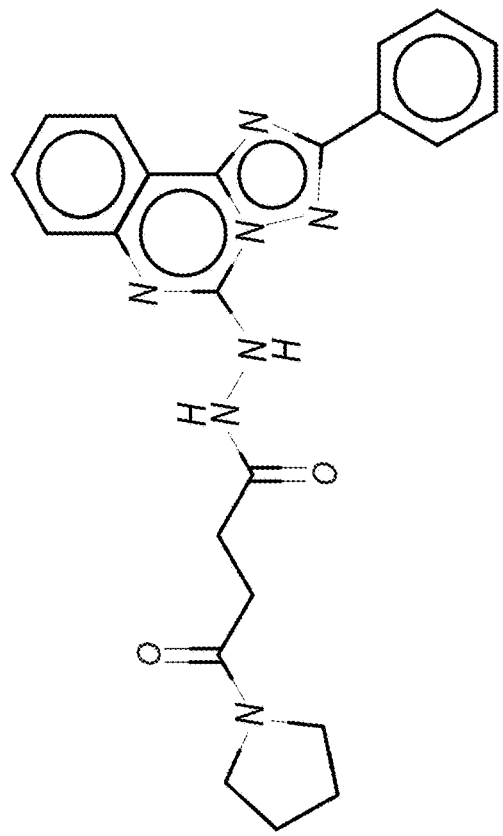

FIG. 24 (Continued)
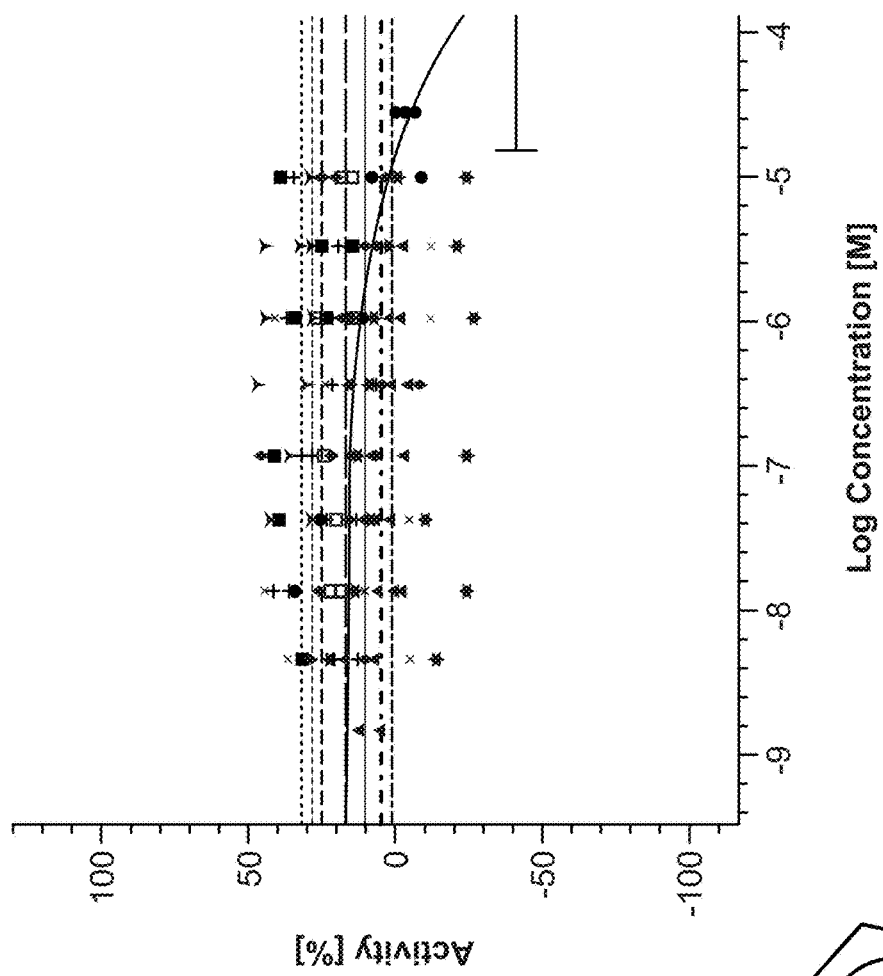
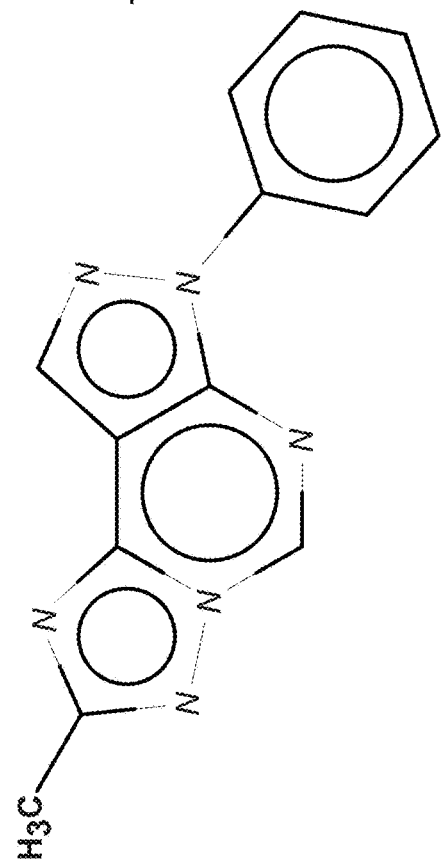

FIG. 24 (Continued)
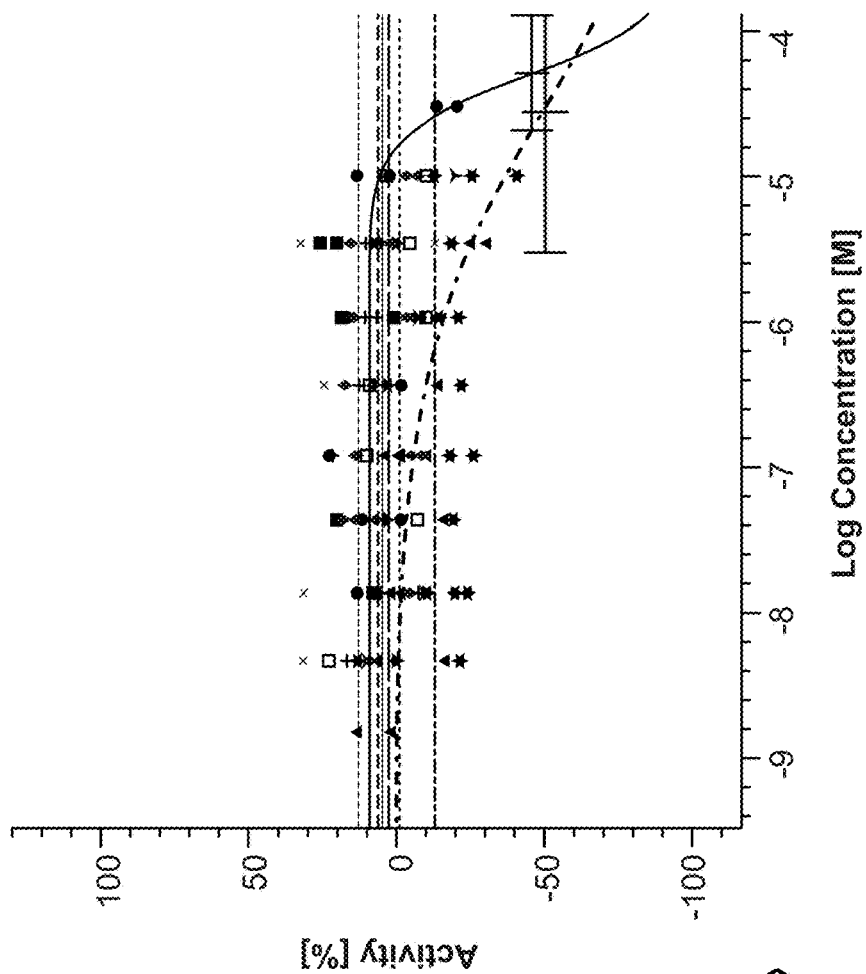
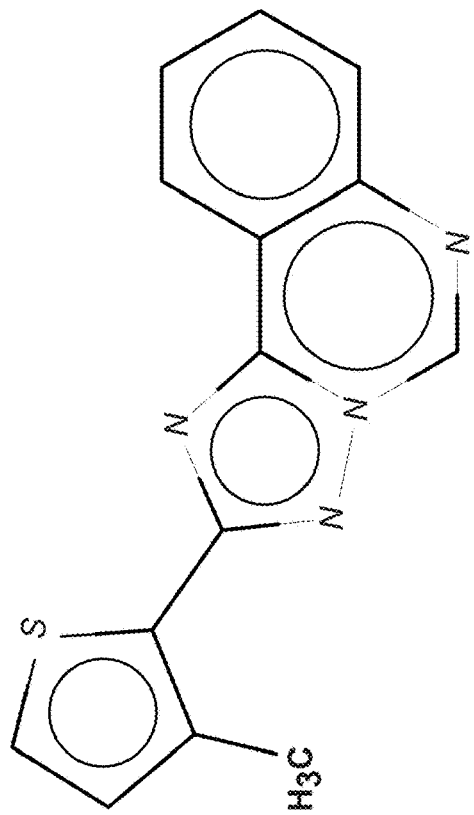

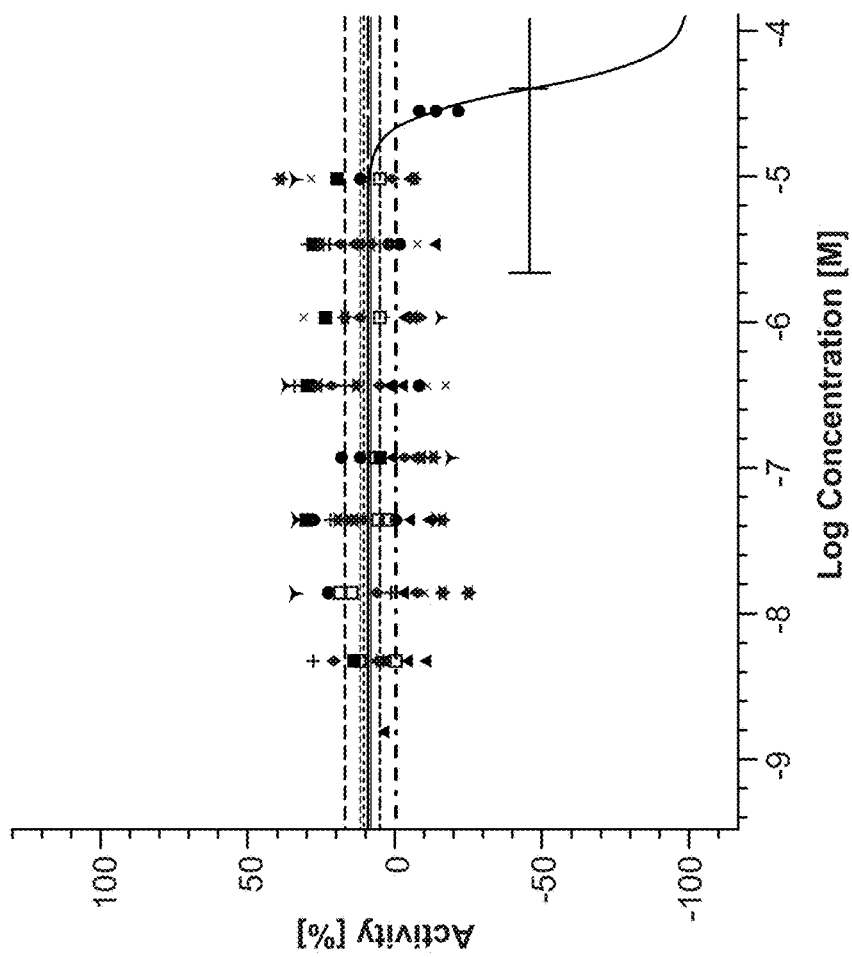
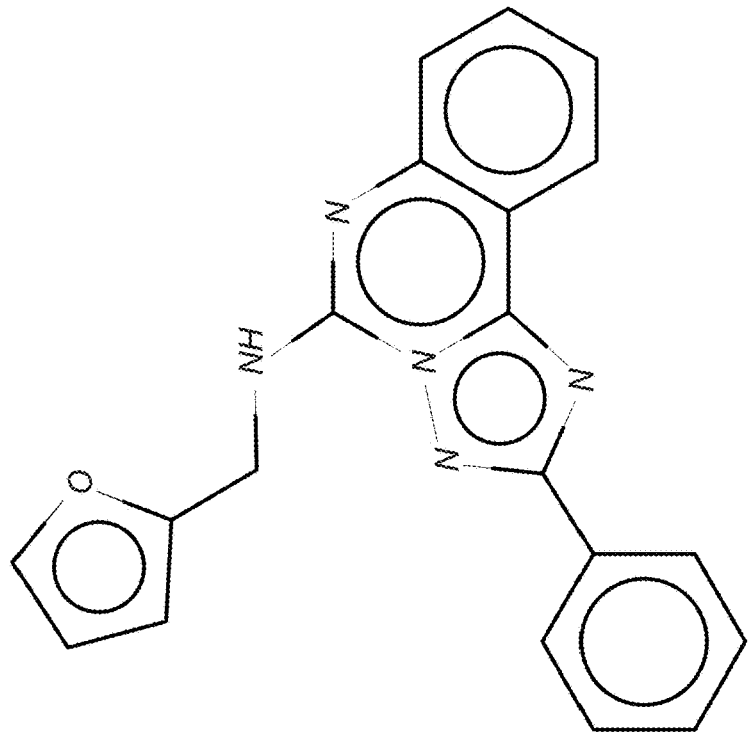
FIG. 24 (Continued)

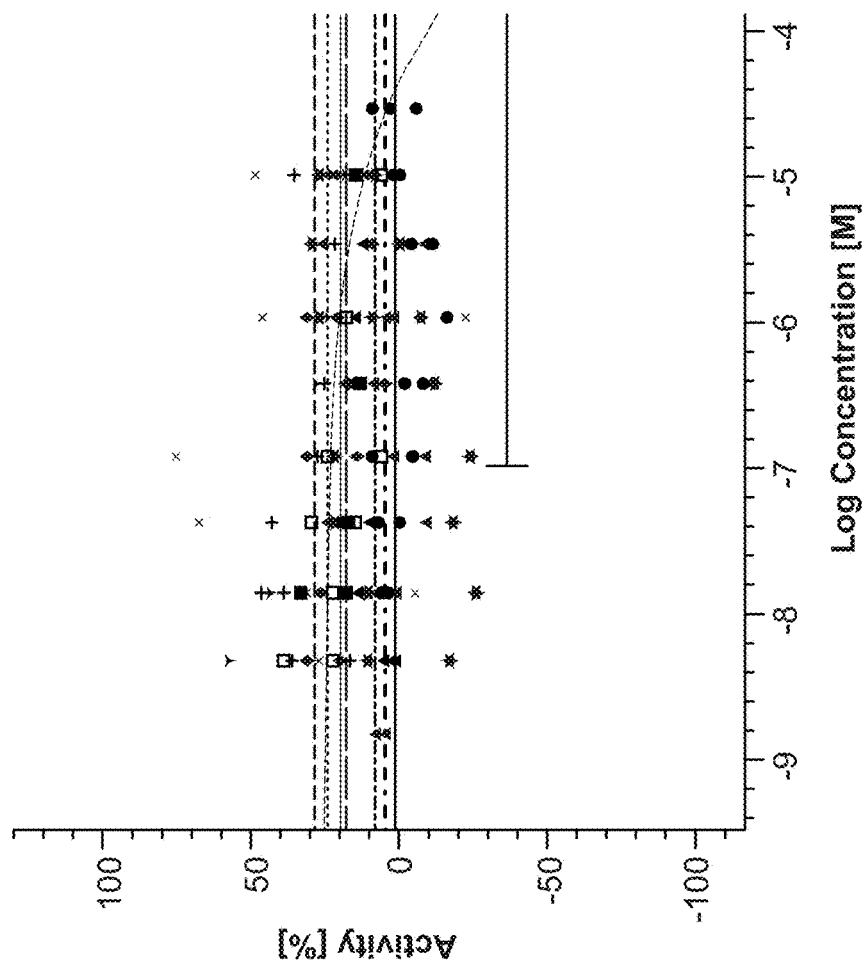
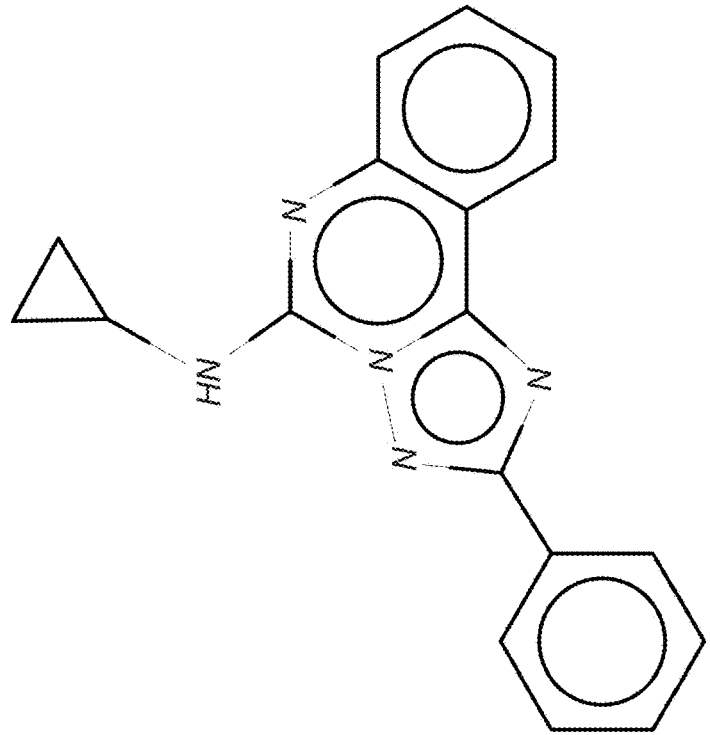
FIG. 24 (Continued)

FIG. 24 (Continued)
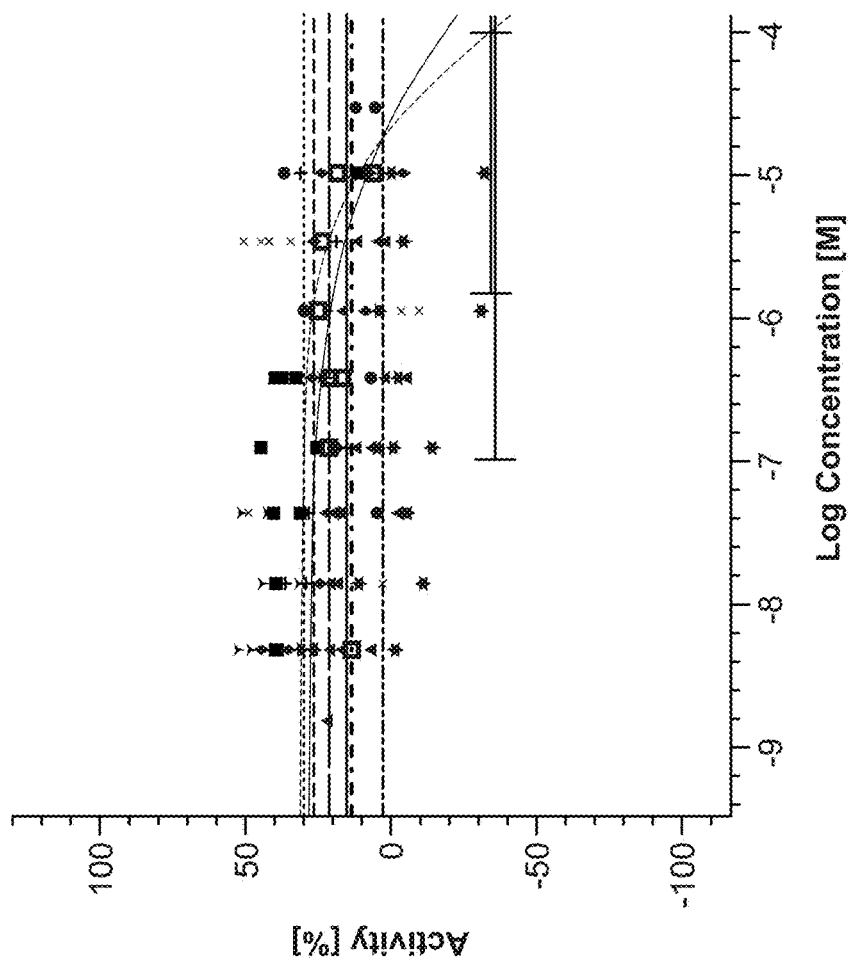
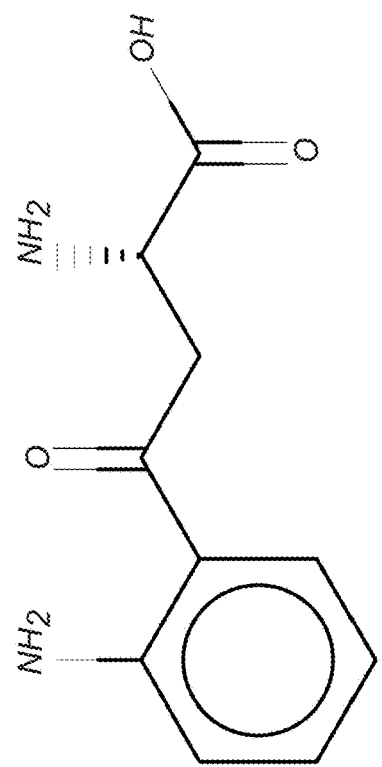

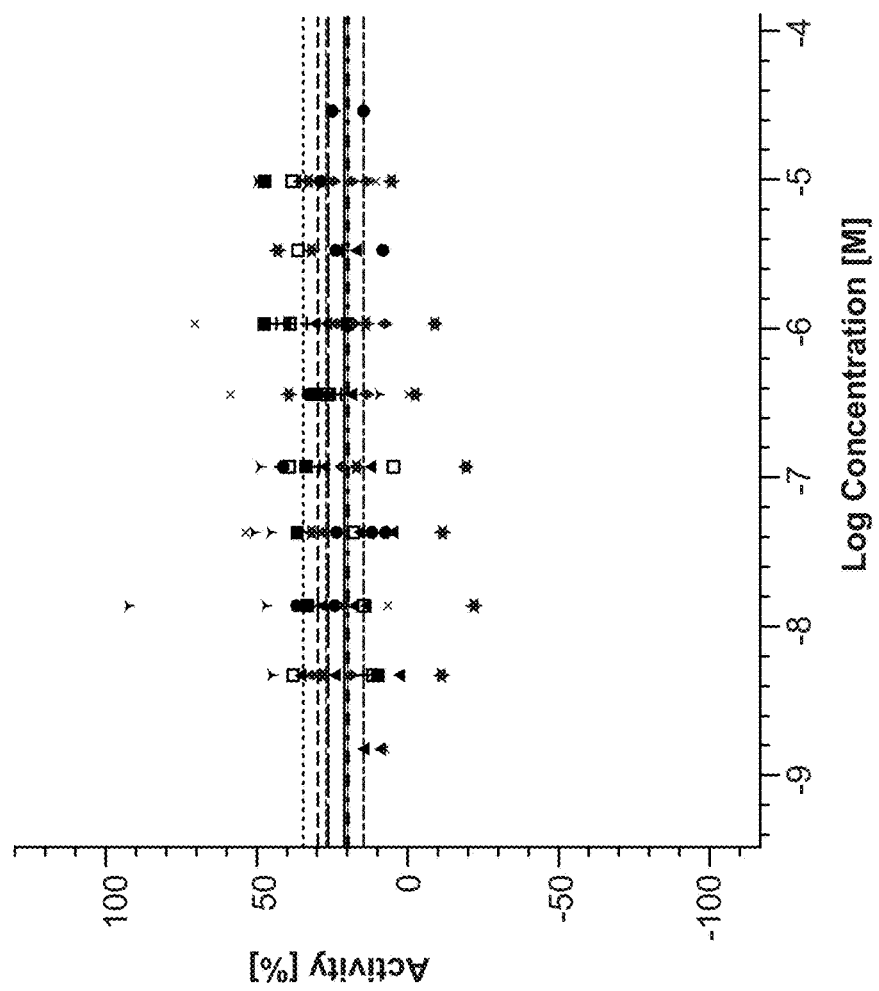
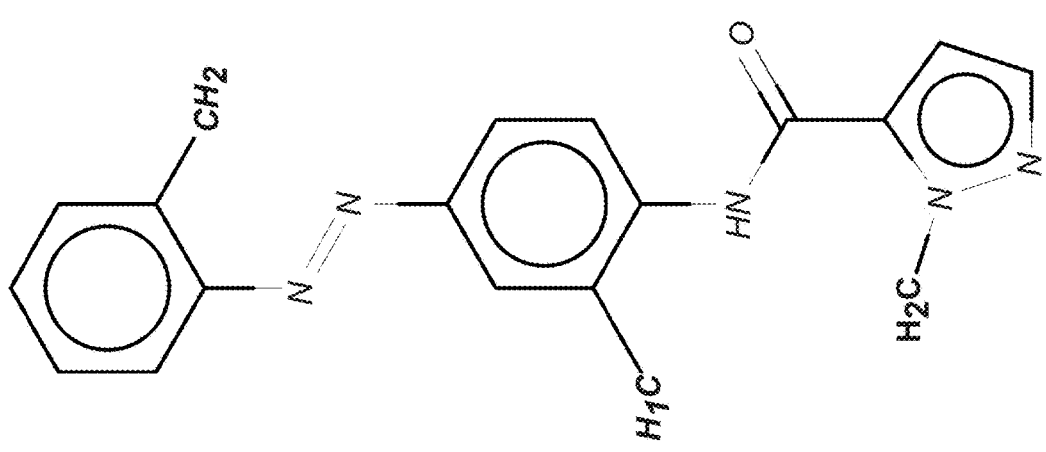
FIG. 24 (Continued)

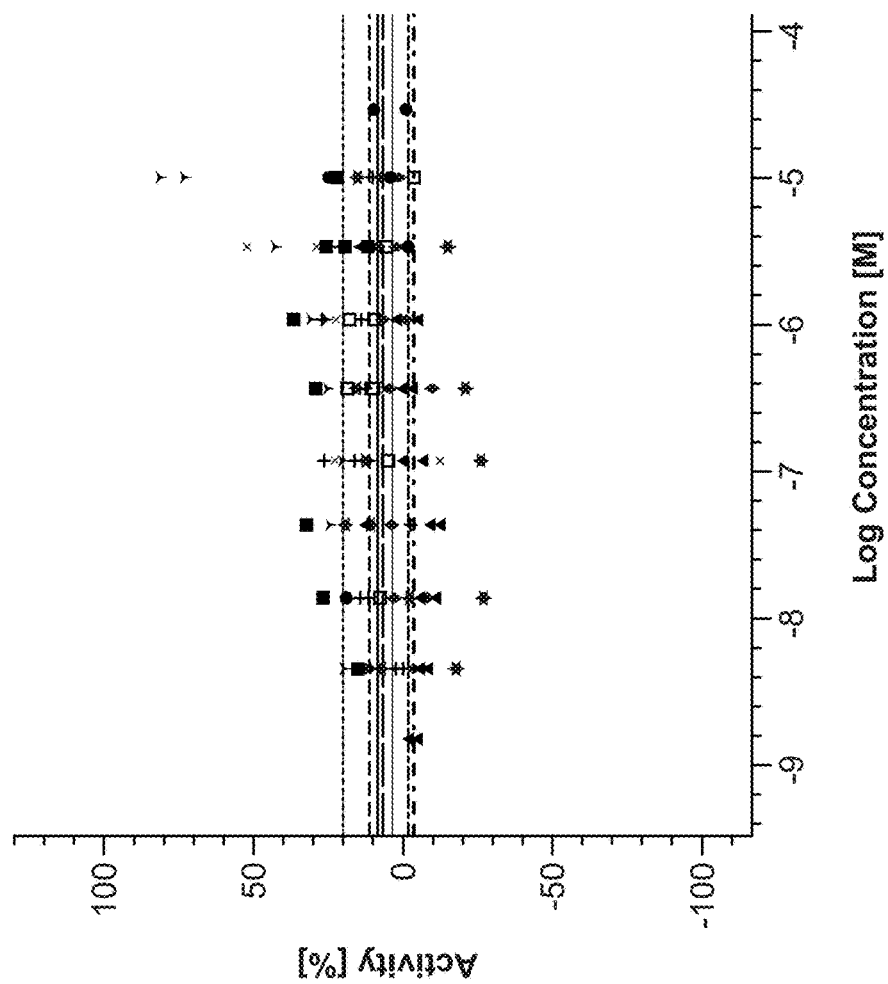
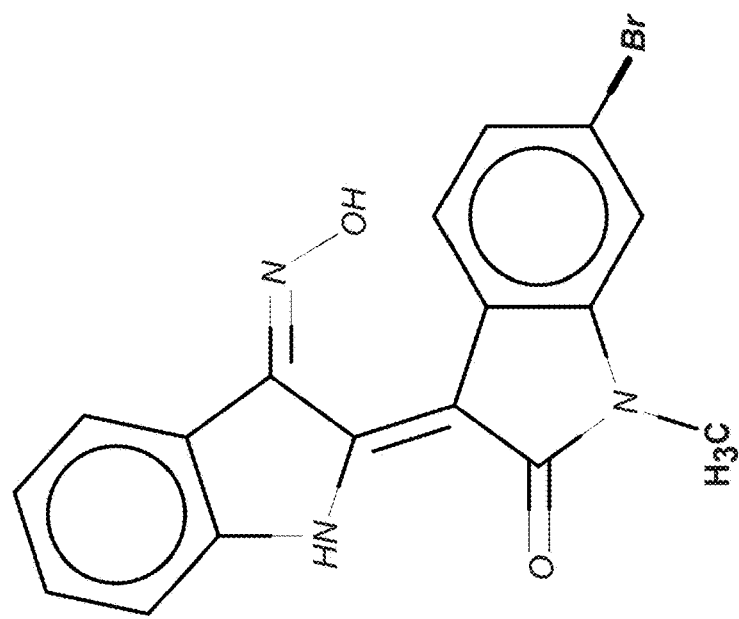
FIG. 24 (Continued)

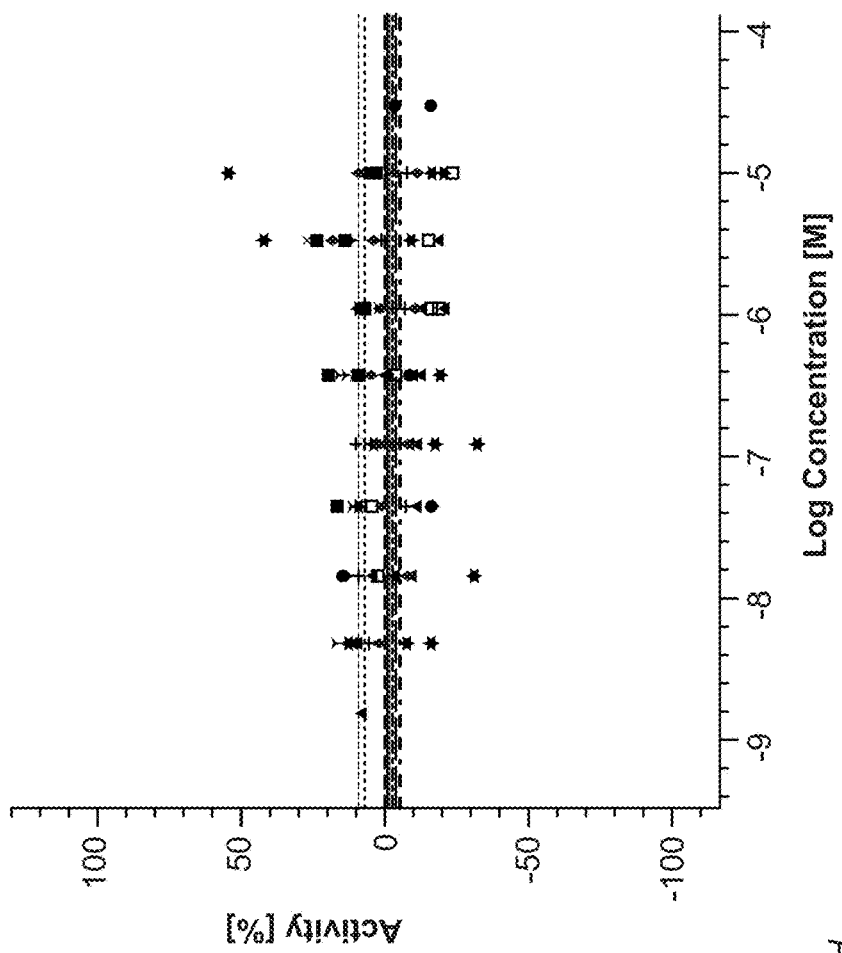
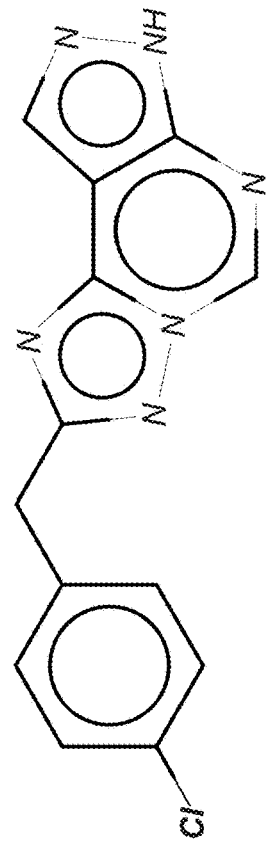
FIG. 24 (Continued)

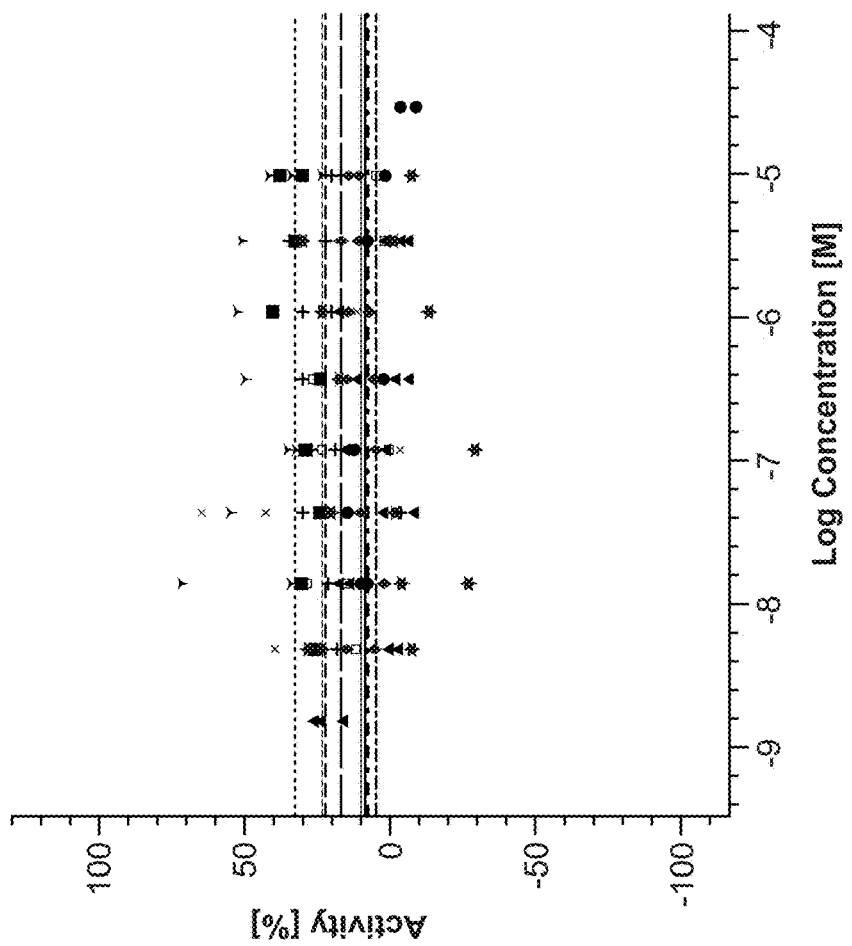
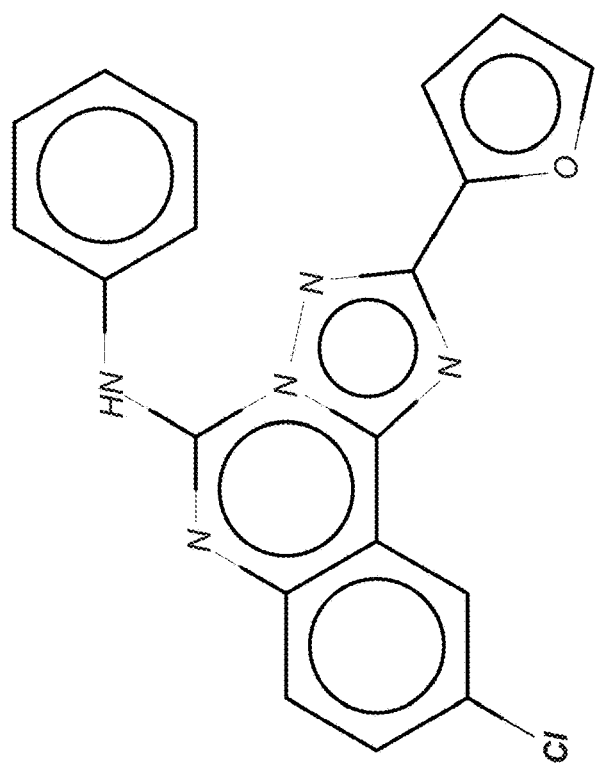
FIG. 24 (Continued)

FIG. 24 (Continued)
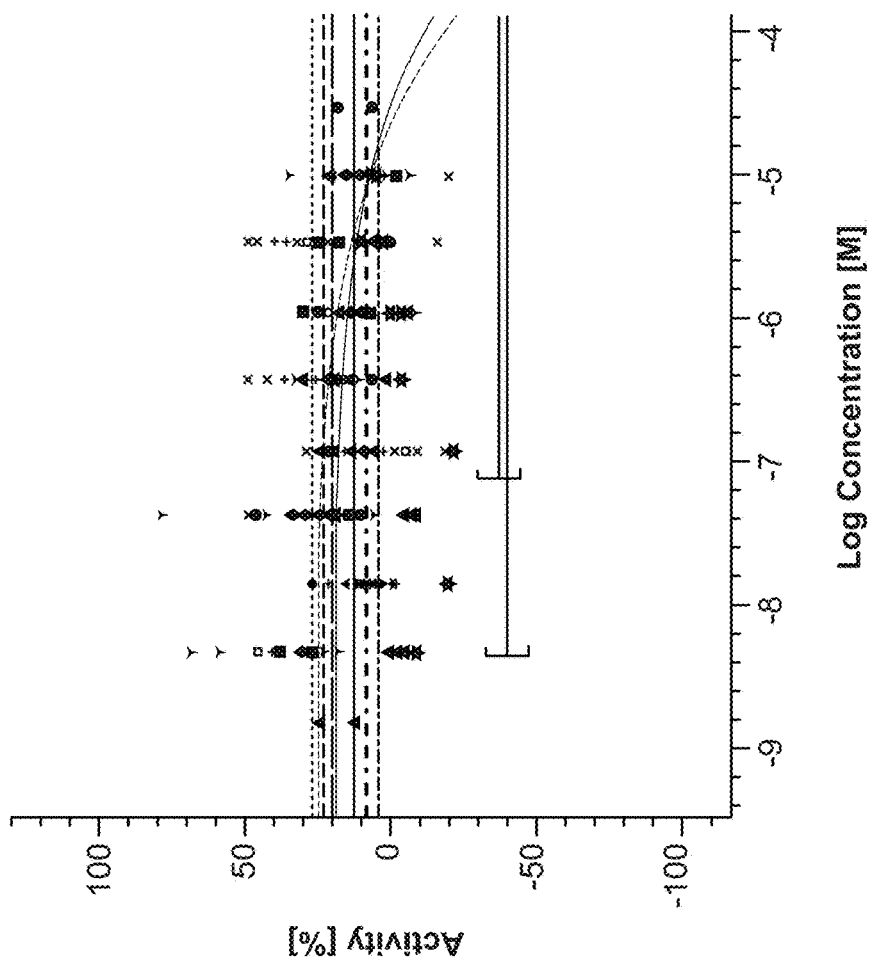
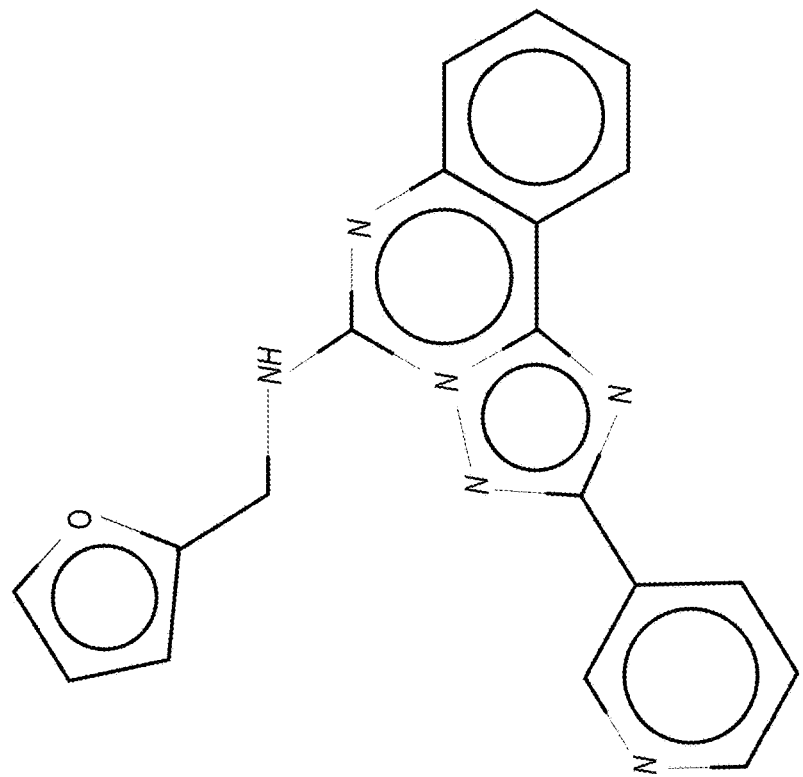

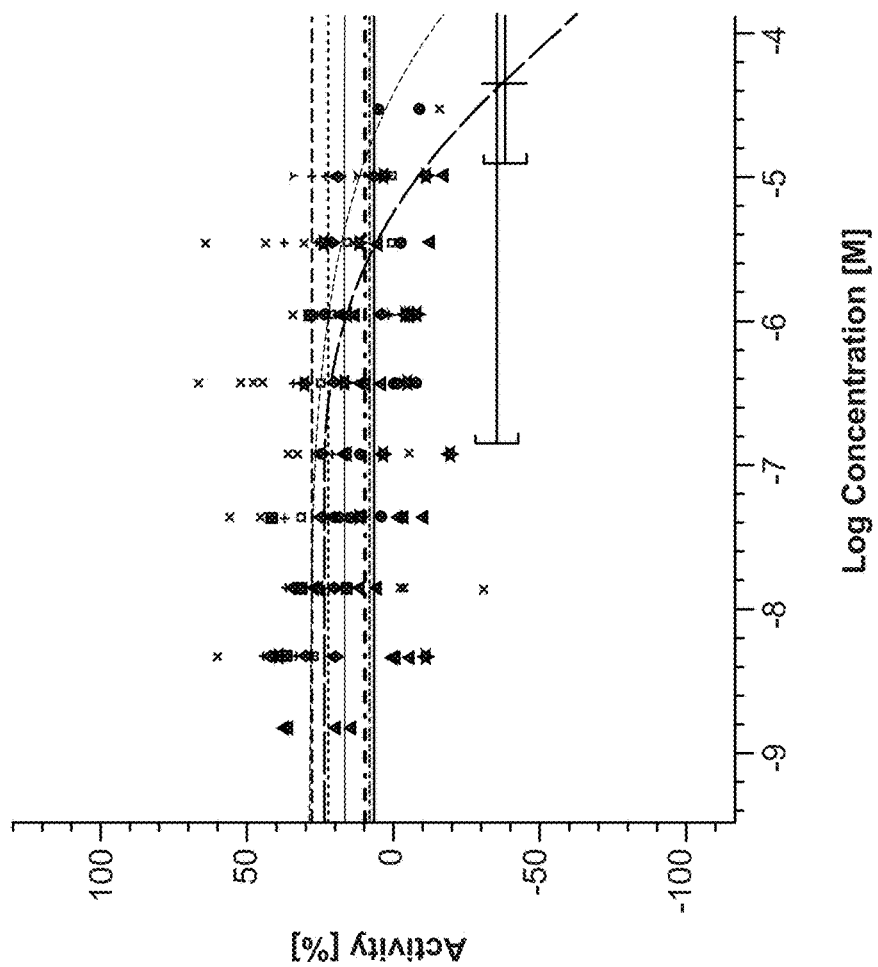
FIG. 24 (Continued)
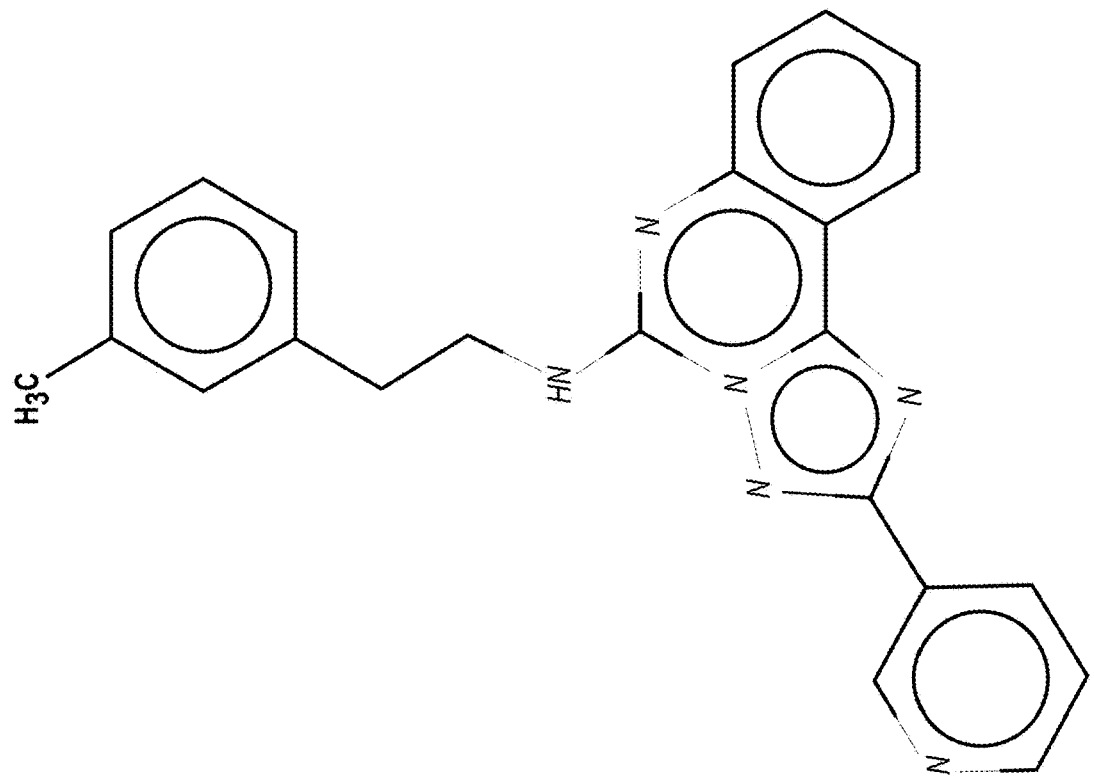

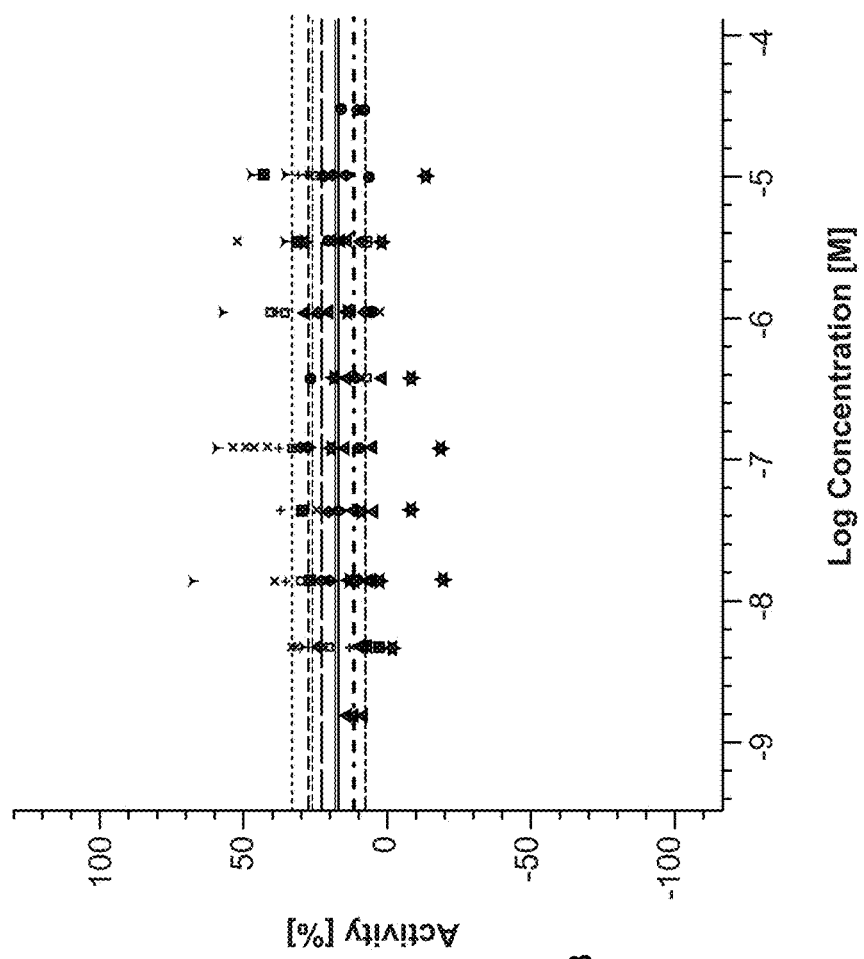
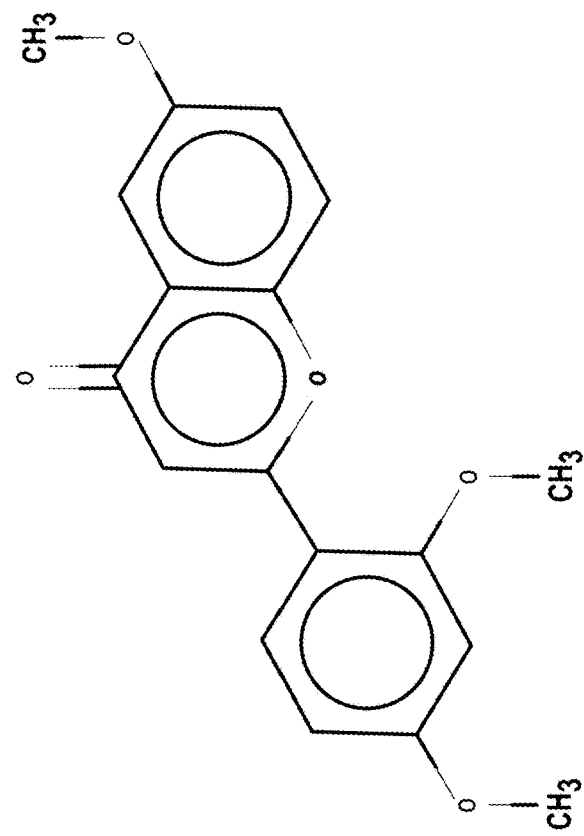
FIG. 24 (Continued)

FIG. 24 (Continued)
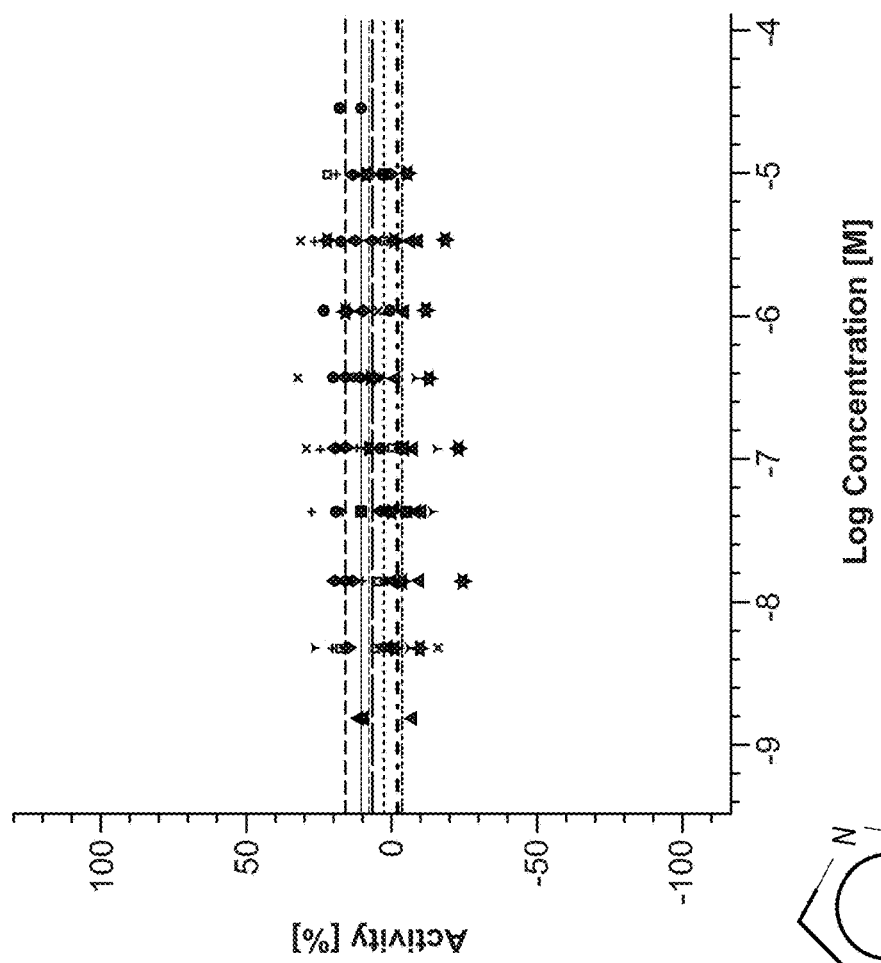
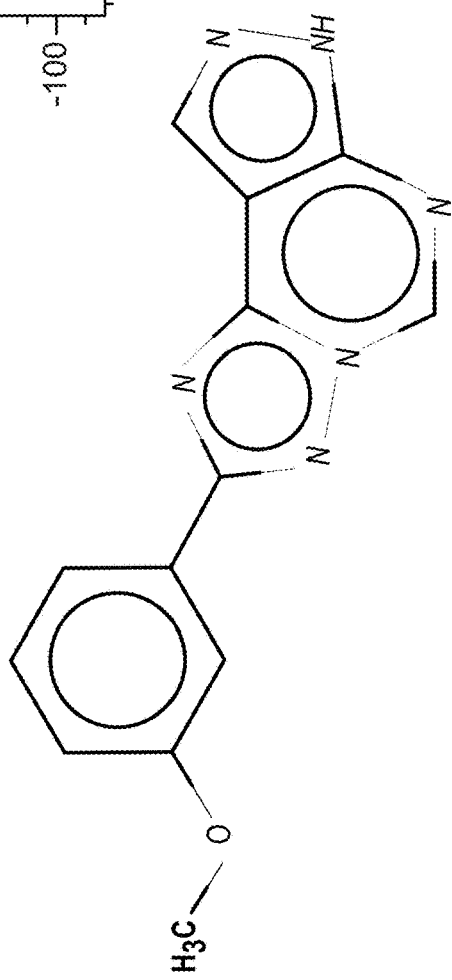

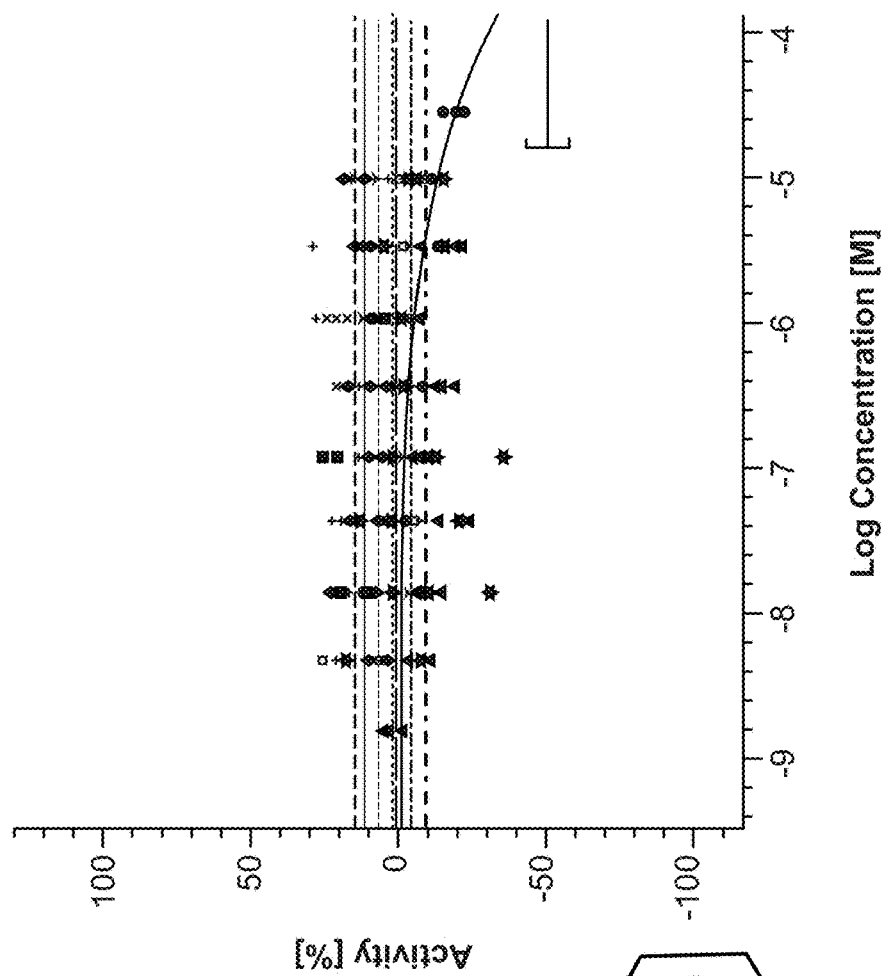
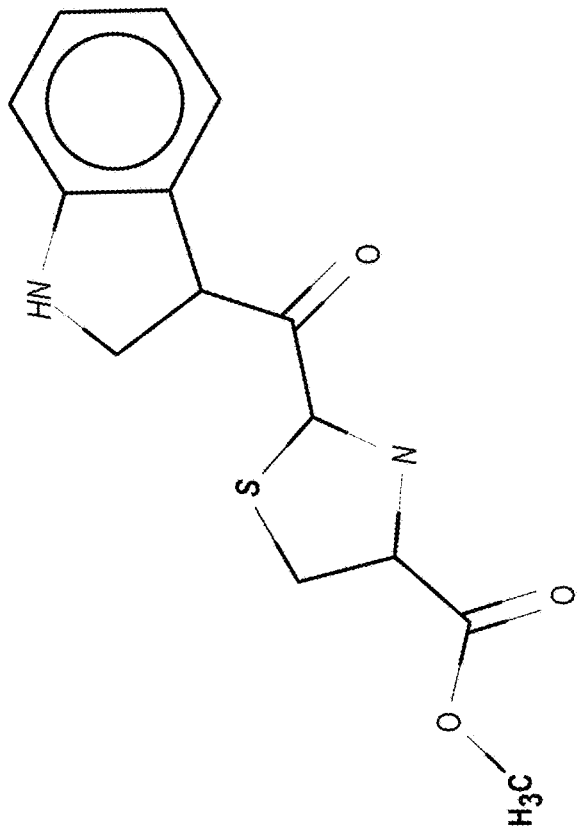
FIG. 24 (Continued)

FIG. 24 (Continued)
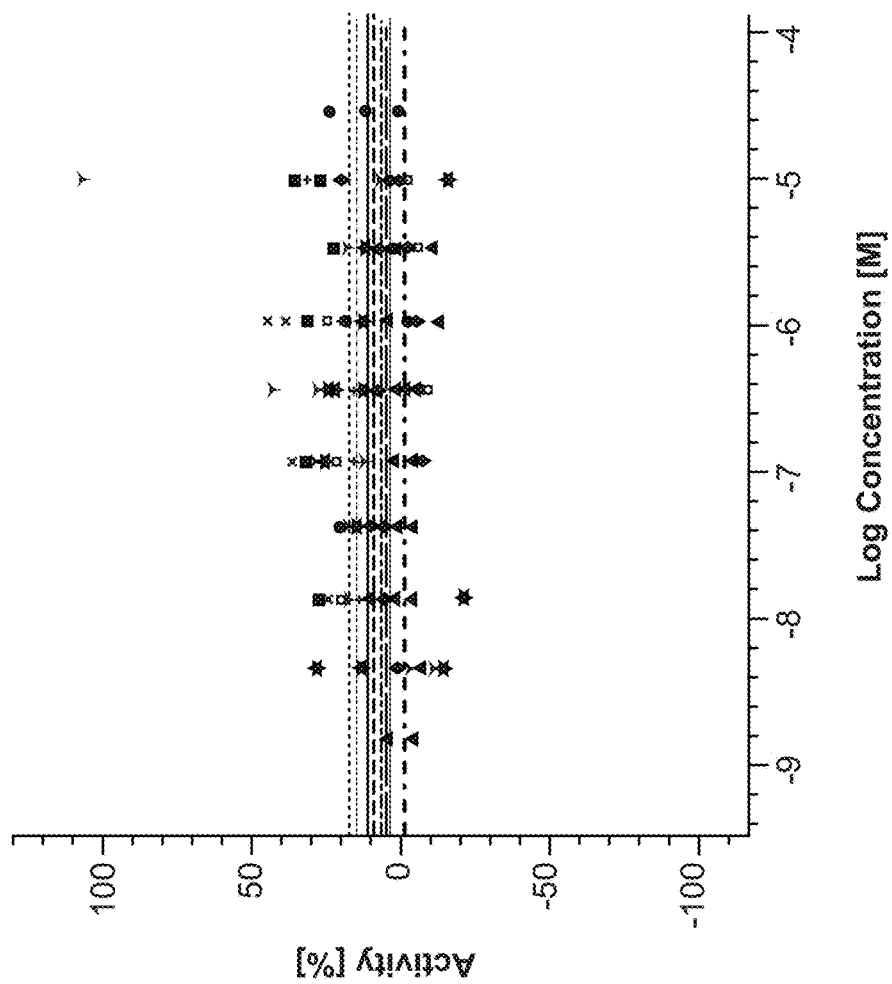
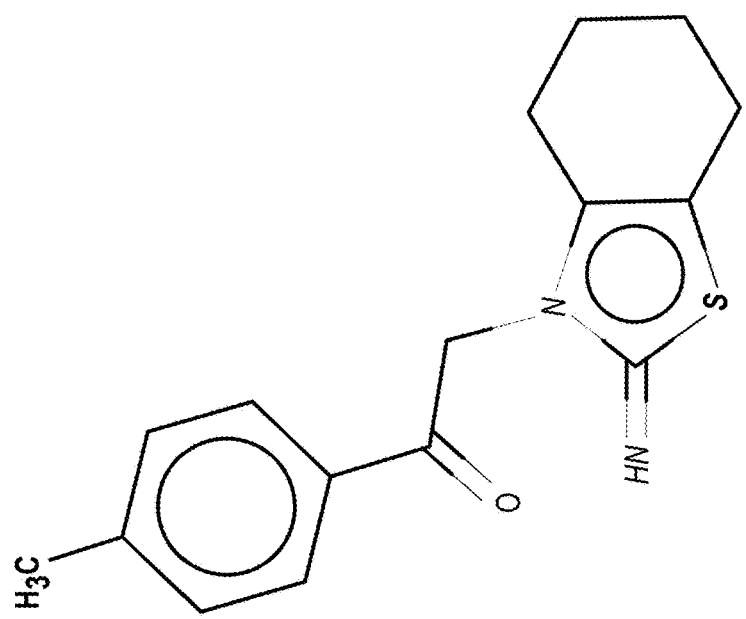

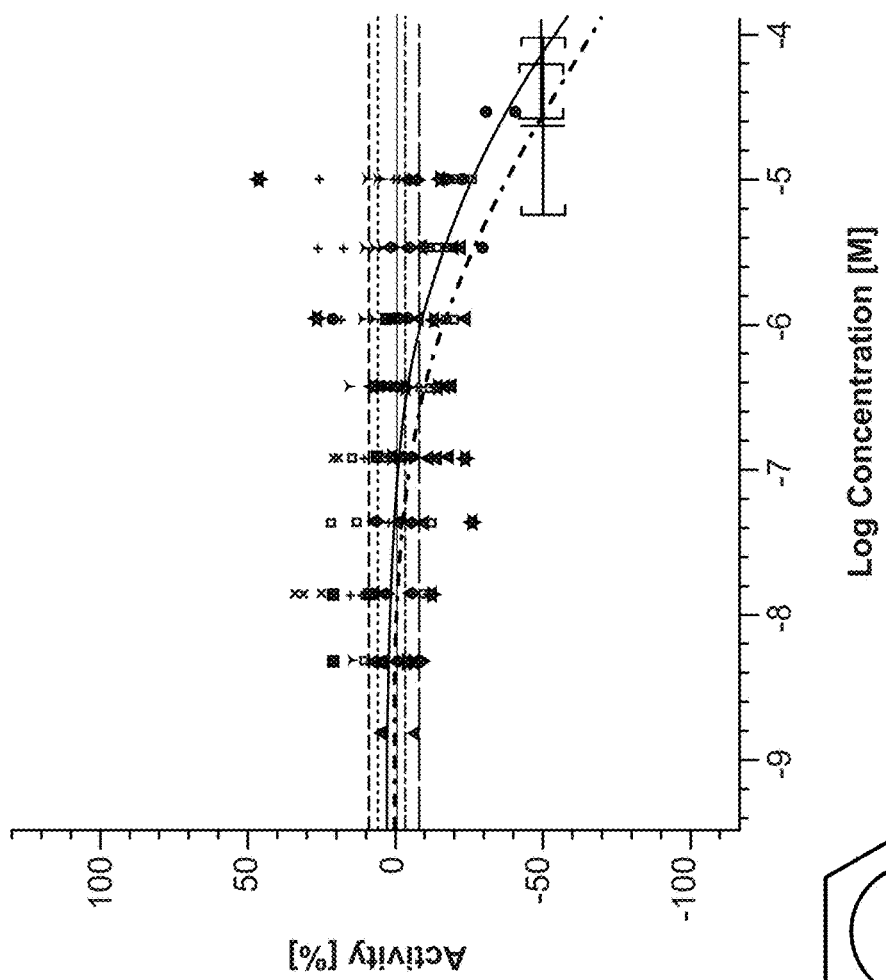
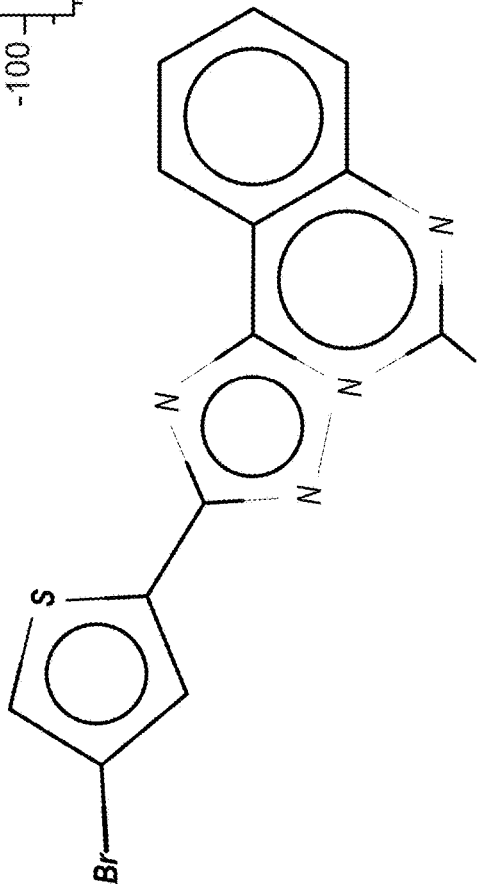
FIG. 24 (Continued)

FIG. 24 (Continued)
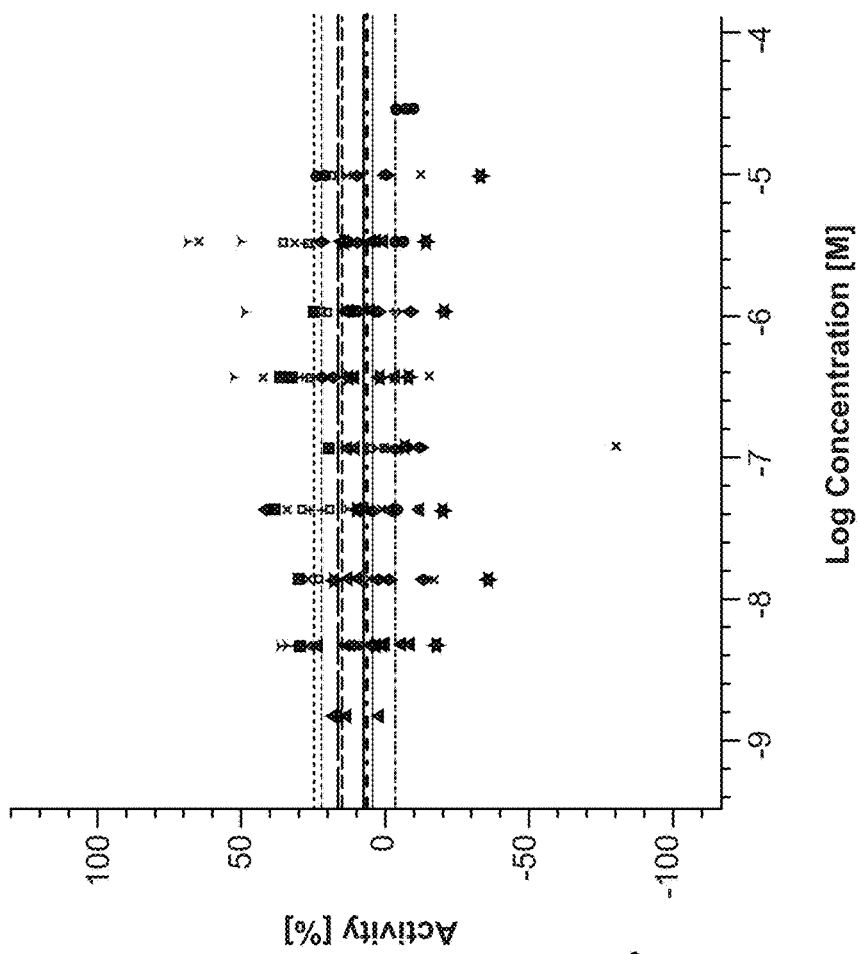
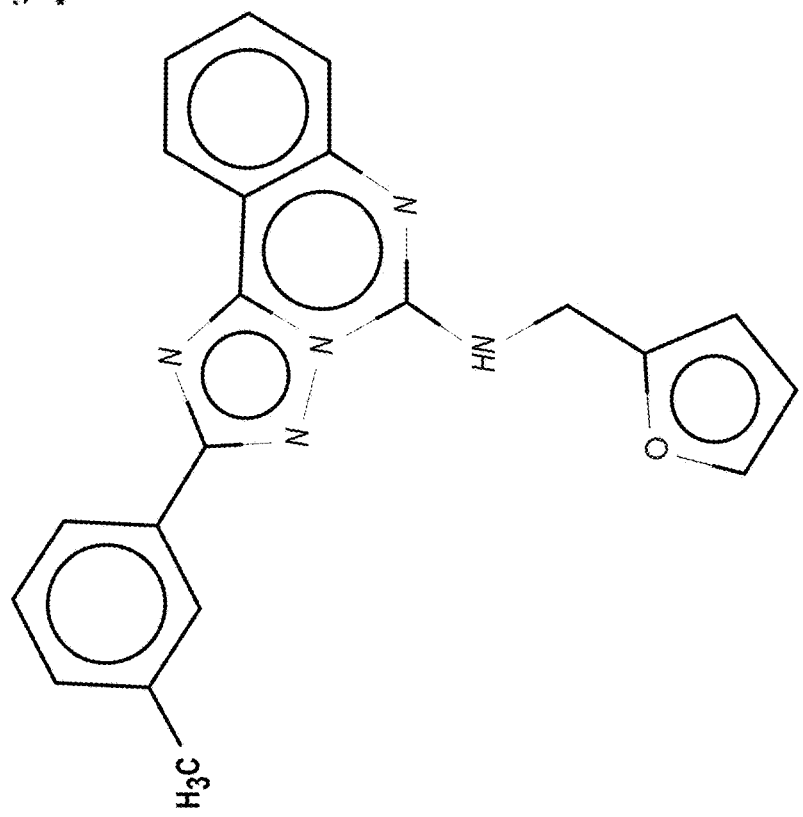

FIG. 24 (Continued)
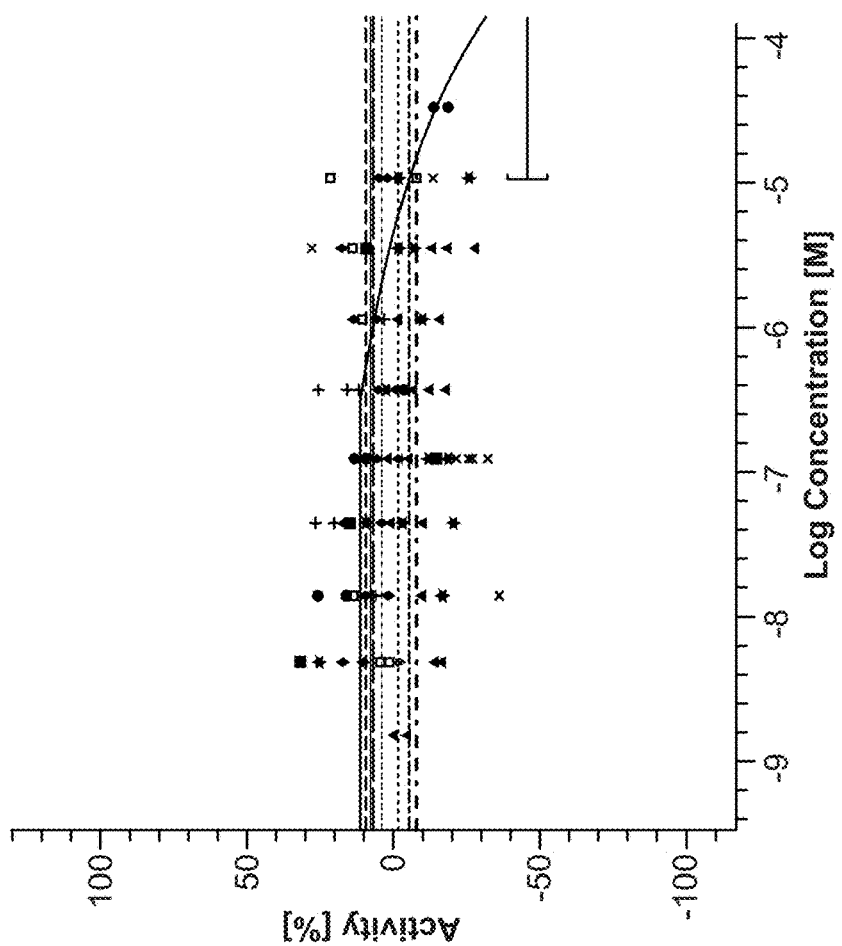
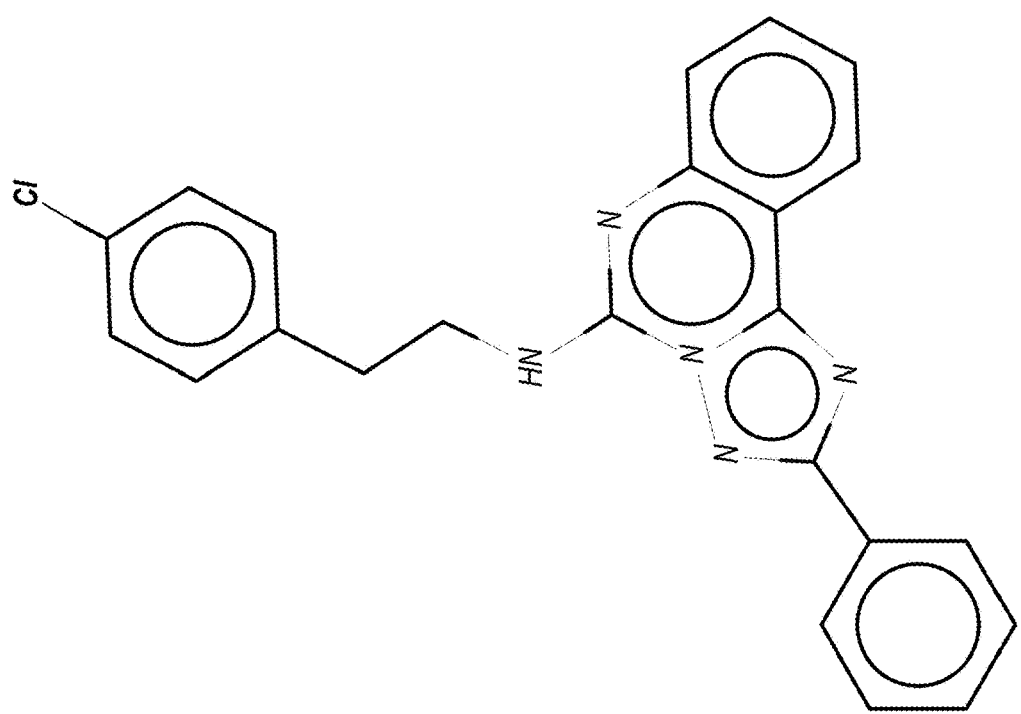

FIG. 24 (Continued)
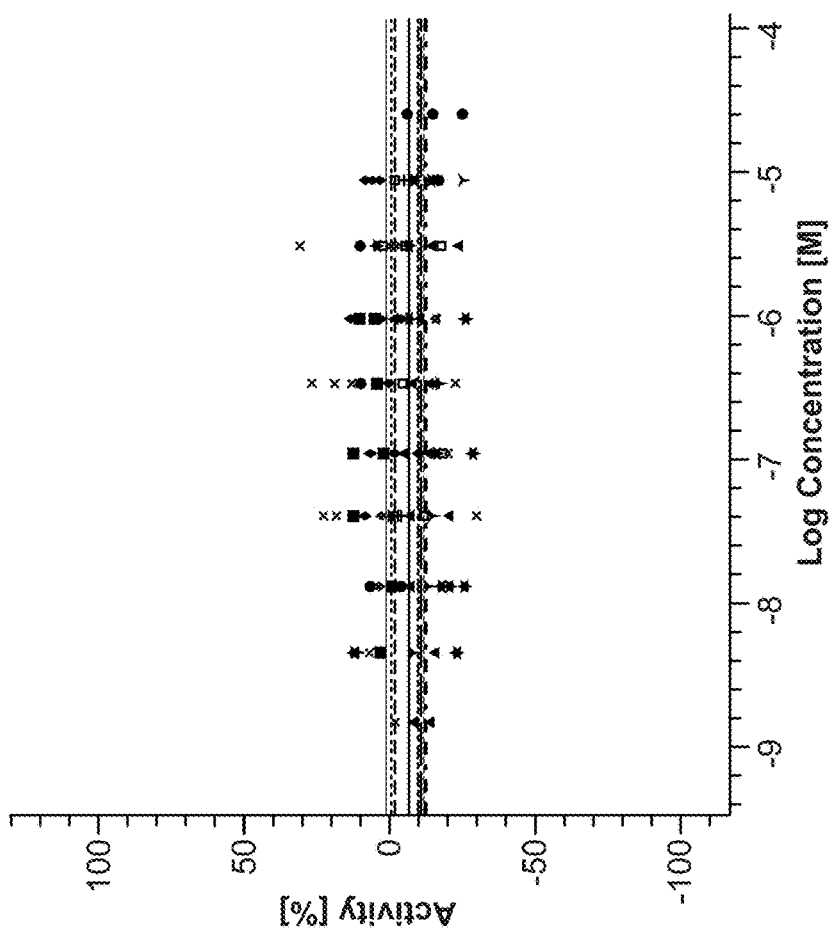
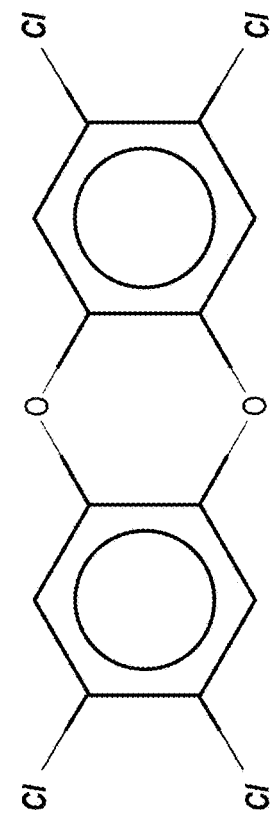

FIG. 24 (Continued)
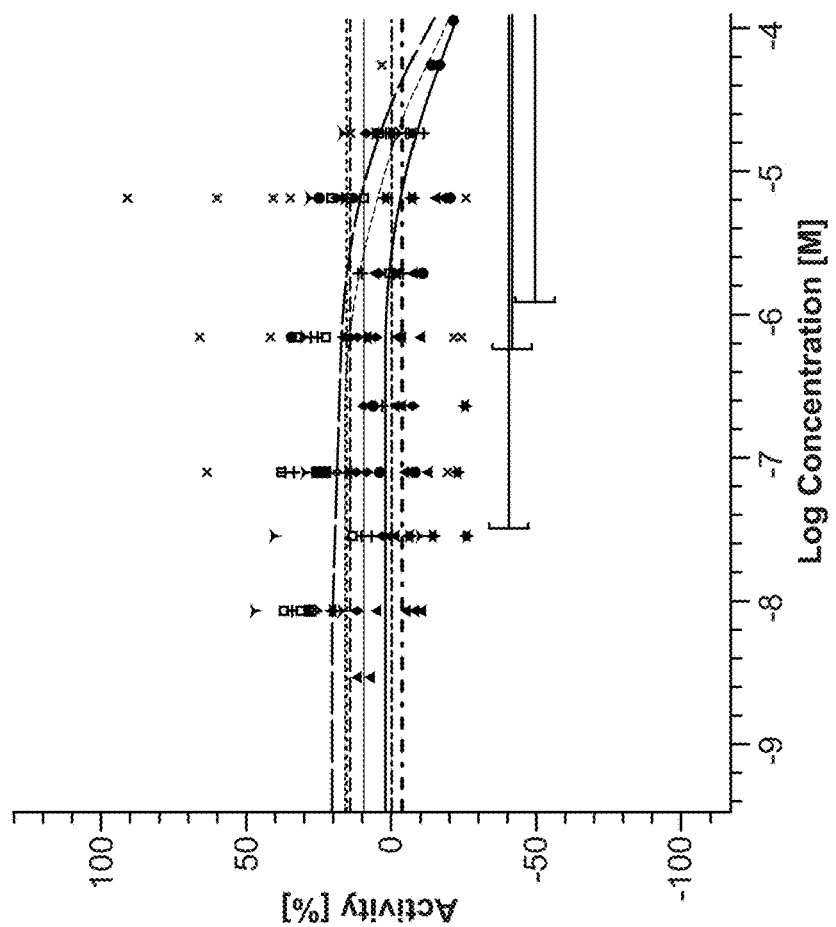
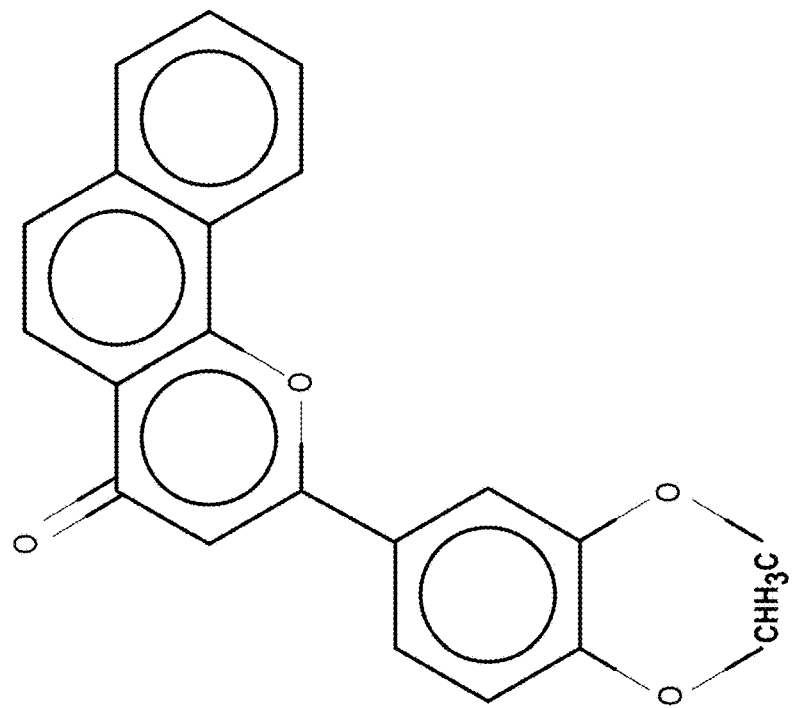

FIG. 24 (Continued)
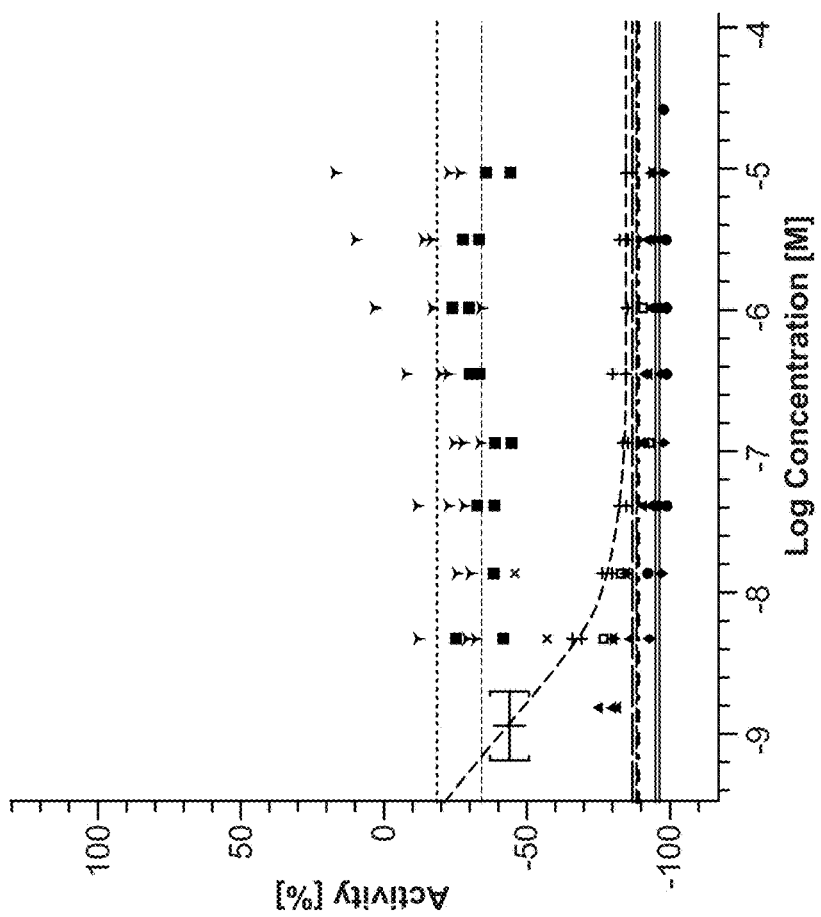
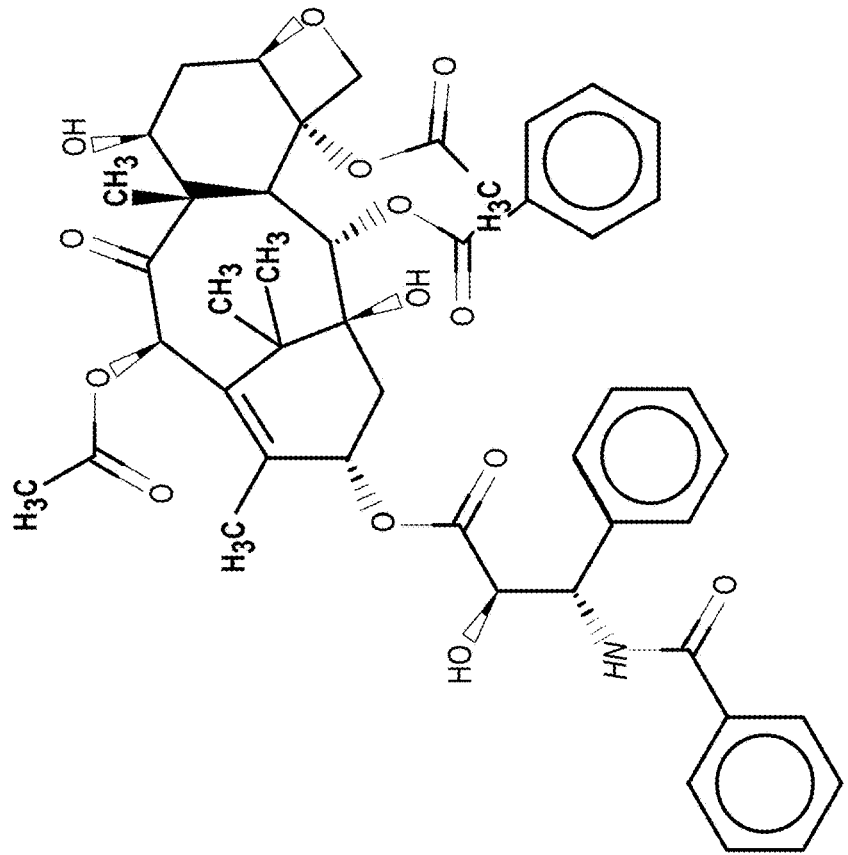

FIG. 24 (Continued)
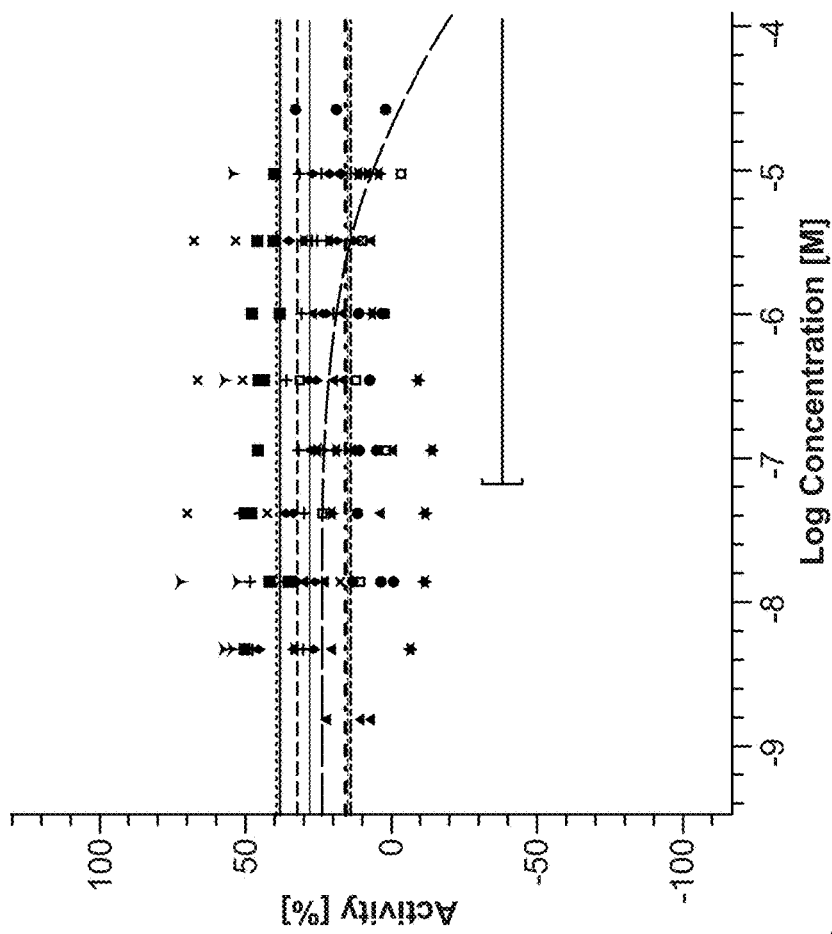
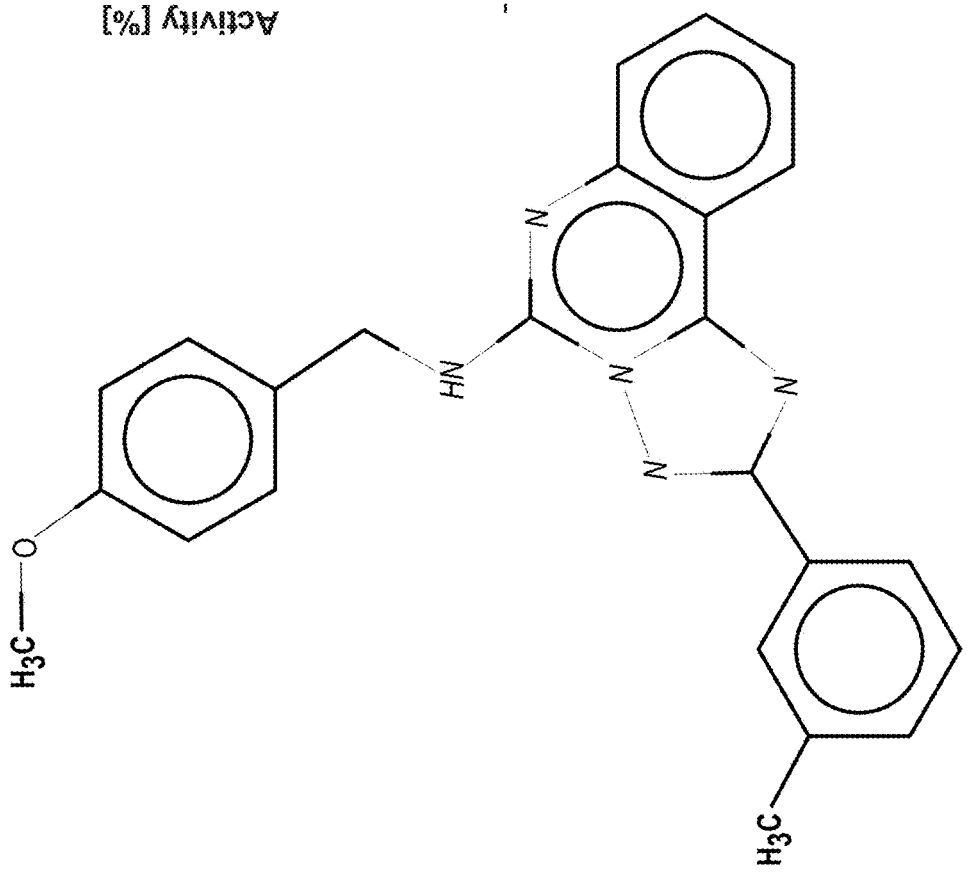

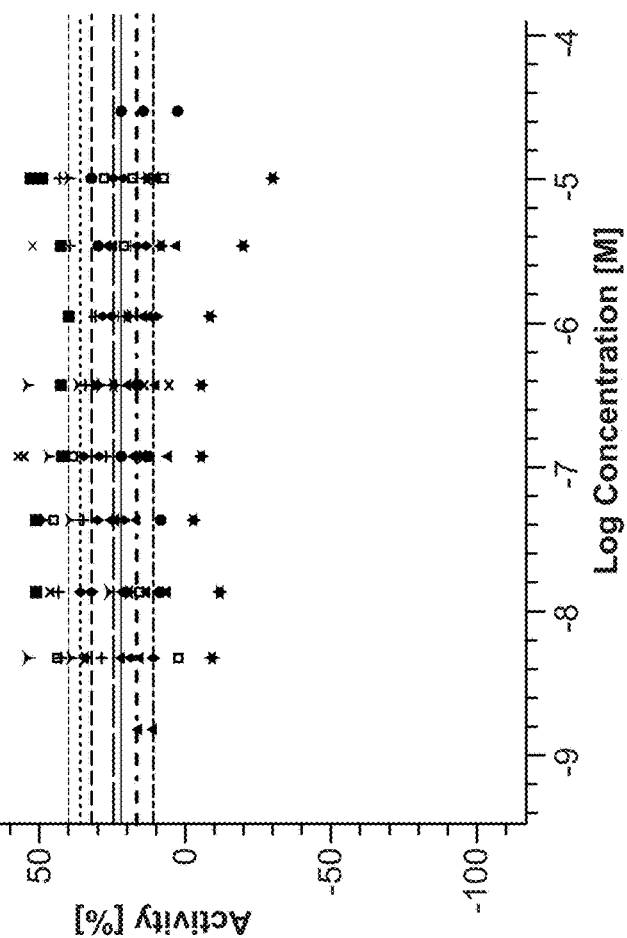
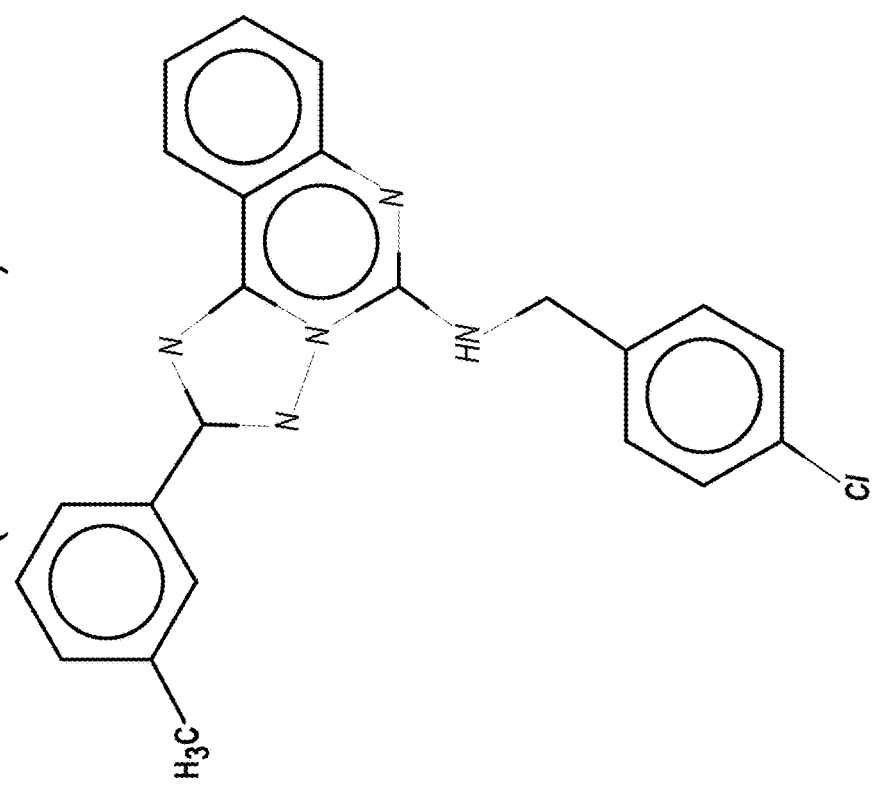
FIG. 24 (Continued)

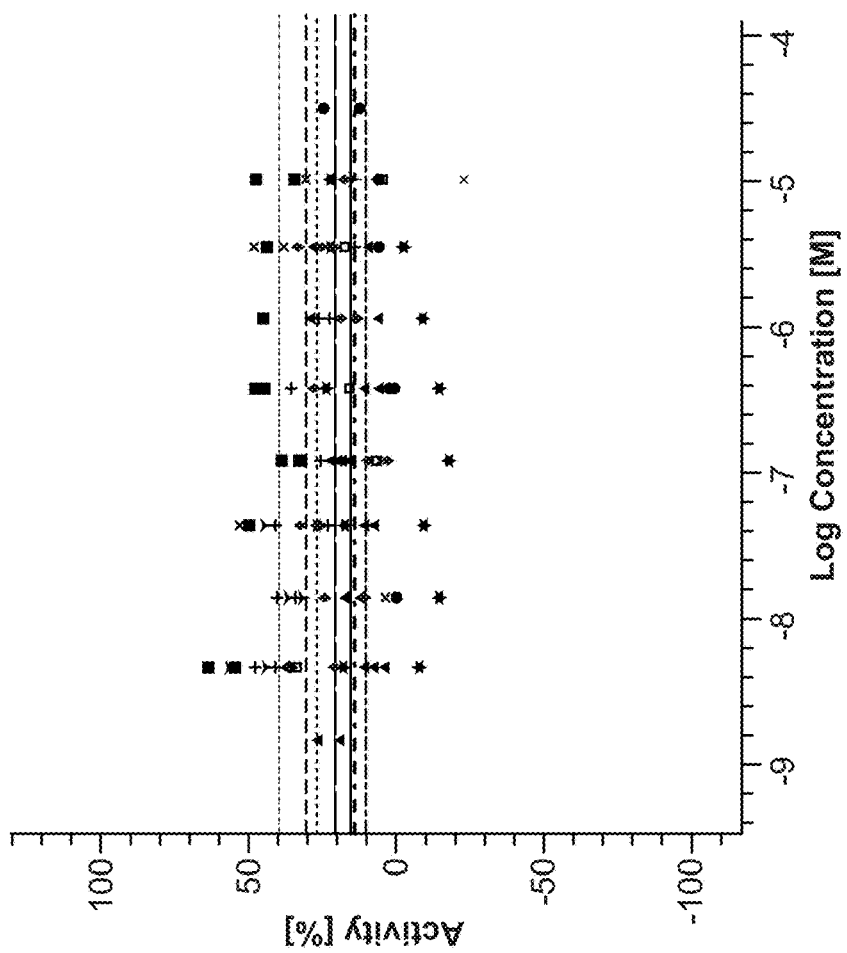
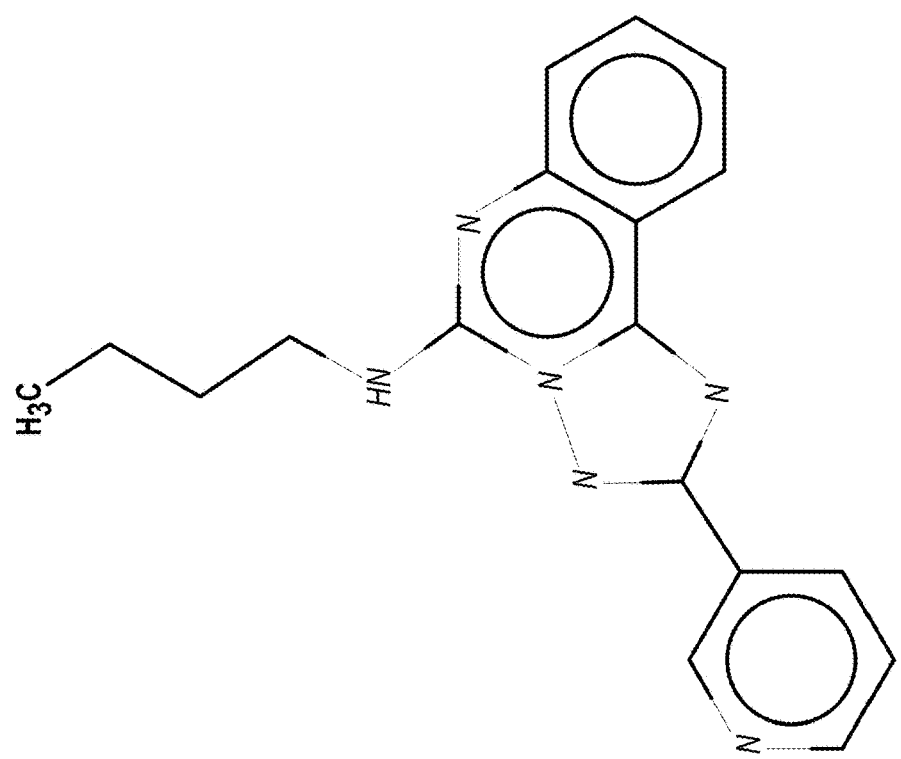
FIG. 24 (Continued)

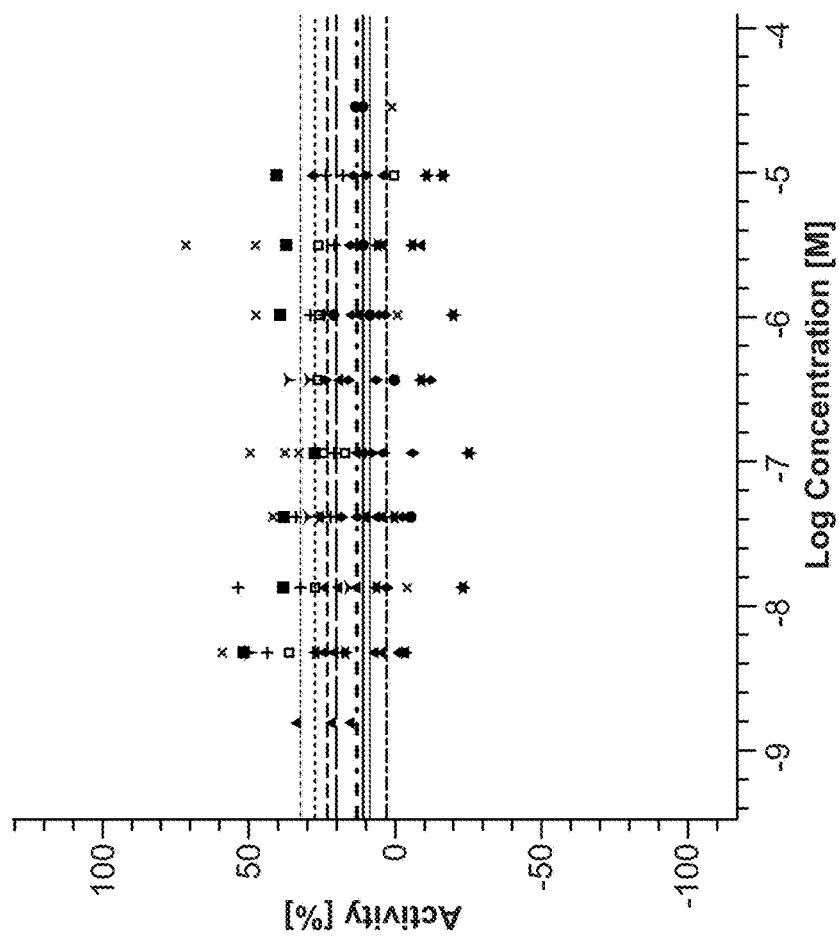
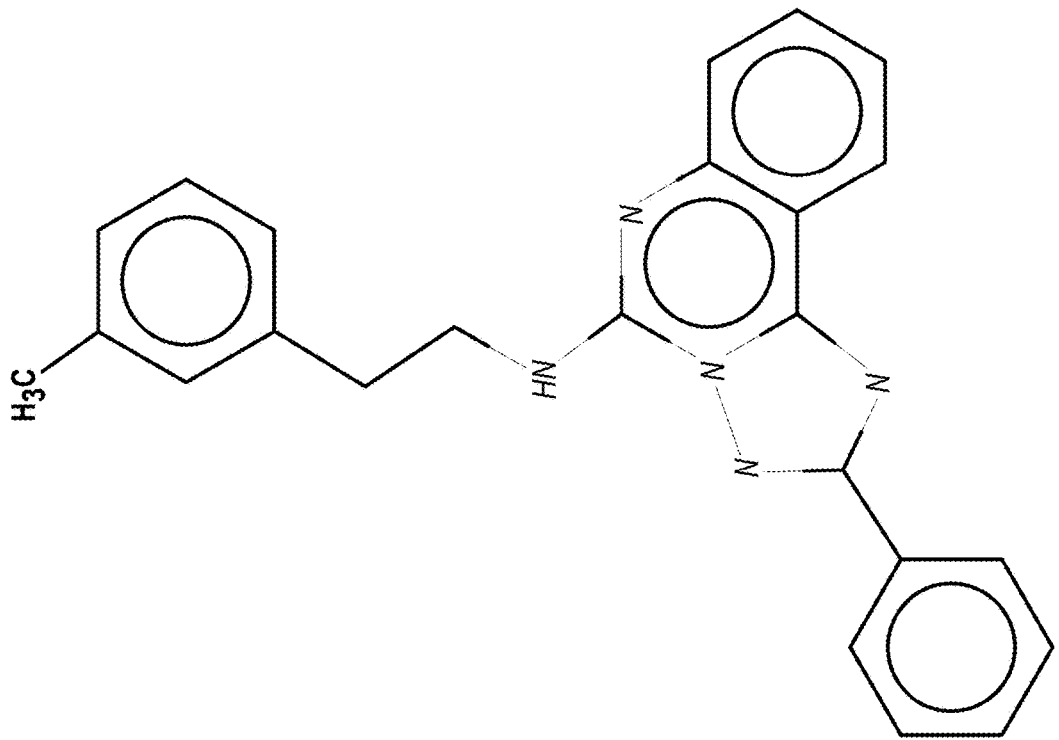
FIG. 24 (Continued)

SEQUENCE LISTING

<160> NUMBER OF SEQ ID NOS: 8

<210> SEQ ID NO 1
<211> LENGTH: 3396
<212> TYPE: DNA
<213> ORGANISM: Homo sapiens

<400> SEQUENCE: 1

```
gggcttcctc ttcgcccggg tggcgttggg cccgcgcggg cgctcgggtg actgcagctg      60
ctcagctccc ctcccccgcc ccgcgccgcg cggccgcccg tcgcttcgca cagggctgga     120
tggttgtatt gggcagggtg gctccaggat gttaggaact gtgaagatgg aagggcatga     180
aaccagcgac tggaacagct actacgcaga cacgcaggag gcctactcct ccgtcccggt     240
cagcaacatg aactcaggcc tgggctccat gaactccatg aacacctaca tgaccatgaa     300
caccatgact acgagcggca acatgacccc ggcgtccttc aacatgtcct atgccaaccc     360
gggcctaggg gccggcctga gtcccggcgc agtagccggc atgccggggg gctcggcggg     420
cgccatgaac agcatgactg cggccggcgt gacggccatg ggtacggcgc tgagcccgag     480
cggcatgggc gccatgggtg cgcagcaggc ggcctccatg aatggcctgg cccctacgc      540
ggccgccatg aacccgtgca tgagcccat ggcgtacgcg ccgtccaacc tgggccgcag     600
ccgcgcgggc ggcggcggcg acgccaagac gttcaagcgc agctacccgc acgccaagcc     660
gccctactcg tacatctcgc tcatcaccat ggccatccag caggcgccca gcaagatgct     720
cacgctgagc gagatctacc agtggatcat ggacctcttc ccctattacc ggcagaacca     780
gcagcgctgg cagaactcca tccgccactc gctgtccttc aatgactgct tcgtcaaggt     840
ggcacgctcc ccggacaagc cgggcaaggg ctcctactgg acgctgcacc cggactccgg     900
caacatgttc gagaacggct gctacttgcg ccgccagaag cgcttcaagt gcgagaagca     960
gccgggggcc ggcggcgggg cgggagcgg aagcgggggc agcggcgcca agggcggccc    1020
tgagagccgc aaggaccct ctggcgcctc taaccccagc gccgactcgc ccctccatcg    1080
gggtgtgcac gggaagaccg gccagctaga gggcgcgccg gcccccgggc ccgccgccag    1140
cccccagact ctggaccaca gtggggcgac ggcgacaggg ggcgcctcgg agttgaagac    1200
tccagcctcc tcaactgcgc ccccataag ctccgggccc ggggcgctgg cctctgtgcc    1260
cgcctctcac ccggcacacg gcttggcacc ccacgagtcc cagctgcacc tgaaagggga    1320
cccccactac tccttcaacc acccgttctc catcaacaac ctcatgtcct cctcggagca    1380
gcagcataag ctggacttca aggcatacga acaggcactg caatactcgc cttacggctc    1440
tacgttgccc gccagcctgc ctctaggcag cgcctcggtg accaccagga gccccatcga    1500
gccctcagcc ctggagccgg cgtactacca aggtgtgtat tccagacccg tcctaaacac    1560
ttcctagctc ccgggactgg ggggtttgtc tggcatagcc atgctggtag caagagagaa    1620
aaaatcaaca gcaaacaaaa ccacacaaac caaaccgtca acagcataat aaaatcccaa    1680
caactatttt tatttcattt ttcatgcaca accttttcccc cagtgcaaaa gactgttact    1740
ttattattgt attcaaaatt cattgtgtat attactacaa agacaacccc aaaccaattt    1800
ttttcctgcg aagtttaatg atccacaagt gtatatatga aattctcctc cttccttgcc    1860
cccctctctt tcttccctct ttcccctcca gacattctag tttgtggagg gttatttaaa    1920
```

|  |  |  |  |  |
|---|---|---|---|---|
| aaaacaaaaa | aggaagatgg | tcaagtttgt | aaaatatttg tttgtgctttt ttccccctcc | 1980 |
| ttacctgacc | ccctacgagt | ttacaggtct | gtggcaatac tcttaaccat aagaattgaa | 2040 |
| atggtgaaga | aacaagtata | cactagaggc | tcttaaaagt attgaaagac aatactgctg | 2100 |
| ttatatagca | agacataaac | agattataaa | catcagagcc atttgcttct cagtttacat | 2160 |
| ttctgataca | tgcagatagc | agatgtcttt | aaatgaaata catgtatatt gtgtatggac | 2220 |
| ttaattatgc | acatgctcag | atgtgtagac | atcctccgta tatttacata acatatagag | 2280 |
| gtaatagata | ggtgatatac | atgatacatt | ctcaagagtt gcttgaccga aagttacaag | 2340 |
| gaccccaacc | cctttgtcct | ctctacccac | agatggccct gggaatcaat tcctcaggaa | 2400 |
| tgccctcaa | gaactctgct | tcttgctttg | cagagtgcca tggtcatgtc attctgaggt | 2460 |
| cacataacac | ataaaattag | tttctatgag | tgtataccat ttaaagaatt ttttttttcag | 2520 |
| taaaagggaa | tattacaatg | ttggaggaga | gataagttat agggagctgg atttcaaaac | 2580 |
| gtggtccaag | attcaaaaat | cctattgata | gtggccattt taatcattgc catcgtgtgc | 2640 |
| ttgtttcatc | cagtgttatg | cactttccac | agttggacat ggtgttagta tagccagacg | 2700 |
| ggtttcatta | ttatttctct | ttgctttctc | aatgttaatt tattgcatgg tttattcttt | 2760 |
| ttctttacag | ctgaaattgc | tttaaatgat | ggttaaaatt acaaattaaa ttgttaattt | 2820 |
| ttatcaatgt | gattgtaatt | aaaaatattt | tgatttaaat aacaaaaata ataccagatt | 2880 |
| ttaagccgtg | gaaaatgttc | ttgatcattt | gcagttaagg actttaaata aatcaaatgt | 2940 |
| taacaaaaga | gcatttctgt | tatttttttt | cacttaacta aatccgaagt gaatatttct | 3000 |
| gaatacgata | ttttttcaaat | tctagaactg | aatataaatg acaaaaatga aaataaaatt | 3060 |
| gttttgtctg | ttgttataat | gaatgtgtag | ctagtaaaaa ggagtgaaag aaattcaagt | 3120 |
| aaagtgtata | agttgattta | atattccaag | agttgagatt tttaagattc tttattccca | 3180 |
| gtgatgttta | cttcattttt | ttttttttt | ttgacaccgg cttaagcctt ctgtgtttcc | 3240 |
| tttgagcctt | ttcactacaa | aatcaaatat | taatttaact accttcctc cttccccaat | 3300 |
| gtatcacttt | tctttatctg | agaattcttc | caatgaaaat aaaatatcag ctgtggctga | 3360 |
| tagaattaag | ttgtgtccaa | aaaaaaaaaa | aaaaaa | 3396 |

```
<210> SEQ ID NO 2
<211> LENGTH: 472
<212> TYPE: PRT
<213> ORGANISM: Homo sapiens

<400> SEQUENCE: 2
```

Met Leu Gly Thr Val Lys Met Glu Gly His Glu Thr Ser Asp Trp Asn
1               5                   10                  15

Ser Tyr Tyr Ala Asp Thr Gln Glu Ala Tyr Ser Ser Val Pro Val Ser
                20                  25                  30

Asn Met Asn Ser Gly Leu Gly Ser Met Asn Ser Met Asn Thr Tyr Met
            35                  40                  45

Thr Met Asn Thr Met Thr Thr Ser Gly Asn Met Thr Pro Ala Ser Phe
        50                  55                  60

Asn Met Ser Tyr Ala Asn Pro Gly Leu Gly Ala Gly Leu Ser Pro Gly
65                  70                  75                  80

Ala Val Ala Gly Met Pro Gly Gly Ser Ala Gly Ala Met Asn Ser Met
                85                  90                  95

Thr Ala Ala Gly Val Thr Ala Met Gly Thr Ala Leu Ser Pro Ser Gly
            100                 105                 110

```
Met Gly Ala Met Gly Ala Gln Gln Ala Ala Ser Met Asn Gly Leu Gly
            115                 120                 125

Pro Tyr Ala Ala Ala Met Asn Pro Cys Met Ser Pro Met Ala Tyr Ala
        130                 135                 140

Pro Ser Asn Leu Gly Arg Ser Arg Ala Gly Gly Gly Asp Ala Lys
145                 150                 155                 160

Thr Phe Lys Arg Ser Tyr Pro His Ala Lys Pro Pro Tyr Ser Tyr Ile
                165                 170                 175

Ser Leu Ile Thr Met Ala Ile Gln Gln Ala Pro Ser Lys Met Leu Thr
            180                 185                 190

Leu Ser Glu Ile Tyr Gln Trp Ile Met Asp Leu Phe Pro Tyr Tyr Arg
        195                 200                 205

Gln Asn Gln Gln Arg Trp Gln Asn Ser Ile Arg His Ser Leu Ser Phe
    210                 215                 220

Asn Asp Cys Phe Val Lys Val Ala Arg Ser Pro Asp Lys Pro Gly Lys
225                 230                 235                 240

Gly Ser Tyr Trp Thr Leu His Pro Asp Ser Gly Asn Met Phe Glu Asn
                245                 250                 255

Gly Cys Tyr Leu Arg Arg Gln Lys Arg Phe Lys Cys Glu Lys Gln Pro
            260                 265                 270

Gly Ala Gly Gly Gly Gly Ser Gly Ser Gly Gly Ser Gly Ala Lys
        275                 280                 285

Gly Gly Pro Glu Ser Arg Lys Asp Pro Ser Gly Ala Ser Asn Pro Ser
    290                 295                 300

Ala Asp Ser Pro Leu His Arg Gly Val His Gly Lys Thr Gly Gln Leu
305                 310                 315                 320

Glu Gly Ala Pro Ala Pro Gly Pro Ala Ala Ser Pro Gln Thr Leu Asp
                325                 330                 335

His Ser Gly Ala Thr Ala Thr Gly Gly Ala Ser Glu Leu Lys Thr Pro
            340                 345                 350

Ala Ser Ser Thr Ala Pro Pro Ile Ser Ser Gly Pro Gly Ala Leu Ala
        355                 360                 365

Ser Val Pro Ala Ser His Pro Ala His Gly Leu Ala Pro His Glu Ser
    370                 375                 380

Gln Leu His Leu Lys Gly Asp Pro His Tyr Ser Phe Asn His Pro Phe
385                 390                 395                 400

Ser Ile Asn Asn Leu Met Ser Ser Glu Gln Gln His Lys Leu Asp
                405                 410                 415

Phe Lys Ala Tyr Glu Gln Ala Leu Gln Tyr Ser Pro Tyr Gly Ser Thr
            420                 425                 430

Leu Pro Ala Ser Leu Pro Leu Gly Ser Ala Ser Val Thr Thr Arg Ser
        435                 440                 445

Pro Ile Glu Pro Ser Ala Leu Glu Pro Ala Tyr Tyr Gln Gly Val Tyr
    450                 455                 460

Ser Arg Pro Val Leu Asn Thr Ser
465                 470

<210> SEQ ID NO 3
<211> LENGTH: 996
<212> TYPE: DNA
<213> ORGANISM: Homo sapiens

<400> SEQUENCE: 3
aatcacttgg ggaaaggaag gttcgtttct gagttagcaa caagtaaatg cagcactagt    60
```

```
gggtgggatt gaggtatgcc ctggtgcata aatagagact cagctgtgct ggcacactca      120
gaagcttgga ccgcatccta gccgccgact cacacaaggc aggtgggtga ggaaatccag      180
agttgccatg gagaaaattc cagtgtcagc attcttgctc cttgtggccc tctcctacac      240
tctggccaga gataccacag tcaaacctgg agccaaaaag gacacaaagg actctcgacc      300
caaactgccc cagaccctct ccagaggttg gggtgaccaa ctcatctgga ctcagacata      360
tgaagaagct ctatataaat ccaagacaag caacaaaccc ttgatgatta ttcatcactt      420
ggatgagtgc ccacacagtc aagctttaaa gaaagtgttt gctgaaaata agaaatcca      480 gaaattggca gagcagtttg tcctcctcaa tctggtttat gaaacaactg acaaacacct      540
ttctcctgat ggccagtatg tccccaggat tatgtttgtt gacccatctc tgacagttag      600
agccgatatc actggaagat attcaaatcg tctctatgct tacgaacctg cagatacagc      660
tctgttgctt gacaacatga gaaagctct caagttgctg aagactgaat tgtaaagaaa      720
aaaaatctcc aagcccttct gtctgtcagg ccttgagact tgaaaccaga agaagtgtga      780
gaagactggc tagtgtggaa gcatagtgaa cacactgatt aggttatggt ttaatgttac      840
aacaactatt ttttaagaaa aacaagtttt agaaatttgg tttcaagtgt acatgtgtga      900
aaacaatatt gtatactacc atagtgagcc atgattttct aaaaaaaaaa ataaatgttt      960
tgggggtgtt ctgttttctc caaaaaaaaa aaaaaa                                996
```

<210> SEQ ID NO 4
<211> LENGTH: 175
<212> TYPE: PRT
<213> ORGANISM: Homo sapiens

<400> SEQUENCE: 4

```
Met Glu Lys Ile Pro Val Ser Ala Phe Leu Leu Leu Val Ala Leu Ser
 1               5                  10                  15

Tyr Thr Leu Ala Arg Asp Thr Thr Val Lys Pro Gly Ala Lys Lys Asp
            20                  25                  30

Thr Lys Asp Ser Arg Pro Lys Leu Pro Gln Thr Leu Ser Arg Gly Trp
        35                  40                  45

Gly Asp Gln Leu Ile Trp Thr Gln Thr Tyr Glu Glu Ala Leu Tyr Lys
    50                  55                  60

Ser Lys Thr Ser Asn Lys Pro Leu Met Ile Ile His His Leu Asp Glu
65                  70                  75                  80

Cys Pro His Ser Gln Ala Leu Lys Lys Val Phe Ala Glu Asn Lys Glu
                85                  90                  95

Ile Gln Lys Leu Ala Glu Gln Phe Val Leu Leu Asn Leu Val Tyr Glu
            100                 105                 110

Thr Thr Asp Lys His Leu Ser Pro Asp Gly Gln Tyr Val Pro Arg Ile
        115                 120                 125

Met Phe Val Asp Pro Ser Leu Thr Val Arg Ala Asp Ile Thr Gly Arg
    130                 135                 140

Tyr Ser Asn Arg Leu Tyr Ala Tyr Glu Pro Ala Asp Thr Ala Leu Leu
145                 150                 155                 160

Leu Asp Asn Met Lys Lys Ala Leu Lys Leu Lys Thr Glu Leu
                165                 170                 175
```

<210> SEQ ID NO 5
<211> LENGTH: 767
<212> TYPE: DNA
<213> ORGANISM: Homo sapiens

<400> SEQUENCE: 5

```
agaaacatcc agaatacatt tccaacaaga gcactggcca agtcagcttc ttctgagaga    60
gtctctagaa gacatgatgc tacactcagc tttgggtctc tgcctcttac tcgtcacagt   120
ttcttccaac cttgccattg caataaaaaa ggaaaagagg cctcctcaga cactctcaag   180
aggatgggga gatgacatca cttgggtaca aacttatgaa gaaggtctct tttatgctca   240
aaaaagtaag aagccattaa tggttattca tcacctggag gattgtcaat actctcaagc   300
actaaagaaa gtatttgccc aaaatgaaga aatacaagaa atggctcaga ataagttcat   360
catgctaaac cttatgcatg aaaccactga taagaattta tcacctgatg gcaatatgt   420
gcctagaatc atgtttgtag acccttcttt aacagttaga gctgacatag ctggaagata   480
ctctaacaga ttgtacacat atgagcctcg ggatttaccc ctattgatag aaaacatgaa   540
gaaagcatta agacttattc agtcagagct ataagagatg atggaaaaaa gccttcactt   600
caaagaagtc aaatttcatg aagaaaacct ctggcacatt gacaaatact aaatgtgcaa   660
gtatatagat tttgtaatat tactatttag ttttttttaat gtgtttgcaa tagtcttatt   720
aaaataaatg ttttttaaat ctgagactga aaaaaaaaaa aaaaaaa                  767
```

<210> SEQ ID NO 6
<211> LENGTH: 166
<212> TYPE: PRT
<213> ORGANISM: Homo sapiens

<400> SEQUENCE: 6

```
Met Met Leu His Ser Ala Leu Gly Leu Cys Leu Leu Val Thr Val
1               5                   10                  15
Ser Ser Asn Leu Ala Ile Ala Ile Lys Lys Glu Lys Arg Pro Pro Gln
            20                  25                  30
Thr Leu Ser Arg Gly Trp Gly Asp Ile Thr Trp Val Gln Thr Tyr
        35                  40                  45
Glu Glu Gly Leu Phe Tyr Ala Gln Lys Ser Lys Lys Pro Leu Met Val
    50                  55                  60
Ile His His Leu Glu Asp Cys Gln Tyr Ser Gln Ala Leu Lys Lys Val
65                  70                  75                  80
Phe Ala Gln Asn Glu Glu Ile Gln Glu Met Ala Gln Asn Lys Phe Ile
                85                  90                  95
Met Leu Asn Leu Met His Glu Thr Thr Asp Lys Asn Leu Ser Pro Asp
            100                 105                 110
Gly Gln Tyr Val Pro Arg Ile Met Phe Val Asp Pro Ser Leu Thr Val
        115                 120                 125
Arg Ala Asp Ile Ala Gly Arg Tyr Ser Asn Arg Leu Tyr Thr Tyr Glu
    130                 135                 140
Pro Arg Asp Leu Pro Leu Leu Ile Glu Asn Met Lys Lys Ala Leu Arg
145                 150                 155                 160
Leu Ile Gln Ser Glu Leu
                165
```

<210> SEQ ID NO 7
<211> LENGTH: 850
<212> TYPE: DNA
<213> ORGANISM: Homo sapiens

<400> SEQUENCE: 7

```
cgggagcaag agagaaggag gcccagacag tgagggcagg agggagagaa gagacgcaga    60
```

```
aggagagcga gcgagagaga aagggttctg gattggaggg gagagcaagg gagggaggaa        120
ggcggtgaga gaggcggggg cctcgggagg gtgaaaggag ggaggagaag ggcggggcac        180
ggaggcccga gcgagggaca agactccgac tccagctctg actttttcg cggctctcgg        240 cttccactgc agccatgtca ctcctcttgc tggtggtctc agcccttcac atcctcattc        300
ttatactgct tttcgtggcc actttggaca gtcctggtg gactctccct gggaaagagt        360
ccctgaatct ctggtacgac tgcacgtgga caacgacac caaaacatgg gcctgcagta        420
atgtcagcga gaatggctgg ctgaaggcgg tgcaggtcct catggtgctc tccctcattc        480
tctgctgtct ctccttcatc ctgttcatgt tccagctcta caccatgcga cgaggaggtc        540
tcttctatgc caccggcctc tgccagcttt gcaccagcgt ggcggtgttt actggcgcct        600
tgatctatgc cattcacgcc gaggagatcc tggagaagca cccgcgaggg ggcagcttcg        660
gatactgctt cgccctggcc tgggtggcct tcccctcgc cctggtcagc ggcatcatct        720
acatccacct acggaagcgg gagtgagcgc ccgcctcgc tcggctgccc ccgcccttc         780 ccggcccccc tcgccgcgcg tcctccaaaa aataaaacct taaccgcgga aaaaaaaaa        840 aaaaaaaaaa                                                                850

<210> SEQ ID NO 8
<211> LENGTH: 163
<212> TYPE: PRT
<213> ORGANISM: Homo sapiens

<400> SEQUENCE: 8

Met Ser Leu Leu Leu Leu Val Val Ser Ala Leu His Ile Leu Ile Leu
1               5                   10                  15

Ile Leu Leu Phe Val Ala Thr Leu Asp Lys Ser Trp Trp Thr Leu Pro
            20                  25                  30

Gly Lys Glu Ser Leu Asn Leu Trp Tyr Asp Cys Thr Trp Asn Asn Asp
        35                  40                  45

Thr Lys Thr Trp Ala Cys Ser Asn Val Ser Glu Asn Gly Trp Leu Lys
    50                  55                  60

Ala Val Gln Val Leu Met Val Leu Ser Leu Ile Leu Cys Cys Leu Ser
65                  70                  75                  80

Phe Ile Leu Phe Met Phe Gln Leu Tyr Thr Met Arg Arg Gly Gly Leu
                85                  90                  95

Phe Tyr Ala Thr Gly Leu Cys Gln Leu Cys Thr Ser Val Ala Val Phe
            100                 105                 110

Thr Gly Ala Leu Ile Tyr Ala Ile His Ala Glu Glu Ile Leu Glu Lys
        115                 120                 125

His Pro Arg Gly Gly Ser Phe Gly Tyr Cys Phe Ala Leu Ala Trp Val
    130                 135                 140

Ala Phe Pro Leu Ala Leu Val Ser Gly Ile Ile Tyr Ile His Leu Arg
145                 150                 155                 160

Lys Arg Glu
```

ARYL HYDROCARBON RECEPTOR (AHR) ACTIVATOR COMPOUNDS AS CANCER THERAPEUTICS

CROSS REFERENCE TO RELATED APPLICATIONS

This application claims the benefit of U.S. Provisional Application No. 62/767,474, filed Nov. 14, 2018, entitled "Aryl Hydrocarbon Receptor (AHR) Activator Compounds as Cancer Therapeutics," the entire contents of which are incorporated herein by reference.

FIELD OF THE INVENTION

The invention relates generally to methods, compositions and kits for the identification and treatment of cancer, particularly FOXA1-dependent and/or overexpressing cancers.

BACKGROUND OF THE INVENTION

Identifying therapeutic compounds capable of killing neoplastic cells in an optimally selective manner poses an ongoing challenge for the oncology field. A need exists for agents that are capable of precision killing of neoplastic cells that are characterized by specific molecular traits.

BRIEF SUMMARY OF THE INVENTION

The current disclosure relates, at least in part, to the identification of three compounds previously described as adenosine receptor antagonists, CGS-15943, MRS-1220 and SCH-58261, as well as furan ring moiety-possessing derivatives thereof, as drugs that exhibit enhanced killing of certain neoplasia cells—particularly neoplasia cells that express high levels of the FOXA1 transcription factor and/or gene targets of FOXA1—via a mechanism that appears to involve these compounds' herein described activation of the aryl hydrocarbon receptor (AHR). Treatable cancers include a broad range of cancers characterized by high FOXA1 expression levels (e.g., certain breast cancers, liver cancers and prostate cancers, among others), and particularly luminal and/or ER-positive forms of breast cancer. Compositions and methods for the diagnosis and treatment of subjects and/or cancers that are likely to be responsive to treatment with CGS-15943, MRS-1220 and SCH-58261, as well as furan ring moiety-possessing derivatives thereof, are therefore provided. Certain furan ring-possessing CGS-15943 derivatives identified herein as active for cytotoxic effect are also provided.

A first aspect of the present disclosure is directed to a compound represented by a structure of formula (I) or formula (II):

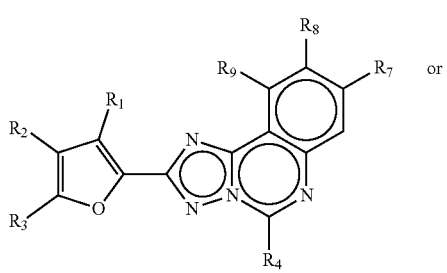

(I)

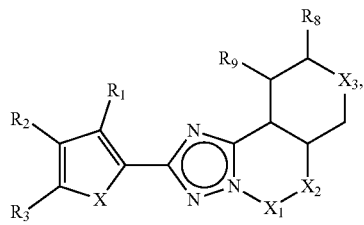

(II)

wherein $R_1$, $R_2$, $R_3$, $R_4$, $R_7$, $R_8$, $R_9$, X, $X_1$, $X_2$, and $X_3$ are as defined herein, or a pharmaceutically acceptable salt, ester, amide, prodrug or stereoisomer thereof.

In one aspect, the instant disclosure provides a method for selecting a treatment for a subject having or at risk of developing a luminal and/or estrogen-receptor positive breast cancer, the method involving: (a) identifying a subject as having or at risk of developing a luminal and/or estrogen-receptor positive breast cancer; and (b) selecting CGS-15943, a CGS-15943 derivative that possesses a furan ring moiety, MRS-1220, a MRS-1220 derivative that possesses a furan ring moiety, SCH-58261 or a SCH-58261 derivative that possesses a furan ring moiety as a treatment for the subject identified as having or at risk of developing a luminal and/or estrogen-receptor positive breast cancer.

In certain embodiments, step (a) includes identifying the presence or absence in the sample of elevated FOXA1 mRNA or protein expression and/or elevated mRNA or protein expression of a FOXA1 gene target, as compared to an appropriate control.

In one embodiment, the method further involves: (c) administering the selected CGS-15943, CGS-15943 derivative, MRS-1220, MRS-1220 derivative, SCH-58261 or SCH-58261 derivative to the subject.

In another aspect, the instant disclosure provides a method for selecting a treatment for a subject having or at risk of developing a cancer, the method involving: (a) obtaining a sample from a subject having or at risk of developing a cancer; (b) identifying the presence or absence in the sample of one or more of the following: high FOXA1 mRNA expression levels, high FOXA1 protein expression levels, high mRNA expression levels of a FOXA1 gene target and/or high protein expression levels of a FOXA1 gene target; and (c) selecting CGS-15943, a CGS-15943 derivative that possesses a furan ring moiety, MRS-1220, a MRS-1220 derivative that possesses a furan ring moiety, SCH-58261 or a SCH-58261 derivative that possesses a furan ring moiety as a treatment for the subject if high FOXA1 mRNA expression levels, high FOXA1 protein expression levels, high mRNA expression levels of a FOXA1 gene target and/or high protein expression levels of a FOXA1 gene target are observed in the sample, thereby selecting a treatment for the subject having or at risk of developing a cancer.

In one embodiment, the FOXA1 gene target is AGR2, AGR3 or EMP3.

In another embodiment, the cancer is a breast cancer, a liver cancer and/or a prostate cancer. Optionally, the cancer is a luminal and/or estrogen-receptor positive breast cancer.

In certain embodiments, step (b) includes identifying the presence or absence in the sample of elevated FOXA1 mRNA expression, as compared to an appropriate control.

In some embodiments, CGS-15943 or a CGS-15943 derivative possessing a furan ring moiety is selected as a treatment for the subject. Optionally, the CGS-15943 derivative is a CGS-15943 derivative of FIGS. 8A and 8D.

In another embodiment, the method further involves: (d) administering the selected CGS-15943, CGS-15943 derivative, MRS-1220, MRS-1220 derivative, SCH-58261 or SCH-58261 derivative to the subject.

In certain embodiments, the identifying step involves use of a kit of the instant disclosure.

In one embodiment, the subject is human.

Another aspect of the instant disclosure provides a method for treating or preventing a luminal and/or estrogen-receptor positive breast cancer in a subject, the method involving: (a) identifying a subject as having or at risk of developing a luminal and/or estrogen-receptor positive breast cancer; and (b) administering CGS-15943, a CGS-15943 derivative that possesses a furan ring moiety, MRS-1220, a MRS-1220 derivative that possesses a furan ring moiety, SCH-58261 or a SCH-58261 derivative that possesses a furan ring moiety to the subject identified as having or at risk of developing a luminal and/or estrogen-receptor positive breast cancer, thereby treating or preventing a luminal and/or estrogen-receptor positive breast cancer in the subject.

An additional aspect of the instant disclosure provides a method for treating or preventing a cancer in a subject, the method involving: (a) obtaining a sample from a subject having or at risk of developing a cancer; (b) identifying the presence or absence in the sample of one or more of the following: high FOXA1 mRNA expression levels, high FOXA1 protein expression levels, high mRNA expression levels of a FOXA1 gene target and/or high protein expression levels of a FOXA1 gene target; and (c) administering CGS-15943, a CGS-15943 derivative that possesses a furan ring moiety, MRS-1220, a MRS-1220 derivative that possesses a furan ring moiety, SCH-58261 or a SCH-58261 derivative that possesses a furan ring moiety to the subject if high FOXA1 mRNA expression levels, high FOXA1 protein expression levels, high mRNA expression levels of a FOXA1 gene target and/or high protein expression levels of a FOXA1 gene target are observed in the sample, thereby treating or preventing a cancer in the subject.

Another aspect of the instant disclosure provides a method for selecting a treatment for a subject having or at risk of developing a luminal and/or estrogen-receptor positive breast cancer, the method involving: (a) identifying a subject as having or at risk of developing a luminal and/or estrogen-receptor positive breast cancer; and (b) selecting an aryl hydrocarbon receptor activator as a treatment for the subject identified as having or at risk of developing a luminal and/or estrogen-receptor positive breast cancer.

In an additional aspect, the instant disclosure provides a method for selecting a treatment for a subject having or at risk of developing a cancer, the method involving: (a) obtaining a sample from a subject having or at risk of developing a cancer; (b) identifying the presence or absence in the sample of one or more of the following: high FOXA1 mRNA expression levels, high FOXA1 protein expression levels, high mRNA expression levels of a FOXA1 gene target and/or high protein expression levels of a FOXA1 gene target; and (c) selecting an aryl hydrocarbon receptor activator as a treatment for the subject if high FOXA1 mRNA expression levels, high FOXA1 protein expression levels, high mRNA expression levels of a FOXA1 gene target and/or high protein expression levels of a FOXA1 gene target are observed in the sample, thereby selecting a treatment for the subject having or at risk of developing a cancer.

In certain embodiments, the aryl hydrocarbon receptor activator is 2,3,7,8-Tetrachlorodibenzo-p-dioxin (TCDD), indirubin, β-naphthoflavone, L-kynurenine, 3-methylcholanthrene, YH439, CGS-15943, a CGS-15943 derivative, MRS-1220, a MRS-1220 derivative, SCH-58261 and/or a SCH-58261 derivative.

In some embodiments, the aryl hydrocarbon receptor activator is a compound shown in FIG. 24.

In certain embodiments, the aryl hydrocarbon receptor activator is a composition disclosed herein.

In embodiments, the method further involves administering the selected aryl hydrocarbon receptor activator to the subject.

In some embodiments, the identifying step involves use of a kit of the instant disclosure.

In an additional aspect, the instant disclosure provides a method for treating or preventing a luminal and/or estrogen-receptor positive breast cancer in a subject, the method involving: (a) identifying a subject as having or at risk of developing a luminal and/or estrogen-receptor positive breast cancer; and (b) administering an aryl hydrocarbon receptor activator to the subject identified as having or at risk of developing a luminal and/or estrogen-receptor positive breast cancer, thereby treating or preventing a luminal and/or estrogen-receptor positive breast cancer in the subject.

Another aspect of the instant disclosure provides a method for treating or preventing a cancer in a subject, the method involving: (a) obtaining a sample from a subject having or at risk of developing a cancer; (b) identifying the presence or absence in the sample of one or more of the following: high FOXA1 mRNA expression levels, high FOXA1 protein expression levels, high mRNA expression levels of a FOXA1 gene target and/or high protein expression levels of a FOXA1 gene target; and (c) administering an aryl hydrocarbon receptor activator to the subject if high FOXA1 mRNA expression levels, high FOXA1 protein expression levels, high mRNA expression levels of a FOXA1 gene target and/or high protein expression levels of a FOXA1 gene target are observed in the sample, thereby treating or preventing a cancer in the subject.

Another aspect of the instant disclosure provides a kit for identifying high expression of FOXA1 mRNA or protein in a sample, the kit consisting essentially of an oligonucleotide for detection of FOXA1 mRNA or an anti-FOXA1 antibody (optionally a labeled anti-FOXA1 antibody or where the kit includes a labeled secondary antibody that binds the anti-FOXA1 antibody), and instructions for its use.

In one embodiment, the sample is a cancer sample. Optionally, the cancer sample is a breast cancer sample, a liver cancer sample and/or a prostate cancer sample. In a related embodiment, the cancer sample is a luminal and/or estrogen-receptor positive breast cancer sample.

In another embodiment, the sample is a tissue sample of a subject having a breast cancer, a liver cancer and/or a prostate cancer. Optionally, the subject has a luminal and/or estrogen-receptor positive breast cancer.

An additional aspect of the instant disclosure provides a pharmaceutical composition for treating a subject having a breast cancer, a liver cancer and/or a prostate cancer, the pharmaceutical composition including a therapeutically effective amount of CGS-15943, a CGS-15943 derivative that possesses a furan ring moiety, MRS-1220, a MRS-1220 derivative that possesses a furan ring moiety, SCH-58261 or a SCH-58261 derivative that possesses a furan ring moiety, and a pharmaceutically acceptable carrier.

Another aspect of the instant disclosure provides a pharmaceutical composition for treating a subject having a cancer that is a breast cancer, a liver cancer and/or a prostate cancer, the pharmaceutical composition including a therapeutically effective amount of an aryl hydrocarbon receptor activator and a pharmaceutically acceptable carrier.

In one embodiment, the cancer is a luminal and/or estrogen-receptor positive breast cancer.

In certain embodiments, the CGS-15943 derivative is a derivative shown in FIGS. 8A, 8D, 21, 23 and/or 24.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

By "agent" is meant any small compound (e.g., small molecule), antibody, nucleic acid molecule, or polypeptide, or fragments thereof or cellular therapeutics such as allogeneic transplantation and/or CART-cell therapy.

The term "cancer" refers to a malignant neoplasm (Stedman's Medical Dictionary, 25th ed.; Hensyl ed.; Williams & Wilkins: Philadelphia, 1990). Exemplary cancers include, but are not limited to, melanoma and ovarian cancer (e.g., cystadenocarcinoma, ovarian embryonal carcinoma, ovarian adenocarcinoma), with ovarian cancer specifically including clear cell ovarian cancer. Additional exemplary cancers include, but are not limited to, colorectal cancer (e.g., colon cancer, rectal cancer, colorectal adenocarcinoma), endometrial cancer (e.g., uterine cancer, uterine sarcoma), esophageal cancer (e.g., adenocarcinoma of the esophagus, Barrett's adenocarcinoma), and gastric cancer (e.g., stomach adenocarcinoma (STAD)), including, e.g., colon adenocarcinoma (COAD), oesophageal carcinoma (ESCA), rectal adenocarcinoma (READ) and uterine corpus endometrial carcinoma (UCEC). Other exemplary forms of cancer include, but are not limited to, diffuse large B-cell lymphoma (DLBCL), as well as the broader class of lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; hematopoietic cancers (e.g., myeloid malignancies (e.g., acute myeloid leukemia (AML) (e.g., B-cell AML, T-cell AML), myelodysplastic syndrome, myeloproliferative neoplasm, chronic myelomonocytic leukemia (CMML) and chronic myelogenous leukemia (CML) (e.g., B-cell CML, T-cell CML)) and lymphocytic leukemia such as acute lymphocytic leukemia (ALL) (e.g., B-cell ALL, T-cell ALL) and chronic lymphocytic leukemia (CLL) (e.g., B-cell CLL, T-cell CLL)); brain cancer (e.g., meningioma, glioblastomas, glioma (e.g., astrocytoma, oligodendroglioma), medulloblastoma); lung cancer (e.g., bronchogenic carcinoma, small cell lung cancer (SCLC), non-small cell lung cancer (NSCLC), adenocarcinoma of the lung); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, luminal A breast cancer, luminal B breast cancer, estrogen receptor (ER)-positive forms of breast cancer, etc.); bronchus cancer; carcinoid tumor; cervical cancer (e.g., cervical adenocarcinoma); choriocarcinoma; chordoma; craniopharyngioma; connective tissue cancer; epithelial carcinoma; ependymoma; endotheliosarcoma (e.g., Kaposi's sarcoma, multiple idiopathic hemorrhagic sarcoma); Ewing's sarcoma; ocular cancer (e.g., intraocular melanoma, retinoblastoma); familiar hypereosinophilia; gall bladder cancer; gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

As used herein, the term "next-generation sequencing" or "NGS" can refer to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (ion Torrent); and DNA nanoball sequencing (Complete Genomics). Descriptions of certain NGS platforms can be found in the following: Shendure, er al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3): 333-43; and Zhang et al., "The impact of next-generation sequencing on genomics", J Genet Genomics, 201, 38(3): 95-109.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease or condition in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "pharmaceutically acceptable salts, esters, amides, and prodrugs" as used herein refers to those carboxylate salts, amino acid addition salts, esters, amides, and prodrugs of the compounds of the present disclosure which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the disclosure.

The term "salts" refers to the relatively non-toxic, inorganic and organic acid addition salts of compounds of the present disclosure. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methylamine, dimethylamine, trimethylamine, triethylamine, ethylamine, and the like. (See, for example, S. M. Barge et al., "Pharmaceutical Salts," J. Pharm. Sci., 1977, 66: 1-19 which is incorporated herein by reference.)

A "therapeutically effective amount" of an agent described herein is an amount sufficient to provide a therapeutic benefit in the treatment of a condition or to delay or minimize one or more symptoms associated with the condition. A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A shows a heatmap of PRISM viability data showing the respective killing patterns for a variety of adenosine receptor antagonists and agonists. FIG. 1B shows a group of three chemical structures, CGS-15943, MRS-1220 and SCH-58261, which were identified as possessing related cell killing effects dependent upon FOXA1 and/or FOXA1 gene targets (here, AGR2). The observed effects for CGS-15943, MRS-1220 and SCH-58261 were distinguishable from other previously characterized adenosine receptor antagonist compounds, meaning that these three compounds likely exerted their effects via a mechanism distinct from their shared activities as adenosine receptor antagonists. FIG. 1C shows a schematic diagram demonstrating the dependence of AGR2 on FOXA1 (AGR2 is a known downstream target of the FOXA1 transcription factor).

FIGS. 2A to 2C show a group of tables and plots demonstrating top predictive expression features included FOXA1 and the FOXA1 targets, AGR2 and AGR3. FIG. 2A is a table of protein targets and their predicted Pearson correlation coefficients and Global.Z values. FIG. 2B is a correlation plot of Z scores for CGS-15943 (BRD-K49049886-001-08-7) vs. all features in GE. FIG. 2C is a dot-plot for CGS-15943 vs. AGR2 in GE.

FIG. 4A shows a dot-plot of different cancers and the odds of killing that cancer type for CGS-15943. FIG. 4B is a heatmap depicting the selective killing pattern of CGS-15943, which demonstrated increased killing activity for luminal breast cancer cell lines.

FIG. 6A depicts the compound repurposing library employed, in which 59 compounds had been previously identified as targeting adenosine receptors in some manner. 23 such compounds were identified as adenosine receptor antagonists, while nine such compounds were identified as adenosine receptor agonists. FIG. 6B depicts an illustration of the breast cancer lines that were dosed with the selected 32 compounds. CGS-15943, MRS-1220, and SCH-58261 were the only compounds among these 32 that were found to be cytotoxic to the breast cancer cell lines assayed.

FIGS. 7A and 7B show a group of illustrations depicting the structure activity relationship ("SAR") of assayed CGS-15943 analogs, which further indicated that the cytotoxic effects observed for CGS-15943 occurred via an off-target mechanism. FIG. 7A schematically illustrates the chemical structure of CGS-15943, showing that the furan ring was essential for its observed cytotoxic effect, whereas the amino-group was not required and multiple substituents could be tolerated at the $R_1$ position. FIG. 7B presents a model of the interactions previously described for the binding of CGS-15943 to the A2a receptor, which highlights the importance of the amino-group to this interaction.

FIG. 8A shows table of various selectively cytotoxic analogs of CGS-15943 (including of CGS-15943) and their respective $IC_{50}$ values observed for killing of ZR75, MDA-MB-468 and HCC1395 cell lines. FIG. 8B shows a table of different non-furan ring presenting CGS-15943 analogs and their respective (non-cytotoxic) $IC_{50}$ values for ZR75, MDA-MB-468 and HCC1395 cell lines. FIG. 8C shows a table of additional non-furan ring presenting CGS-15943 analogs and their respective (non-cytotoxic) $IC_{50}$ values for ZR75, MDA-MB-468 and HCC1395 cell lines. FIG. 8D shows a table of the furan ring-presenting CGS-15943 analog "BRD-K81225797-001-02-3" and its observed $IC_{50}$ value for killing of ZR75, MDA-MB-468, and HCC1395 (where selective killing was again observed for the former two sensitive cell lines, and not for the latter resistant cell line), as compared to additional non-furan ring presenting CGS-15943 analogs and their respective (non-cytotoxic) $IC_{50}$ values for ZR75, MDA-MB-468 and HCC1395 cell lines.

FIG. 9A presents an immunoblot demonstrating AGR2 knockout in ZR-75-1 cells, as compared to a β-actin control. FIG. 9B presents an immunoblot demonstrating AGR2 knockout in MDA-MB-468 cells, as compared to a β-actin control.

FIG. 10A shows dose-response curves of cell killing for the indicated treatments (including CGS-15943, MRS-1220, Paclitaxel, SCH-58261, Thapsigargin and Tunicamycin) in ZR-75-1_AGR2_WT-120H (wild-type) cells. FIG. 10B shows dose-response curves of cell killing for the indicated treatments (including CGS-15943, MRS-1220, Paclitaxel, SCH-58261, Thapsigargin and Tunicamycin) in ZR-75-1_AGR2_sg1-120H (AGR2 knockout) cells. FIG. 10C shows dose-response curves of cell killing for the indicated treatments (including CGS-15943, MRS-1220, Paclitaxel, SCH-58261, Thapsigargin and Tunicamycin) in ZR-75-1_AGR2_sg2-120H (AGR2 knockout) cells. FIG. 10D shows a table that summarizes the observed IC50 values observed for each indicated agent. Notably, AGR2 knockout did not significantly affect such values for any treatment that exhibited cytotoxicity.

FIG. 11A shows the outcome of a genome-wide modifier screen of the MDA-MB-468 breast cancer cell line that identified AHR and ARNT as hits. FIG. 11B shows the similar outcome of a genome-wide modifier screen of the ZR-75-1 breast cancer cell line that also yielded AHR and ARNT as hits, in addition to PGRMC1, POR and CYP1A1.

FIG. 12A depicts a viability plot for various assayed cells of different levels of AHR expression, in the presence of 625 nM CGS-15943, with FOXA1 levels also indicated by dot color. FIG. 12B is a pearson correlation plot of AHR and FOXA1 for various inhibitors, further noting the presence of CGS-15943 and MRS-1220 at low robust Z score values.

FIG. 13A shows dose-response curves for CGS-15943 treatment of MDA-MB-468 breast cancer cells having no AHR knockdown (parental Cas9 or GFP sg1) or possessing CRISPR-Cas9-mediated knockdown of AHR (AHR sg3 and AHR sg4). FIG. 13B shows dose-response curves for CGS-15943 treatment of ZR-75-1 breast cancer cells having no AHR knockdown (parental Cas9 or GFP sg1) or possessing CRISPR-Cas9-mediated knockdown of AHR (AHR sg3 and AHR sg4).

FIG. 19 depicts a table of studies performed for preclinical testing of CGS-15943. Only limited PK data have been identified as available.

FIG. 20A shows that CGS-15943 was cleared from plasma over time post-injection, at either 3 mg/kg or 15 mg/kg. FIG. 20B shows a table that summarizes the CGS-15943 plasma clearance results obtained in FIG. 20A.

FIG. 23 shows information for 78 compounds that were tested for cytotoxicity (see FIG. 24 below), including compound names, structure, SMILES string, and solubility (O4) data.

DETAILED DESCRIPTION OF THE INVENTION

Figure 1A:
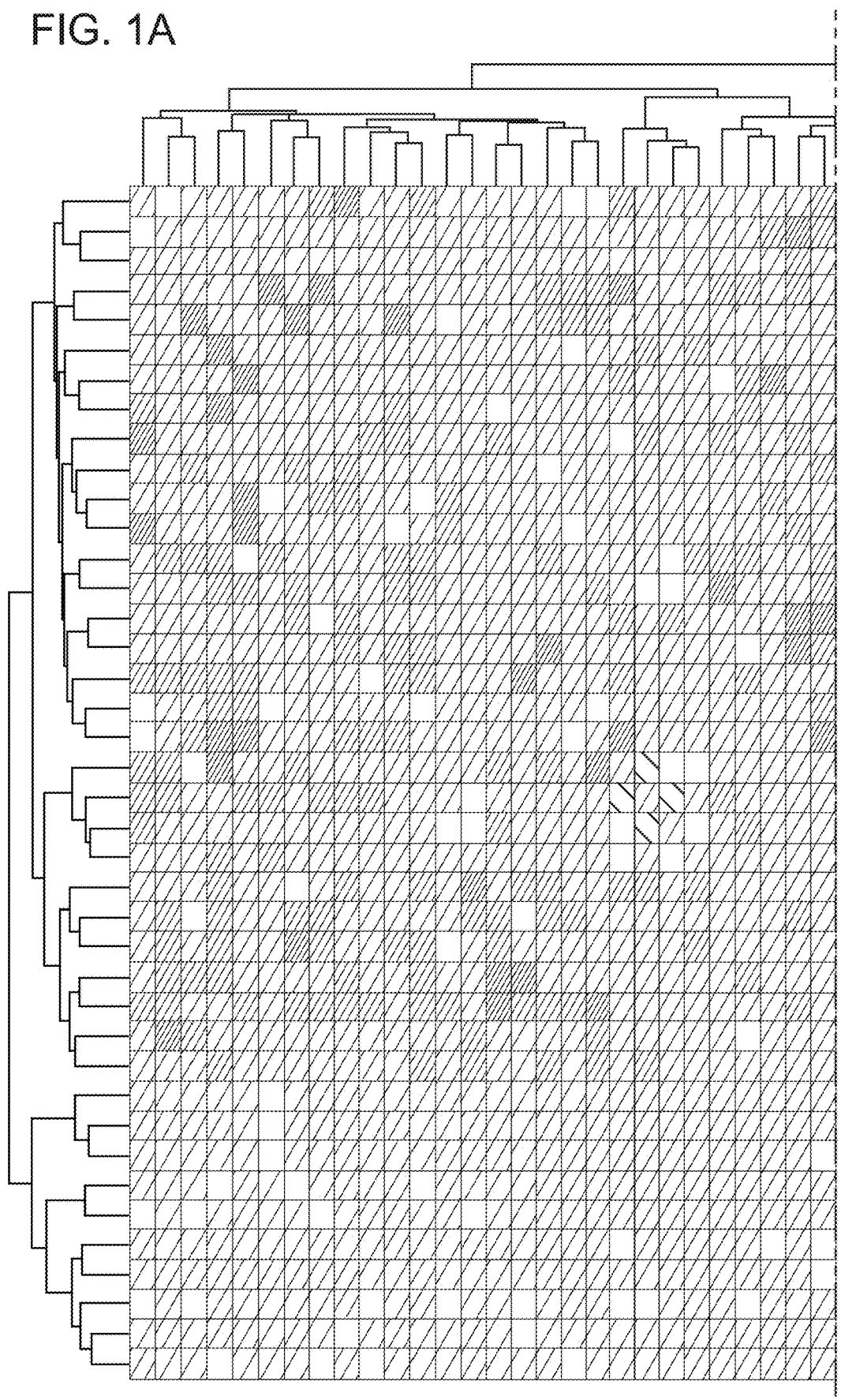
FIGS. 1A to 1C show a series of heatmaps, chemical structures, and diagrams that illustrate the similar cell killing effects observed in PRISM assays for three compounds previously characterized as adenosine receptor antagonists, CGS-15943, MRS-1220 and SCH-58261.
Figure 1A:
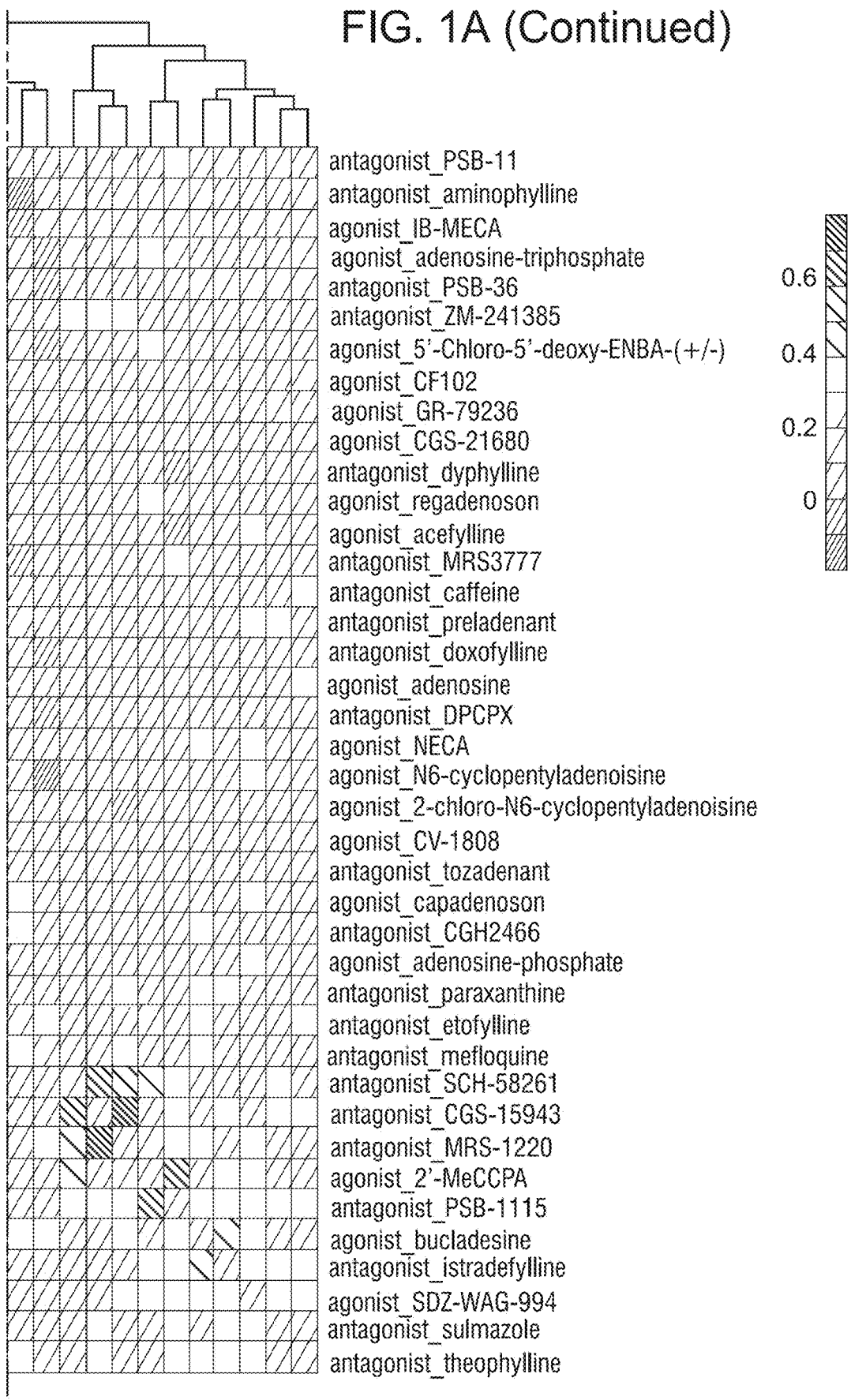

The present disclosure is directed, at least in part, to the discovery that certain types of cancer, particularly those characterized by high expression and/or overexpression of FOXA1 and/or FOXA1 gene targets (e.g., AGR2, AGR3 and EMP3) are particularly susceptible to treatment with CGS-15943, MRS-1220 or SCH-58261, or to treatment with furan ring-possessing derivatives of CGS-15943. Indeed, CGS-15943, MRS-1220 and SCH-58261 were identified via genomic screening methods as the three agents among drugs present in a drug repurposing library that exhibited progressively enhanced killing of neoplasia cell lines as FOXA1 and/or FOXA1 gene target expression levels rose across such screened neoplasia cell lines. Cancers particularly including breast, liver and prostate cancers, among others, have therefore herein been identified as susceptible to treatment with CGS-15943, MRS-1220 and SCH-58261 and/or derivatives thereof (including certain furan ring-possessing derivatives of CGS-15943 that were also specifically exemplified as cytotoxic to cancer cell lines that exhibited high FOXA1 and/or FOXA1 gene target expression levels). Such cancers particularly include luminal and/or estrogen receptor (ER)-positive forms of breast cancer. The instant disclosure therefore provides compositions and methods for the diagnosis and treatment of cancer that employ CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety, either alone (i.e., as a monotherapy, optionally in certain classes of cancer, such as luminal and/or ER-positive breast cancer) or in combination with other chemotherapeutic drugs.

The instant discovery was made using large-scale multiplex profiling of existing drugs against 578 cancer cell lines, employing a PRISM multiplexed cellular viability assay. Across more than 4,000 compounds, three compounds, CGS-15943, MRS-1220 and SCH-58261, were identified for which high FOXA1 or FOXA1 transcriptional target (including AGR2, AGR3 and EMP3, as well as FOXA1 itself) gene expression similarly predicted cell line sensitivity. In confirmatory studies, it was identified that: 1) other adenosine receptor antagonists lacked this activity, which indicated an alternate, non-adenosine receptor target, 2) AHR and ARNT were identified as required for CGS-15943 killing via genome-wide CRISPR modifier screens, 3) AHR and ARNT knockout were observed to rescue individual cell lines from CGS-15943-mediated cytotoxic killing and 4) co-treatment with an AHR small molecule antagonist also rescued treated cell lines from CGS-15943-mediated cytotoxic killing. These results were consistent with CGS-15943 killing cancer cells in a manner dependent on AHR activation, likely through a direct binding interaction.

CGS-15943, MRS-1220 and SCH-58261 (and improved and/or novel derivatives of such compounds) have therefore been identified as agents for use in treating or preventing cancers that exhibit activation of and/or dependency on FOXA1 (particularly including breast, prostate, and liver cancer, notably including luminal and/or ER-positive forms of breast cancer). Expression of FOXA1, AGR2, AGR3, EMP3 or other FOXA1 targets can also be used a predictive biomarker for such cancers and therefore a cancer's susceptibility to the agents of the instant disclosure. In addition, since a high percentage of luminal/ER-positive breast cancers have been identified as expressing FOXA1, that entire disease type can be targeted with the agents of the instant disclosure, even absent profiling of such cancers for FOXA1 and/or FOXA1 target gene expression status.

CGS-15943 has the following structure:

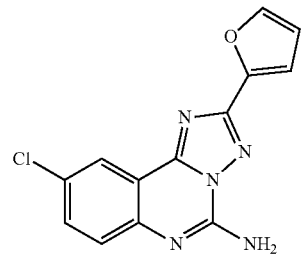 [SMILES: Nc1nc2ccc(Cl)cc2c2nc(-c3ccco3)nn12]

CGS-15943 has been previously characterized as a drug which acts as a potent and reasonably selective antagonist for the adenosine receptors A1 and A2A, having a Ki of 3.3 nM at A2A and 21 nM at A1. It was one of the first adenosine receptor antagonists discovered that is not a xanthine derivative, instead being a triazoloquinazoline (Williams et al. *The Journal of Pharmacology and Experimental Therapeutics.* 241: 415-20; Ghai et al. *The Journal of Pharmacology and Experimental Therapeutics.* 242: 784-90). Consequently, CGS-15943 has been described as having the advantage over most xanthine derivatives that it is not a phosphodiesterase inhibitor, and so has more a specific pharmacological effects profile. It has previously been observed to produce similar effects to caffeine in animal studies, though with higher potency (Holtzman S G. *Life Sciences.* 49: 1563-70; Griebel et al. *Psychopharmacology.* 103: 541-4; Howell and Byrd. *The Journal of Pharmacology and Experimental Therapeutics.* 267: 432-9; Holtzman S G. *The Journal of Pharmacology and Experimental Therapeutics.* 277: 739-46; Weerts and Griffiths. *Psychopharmacology.* 168: 155-63). Exemplary dosages of CGS-15943 include, e.g., 0.01-20 mg/kg, i.v. or i.p.

Figure 8A:
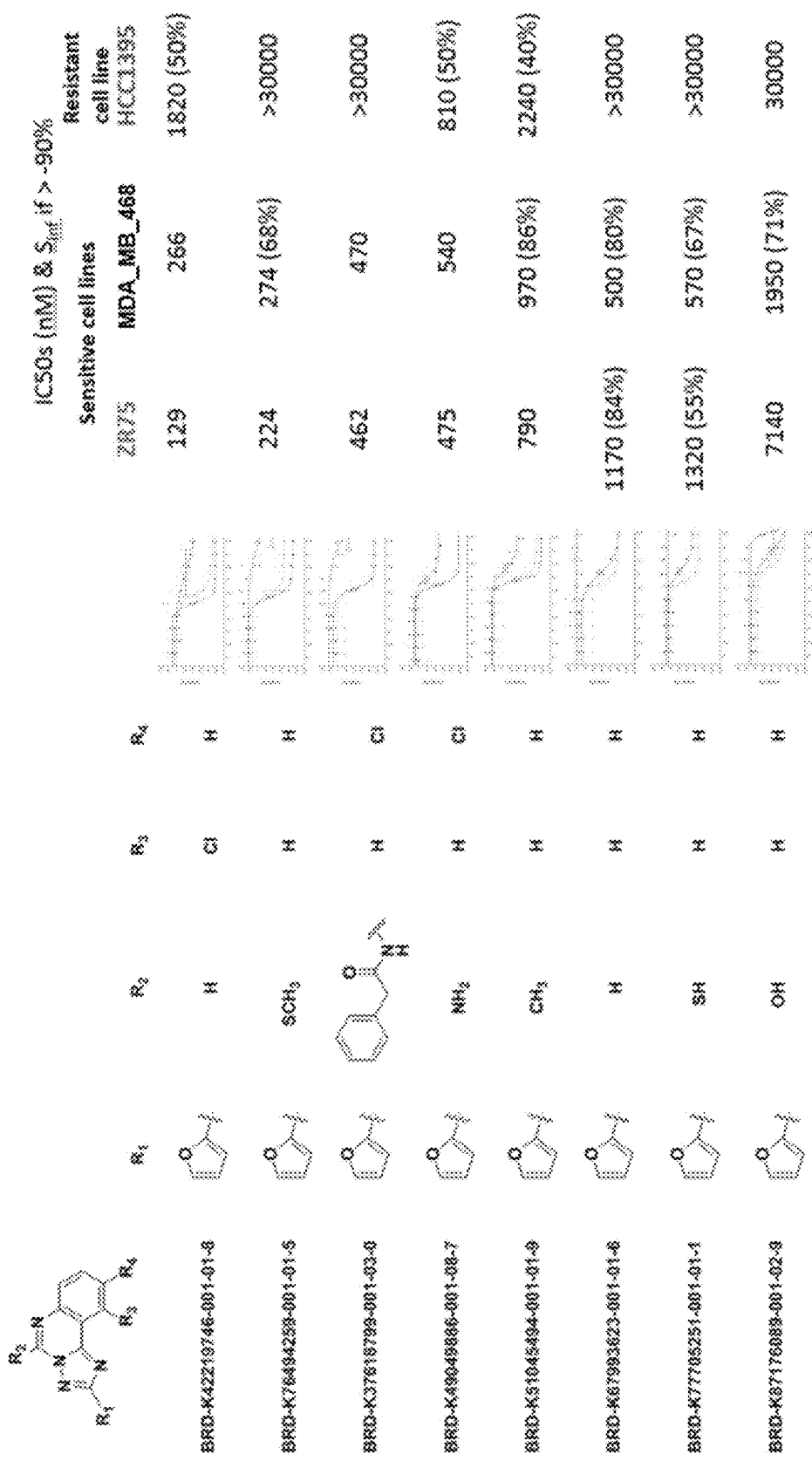
FIGS. 8A to 8D show a series of tables depicting different analogs of CGS-15943, with their respective $IC_{50}$ values, as tested in different sensitive (ZR75 and MBA_MB_468) and resistant (HCC1395) cell lines.
Figure 8B:
Figure 8C:
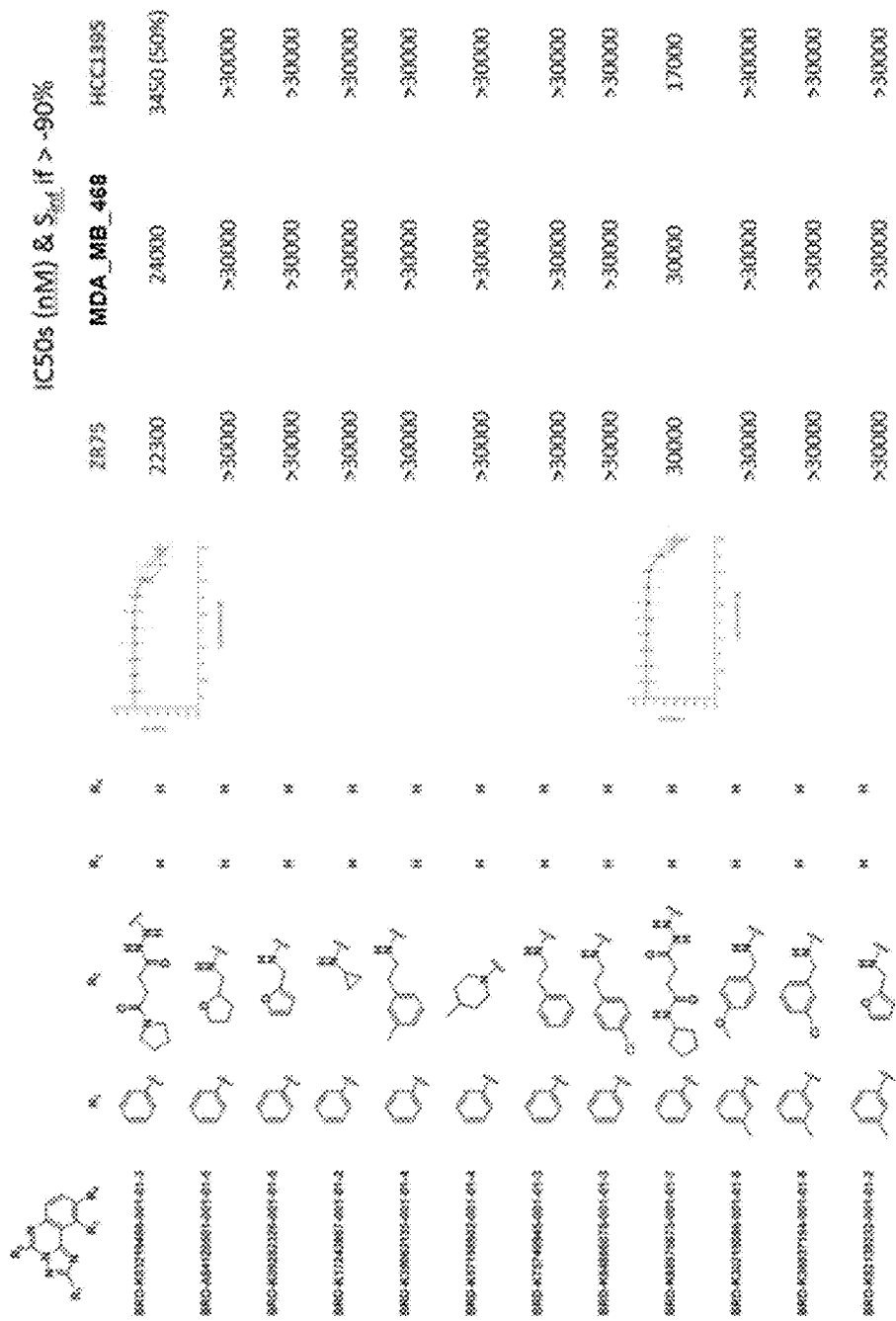
Figure 8D:
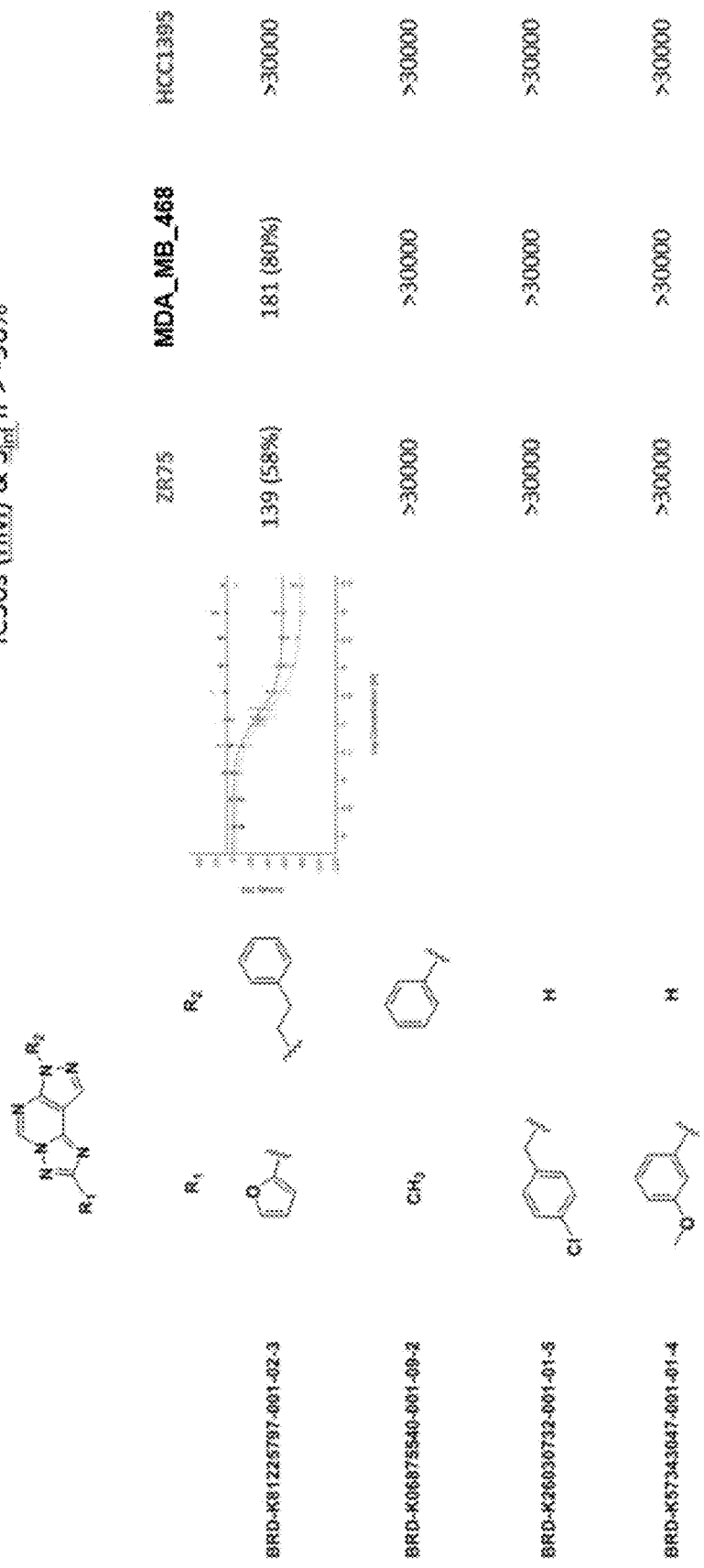

As presented in FIGS. 8A and 8D, a number of furan ring-possessing derivatives of CGS-15943 were also obtained and found to exhibit cytotoxicity against CGS-15943-susceptible cell lines.

MRS-1220 has the following structure:

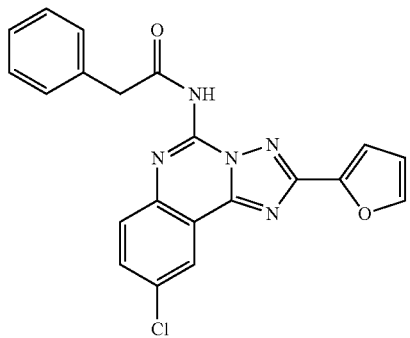 [SMILES: O=C(Cc1ccccc1)Nc1nc2ccc(Cl)cc2c2nc(-c3ccco3)nn12]

MRS-1220 has been previously characterized as a highly potent, selective $hA_3$ adenosine receptor antagonist. Exemplary dosages of MRS-1220 include, e.g., 0.01-20 mg/kg, i.v. or i.p.

SCH-58261 has the following structure:

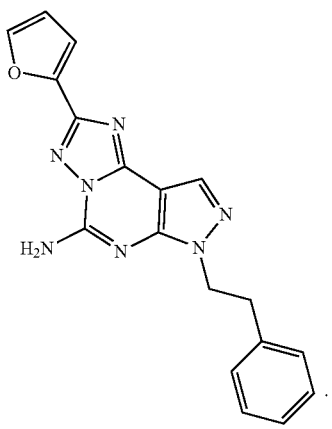 [SMILES: Nc1nc2c(cnn2CCc2ccccc2)c2nc(-c3ccco3)nn12]

SCH-58261 has been previously characterized as a potent, highly selective adenosine receptor A2A antagonist, with Ki values of 1-2, 289 and >10000 nM at A2A, A1 and A3 receptors, respectively. Exemplary dosages of SCH-58261 include, e.g., 0.01-20 mg/kg, i.v. or i.p.

CGS-15943 has been previously implicated for certain forms of immunotherapy, yet has been described for the specific purpose of blocking adenosine receptors in combination therapies (WO 2017019896). In contrast, the instant identification of AHR-dependent cytotoxicity of such compounds against high-FOXA1 cancers does not appear to have been previously described. Indeed, data presented herein have shown that the previously reported role of CGS-15943 in blocking adenosine receptors appears to be unrelated to the actual single-agent anti-cancer activity described herein for CGS-15943, MRS-1220 and SCH-58261, each of which appears to act via activation of AHR.

Meanwhile, whereas certain known AHR agonists have previously been suggested to be useful in the treatment of cancer (PMID 15634650), CGS-15943, MRS-1220 and SCH-58261 do not appear to have been previously identified as AHR agonists.

A variety of CGS analogs are disclosed herein, a number of which are represented by formulas (I) and (II):

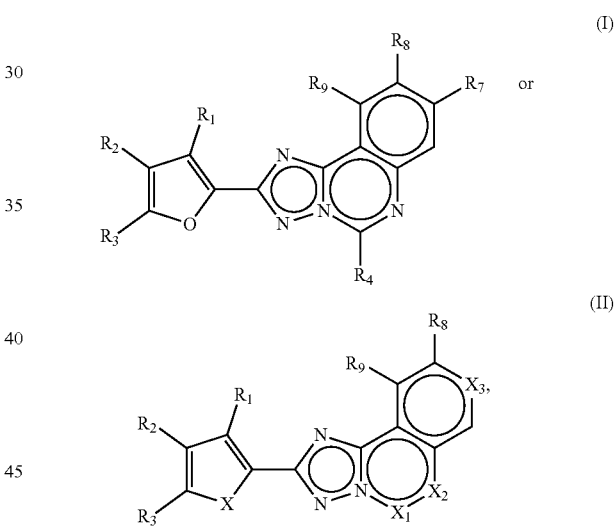

wherein:
$R_1$, $R_2$, and $R_3$ independently represent H or Me, provided that only one of $R_1$, $R_2$, and $R_3$ may represent methyl, or wherein $R_2$, and $R_3$ together with the other atoms to which they are bound form an optionally substituted phenyl group;

$R_4$ represents H, methyl, or $NR_5R_6$ wherein $R_5$ and $R_6$ independently represent H, methyl, or phenyl, provided that only one of $R_5$ and $R_6$ may represent phenyl;

$R_7$, $R_8$, and $R_9$ independently represent H, F, Cl, Br, methoxy, or optionally substituted C1-C3 alkyl (e.g., $CF_3$);

X represents O or N—$R_{10}$, wherein $R_{10}$ represents H or methyl;

$X_1$ represents C=O or $CR_4$;

$X_2$ represents N or NH;

and $X_3$ represents $CR_7$ or N, provided that $X_2$ represents NH when $X_1$ represents C=O, at least one of $R_7$, $R_8$, and R₉ represents F, Cl, Br, methoxy, or optionally substituted C1-C3 alkyl (e.g., CF₃);

and further provided that if $R_1$, $R_2$ and $R_3$ independently represent H and $R_8$ represents Cl, $R_4$ cannot represent $NR_5R_6$ wherein $R_5$ and $R_6$ both represent H;

or a pharmaceutically acceptable salt, ester, amide, prodrug or stereoisomer thereof.

In some embodiments, $R_1$, $R_2$, and $R_3$ independently represent H.

In certain embodiments, $R_1$ represents methyl and $R_2$ and $R_3$ each represents H.

In some embodiments, $R_3$ represents methyl and $R_1$ and $R_2$ each represents H.

In some embodiments, both $R_1$ and $R_3$ represent methyl and $R_2$ represents H.

In certain embodiments $R_2$ and $R_3$ together with the other atoms to which they are bound form an optionally substituted phenyl group.

In some embodiments, $R_4$ represents H.

In some embodiments, $R_4$ represents methyl. In certain embodiments, $R_4$ represents $NR_5R_6$, $R_5$ represents H and $R_6$ represents methyl.

In some embodiments, $R_4$ represents $NR_5R_6$, $R_5$ and $R_6$ represent methyl.

In certain embodiments, $R_4$ represents $NR_5R_6$, $R_5$ represents H and $R_6$ represents phenyl.

In some embodiments, $R_4$ represents $NR_5R_6$, $R_5$ represents methyl and $R_6$ represents methyl.

In certain embodiments, $R_8$ represents Cl and $R_7$ and $R_9$ each represents H.

In some embodiments, $R_8$ represents F and $R_7$ and $R_9$ each represents H.

In some embodiments, $R_8$ represents Br and $R_7$ and $R_9$ each represents H.

In certain embodiments, $R_8$ represents $CF_3$ and $R_7$ and $R_9$ each represents H.

In some embodiments, $R_8$ represents methoxy and $R_7$ and $R_8$ each represents H.

In some embodiments, $R_9$ represents $CF_3$ and $R_7$ and $R_8$ each represents H.

In some embodiments, $R_9$ represents methoxy and $R_7$ and $R_8$ each represents H.

In some embodiments, X represents O. In certain embodiments, X represents $NR_{10}$, wherein $R_{10}$ represents methyl.

In some embodiments, $X_1$ represents C=O and $X_2$ represents NH.

In some embodiments, $X_3$ represents N.

In some embodiments, the compound of formula (I) is selected from the group consisting of:

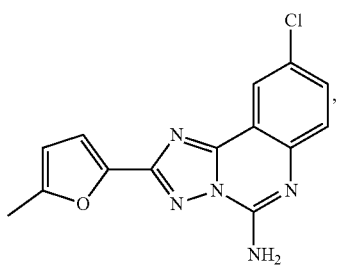
(BRO-013)

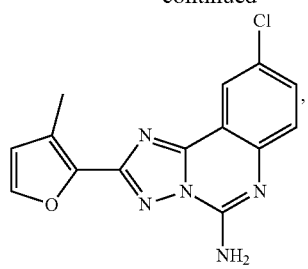
(BRO-017)

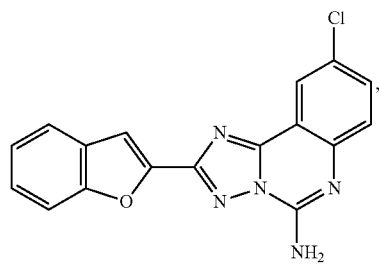
(BRO-019)

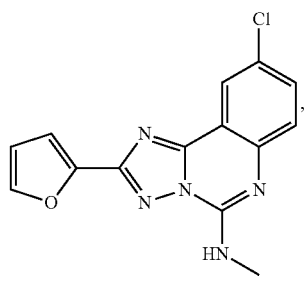
(BRO-025)

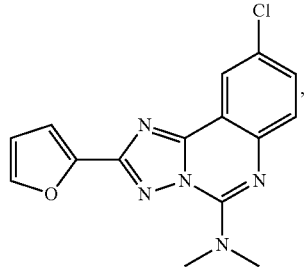
(BRO-021)

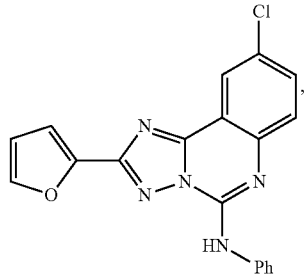
(BRO-022)

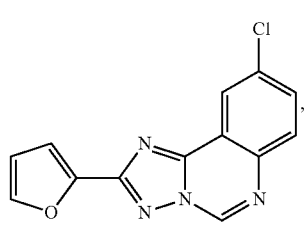

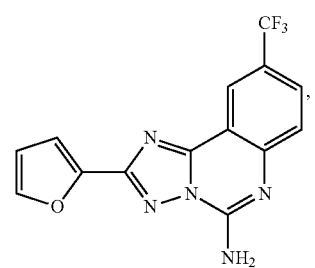
(BRO-024)
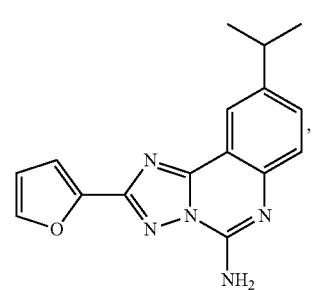
(BRO-025)
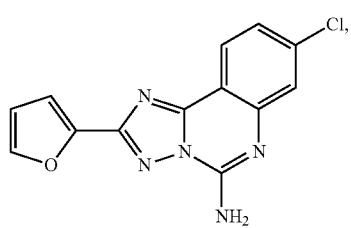
(BRO-026)
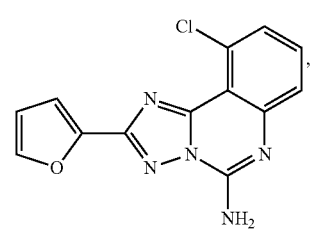
(BRO-027)
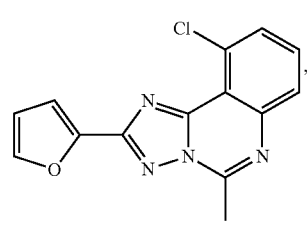
(B1)
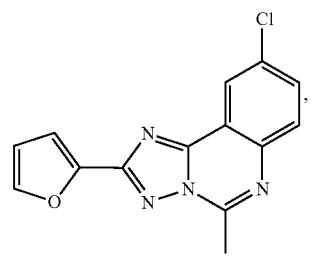
(B2)
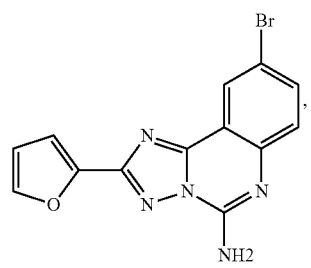
(A14)
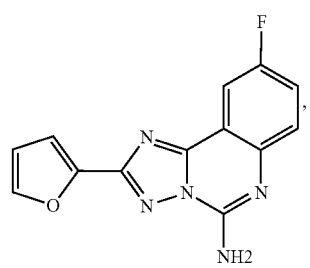
(BRO-023)
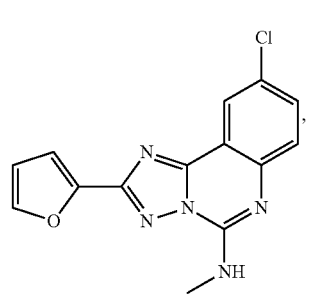
(BRO-019)
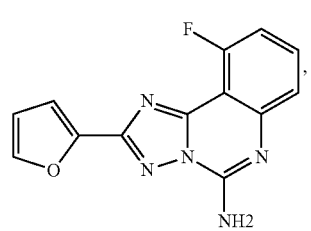
(A17)
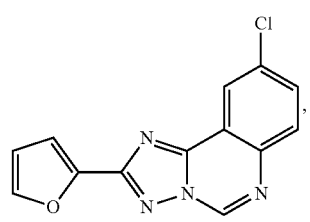
(BRO-022)
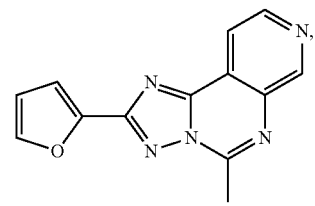
(B7)

-continued

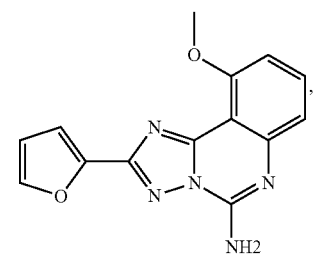
(A16)

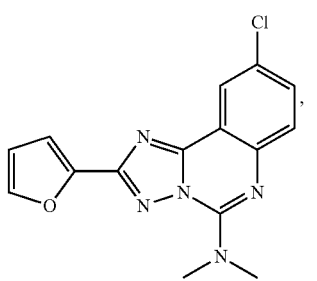
(BRO-027)

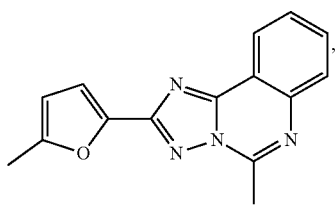
(B5)

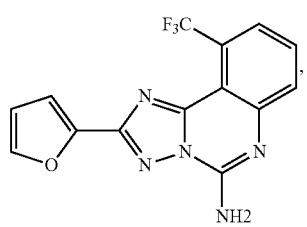
(A2)

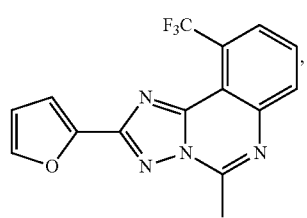
(B3)

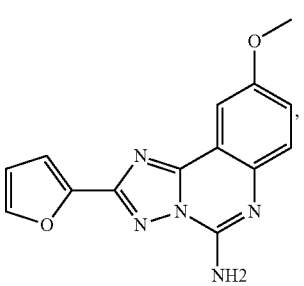
(A15)

-continued

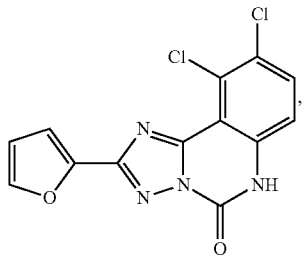
(A1)

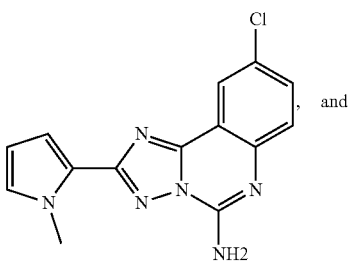
(BRO-018)

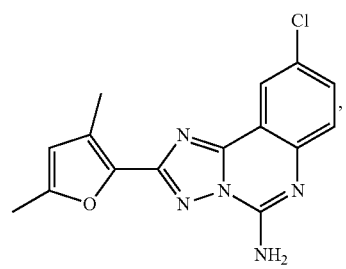
(BRO-014)

or a pharmaceutically acceptable salt, ester, amide, prodrug or stereoisomer thereof.

FOXA1 and FOXA1 Gene Targets

FOXA1 is a forkhead box transcription factor that acts on condensed chromatin and at distal enhancer sites as pioneer factor. It is highly expressed in hepatocytes and luminal breast cancers, but it has heretofore presented a challenging pharmacological target since it is a transcription factor. FOXA1 has been characterized as a lineage-selective dependency in multiple cancer types, most notably luminal breast cancer. FOXA1 activation has also been observed in some models of prostate cancer and liver cancer. While directly targeting FOXA1 has been identified as a promising approach for cancer therapy, no specific small molecule inhibitors have been reported.

Known and notable FOXA1 gene targets include AGR2 (anterior gradient homology 2, a known proto-oncogene and disulfide isomerase), AGR3 (anterior gradient homology 2, a member of the disulfide isomerase (PDI) family of endoplasmic reticulum (ER) proteins that catalyze protein folding and thiol-disulfide interchange reactions, previously described as associated with AGR2) and EMP3 (epithelial membrane protein 3, a member of the PMP-22/EMP/MP20 family of proteins. The protein contains four transmembrane domains and two N-linked glycosylation sites. EMP3 has been characterized as involved in cell proliferation, cell-cell interactions and is believed to function as a tumor suppressor. Alternative splicing results in multiple transcript variants).

It has been discovered herein that three existing preclinical compounds selectively kill breast cancer cells as well as other cancer cell types that exhibit FOXA1 activation. All three compounds share structural similarity and were originally developed to antagonize adenosine receptors. As disclosed herein, AGR2 expression has been identified as a predictive biomarker for drug-induced effects of the instant disclosure, but AGR2 was not functionally required for the observed drug responses.

Through genome-wide CRISPR modifier screens, it has been determined herein that the AHR (aryl hydrocarbon receptor) protein is likely a novel target of these molecules necessary for their effects, as AHR has been described herein as required for their cytotoxic activity.

Exemplary human FOXA1, AGR2, AGR3 and EMP3 mRNA and protein sequences are:

*Homo sapiens* forkhead box A1 (FOXA1), mRNA, NCBI Ref No. NM_004496.3 (SEQ ID NO: 1):

```
GGGCTTCCTCTTCGCCCGGGTGGCGTTGGGCCCGCGCGGGCGCTCGGGTGACT
GCAGCTGCTCAGCTCCCCTCCCCCGCCCCGCGCCGCGCGGCCGCCCGTCGCTTCGCAC
AGGGCTGGATGGTTGTATTGGGCAGGGTGGCTCCAGGATGTTAGGAACTGTGAAGAT
GGAAGGGCATGAAACCAGCGACTGGAACAGCTACTACGCAGACACGCAGGAGGCCT
ACTCCTCCGTCCCGGTCAGCAACATGAACTCAGGCCTGGGCTCCATGAACTCCATGAA
CACCTACATGACCATGAACACCATGACTACGAGCGGCAACATGACCCCGGCGTCCTTC
AACATGTCCTATGCCAACCCGGGCCTAGGGCCGGCCTGAGTCCCGGCGCAGTAGCC
GGCATGCCGGGGGCTCGGCGGGCGCCATGAACAGCATGACTGCGGCCGGCGTGACG
GCCATGGGTACGGCGCTGAGCCCGAGCGGCATGGGCGCCATGGGTGCGCAGCAGGCG
GCCTCCATGAATGGCCTGGGCCCCTACGCGGCCGCCATGAACCCGTGCATGAGCCCCA
TGGCGTACGCGCCGTCCAACCTGGGCCGCAGCCGCGCGGGCGGCGGCGGCGACGCCA
AGACGTTCAAGCGCAGCTACCCGCACGCCAAGCCGCCCTACTCGTACATCTCGCTCAT
CACCATGGCCATCCAGCAGGCGCCCAGCAAGATGCTCACGCTGAGCGAGATCTACCA
GTGGATCATGGACCTCTTCCCCTATTACCGGCAGAACCAGCAGCGCTGGCAGAACTCC
ATCCGCCACTCGCTGTCCTTCAATGACTGCTTCGTCAAGGTGGCACGCTCCCCGGACA
AGCCGGGCAAGGGCTCCTACTGGACGCTGCACCCGGACTCCGGCAACATGTTCGAGA
ACGGCTGCTACTTGCGCCGCCAGAAGCGCTTCAAGTGCGAGAAGCAGCCGGGGGCCG
GCGGCGGGGCGGGAGCGGAAGCGGGGCAGCGGCGCCAAGGGCGGCCCTGAGAGC
CGCAAGGACCCCTCTGGCGCCTCTAACCCCAGCGCCGACTCGCCCCTCCATCGGGGTG
TGCACGGGAAGACCGGCCAGCTAGAGGGCGCGCCGGCCCCCGGGCCCGCCGCCAGCC
CCCAGACTCTGGACCACAGTGGGGCGACGGCGACAGGGGGCGCCTCGGAGTTGAAGA
CTCCAGCCTCCTCAACTGCGCCCCCCATAAGCTCCGGGCCCGGGGCGCTGGCCTCTGT
GCCCGCCTCTCACCCGGCACACGGCTTGGCACCCCACGAGTCCCAGCTGCACCTGAAA
GGGGACCCCCACTACTCCTTCAACCACCCGTTCTCCATCAACAACCTCATGTCCTCCTC
GGAGCAGCAGCATAAGCTGGACTTCAAGGCATACGAACAGGCACTGCAATACTCGCC
TTACGGCTCTACGTTGCCCGCCAGCCTGCCTCTAGGCAGCGCCTCGGTGACCACCAGG
AGCCCCATCGAGCCCTCAGCCCTGGAGCCGGCGTACTACCAAGGTGTGTATTCCAGAC
CCGTCCTAAACACTTCCTAGCTCCCGGGACTGGGGGGTTTGTCTGGCATAGCCATGCT
GGTAGCAAGAGAGAAAAAATCAACAGCAAACAAAACCACACAAACCAAACCGTCAA
CAGCATAATAAAATCCCAACAACTATTTTTATTTCATTTTTCATGCACAACCTTTCCCC
CAGTGCAAAAGACTGTTACTTTATTATTGTATTCAAAATTCATTGTGTATATTACTACA
AAGACAACCCCAAACCAATTTTTTTCCTGCGAAGTTTAATGATCCACAAGTGTATATA
TGAAATTCTCCTCCTTCCTTGCCCCCCTCTCTTTCTTCCCTCTTTCCCCTCCAGACATTC
TAGTTTGTGGAGGGTTATTTAAAAAAACAAAAAAGGAAGATGGTCAAGTTTGTAAAA
TATTTGTTTGTGCTTTTTCCCCCTCCTTACCTGACCCCCTACGAGTTTACAGGTCTGTGG
CAATACTCTTAACCATAAGAATTGAAATGGTGAAGAAACAAGTATACACTAGAGGCT
CTTAAAAGTATTGAAAGACAATACTGCTGTTATATAGCAAGACATAAACAGATTATA
```

-continued

```
AACATCAGAGCCATTTGCTTCTCAGTTTACATTTCTGATACATGCAGATAGCAGATGT
CTTTAAATGAAATACATGTATATTGTGTATGGACTTAATTATGCACATGCTCAGATGT
GTAGACATCCTCCGTATATTTACATAACATATAGAGGTAATAGATAGGTGATATACAT
GATACATTCTCAAGAGTTGCTTGACCGAAAGTTACAAGGACCCCAACCCCTTTGTCCT
CTCTACCCACAGATGGCCCTGGGAATCAATTCCTCAGGAATTGCCCTCAAGAACTCTG
CTTCTTGCTTTGCAGAGTGCCATGGTCATGTCATTCTGAGGTCACATAACACATAAAA
TTAGTTTCTATGAGTGTATACCATTTAAAGAATTTTTTTTCAGTAAAAGGGAATATTA
CAATGTTGGAGGAGAGATAAGTTATAGGGAGCTGGATTTCAAAACGTGGTCCAAGAT
TCAAAAATCCTATTGATAGTGGCCATTTTAATCATTGCCATCGTGTGCTTGTTTCATCC
AGTGTTATGCACTTTCCACAGTTGGACATGGTGTTAGTATAGCCAGACGGGTTTCATT
ATTATTTCTCTTTGCTTTCTCAATGTTAATTTATTGCATGGTTTATTCTTTTTCTTTACAG
CTGAAATTGCTTTAAATGATGGTTAAAATTACAAATTAAATTGTTAATTTTTATCAATG
TGATTGTAATTAAAAATATTTTGATTTAAATAACAAAAATAATACCAGATTTTAAGCC
GTGGAAAATGTTCTTGATCATTTGCAGTTAAGGACTTTAAATAAATCAAATGTTAACA
AAAGAGCATTTCTGTTATTTTTTTCACTTAACTAAATCCGAAGTGAATATTTCTGAAT
ACGATATTTTTCAAATTCTAGAACTGAATATAAATGACAAAAATGAAAATAAAATTGT
TTTGTCTGTTGTTATAATGAATGTGTAGCTAGTAAAAAGGAGTGAAAGAAATTCAAGT
AAAGTGTATAAGTTGATTTAATATTCCAAGAGTTGAGATTTTTAAGATTCTTTATTCCC
AGTGATGTTTACTTCATTTTTTTTTTTTTTGACACCGGCTTAAGCCTTCTGTGTTTC
CTTTGAGCCTTTTCACTACAAAATCAAATATTAATTTAACTACCTTTCCTCCTTCCCCA
ATGTATCACTTTTCTTTATCTGAGAATTCTTCCAATGAAAATAAAATATCAGCTGTGGC
TGATAGAATTAAGTTGTGTCCAAAAAAAAAAAAAAAAAA
```

*Homo sapiens* forkhead box A1 (FOXA1), protein, NCBI Ref No. NP_004487.2 (SEQ ID NO: 2):

```
MLGTVKMEGHETSDWNSYYADTQEAYSSVPVSNMNSGLGSMNSMNTYM
TMNTMTTSGNMTPASFNMSYANPGLGAGLSPGAVAGMPGGSAGAMNSM
TAAGVTAMGTALSPSGMGAMGAQQAASMNGLGPYAAAMNPCMSPMAYA
PSNLGRSRAGGGGDAKTFKRSYPHAKPPYSYISLITMAIQQAPSKMLT
LSEIYQWIMDLFPYYRQNQQRWQNSIRHSLSFNDCFVKVARSPDKPGK
GSYWTLHPDSGNMFENGCYLRRQKRFKCEKQPGAGGGGGSGGGSGAK
GGPESRKDPSGASNPSADSPLHRGVHGKTGQLEGAPAPGPAASPQTLD
HSGATATGGASELKTPASSTAPPISSGPGALASVPASHPAHGLAPHES
QLHLKGDPHYSENHPFSINNLMSSSEQQHKLDFKAYEQALQYSPYGST
LPASLPLGSASVTTRSPIEPSALEPAYYQGVYSRPVLNTS
```

*Homo sapiens* anterior gradient 2, protein disulphide isomerase family member (AGR2), mRNA, NCBI Ref. No. NM_006408.3 (SEQ ID NO: 3):

```
AATCACTTGGGGAAAGGAAGGTTCGTTTCTGAGTTAGCAACAAGTAAA
TGCAGCACTAGTGGGTGGGATTGAGGTATGCCCTGGTGCATAAATAGA
GACTCAGCTGTGCTGGCACACTCAGAAGCTTGGACCGCATCCTAGCCG
CCGACTCACACAAGGCAGGTGGGTGAGGAAATCCAGAGTTGCCATGGA
GAAAATTCCAGTGTCAGCATTCTTGCTCCTTGTGGCCCTCTCCTACAC
TCTGGCCAGAGATACCACAGTCAAACCTGGAGCCAAAAAGGACACAAA
GGACTCTCGACCCAAACTGCCCCAGACCCTCTCCAGAGGTTGGGGTGA
CCAACTCATCTGGACTCAGACATATGAAGAAGCTCTATATAAATCCAA
GACAAGCAACAAACCCTTGATGATTATTCATCACTTGGATGAGTGCCC
ACACAGTCAAGCTTTAAAGAAAGTGTTTGCTGAAAATAAAGAAATCCA
GAAATTGGCAGAGCAGTTTGTCCTCCTCAATCTGGTTTATGAAACAAC
TGACAAACACCTTTCTCCTGATGGCCAGTATGTCCCCAGGATTATGTT
TGTTGACCCATCTCTGACAGTTAGAGCCGATATCACTGGAAGATATTC
AAATCGTCTCTATGCTTACGAACCTGCAGATACAGCTCTGTTGCTTGA
CAACATGAAGAAGCTCTCAAGTTGCTGAAGACTGAATTGTAAAGAAA
AAAAATCTCCAAGCCCTTCTGTCTGTCAGGCCTTGAGACTTGAAACCA
GAAGAAGTGTGAGAAGACTGGCTAGTGTGGAAGCATAGTGAACACACT
GATTAGGTTATGGTTTAATGTTACAACAACTATTTTTTAAGAAAAACA
AGTTTTAGAAATTTGGTTTCAAGTGTACATGTGTGAAAACAATATTGT
```

```
ATACTACCATAGTGAGCCATGATTTTCTAAAAAAAAAAATAAATGTTT

TGGGGGTGTTCTGTTTTCTCCAAAAAAAAAAAAAAA
```

Homo sapiens anterior gradient 2, protein disulphide isomerase family member (AGR2), protein ("anterior gradient protein 2 homolog precursor"), NCBI Ref. No. NP_006399.1 (SEQ ID NO: 4):

```
MEKIPVSAFLLLVALSYTLARDTTVKPGAKKDTKDSRPKLPQTLSRGW

GDQLIWTQTYEEALYKSKTSNKPLMIIHHLDECPHSQALKKVFAENKE

IQKLAEQFVLLNLVYETTDKHLSPDGQYVPRIMFVDPSLTVRADITGR

YSNRLYAYEPADTALLLDNMKKALKLLKTEL
```

Homo sapiens anterior gradient 3, protein disulphide isomerase family member (AGR3), mRNA, NCBI Ref. No. NM_176813.4 (SEQ ID NO: 5):

```
AGAAACATCCAGAATACATTTCCAACAAGAGCACTGGCCAAGTCAGCT

TCTTCTGAGAGAGTCTCTAGAAGACATGATGCTACACTCAGCTTTGGG

TCTCTGCCTCTTACTCGTCACAGTTTCTTCCAACCTTGCCATTGCAAT

AAAAAAGGAAAAGAGGCCTCCTCAGACACTCTCAAGAGGATGGGGAGA

TGACATCACTTGGGTACAAACTTATGAAGAAGGTCTCTTTTATGCTCA

AAAAAGTAAGAAGCCATTAATGGTTATTCATCACCTGGAGGATTGTCA

ATACTCTCAAGCACTAAAGAAAGTATTTGCCCAAAATGAAGAAATACA

AGAAATGGCTCAGAATAAGTTCATCATGCTAAACCTTATGCATGAAAC

CACTGATAAGAATTTATCACCTGATGGGCAATATGTGCCTAGAATCAT

GTTTGTAGACCCTTCTTTAACAGTTAGAGCTGACATAGCTGGAAGATA

CTCTAACAGATTGTACACATATGAGCCTCGGGATTTACCCCTATTGAT

AGAAAACATGAAGAAAGCATTAAGACTTATTCAGTCAGAGCTATAAGA

GATGATGGAAAAAAGCCTTCACTTCAAAGAAGTCAAATTTCATGAAGA

AAACCTCTGGCACATTGACAAATACTAAATGTGCAAGTATATAGATTT

TGTAATATTACTATTTAGTTTTTTTAATGTGTTTGCAATAGTCTTATT

AAAATAAATGTTTTTAAATCTGAGACTGAAAAAAAAAAAAAAAAAA
```

Homo sapiens anterior gradient 3, protein disulphide isomerase family member (AGR3), protein ("anterior gradient protein 3 precursor"), NCBI Ref. No. NM_176813.4 (SEQ ID NO: 6):

```
MMLHSALGLCLLLVTVSSNLAIAIKKEKRPPQTLSRGWGDDITWVQTY

EEGLFYAQKSKKPLMVIHHLEDCQYSQALKKVFAQNEEIQEMAQNKFI

MLNLMHETTDKNLSPDGQYVPRIMFVDPSLTVRADIAGRYSNRLYTYE

PRDLPLLIENMKKALRLIQSEL
```

Homo sapiens epithelial membrane protein 3 (EMP3), transcript variant 1, mRNA, NCBI Ref. No. NM_001425.2 (SEQ ID NO: 7):

```
CGGGAGCAAGAGAGAAGGAGGCCCAGACAGTGAGGGCAGGAGGGAGAG

AAGAGACGCAGAAGGAGAGCGAGCGAGAGAGAAAGGGTTCTGGATTGG

AGGGGAGAGCAAGGGAGGGAGGAAGGCGGTGAGAGAGGCGGGGCCTC

GGGAGGGTGAAAGGAGGGAGGAGAAGGGCGGGGCACGGAGGCCCGAGC

GAGGGACAAGACTCCGACTCCAGCTCTGACTTTTTTCGCGGCTCTCGG

CTTCCACTGCAGCCATGTCACTCCTCTTGCTGGTGGTCTCAGCCCTTC

ACATCCTCATTCTTATACTGCTTTTCGTGGCCACTTTGGACAAGTCCT

GGTGGACTCTCCCTGGGAAAGAGTCCCTGAATCTCTGGTACGACTGCA

CGTGGAACAACGACACCAAAACATGGGCCTGCAGTAATGTCAGCGAGA

ATGGCTGGCTGAAGGCGGTGCAGGTCCTCATGGTGCTCTCCCTCATTC

TCTGCTGTCTCTCCTTCATCCTGTTCATGTTCCAGCTCTACACCATGC

GACGAGGAGGTCTCTTCTATGCCACCGGCCTCTGCCAGCTTTGCACCA

GCGTGGCGGTGTTTACTGGCGCCTTGATCTATGCCATTCACGCCGAGG

AGATCCTGGAGAAGCACCCGCGAGGGGGCAGCTTCGGATACTGCTTCG

CCCTGGCCTGGGTGGCCTTCCCCCTCGCCCTGGTCAGCGGCATCATCT

ACATCCACCTACGGAAGCGGGAGTGAGCGCCCCGCCTCGCTCGGCTGC

CCCCGCCCCTTCCCGGCCCCCCTCGCCGCGCGTCCTCCAAAAAATAAA

ACCTTAACCGCGGAAAAAAAAAAAAAAAAAAAAA
```

Homo sapiens epithelial membrane protein 3 (EMP3), protein, NCBI Ref. No. NP_001416.1 (SEQ ID NO: 8):

```
MSLLLLVVSALHILILILLFVATLDKSWWTLPGKESLNLWYDCTWNND

TKTWACSNVSENGWLKAVQVLMVLSLILCCLSFILFMFQLYTMRRGGL

FYATGLCQLCTSVAVFTGALIYAIHAEEILEKHPRGGSFGYCFALAWV

AFPLALVSGIIYIHLRKRE
```

Aryl Hydrocarbon Receptor (AHR) and AhR Nuclear Translocator (ARNT)

The aryl hydrocarbon receptor (AhR or AHR or ahr or ahR) is a protein that in humans is encoded by the AHR gene. The aryl hydrocarbon receptor is a transcription factor that regulates gene expression. It was originally believed to function primarily as a sensor of xenobiotic chemicals and also as the regulator of enzymes such as cytochrome P450s that metabolize these chemicals. The most notable of these xenobiotic chemicals are aromatic (aryl) hydrocarbons from which the receptor derives its name.

More recently, it has been discovered that AhR is activated (or deactivated) by a number of endogenous indole derivatives such as kynurenine (see below). In addition to regulating metabolism enzymes, the AhR has roles in regulating immunity, stem cell maintenance, and cellular differentiation (Esser C. *Methods in Molecular Biology*. 1371. pp. 239-57; Kawajiri and Fujii-Kuriyama. *Experimental Animals*. 66: 75-89; Gutiérrez-Vázquez and *Quintana. Immunity*. 48: 19-33).

The aryl hydrocarbon receptor is a member of the family of basic helix-loop-helix transcription factors. AHR binds several exogenous ligands such as natural plant flavonoids, polyphenolics and indoles, as well as synthetic polycyclic aromatic hydrocarbons and dioxin-like compounds. AhR is a cytosolic transcription factor that is normally inactive, bound to several co-chaperones.

The aryl hydrocarbon receptor (AhR or AHR herein) is involved in the induction of several enzymes that participate in xenobiotic metabolism. The ligand-free, cytosolic form of the aryl hydrocarbon receptor is complexed to heat shock protein 90. Binding of ligand, which includes dioxin and polycyclic aromatic hydrocarbons, results in translocation of the ligand-binding subunit only to the nucleus. Induction of enzymes involved in xenobiotic metabolism occurs through binding of the ligand-bound AHR to xenobiotic responsive elements in the promoters of genes for these enzymes.

AhR has been previously described to bind a wide range of aromatic substrates including agonists, antagonists, and modulators (Denison et al. *Tox. Sci.* 2014). AhR ligands have been generally classified into two categories, synthetic or naturally occurring. The first ligands to be discovered were synthetic and members of the halogenated aromatic hydrocarbons (polychlorinated dibenzodioxins, dibenzofurans and biphenyls) and polycyclic aromatic hydrocarbons (3-methylcholanthrene, benzo[a]pyrene, benzanthracenes and benzoflavones; Denison et al. *Chemico-Biological Interactions* (Submitted manuscript). 141: 3-24; Denison and Nagy. *Annual Review of Pharmacology and Toxicology.* 43: 309-34).

Research has focused on naturally occurring compounds with the hope of identifying an endogenous ligand. Naturally occurring compounds that have been identified as ligands of Ahr include derivatives of tryptophan such as indigo dye and indirubin (Adachi et al. *The Journal of Biological Chemistry.* 276: 31475-8), tetrapyrroles such as bilirubin (Sinal and Bend. *Molecular Pharmacology.* 52: 590-9), the arachidonic acid metabolites lipoxin A4 and prostaglandin G (Seidel et al. *Journal of Biochemical and Molecular Toxicology.* 15: 187-96), modified low-density lipoprotein (McMillan and Bradfield. *Proceedings of the National Academy of Sciences of the United States of America.* 104: 1412-7) and several dietary carotenoids (Denison and Nagy). One assumption made in the search for an endogenous ligand is that the ligand will be a receptor agonist. However, work by Savouret et al. has shown this may not be the case since their findings demonstrate that 7-ketocholesterol competitively inhibits Ahr signal transduction (Savouret et al. *The Journal of Biological Chemistry.* 276: 3054-9).

Carbidopa is a selective aryl hydrocarbon receptor modulator (SAhRM; Safe, Stephen. *Biochemical Journal.* 474: 3763-3765).

Upon ligand binding to chemicals such as 2,3,7,8-tetrachlorodibenzo-p-dioxin (TCDD), the chaperones dissociate resulting in AhR translocating into the nucleus and dimerizing with ARNT (AhR nuclear translocator), leading to changes in gene transcription.

The ARNT gene encodes the aryl hydrocarbon receptor nuclear translocator protein that forms a complex with ligand-bound aryl hydrocarbon receptor (AhR or AHR herein), and is required for receptor function. The encoded protein has also been identified as the beta subunit of a heterodimeric transcription factor, hypoxia-inducible factor 1 (HIF1). A t(1;12)(q21;p13) translocation, which results in a TEL-ARNT fusion protein, is associated with acute myeloblastic leukemia. Three alternatively spliced variants encoding different isoforms have been described for this gene.

Known AHR Agonists

A number of AHR agonists have been previously described, possessing a variety of structures. Exemplary known AHR agonists include TCDD, indirubin, β-naphthoflavone, L-kynurenine, 3-methylcholanthrene and YH439, which have the following structures:

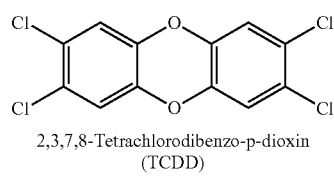

2,3,7,8-Tetrachlorodibenzo-p-dioxin
(TCDD)

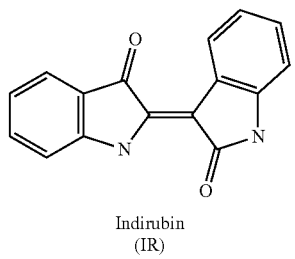

Indirubin
(IR)

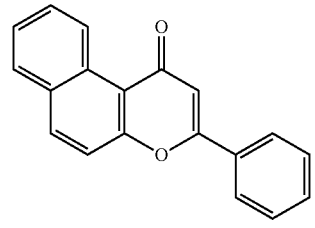

β-Naphthoflavone
(βNF)

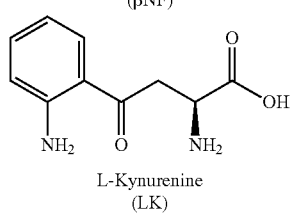

L-Kynurenine
(LK)

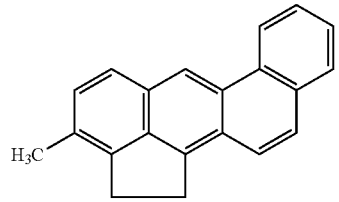

3-Methylcholanthrene
(3MC)

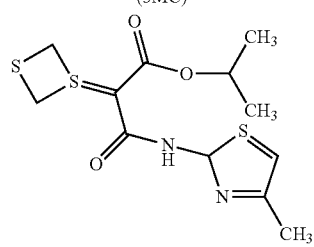

YH439

Identification of FOXA1 High/Overexpressing and/or FOXA1 Gene Target High/Overexpressing Cells, Tissues and/or Cancers Identification of a tissue, tumor and/or cancer of a subject as exhibiting elevated levels of FOXA1 and/or FOXA1 gene target expression (including FOXA1 and/or FOXA1 gene target overexpression) can be performed by any method available in the art. Certain methods and compositions described herein relate to identification of a cell, cell line, sample, tissue and/or subject having or at risk of developing a cancer that exhibits elevated levels of FOXA1 and/or FOXA1 gene target expression (including FOXA1 and/or FOXA1 gene target overexpression) at the mRNA or protein level, based upon gene-specific assessment of FOXA1 and/or FOXA1 gene target mRNA or protein performed upon the cell, cell line, sample, tissue and/or subject having or at risk of developing a cancer that exhibits elevated levels of FOXA1 and/or FOXA1 gene target expression. In certain embodiments, detection of elevated FOXA1 and/or FOXA1 gene target levels can readily be performed, e.g., via assessment of mRNA expression levels (e.g., via real-time PCR or other such quantitative method). In related embodiments, assessment of FOXA1 and/or FOXA1 gene target mRNA expression can be performed via art-recognized, oligonucleotide-mediated approaches, including, e.g., northern blotting, expression profiling using RT-PCR and/or next-generation sequencing performed upon cellular transcriptomes.

In some embodiments, detection of elevated FOXA1 and/or FOXA1 gene target levels can readily be performed, e.g., via immunoassay for detection of FOXA1 and/or FOXA1 gene target protein levels.

Protein levels of FOXA1 and/or FOXA1 gene target(s) can be quantitated in a variety of ways well known in the art, such as immunoprecipitation, Western blot analysis (immunoblotting), ELISA or fluorescence-activated cell sorting (FACS). Antibodies directed to FOXA1 and/or FOXA1 gene target(s) can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Treatable Cancers

A number of cancers have been described in the art as exhibiting elevated levels of FOXA1 and/or FOXA1 gene target(s). As noted herein, exemplary types of cancer that have been identified as exhibiting elevated expression of FOXA1 and/or FOXA1 gene target(s) include breast (particularly luminal and/or ER-positive breast cancers), liver and prostate cancers. The range of cancers presently contemplated as treatable using CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety as described herein is not in any way limited to these aforementioned types of cancer.

As used in this context, to "treat" means to ameliorate at least one symptom of the cancer. For example, a treatment can result in a reduction in tumor size, tumor growth, cancer cell number, cancer cell growth, or metastasis or risk of metastasis.

For example, the methods can include selecting and/or administering a treatment that includes a therapeutically effective amount of CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety and/or other agent capable of selectively killing cells that exhibit high mRNA or protein expression of FOXA1 and/or a FOXA1 gene target. In certain embodiments, CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety and/or other agent capable of selectively killing cells that exhibit high mRNA or protein expression of FOXA1 and/or a FOXA1 gene target may be administered in combination with an additional therapeutic agent, optionally a chemotherapeutic agent including Letrozole, Anastrozole, Exemestane, Doxorubicin, Liposomal doxorubicin, Cyclophosphamide, Capecitabine, Docetaxel, Paclitaxel, Nab-paclitaxel, Trastuzumab, Ado-trastuzumab emtansine, Pertuzumab, Neratinib, Carboplatin, Cisplatin, Gemcitabine, Tamoxifen, Methotrexate, 5-Fluorouracil, Vinorelbine, Palbociclib, Abemaciclib, Fulvestrant, Olaparib, Eribulin, sorafenib, lenvatinib, nivolumab, oxaliplatin, Leuprolide, Degarelix, Goserelin, Bicalutamide, Triptorelin, Abiraterone, Enzalutamide, Etoposide, Cabazitaxel, and/or other chemotherapeutic agents, particularly those commonly used for treating breast, liver and prostate cancers.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety, which achieves a half-maximal inhibition of symptoms and/or a half-maximal extent of killing of targeted cancer cells) as determined in cell culture. Such information can be used to more accurately determine useful doses in humans. Levels in plasma may be measured, for example, by high performance liquid chromatography.

Combination Treatments

The compositions and methods of the present disclosure may be used in the context of a number of therapeutic or prophylactic applications. In order to increase the effectiveness of a treatment with the compositions of the present disclosure, e.g., CGS-15943, MRS-1220, SCH-58261 and/or a furan ring-possessing CGS-15943, MRS-1220, SCH-58261 derivative can be selected and/or administered as a single agent, or to augment the efficacy of another therapy (second therapy), it may be desirable to combine these compositions and methods with one another, or with other agents and methods effective in the treatment, amelioration, or prevention of diseases and pathologic conditions, for example, cancers characterized by high FOXA1 expression levels (e.g., luminal and/or ER-positive forms of breast cancer).

In certain embodiments of the instant disclosure, one or more chemotherapeutic drugs that are unrelated to CGS-15943, MRS-1220 and/or SCH-58261 can be co-administered with CGS-15943, MRS-1220, SCH-58261 or related compound, or can be administered in advance of CGS-15943, MRS-1220, SCH-58261 or related compound administration. Examples of such non-CGS-15943, MRS-1220, SCH-58261 or related compound chemotherapeutics include Letrozole, Anastrozole, Exemestane, Doxorubicin, Liposomal doxorubicin, Cyclophosphamide, Capecitabine, Docetaxel, Paclitaxel, Nab-paclitaxel, Trastuzumab, Ado-trastuzumab emtansine, Pertuzumab, Neratinib, Carboplatin, Cisplatin, Gemcitabine, Tamoxifen, Methotrexate, 5-Fluorouracil, Vinorelbine, Palbociclib, Abemaciclib, Fulvestrant, Olaparib, Eribulin, sorafenib, lenvatinib, nivolumab, oxaliplatin, Leuprolide, Degarelix, Goserelin, Bicalutamide, Triptorelin, Abiraterone, Enzalutamide, Etoposide, Cabazitaxel, and other chemotherapeutic agents, particularly those commonly used for treating breast, liver and prostate cancers. It is also expressly contemplated that compounds of the instant disclosure can be combined with hormone therapy (including ovarian ablation (e.g., oophorectomy or radiation treatment, administration of GnRH agonists (LH-RH agonists)), administration of ovarian suppression drugs (e.g., goserelin and leuprolide), estrogen production blockers (e.g., aromatase inhibitors, such as anastrozole, letrozole, and exemestane), blockers of estrogen effects (e.g., selective estrogen receptor modulators (SERMs) such as tamoxifen and toremifene), and/or other anti-estrogen drugs (e.g., fulvestrant)) or with administration of a cyclin-dependent kinase (CDK) inhibitor (e.g., 3α-Amino-5α-androstane, 7x, AG-024322, AMG 925, AT7519, AZD5438, BAY 1000394, BML-259. Compound 1, Compound 530, CR8, Dinaciclib, F07#13, Fascaplysin, Flavopiridol, Kenpaullone, LY2835219, NBI1, NU2058, Olomoucine, P276-00, PD-0332991, PHA-793887, Purvalanol A/B, R547, RGB-286638, Roscovitine, Ryuvidine, SNS-032, SU 9516, VMY-1-101, VMY-1-103, etc.), particularly for treating or preventing breast cancer in a subject.

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary. It also is contemplated that various standard therapies may be applied in combination with the described therapies.

Pharmaceutical Compositions

Agents of the present disclosure can be incorporated into a variety of formulations for therapeutic use (e.g., by administration) or in the manufacture of a medicament (e.g., for treating or preventing cancer, e.g., a cancer that exhibits high FOXA1 or high FOXA1 gene target expression and/or is a luminal or ER-positive form of breast cancer) by combining the agents with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols.

Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, non-therapeutic, nonimmunogenic stabilizers, excipients and the like. The compositions can also include additional substances to approximate physiological conditions, such as pH adjusting and buffering agents, toxicity adjusting agents, wetting agents and detergents.

Further examples of formulations that are suitable for various types of administration can be found in Remington's Pharmaceutical Sciences, Mace Publishing Company, Philadelphia, PA, 17th ed. (1985). For a brief review of methods for drug delivery, see, Langer, Science 249: 1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink.

Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences 66 (1977): 1-19, incorporated herein by reference. The salts can be prepared in situ during the final isolation and purification of the compounds of the application, or separately by reacting a free base or free acid function with a suitable reagent, as described generally below. For example, a free base function can be reacted with a suitable acid. Furthermore, where the compounds to be administered of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound (e.g., an FDA-approved compound where administered to a human subject) or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethyl succinates.

Furthermore, the term "pharmaceutically acceptable prodrugs" as used herein refers to those prodrugs of certain compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of an agent of the instant disclosure, for example by hydrolysis in blood. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, (1987), both of which are incorporated herein by reference.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in a subject and/or tissue of a subject, e.g., to prevent rapid clearance of a formulation by the subject. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent, such as CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the individual instant disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an agent described herein may be used (e.g., administered to an individual, such as a human individual, in need of treatment with CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety) in accord with known methods, such as oral administration, intravenous administration as a bolus or by continuous infusion over a period of time, by intramuscular, intraperitoneal, intracerobrospinal, intracranial, intraspinal, subcutaneous, intraarticular, intrasynovial, intrathecal, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

For in vivo administration of any of the agents of the present disclosure, normal dosage amounts may vary from about 10 ng/kg up to about 100 mg/kg of an individual's and/or subject's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An effective amount of an agent of the instant disclosure may vary, e.g., from about 0.001 mg/kg to about 1000 mg/kg or more in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An exemplary dosing regimen may include administering an initial dose of an agent of the disclosure of about 200 µg/kg, followed by a weekly maintenance dose of about 100 µg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the agent(s) administered, can vary over time independently of the dose used.

Pharmaceutical compositions described herein can be prepared by any method known in the art of pharmacology. In general, such preparatory methods include the steps of bringing the agent or compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, German® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadow foam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such as magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of an agent (e.g., CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety) described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Drugs provided herein can be formulated in dosage unit form for ease of administration and uniformity of dosage. It will be understood, however, that the total daily usage of the agents described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for oral delivery or intravenous injection to a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent (e.g., CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety) described herein.

As noted elsewhere herein, a drug of the instant disclosure may be administered via a number of routes of administration, including but not limited to: subcutaneous, intravenous, intrathecal, intramuscular, intranasal, oral, transepidermal, parenteral, by inhalation, or intracerebroventricular.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

In some embodiments of the present disclosure, a formulation as herein defined is administered to the subject by bolus administration.

A drug or other therapy of the instant disclosure is administered to the subject in an amount sufficient to achieve a desired effect at a desired site (e.g., reduction of cancer size, cancer cell abundance, symptoms, etc.) determined by a skilled clinician to be effective. In some embodiments of the disclosure, the agent is administered at least once a year. In other embodiments of the disclosure, the agent is administered at least once a day. In other embodiments of the disclosure, the agent is administered at least once a week. In some embodiments of the disclosure, the agent is administered at least once a month.

Additional exemplary doses for administration of an agent of the disclosure to a subject include, but are not limited to, the following: 1-20 mg/kg/day, 2-15 mg/kg/day, 5-12 mg/kg/day, 10 mg/kg/day, 1-500 mg/kg/day, 2-250 mg/kg/day, 5-150 mg/kg/day, 20-125 mg/kg/day, 50-120 mg/kg/day, 100 mg/kg/day, at least 10 µg/kg/day, at least 100 µg/kg/day, at least 250 µg/kg/day, at least 500 µg/kg/day, at least 1 mg/kg/day, at least 2 mg/kg/day, at least 5 mg/kg/day, at least 10 mg/kg/day, at least 20 mg/kg/day, at least 50 mg/kg/day, at least 75 mg/kg/day, at least 100 mg/kg/day, at least 200 mg/kg/day, at least 500 mg/kg/day, at least 1 g/kg/day, and a therapeutically effective dose that is less than 500 mg/kg/day, less than 200 mg/kg/day, less than 100 mg/kg/day, less than 50 mg/kg/day, less than 20 mg/kg/day, less than 10 mg/kg/day, less than 5 mg/kg/day, less than 2 mg/kg/day, less than 1 mg/kg/day, less than 500 µg/kg/day, and less than 500 µg/kg/day.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent (e.g., CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety) described herein. In certain embodiments, a dose described herein includes independently between 1 mg and 3 mg, inclusive, of an agent (e.g., CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety) described herein. In certain embodiments, a dose described herein includes independently between 3 mg and 10 mg, inclusive, of an agent (e.g., CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety) described herein. In certain embodiments, a dose described herein includes independently between 10 mg and 30 mg, inclusive, of an agent (e.g., CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety) described herein. In certain embodiments, a dose described herein includes independently between 30 mg and 100 mg, inclusive, of an agent (e.g., CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety) described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that an agent (e.g., CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety) or composition, as described herein, can be administered in combination with one or more additional pharmaceutical agents (e.g., therapeutically and/or prophylactically active agents), which are different from the agent or composition and may be useful as, e.g., combination therapies.

The agents or compositions can be administered in combination with additional pharmaceutical agents that improve their activity (e.g., activity (e.g., potency and/or efficacy) in treating a disease (e.g., cancer) in a subject in need thereof, in preventing a disease in a subject in need thereof, in reducing the risk of developing a disease in a subject in need thereof, etc. in a subject or cell. In certain embodiments, a pharmaceutical composition described herein including an agent (e.g., CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety) described herein and an additional pharmaceutical agent shows a synergistic effect that is absent in a pharmaceutical composition including one of the agent and the additional pharmaceutical agent, but not both.

In some embodiments of the disclosure, a therapeutic agent distinct from a first therapeutic agent of the disclosure is administered prior to, in combination with, at the same time, or after administration of the agent of the disclosure. In some embodiments, the second therapeutic agent is selected from the group consisting of a chemotherapeutic, an immunotherapy, an antioxidant, an antiinflammatory agent, an antimicrobial, a steroid, etc.

The agent or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, additional CGS-15943 derivatives, MRS-1220 derivatives, SCH-58261 derivatives (optionally possessing a furan ring moiety), other anti-cancer agents, immunotherapy and/or immunomodulatory agents, anti-proliferative agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the agents described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Dosages for a particular agent of the instant disclosure may be determined empirically in individuals who have been given one or more administrations of the agent.

Administration of an agent of the present disclosure can be continuous or intermittent, depending, for example, on the recipient's physiological condition, whether the purpose of the administration is therapeutic or prophylactic, and other factors known to skilled practitioners. The administration of an agent may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the instant disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Kits

The instant disclosure also provides kits containing agents of this disclosure for use in the methods of the present disclosure. Kits of the instant disclosure may include one or more containers comprising an agent (e.g., CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety) of this disclosure and/or may contain agents (e.g., oligonucleotide primers, probes, etc.) for identifying a cancer or subject as having a luminal and/or ER-positive form or breast cancer and/or as exhibiting elevated FOXA1 and/or FOXA1 gene target levels. In some embodiments, the kits further include instructions for use in accordance with the methods of this disclosure. In some embodiments, these instructions comprise a description of administration of the agent to treat or diagnose, e.g., a cancer that exhibits elevated expression of FOXA1 and/or FOXA1 gene targets, according to any of the methods of this disclosure. In some embodiments, the instructions comprise a description of how to detect a cancer or subject as a luminal and/or ER-positive form or breast cancer and/or as exhibiting elevated FOXA1 and/or FOXA1 gene target levels, for example in an individual, in a tissue sample, or in a cell. The kit may further comprise a description of selecting an individual suitable for treatment based on identifying whether that subject has a luminal and/or ER-positive form or breast cancer and/or a cancer that exhibits elevated FOXA1 and/or FOXA1 gene target levels.

The instructions generally include information as to dosage, dosing schedule, and route of administration for the intended treatment. The containers may be unit doses, bulk packages (e.g., multi-dose packages) or sub-unit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a cancer or subject having a luminal and/or ER-positive form or breast cancer and/or a cancer exhibiting elevated FOXA1 and/or FOXA1 gene target levels, in a subject. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). In certain embodiments, at least one active agent in the composition is CGS-15943, a CGS-15943 derivative that possesses a furan ring moiety, MRS-1220, a MRS-1220 derivative that possesses a furan ring moiety, SCH-58261 and/or a SCH-58261 derivative that possesses a furan ring moiety. The container may further comprise a second pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

PRISM Screening

Parental cell lines were obtained from the Cancer Cell Line Encyclopedia (CCLE) project (1). PRISM cell line barcoding, pooling, and screening was performed as previously described with several improvements to the original method (2). First, the lentiviral vector was modified to encode the unique barcode identifier at the end of the puromycin resistance gene. This enables barcodes to be detected using a variant of the mRNA capture and Luminex detection method developed for the L1000 gene expression assay (3). Second, a set of ten inert barcodes were spiked-in to each well of each plate after cell lysis to control for variation in PCR amplification as detailed below.

Data Processing

Luminex technology produced .lxb files containing data for each Luminex bead observed during detection. These .lxb files were processed to compute Median Fluorescence Intensity (MFI) values, calculated as the median of the values obtained for all beads corresponding to a single PRISM barcode.

MFI values were log-transformed (log MFI) and used to perform basic quality control. To detect probable screening artifacts, log MFI values were centered to the median log MFI for each cell line on each plate in order to put the measurements from each cell line on the same scale. For each well on each plate, the median of these centered values was then standardized according to the global median and global MAD across all plate wells in the same position. Data from wells with a standardized score of greater than 5 or less than −5 were excluded from all further processing steps.

For each cell line on each plate, the distribution of MFI values observed for the DMSO-treated negative controls was compared to that of the positive controls using a robust form of the Strictly Standardized Mean Difference (SSMD*) '. Specifically, SSMD* was calculated as:

$$\frac{(\mu_- - \mu_+)}{\sqrt{\sigma_-^2 + \sigma_+^2}}$$

Data corresponding to SSMD values less than 2 were removed before calculating cell viability.

The data in the instant disclosure were produced according to two different screening protocols. In the PR500 protocol, ten inert barcodes were spiked-in to each well of each plate after cell lysis. For data produced using the PR500 protocol, normalized MFI (nMFI) values were computed by taking the ratio of each MFI value against the median of the inert barcodes within each well. For data produced before the PR500 protocol was introduced, nMFI values were set equal to MFI values.

Cell viability was calculated as the ratio of nMFI to the median of the nMFI from the DMSO-treated negative controls for each cell line on each plate. Batch effects produced from variable detection and assay conditions were then removed using ComBat (4). The final viability values were calculated as the median of the batch-corrected cell viabilities from biological replicates for each cell line, compound and dose.

Dose Response

Measures of dose response were obtained by fitting 3-parameter logistic curves to viability values for each compound and cell line using the R package 'drc'. Following the practice of Smirnov and Safikhani (5), viability was truncated at 1.0 and fit as a function of drug concentration according to:

$$V(c) = E_\infty + \frac{1 - E_\infty}{1 + e^{HS(c - EC50)}}$$

where all concentrations are in the natural logarithm scale. IC50 values were defined as the concentration c at which V(c)=0.5, given by the formula:

$$IC50 = -\frac{\log(1 - 2E_\infty)}{HS} + EC50$$

The Area Under the dose response Curve (AUC) was calculated using the normalized integral:

$$\frac{\int_{c_{min}}^{c_{max}} V(c)\,dc}{c_{max} - c_{min}}$$

-continued where $$\int V(c)dc = \frac{(E_\infty - 1)\log(1 + e^{-HS(c-EC50)})}{HS} + E_\infty c + const$$

The formulation above puts AUC values on a scale between 0 and 1, where lower AUC values indicate increased sensitivity to the treatment.

Nomination for Secondary Screen

Compounds from the primary screen were labeled as candidates for secondary screening using a combination of cell killing metrics and goodness-of-fit measures obtained from the ATLANTIS method (6). Metrics considered were profile mean, variance, skewness, number of sensitive cell lines as well as the 75th, 25th, 10th and 5th quantiles of each profile's distribution. Cell lines were defined as sensitive to a compound if their median log fold change after batch correction was below 2 standard deviations of the distribution of DMSO controls. ATLANTIS model R2 values of above 0.1 were considered strong models. Subject to compound availability and manual curation, candidates were progressed to secondary profiling at 8 point dose.

Antibodies and Reagents

FOXA1 antibody was obtained from AbCam (ab23738). FoxA1/HNF3α antibody (D7P9B) and AhR antibody (83200S) were obtained from Cell Signaling. pH2A.X sc-517348 antibody was obtained from Santa Cruz Biotechnology. CYP1A1 antibody PA1-340 was obtained from Thermo Fisher. β-Actin (8H10D10) mouse mAb 3700S, PARP (46D11) rabbit mAb #9532 and estrogen receptor alpha 8644S antibody were obtained from Cell Signaling.

Compounds CGS15943, SCH58261, MRS1220 and Phortress were obtained from Tocris (catalog numbers 1699, 2270, 1217 and 4995, respectively). Aminoflavone was provided by the National Cancer Institute. 6',2',4-trimethylflavone, ITE, L-Kynurenine, FITZ and CH223191 were obtained from Tocris (catalog numbers 3859, 1803, 4393, 5304 and 3858, respectively). NucleoSpin® Blood XL Columns were obtained from Machu)/Nagel (Catalog No. 740950.50). Paclitaxel and Doxorubicin were obtained from Selleck (Catalog Nos. S1150 and S1208, respectively). Dimethyl sulfoxide was obtained from Sigma.

Cell Lines

MDA-MB-468, ZR-75-1, and MDA-MB-231 cell lines were obtained from the Cancer Cell Line Encyclopedia (CCLE) project.

Cloning

XP003, XP023, psPAX, and pMD2.G vectors were acquired from the Broad Genetic Perturbation Platform (GPP). Oligos for sgRNAs designs were generated using Broad GPP sgRNA guide generator resource (www.broadinstitute.org/gpp/db/analysis-tools/sgrna-design) and the respective oligos were synthesized by Integrated DNA Technologies. In order to clone the sgRNAs into either the XPR003 guide only or XPRO23 all-in-one crispr lentiviral expression systems the protocol available on the Broad GPP website (www.broadinstitute.org/gpp/db/resources/protocols) was followed.

Viral Vector Generation

In order to generate viral vectors, HEK293T cells were seeded in 6 well plates at a density of 1.5E6 cells per well. Cells were then transfected with a mixture of TransIT®-LT1 Transfection Reagent (MirusBio #M1R2304), psPAX2, pMD2.G, lentiviral plasmid diluted in Opti-MEM™ (Thermo #31985062). The following day media was changed DMEM (Thermo #10566016) with 30% FBS (Sigma 18A079). 72 hrs after transfection, virus containing media was collected and run through a 0.2 uM filter to remove cellular debris. Virus was aliquoted and stored short term at −20° C. until infection day.

Lentiviral Infection

A mixture of 3E6 cells, virus, and media with 4 μg/mL polybrene (Millipore) at a total volume of 2 mL was plated per well of a 12 well plate. Cells were centrifuged at 2000 RPM for 2 hours at 30° C. After removal from incubator, 2 mL of fresh media was added to each well and cells were allowed to incubate at 37° C. overnight. The following day cells were selected for with puromycin for 3-10 days, or until the non-infected control cell were completely non-viable.

CellTiter-Glo® Cellular Viability Assay

Cell viability was assayed using a modified manufacturer's protocol for CellTiter-Glo® (Promega #G7573). Cells were seeded at a density of 2000 cells per well in a 96 well black, clear bottom plate (Corning #89091-012) in 100 uL total media per well. The following day different concentrations of compounds at various doses were printed in triplicate in a random well format using the Tecan D300e Digital Dispenser. After 120H, 60 μL of a 1:3 solution of CellTiter-Glo reagent in 1×PBS (Corning #01018002) was added per well and allowed to incubate at RT for 10 mins. Luminescence was measured with an integration time of 0.1 s using Envision Microplates Reader (PERKIN ELMER #2105-0010). Biological replicates were averaged and normalized to vehicle control. Dose curves were generated using Graphpad Prism.

Western Immunoblotting

Adherent cells were washed once with cold 1×PBS (Corning #01018002) and lysed with RIPA buffer (Sigma #R0278) supplemented by protease and phosphatase inhibitors (Sigma). Protein content was quantified using the DC Protein Assay (BioRad #5000111). Samples were reduced with (loading buffer) and boiled at 95° C. before being resolved by SDS gel electrophoresis on 4-20% Tris/glycine gels (Invitrogen). Proteins were transferred using the IBlot2 (Thermo #IB21001) onto the iBlot™ 2 nitrocellulose Transfer Stacks (Thermo #IB23001). The membranes were then blocked in Odyssey Blocking Buffer (Li-COR #927-40000) for one hour, and then probed overnight with primary antibodies diluted in blocking buffer. The following day, membranes were washed 3×5 mins with 1×TBST and then probed with LiCOR Infrared secondary antibodies for 1 hour at room temperature. Membranes were washed an additional 3×5 mins in 1×TBST and then imaged using the LiCOR Imager.

CRISPR Genome-Wide Knockout Modifier Screen

Cas9-derivatized cells were infected with the Brunello virus library, as described in Doench et al. (Nat. Biotechnol. 2016 Jan. 18. doi: 10.1038/nbt.3437). Virus was titered to achieve an MOI of 0.3-0.6. The following day, cells were trypsinized and split into two biological replicates and selected for with puromycin for 7 days. After selection, replicates were seeded into a drug arm of either 400 nM or 700 nM of CGS15943, 1.7 μM MRS1220, or vehicle control. Cells were maintained at 37° C. and 5% $CO_2$ in CellSTACK 1272 $cm^2$ 2-STACK flasks (Corning #3269) in DMEM with 10% FBS. Cells were trypsinized and reseeded every 7 days at a bottleneck of 40 million cells in order to maintain library representation. Media and drug was refreshed every 3-4 days. Cell pellets were harvested before initial seeding and every passage up to 30 days of drug treatment. Genomic DNA was isolated from cell pellets using the NucleoSpin® Blood XL Columns (Machery Nagel #740950.50) following the manufacturer's protocol. Genomic DNA sequencing and analysis was performed by the Broad Genetic Perturbation Platform protocol using standard protocols.

Synergy/Antagonism Testing 1000 cells per well were seeded in 384 well clear bottom tissue culture plates and incubated overnight at 37° C. and 4% $CO_2$. The following day, compounds were dispensed in a combination grid format using the Tecan Digital Dispenser. Plates were incubated for 5 days and then viability was assayed using CellTiter-Glo® Cellular Viability Assay. Analysis and Synergy plots were generated using the publicly available Combenefit software package.

In-Vivo Pharmacokinetics

A study was performed to investigate the plasma pharmacokinetics of CGS-15943 (BRD-K49049886-001-12-9) in male NOD SCID mice following a single intraperitoneal administration at 3 and 15 mg/kg dose. A group of eighteen male mice were divided in to two groups with nine mice in each group. Animals in Group 1 and Group 2 were administered intraperitoneally with BRD-K49049886-001-12-9 solution formulation prepared in 7.5% NMP, 7.5% Solutol, 30% PEG-400 and 55% HPβCD (20% w/v) at 3 and 15 mg/kg dose respectively. The blood samples were collected under light isoflurane anesthesia at pre-dose, 0.08, 0.25, 0.5, 1, 2, 4, 8 and 24 hr (IP) in labeled micro centrifuge tube containing K2EDTA as anticoagulant. Immediately after blood collection, plasma was harvested by centrifugation and stored at −70° C. until analysis. All samples were processed for analysis by protein precipitation using acetonitrile and analyzed with fit-for-purpose LC-MS/MS method (LLOQ=2.05 ng/mL). Pharmacokinetic parameters were calculated using the non-compartmental analysis tool of Phoenix WinNonlin® (Version 7.0).

Example 2: Synthesis of BRO-014 (BRD-K71257481-001-01-1)

Name: 9-chloro-2-(3,5-dimethylfuran-2-yl)-[1,2,4]triazolo[1,5-c]quinazolin-5-amine

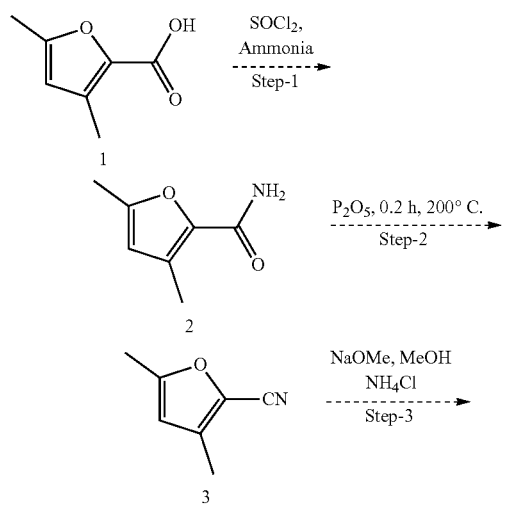

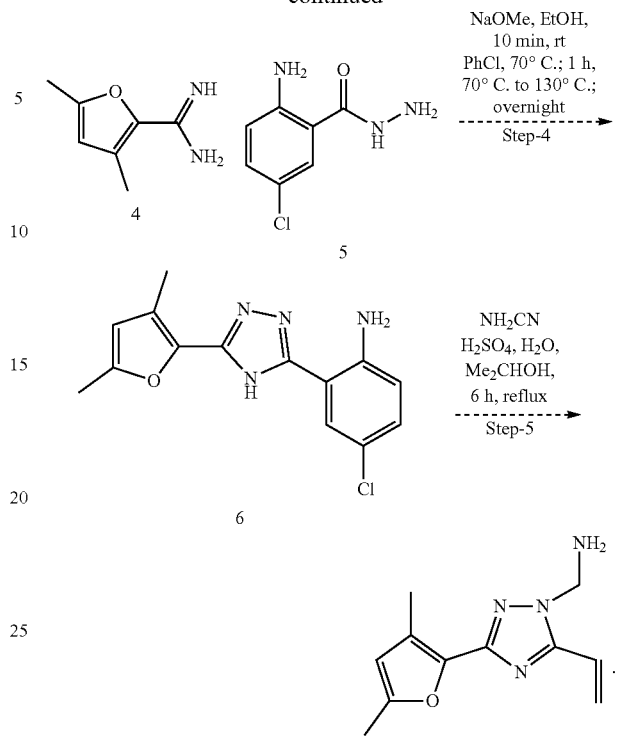

Example 3: Synthesis of BRO-017 (BRD-K01625162-001-01-0)

Name: 2-(benzofuran-2-yl)-9-chloro-[1,2,4]triazolo[1,5-c]quinazolin-5-amine)

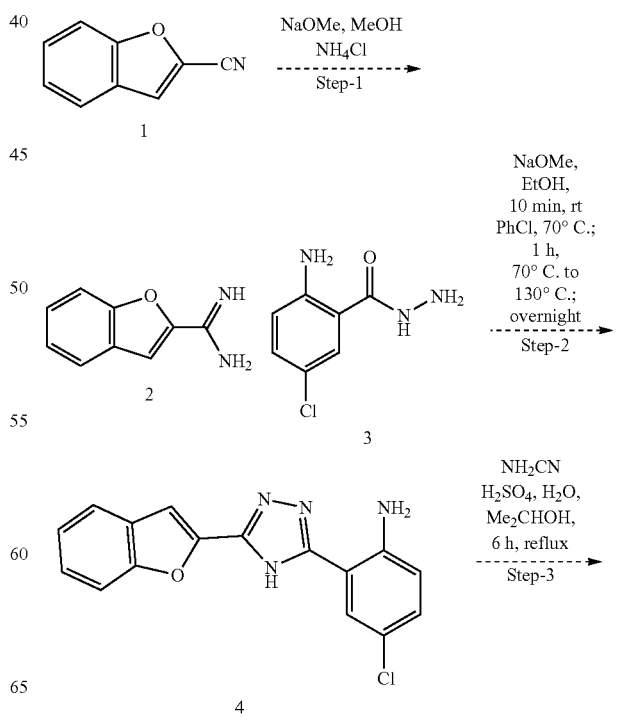

57
-continued
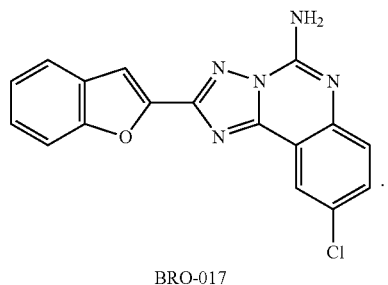
BRO-017
Example 4: Synthesis of BRO-018 (BRD-K89088840-001-01-6)
Name: 9-chloro-2-(1-methyl-1H-pyrrol-2-yl)-[1,2,4]triazolo[1,5-c]quinazolin-5-amine
Example 5: Synthesis of BRO-019 (BRD-K58390791-001-01-2)
Name: 9-chloro-2-(furan-2-yl)-N-methyl-[1,2,4]triazolo[1,5-c]quinazolin-5-amine
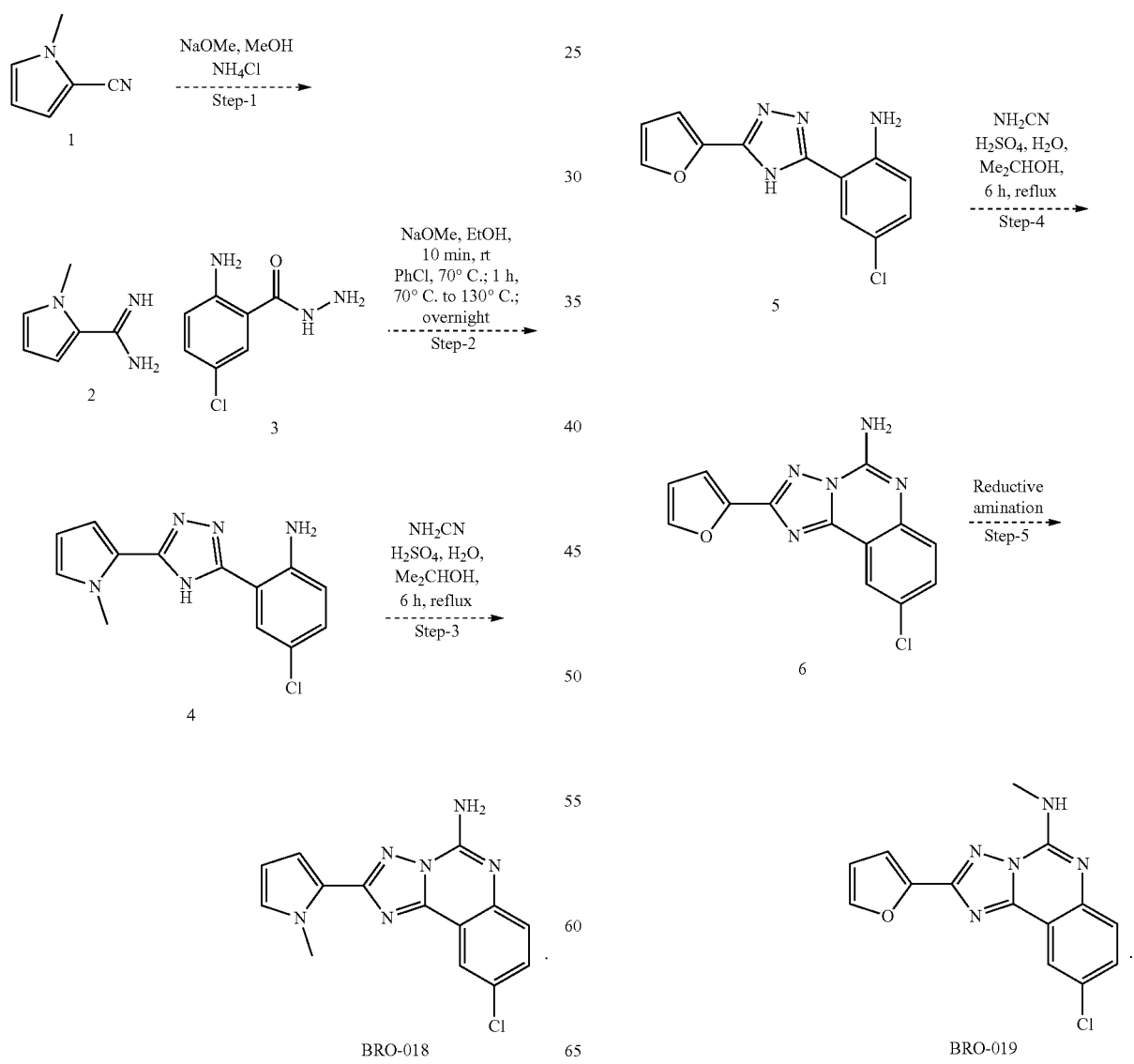

Example 6: Synthesis of BRO-020
(BRD-K10462076-001-01-2)

Name: 9-chloro-2-(furan-2-yl)-N,N-dimethyl-[1,2,4]triazolo[1,5-c]quinazolin-5-amine

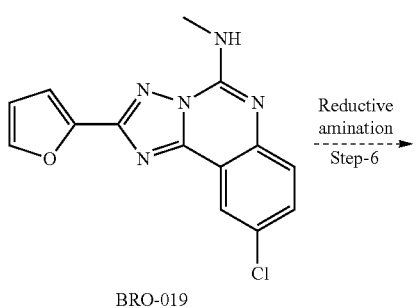

BRO-019

→ Reductive amination, Step-6 →

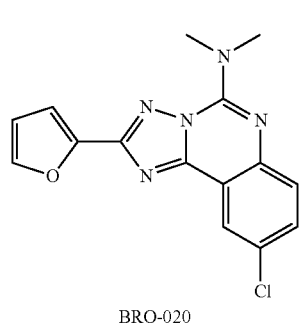

BRO-020

Example 7: Synthesis of BRO-021
(BRD-K33357102-001-01-5)

Name: 9-chloro-2-(furan-2-yl)-N-phenyl-[1,2,4]triazolo[1,5-c]quinazolin-5-amine

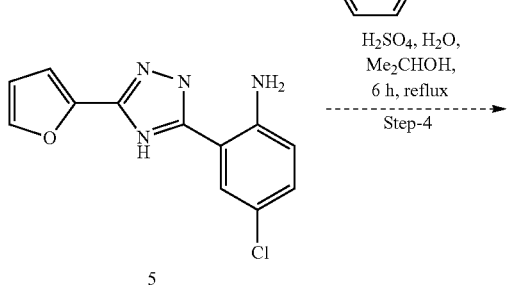

H$_2$SO$_4$, H$_2$O, Me$_2$CHOH, 6 h, reflux
Step-4 →

-continued

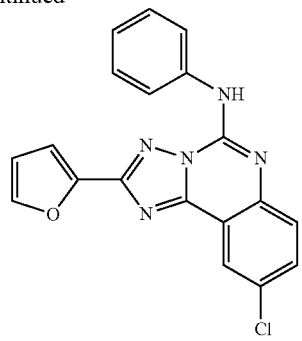

BRO-021

Example 8: Synthesis of BRO-022
(BRD-K85258437-001-01-8)

Name: 9-chloro-2-(furan-2-yl)-[1,2,4]triazolo[1,5-c]quinazoline

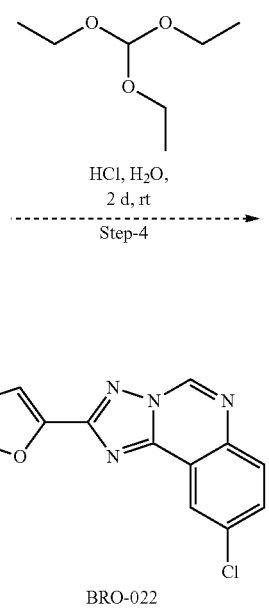

HCl, H$_2$O, 2 d, rt
Step-4 →

BRO-022

Example 9: Synthesis of BRO-023
(BRD-K14579483-001-01-6)

Name: 9-fluoro-2-(furan-2-yl)-[1,2,4]triazolo[1,5-c]quinazolin-5-amine

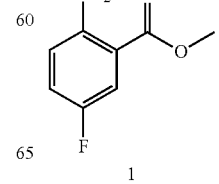

Tri phosgene, THF, > 4 h, rt
N$_2$H$_4$—H$_2$O, EtOH, rt; 2 h, rt
Step-1 →

1

-continued
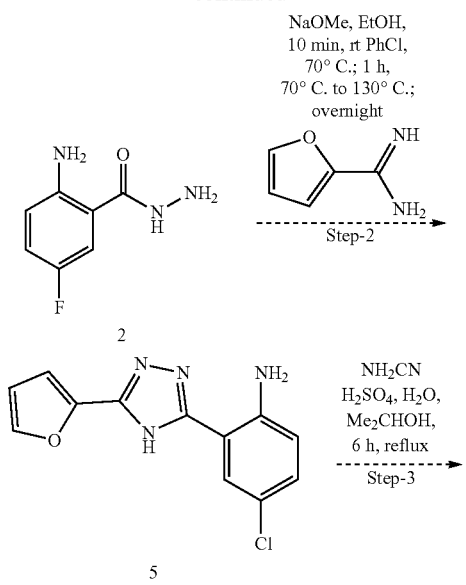
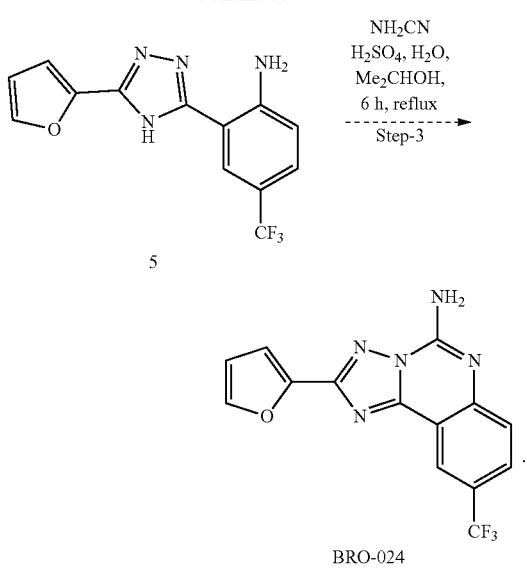
Example 11: Synthesis of BRO-025 (BRD-K72736282-001-01-4)
Name: 2-(furan-2-yl)-9-isopropyl-[1,2,4]triazolo[1,5-c]quinazolin-5-amine
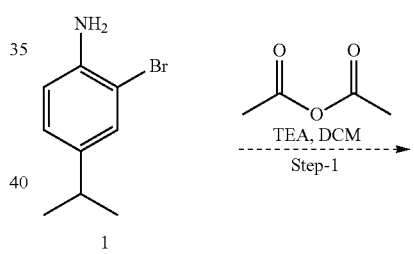
Example 10: Synthesis of BRO-024 (BRD-K02770140-001-01-0)
Name: 2-(furan-2-yl)-9-(trifluoromethyl)-[1,2,4]triazolo[1,5-c]quinazolin-5-amine
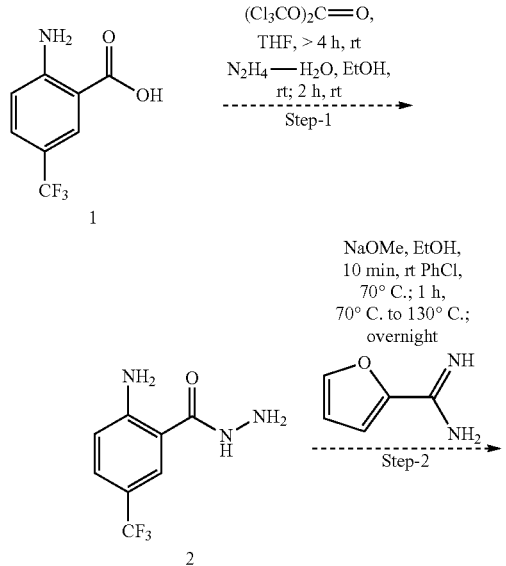

-continued
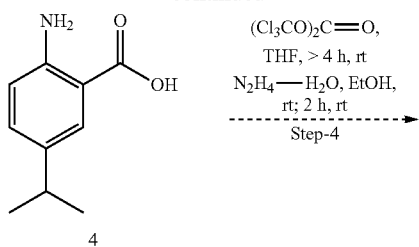
4
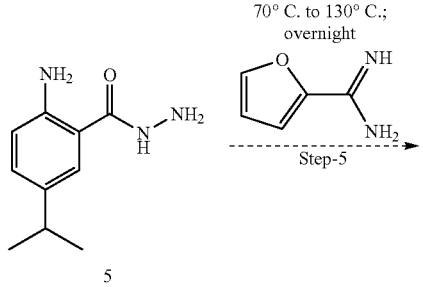
5
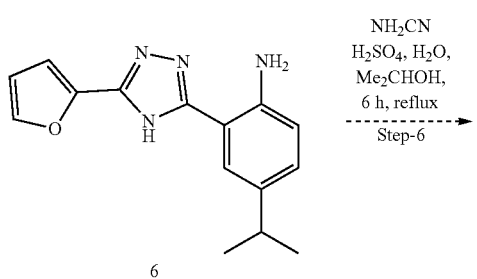
6
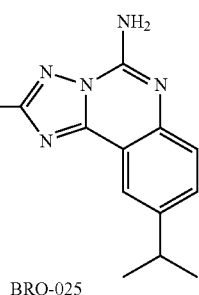
BRO-025
Example 12: Synthesis of BRO-026 (BRD-K80814736-001-01-1)
Name: 8-chloro-2-(furan-2-yl)-[1,2,4]triazolo[1,5-c]quinazolin-5-amine
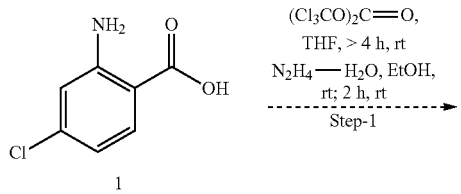
1
-continued
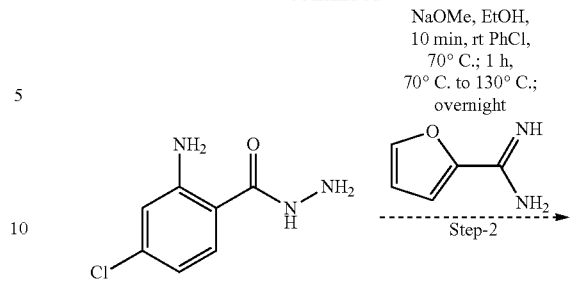
2
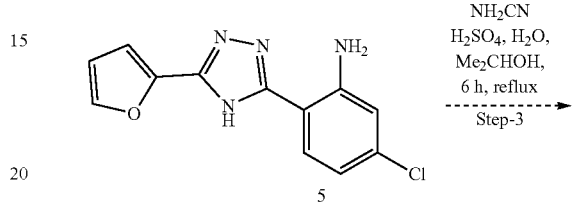
5
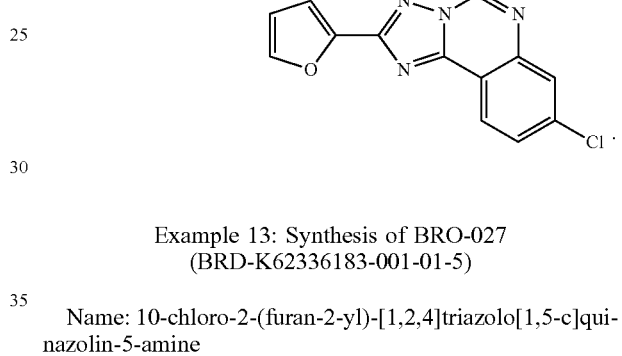
Example 13: Synthesis of BRO-027 (BRD-K62336183-001-01-5)
Name: 10-chloro-2-(furan-2-yl)-[1,2,4]triazolo[1,5-c]quinazolin-5-amine
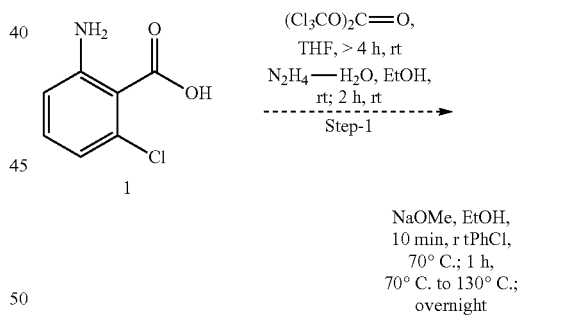
1
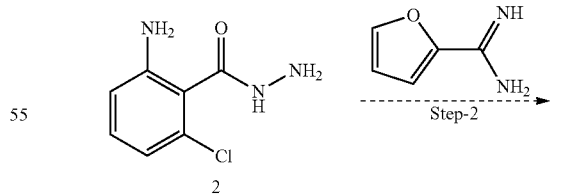
2
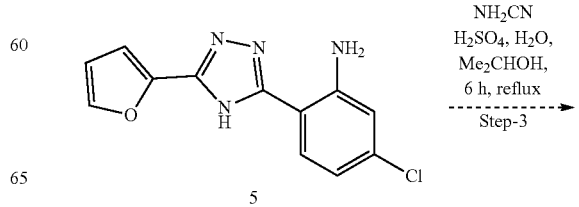
5

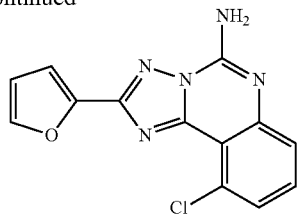
Example 14: Synthesis of BRO-013 (BRD-K62027577-001-01-4)
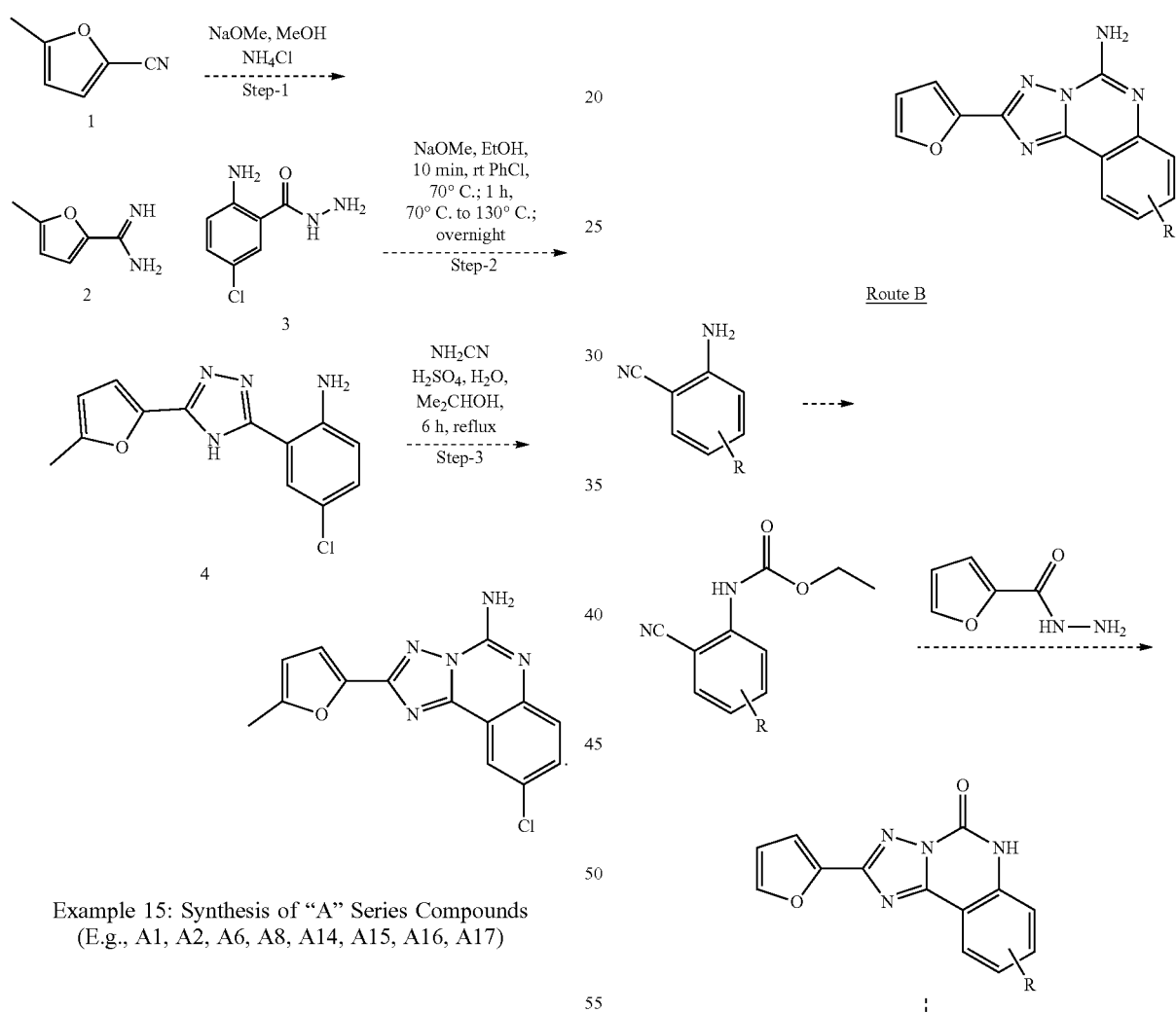
Example 15: Synthesis of "A" Series Compounds (E.g., A1, A2, A6, A8, A14, A15, A16, A17)
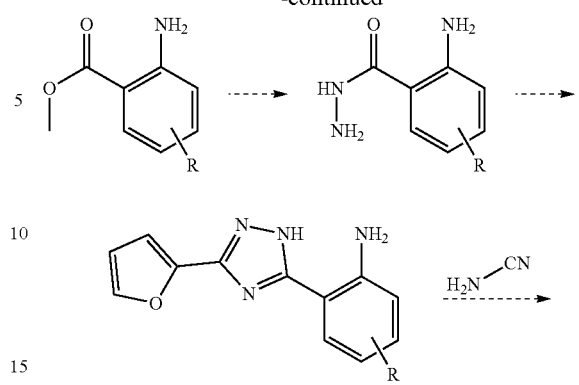
Route B
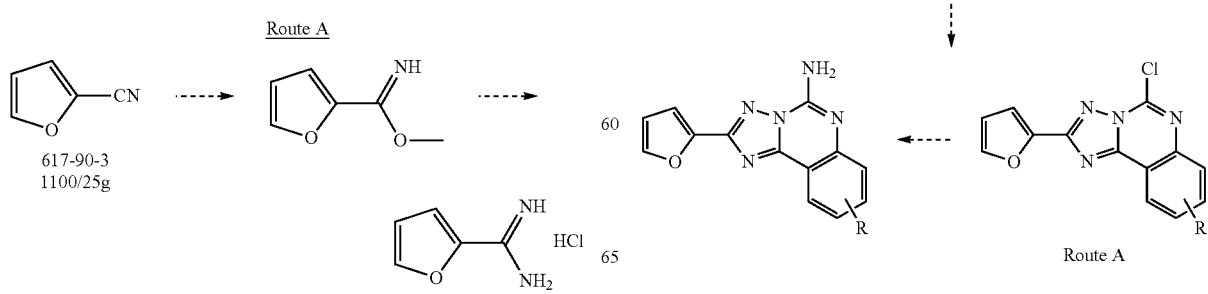
Route A The following compounds A6 and A8 of the "A" series are noted as specifically disclosed herein:

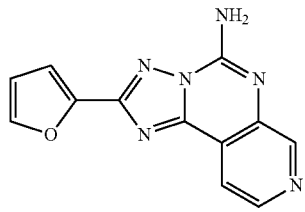
A6

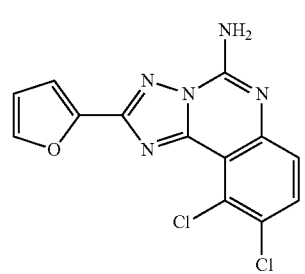
A8

Example 16: Synthesis of "B" Series Compounds (E.g., B1, B2, B3, B5, B7)

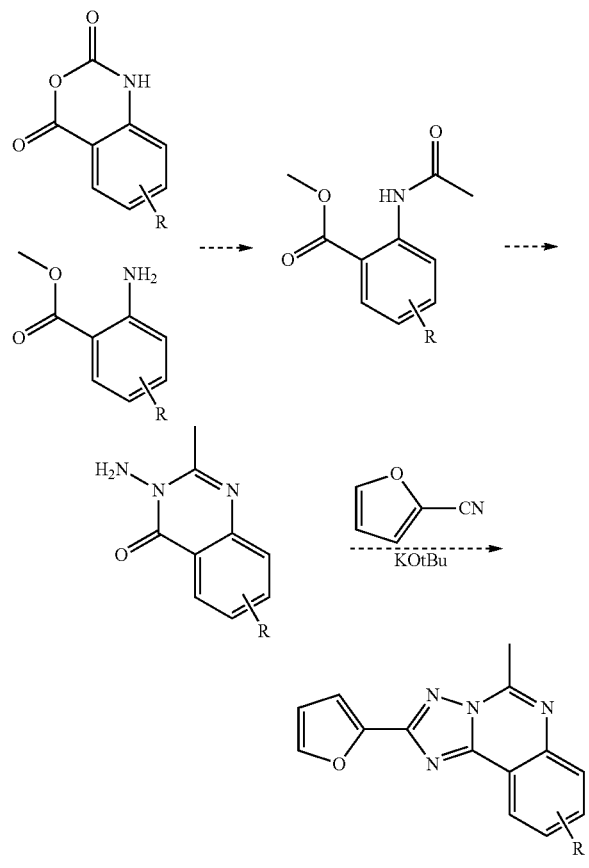

Figure 1B:
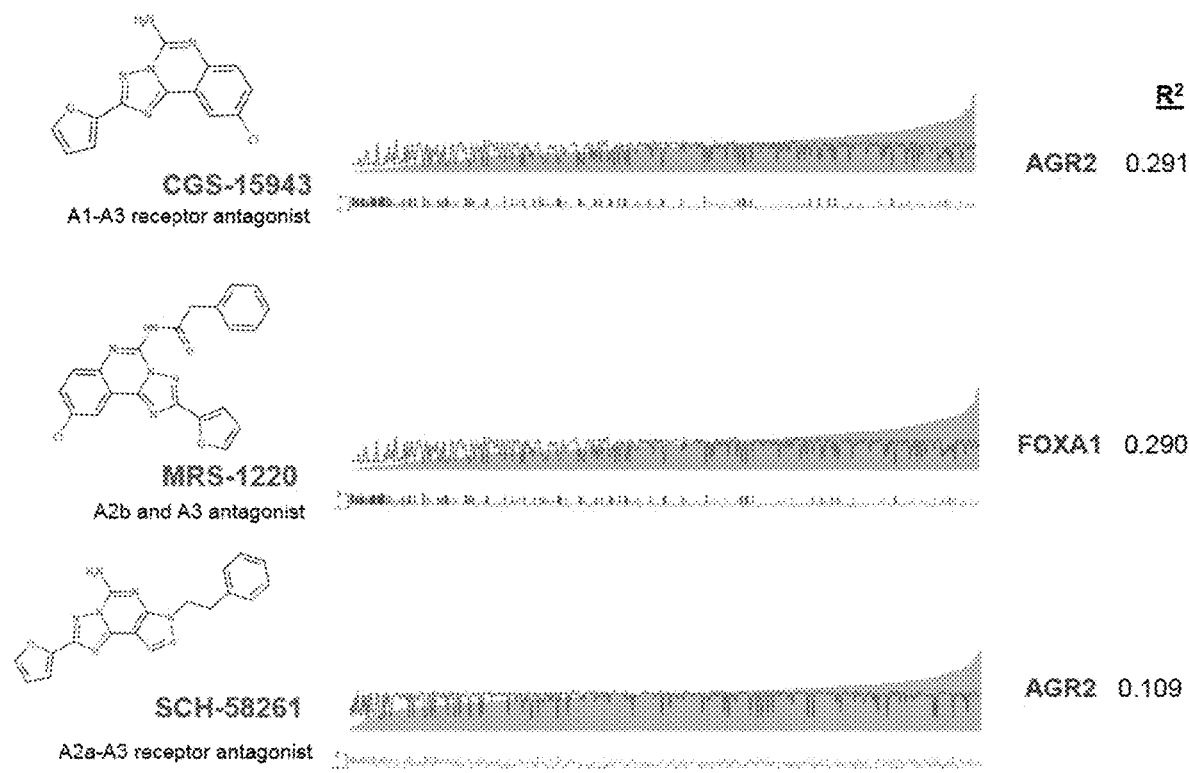
Figure 1C:
Figure 2B:
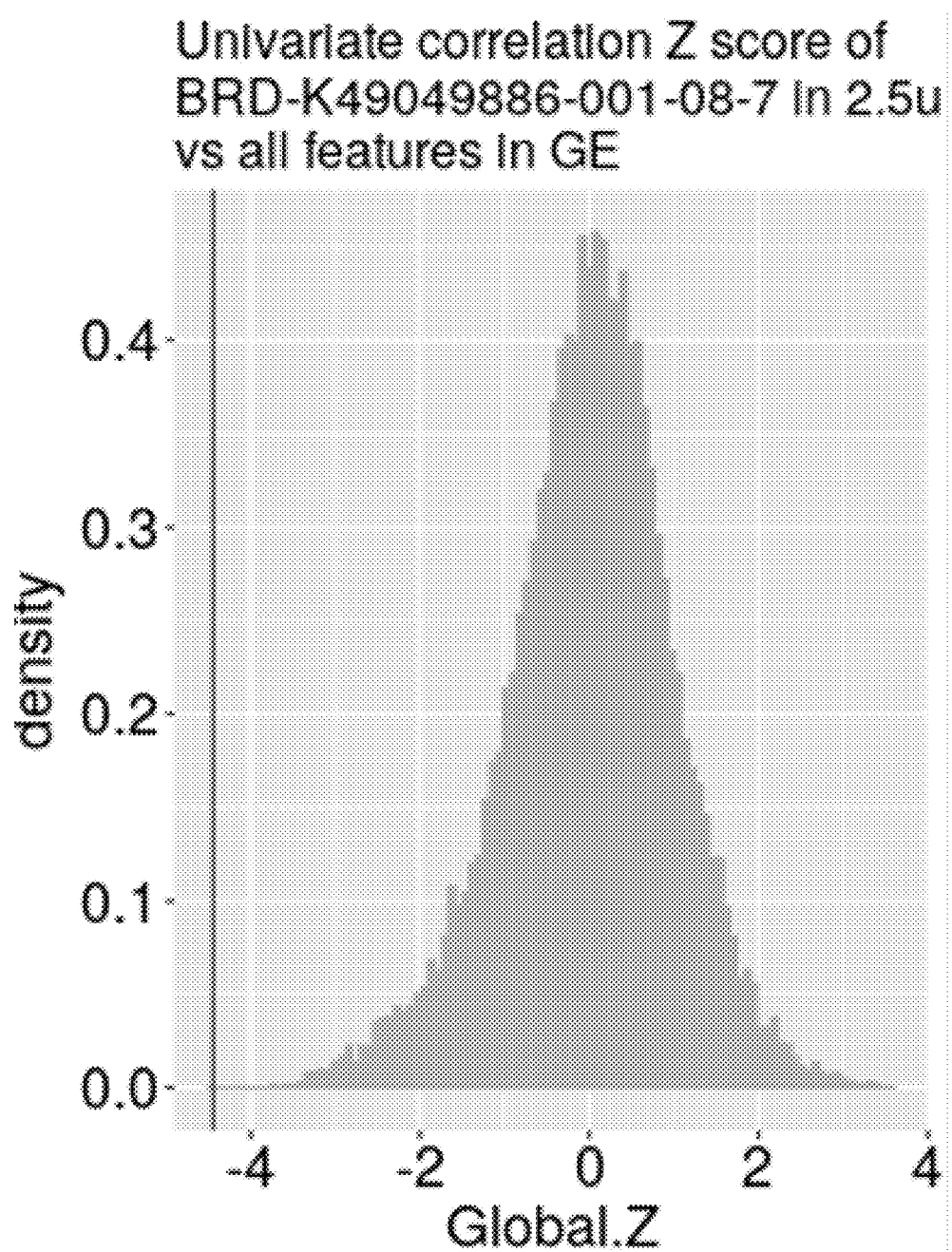
Figure 2C:
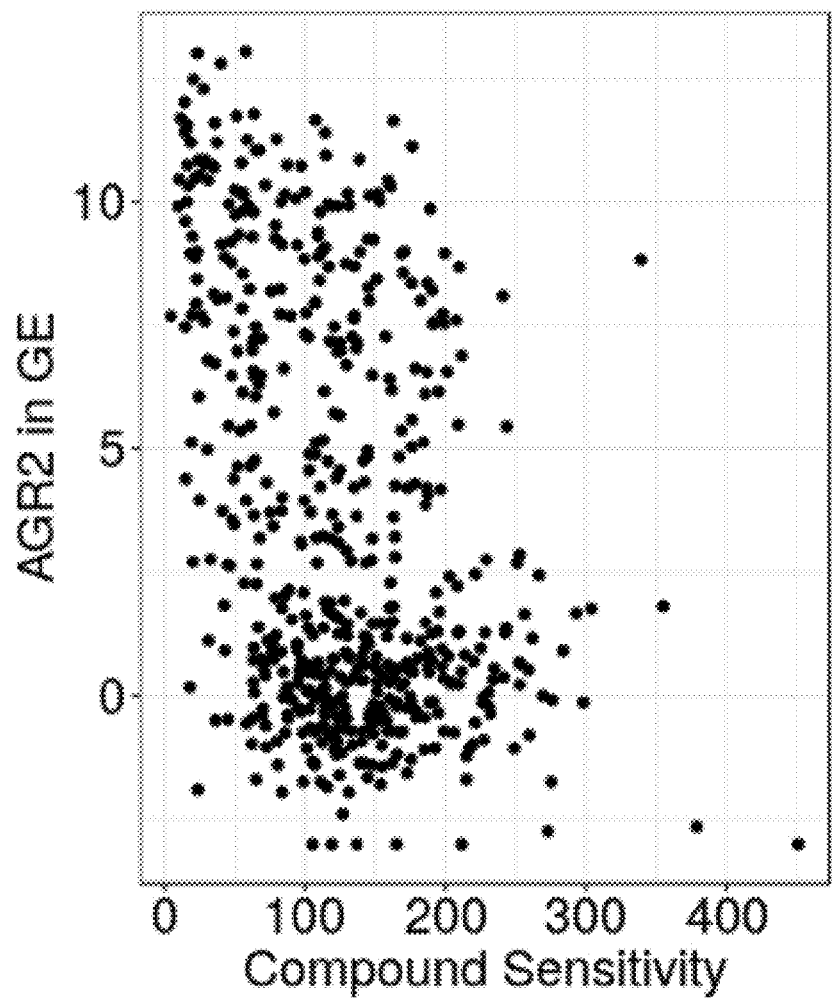

Example 17: PRISM Screening Identified Known Adenosine Receptor Antagonists as Cytotoxic to FOXA1-Dependent Cancer Cell Lines PRISM screening was applied to a drug repurposing library (described in Corsello et al. *Nat. Medicine* 23: 405-408), to identify compounds that were selectively capable of killing cancer cell lines characterized by elevation of FOXA1 and/or FOXA1 target (e.g., AGR2, AGR3, EMP3, etc.) mRNA and/or protein expression levels. Three compounds previously characterized as adenosine receptor antagonists—CGS-15943, MRS-1220, and SCH-58261—were observed to exhibit a shared cell killing profile specific for such FOXA1-dependent cancer cell lines (FIGS. 1A to 1C), a profile distinct from those observed for other compounds of the input cell repurposing library. The top expression features identified for cytotoxicity effects observed for CGS-15943, MRS-1220 and SCH-58261 included FOXA1 and the FOXA1 targets, AGR2 and AGR3 (FIG. 2A-FIG. 2C), which validated the FOXA1-dependency of such compound-mediated cytotoxic effects (FIGS. 2A to 2C). The FOXA1-dependent cytotoxicity effects observed for CGS-15943, MRS-1220 and SCH-58261 were most notably distinguishable from other previously characterized adenosine receptor antagonist compounds, and it was therefore surmised that these compounds likely exerted their effects via a mechanism distinct from their previously characterized activities as adenosine receptor antagonists.

Figure 3:
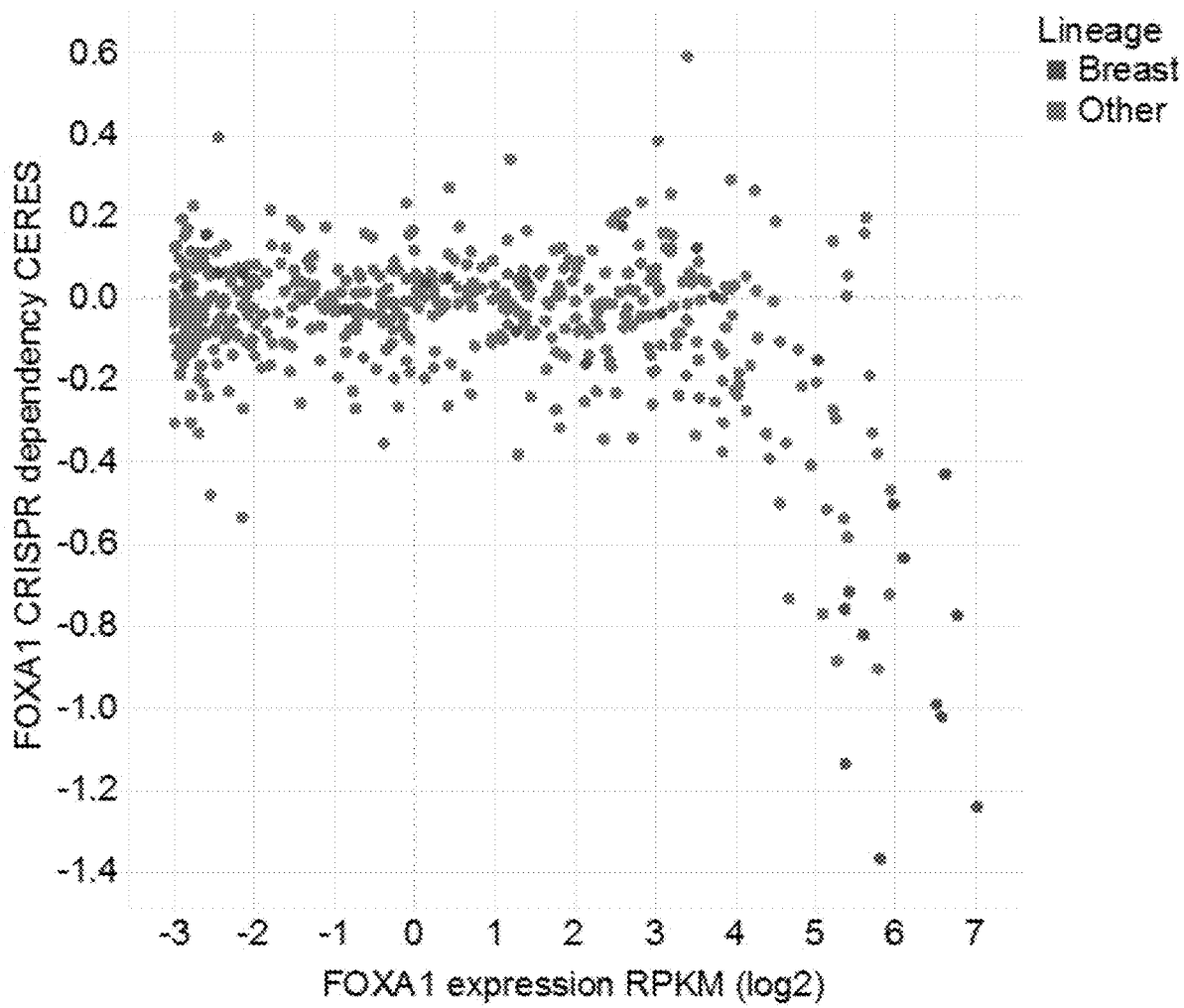
FIG. 3 shows a correlation plot of FOXA1 CRISPR knockout vs FOXA1 expression. FOXA1 was demonstrated as a lineage-specific cancer dependency for luminal breast cancer.
Figure 4A:
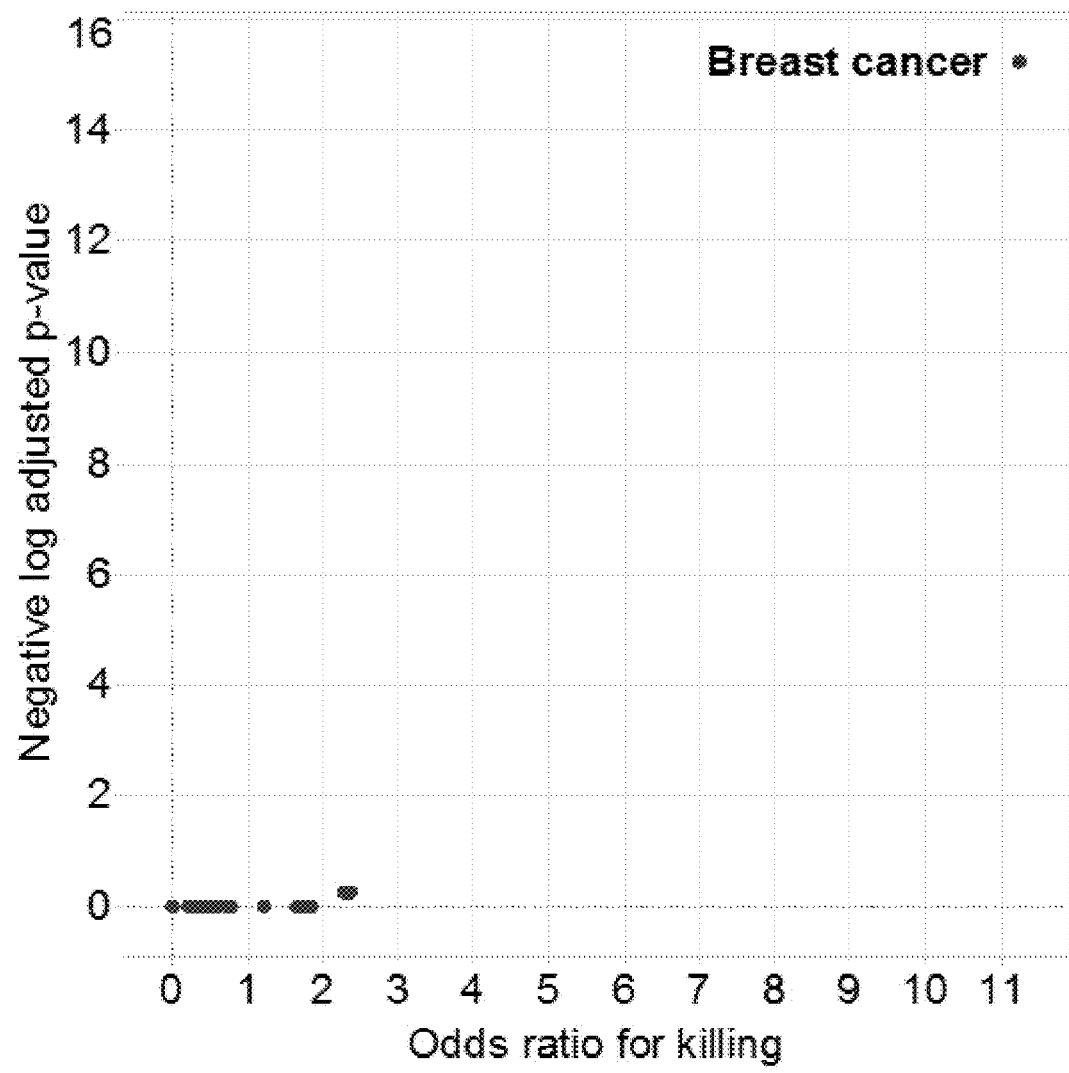
FIGS. 4A and 4B depict a dot-plot and heatmap, respectively, which show selective killing patterns observed for CGS-15943 against assayed cancer lines.
Figure 4B:
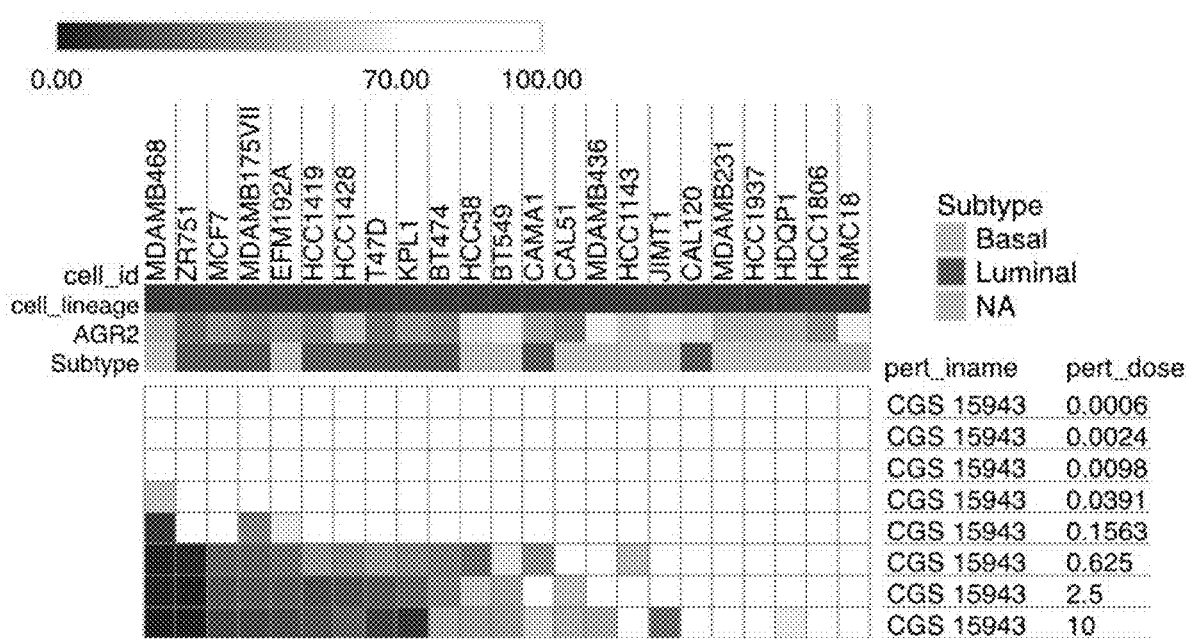
Figure 5:
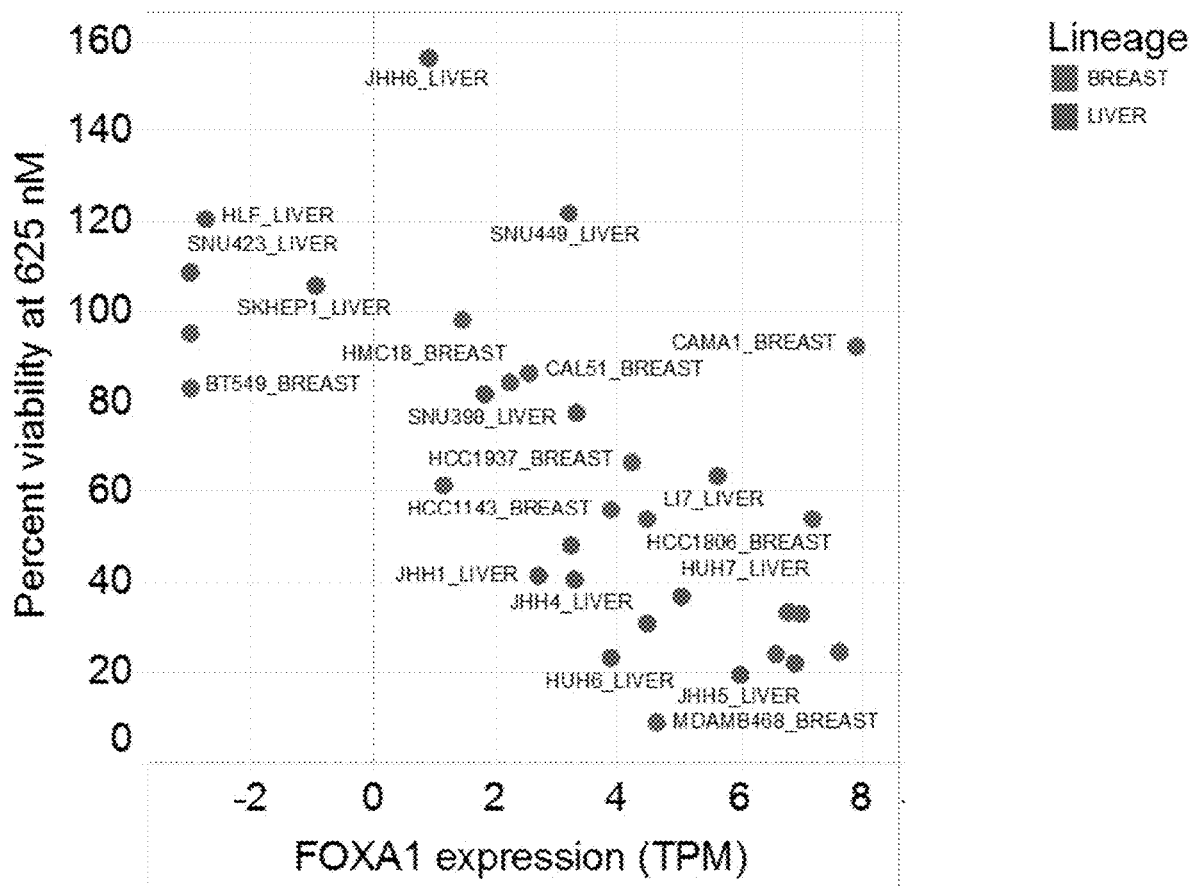
FIG. 5 shows a plot demonstrating that selective killing of FOXA1-high cancer cell lines, which was an effect observed for multiple compounds previously described as adenosine receptor antagonists (CGS-15943, MRS-1220 and SCH-58261).

FOXA1 has been previously characterized as a forkhead box transcription factor that acts on condensed chromatin and at distal enhancer sites as pioneer factor. It has been identified as highly expressed in hepatocytes and luminal breast cancers, but it has presented a challenging pharmacological target since it is a transcription factor. The instant studies demonstrated FOXA1 to be a lineage-specific cancer dependency for luminal breast cancer, via CRISPR-Cas9 knockout of FOXA1 in various cell lines possessing highly varying native levels of FOXA1 expression (FIG. 3). In particular, CGS-15943 exhibited a selective killing pattern across tested cell lines, with enrichment for luminal breast cancer cell lines (FIGS. 4A and 4B). Furthermore, CGS-15943 showed selective killing of FOXA1-high cancer cell lines, as compared to assayed cancer cell lines that possessed lower FOXA1 expression levels (FIG. 5).

Figure 6A:
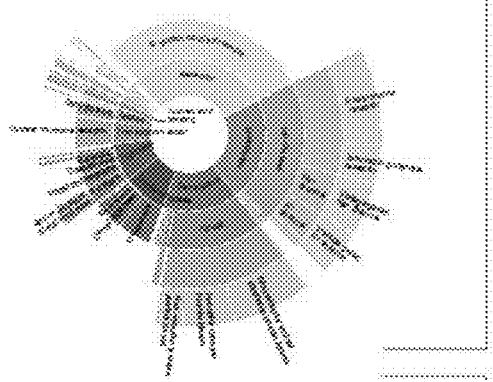
FIGS. 6A and 6B show a diagram and illustration that depict adenosine receptor validation.
Figure 6B:
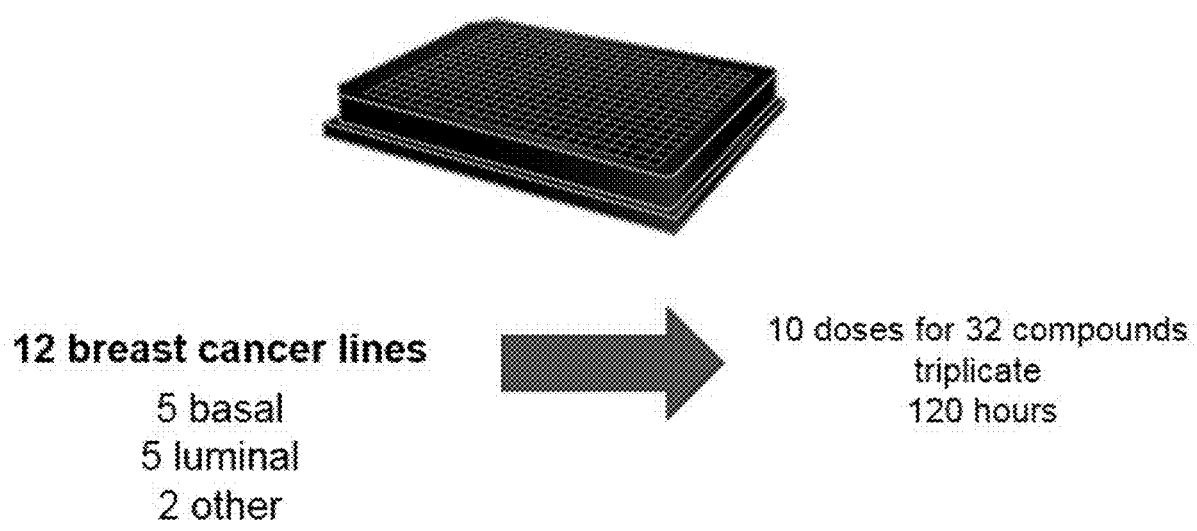
Figure 7B:
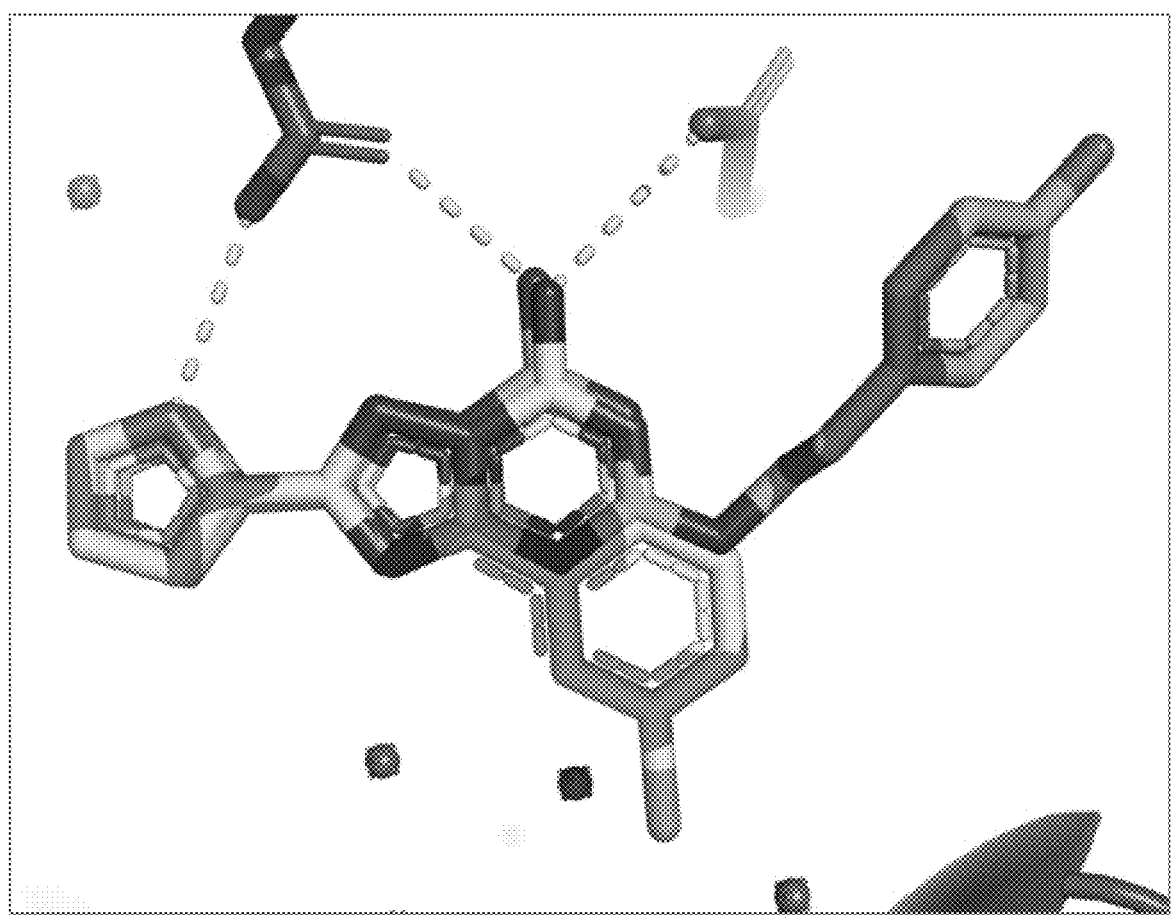

Example 18: CGS-15943 Cancer Cell Killing was Likely Driven by an Off-Target Effect To explore whether the cell-selective cytotoxic effects observed for CGS-15943, MRS-1220 and SCH-58261 occurred via a mechanism distinct from these compounds' previously characterized adenosine receptor antagonist activities, a more directed comparison was made between these compounds and a total of 20 other known adenosine receptor antagonists and a total of nine known adenosine receptor agonists found in the screened compound repurposing library. The compound repurposing library specifically contained a total of 59 compounds that had been previously identified as targeting adenosine receptors in some manner. From this group of compounds, a total of 23 were previously identified as adenosine receptor antagonists (three of which were CGS-15943, MRS-1220 and SCH-58261), while nine had been previously identified as adenosine receptor agonists (FIG. 6A). Twelve different breast cancer cell lines were dosed with the selected 32 compounds, and CGS-15943, MRS-1220, and SCH-58261 were the only compounds identified as cytotoxic to the breast cancer cell lines assayed (FIG. 6B).

Having identified and validated the above-described distinct cell killing activities of CGS-15943, MRS-1220, and SCH-58261, the structures of each of these compounds were examined, and particular structural analogs of CGS-15943 were produced and/or obtained. Initial characterization of structural analogs of CGS-15943 revealed a structure activity relationship ("SAR") for assayed CGS-15943 analogs that further indicated that the cytotoxic effects observed for CGS-15943 occurred via an off-target mechanism. The analog studies supported that the furan ring was essential for its observed cytotoxic effect, whereas the amino-group was not required and multiple substituents were tolerated at the $R_1$ position (FIG. 7A and FIGS. 8A to 8D). Yet the amino-group was previously observed to play an important role in the binding of the CGS-15943 compound to the A2a receptor (FIG. 7B), further demonstrating that cytotoxicity of CGS-15943 occurred independently of A2a adenosine receptor binding. While many existing drugs contain a furan ring (e.g., Prazosin, Furosemide, Lapatinib, Mometasone furoate and Cefuroxime, among others), the effects observed for CGS-15943 were identified as distinct from those of such compounds. Thus, to summarize, CGS-15943 anti-cancer activity was likely driven by an off-target effect as 20 other adenosine receptor antagonists were inactive. Additionally, the CGS-15943 derivatives with expected loss of adenosine receptor binding actually remained active for cytotoxic effect.

Figure 9A:
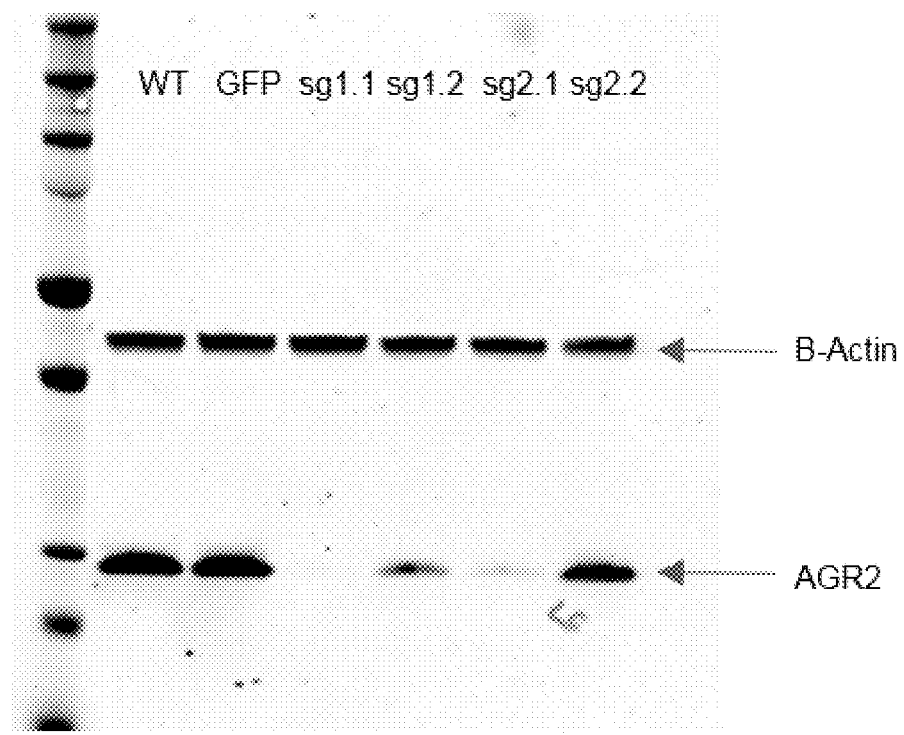
FIGS. 9A and 9B show a pair of immunoblots that demonstrate CRISPR-Cas9-mediated knockout of AGR2 in the indicated cell lines.
Figure 9B:
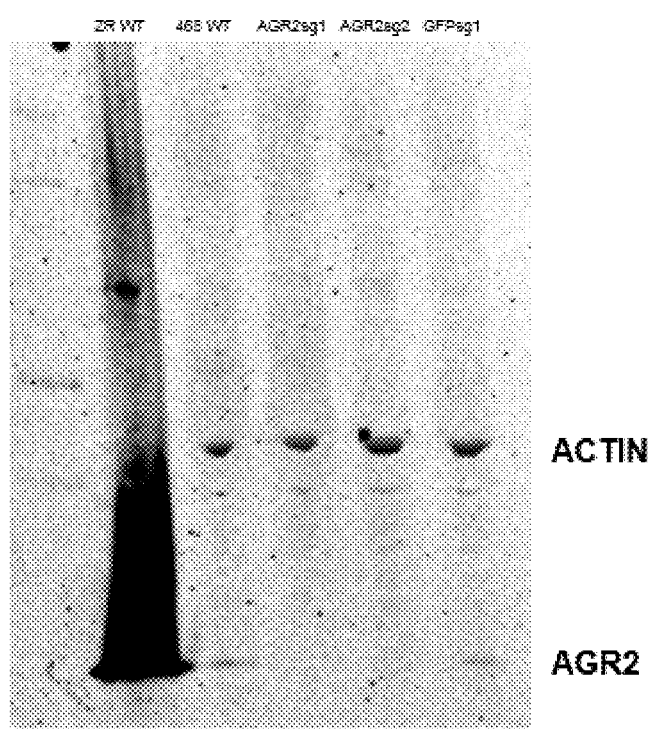
Figure 10A:
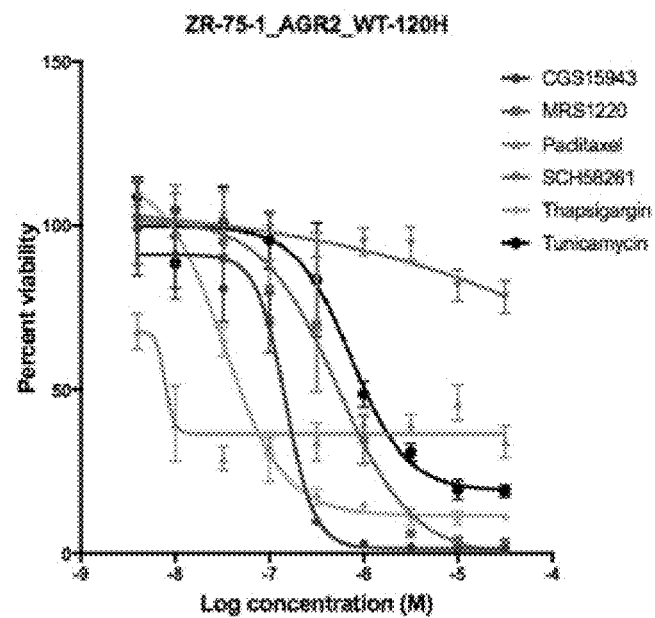
FIGS. 10A to 10D show a series of dose-response curves and a table, which illustrate that CGS-15943 cytotoxicity was not rescued by AGR2 knockout.
Figure 10B:
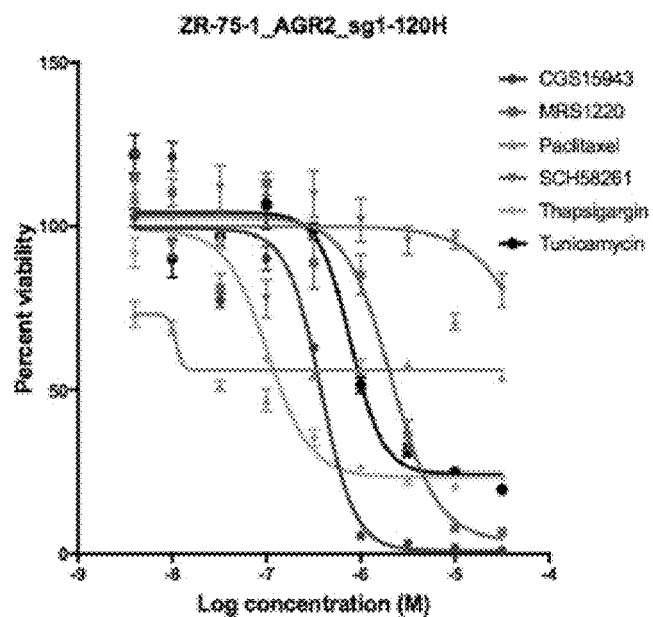
Figures 10C, 10D:
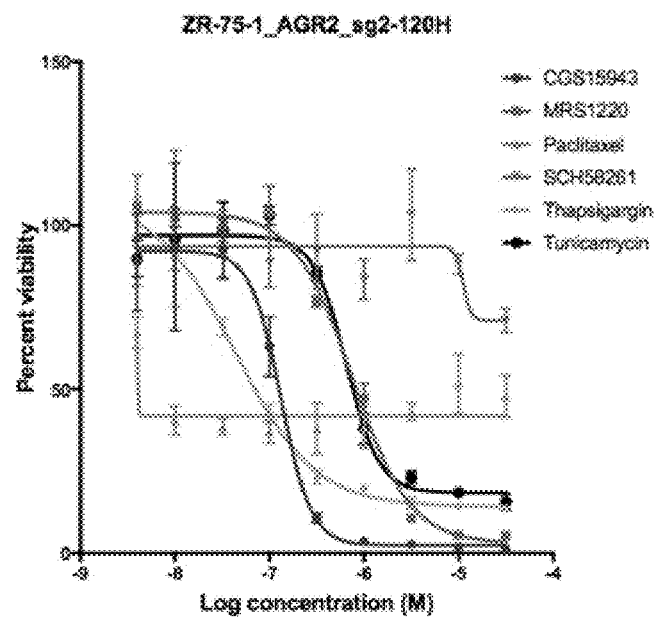

It was then examined whether knockout of the FOXA1 gene target, AGR2, in CGS-15943-susceptible breast cancer cells could rescue such knockout breast cancer cells from CGS-15943 cytotoxicity. Initially, CRISPR-Cas9-mediated knockout of the AGR2 gene was performed in CGS-15943-susceptible breast cancer cell lines ZR-75-1 and MDA-MB-468 (FIGS. 9A and 9B). These breast cancer cell lines harboring an AGR2 knockout were then separately dosed with CGS-15943, MRS-1220, Paclitaxel, SCH-58261, Thapsigargin and Tunicamycin. CGS-15943 cytotoxicity was not rescued by AGR2 knockout (FIG. 10A-FIG. 10D). These results indicated that while AGR2 expression might serve as a predictive biomarker for certain breast cancers, the presence and/or expression of AGR2 was not functionally required for the CGS-15943 cytotoxic drug response observed.

Example 19: Genome-Wide CRISPR-Cas9 Modifier Screens Identified AHR and ARNT

Figure 11A:
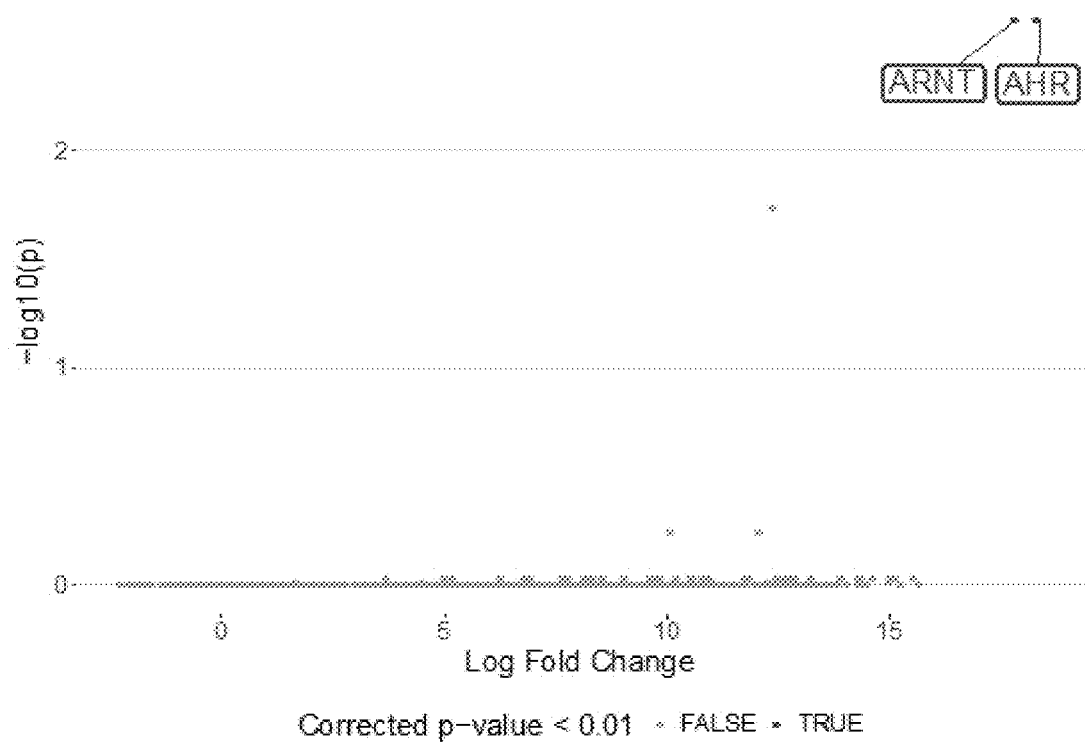
FIGS. 11A and 11B show respective plots obtained from performance of genome-wide modifier screens of breast cancer cell lines MDA-MB-468 and ZR-75-1.
Figure 11B:
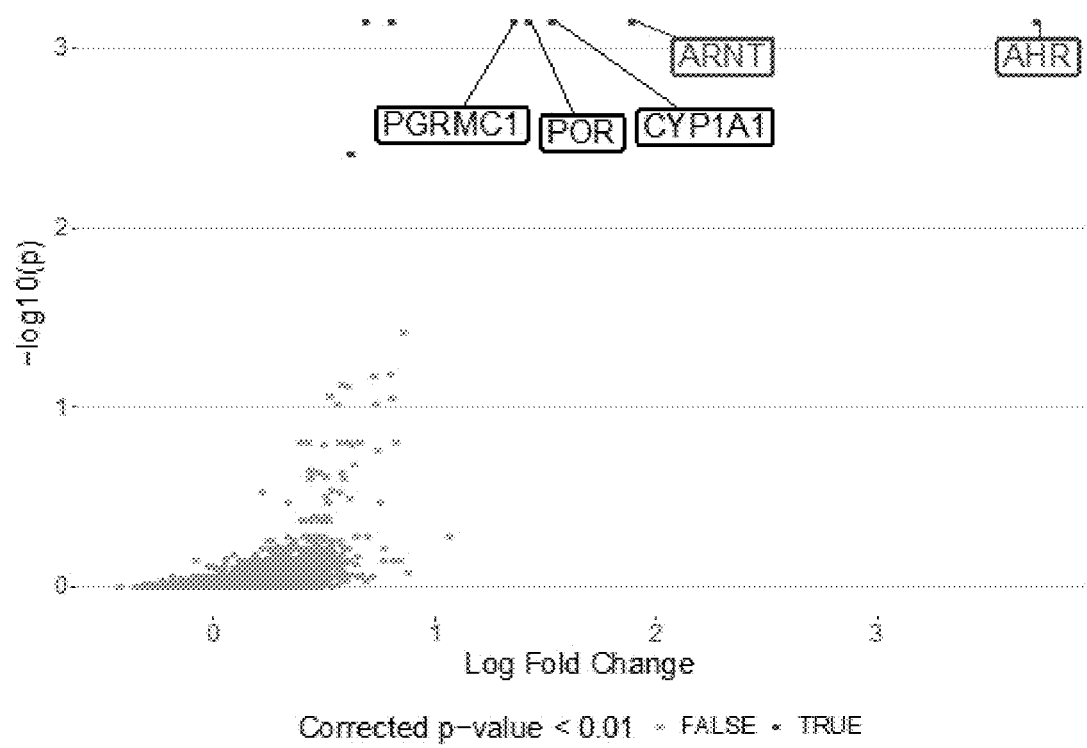
Figure 12A:
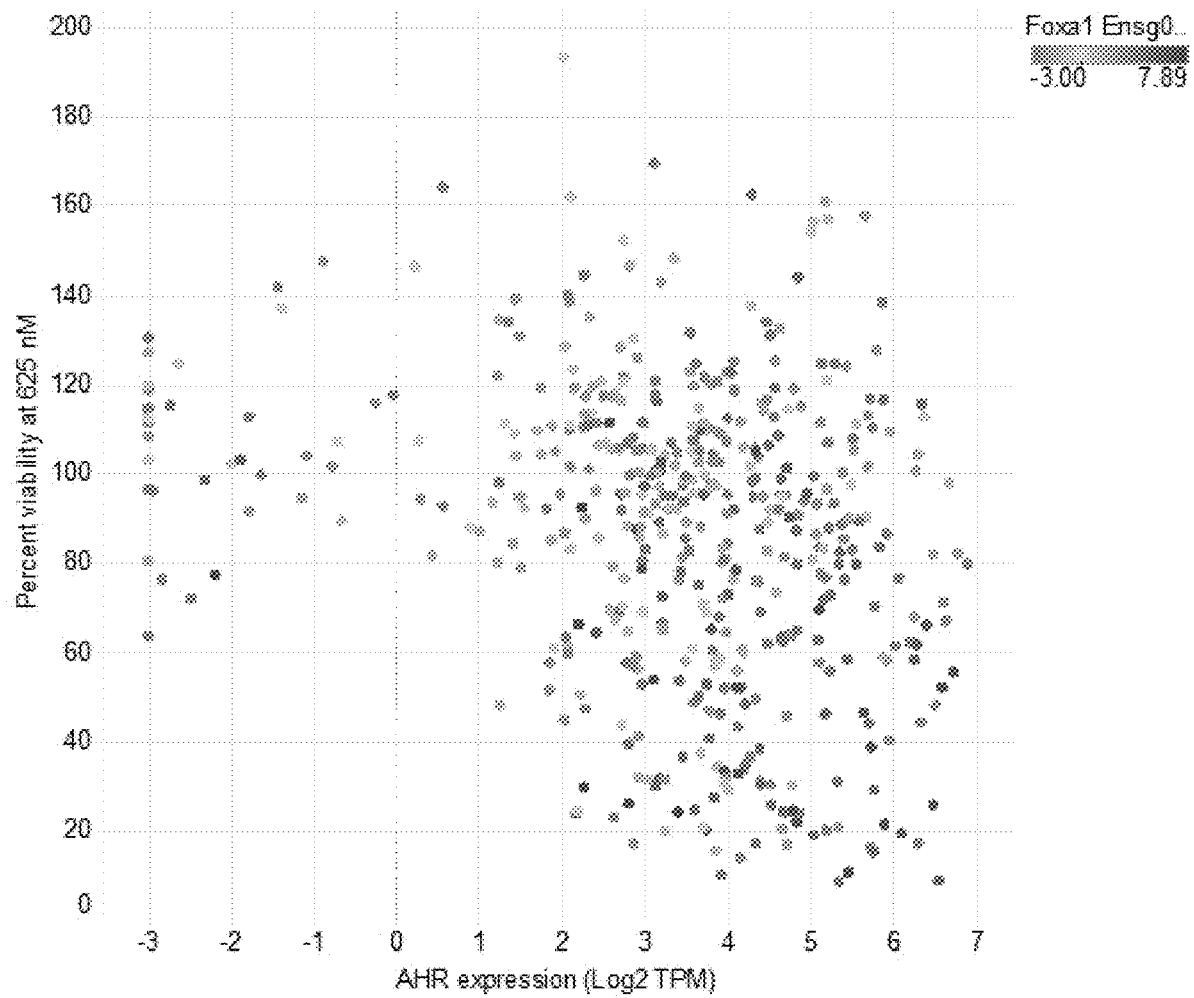
FIGS. 12A and 12B show a viability plot and correlation plot which demonstrated that CGS-15943 activity required intact AHR expression.
Figure 12B:
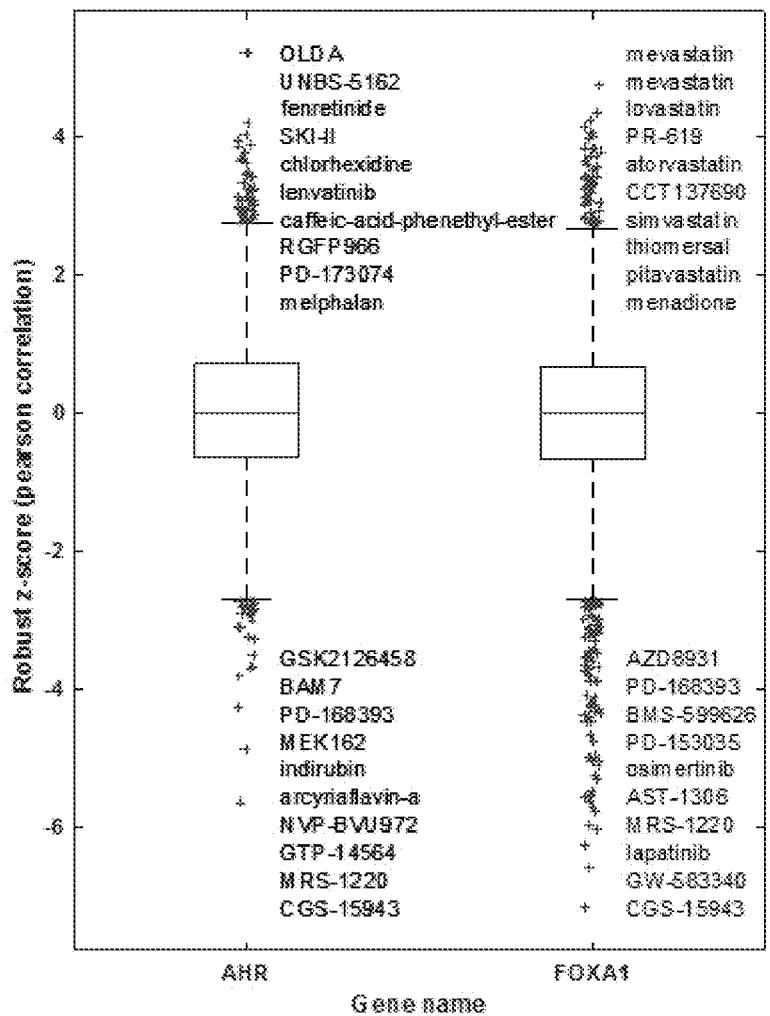

Genome-wide CRISPR-Cas-9 modifier screens were performed upon breast cancer cell lines MDA-MB-468 and ZR-75-1, in an attempt to identify the gene targets through which the observed CGS-15943 cytotoxic effects might be acting. These screens revealed aryl hydrocarbon receptor (AHR) and an associated protein, AhR nuclear translocator (ARNT), as striking hits upon which the cytotoxic effect of CGS-15943 relied in both assayed cell lines (FIGS. 11A and 11B). In addition, the modifier screen of ZR-75-1 revealed not only AHR and ARNT, but also PGRMC1, POR and CYP1A1 as robust hits. PRISM data were then examined for CGS-15943 treatment (dosed at 625 nM), sorting for AHR expressions, which revealed that cell lines elevated for FOXA1 and expressing normal to high levels of AHR exhibited the greatest susceptibility to CGS-15943 (FIG. 12A), consistent with the newly identified relevance of AHR to the observed CGS-15943 cell killing effect. Indeed, CGS-15943 and MRS-1220 were identified as showing high correlation (as reflected in robust z-score, Pearson correlation values) of their effects with both AHR and FOXA1, respectively (FIG. 12B).

Figure 13A:
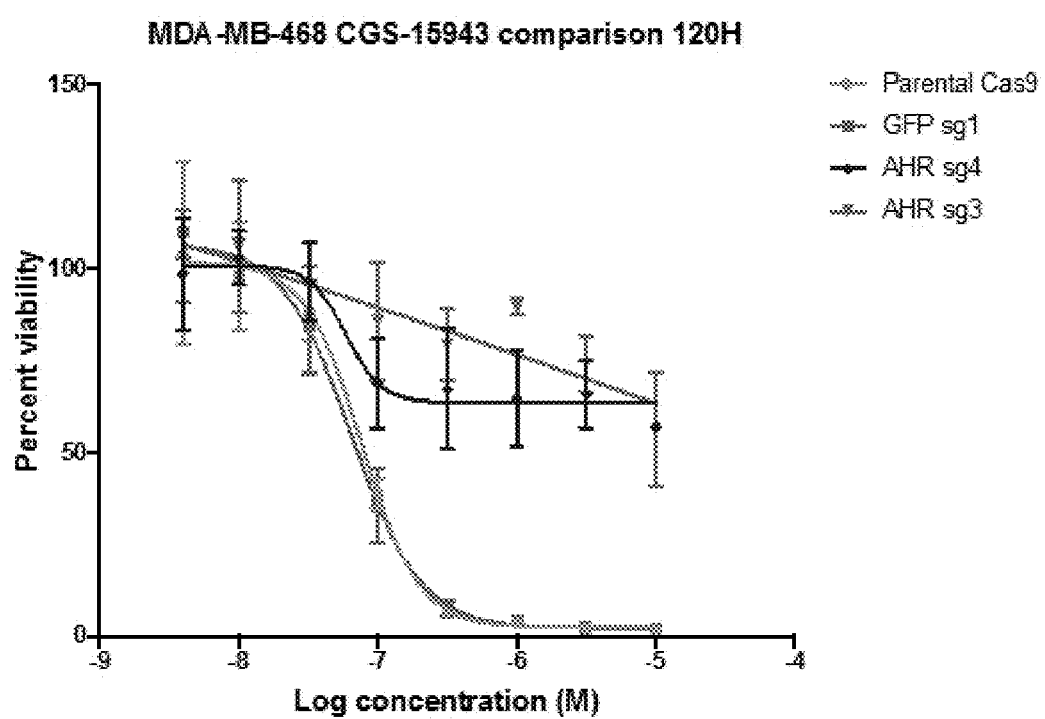
FIGS. 13A and 13B show dose-response curves for CGS-15943 under wild-type and AHR knockout conditions in breast cancer cell lines MDA-MB-468 and ZG-75-1, respectively.
Figure 13B:
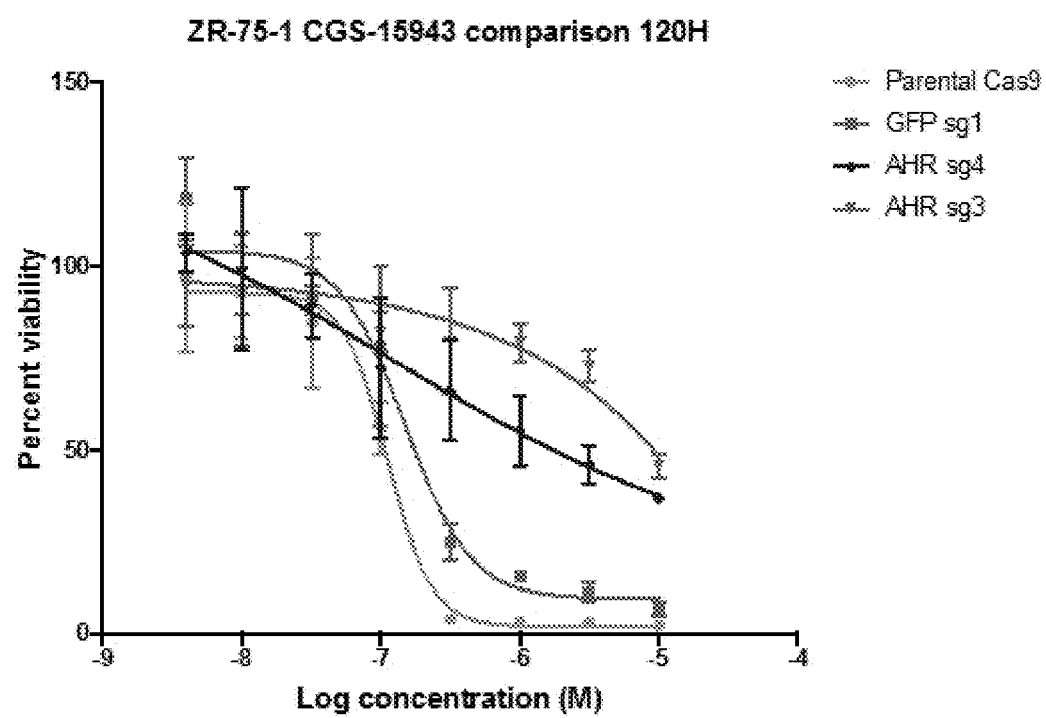

The MDA-MB-468 and ZR-75-1 cell lines were then dosed with CGS-15943 and either CRISPR-Cas9-active AHR knockout-active guide RNAs ("AHR sg3" and AHR sg4" agents) or a GFP knockout-active guide RNA ("GFP sg1") or parental Cas9 as controls. Reflecting the AHR-reliance of the observed CGS-15943 cytotoxicity effect upon these cell lines, robust levels of viability were observed only in AHR knockout cells at elevated doses of CGS-15943, whereas control cells showed dose-responsiveness of cell killing at increasing levels of CGS-15943 (FIGS. 13A and 13B). CGS-15943 activity therefore required intact AHR expression.

Figure 14:
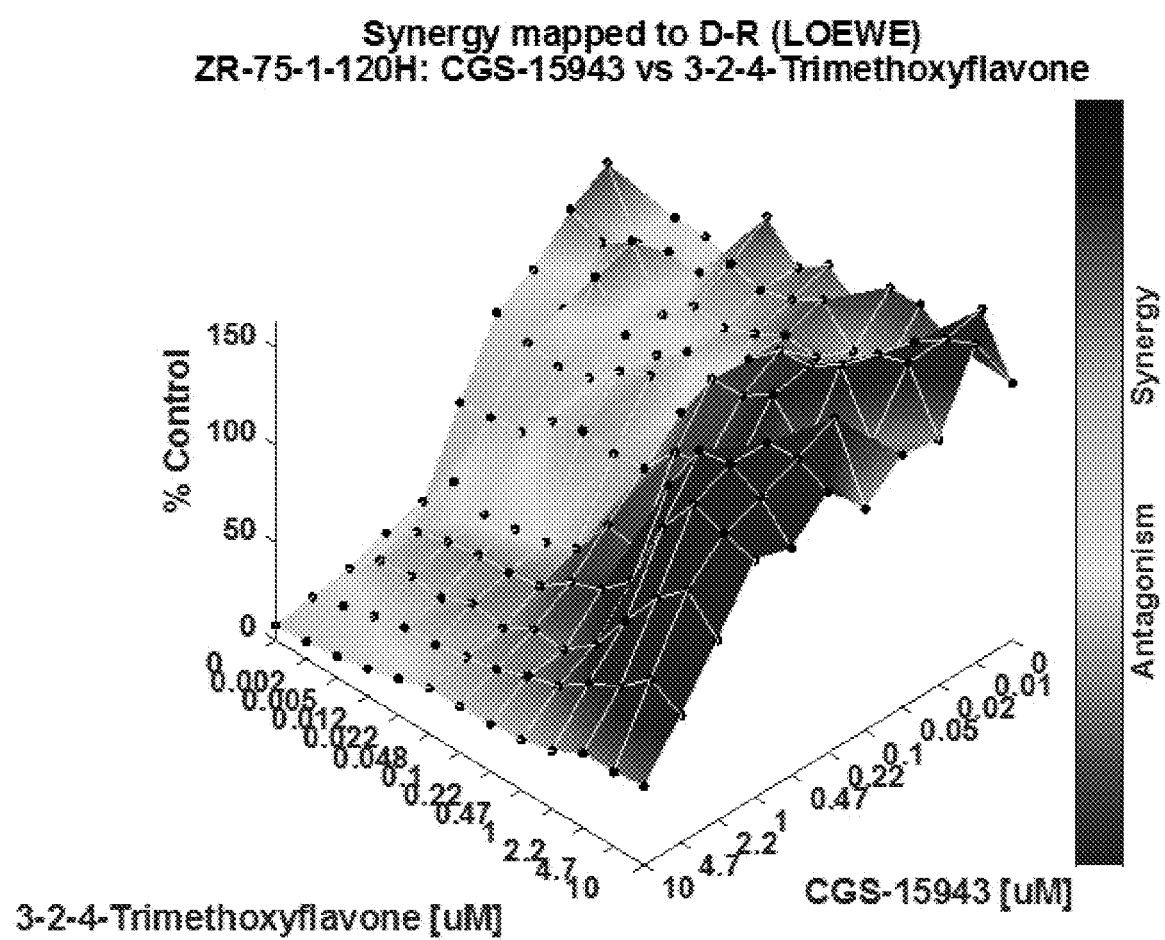
FIG. 14 shows a 3D "Synergy" plot that demonstrates that CGS-15943 and the small molecule AHR antagonist 3-2-4-trimethoxyflavone acted in an antagonistic manner to one another, when assayed in ZR-75-1 breast cancer cells at 120H. In particular, co-treatment with 3-2-4-trimethoxyflavone rescued cells from killing by CGS-15943.

AHR has been previously described to bind a range of endogenous and exogenous aromatic ligands (Denison et al. *Tox. Sci.* 2004, see Table 2), resulting in the formation of a nuclear heterodimer with ARNT. The dimer then binds dioxin-responsive elements and drives gene expression, after nuclear translocation. AHR has been described to bind a wide range of aromatic substrates including agonists, antagonists, and modulators. As shown above, AHR knockout rescued CGS-15943 cytotoxicity. Small molecule antagonists of AHR have been previously described, including the small molecule 3-2-4-trimethoxyflavone, which was also applied to ZR-75-1 cells and exhibited pronounced antagonism to CGS-15943, as assessed via a 3D "Synergy" plot (FIG. 14). In particular, as observed above for AHR knockout, co-treatment with 3-2-4-trimethoxyflavone rescued ZR-75-1 breast cancer cells from killing by CGS-15943.

Figure 15:
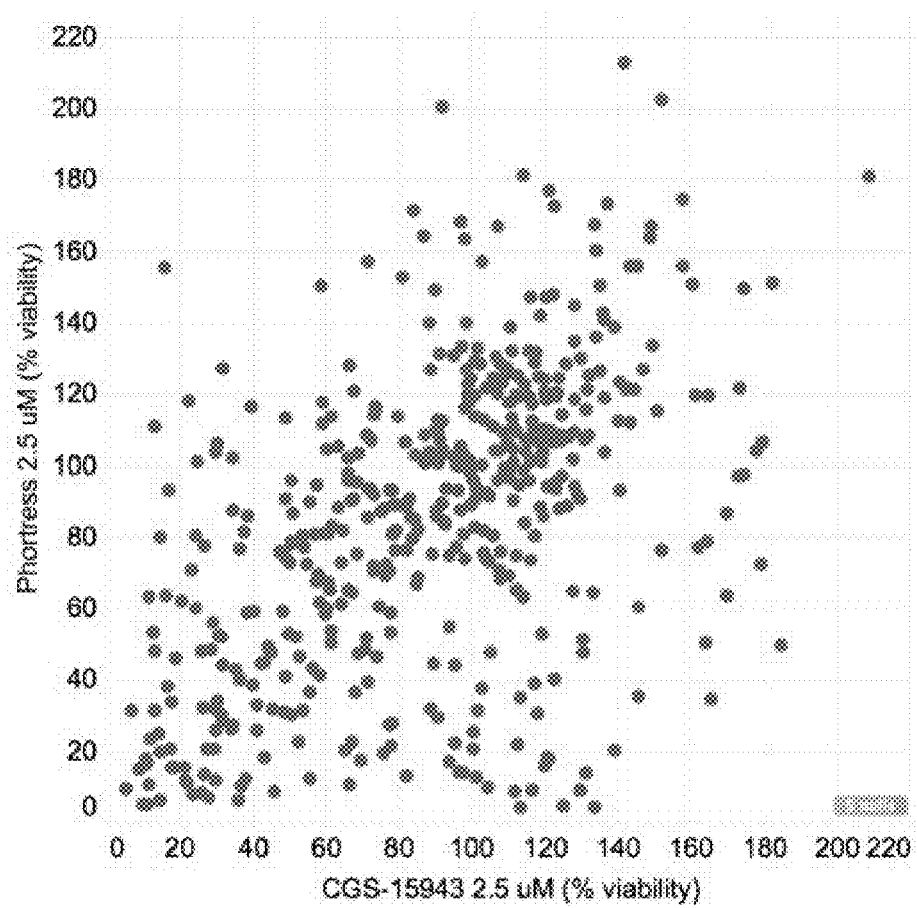
FIG. 15 shows a dot-plot of CGS-15943 and Phortress effects which shows that Phortress was more broadly cytotoxic to the various cell lines assayed in the PRISM population than CGS-15943.
Figure 16:
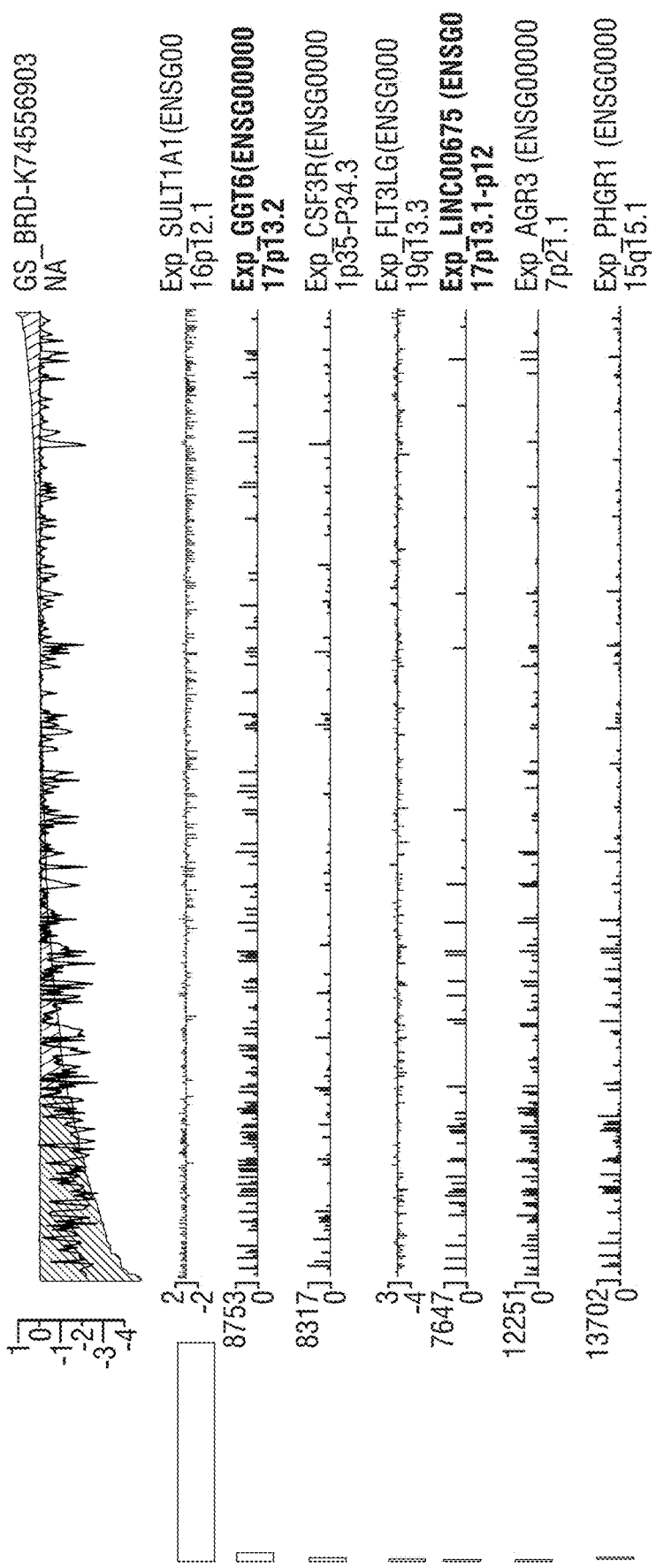
FIG. 16 demonstrates that SULT1A1 sulfotransferase enzyme expression was the top predictor of Phortress activity.
Figure 17:
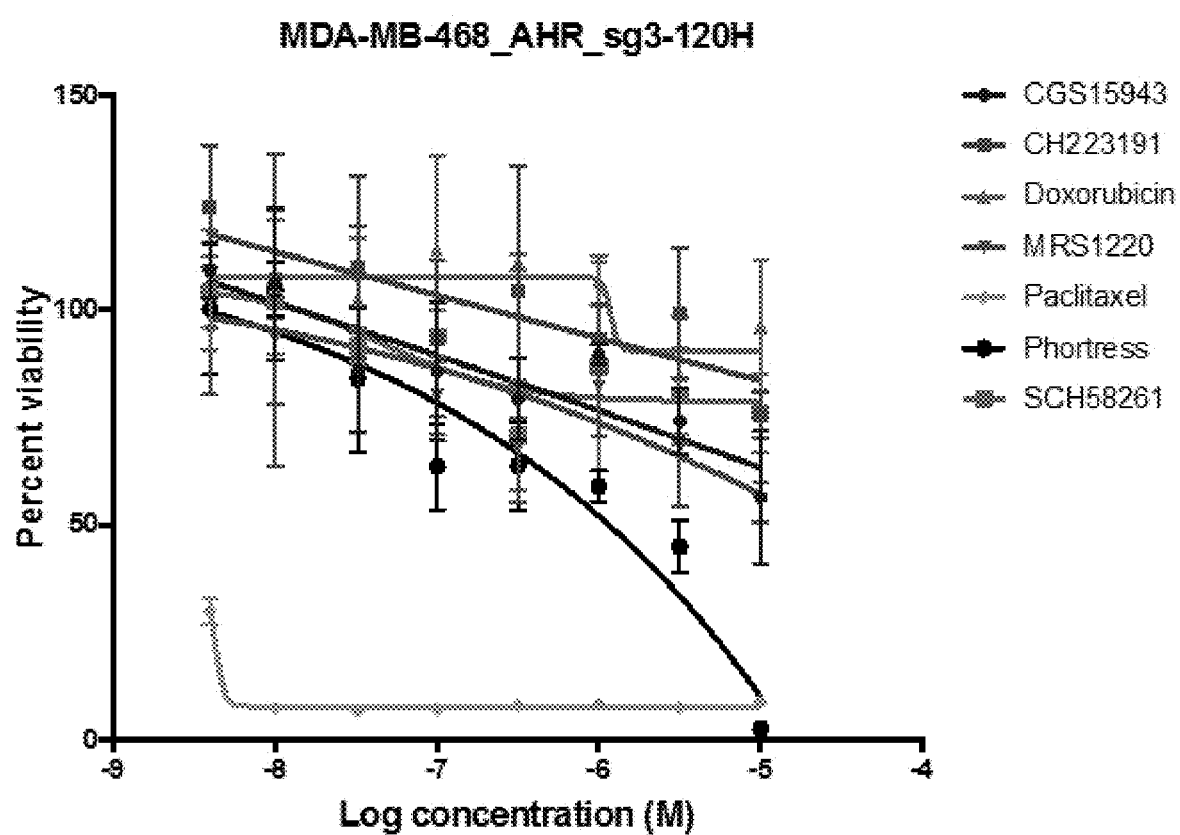
FIG. 17 shows dose-response curves for MDA-MB-468 breast cancer cells possessing AHR knockout (via the AHR_sg3 CRISPR-Cas9 agent), across treatments that included CGS15943, CH223191, Doxorubicin, MRS1220, Paclitaxel, Phortress and SCH58261. Phortress notably exhibited non-specific cytotoxicity at high dose and AHR knockout was observed not to rescue Phortress killing at 10 µM.

The above results were most consistent with CGS-15943 and MRS-1220 compounds acting as AHR agonists; however, not all AHR agonists possessed this property (other AHR agonists did not possess the observed FOXA1-associated pattern of killing), which indicated that other activities of these compounds might also be relevant to their observed effects. Intriguingly, some interaction of FOXA1 and AHR has also been previously reported. Regardless, the strong AHR dependence of CGS-15943 and MRS-1220 cytotoxicity indicated that the mode of action observed for these compounds might be shared with other compounds described as harnessing AHR-dependent cytotoxicity, such as Phortress (a 5F-203 prodrug, as described in Leong et al. *Mol. Cancer Ther.* 3: 1565-75), AFP464 (an aminoflavone prodrug in clinical development), and NK150460 (a discovery-level compound, for which killing was rescued by siRNA targeting ARNT). Phortress has reached Phase I clinical testing and has been described as well-tolerated in solid tumor patients. However, as shown in FIG. 15, the killing profile of Phortress in PRISM cytotoxicity studies was observed to have been broader (Phortress was more broadly cytotoxic to the various cell lines assayed) and CGS-15943. In addition, SULT1A1 sulfotransferase enzyme expression was identified as the top predictor of Phortress activity (FIG. 16), which it was not for CGS-15943. Further, Phortress exhibited non-specific cytotoxicity at high doses, in contrast to CGS-15943 and other tested compounds (FIG. 17)—indeed, AHR knockout did not rescue cells from Phortress killing at 10 μM Phortress doses, in contrast to results observed for CGS-15943. Such results indicated divergence between both the effects and overall modes of action of Phortress and CGS-15943.

Figure 18:
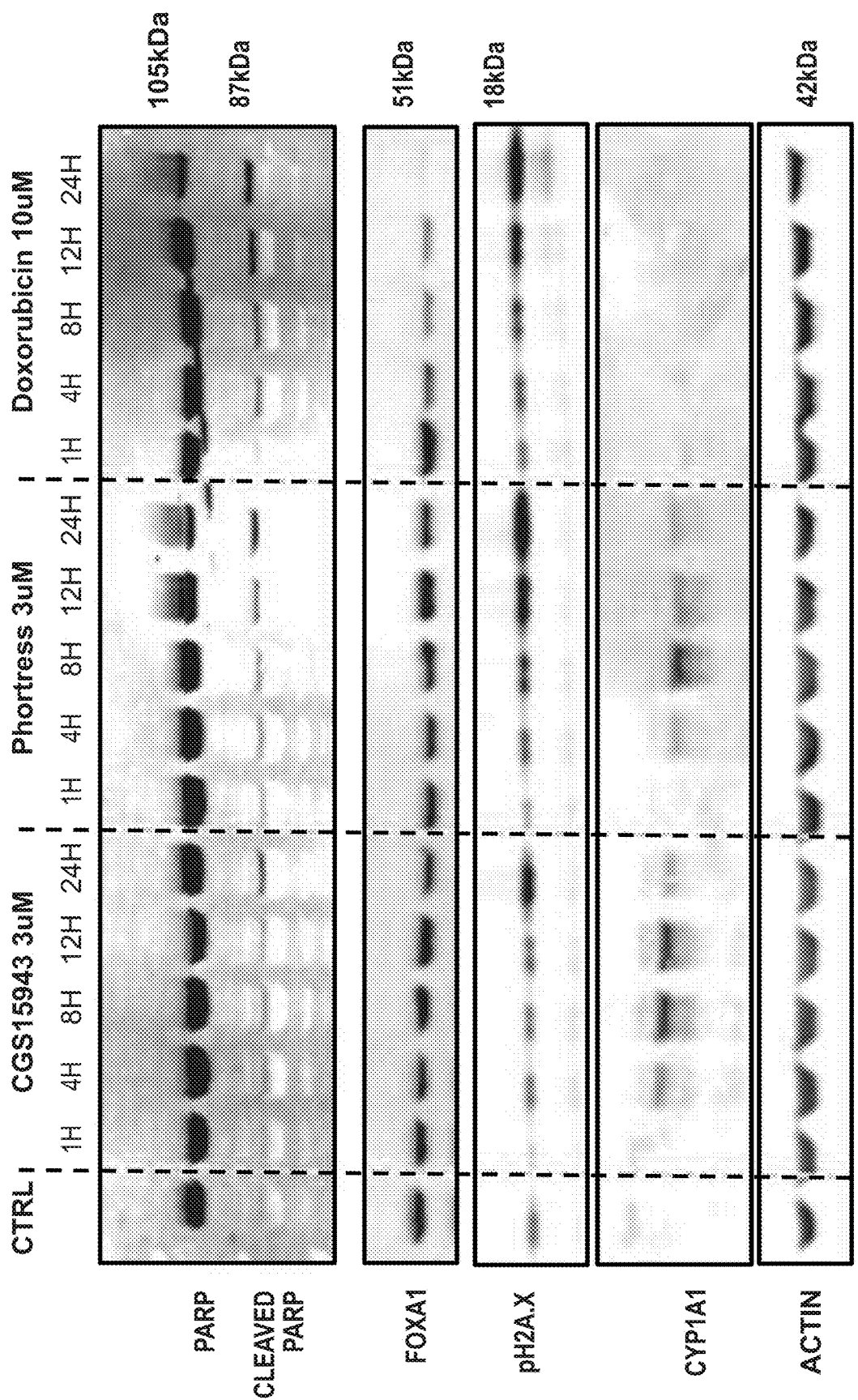
FIG. 18 shows an immunoblot that illustrates that CGS-15943, Phortress and doxorubicin each induced DNA double stranded breaks (as indicated by the accumulation of phosphorylated H2AX (pH2A.X), known to occur at the sites of DNA double-stranded break) and PARP cleavage in treated MDA-MB-468 breast cancer cells within 24 hours. CGS-15943 and Phortress also induced CYP1A1 expression (consistent with aryl hydrocarbon receptor activity) and maintenance of FOXA1 levels in treated cells over the 24 time course, whereas doxorubicin caused a decline in FOXA1 levels and no detectable induction of CYP1A1 expression over the 24 hour time course.

A number of different possible mechanisms existed for CGS-15943 activity. One such possibility was that AHR-mediated transport to nucleus was followed by DNA damage. Another such possibility was that AHR agonism induced P450 expression. A third such possibility was that a unique cytotoxic compound effect was exerted after binding to AHR-FOXA1 complexes. The cytotoxic effects of CGS-15943 was therefore further investigated in experiments that examined whether such effects were at least in part attributable to induction of DNA double-stranded breaks. As shown in FIG. 18, CGS-15943 induced DNA double stranded breaks and PARP cleavage in MDA-MB-468 breast cancer cells within 24 hours of administration, indicating a further mode of action for CGS-15943 activity.

While CGS-15943 has been the subject of preclinical testing, e.g., for treatment of certain forms of melanoma (FIG. 19), the instant studies appear to be the first to identify CGS-15943 (and MRS-1220 and SCH-58261) as agents possessing cytotoxicity against FOXA1-high cell lines/neoplasias, particularly against luminal and/or estrogen-receptor positive breast cancers.

Figures 20A, 20B:
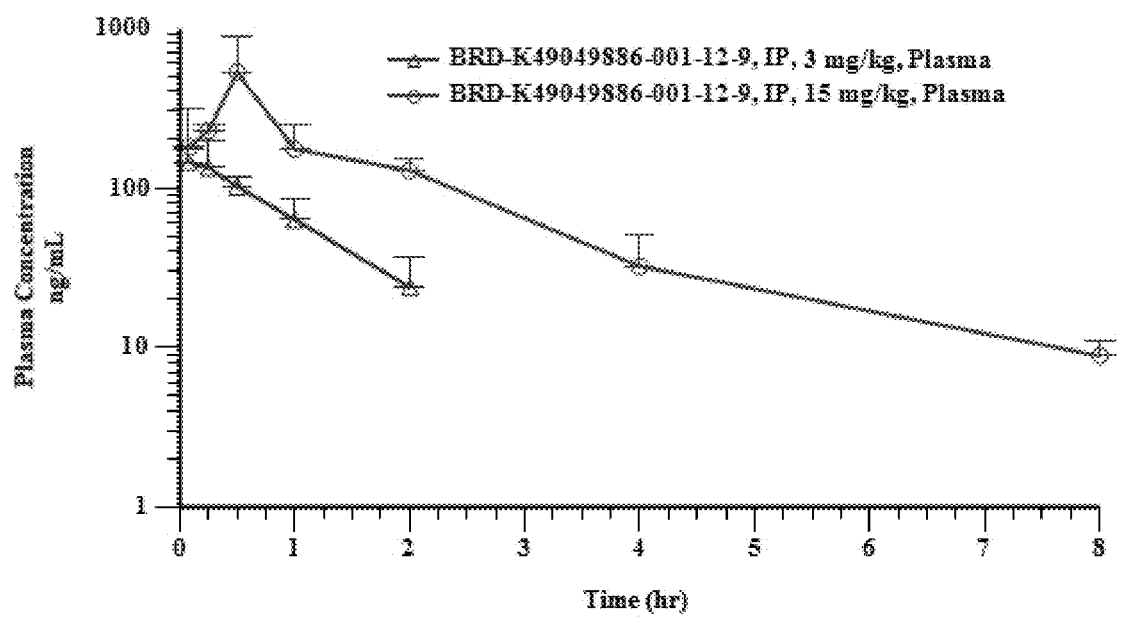
FIGS. 20A and 20B show clearance of injected plasma concentrations of CGS-15943.
Figure 21:
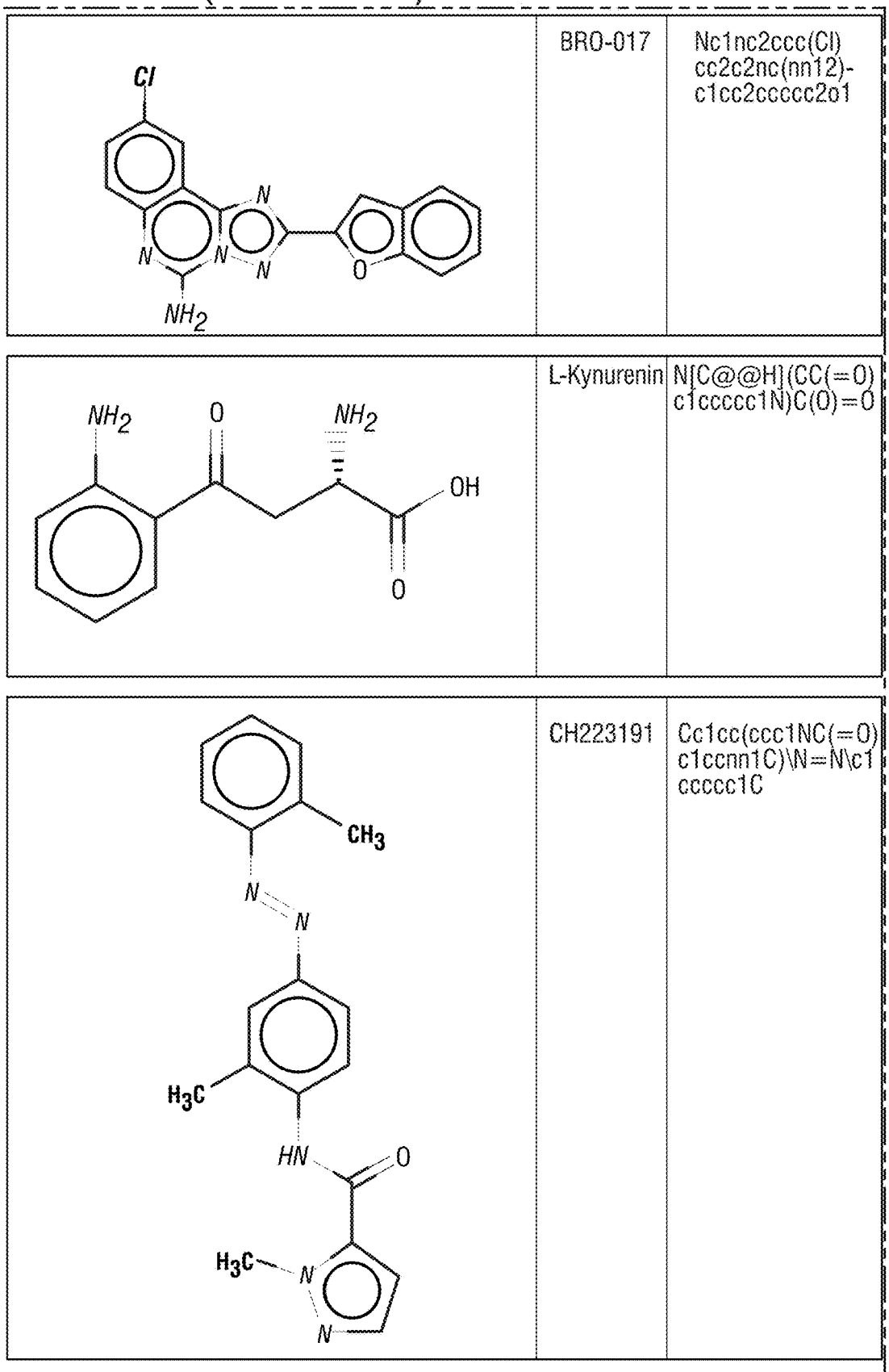
FIG. 21 shows cytotoxic activity results observed in various indicated cell lines for CGS-15943 and a series of CGS-15943 derivatives/analogs of the instant disclosure, as well as various known compounds.
Figure 22:
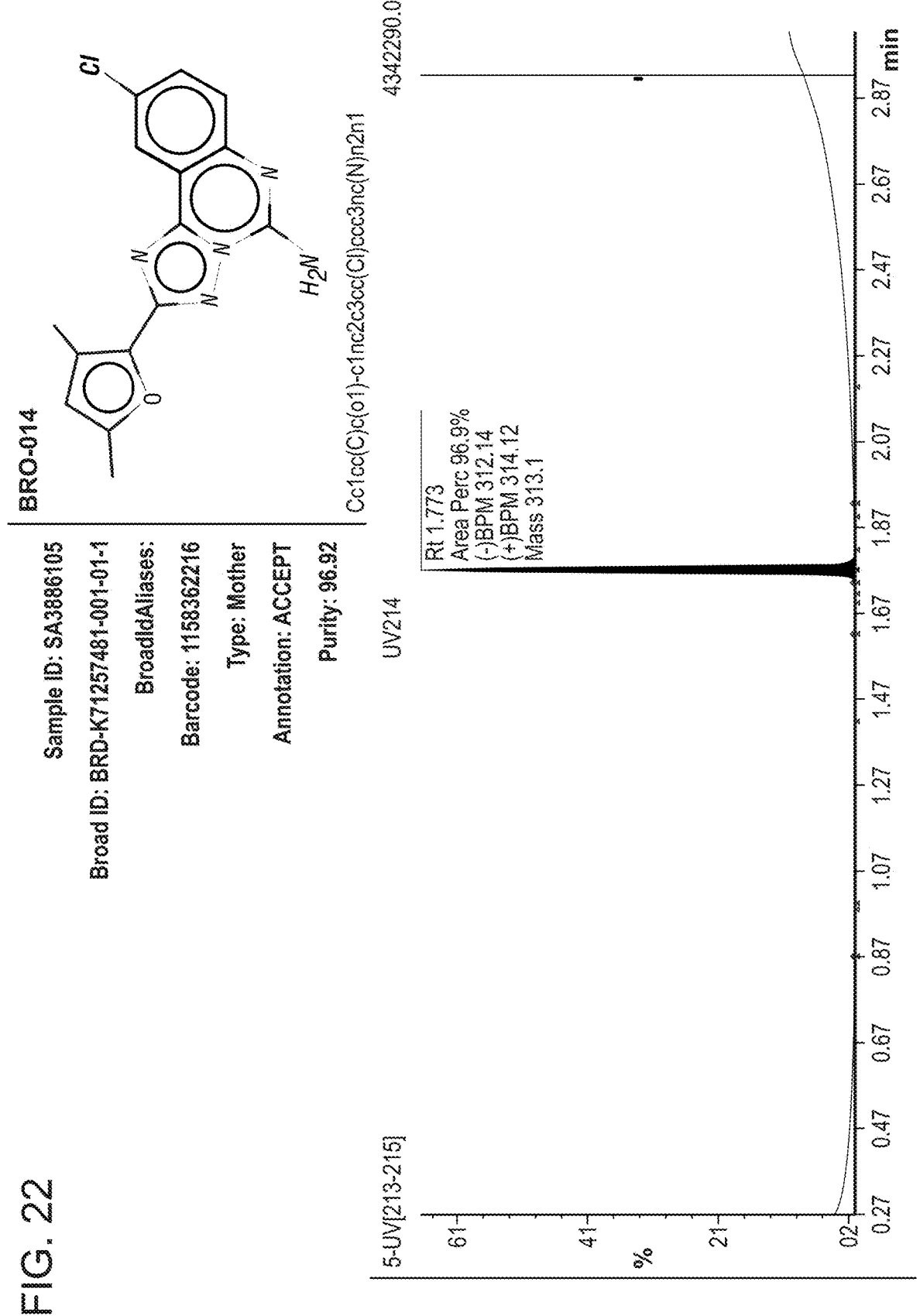
FIG. 22 shows experimental characterization of indicated compounds, performed using LC-MS (liquid chromatography—mass spectrometry).
Figure 22:
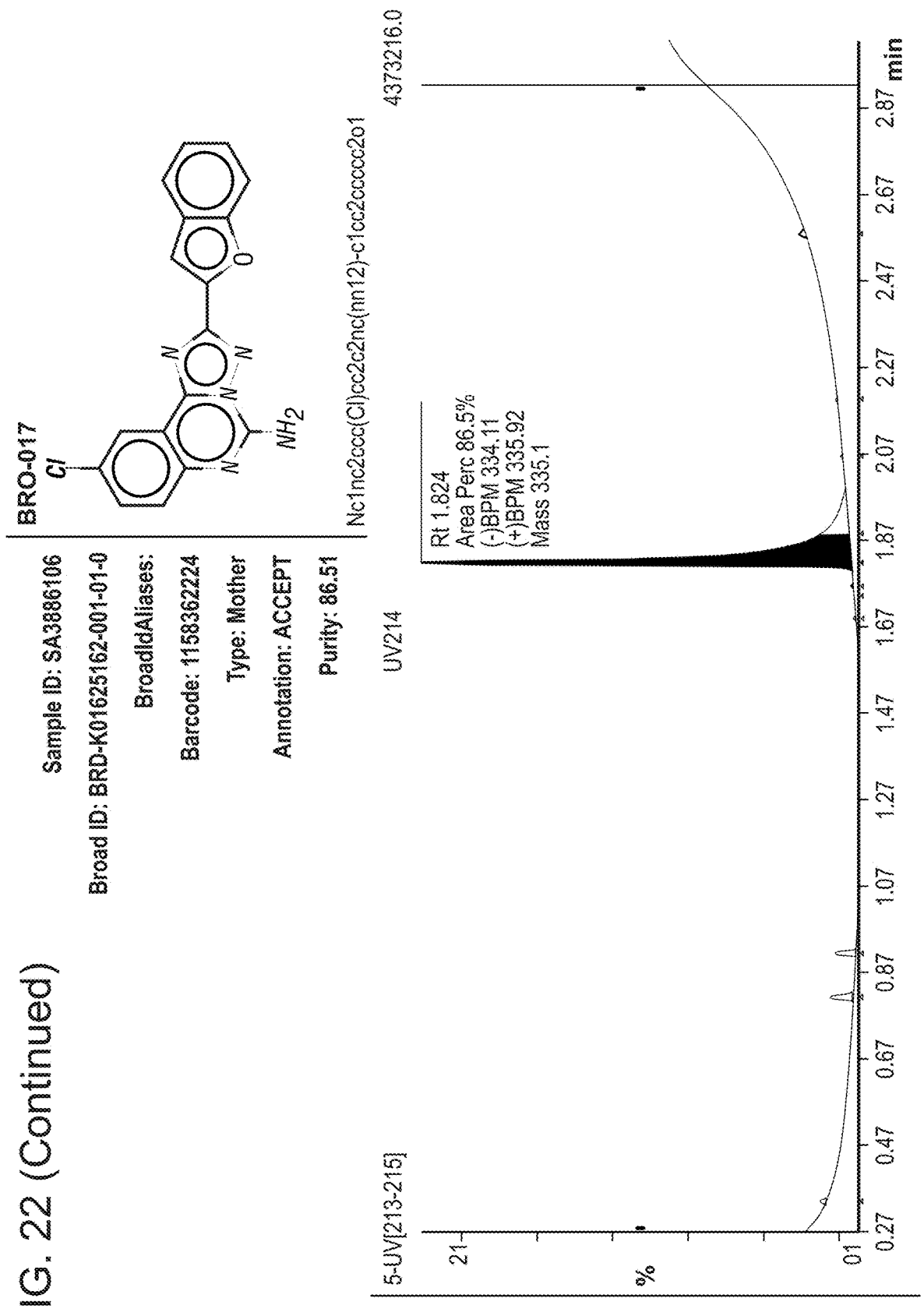
Figure 22:
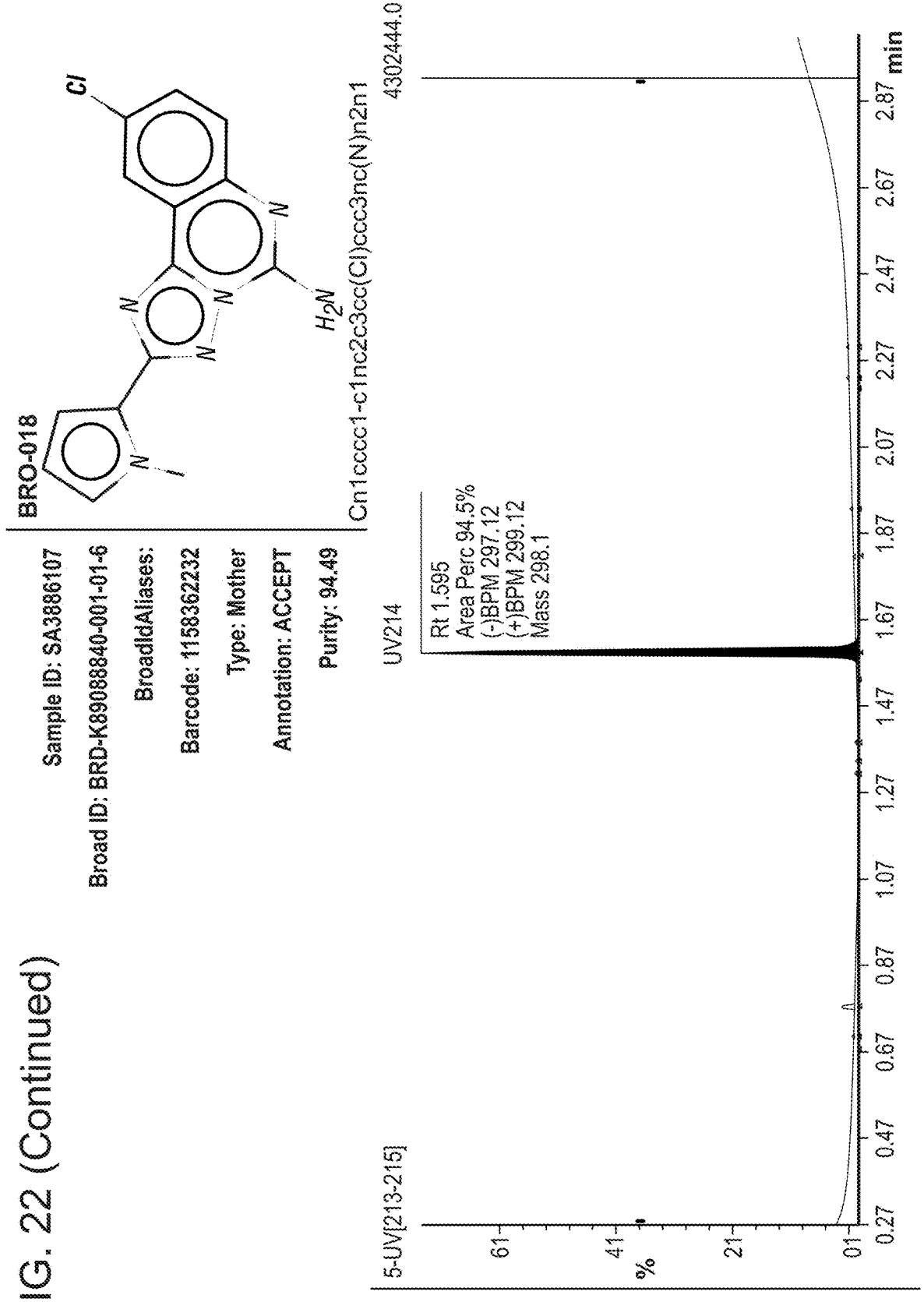
Figure 22:
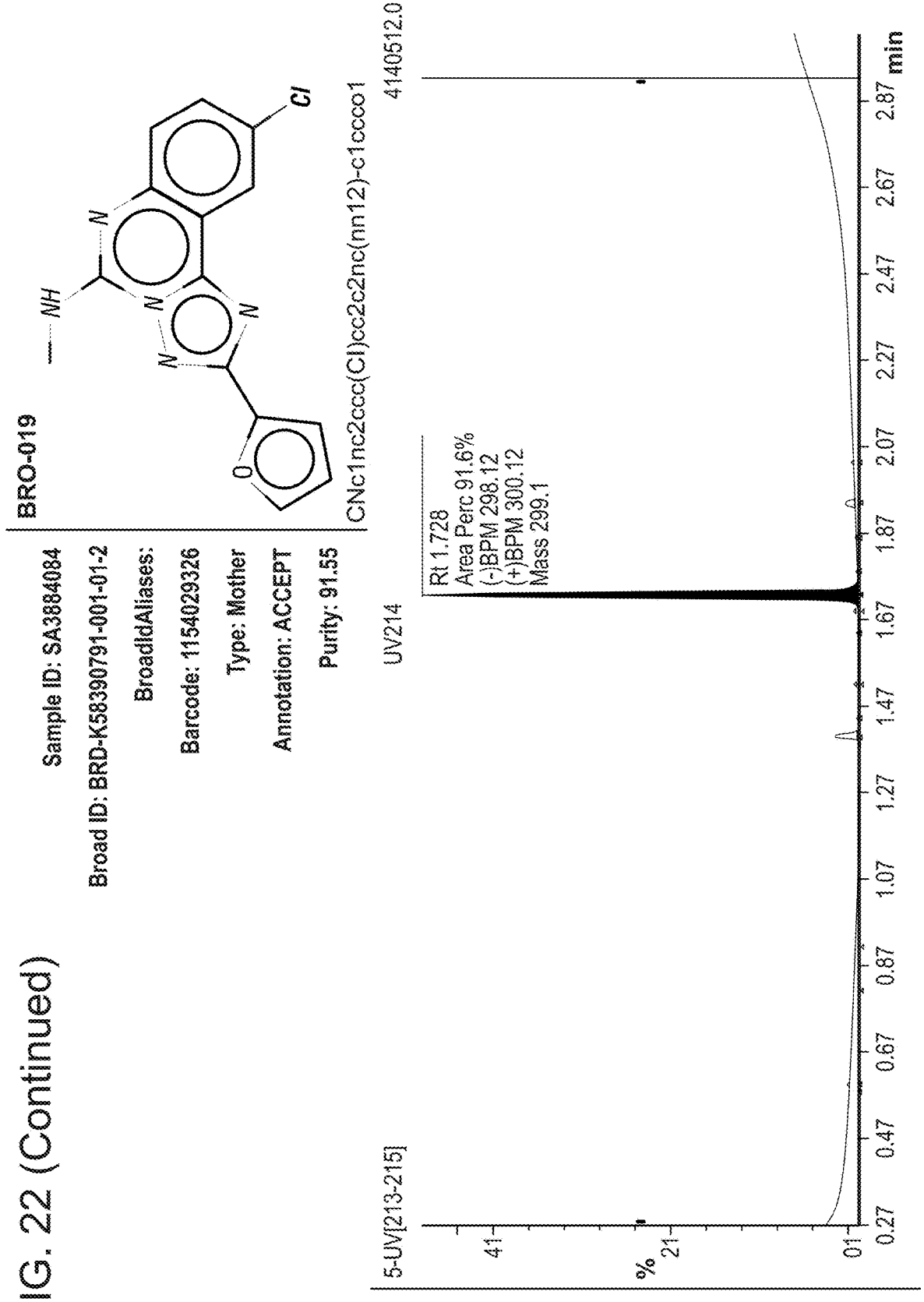
Figure 22:
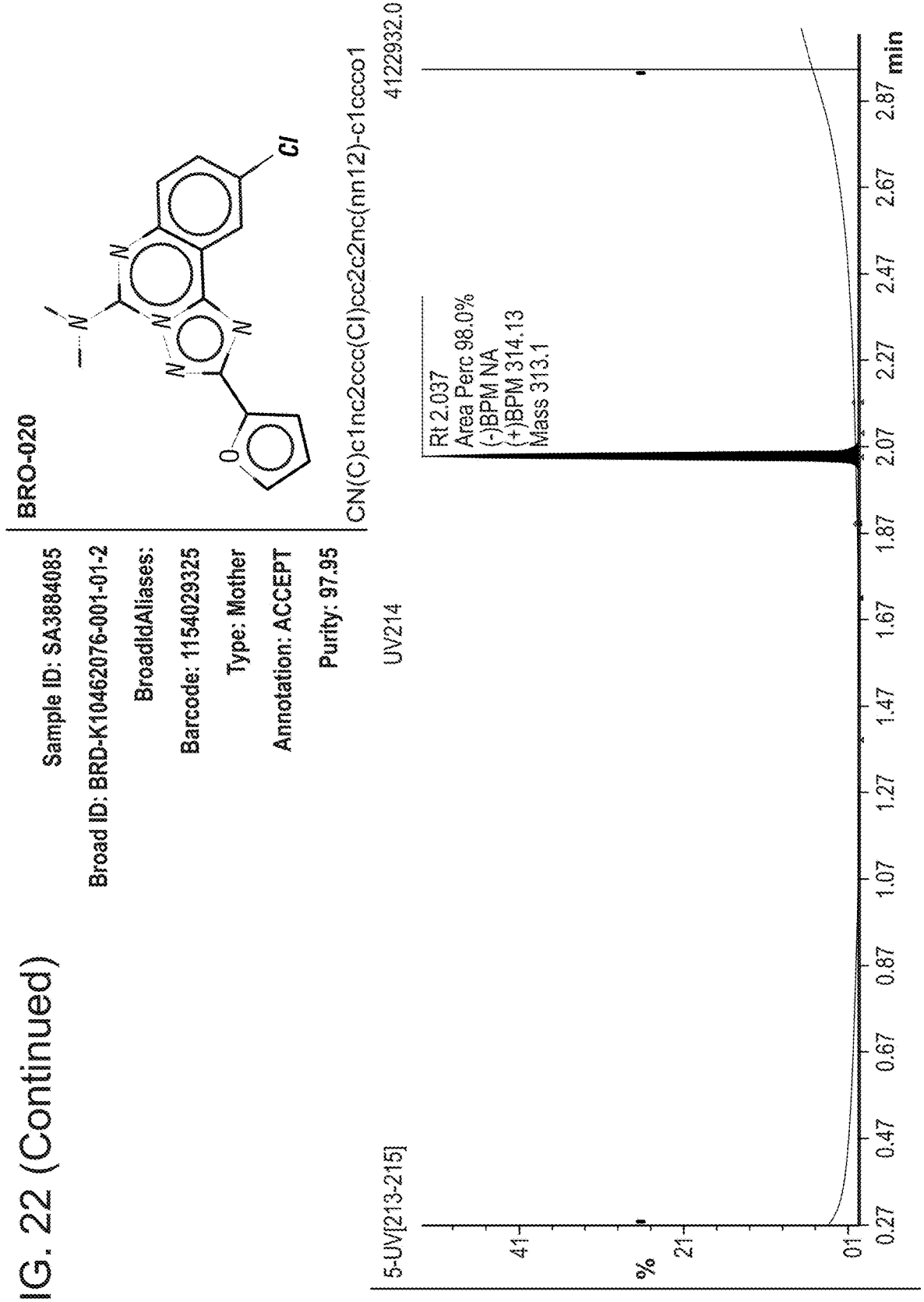
Figure 22:
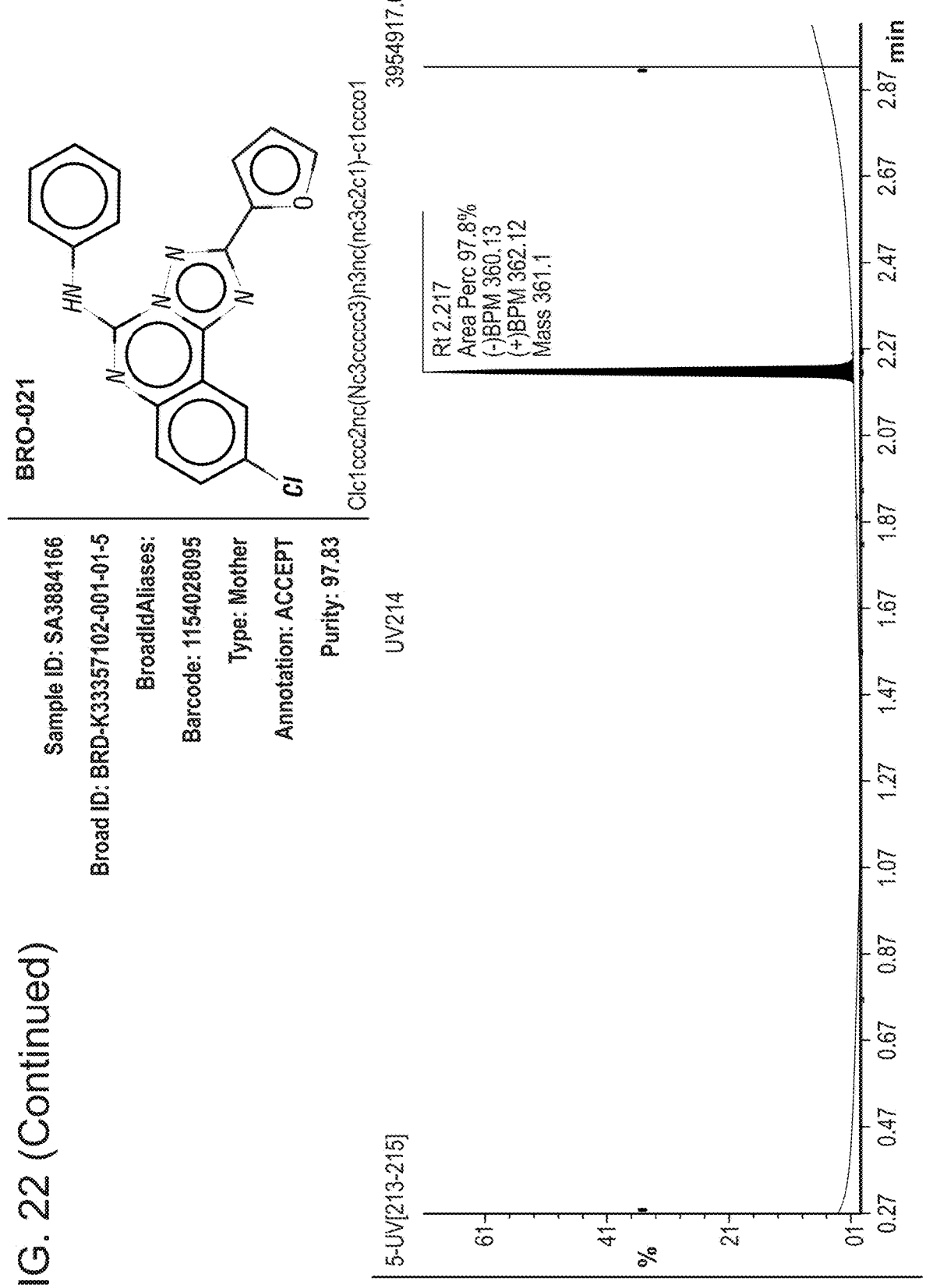
Figure 22:
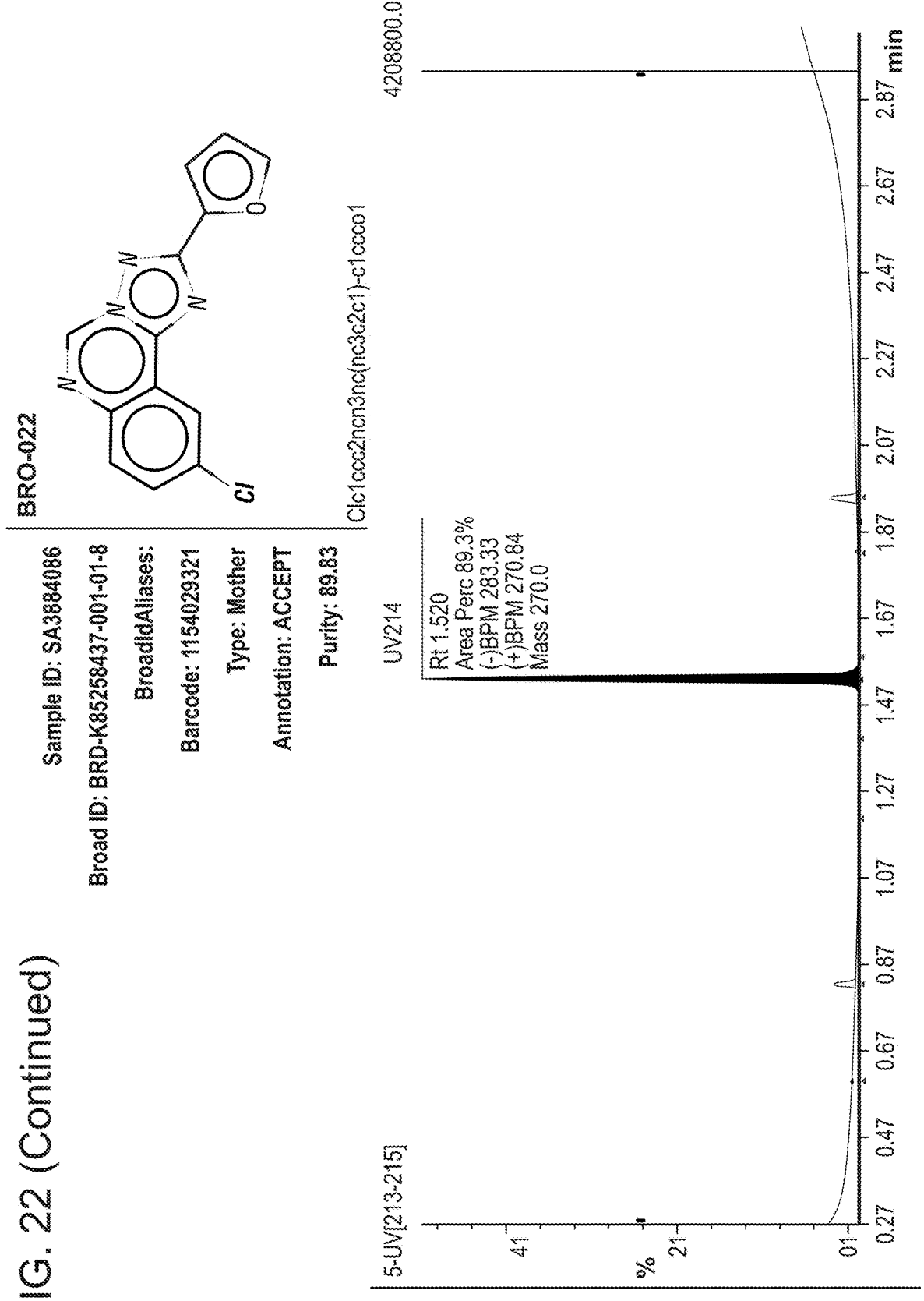
Figure 22:
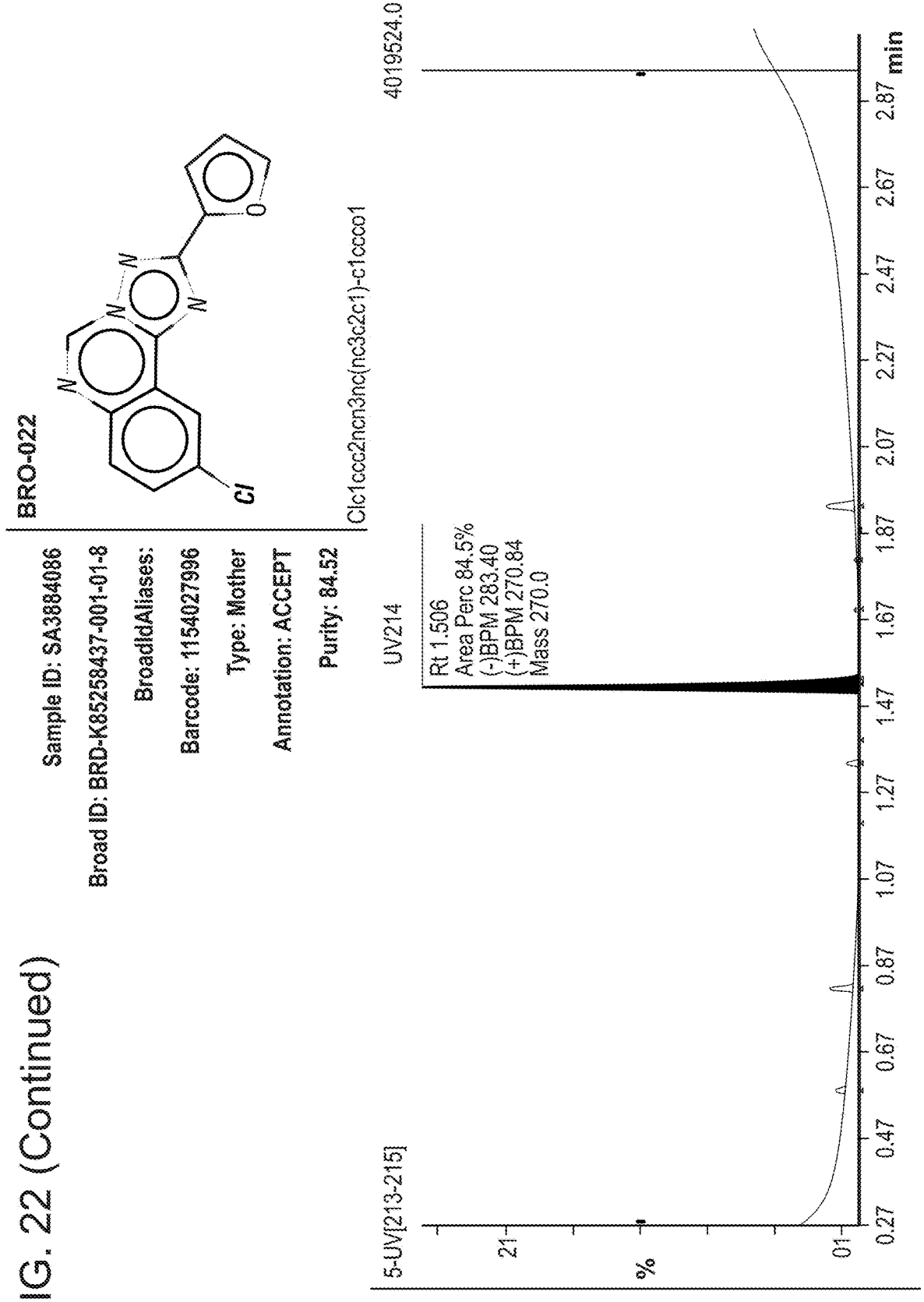
Figure 22:
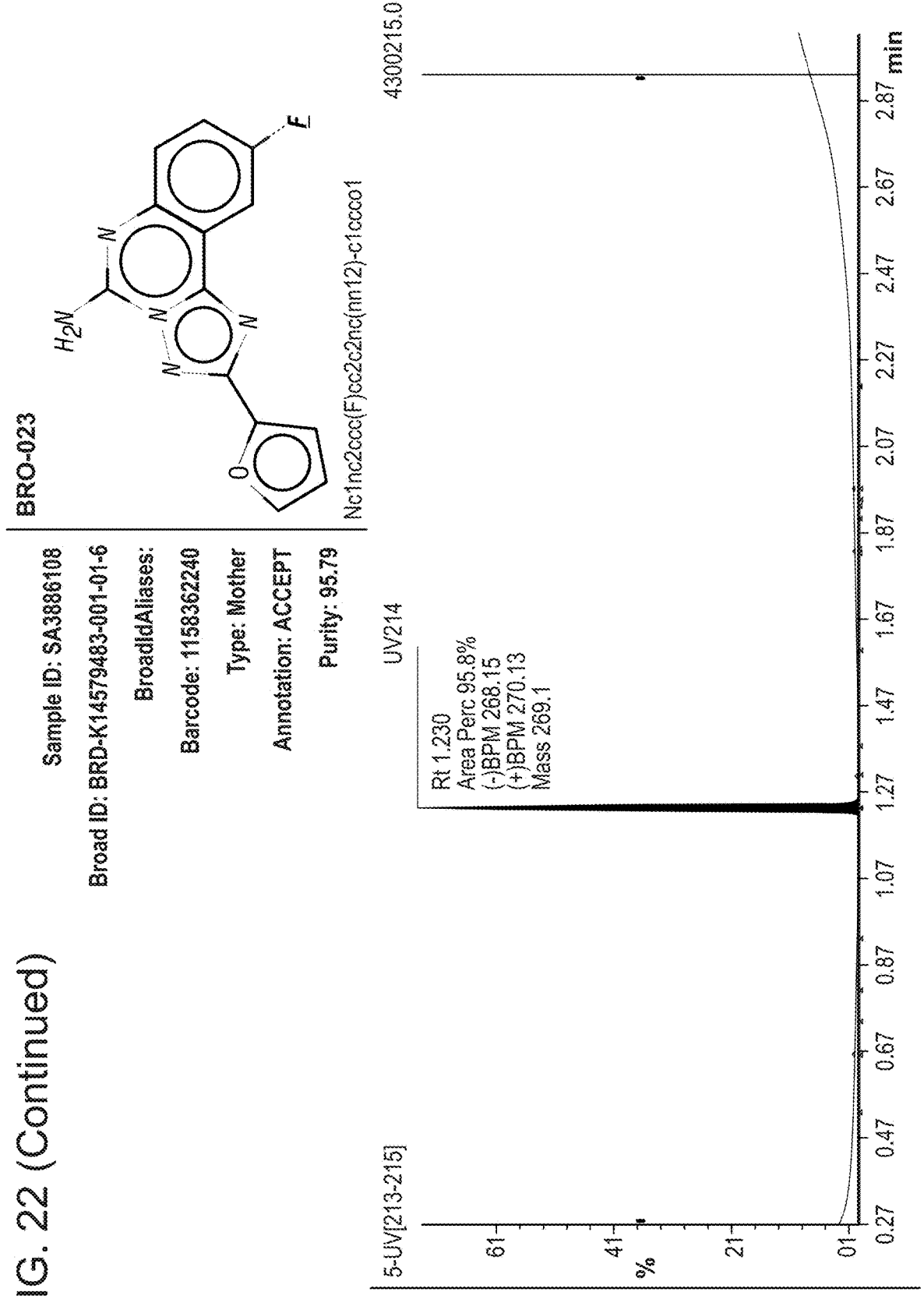
Figure 22:
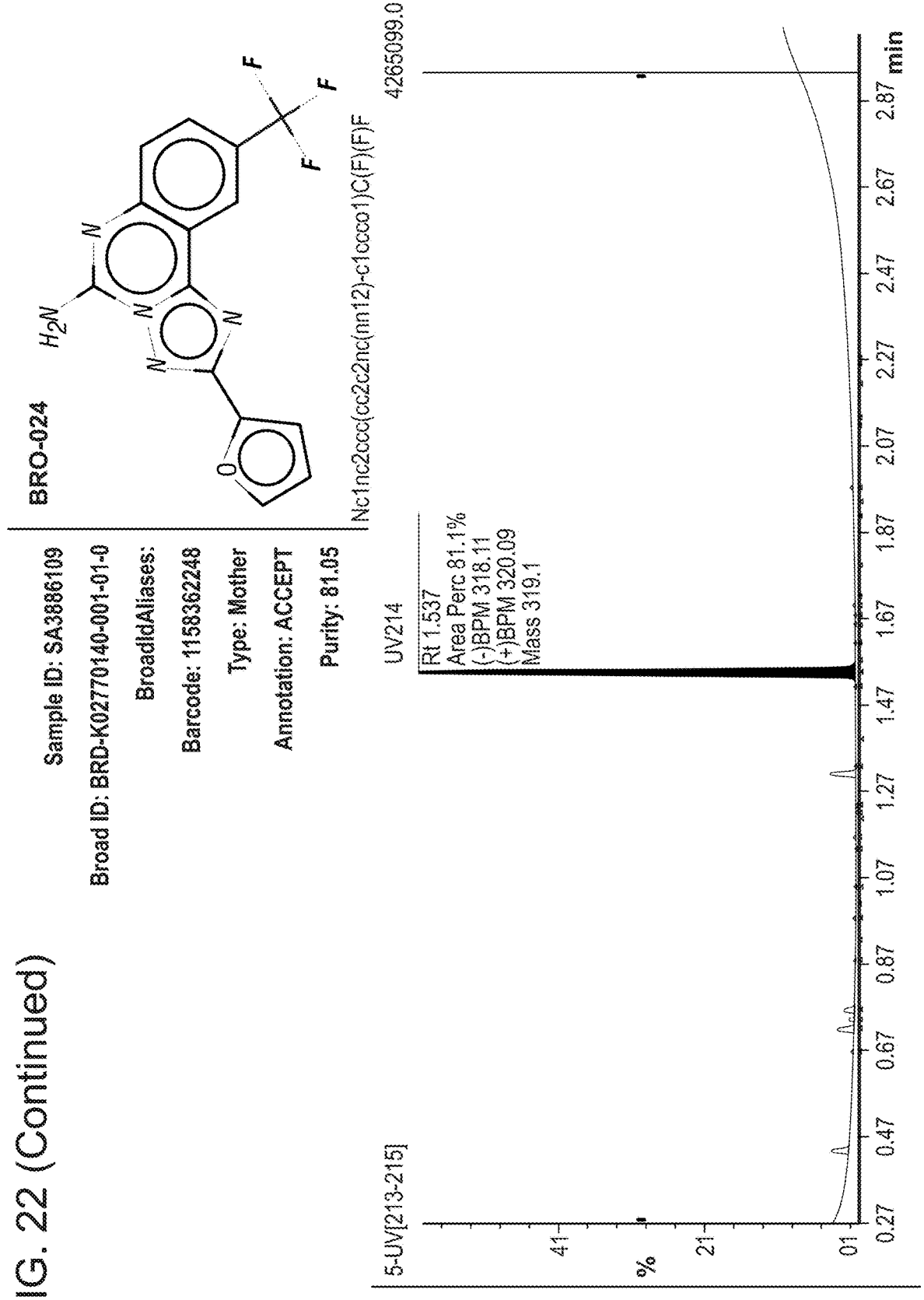
Figure 22:
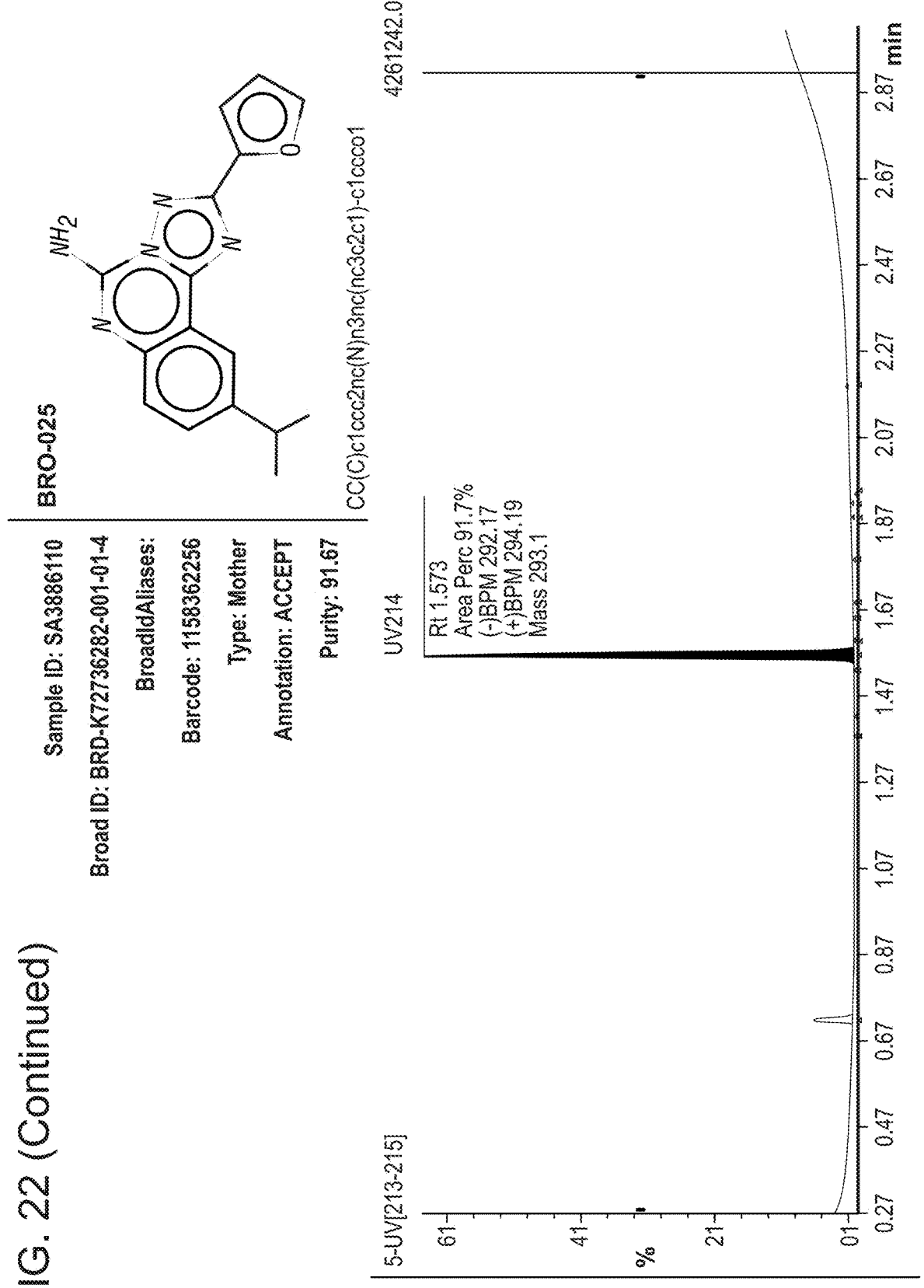
Figure 22:
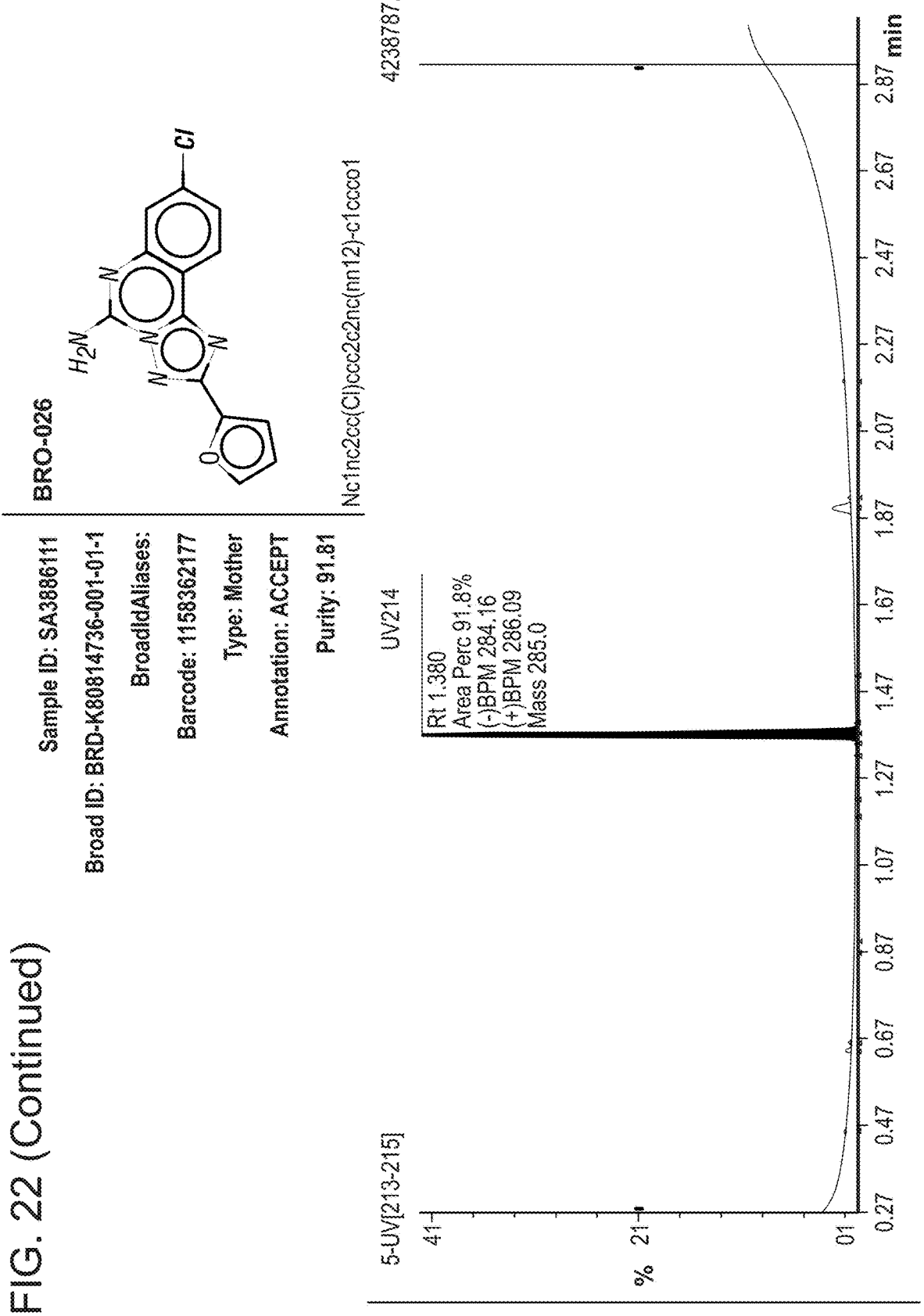
Figure 22:
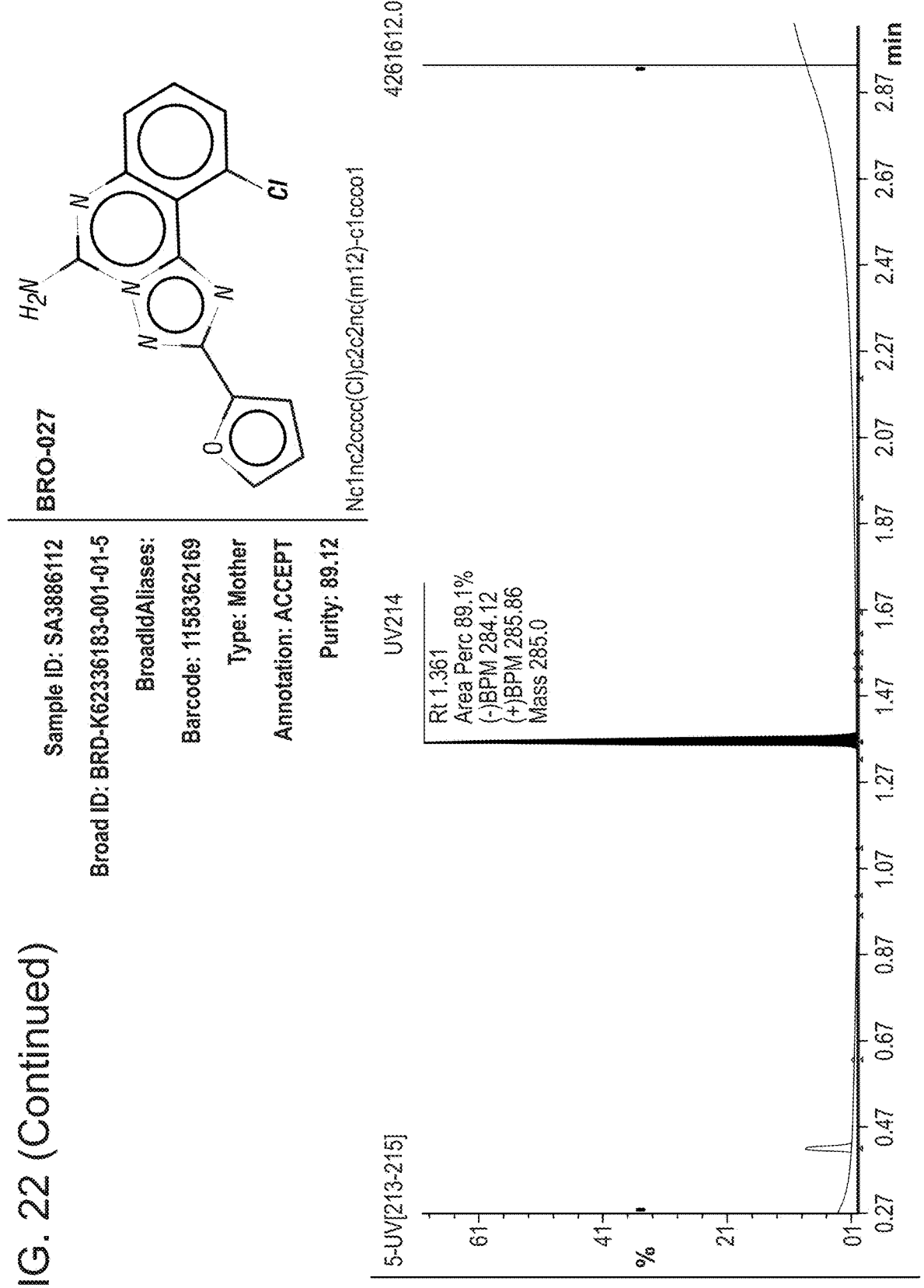
Figure 22:
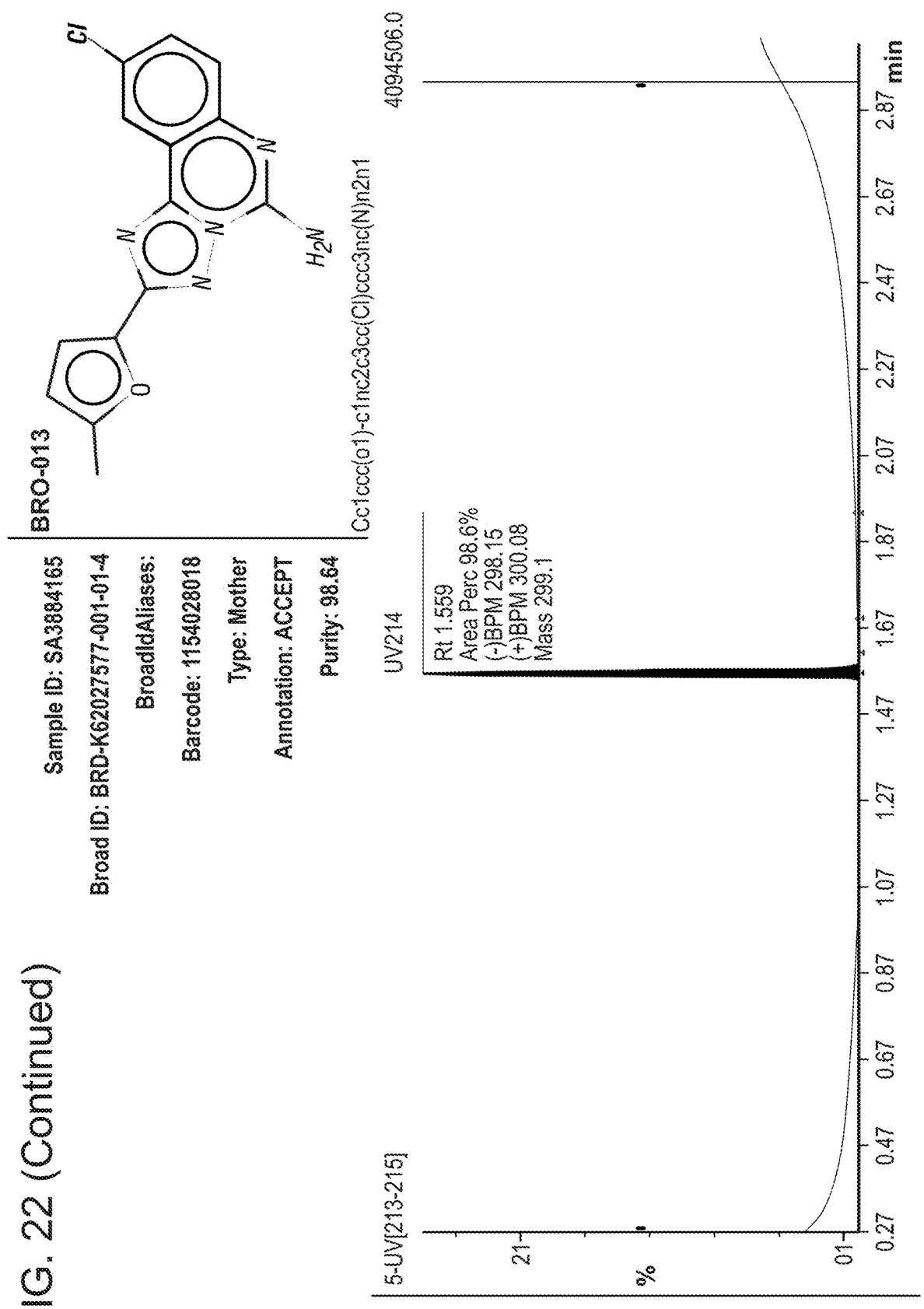
Figure 22:
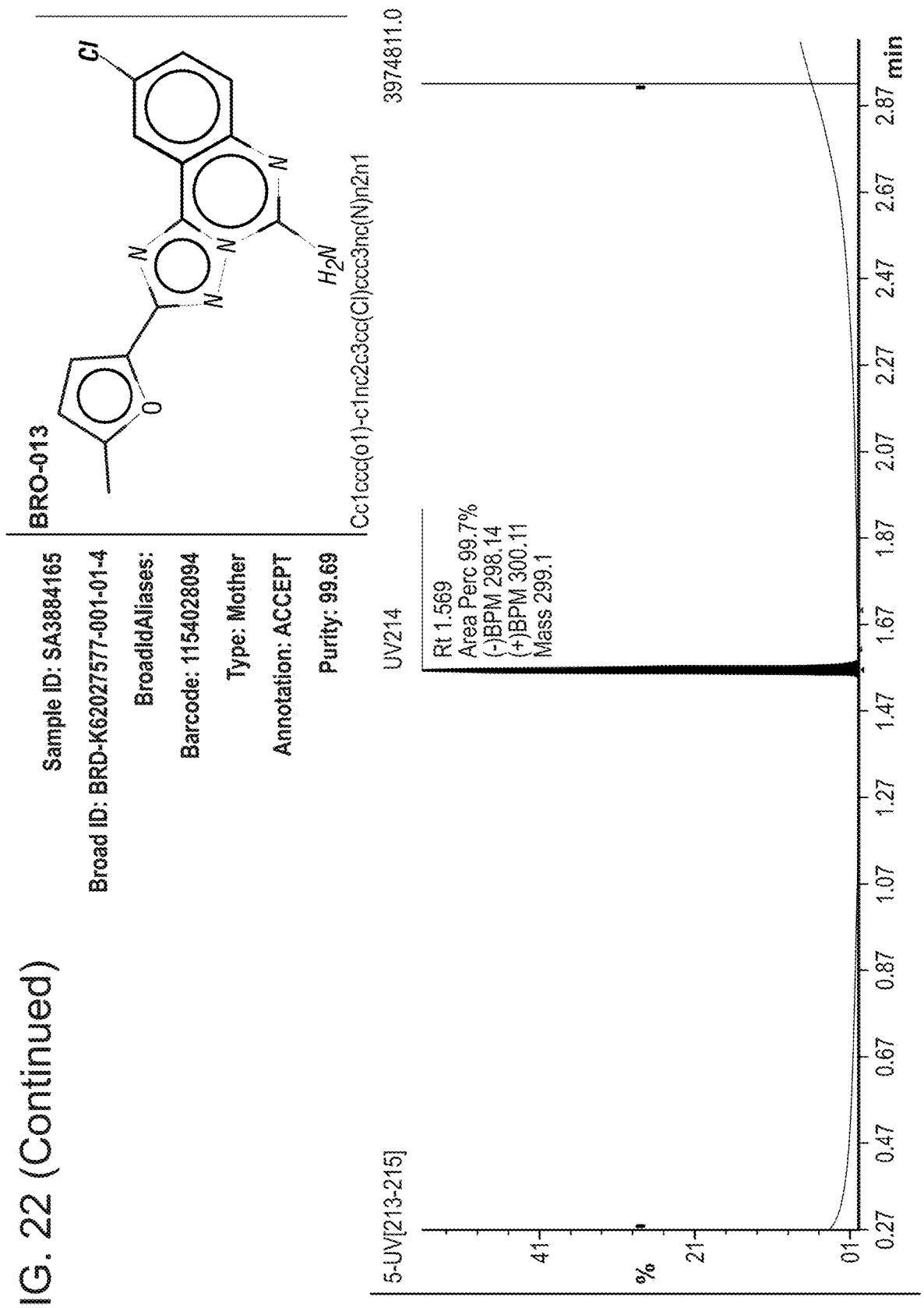

CGS-15943 PK was also preliminarily investigated in animals, with respective plasma-injected 3 mg/kg and 15 mg/kg concentrations of CGS-15943 observed to decay over the time courses indicated in FIG. 20A. A tabular summary of such plasma clearance results has also been provided, as FIG. 20B.

In conclusion, CGS-15943 and MRS-1220 killed FOXA1-high cell lines via an off-target (non-FOXA1/non-AGR2-mediated) effect. SAR studies performed upon CGS-15943 demonstrated that the furan ring of CGS-15943 was required for such effects, a finding that was further reinforced by identification of various active, furan-ring-presenting CGS-15943 derivatives. Genome-wide CRISPR screens then revealed that CGS-15943-targeted cells could be rescued from such cytotoxic effects by AHR or ARNT knockout, or via co-administration of a small molecule antagonist of AHR, which identified the CGS-15943 cytotoxic effect as AHR-dependent.

Example 20: Therapeutic Testing of CGS-15943

The cytotoxic activity of CGS-15943, MRS-1220, SCH-58261, and or derivatives of any of the aforementioned compounds is tested in in vivo xenograft models (optionally mouse xenograft models), with the downstream mechanism for CGS-15943 (or other agent and/or derivative)-induced cell death thereby further investigated. Additional derivatives of CGS-15943, as well as derivatives of MRS-1220 and/or SCH-58261, are also synthesized and tested for cell killing activity.

Figure 24:
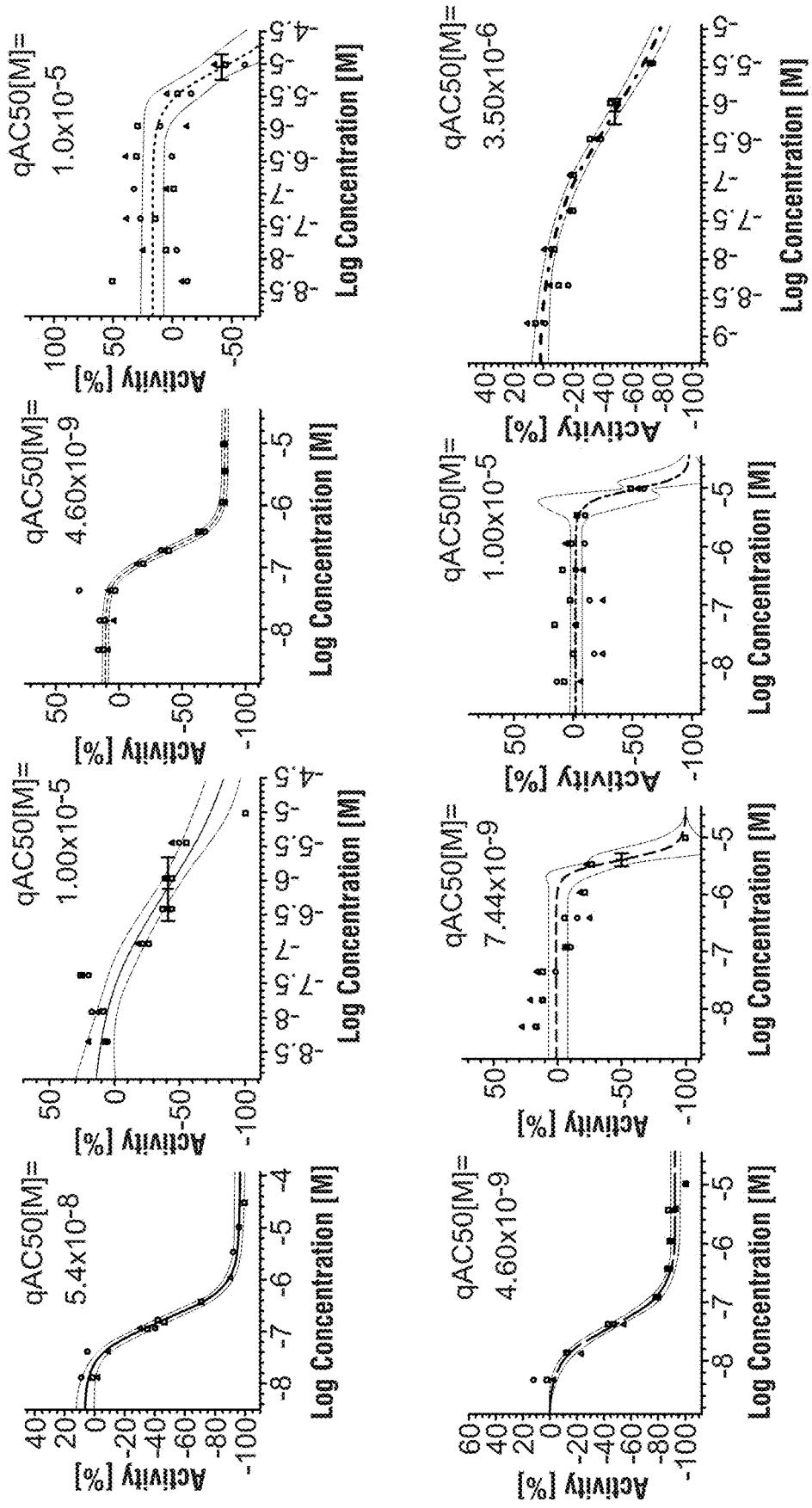
FIG. 24 shows, for each compound tested (for each compound, images proceeding by row, from left to right), the structure, overlaid graphs of all cytotoxicity experiments, and individual graphs depicting percent viability vs log compound concentration (M) for each 5 day cytotoxicity experiment including: MDA-MB-465 wild type, MDA-MB-468 sg4 to AHR, ZR-51 wild type, ZR-51 sg4 to AHR, JHH7 wild type, JHH7 sg3 to AHR, MDA-MB-231 wild type, and MDA-MB-231 over-expressing CYP1A1. The calculated qAC50[M] for each compound in each experiment is also shown.
Figure 24:
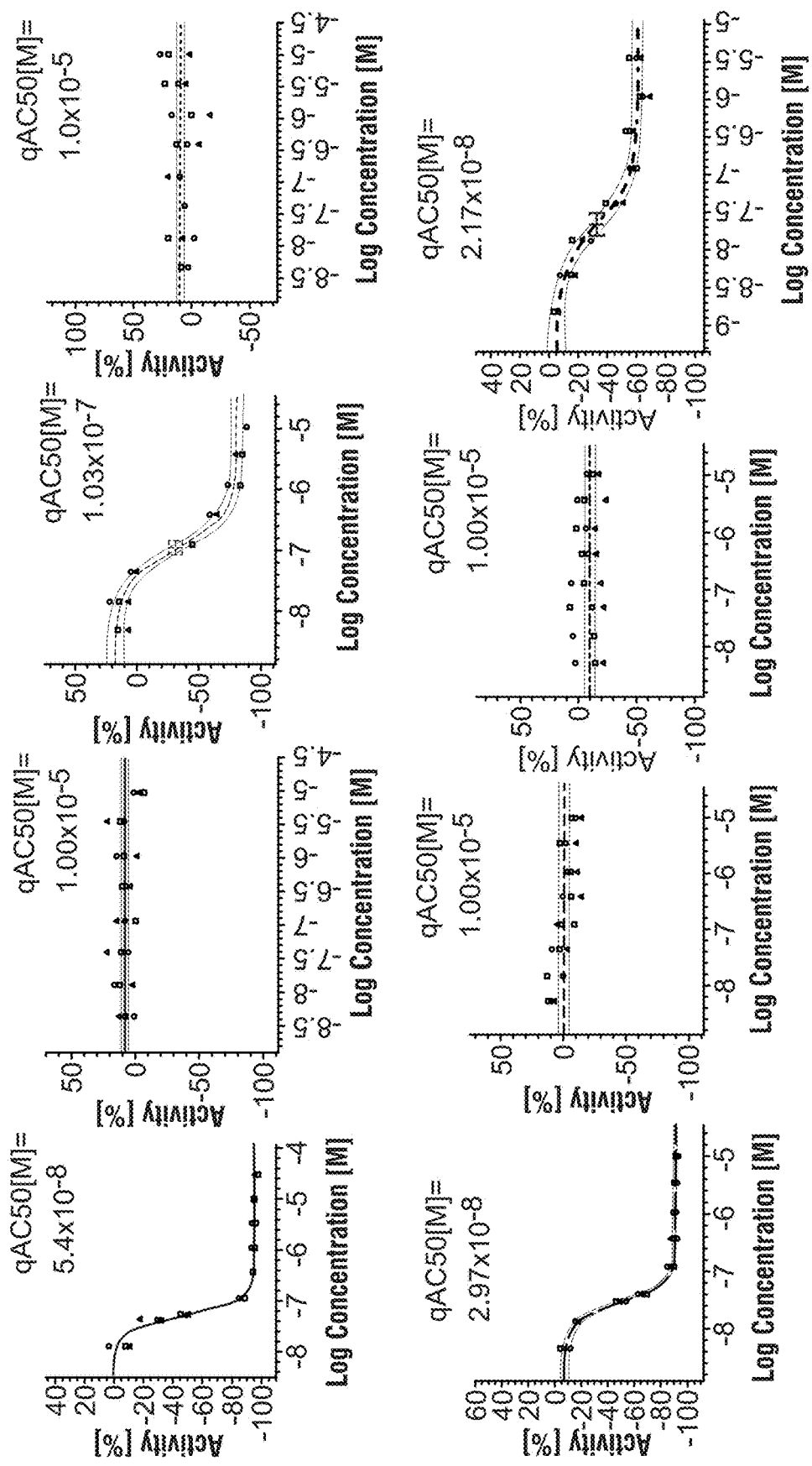
Figure 24:
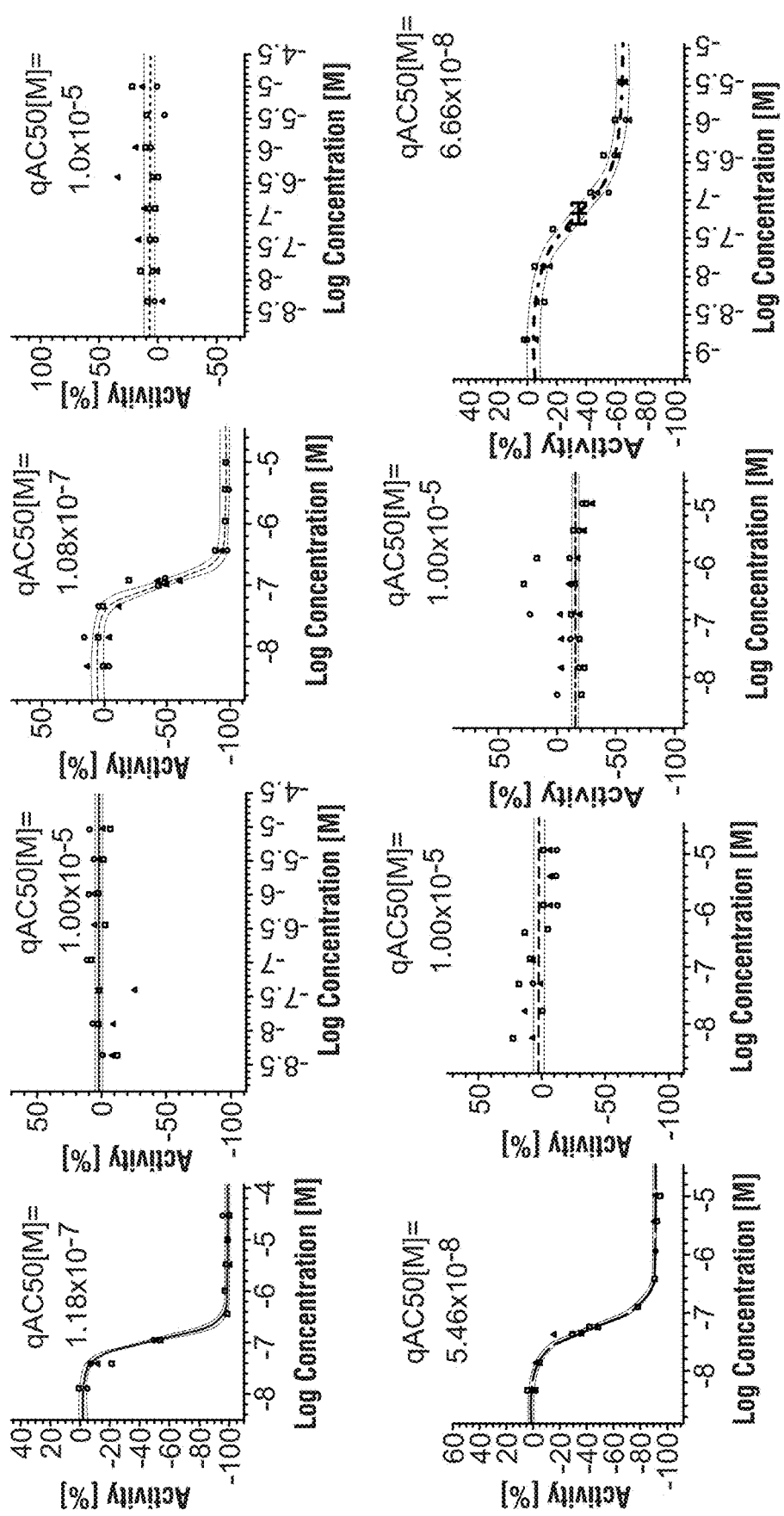
Figure 24:
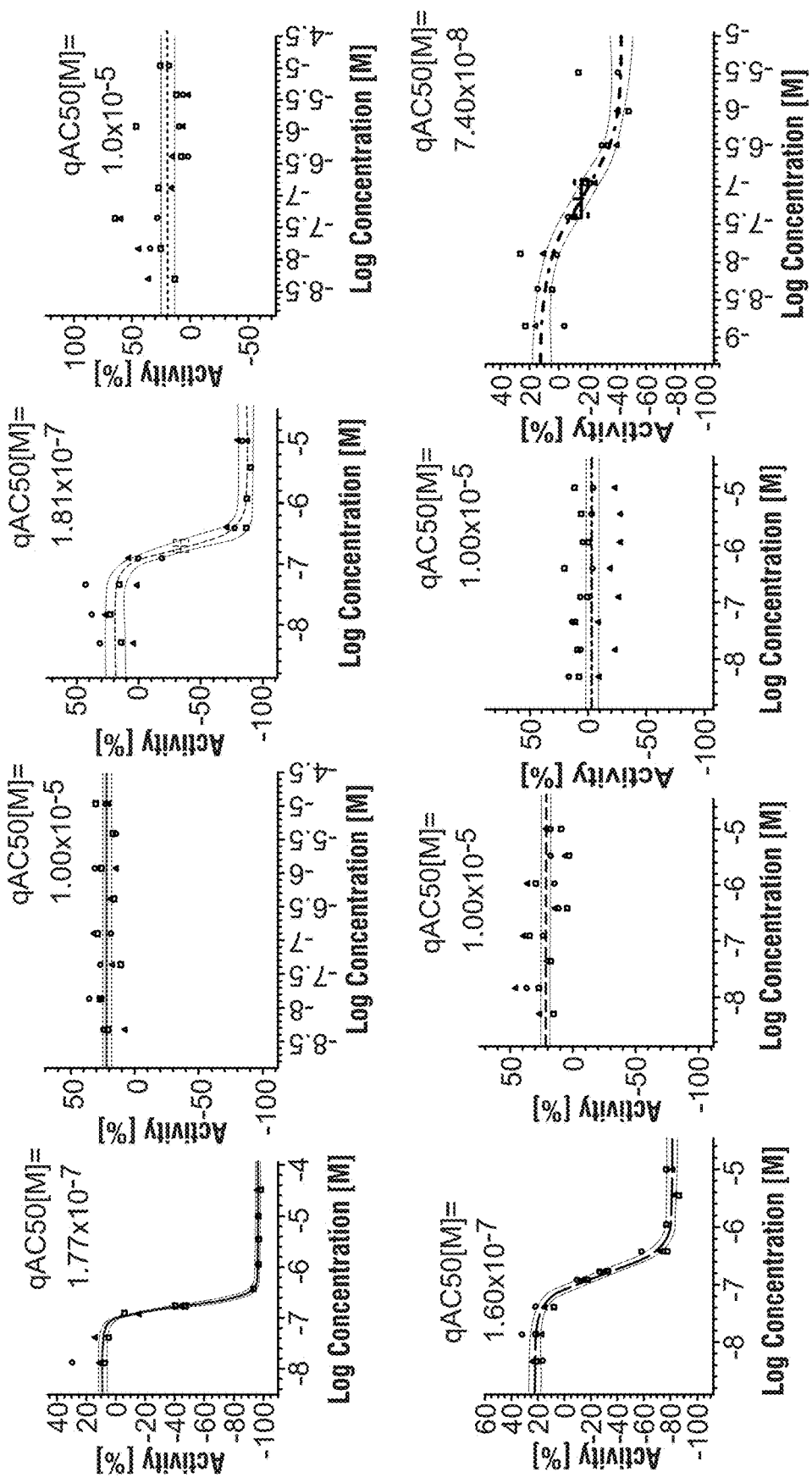
Figure 24:
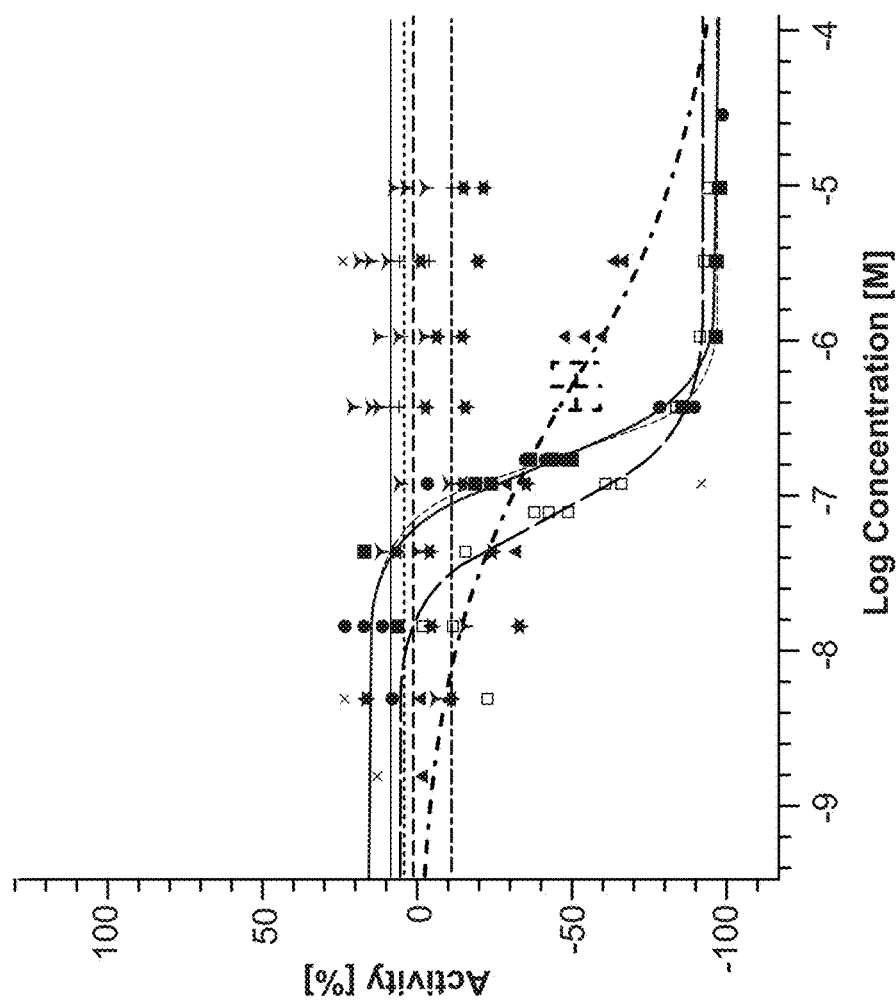
Figure 24:
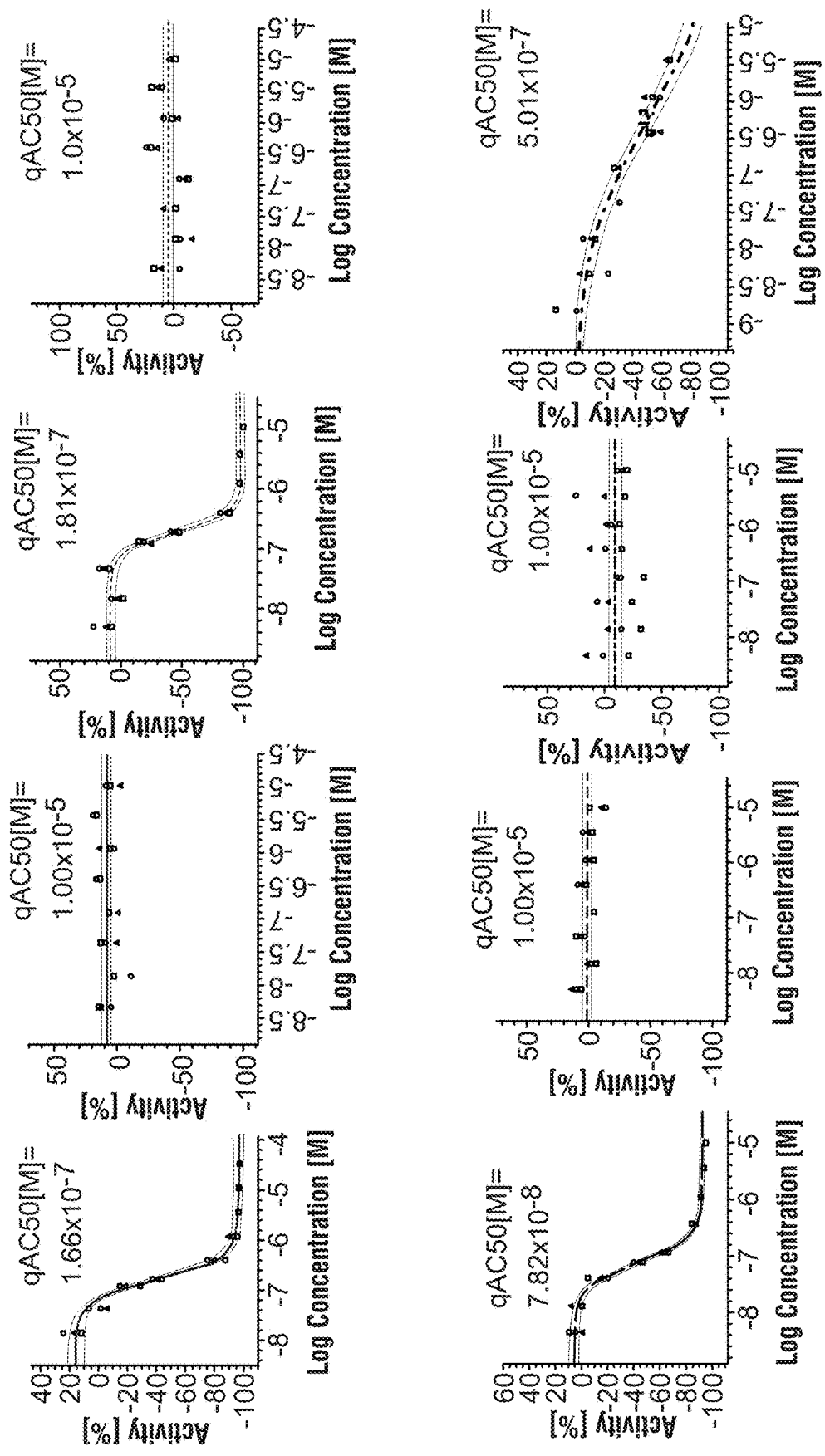
Figure 24:
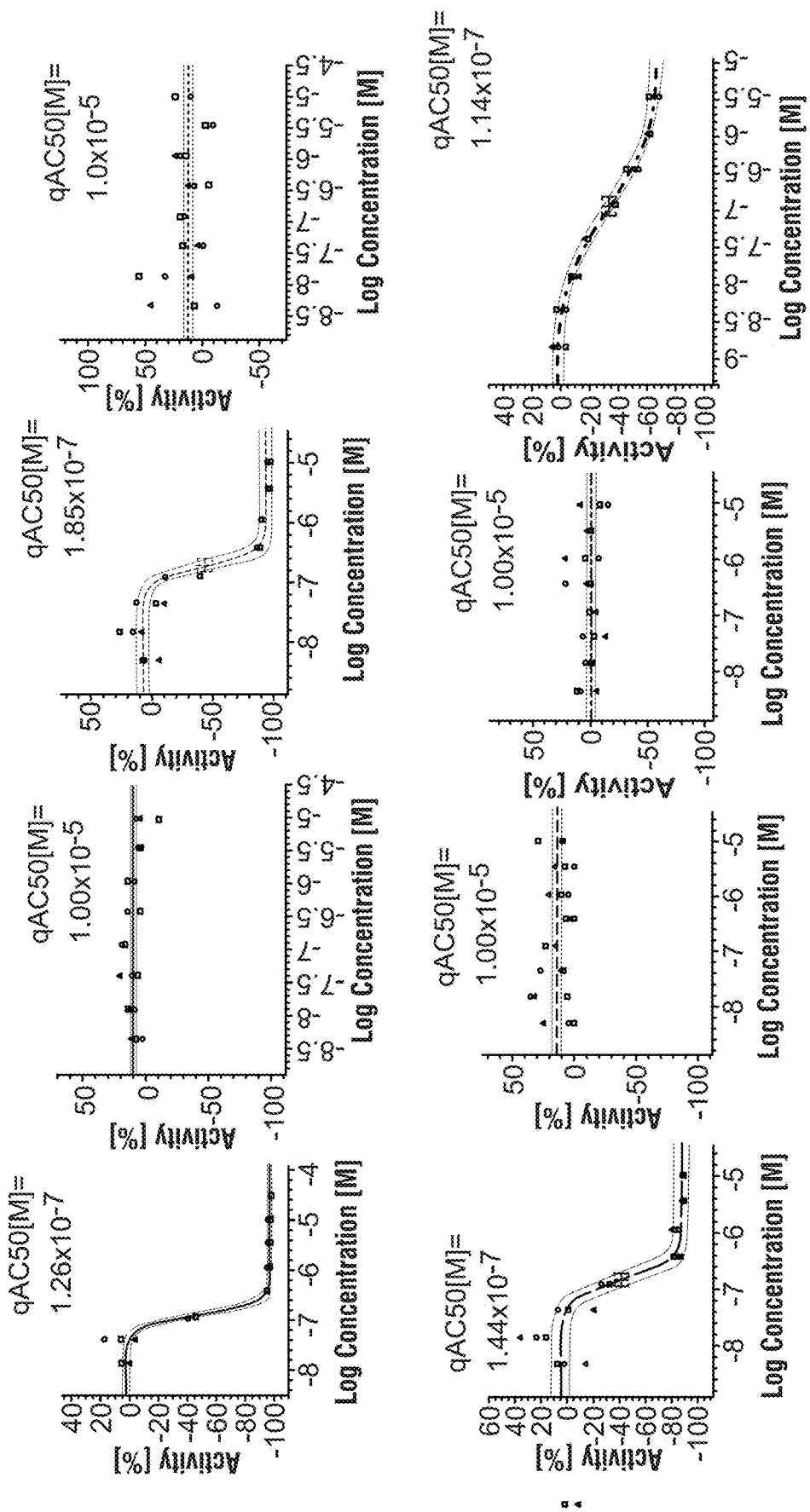
Figure 24:
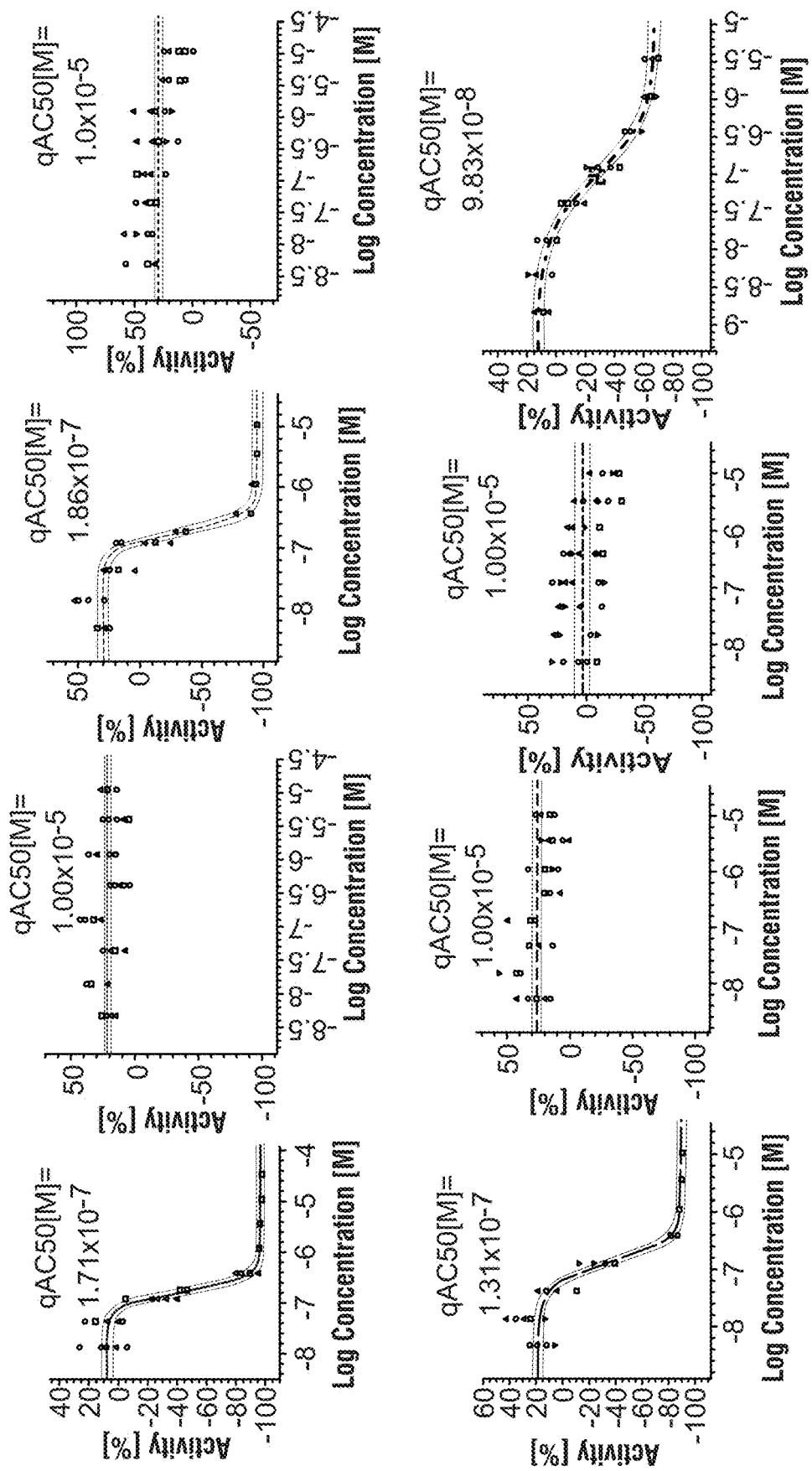
Figure 24:
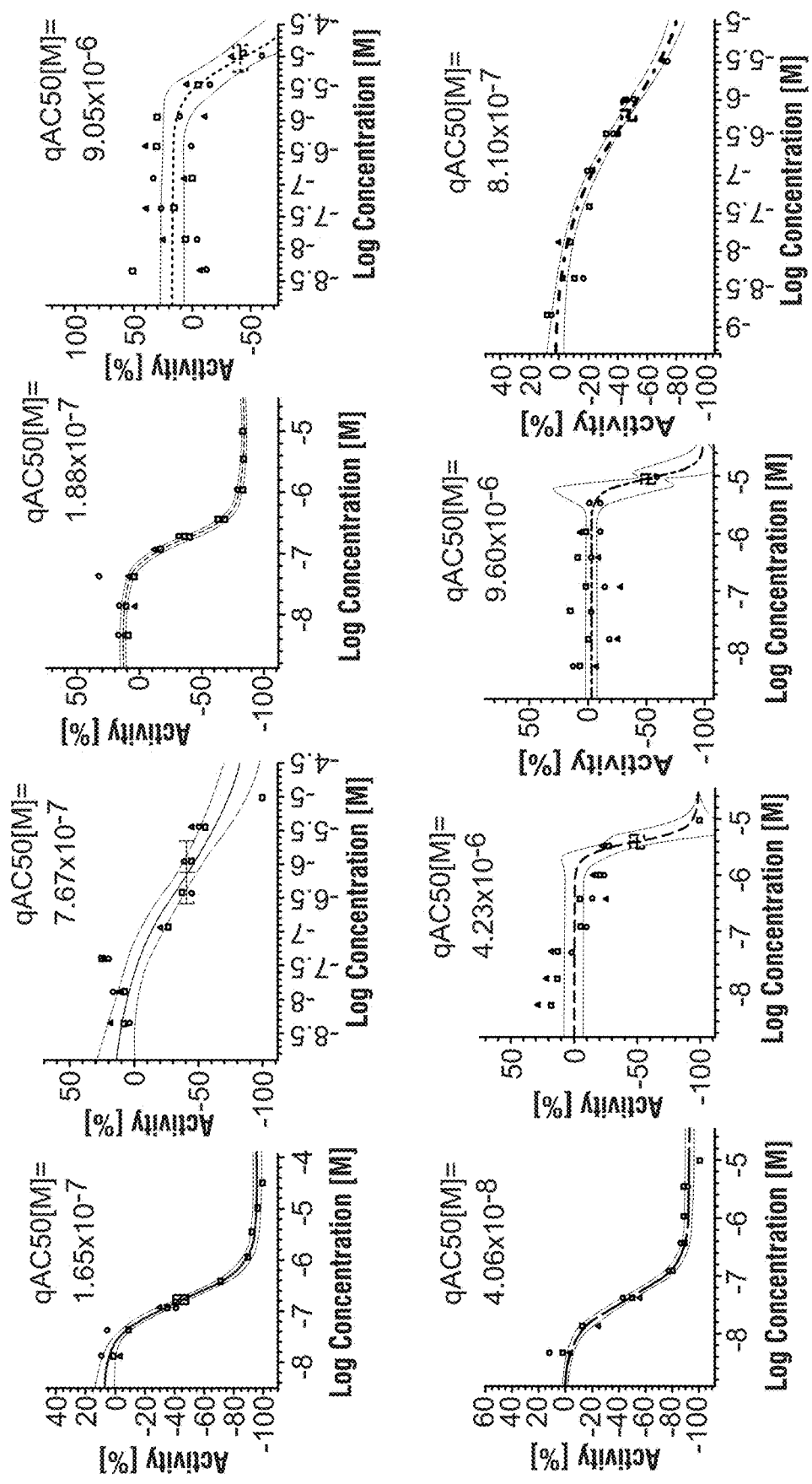
Figure 24:
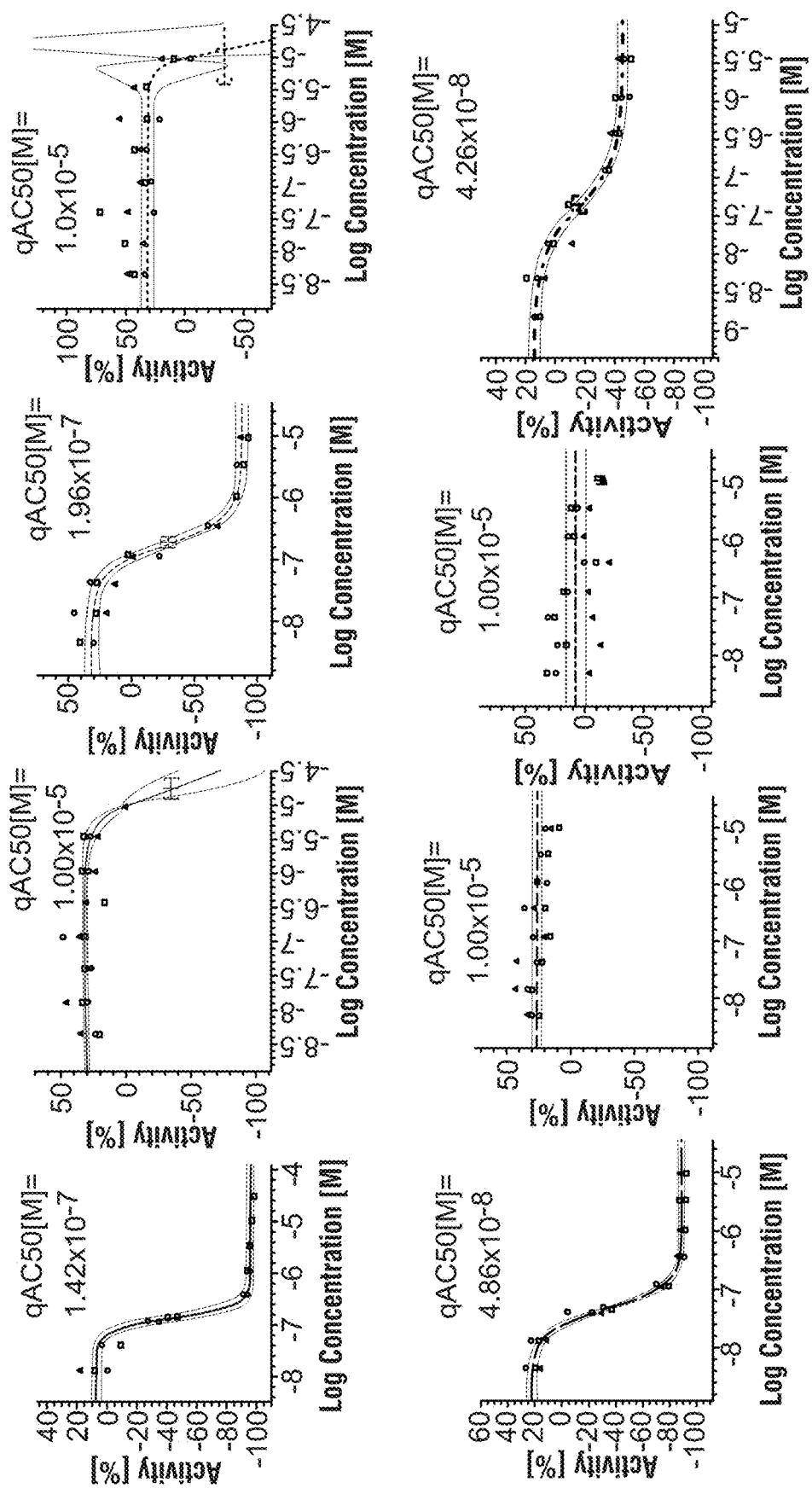
Figure 24:
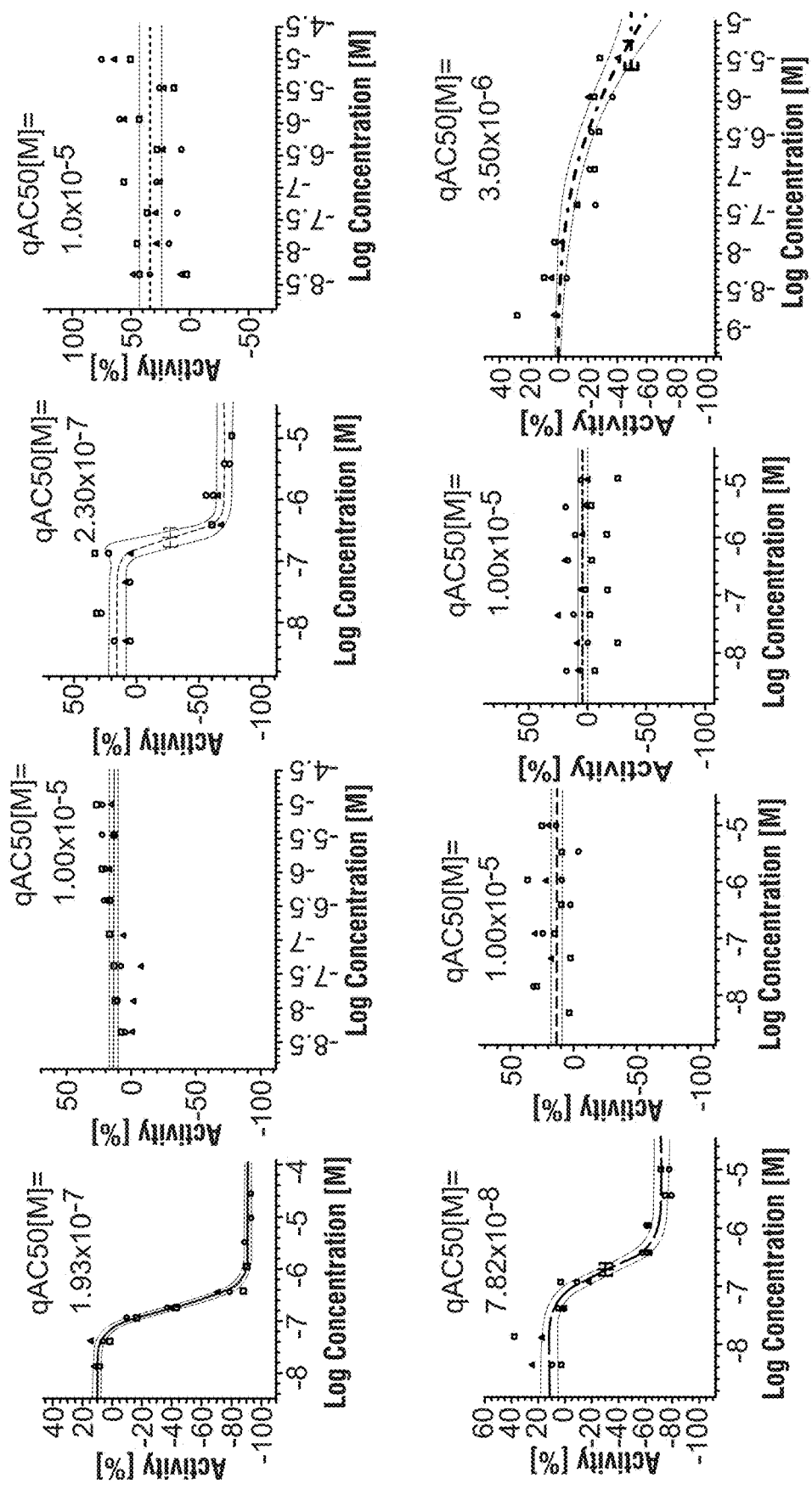
Figure 24:
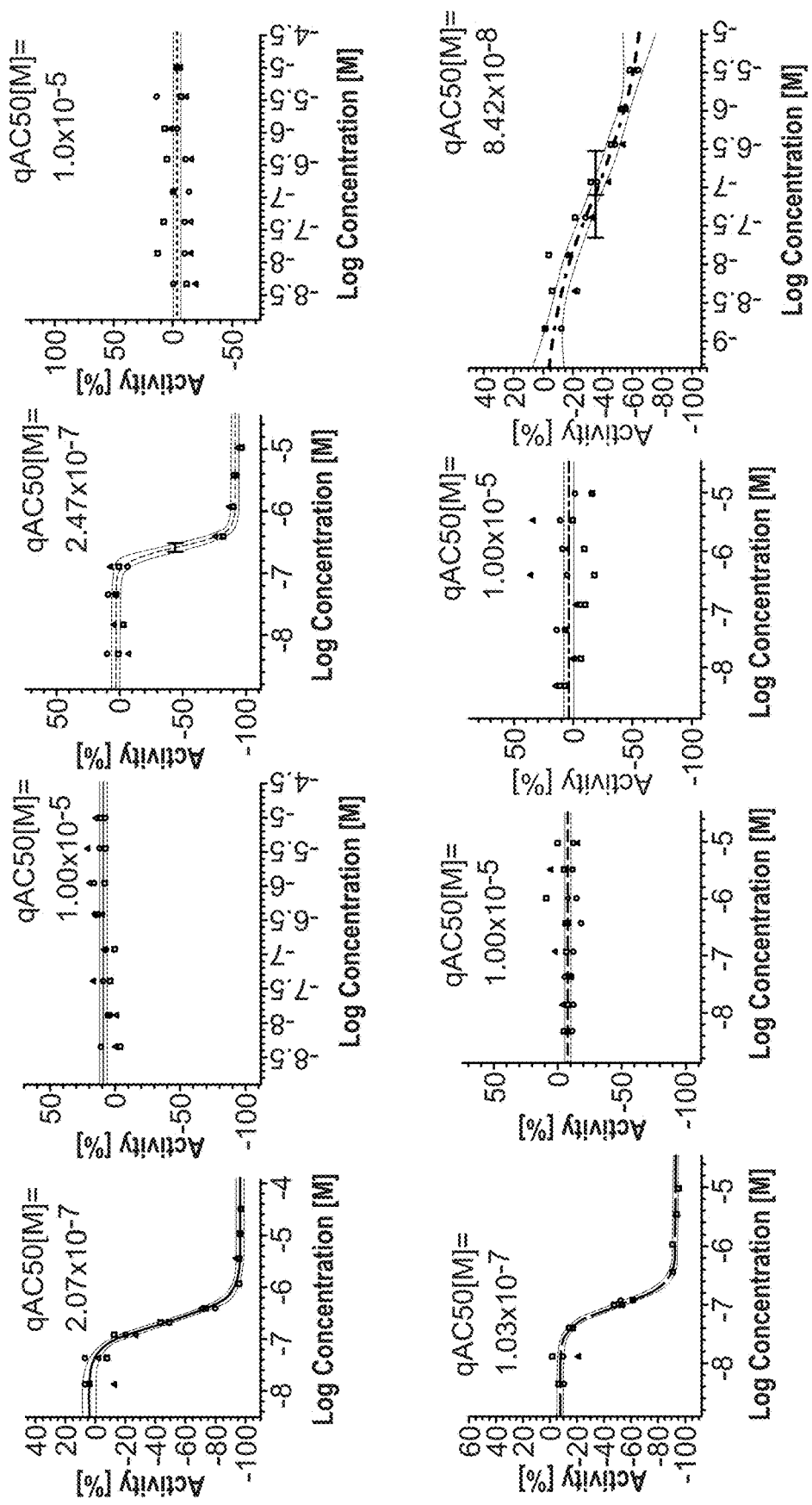
Figure 24:
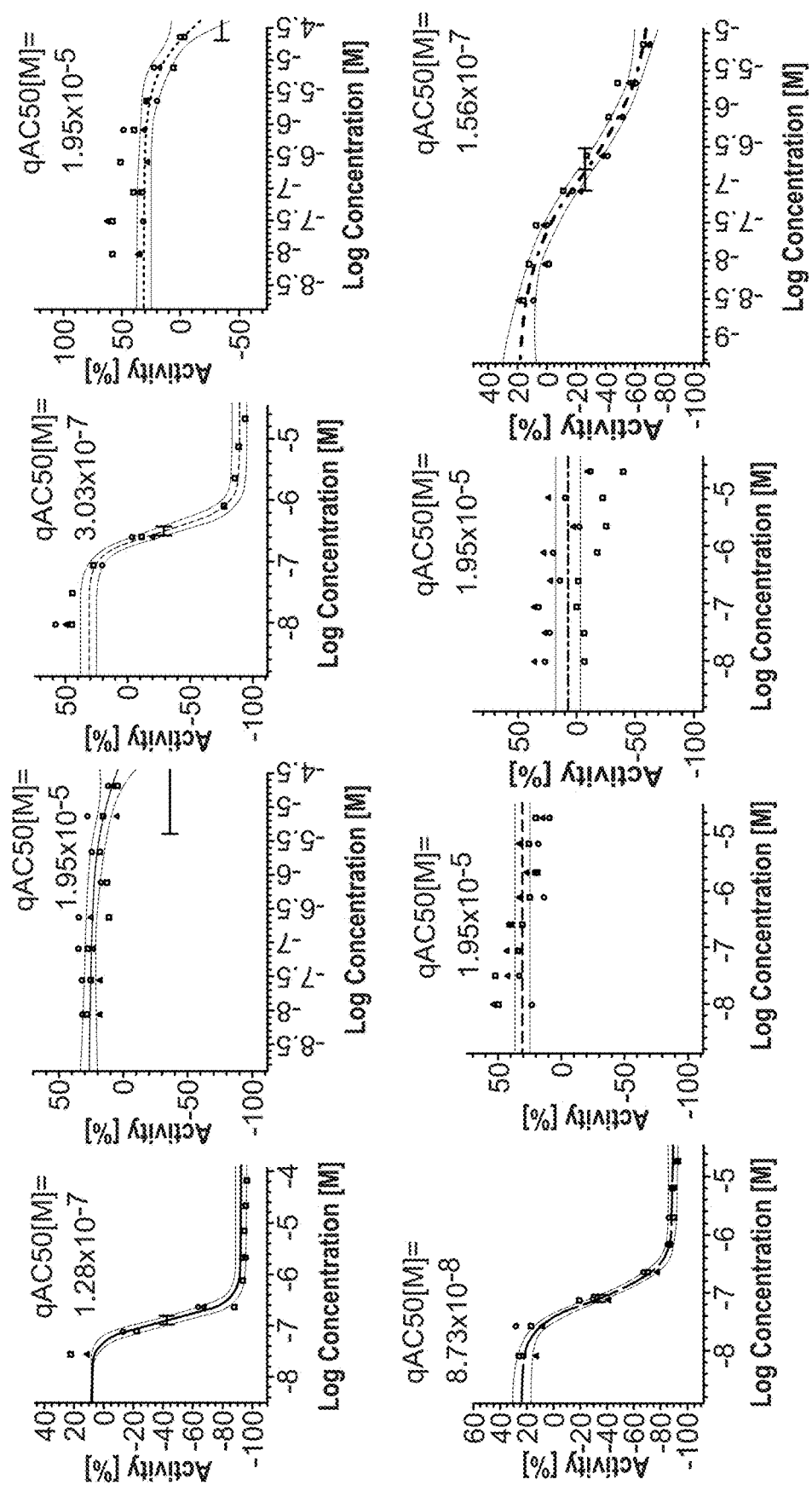
Figure 24:
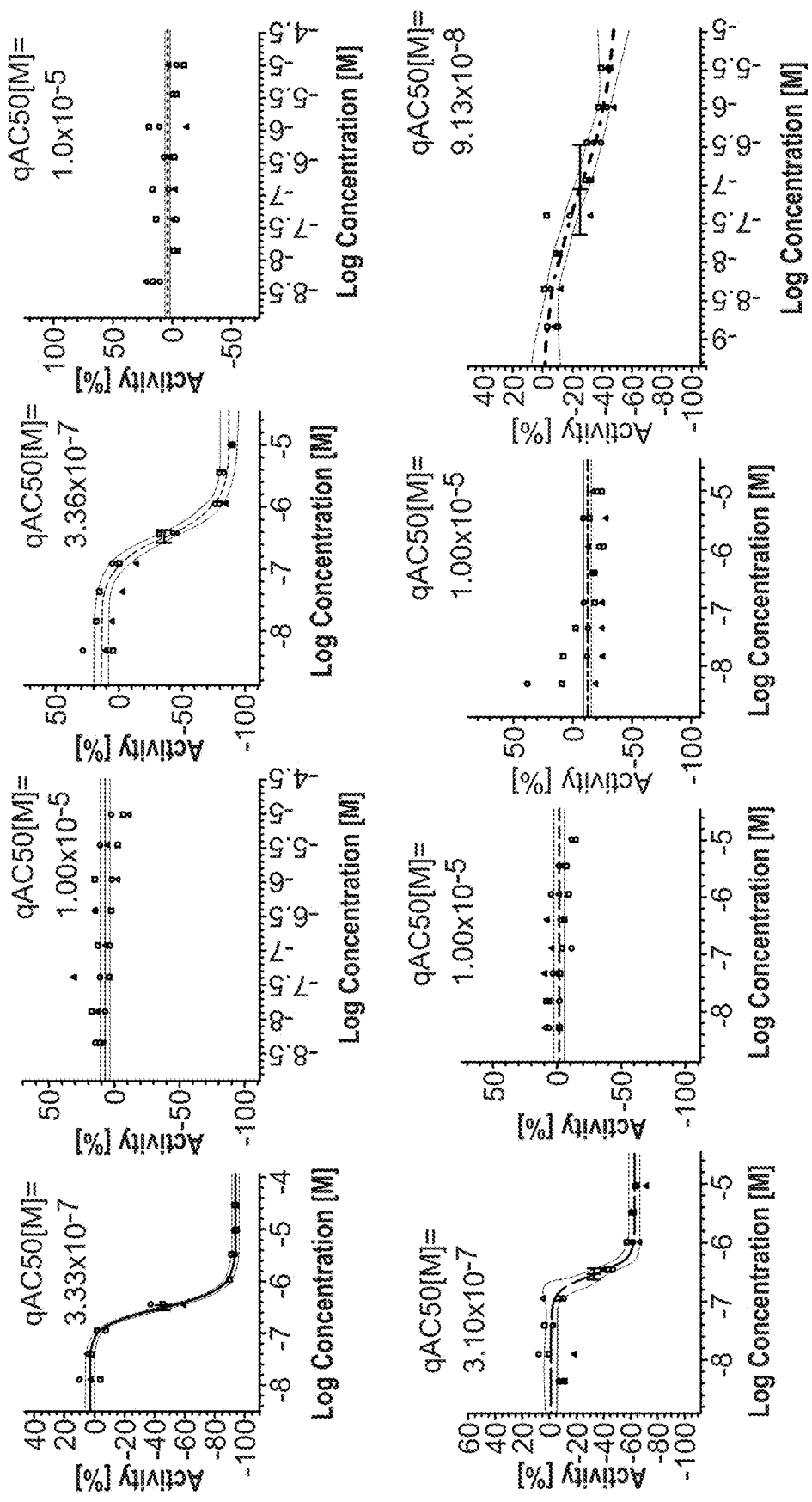
Figure 24:
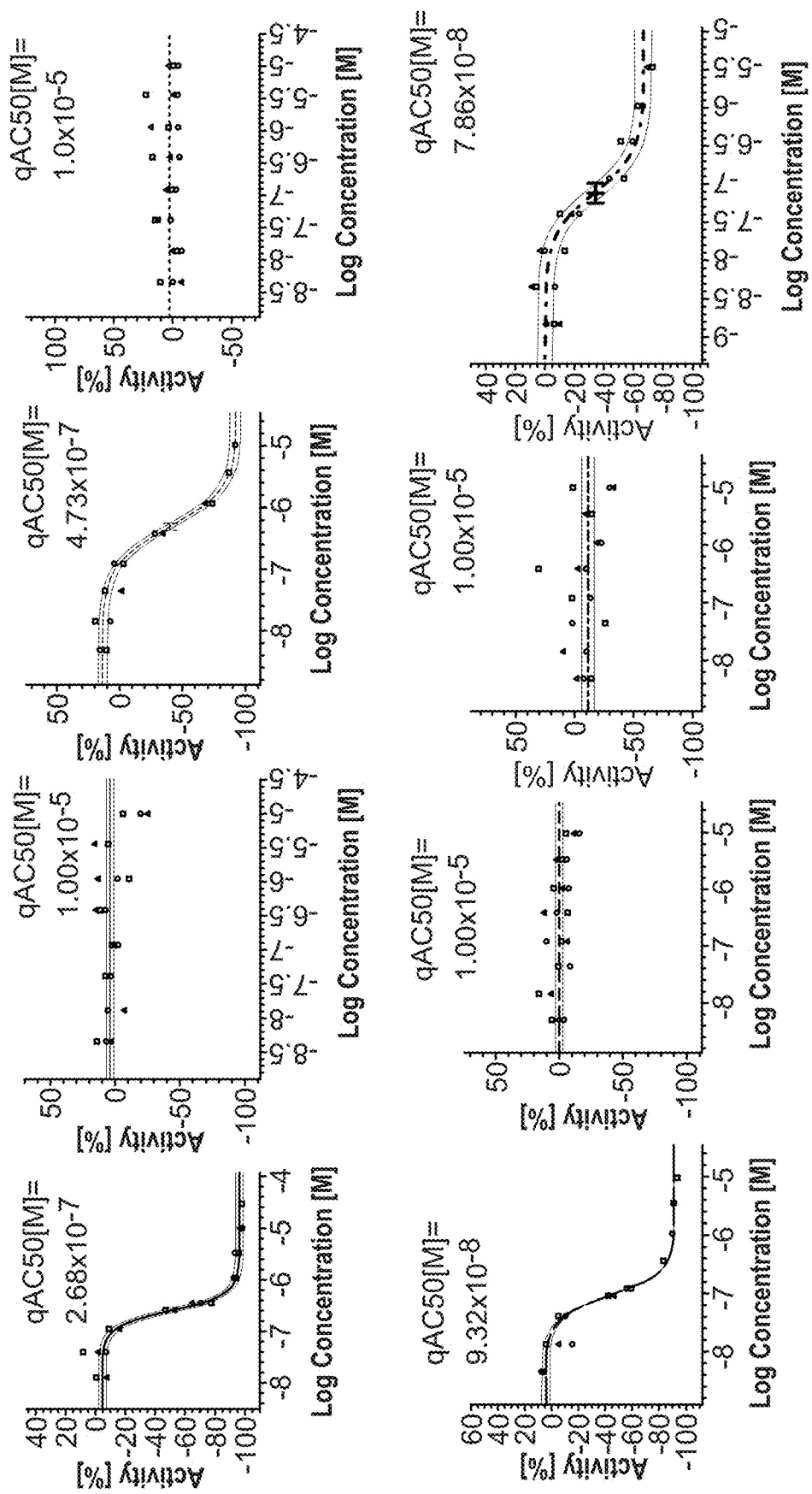
Figure 24:
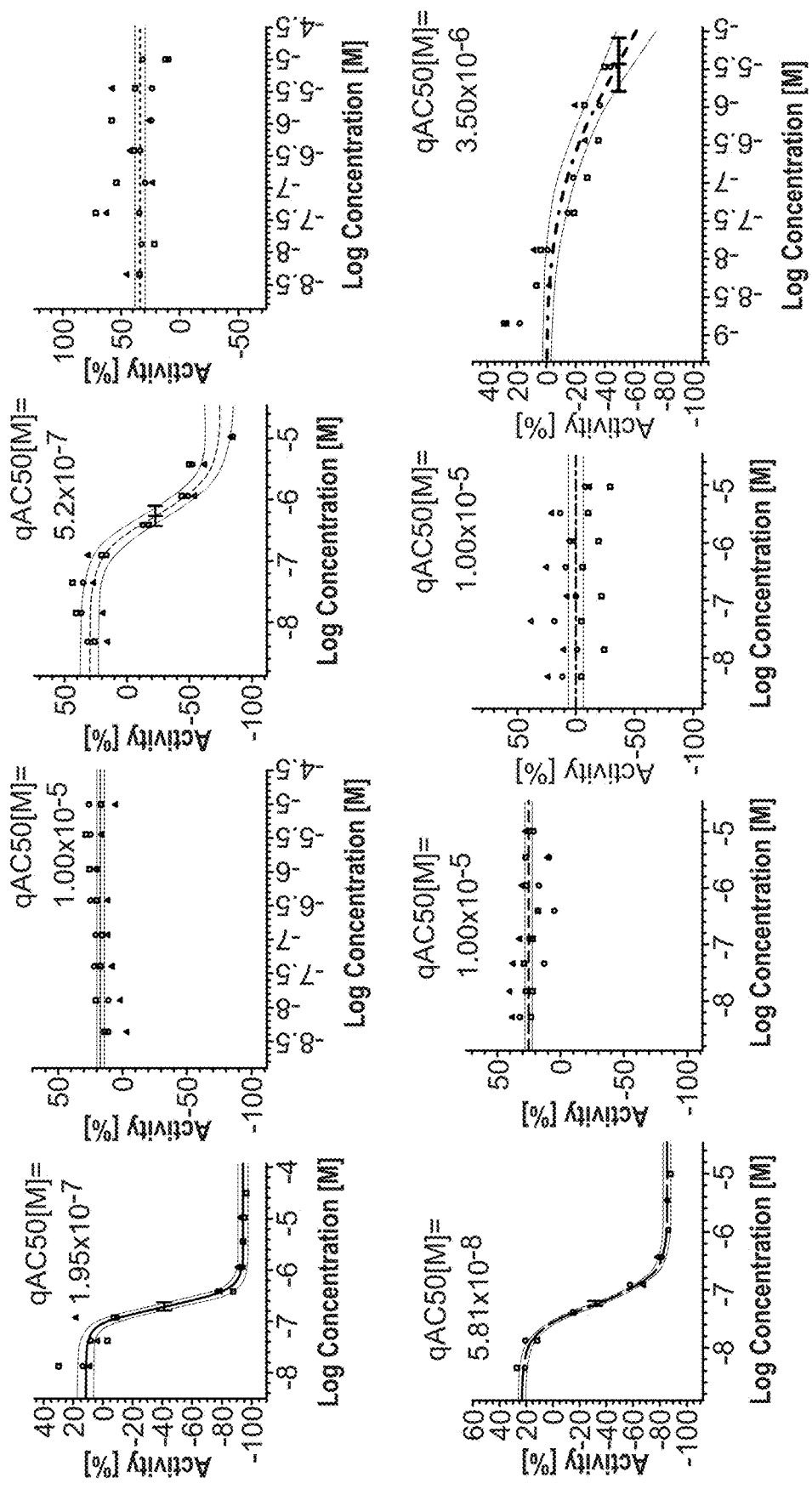
Figure 24:
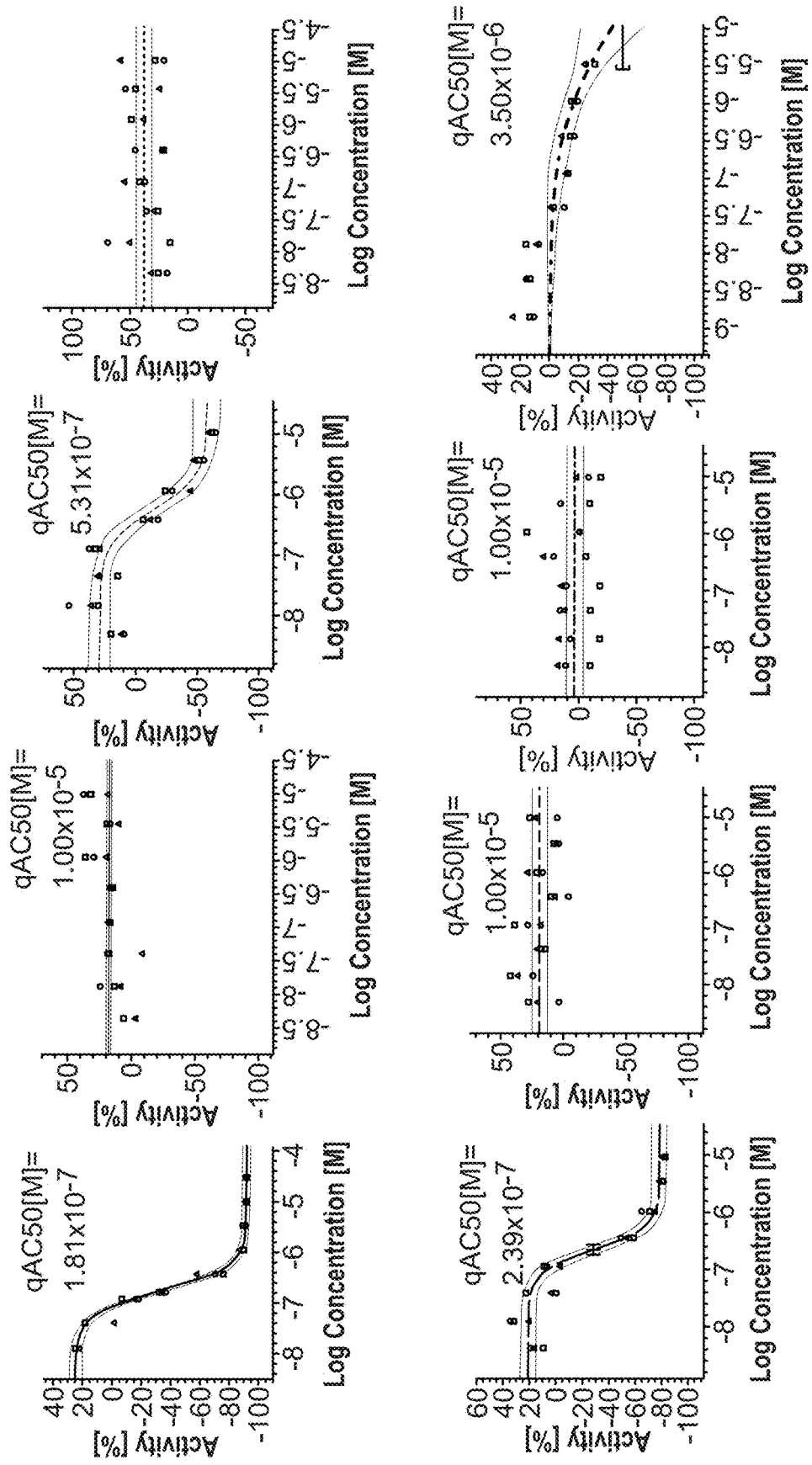
Figure 24:
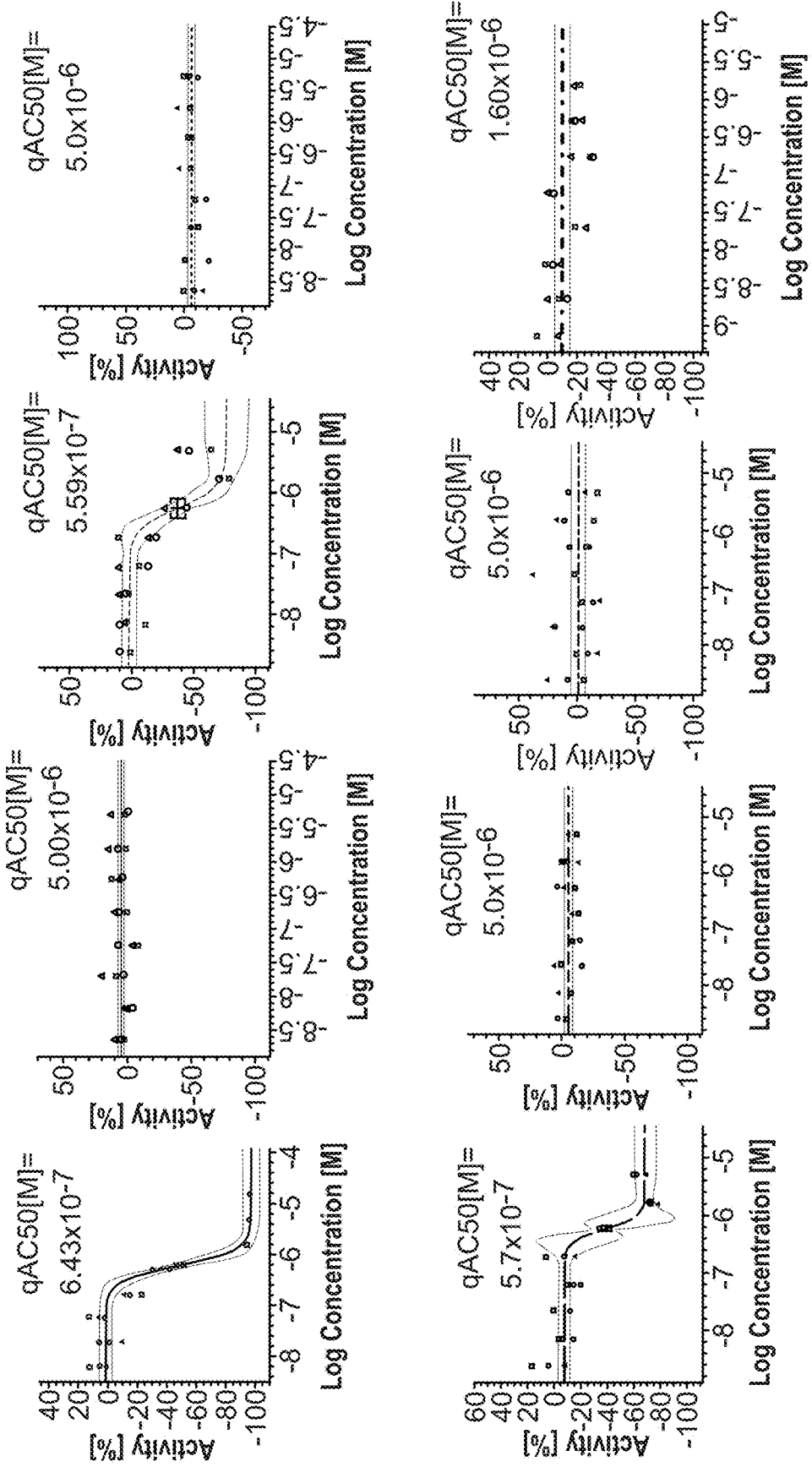
Figure 24:
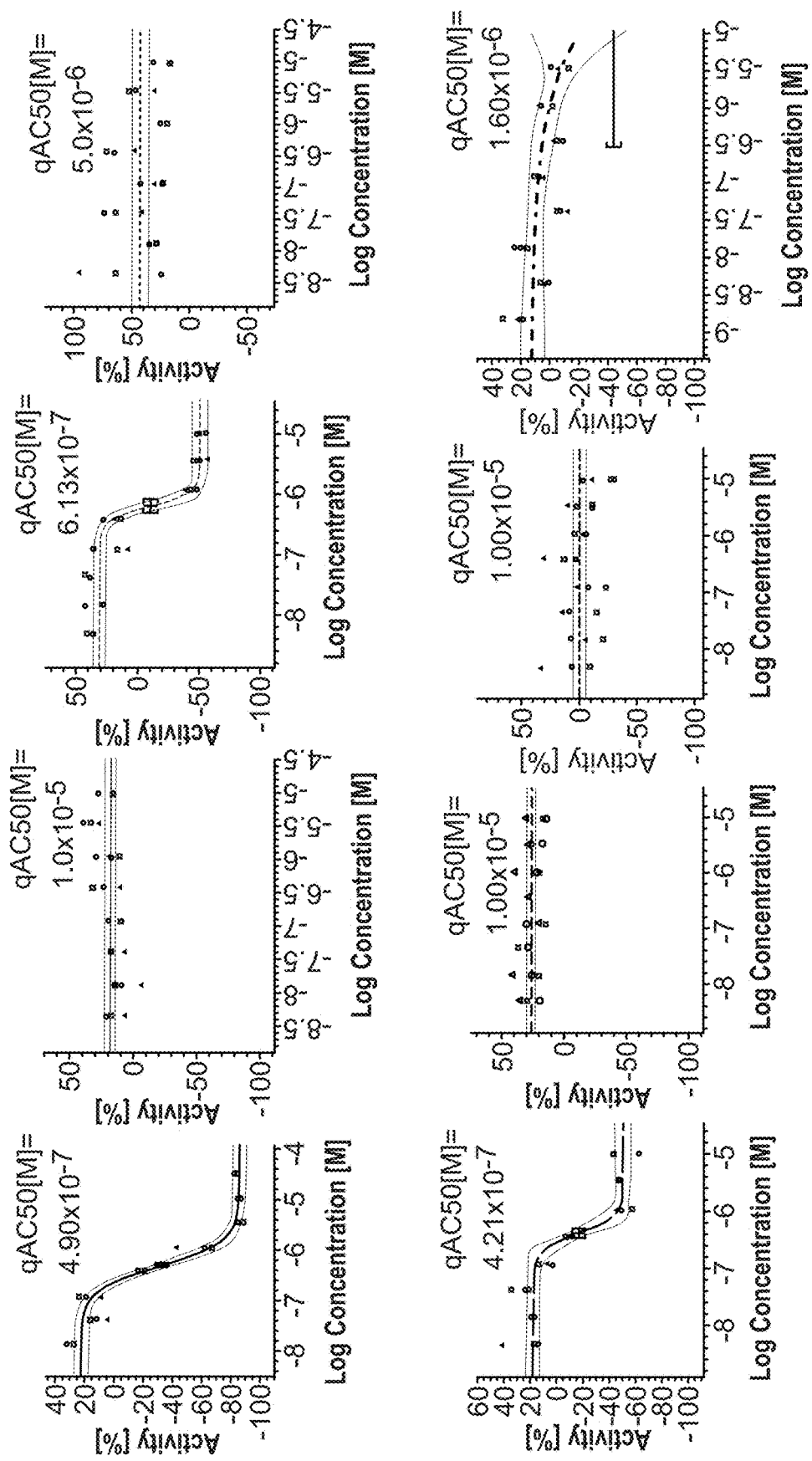
Figure 24:
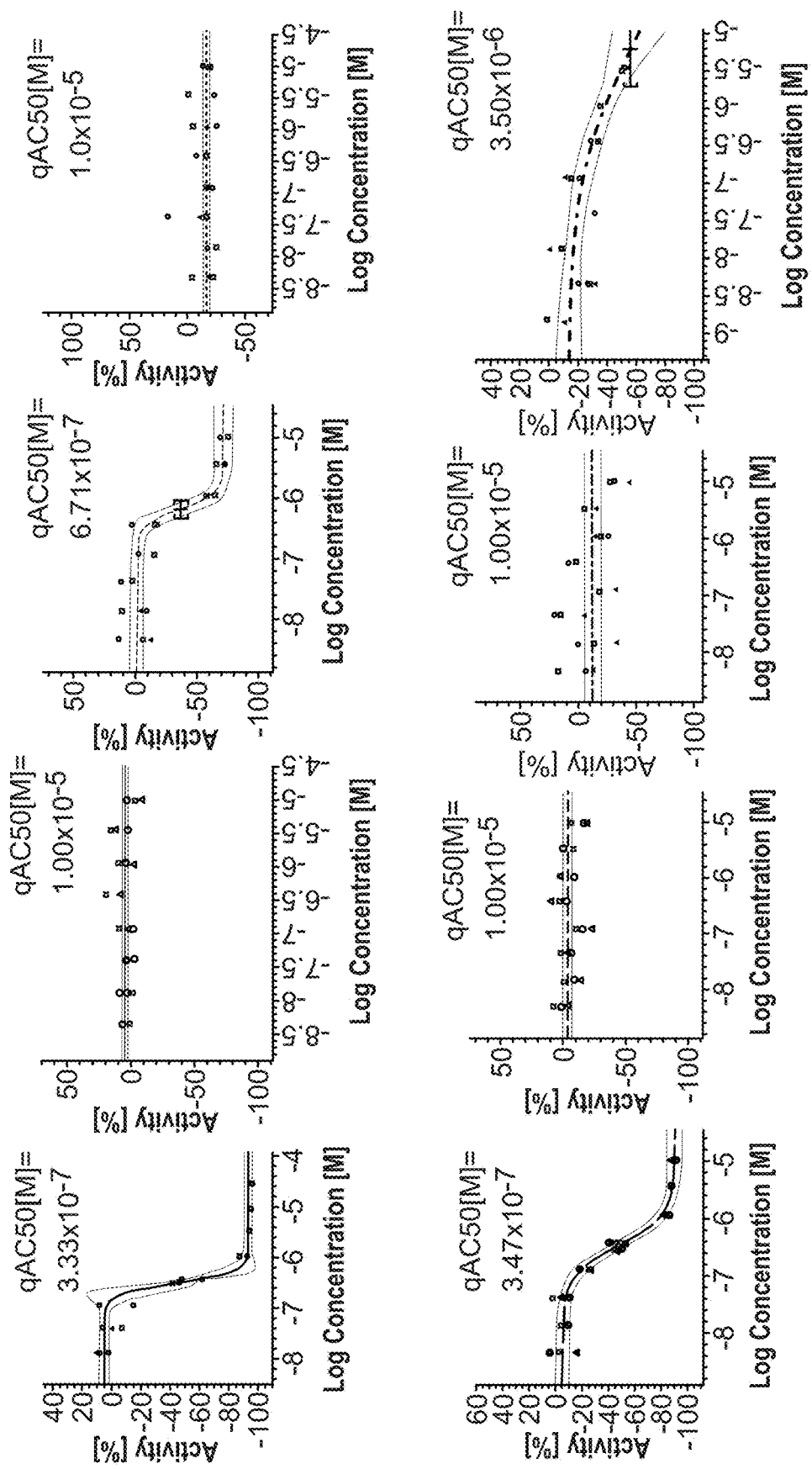
Figure 24:
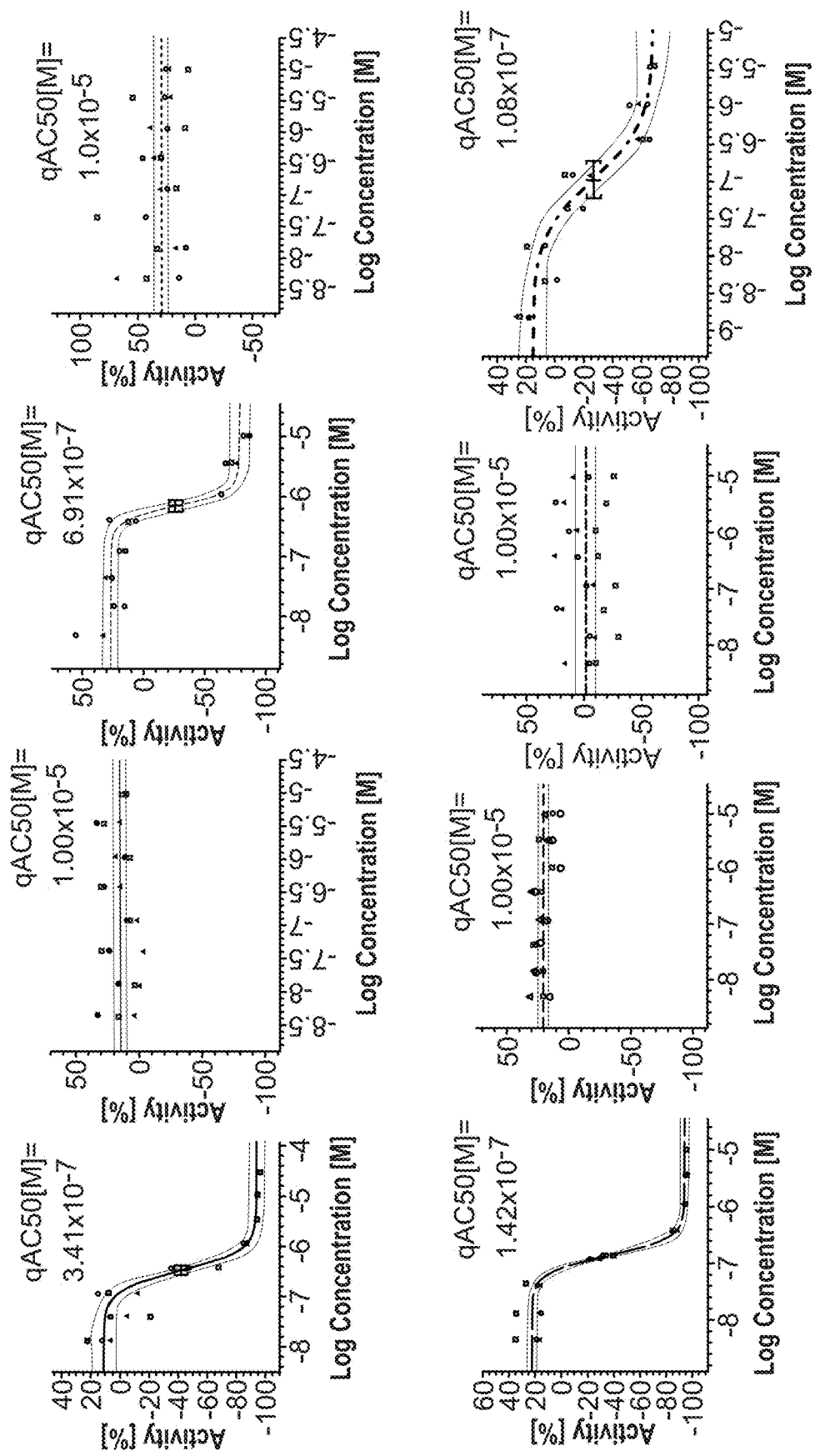
Figure 24:
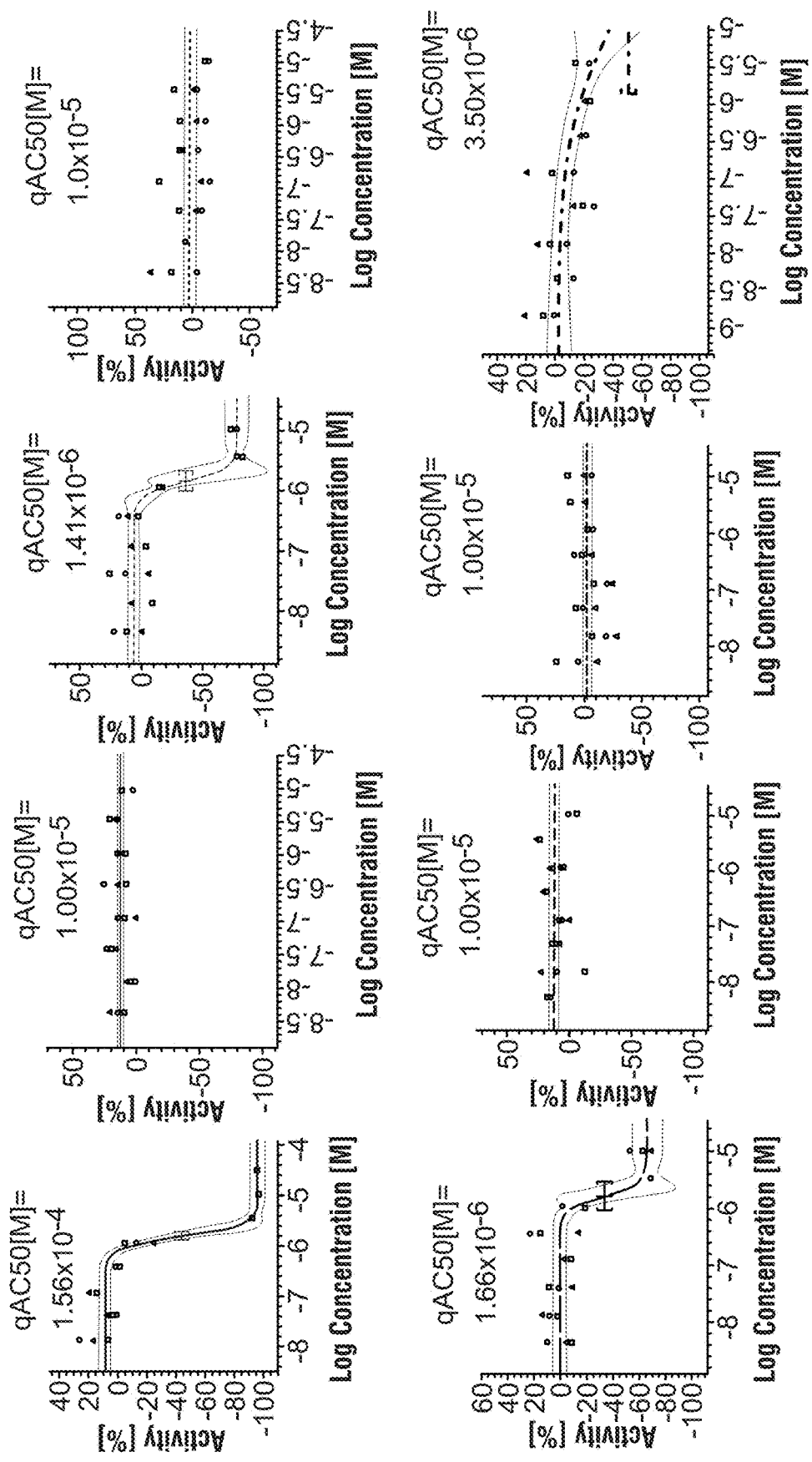
Figure 24:
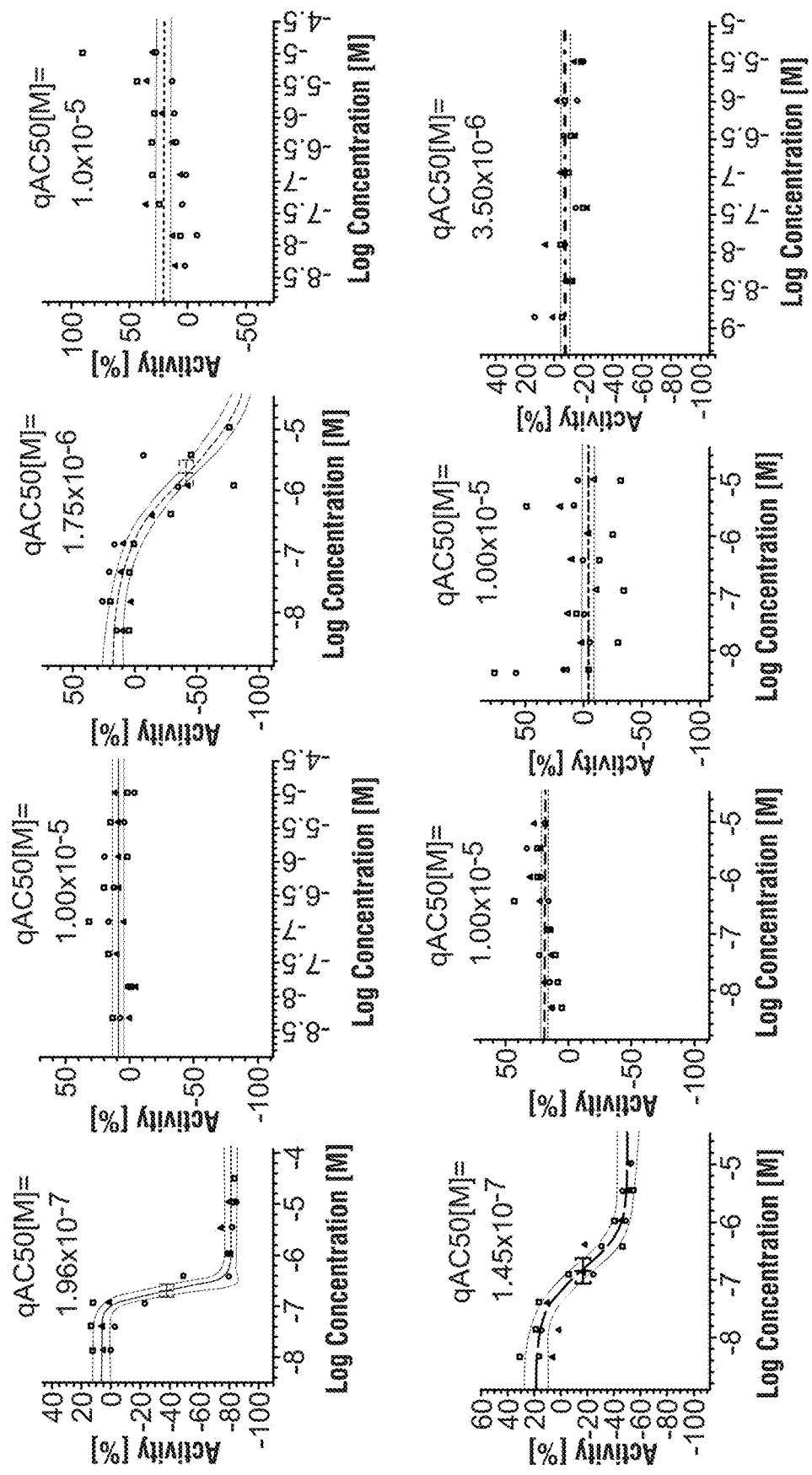
Figure 24:
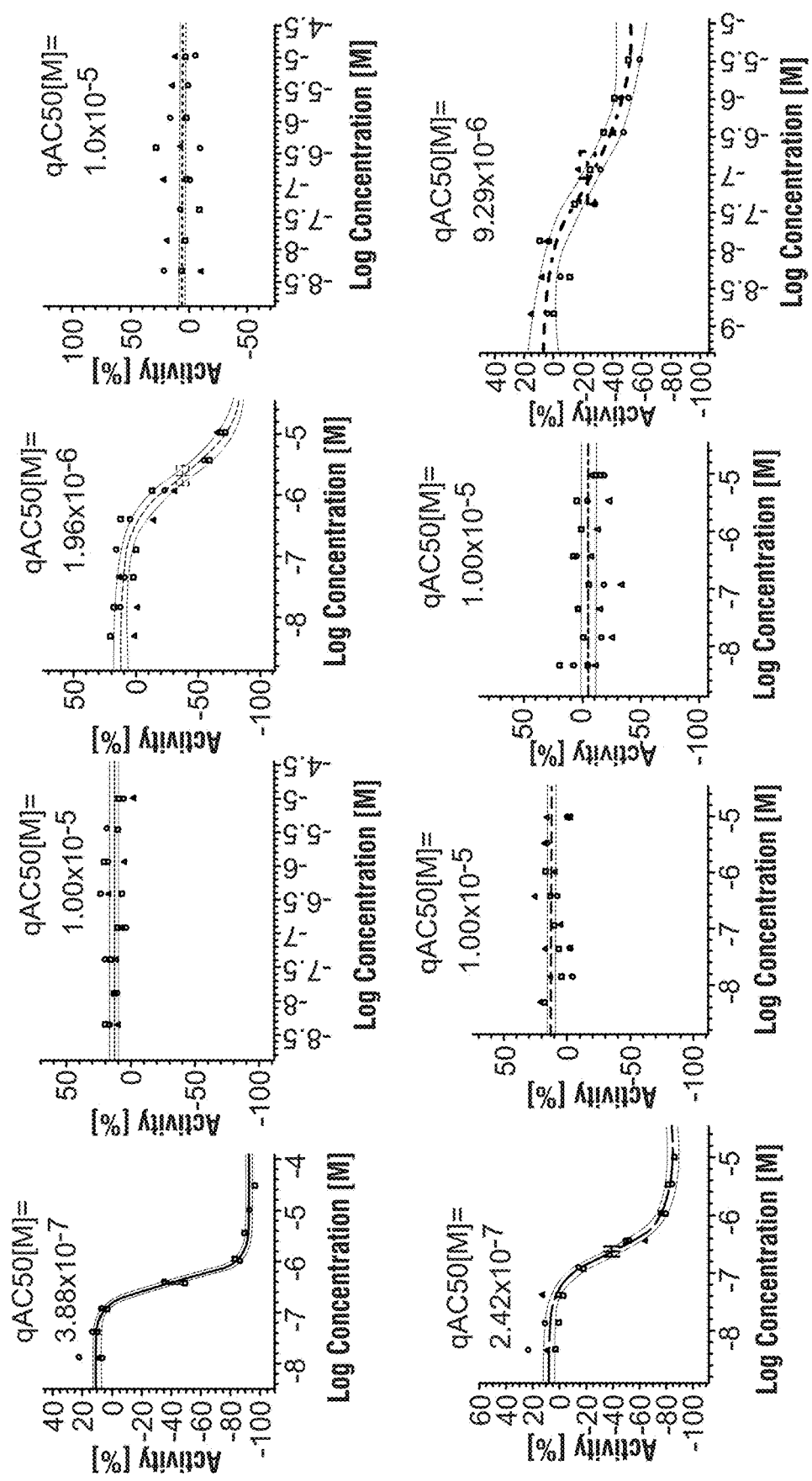
Figure 24:
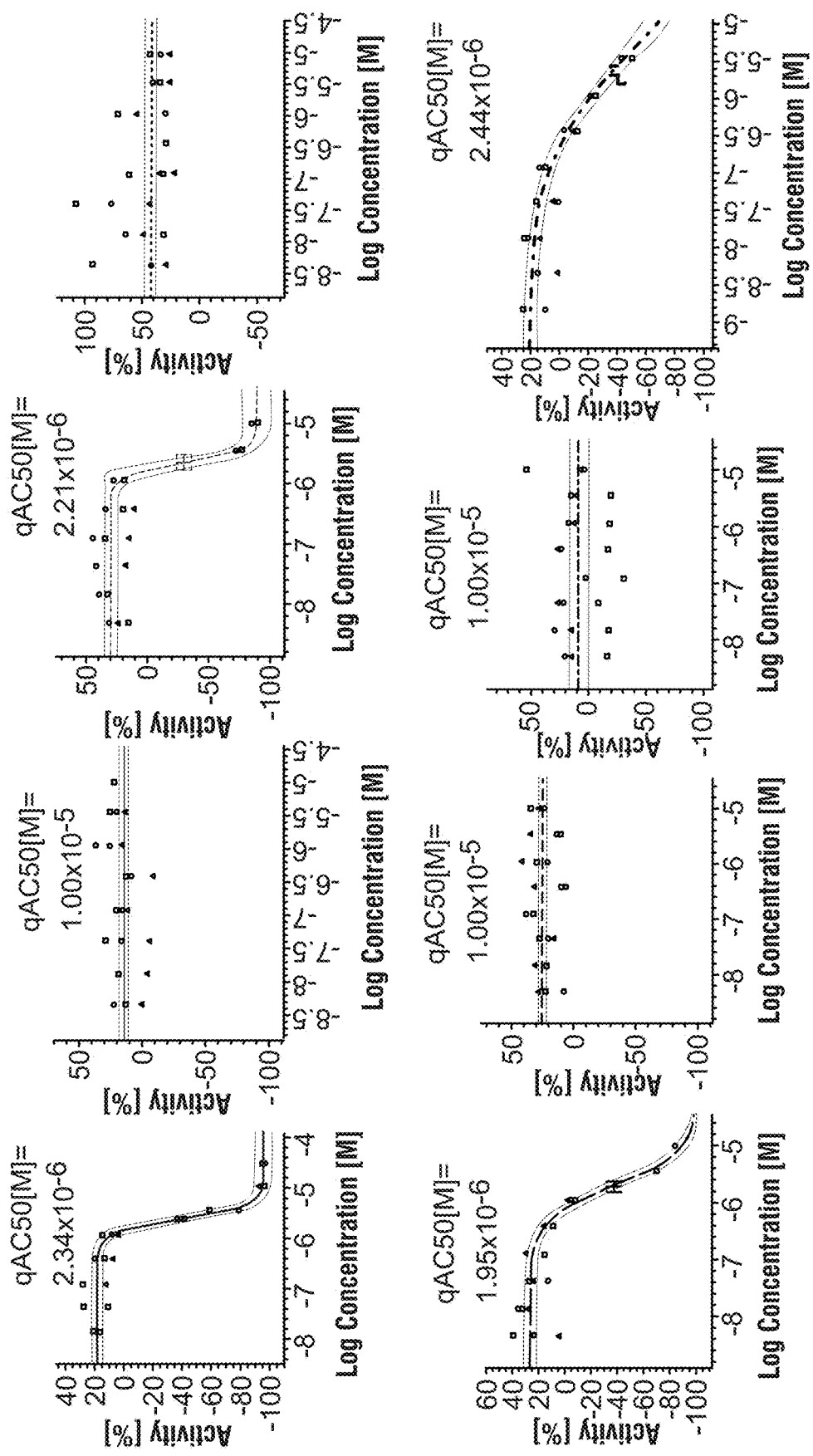
Figure 24:
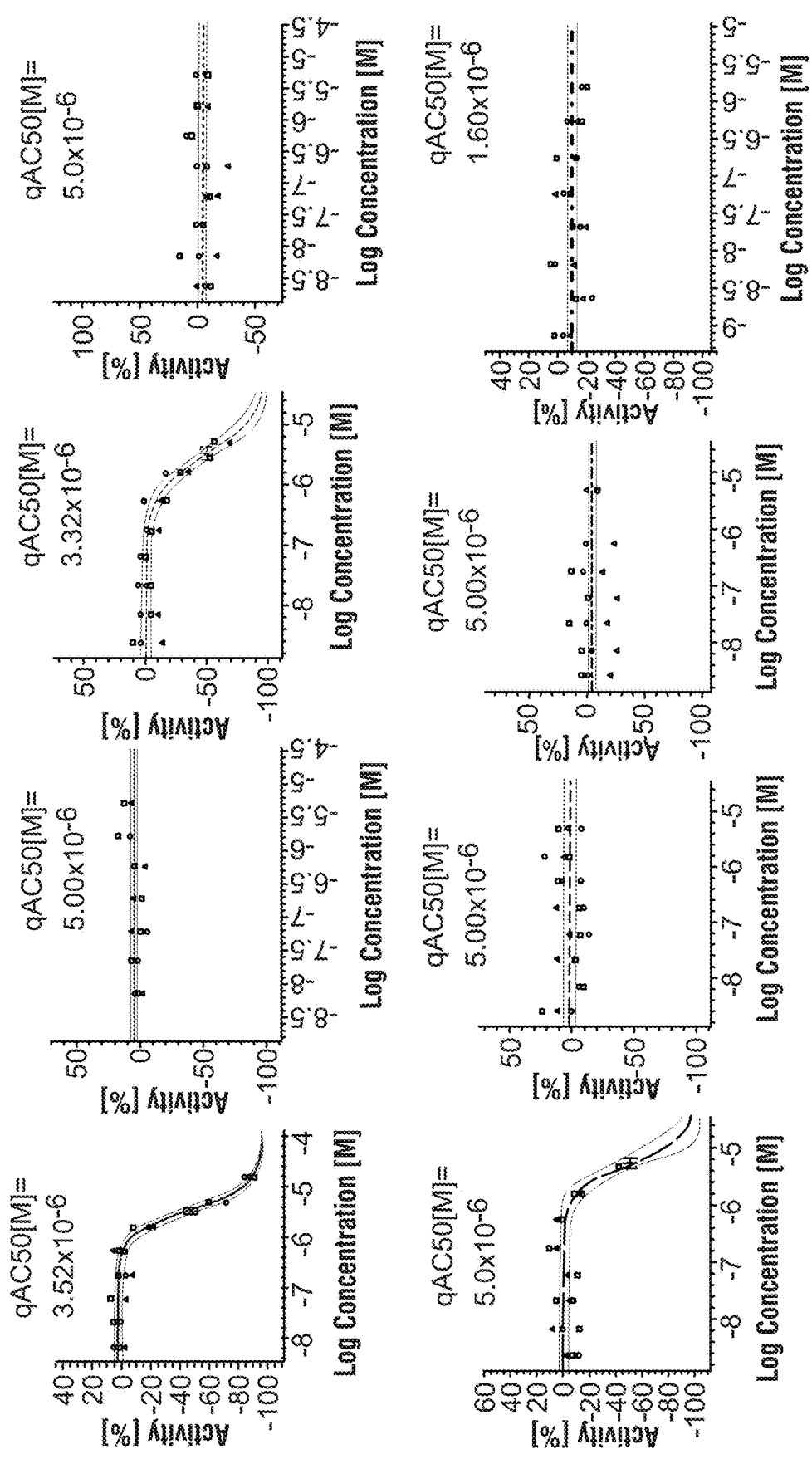
Figure 24:
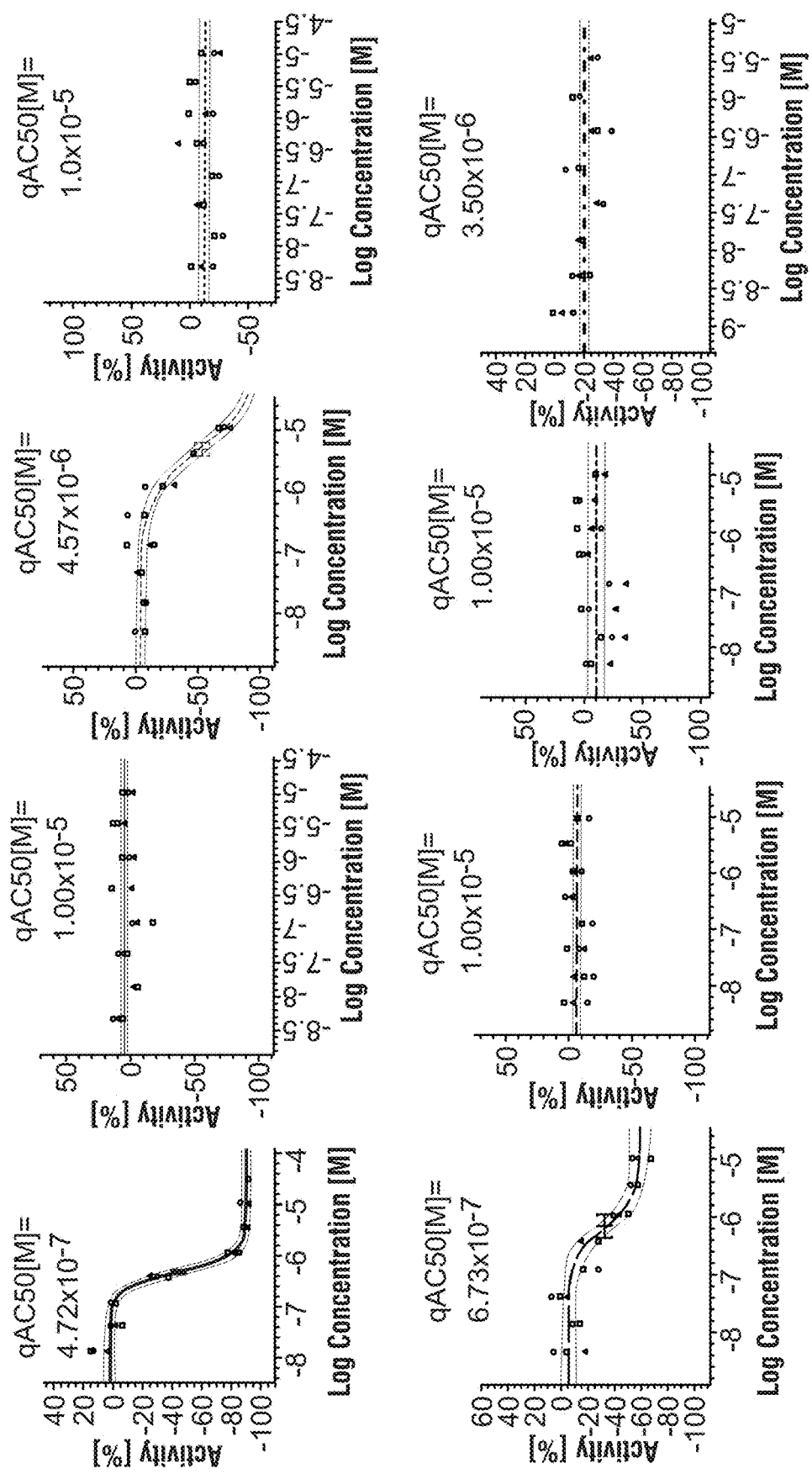
Figure 24:
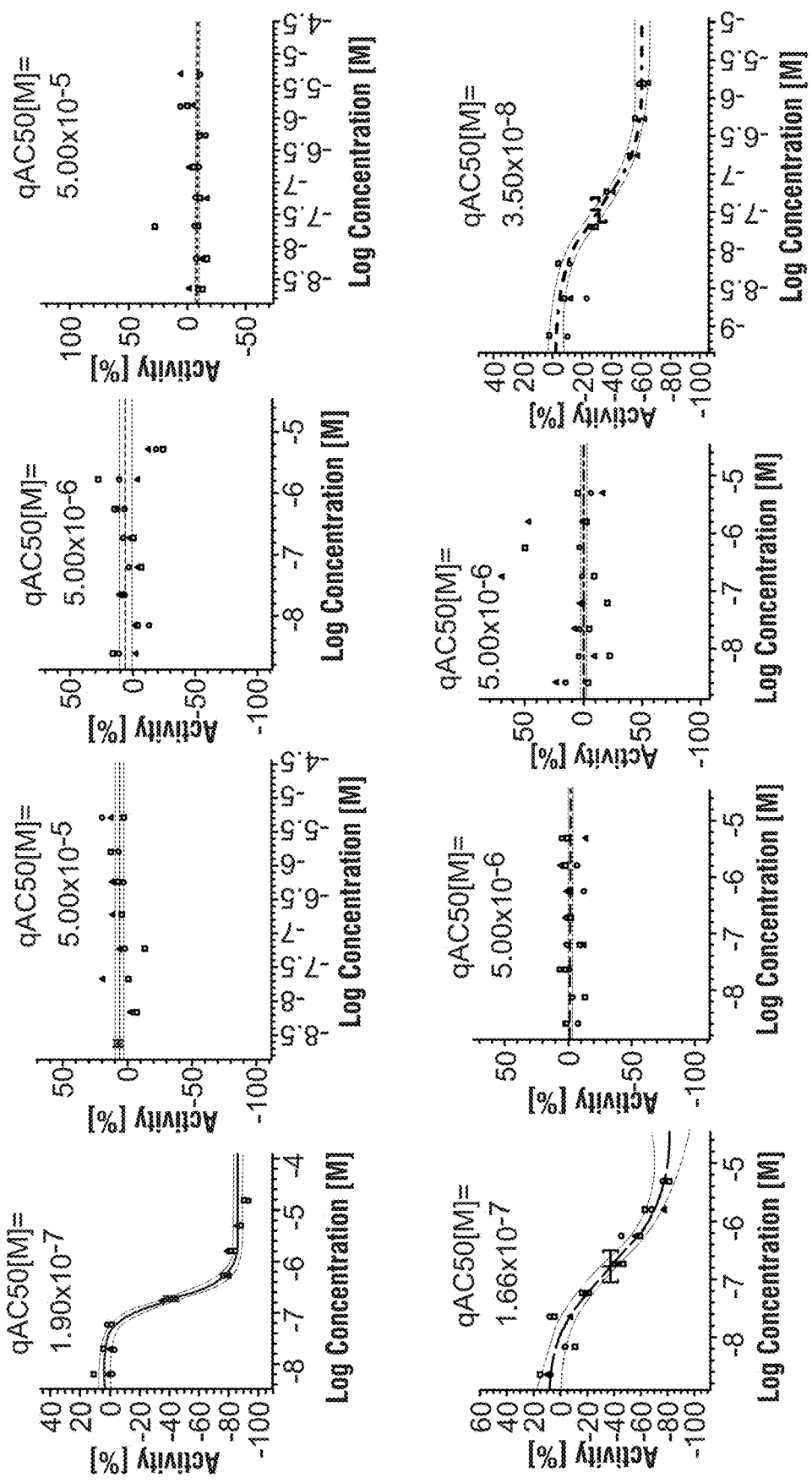
Figure 24:
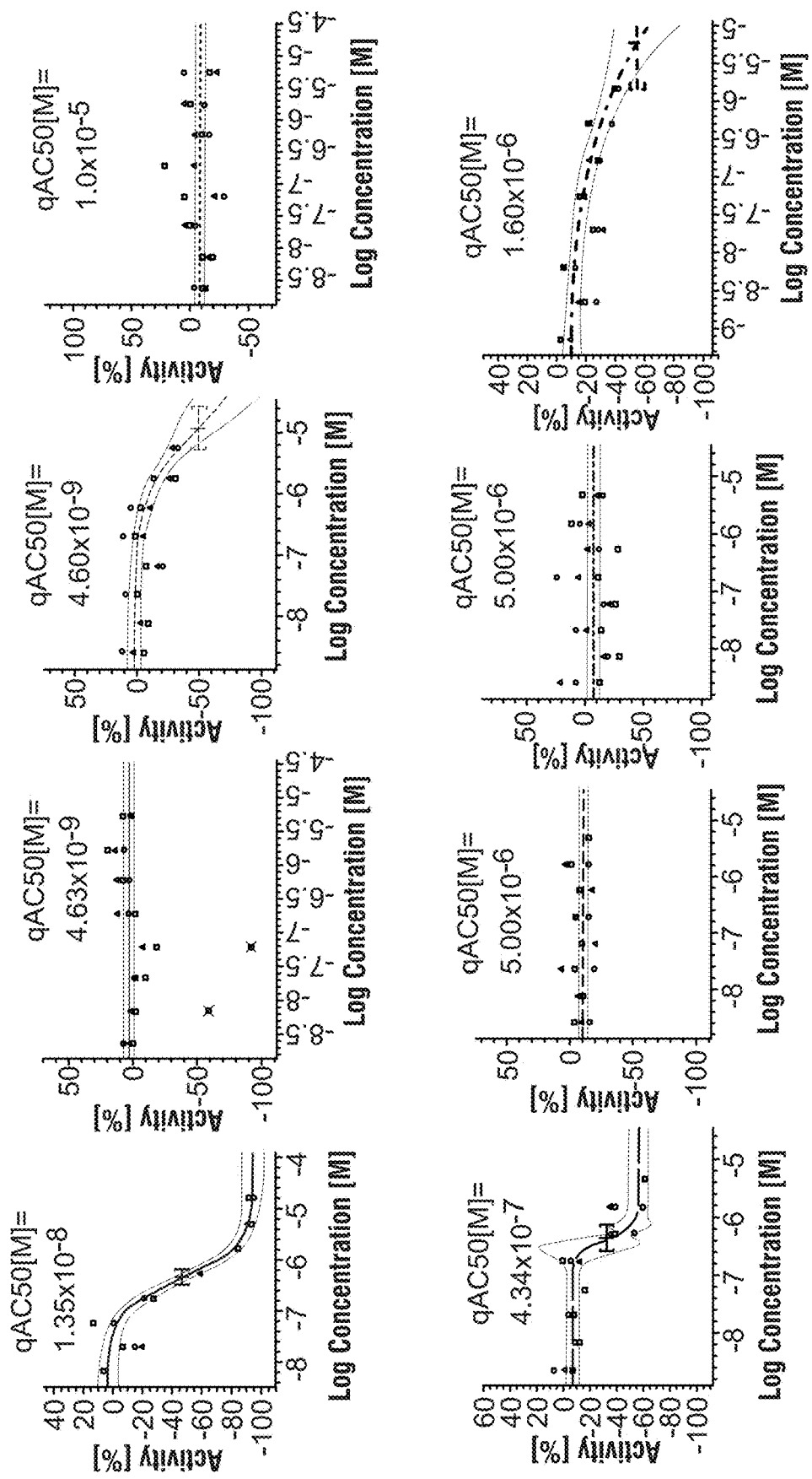
Figure 24:
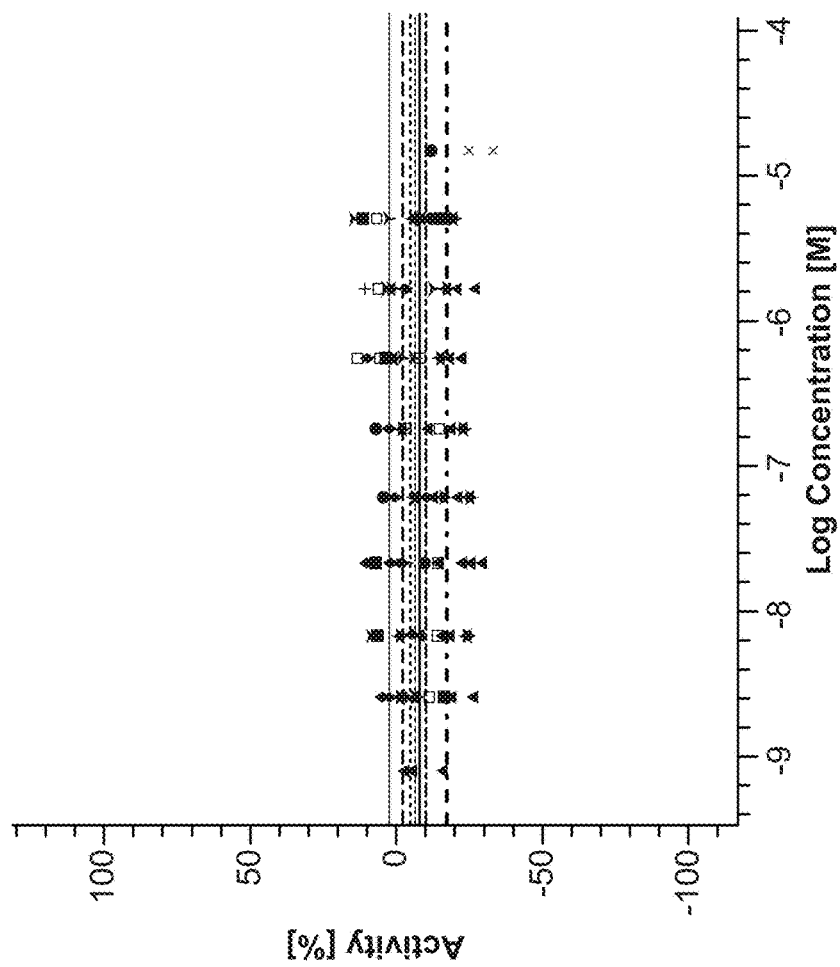
Figure 24:
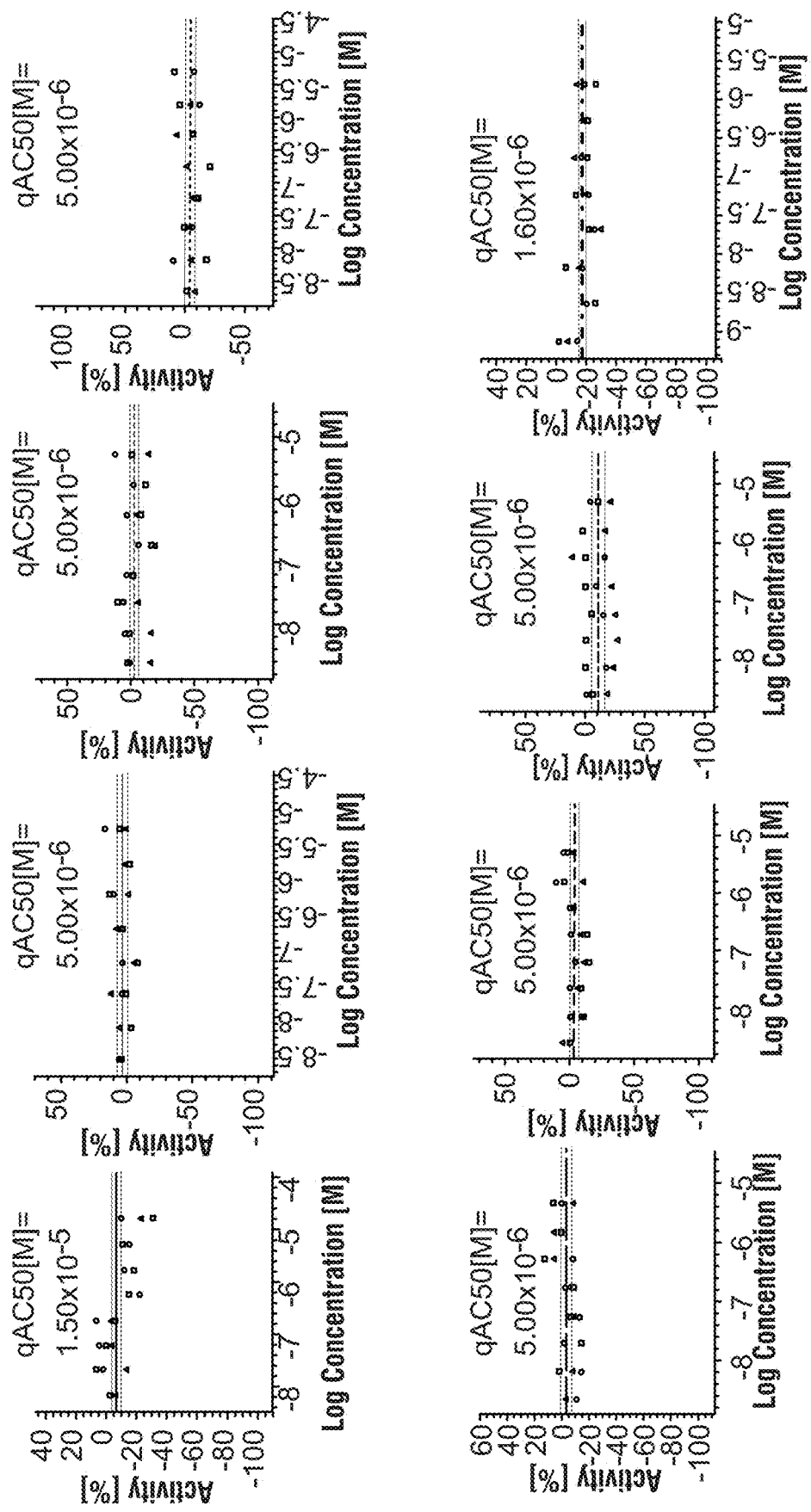
Figure 24:
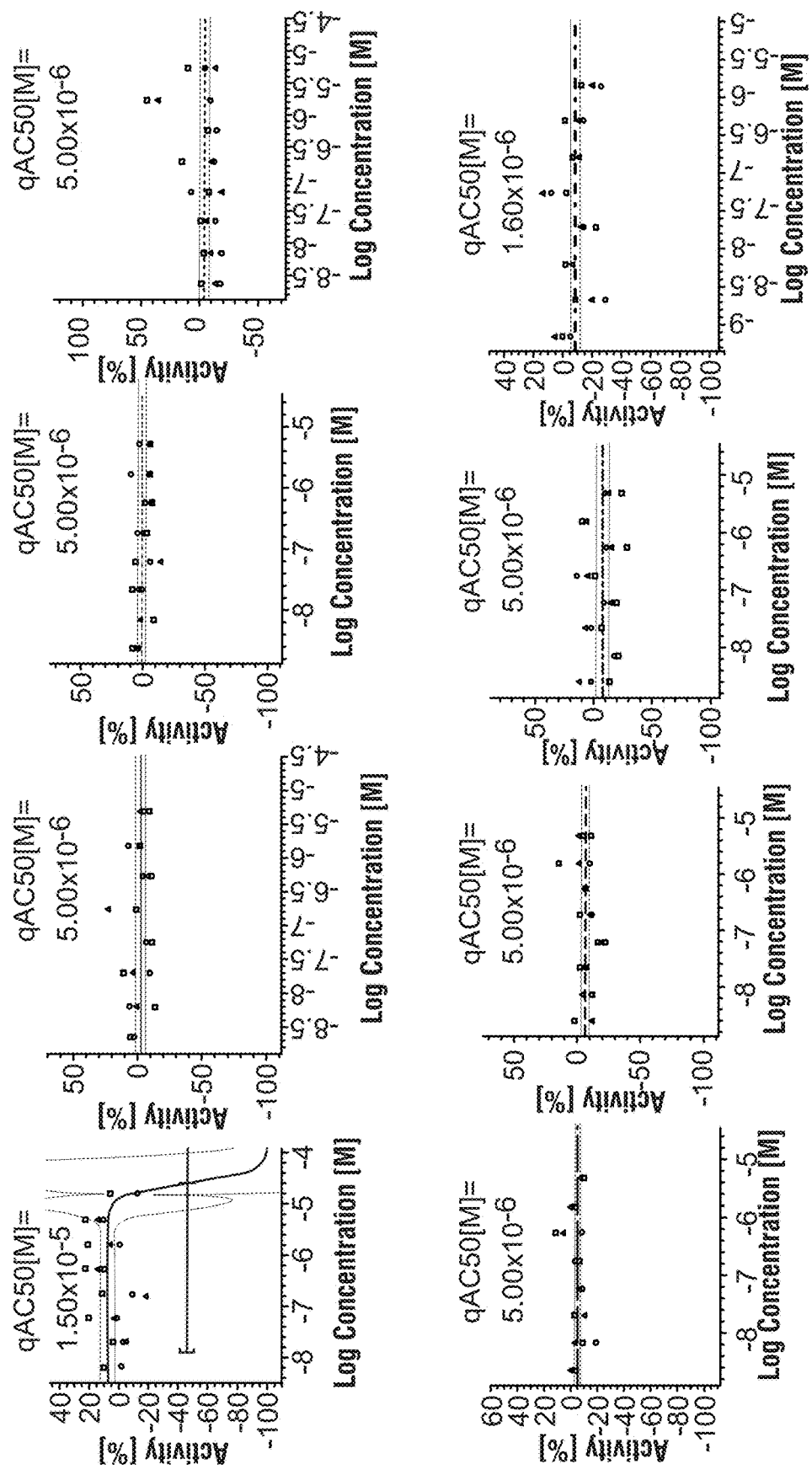
Figure 24:
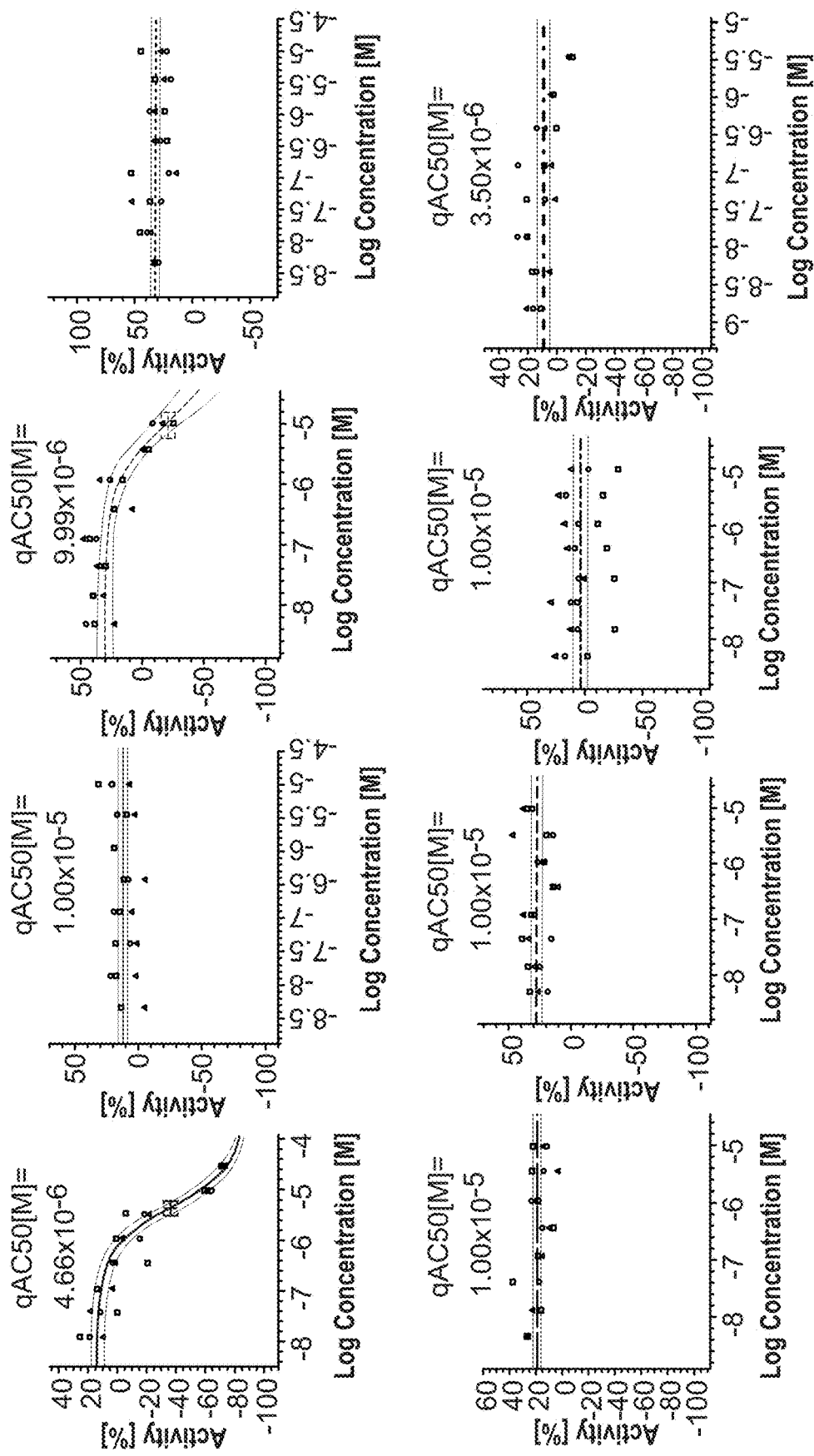
Figure 24:
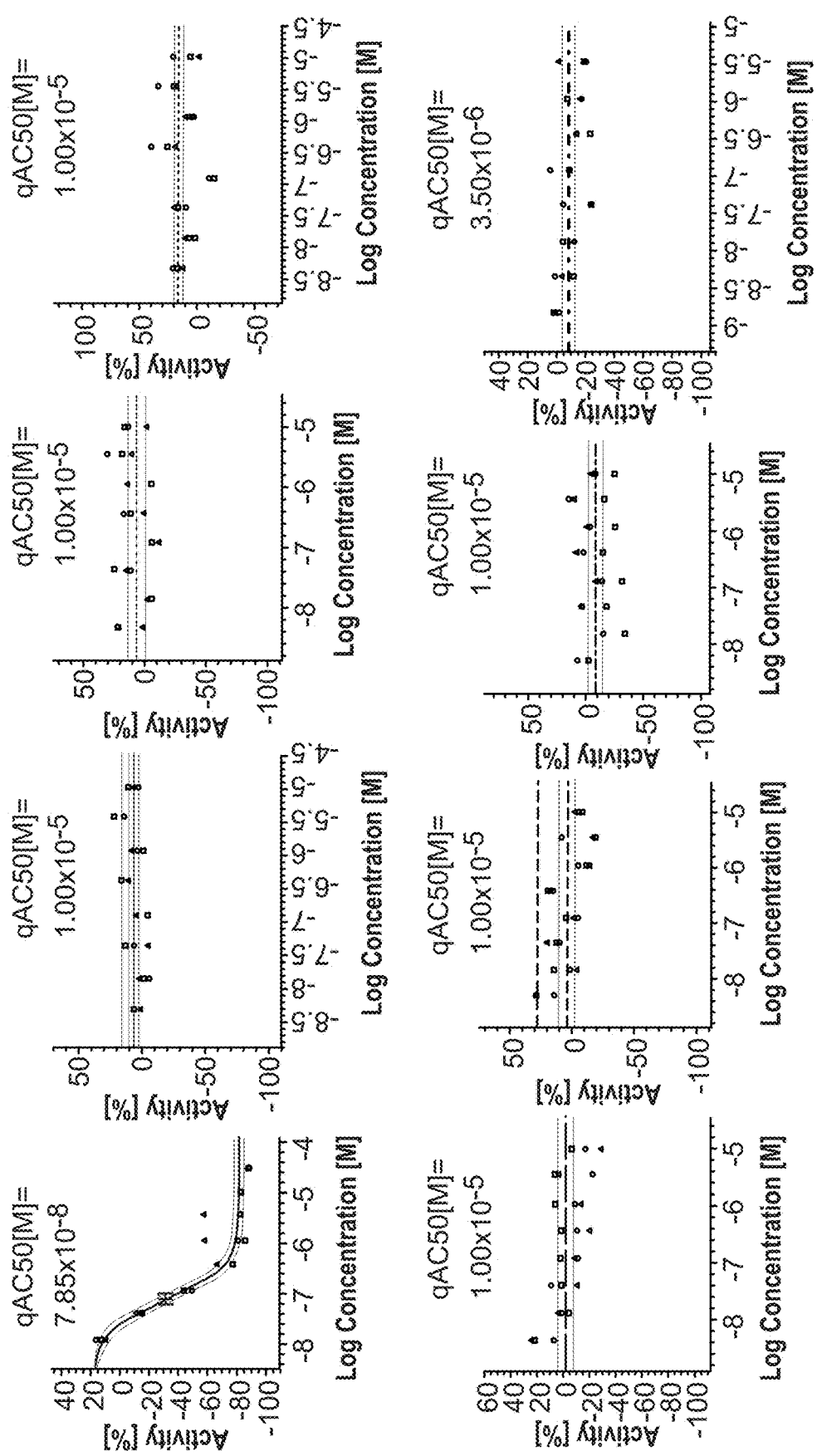
Figure 24:
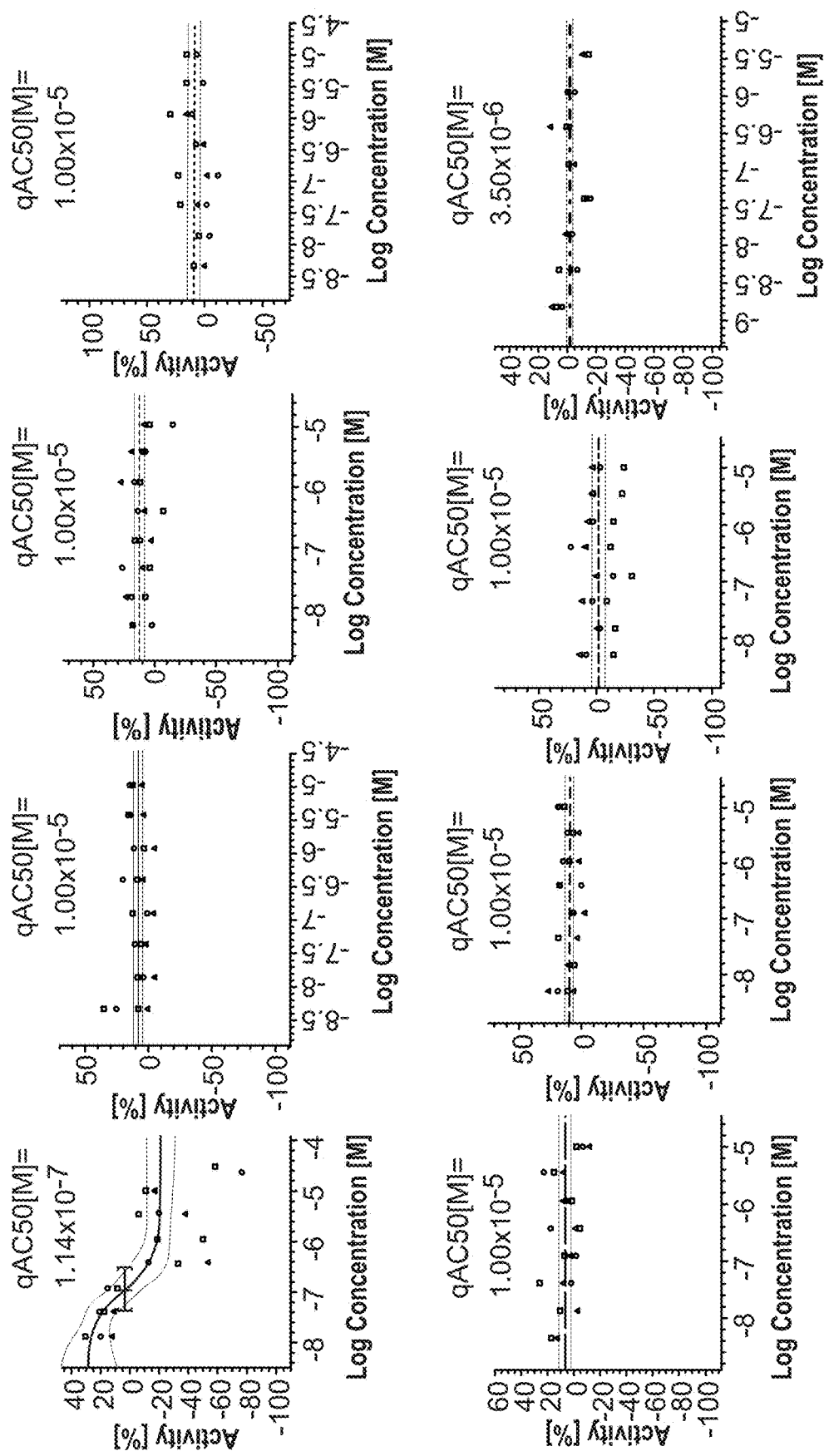
Figure 24:
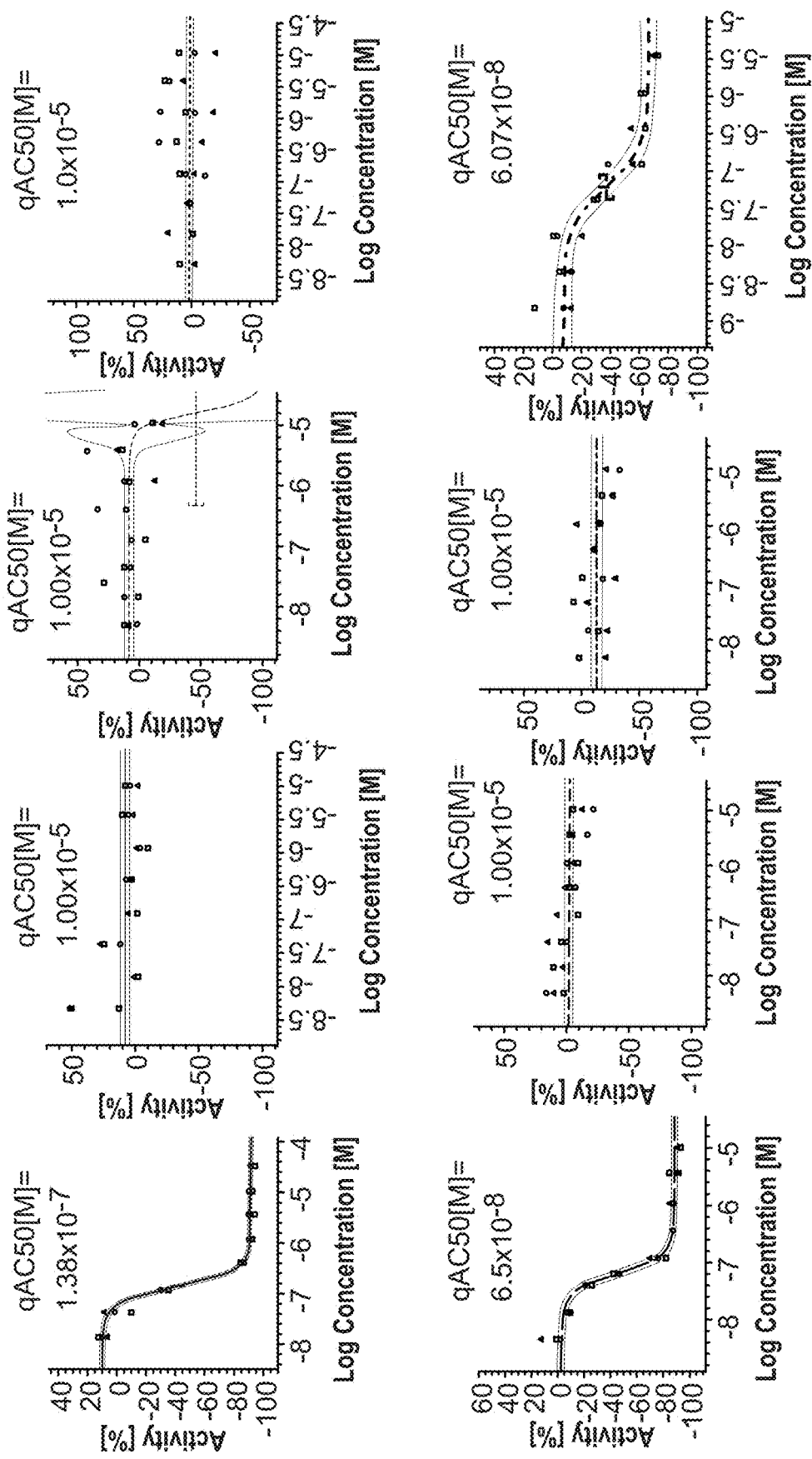
Figure 24:
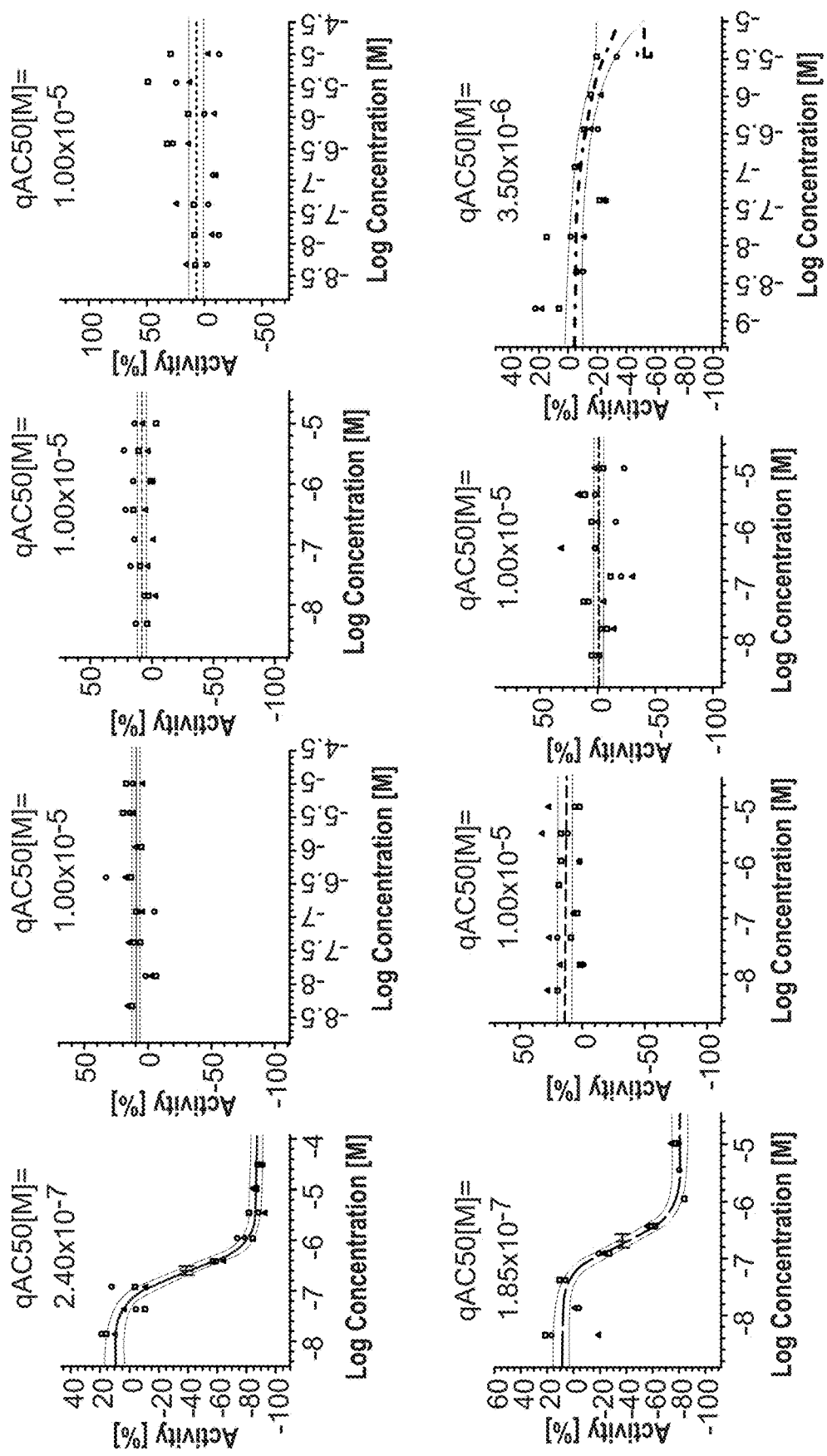
Figure 24:
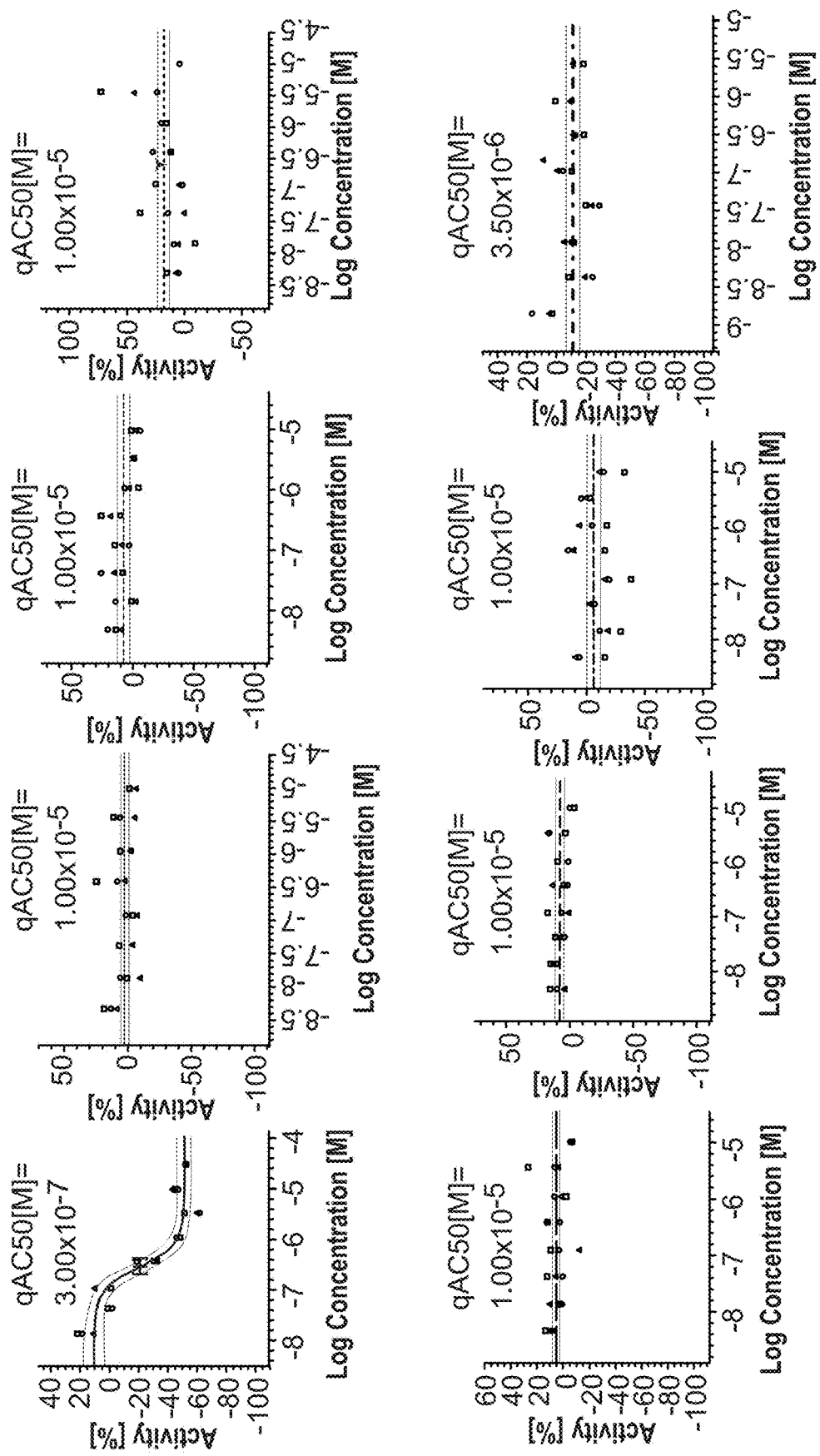
Figure 24:
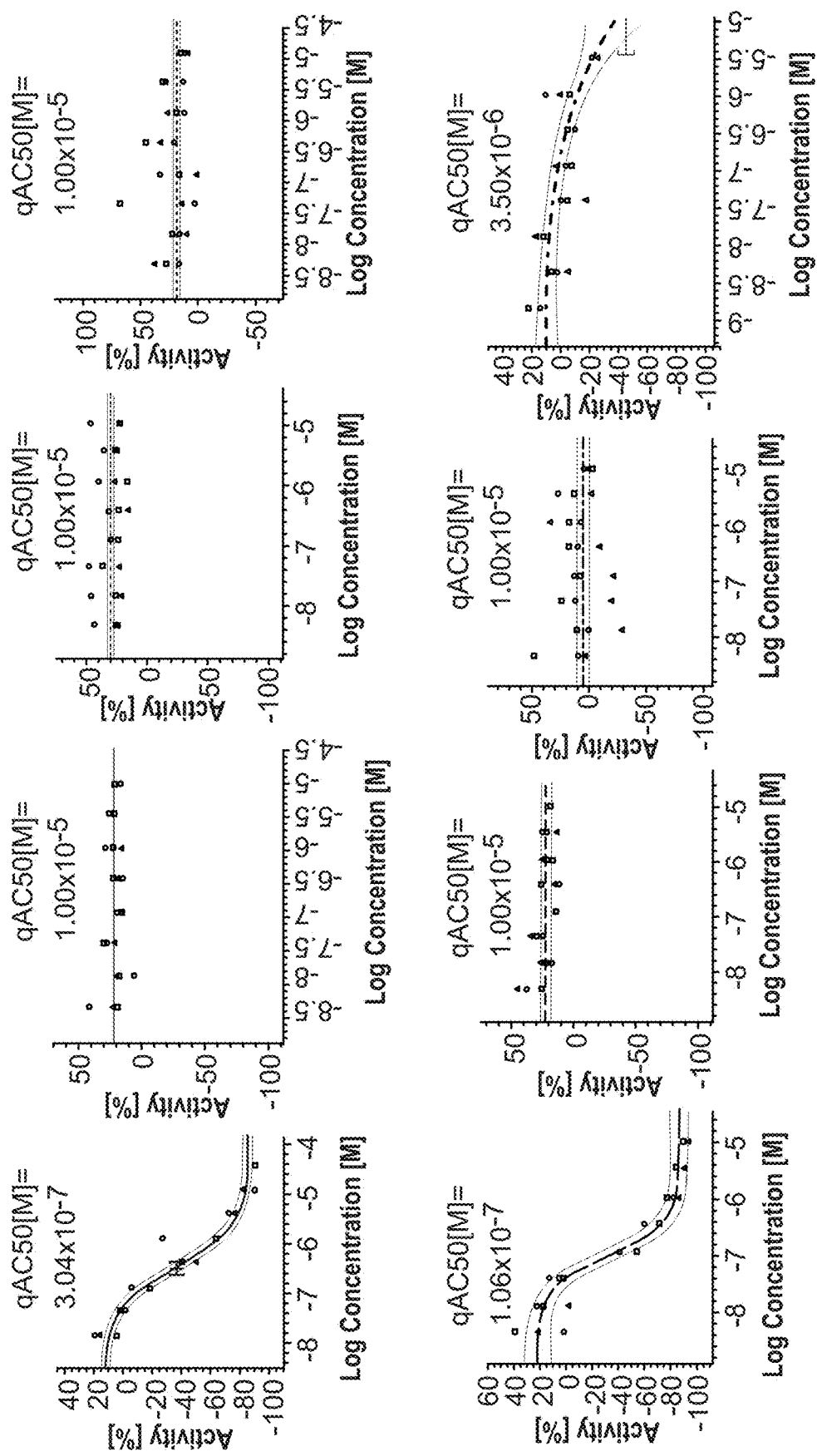
Figure 24:
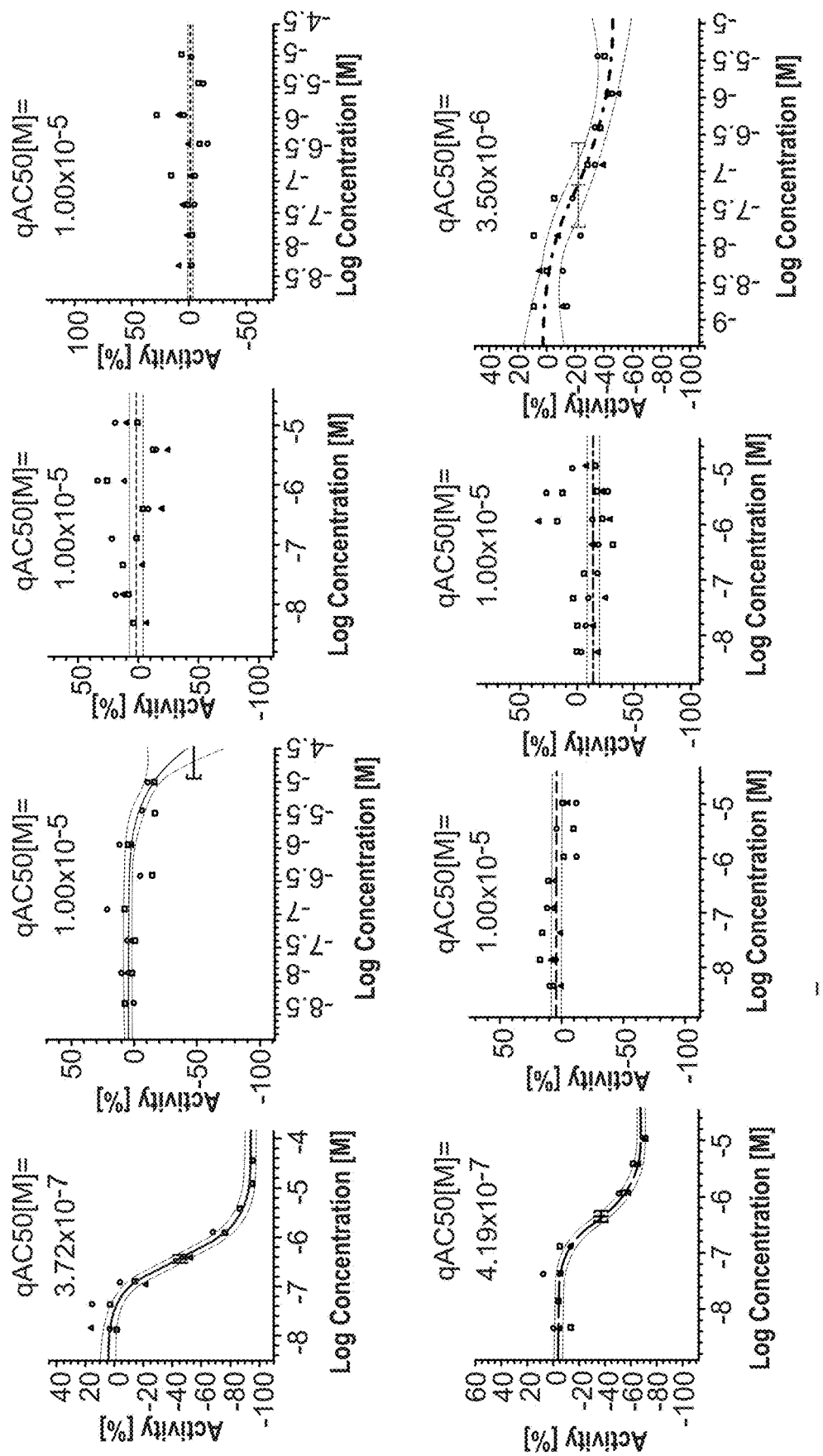
Figure 24:
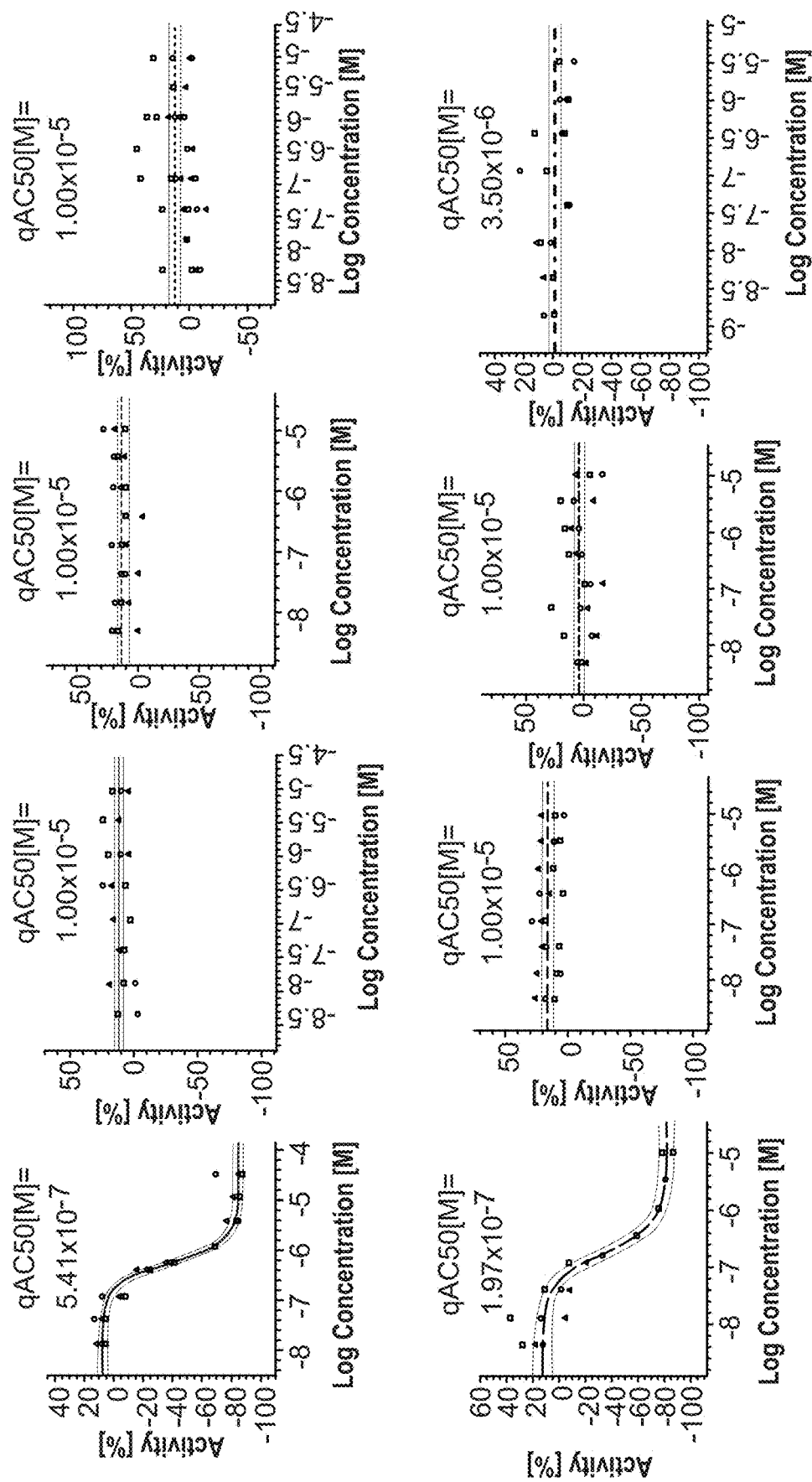
Figure 24:
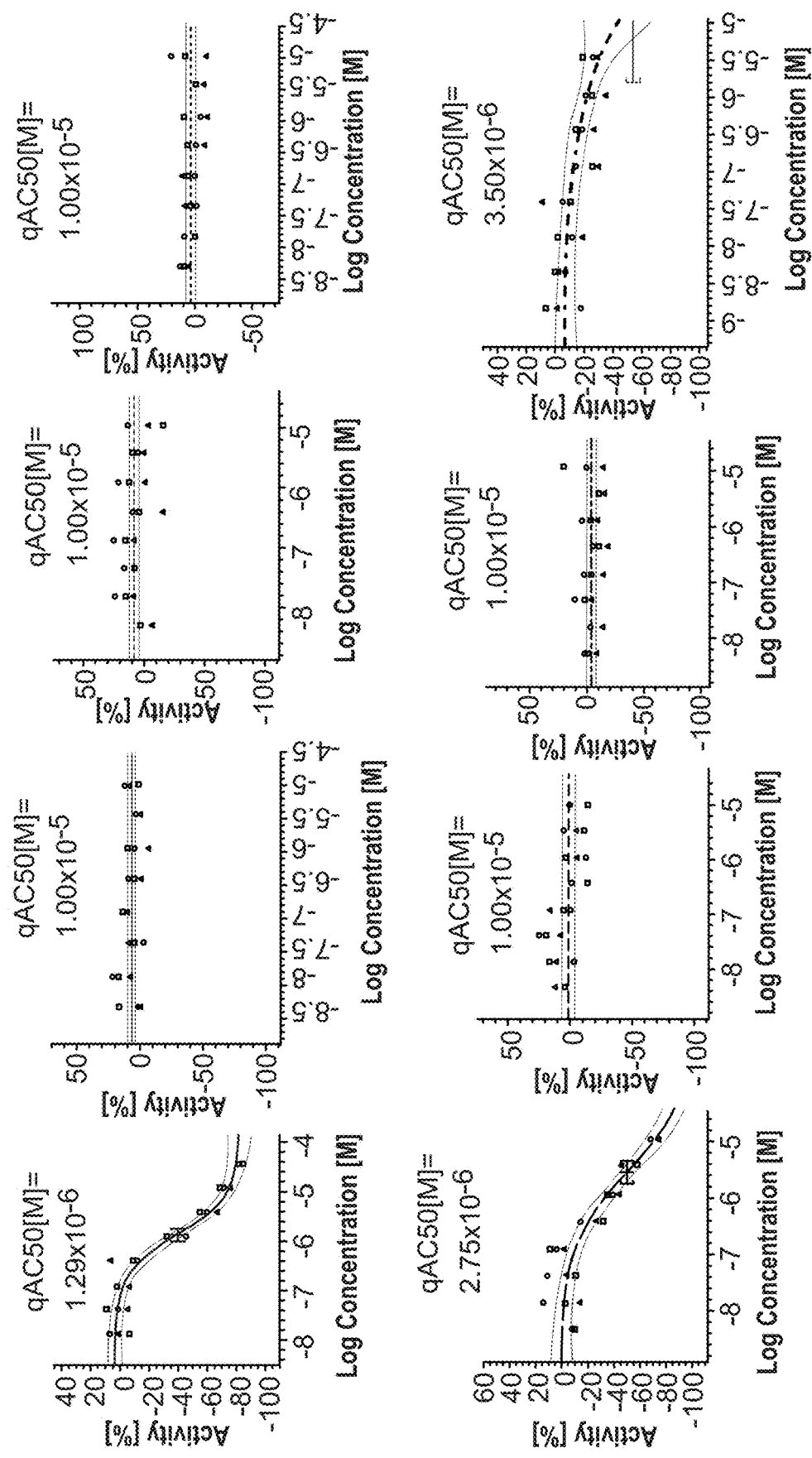
Figure 24:
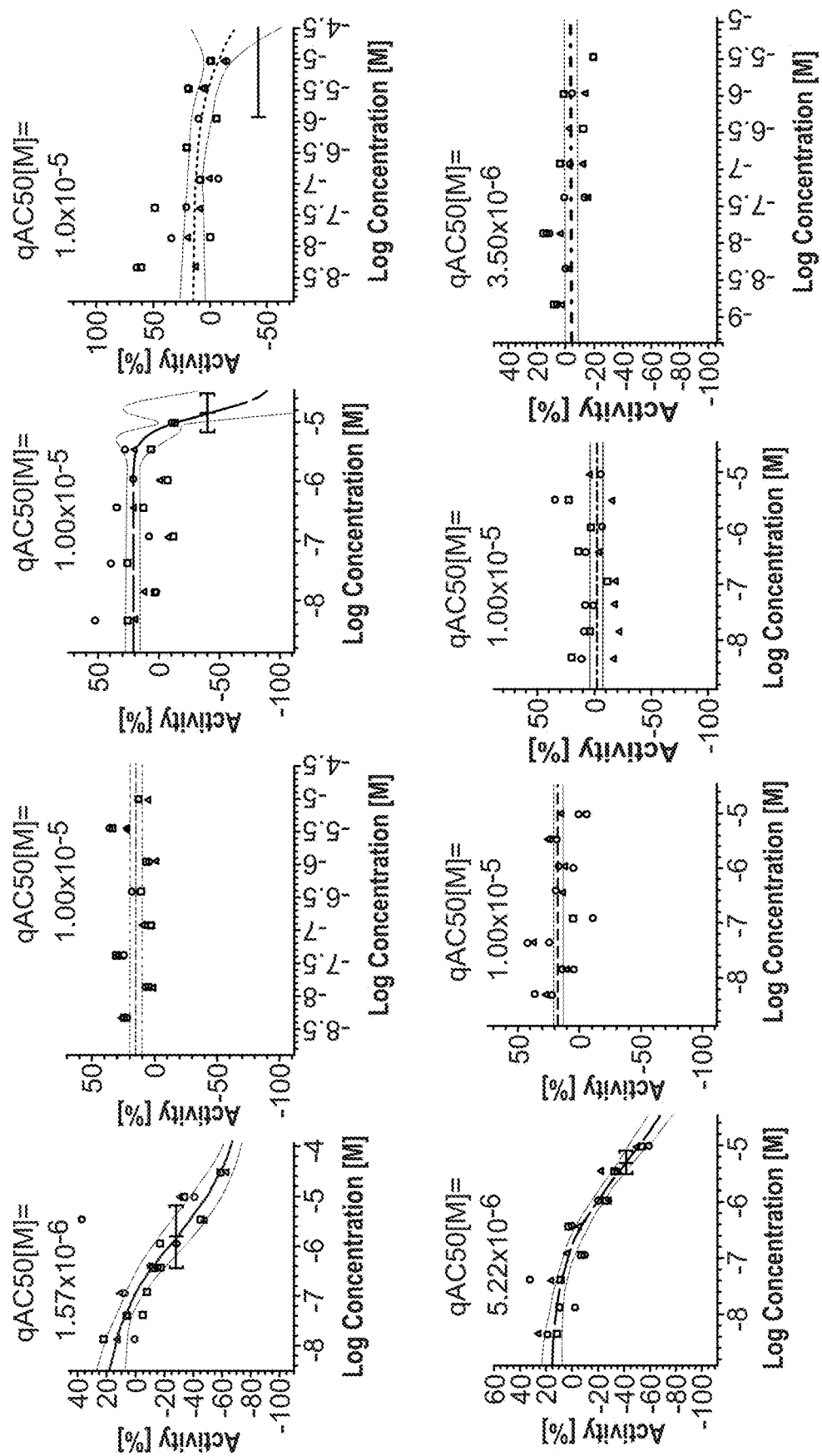
Figure 24:
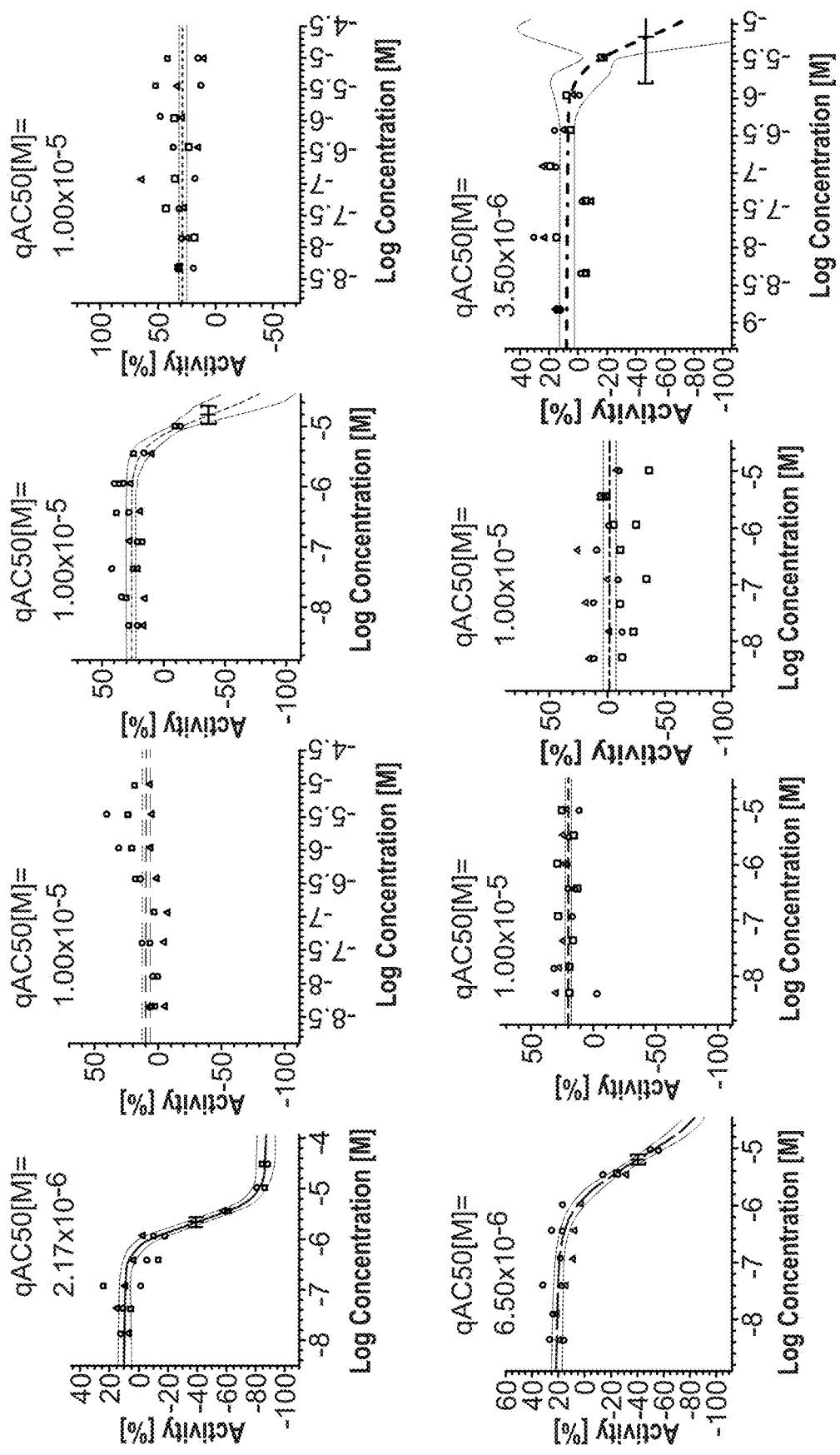
Figure 24:
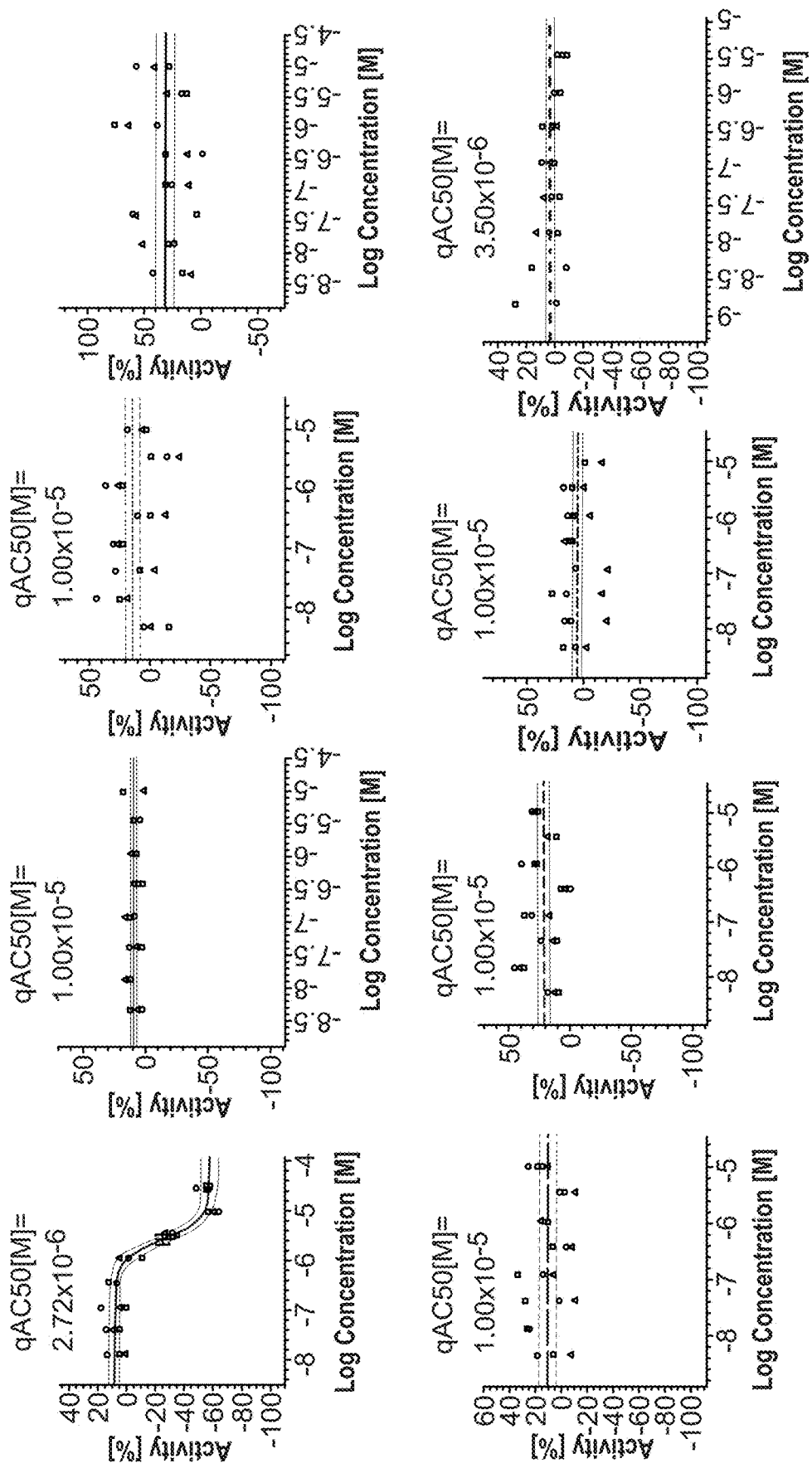
Figure 24:
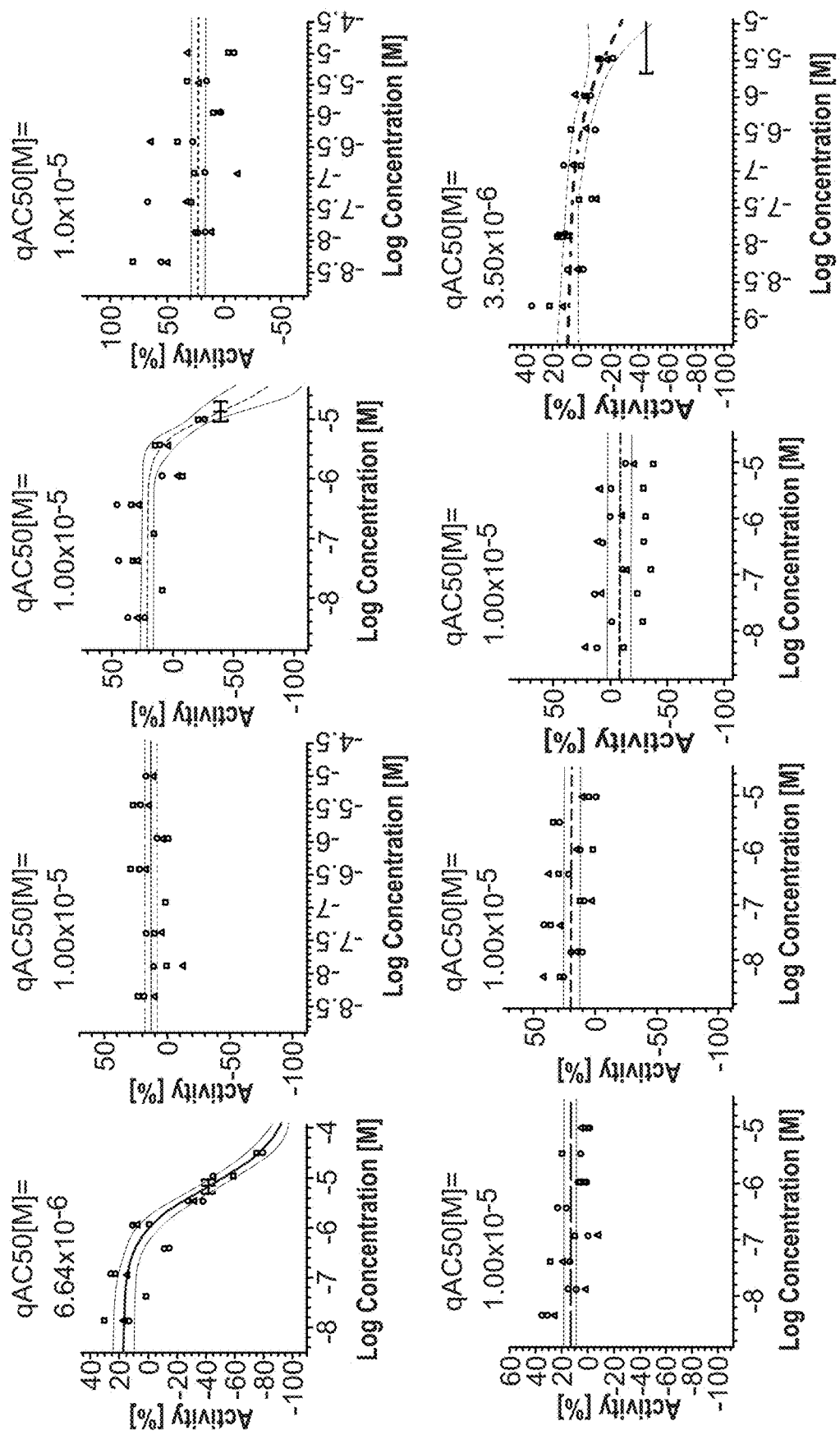
Figure 24:
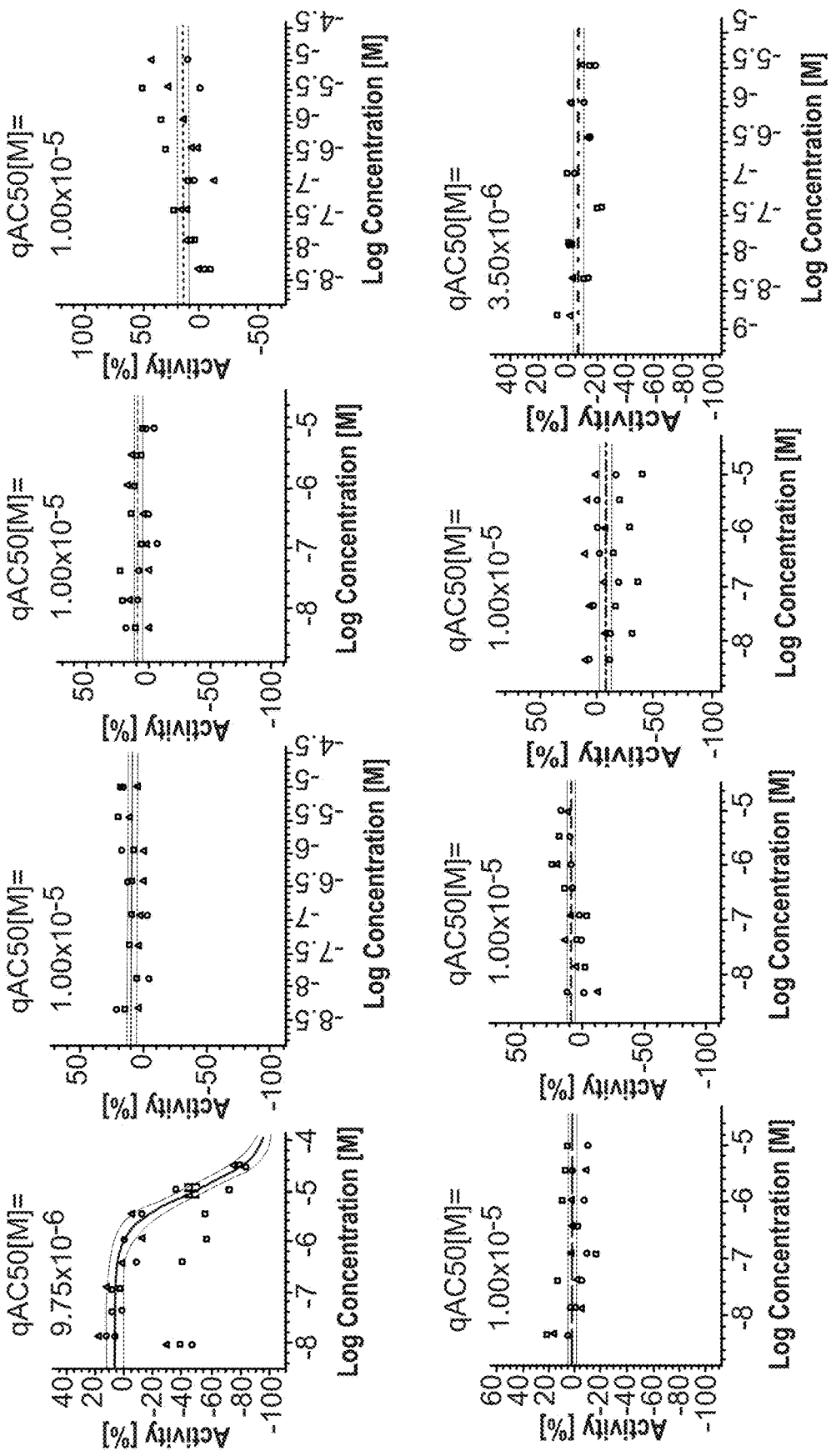
Figure 24:
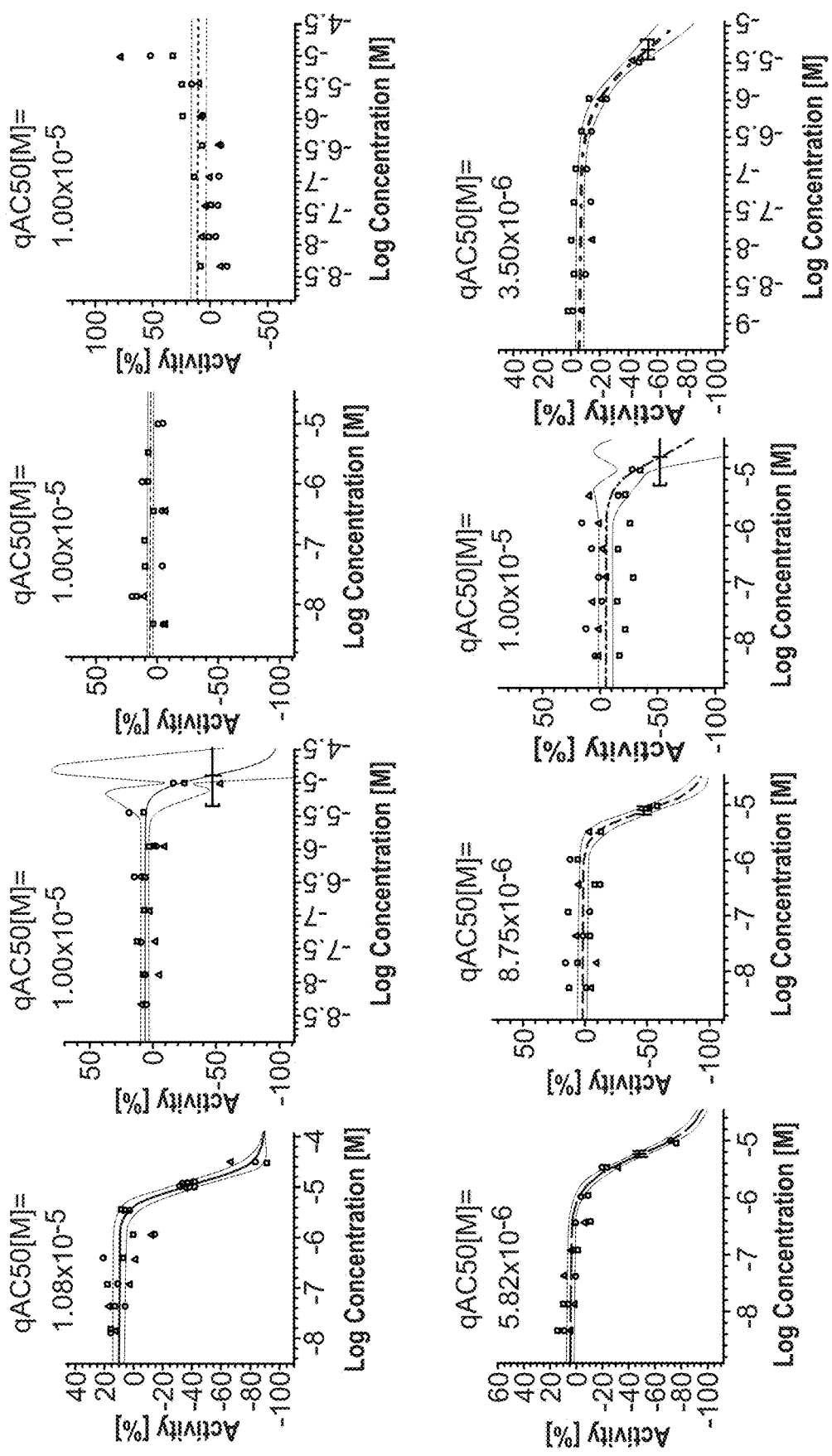
Figure 24:
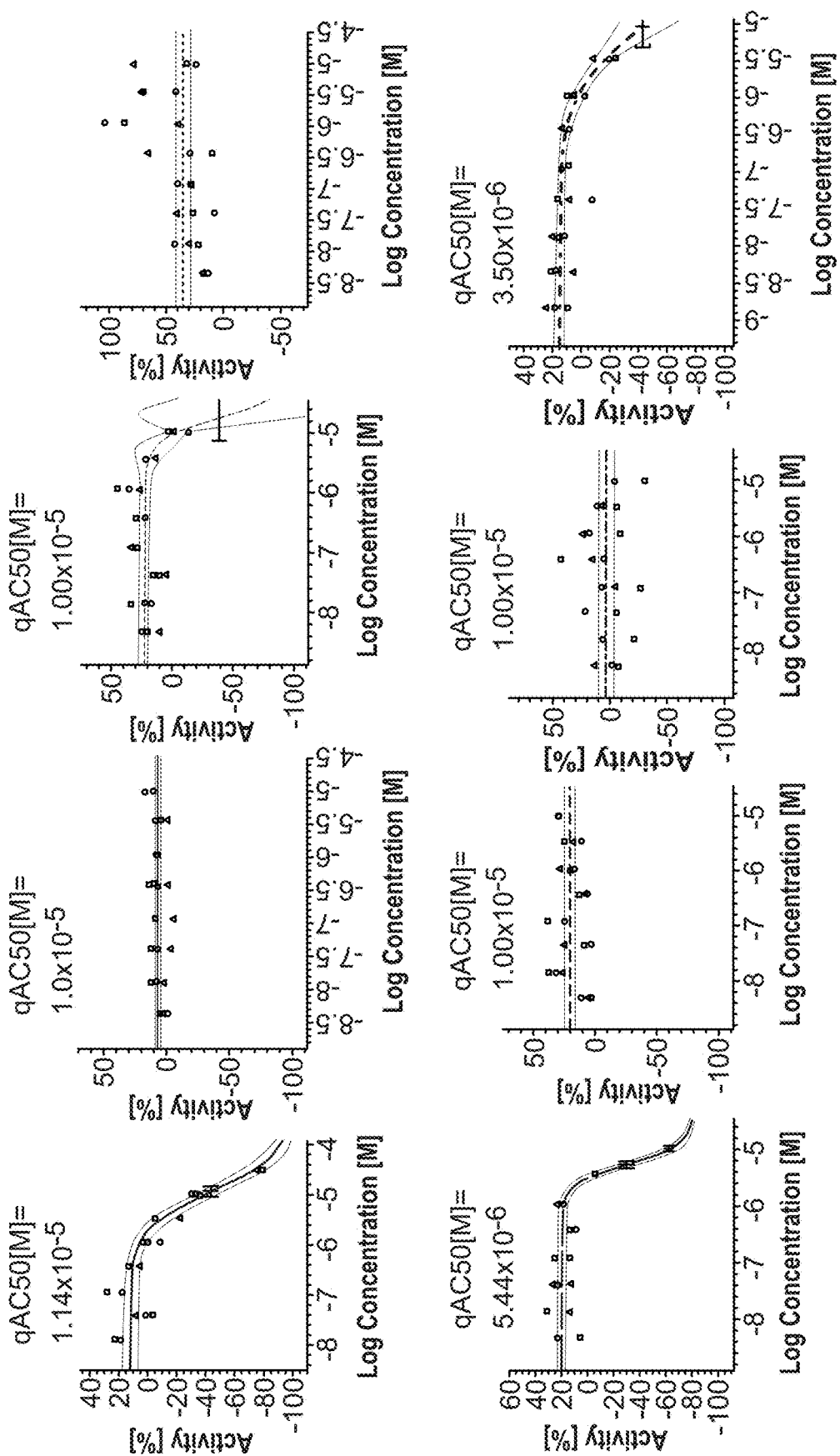
Figure 24:
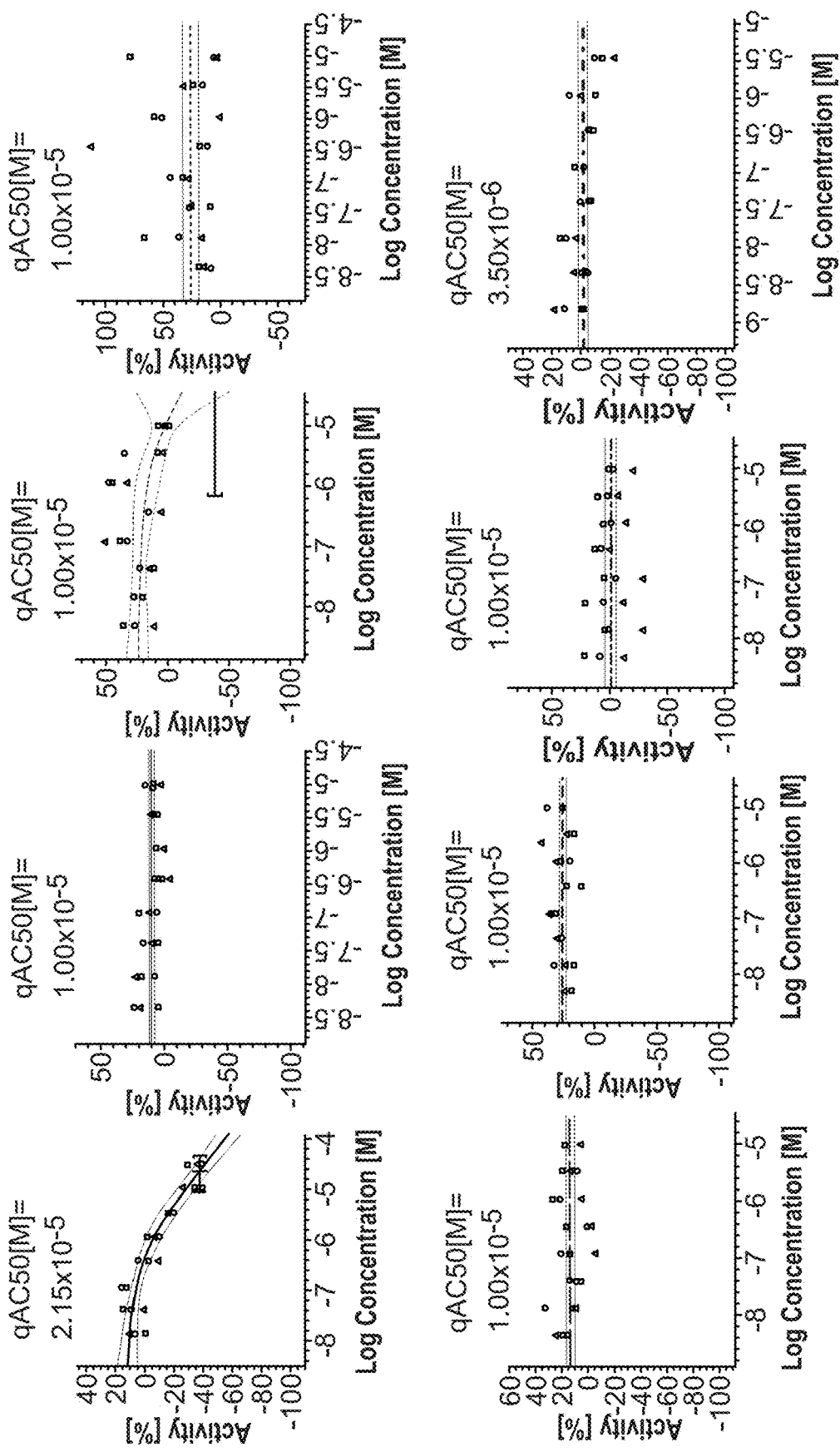
Figure 24:
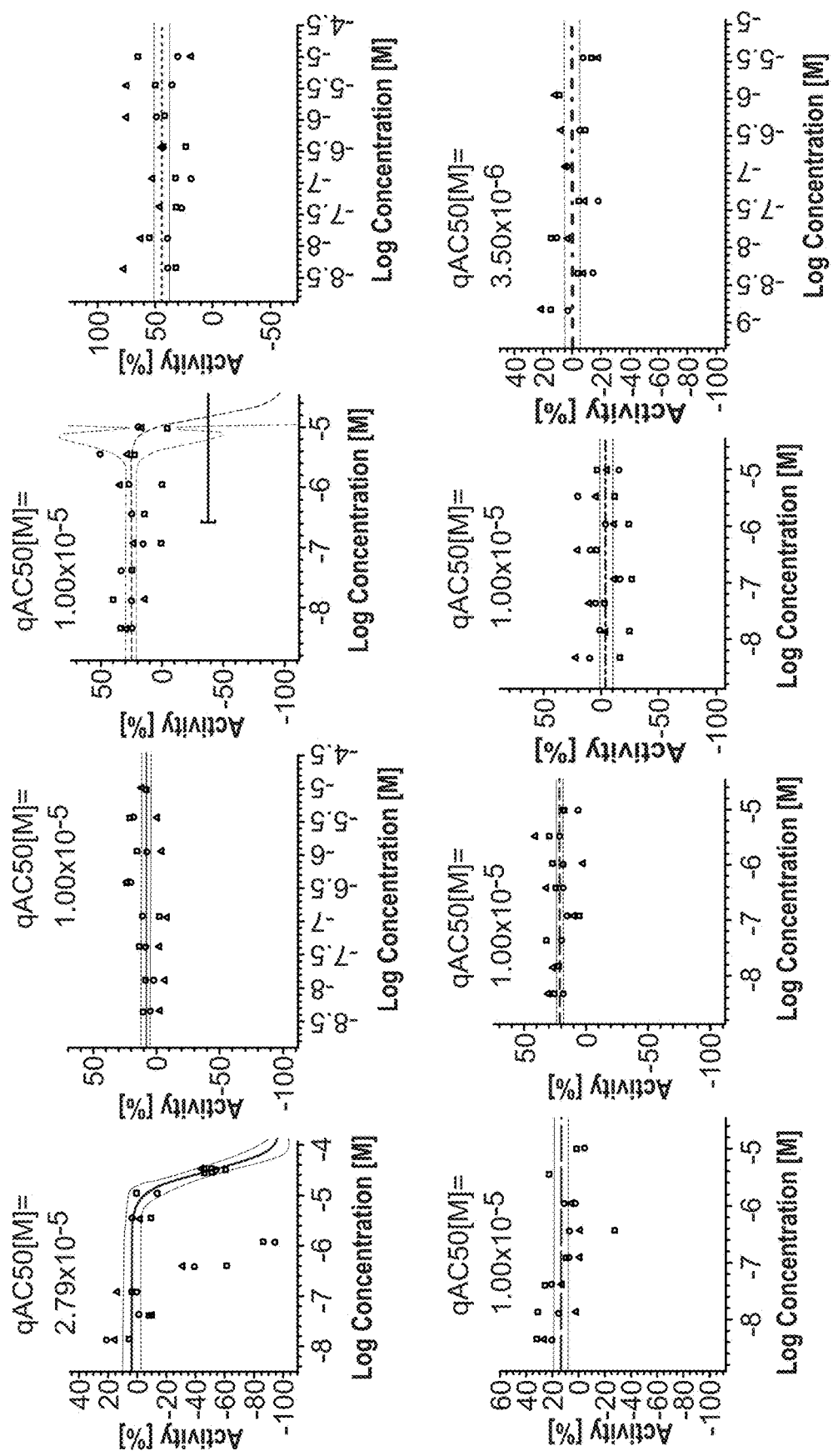
Figure 24:
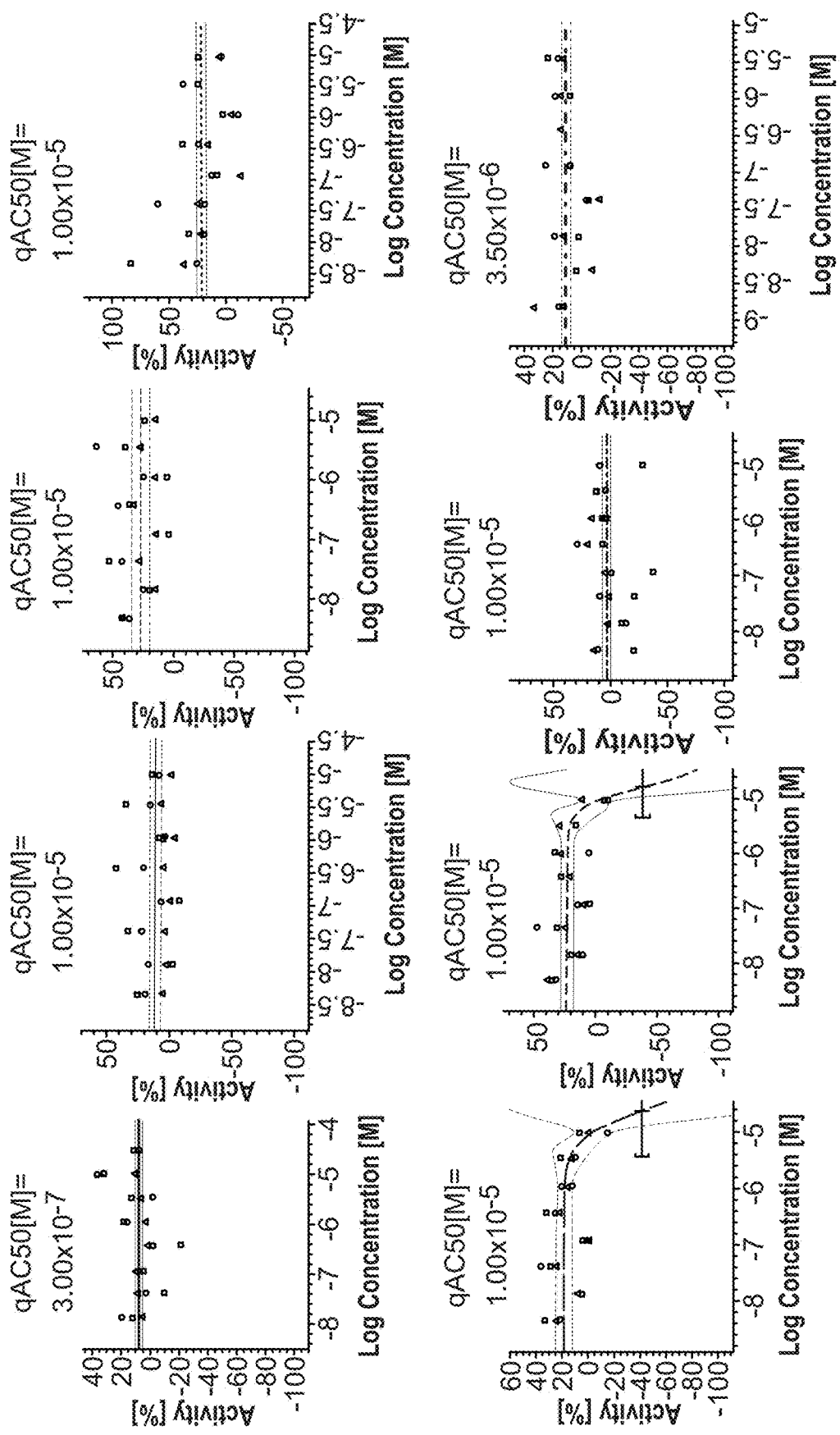
Figure 24:
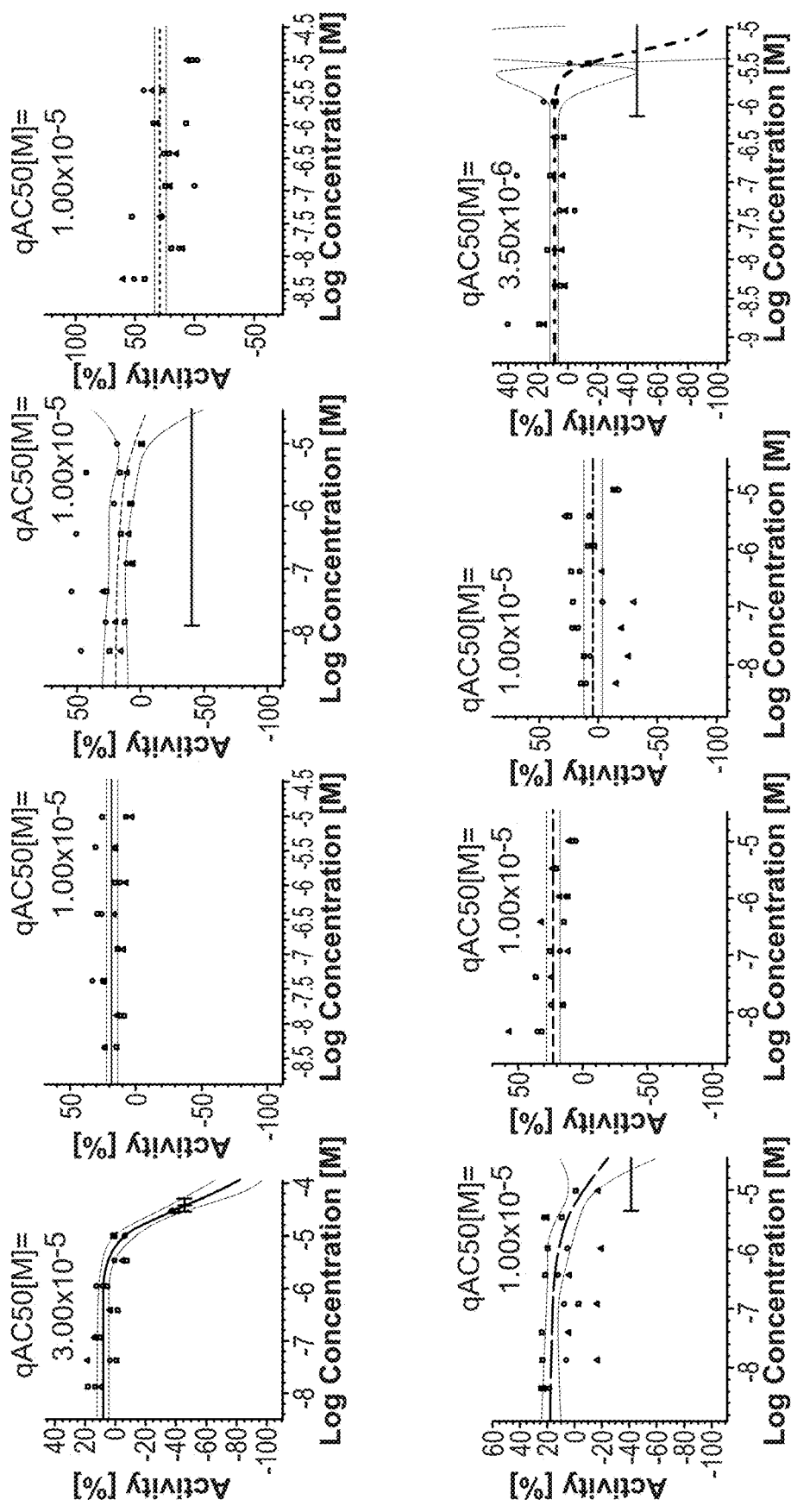
Figure 24:
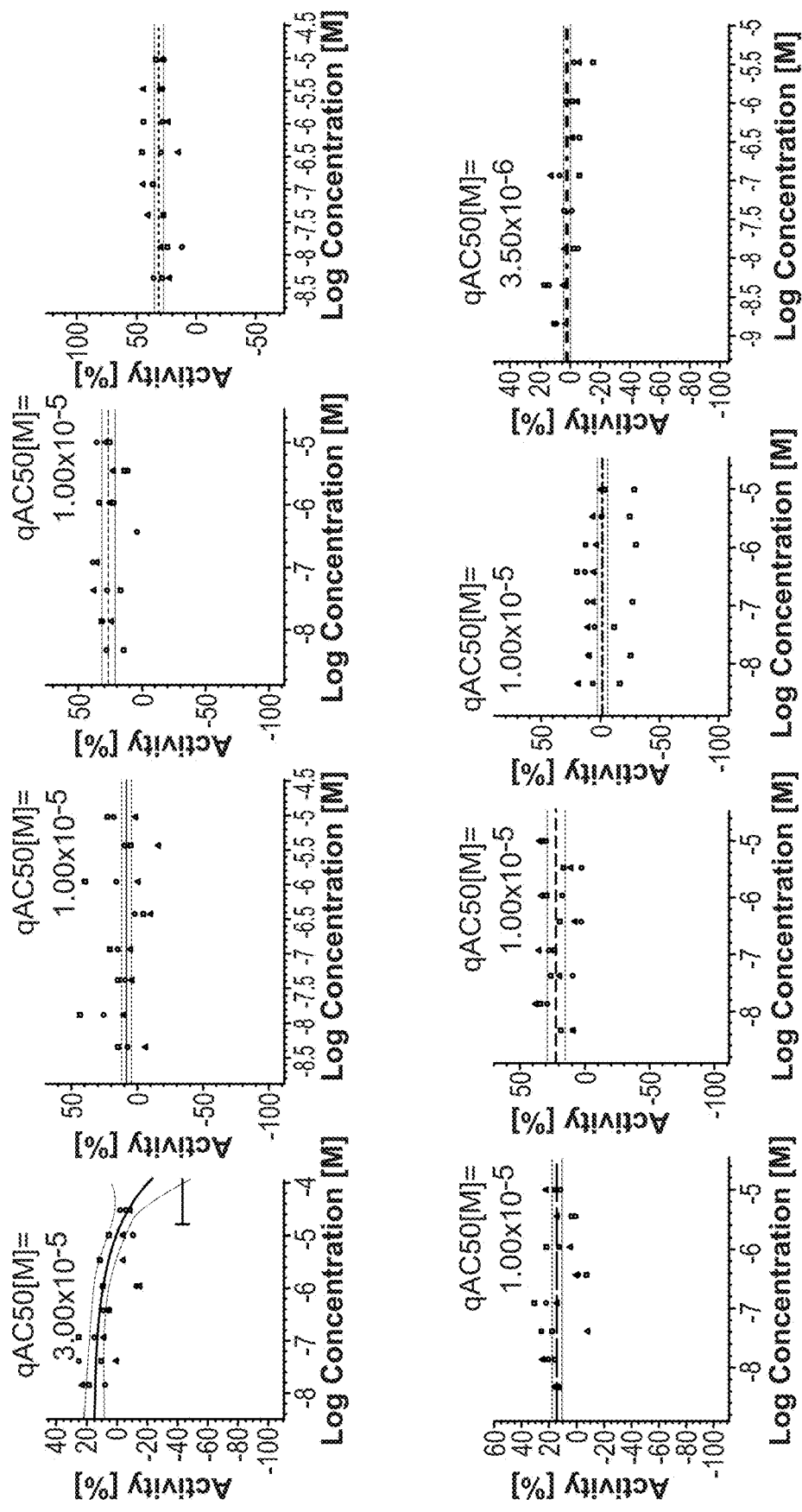
Figure 24:
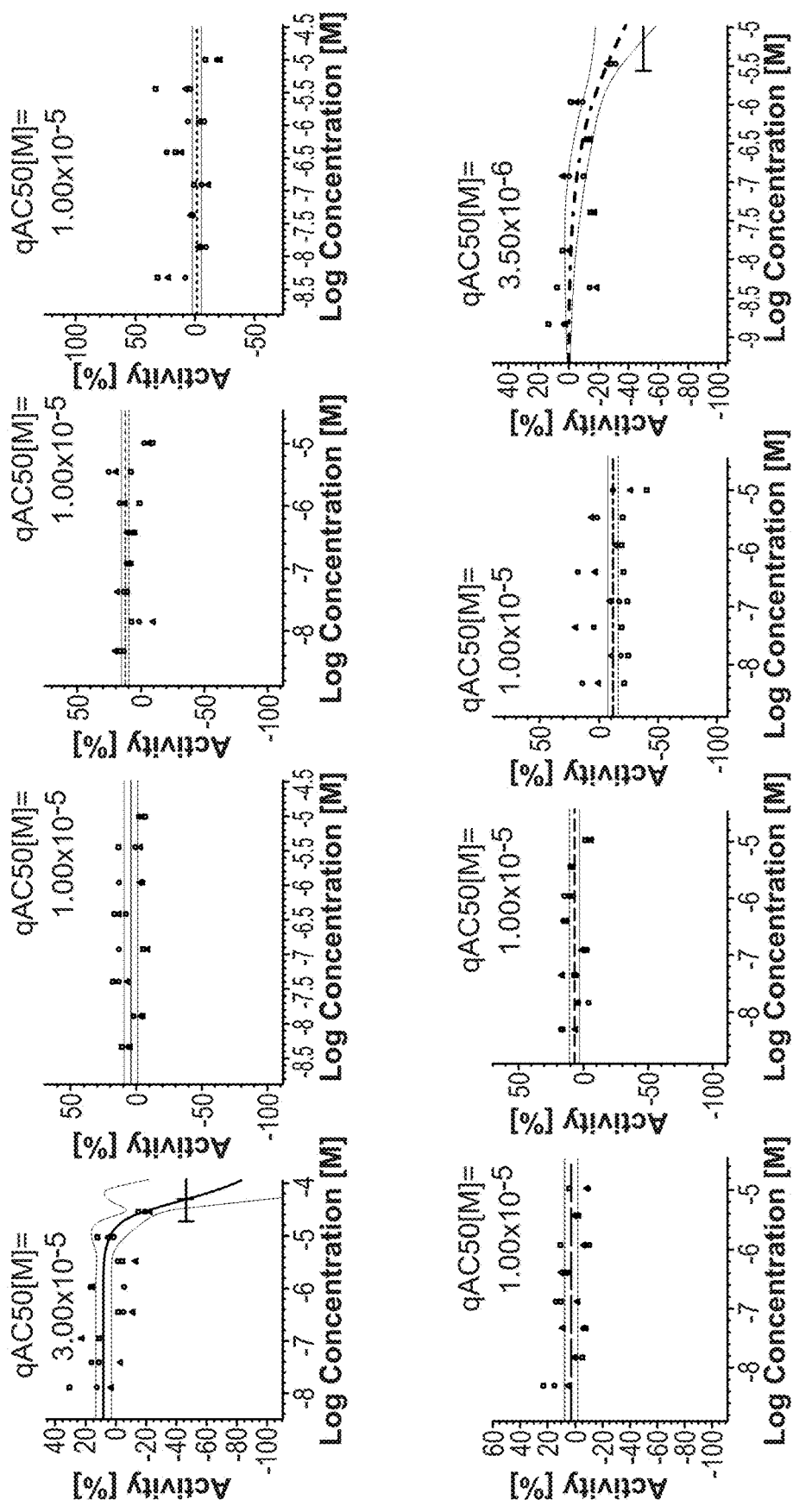
Figure 24:
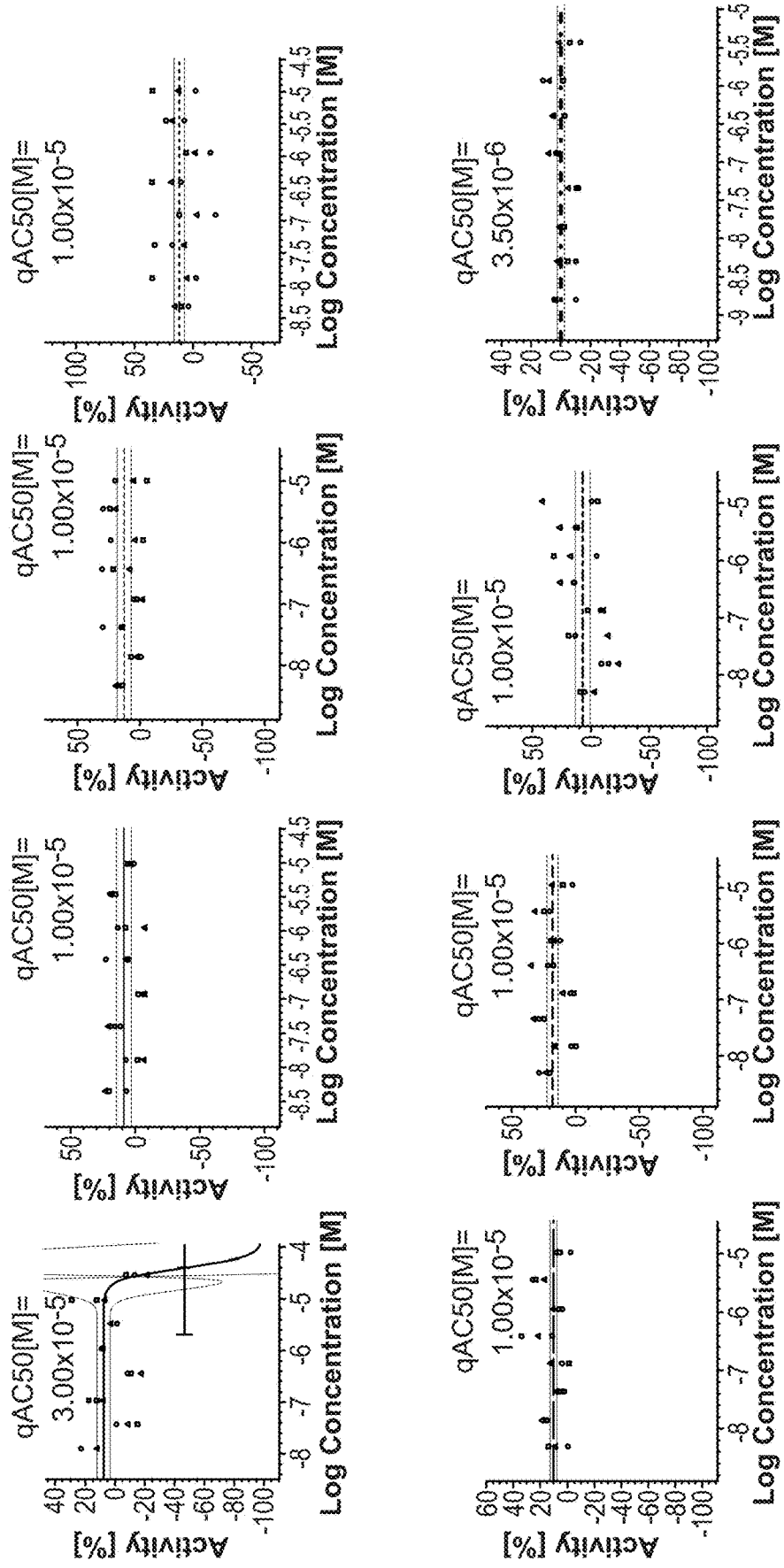
Figure 24:
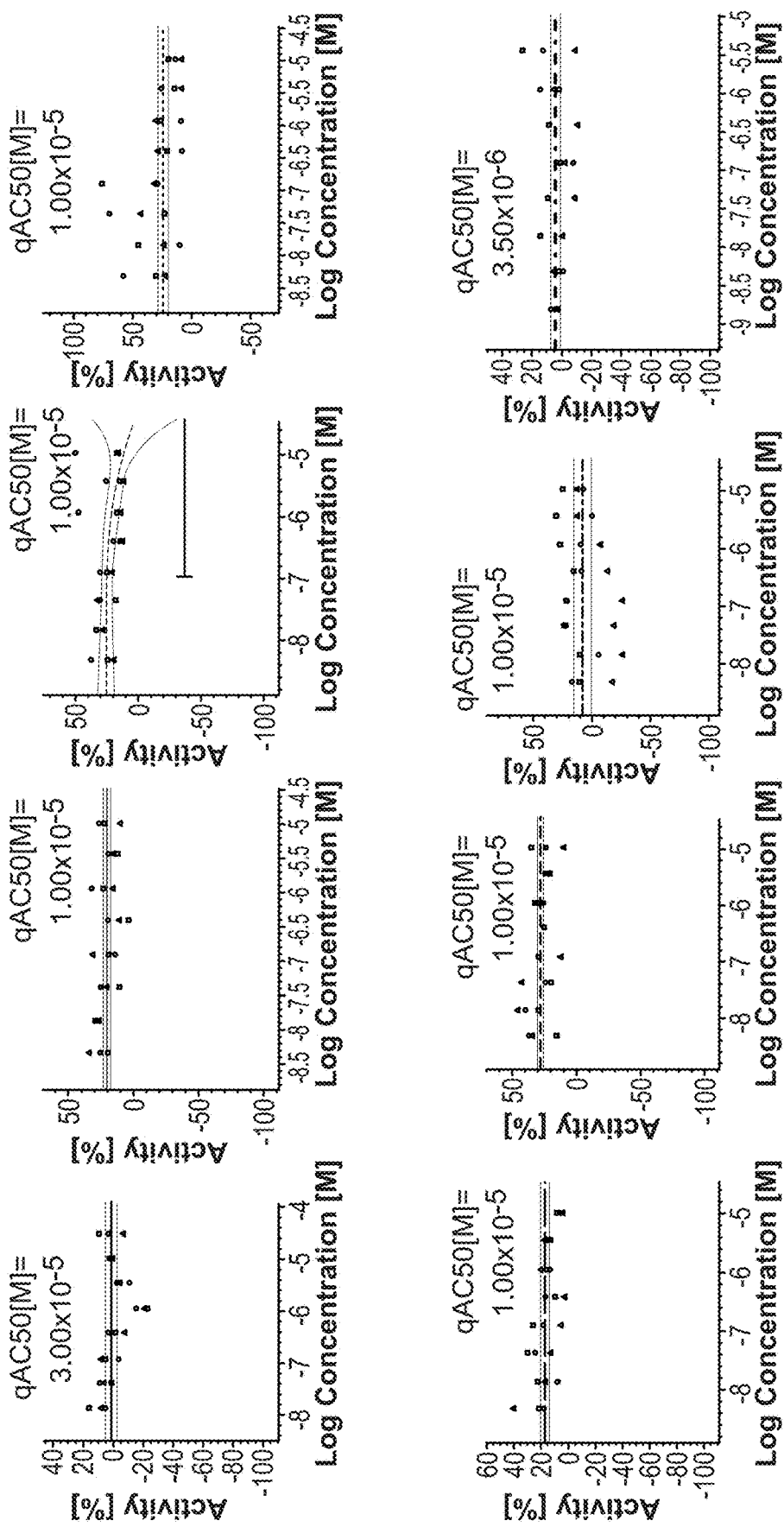
Figure 24:
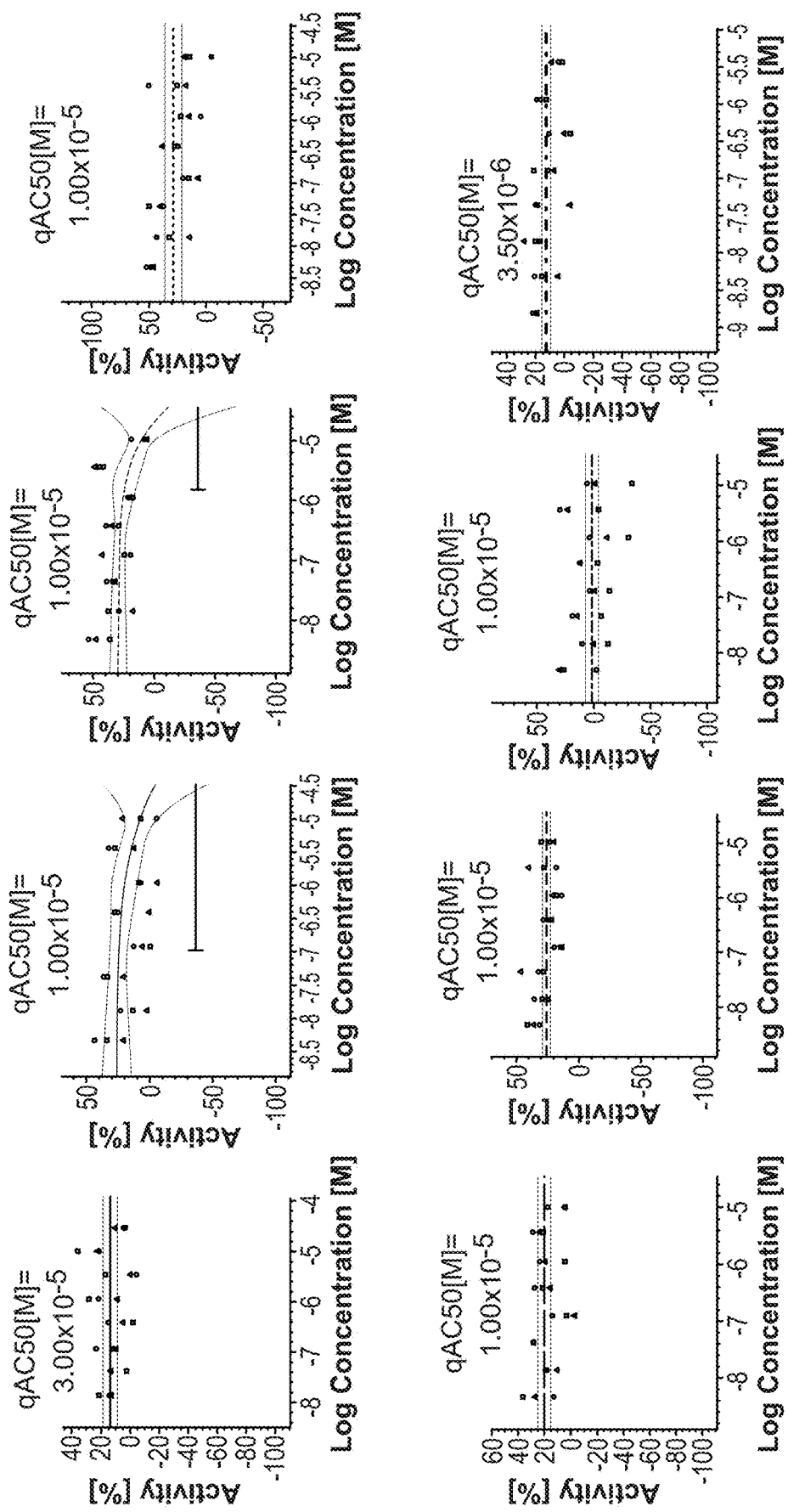
Figure 24:
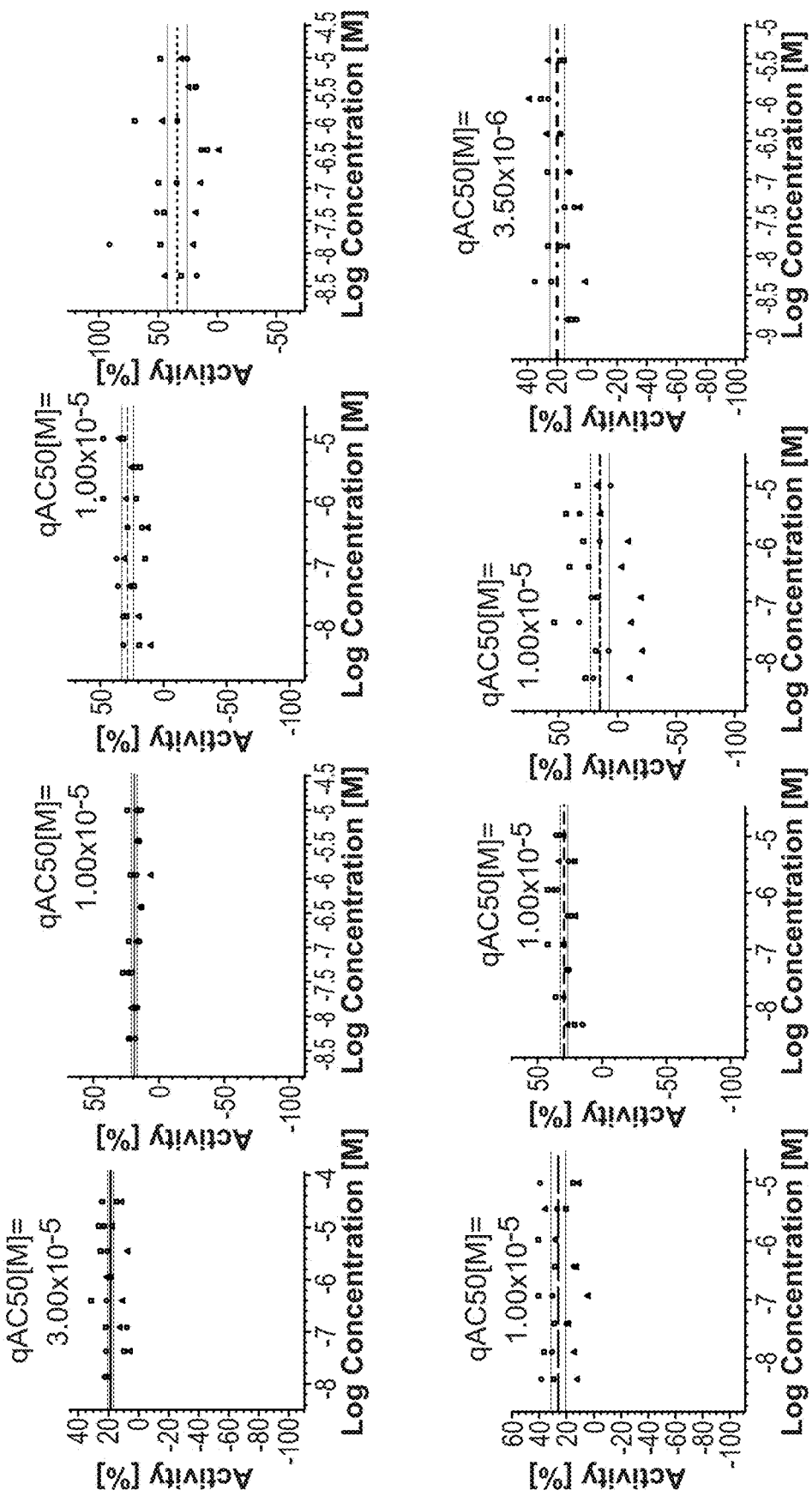
Figure 24:
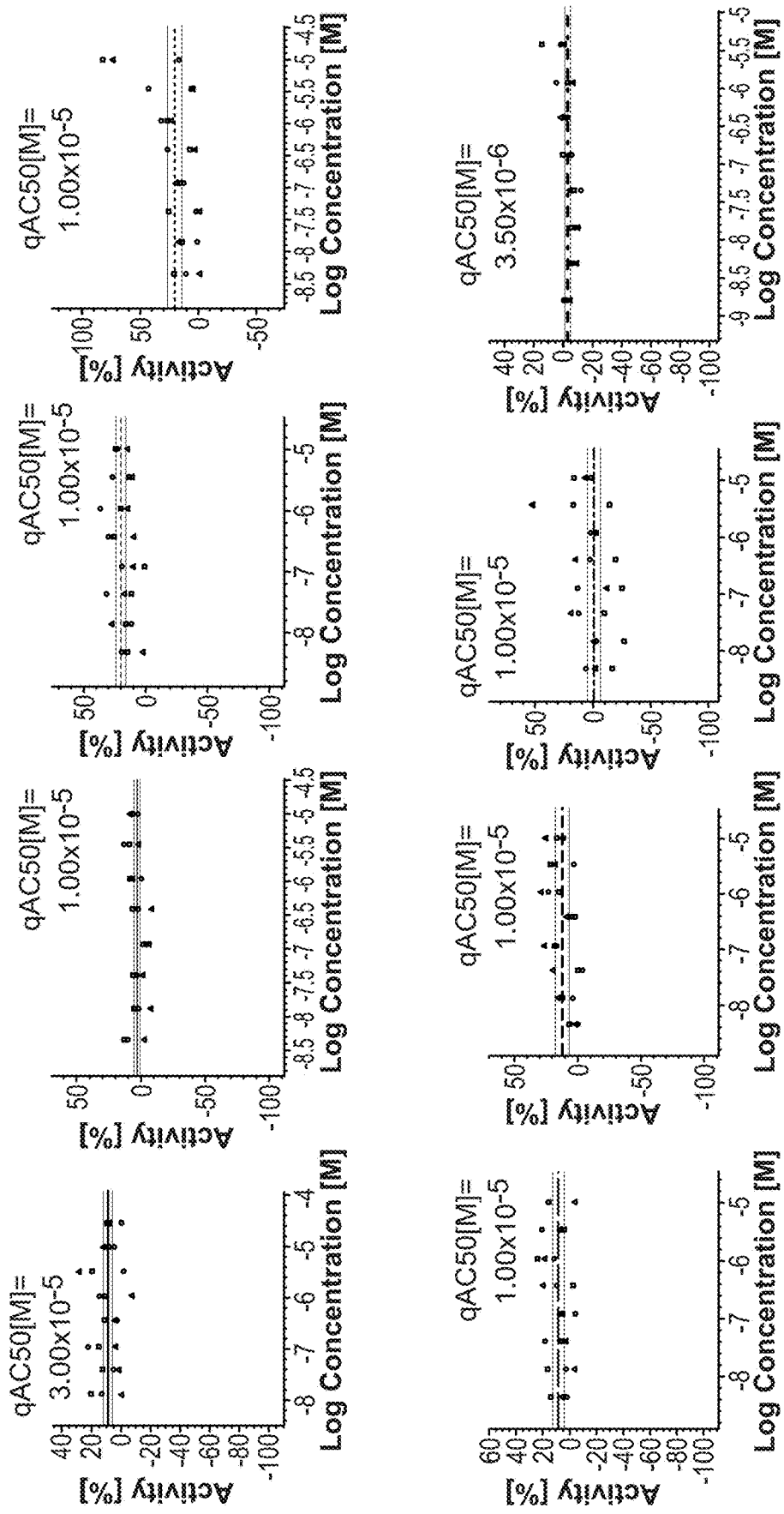
Figure 24:
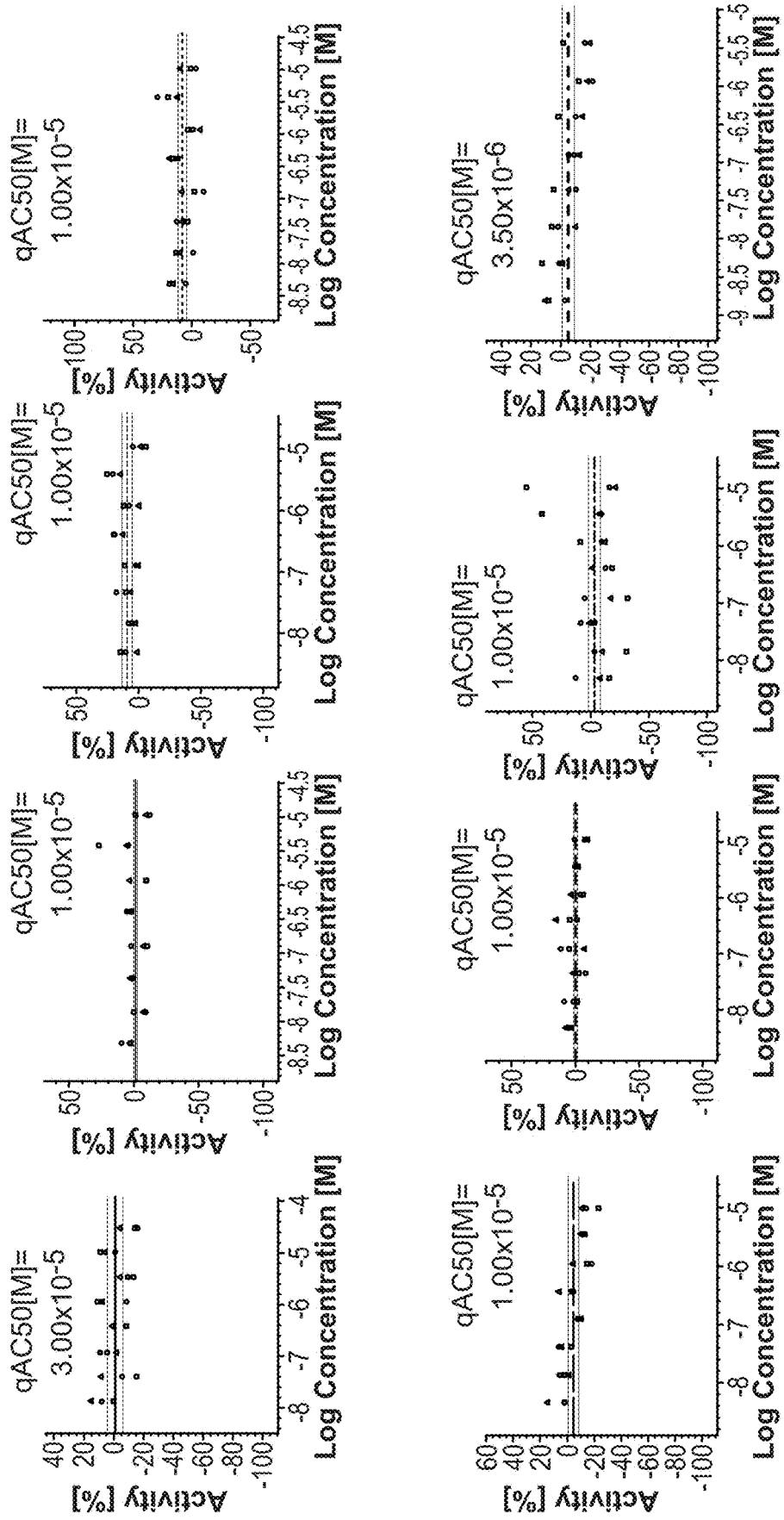
Figure 24:
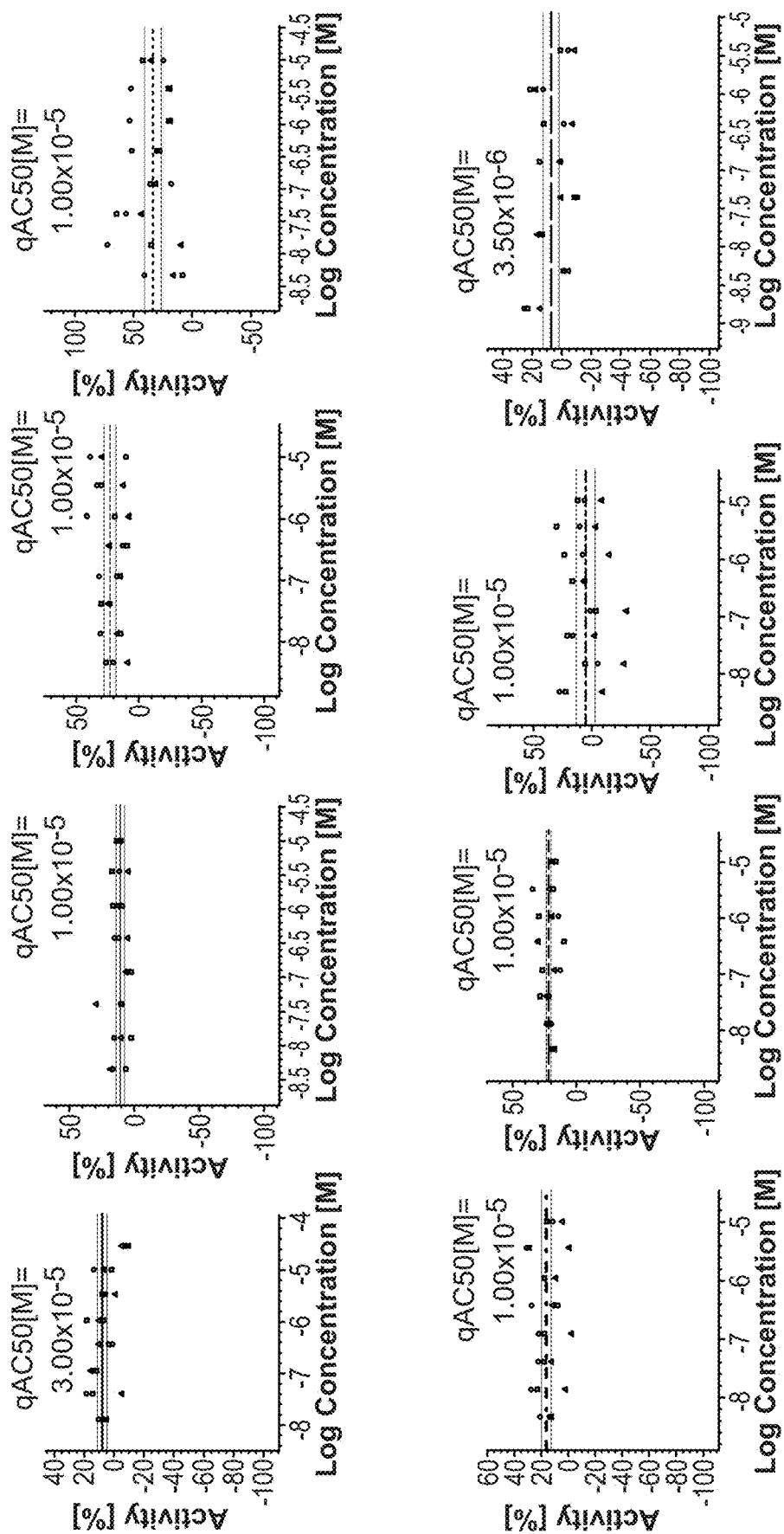
Figure 24:
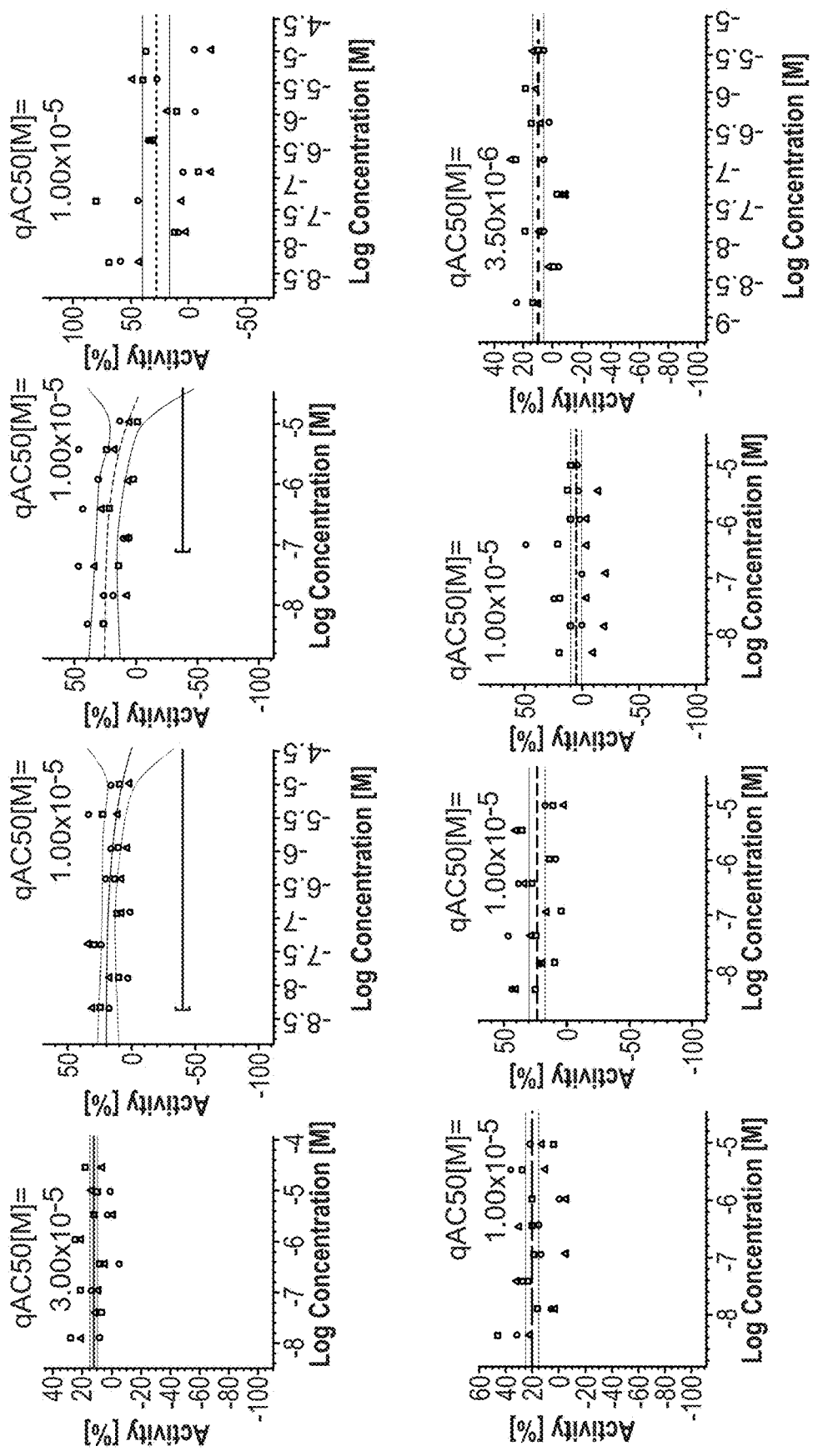
Figure 24:
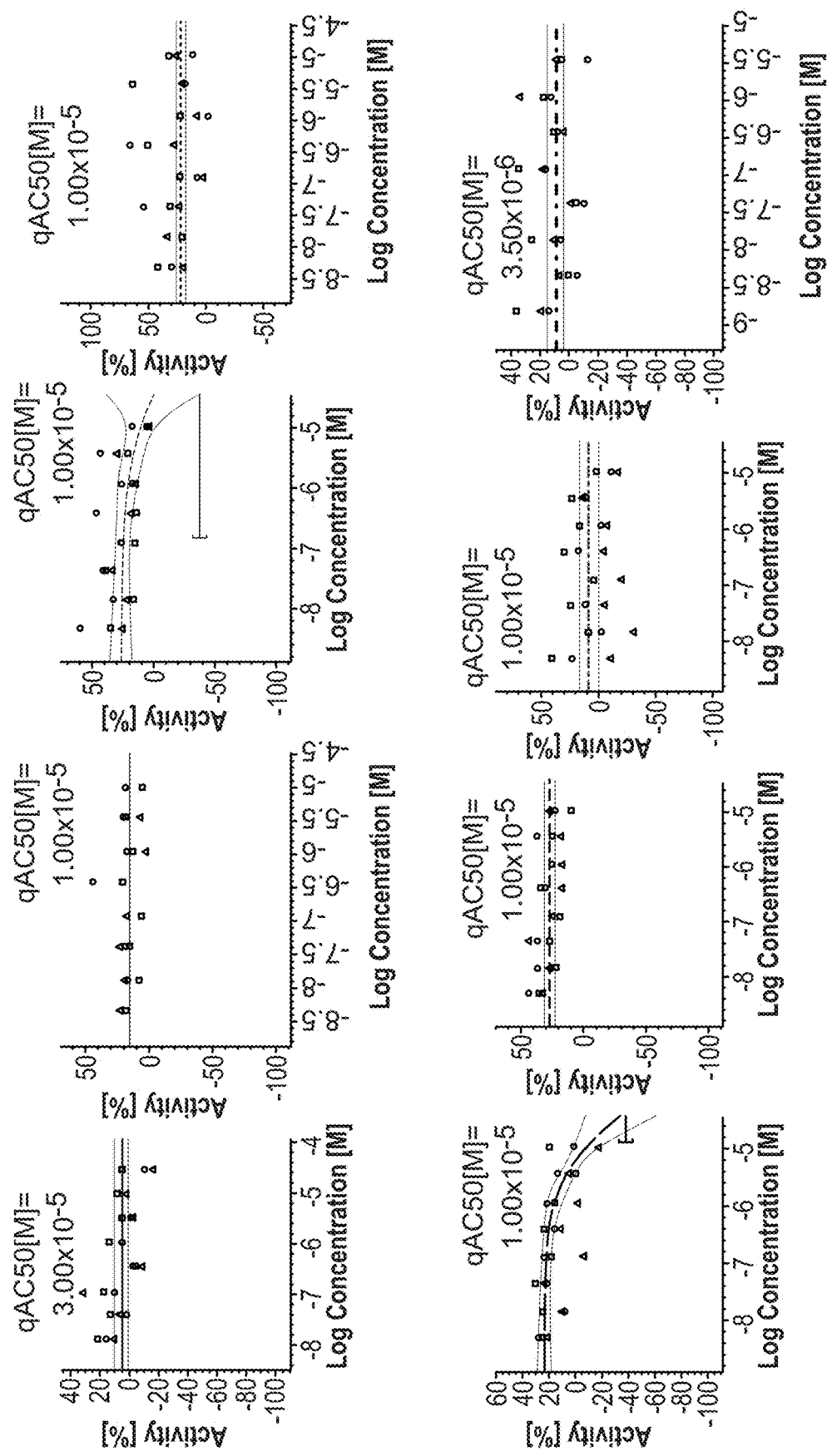
Figure 24:
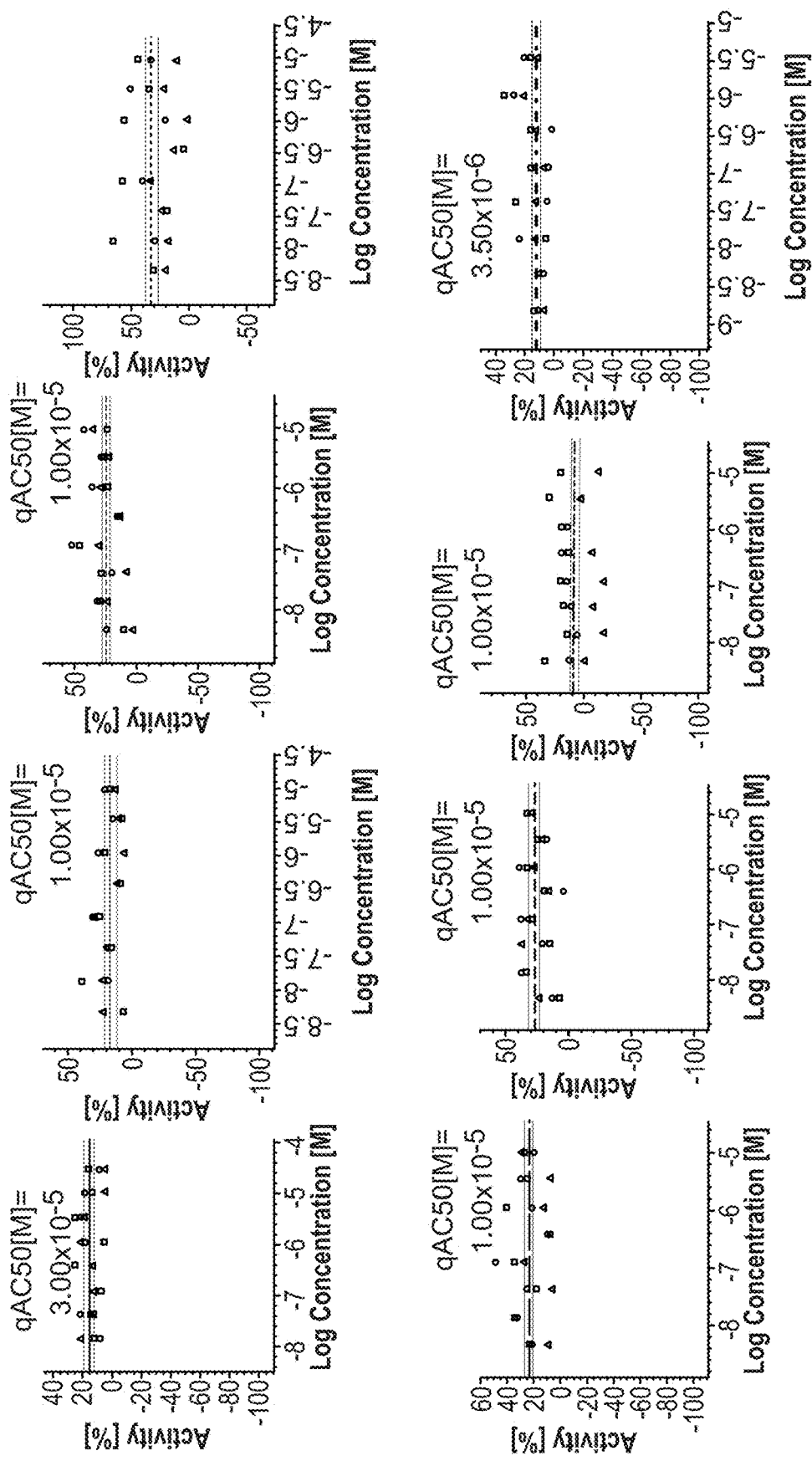
Figure 24:
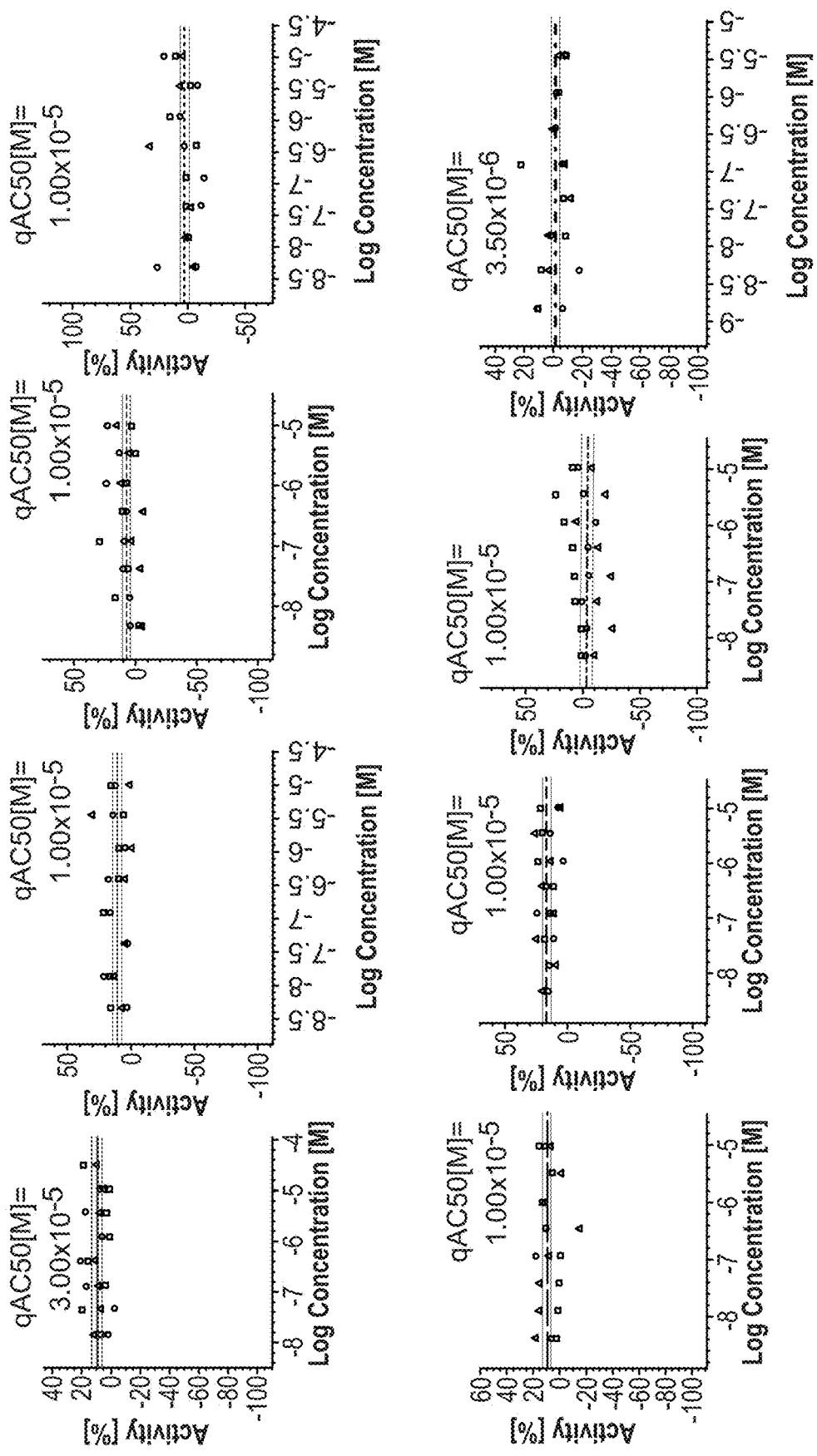
Figure 24:
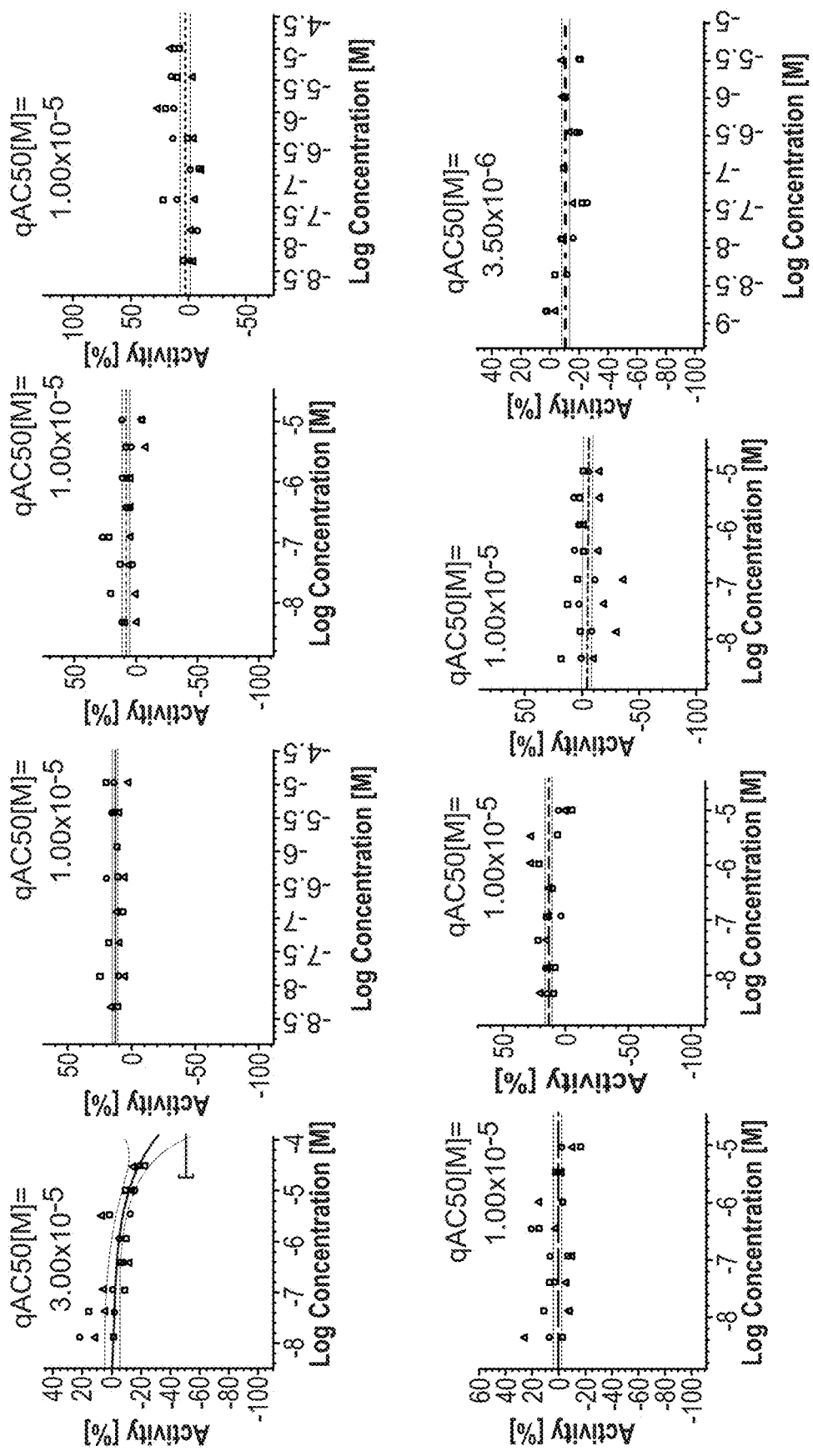
Figure 24:
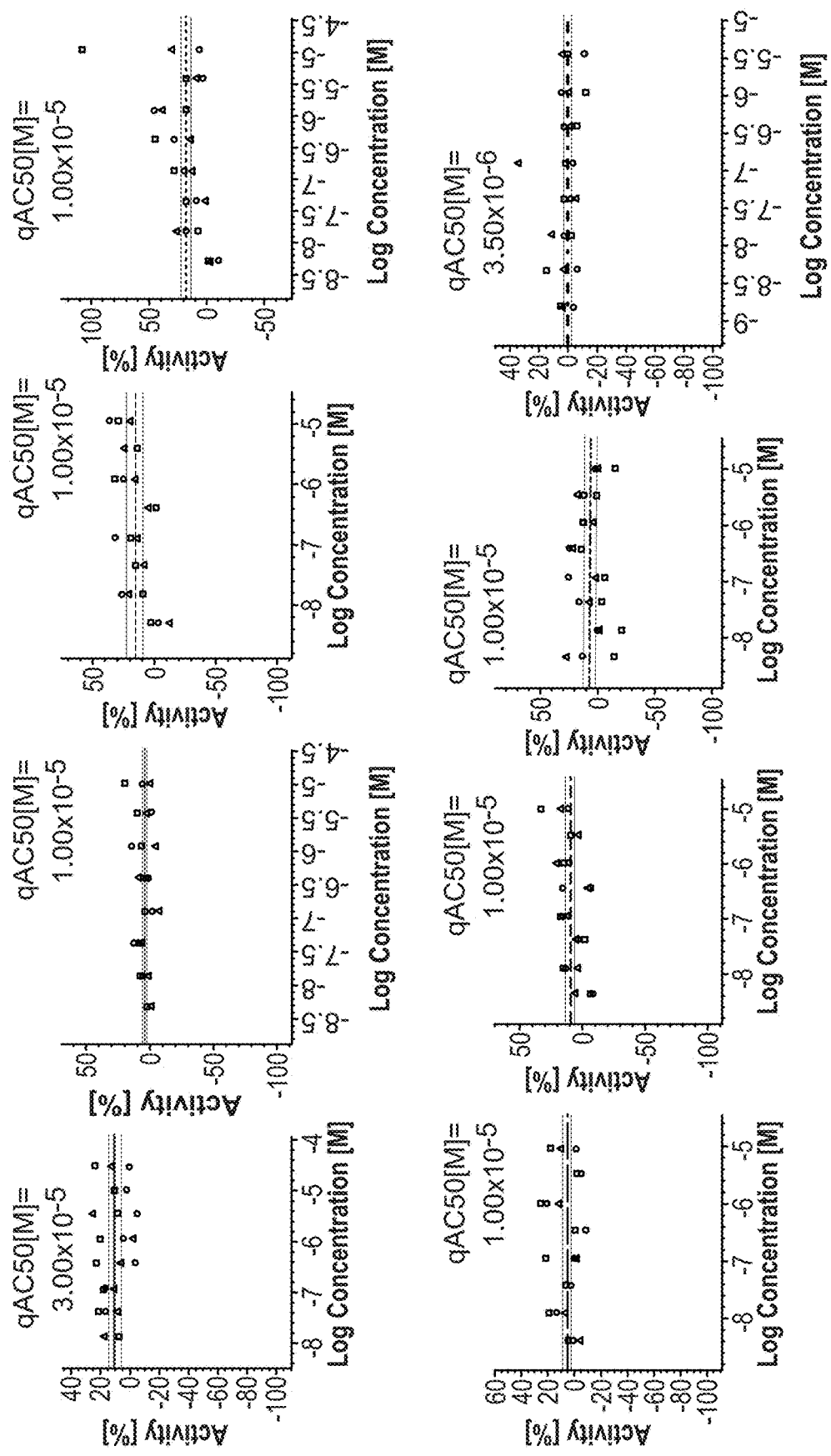
Figure 24:
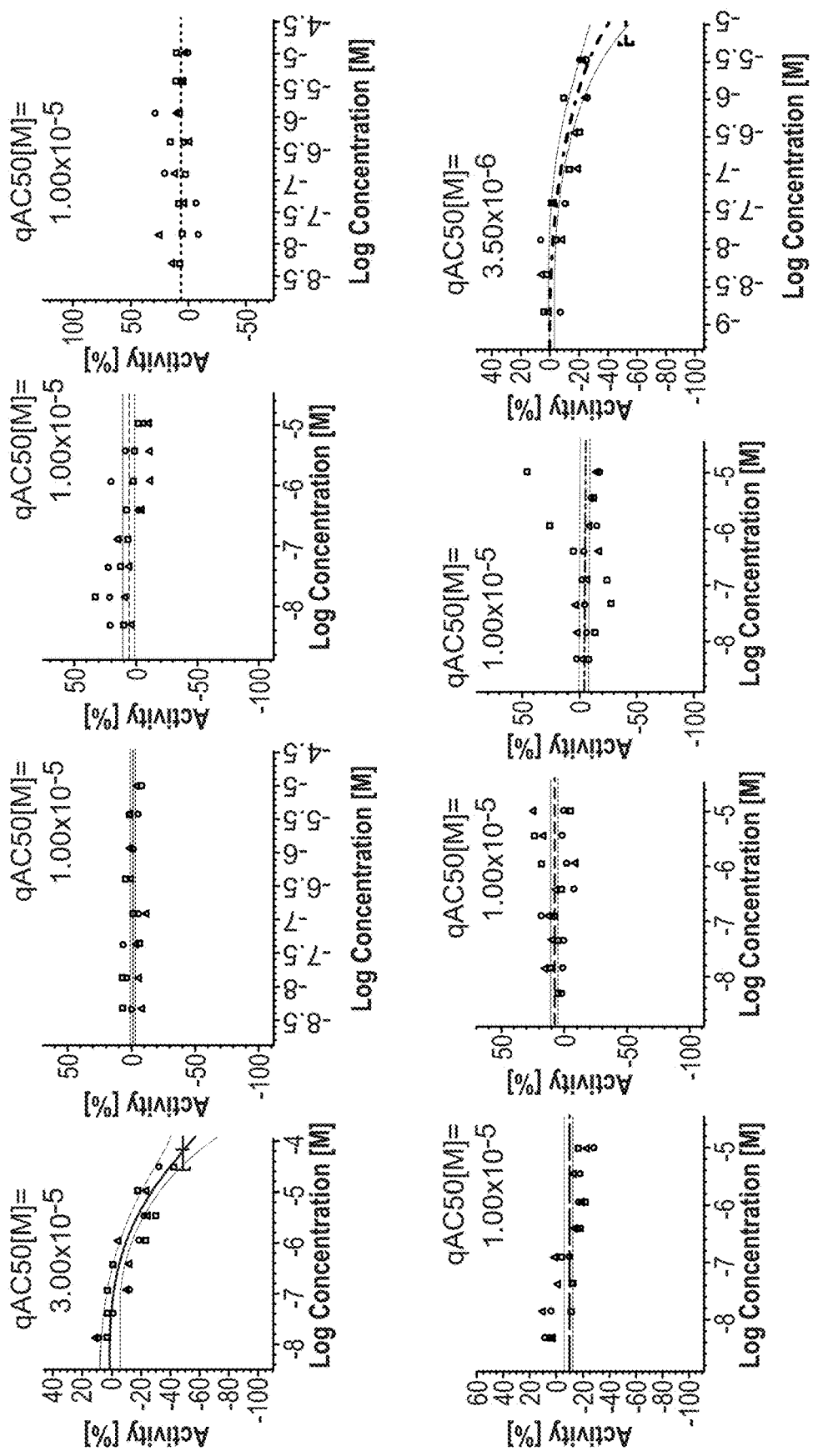
Figure 24:
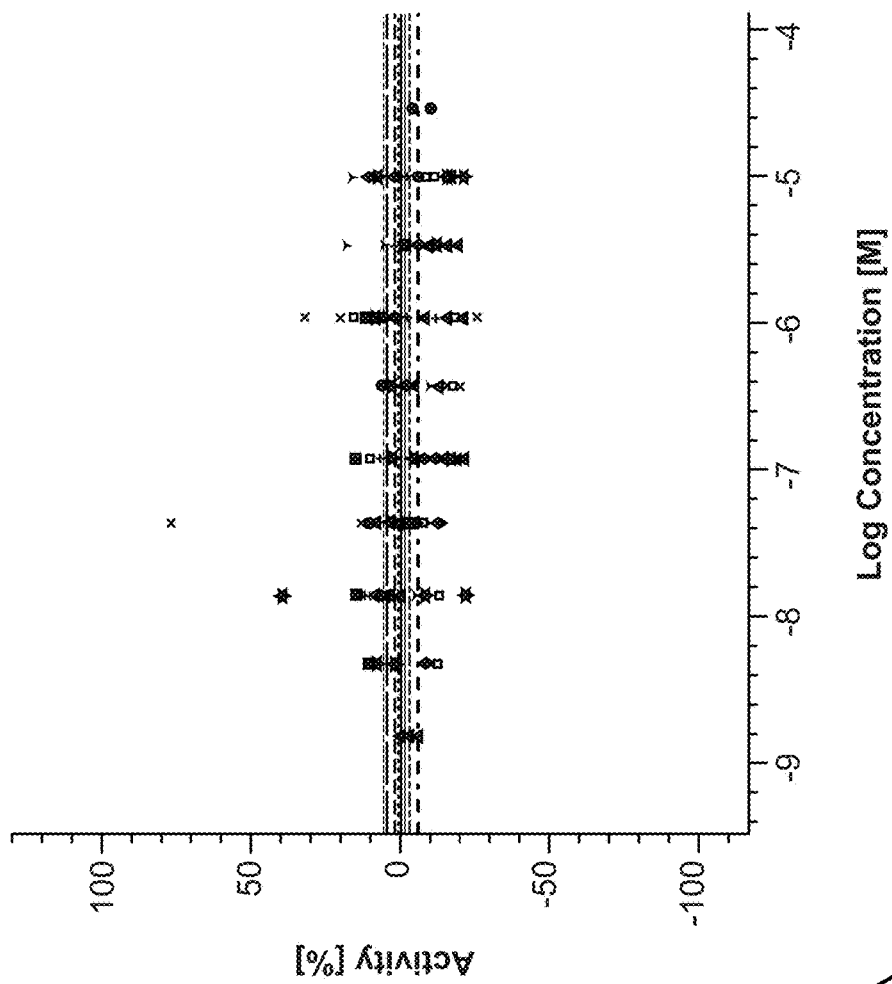
Figure 24:
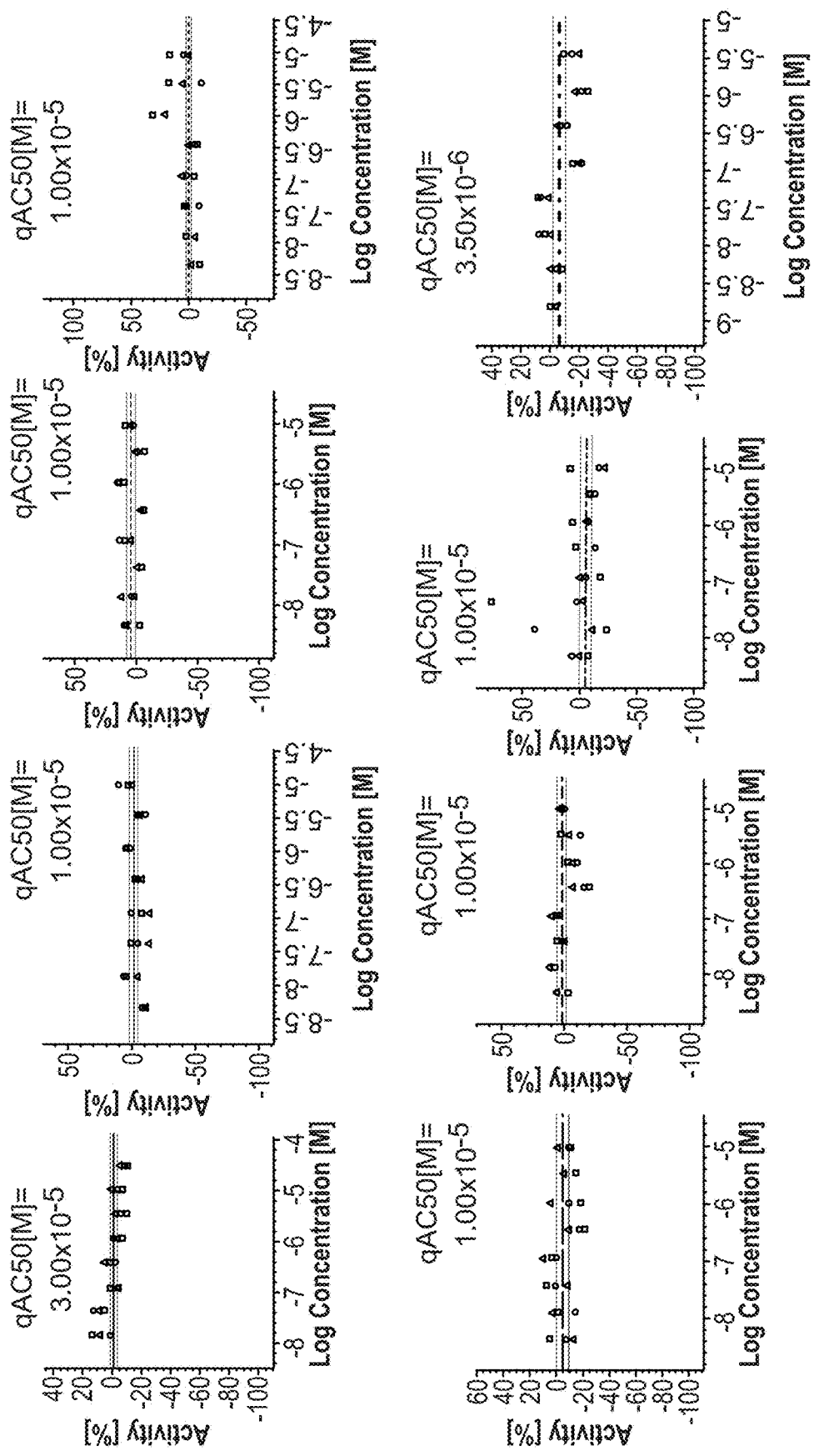
Figure 24:
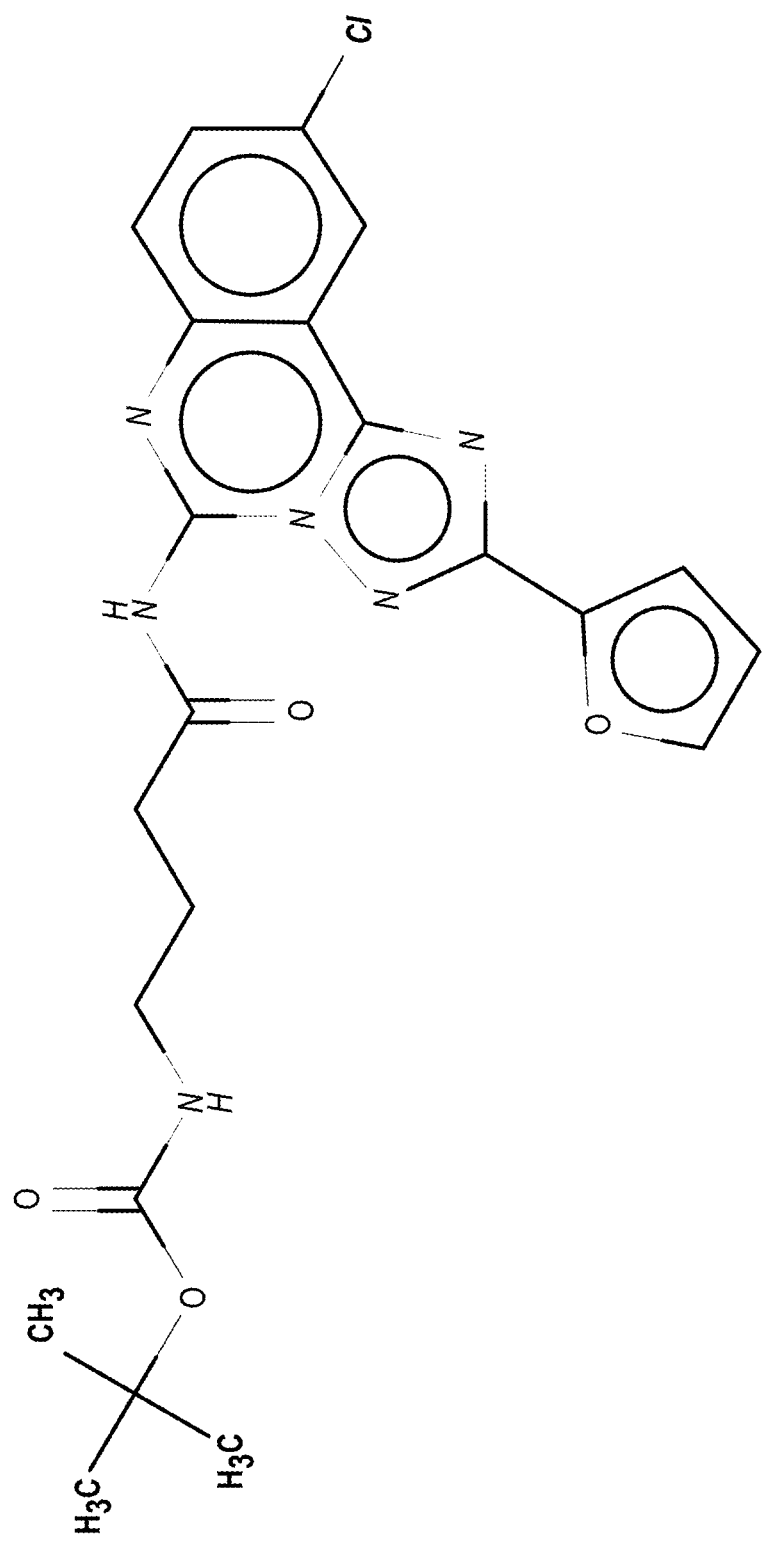
Figure 24:
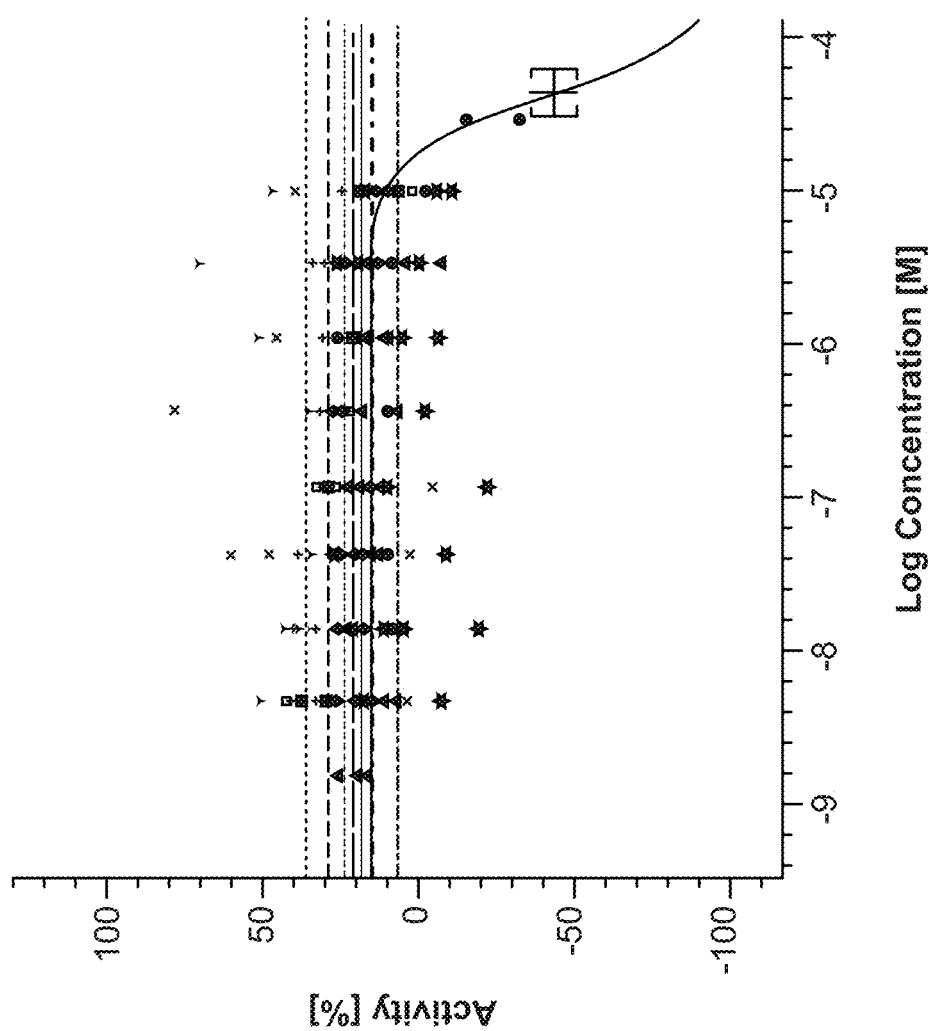
Figure 24:
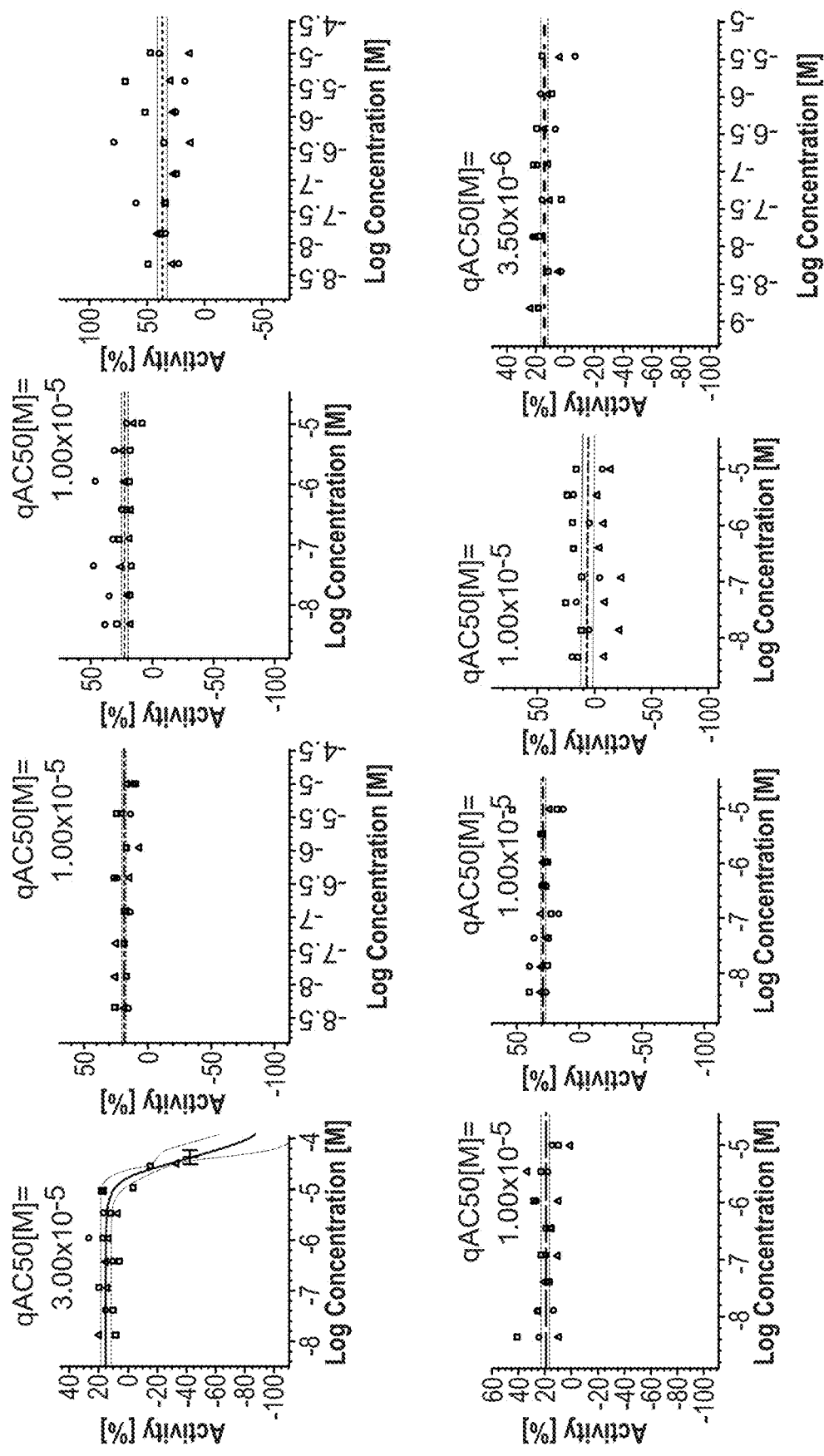
Figure 24:
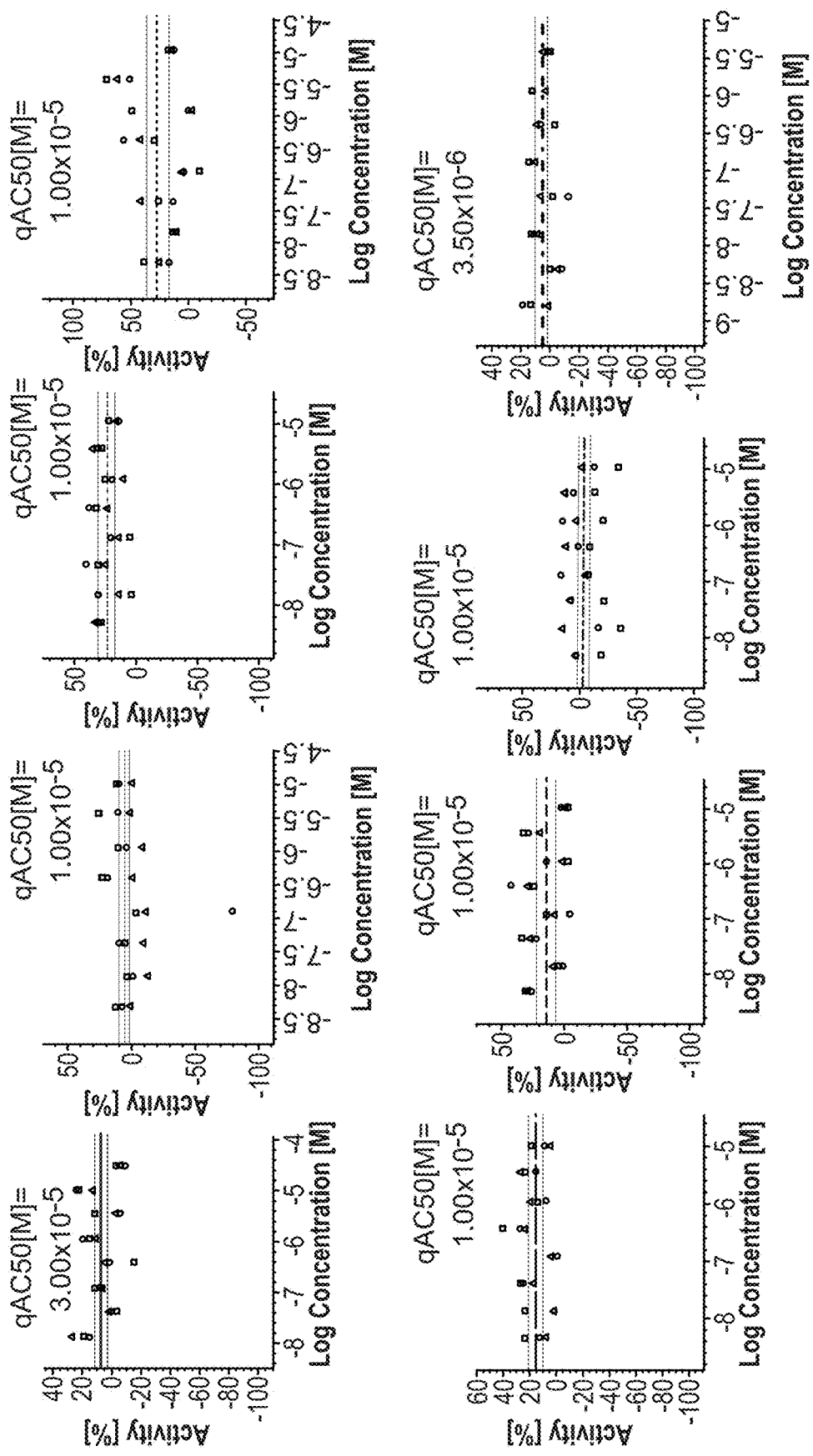
Figure 24:
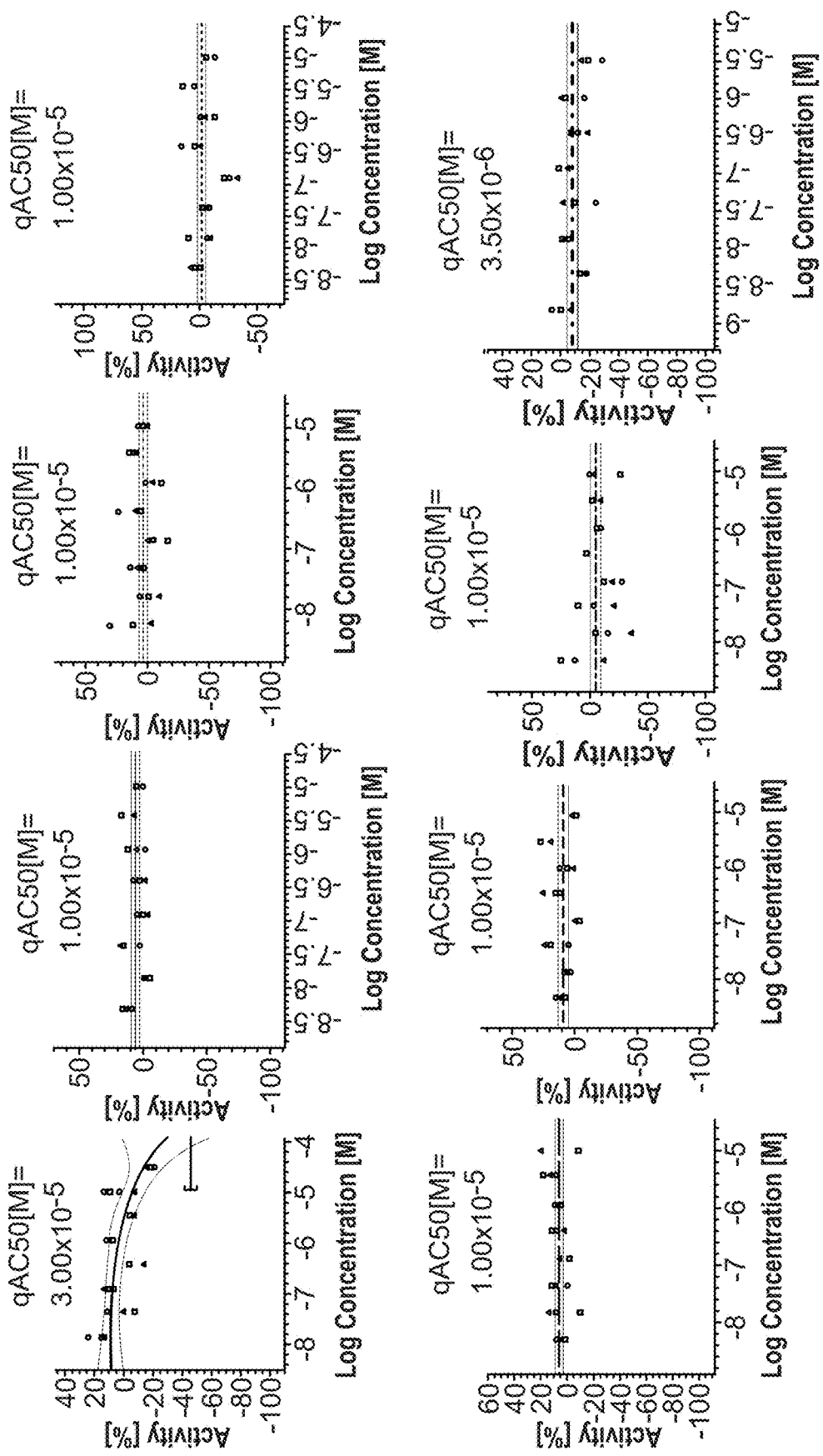
Figure 24:
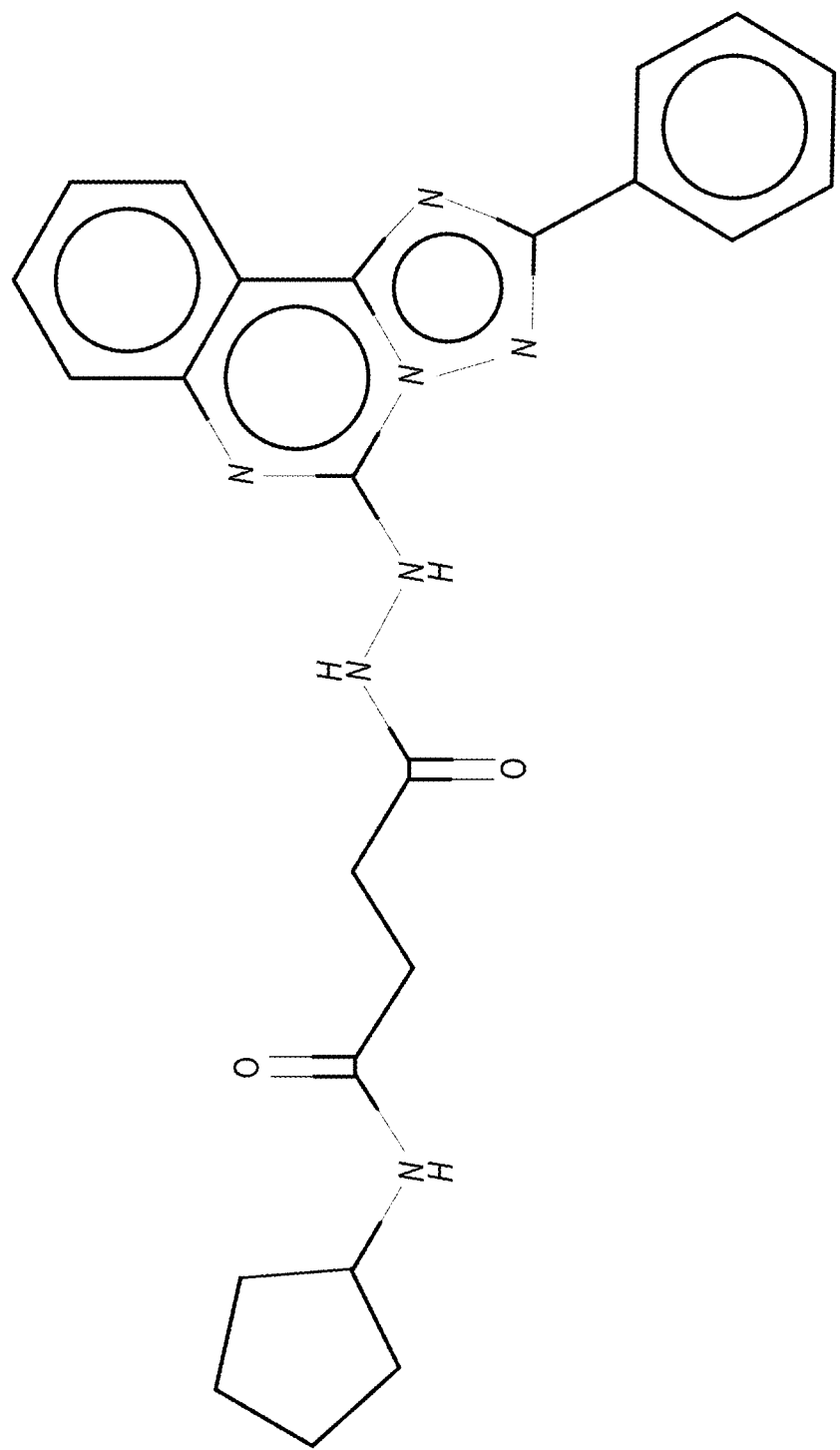
Figure 24:
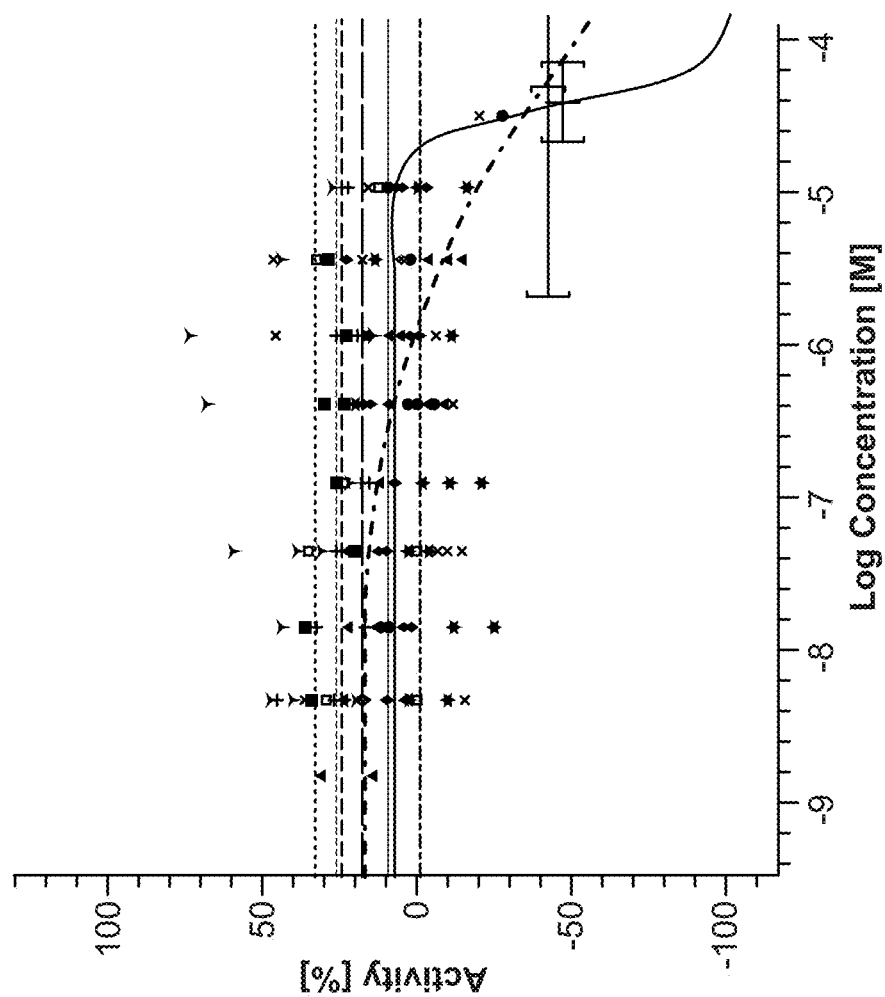
Figure 24:
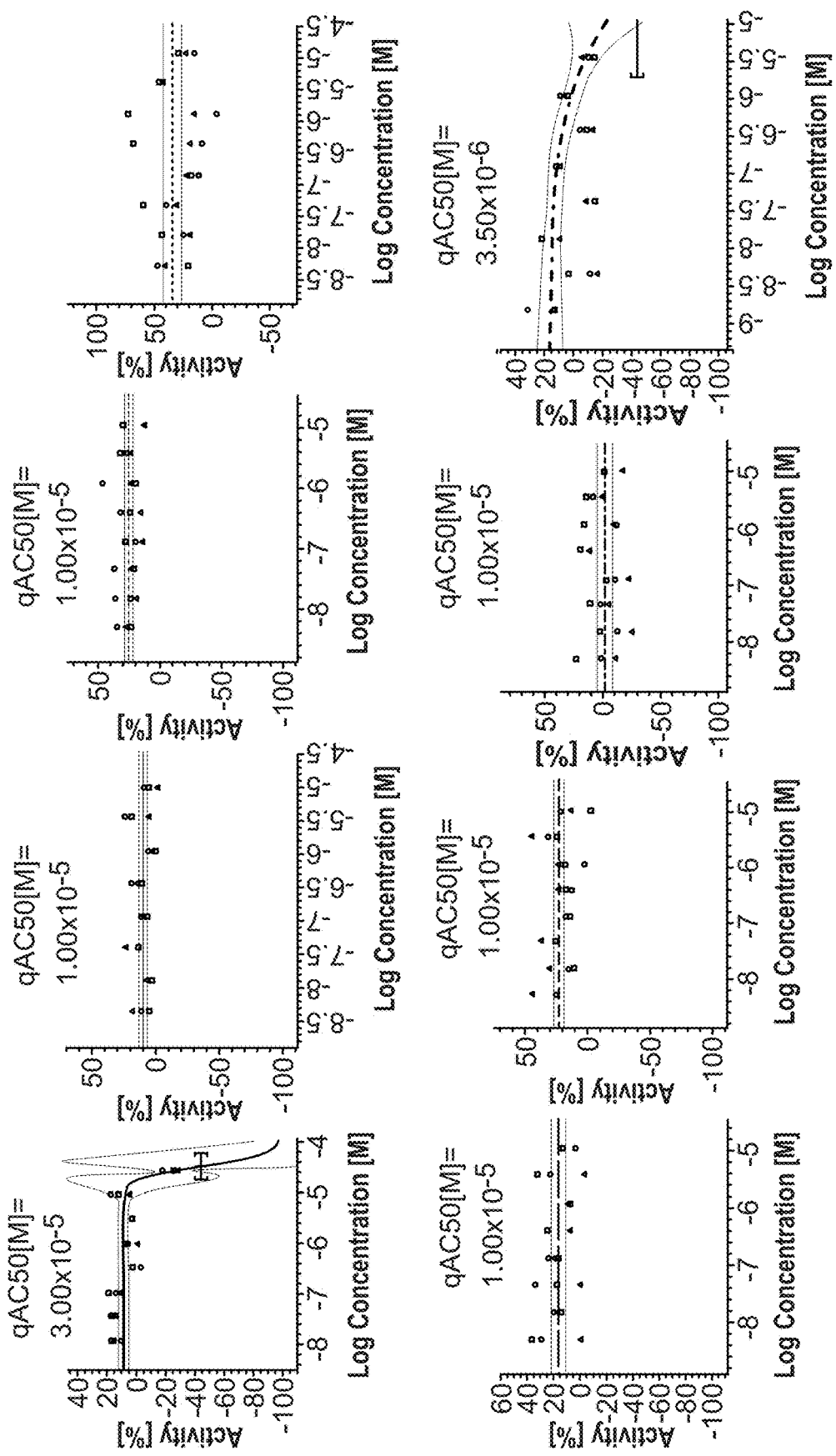
Figure 24:
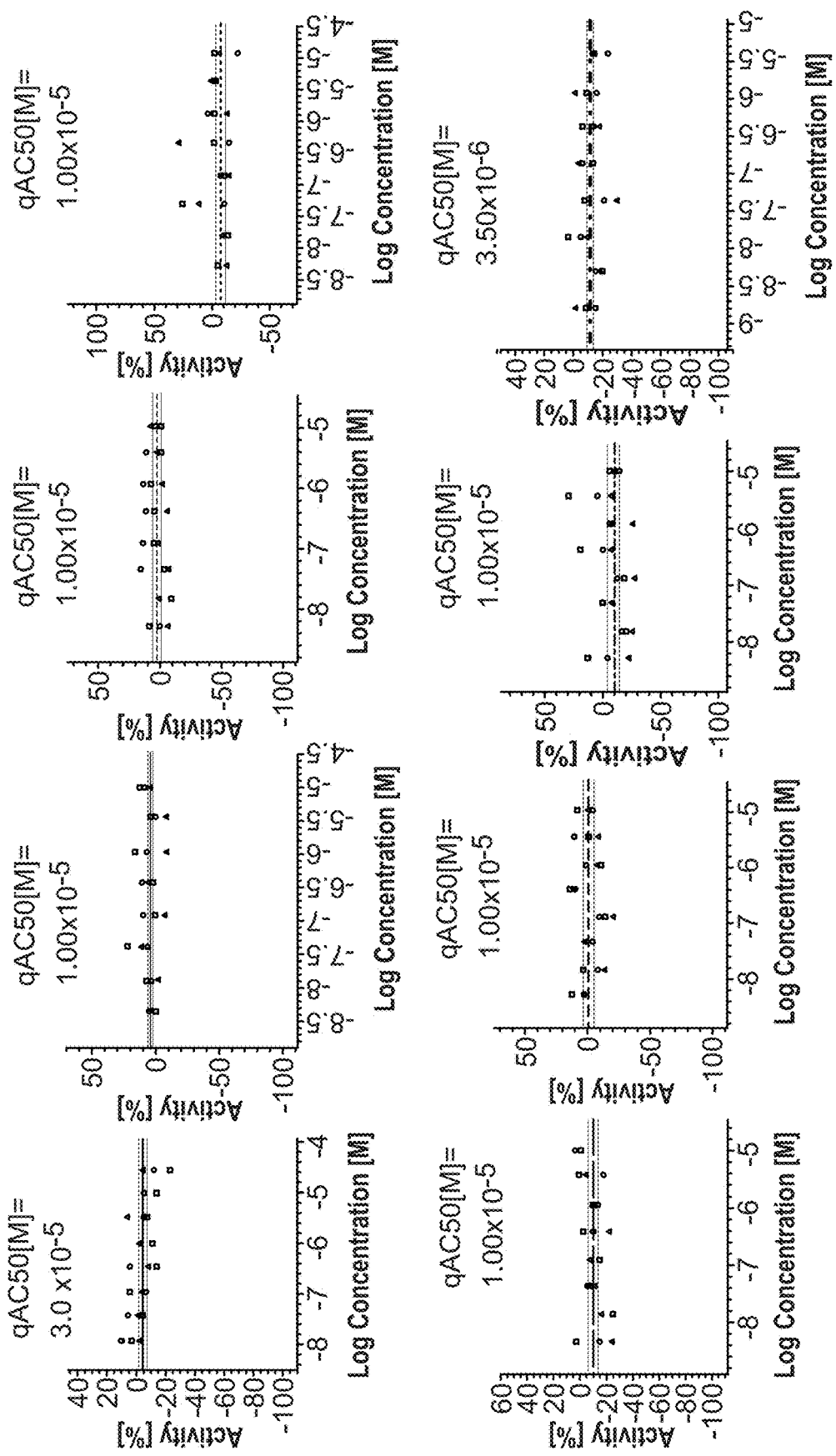
Figure 24:
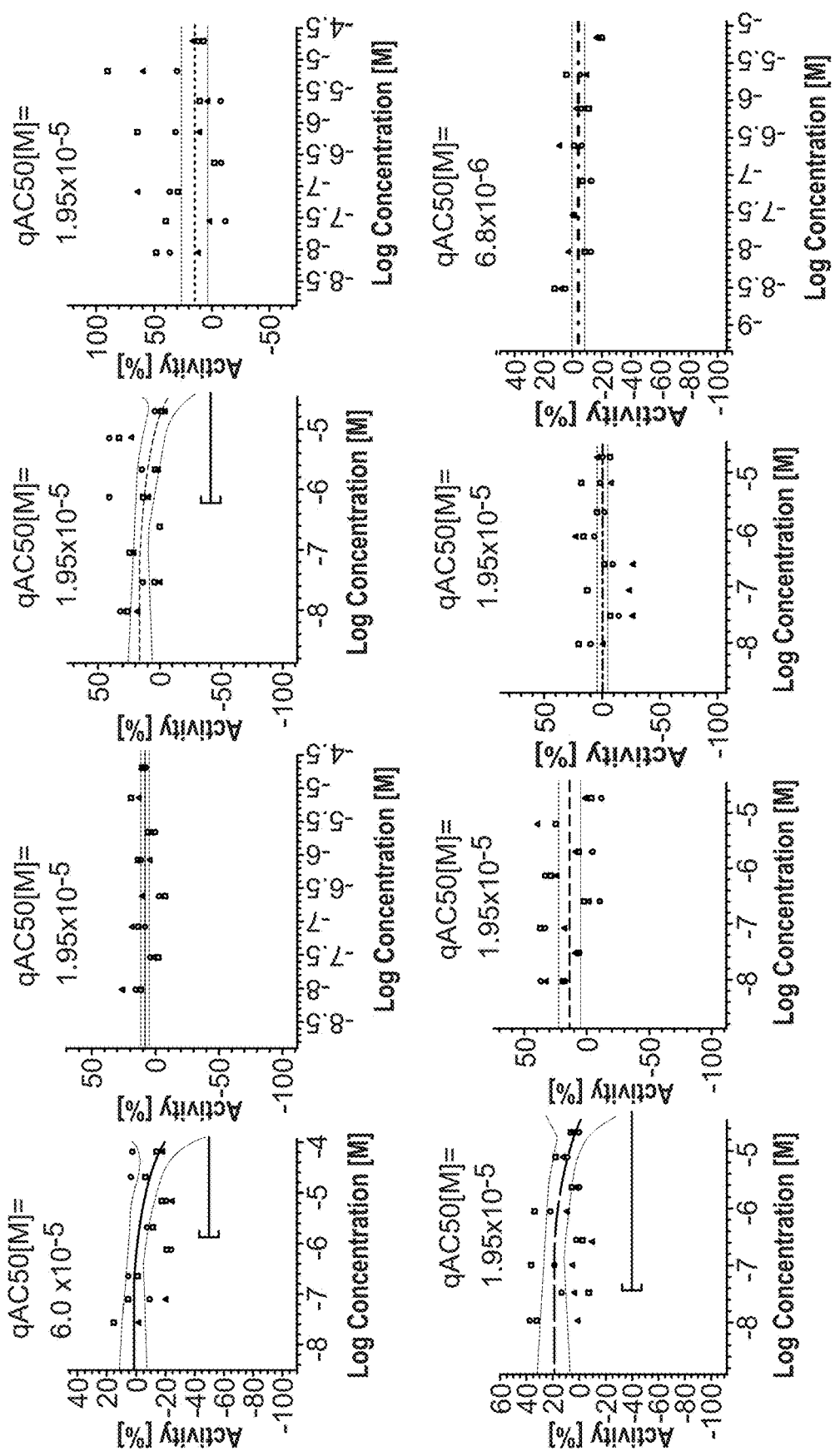
Figure 24:
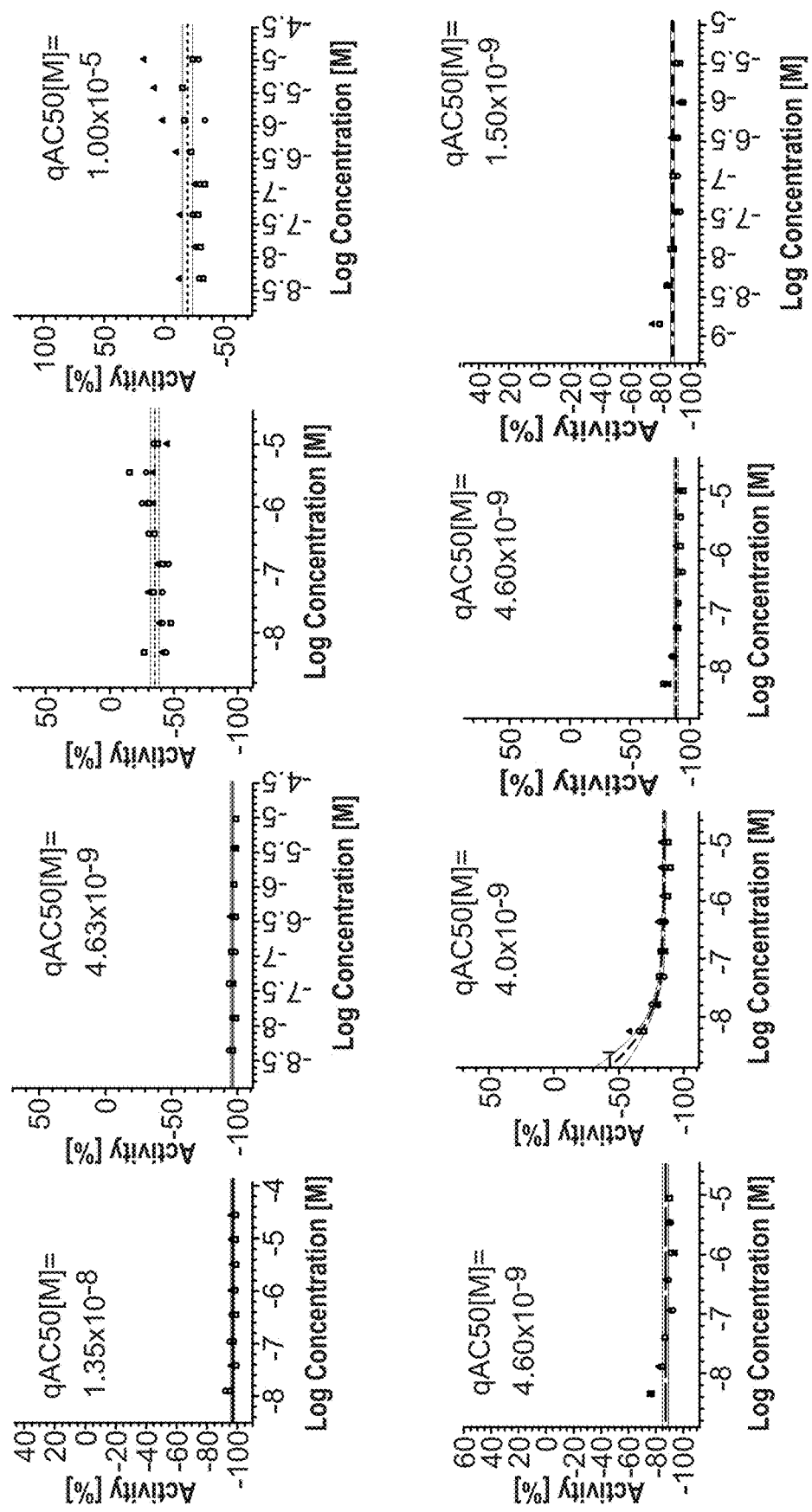
Figure 24:
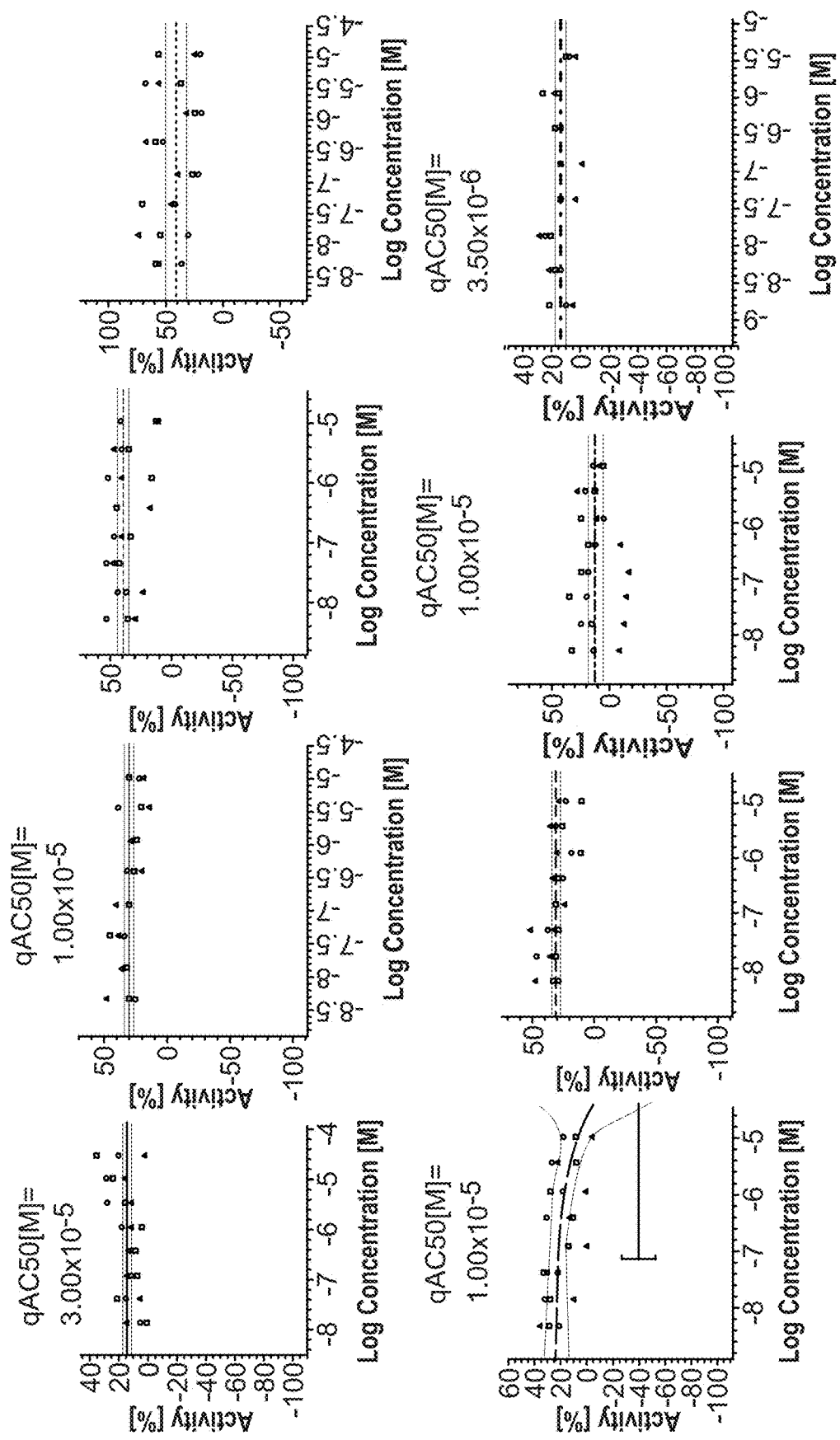
Figure 24:
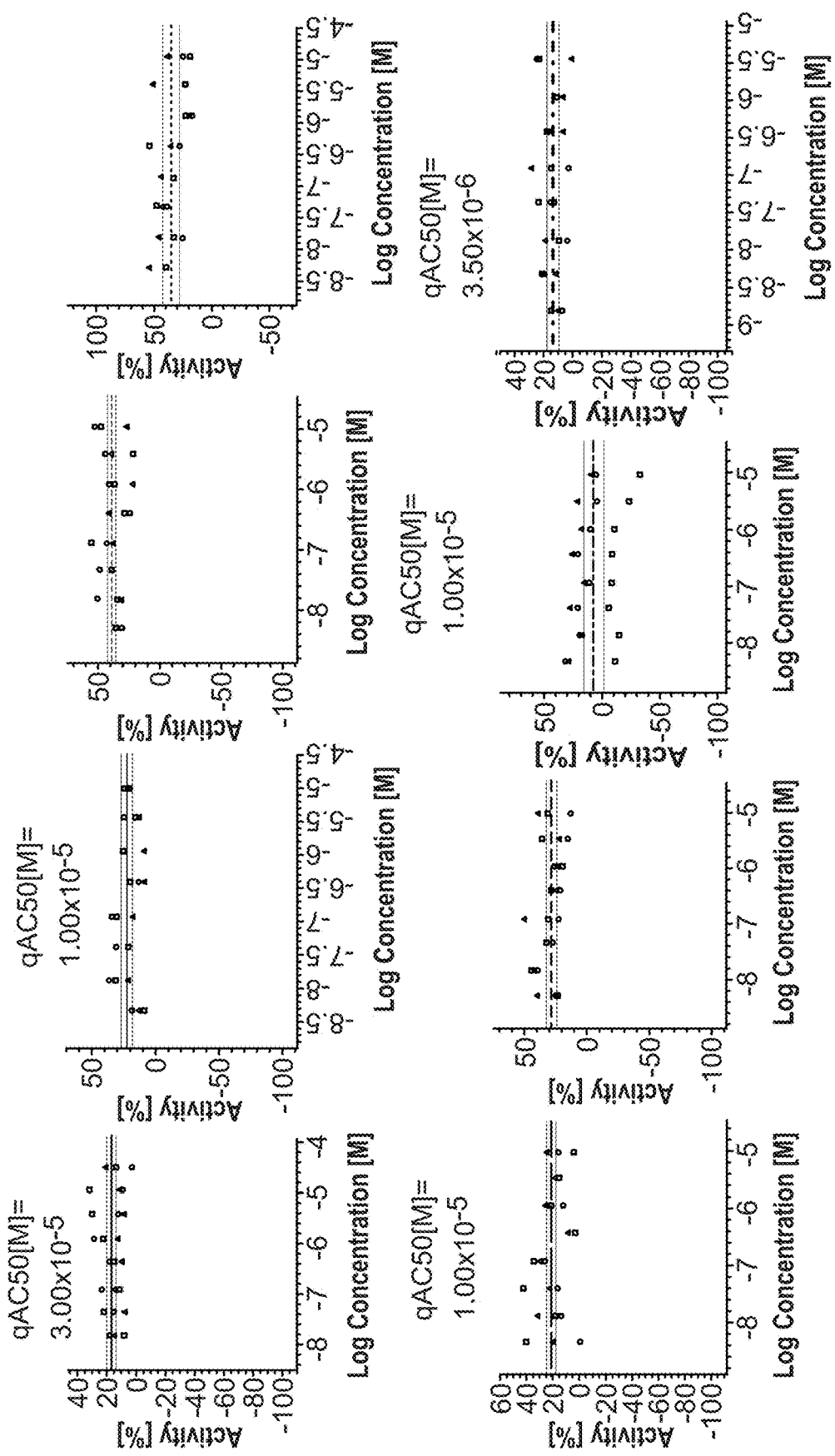
Figure 24:
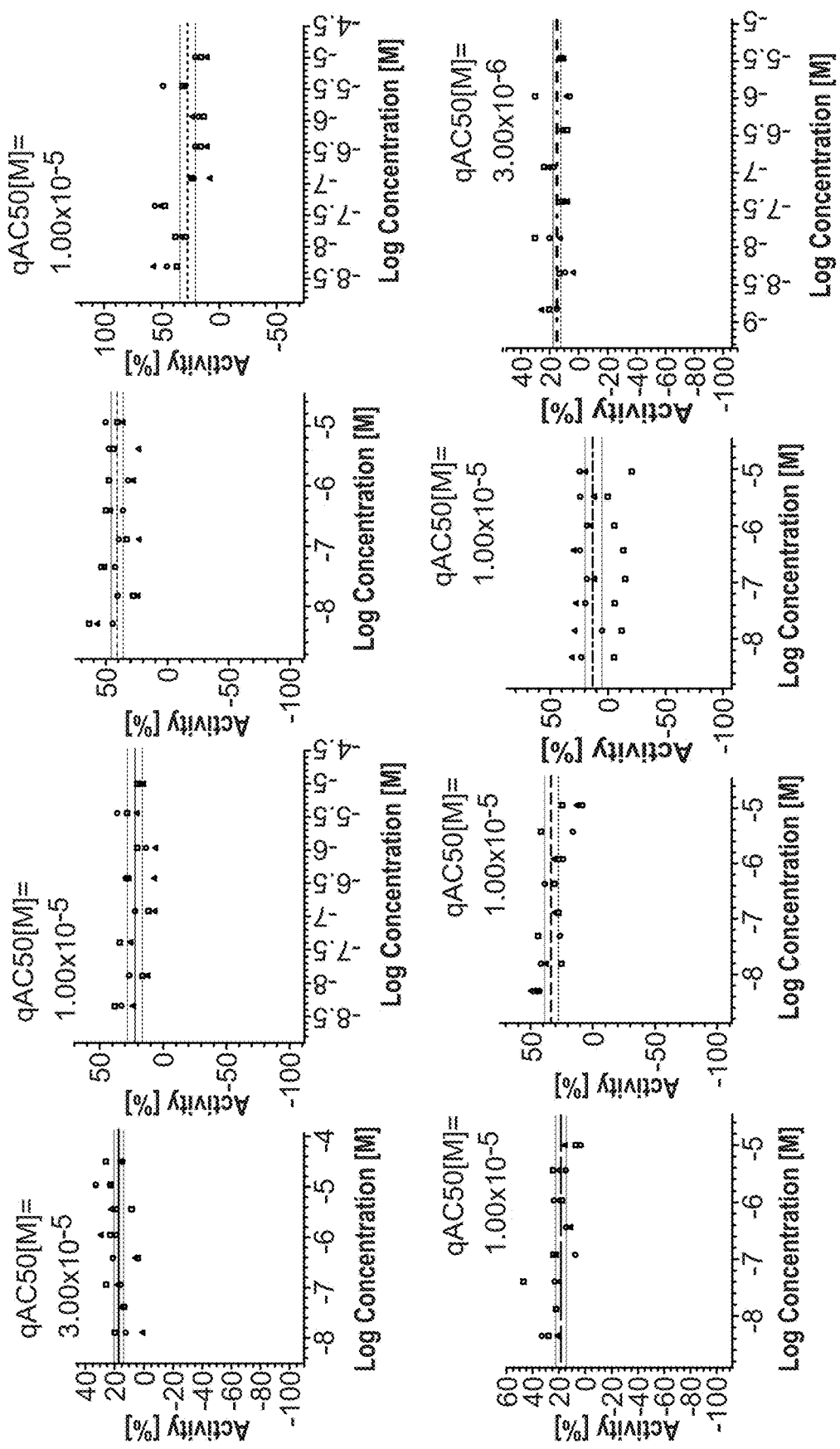
Figure 24:
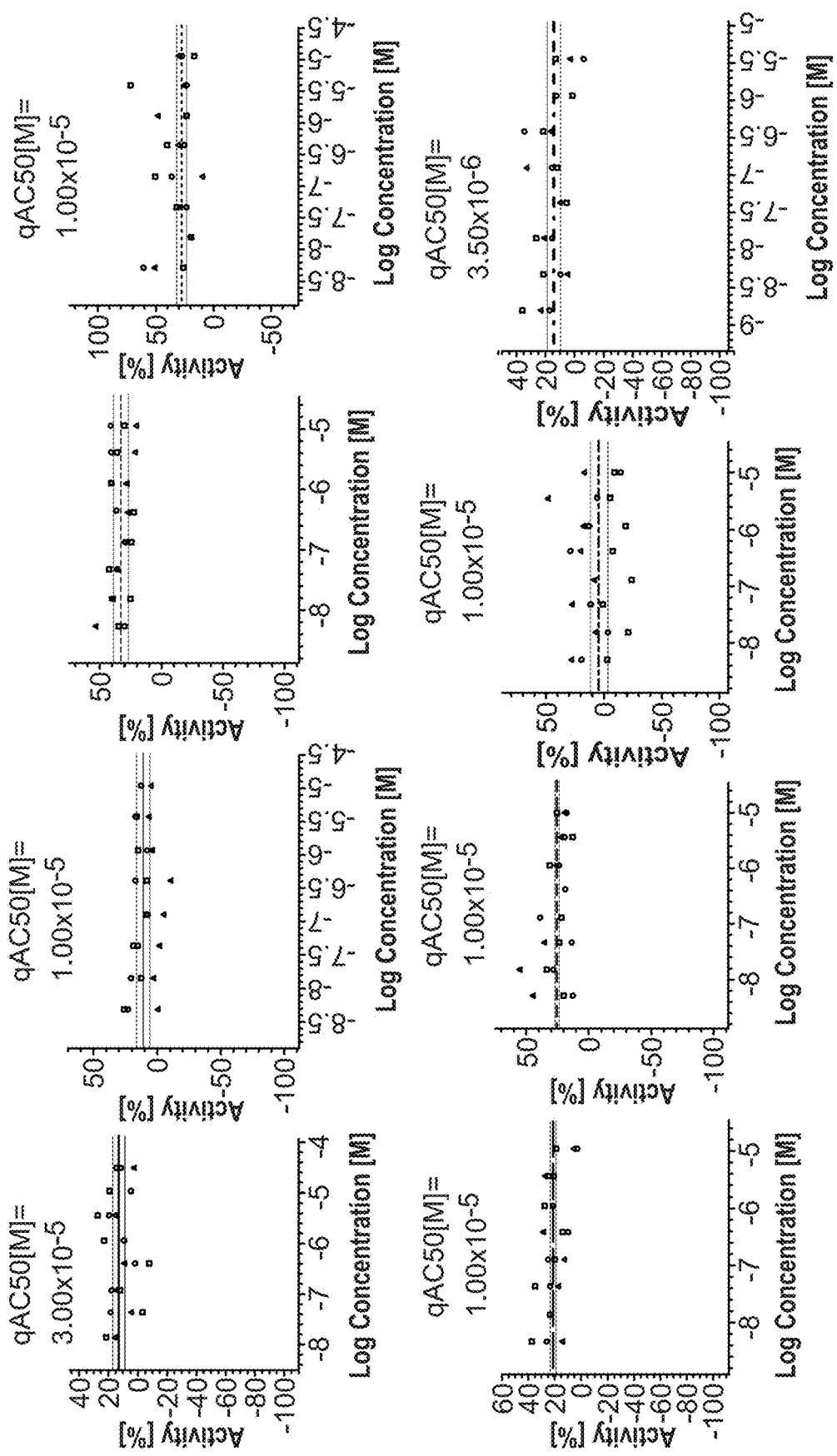

Example 21: Cytotoxicity Assays Identify Compounds Exhibiting High AHR Dependence To determine the AHR-dependence of a compound's cytotoxic effects, MDA-MB-468 and ZR51 breast cancer and JHH7 liver cancer cell lines were screened for cytotoxic response to CGS-15943 and other agents and derivatives. The AHR-dependence of the cytotoxic response of each tested compound was determined by comparing the cytotoxicity of the compound when administered to control cells with that of corresponding cells harboring a single guide (sg) RNA knock out of AHR. Many of the tested compounds exhibited concentration-dependent cytotoxicity in control cell lines and cytotoxic resistance (viability) in AHR knock out cell lines. These results (FIGS. 23 and 24) demonstrated a dependence upon AHR for at least the following tested compounds: B2, B1, A14, 10-chloro-2-(2-furyl)[1,2,4]triazolo[1,5-c]quinazoline, CGS 15943, CGS-15943, BRO-023, 2-(2-furyl)-5-(methylsulfanyl)[1,2,4]triazolo[1,5-c]quinazoline, 2-(2-furyl)-5-methylene-5,6-dihydro[1,2,4]triazolo[1,5-c]quinazoline, Z1222312995, A17, BRO-027, BRO-024, BIMH-20171221_Cpd4, BRO-025, B7, BIMH-20171221_Cpd7, 3-Methylcholanthrene, A16, BIMH-20171221_Cpd2, 2-(2-furyl)[1,2,4]triazolo[1,5-c]quinazoline, BRO-026, B5, Arcyriaflavin A, MRS-1220, A2, SCH-58261, GTP 14564, B3, A15, SCH 442416, 2-(2-furyl)[1,2,4]triazolo[1,5-c]quinazolin-5(6H)-one, A1,2-(2-furyl)[1,2,4]triazolo[1,5-c]quinazolin-5-yl hydrosulfide, BRO-018, BRO-013 and FICZ.

The dependence of each compound's cytotoxic effects upon CYP1A1 was also examined, via screening of MDA-MB-231 breast cancer cell lines for cytotoxic response. The CYP1A1-dependence of the cytotoxic response of to each tested compound was specifically determined by comparing the cytotoxicity of each compound administered to control cells with that of the compound administered to corresponding cells that overexpressed CYP1A1. A majority of the tested compounds exhibited concentration-dependent cytotoxicity in control cells and cytotoxic resistance (viability) in corresponding cells that overexpressed CYP1A1. These results demonstrated a CYP1A1-dependence for the majority of tested compounds, with exemplary CYP1A1-dependent cytotoxic compounds including: B2, B1, A14, 10-chloro-2-(2-furyl)[1,2,4]triazolo[1,5-c]quinazoline, CGS 15943, CGS-15943, BRO-023, 2-(2-furyl)-5-(methyl sulfanyl)[1,2,4]triazolo[1,5-c]quinazoline, 2-(2-furyl)-5-methylene-5,6-dihydro[1,2,4]triazolo[1,5-c]quinazoline, Z1222312995, A17, BRO-027, BRO-024, BIMH-20171221_Cpd4, BRO-025, B7, BIMH-20171221_Cpd7, 3-Methylcholanthrene, A16, BIMH-20171221_Cpd2, 2-(2-furyl)[1,2,4]triazolo[1,5-c]quinazoline, BRO-026, B5, Arcyriaflavin A, MRS-1220, A2, SCH-58261, GTP 14564, B3, A15, SCH 442416, 2-(2-furyl)[1,2,4]triazolo[1,5-c]quinazolin-5(6H)-one, A1,2-(2-furyl)[1,2,4]triazolo[1,5-c]quinazolin-5-yl hydrosulfide, BRO-018, BRO-013 and FICZ.

Example 22: Testing of 5 Molecules for Antagonist Activity on Recombinant Human Adenosine A1, A2A, A2B and A3 Receptors Using cAMP HTRF Assays A panel of five compounds, including CGS-15943 and related and/or derivative compounds either possessing or lacking the amine group identified in Example 18 above (FIG. 7A) as predictive of Adenosine receptor antagonist activity, were examined in additional detail for human Adenosine receptor antagonist activity, Specifically, CGS-15943 and the following four compounds were examined:

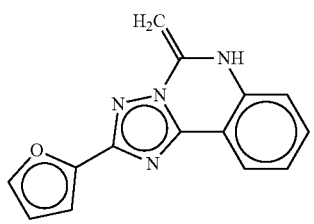

2-(2-furyl)-5-methylene-5,6-dihydro[1,2,4]triazolo[1,5-c]quinazoline

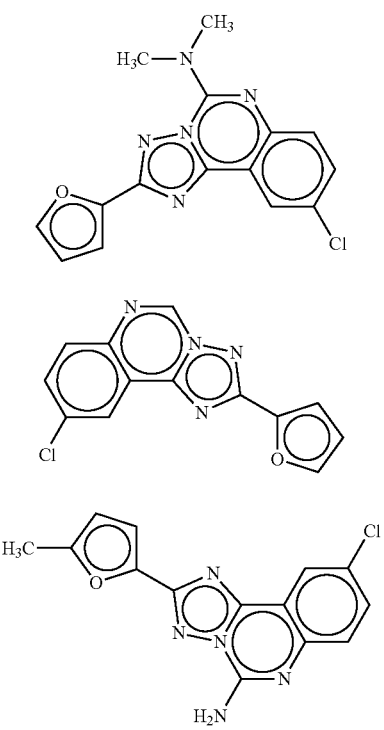

BRO-020

BRO-022

BRO-013

The five compounds were tested for their respective effects (antagonist activity) upon recombinant human Adenosine A1 (FAST-001C), A2A (FAST-002C), A2B (FAST-003C) and A3 (FAST-004C) receptors, using cAMP-HTRF assays. Receptor accession numbers, cellular background and reference compounds are shown in Table 1. The concentrations of the compounds in the cAMP-HTRF assays were as follows: 0.610, 2.44, 9.77, 39.1, 156, 625, 2,500, and 10,000 nM. All assays were performed in duplicate.

For each experiment, reference compounds with known agonist activity for each of the tested receptors were tested at several concentrations in triplicate to obtain a dose-response curve and an estimated EC50/IC50 value. These known reference values served as a control for each experimental run. Values for the reference compounds are indicated in Table 2. For replicate determinations, the maximum variability tolerated in the test was of +/−20% the mean replicate value.

TABLE 1

| Receptor | Accession Number | Cell line | Reference agonist | Reference antagonist |
|---|---|---|---|---|
| A1 | NP_000665.1 | CHO-K1 | CPA | DPCPX |
| A2A | NP_000666.2 | HEK293 | NECA | ZM241385 |
| A2B | NP_000667.1 | HEK293 | NECA | ZM241385 |
| A3 | NP_000668.1 | CHO-K1 | IB-MECA | MRS1220 |

TABLE 2

| Receptor | Ref. Compound | IC50 (nM) | Historical (nM) |
|---|---|---|---|
| A1 | DPCPX | 1.52 | 2.81 |
| A2A | ZM241385 | 18.9 | 10.4 |
| A2B | ZM241385 | 56.1 | 21.9 |
| A3 | MRS1220 | 79.4 | 63.1 |

Dose-response data from test compounds were analyzed with XLfit (IDBS) software using nonlinear regression applied to a sigmoidal dose-response model and the following parameters and equations: XL Fit Model 203: 4 Parameter Logistic Model: A: Bottom; B: TOP; C: Log EC50; D: Hill; fit=(A+((B−A)/(1+(((10^C)/x)^D)))); inv=((10^C)/((((B−A)/(y−A))−1)^(1/D))); and res=(y-fit).

Agonist activity of the five tested compounds (CGS-15943, 2-(2-furyl)-5-methylene-5,6-dihydro[1,2,4]triazolo[1,5-c]quinazoline, BRO-020, BRO-022, and BRO-013) was expressed as a percentage of the activity of the reference agonist at its $EC_{100}$ concentration. Antagonist activity of the five tested compounds, shown in Tables 3-6, has been expressed as a percentage of the inhibition of reference agonist activity at its $EC_{80}$ concentration. Notably, the below-tabulated results confirmed that those compounds possessing the amine group identified in Example 18 above (FIG. 7A) as predictive of Adenosine receptor antagonist activity did indeed possess antagonist activity across all tested Adenosine receptors, while those lacking the amine group exhibited diminished/ablated Adenosine receptor antagonist activity.

TABLE 3

Adenosine A1 Receptor, Dose-response test, antagonist mode

| Compound ID | % Inhibition Average at maximal concentration | IC50 (nM) | Hill Coefficient |
|---|---|---|---|
| 2-(2-furyl)-5-methylene-5,6-dihydro[1,2,4]triazolo[1,5-c]quinazoline | 96.06 | 493 | 1.17 |
| BRO-020 | 81.13 | 72.4 | 0.83 |
| CGS 15943 | 106.39 | 1.44 | 0.92 |
| BRO-022 | 101.32 | 170 | 1.06 |
| BRO-013 | 106.60 | 7.94 | 1.18 |

TABLE 4

Adenosine $_{A2A}$ Receptor, Dose-response test, antagonist mode

| Compound ID | % Inhibition Average at maximal concentration | IC50 (nM) | Hill Coefficient |
|---|---|---|---|
| 2-(2-furyl)-5-methylene-5,6-dihydro[1,2,4]triazolo[1,5-c]quinazoline | 99.17 | 1329 | 1.72 |
| BRO-020 | 18.45 | — | — |
| CGS 15943 | 124.98 | 7.29 | 1.25 |
| BRO-022 | 60.73 | — | — |
| BRO-013 | 111.65 | 27.2 | 1.39 |

TABLE 5

Adenosine $_{A2B}$ Receptor, Dose-response test, antagonist mode

| Compound ID | % Inhibition Average at maximal concentration | IC50 (nM) | Hill Coefficient |
|---|---|---|---|
| 2-(2-furyl)-5-methylene-5,6-dihydro[1,2,4]triazolo[1,5-c]quinazoline | 109.20 | 2141 | 1.80 |
| BRO-020 | 9.09 | — | — |
| CGS 15943 | 119.87 | 21.9 | 1.75 |
| BRO-022 | 97.75 | 2503 | 1.39 |
| BRO-013 | 109.61 | 116 | 1.76 |

TABLE 6

Adenosine A3 Receptor, Dose-response test, antagonist mode

| Compound ID | % Inhibition Average at maximal concentration | IC50 (nM) | Hill Coefficient |
|---|---|---|---|
| 2-(2-furyl)-5-methylene-5,6-dihydro[1,2,4]triazolo[1,5-c]quinazoline | 30.96 | — | — |
| BRO-020 | 8.55 | — | — |
| CGS 15943 | 68.92 | 2087 | 1.66 |
| BRO-022 | 29.54 | — | — |
| BRO-013 | 74.19 | 730 | 1.04 |

REFERENCES

1. Barretina, J. et al. The Cancer Cell Line Encyclopedia enables predictive modelling of anticancer drug sensitivity. *Nature* 483, 603-607 (2012).
2. Yu, C. et al. High-throughput identification of genotype-specific cancer vulnerabilities in mixtures of barcoded tumor cell lines. *Nat. Biotechnol.* 34, 419-423 (2016).
3. Subramanian, A. et al. A Next Generation Connectivity Map: L1000 Platform and the First 1,000,000 Profiles. *Cell* 171, 1437-1452.e17 (2017).
4. Johnson, W. E., Li, C. & Rabinovic, A. Adjusting batch effects in microarray expression data using empirical Bayes methods. *Biostatistics* 8, 118-127 (2007).
5. Smirnov, P. et al. PharmacoGx: an R package for analysis of large pharmacogenomic datasets. *Bioinformatics* 32, 1244-1246 (2016).
6. Tsherniak, A. et al. Defining a Cancer Dependency Map. *Cell* 170, 564-576.e16 (2017).
7. Doench, J. G. et al. Optimized sgRNA design to maximize activity and minimize off-target effects of CRISPR-Cas9. *Nat. Biotechnot* 34, 184-191 (2016).

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:
1. A compound having a structure of formula I:

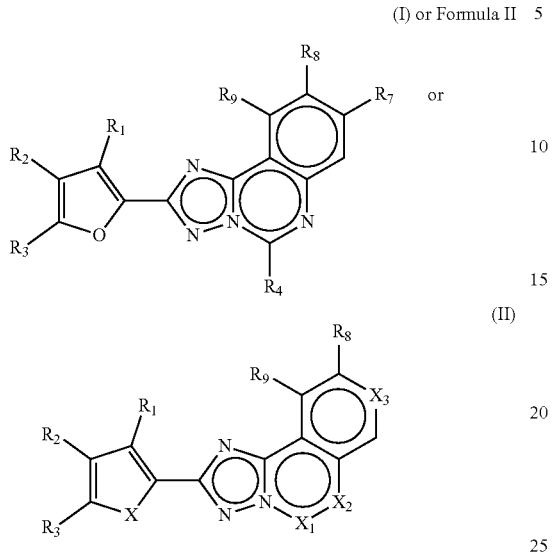

wherein:
$R_1$, $R_2$, and $R_3$ independently represent H or Me,
wherein $R_1$, $R_2$, and $R_3$ independently represent H; or
wherein $R_1$ represents methyl and $R_2$ and $R_3$ each represents H; or
wherein $R_3$ represents methyl and $R_1$ and $R_2$ each represents H; or
wherein both $R_1$ and $R_3$ represent methyl and $R_2$ represents H; or
wherein $R_2$ and $R_3$ together with the other atoms to which they are bound form an optionally substituted phenyl group;
$R_4$ represents H, methyl, or $NR_5R_6$ wherein $R_5$ and $R_6$ independently represent H, methyl, or phenyl, provided that only one of $R_5$ and $R_6$ may represent phenyl;
and wherein $R_7$, $R_8$, and $R_9$ independently represent H, F, Cl, Br, methoxy, or optionally substituted $C_1$-$C_3$ alkyl,
X represents O or N—$R_{10}$, wherein $R_{10}$ represents H or methyl;
$X_1$ represents C—O or $CR_4$;
$X_2$ represents N or NH;
and $X_3$ represents $CR_7$ or N, provided that $X_2$ represents NH when $X_1$ represents C=O, at least one of $R_7$, $R_8$, and $R_9$ represents F, Cl, Br, methoxy, or optionally substituted $C_1$-$C_3$ alkyl;
and further provided that if $R_1$, $R_2$ and $R_3$ independently represent H and $R_5$ represents Cl, $R_4$ cannot represent $NR_5R_6$ wherein $R_5$ and $R_6$ both represent H;
or a pharmaceutically acceptable salt, ester, amide, prodrug or stereoisomer thereof.
2. The compound of claim 1, wherein:
$R_4$ is H;
$R_4$ represents methyl;
$R_4$ represents $NR_5R_6$, $R_5$ represents H and $R_6$ represents Me;
$R_4$ represents $NR_5R_6$, and $R_5$ and $R_6$ represent Me;
$R_4$ represents $NR_5R_6$, $R_5$ represents H and $R_6$ represents phenyl;
$R_4$ represents $NR_5R_6$, $R_5$ represents methyl and $R_6$ represents phenyl;
$R_8$ represents Cl and $R_7$ and $R_9$ each represents H;
$R_8$ represents F and $R_7$ and $R_9$ each represents H;
$R_8$ represents Br and $R_7$ and $R_9$ each represents H;
$R_8$ represents $CF_3$ and $R_7$ and $R_9$ each represents H;
$R_8$ represents methoxy and $R_7$ and $R_8$ each represents H;
$R_9$ represents $CF_3$ and $R_7$ and $R_8$ each represents H;
$R_9$ represents methoxy and $R_7$ and $R_8$ each represents H;
X represents O;
X represents $NR_{10}$, wherein $R_{10}$ represents methyl;
$X_1$ represents C=O and $X_2$ represents NH; and/or
$X_3$ represents N.
3. A compound selected from the group consisting of:

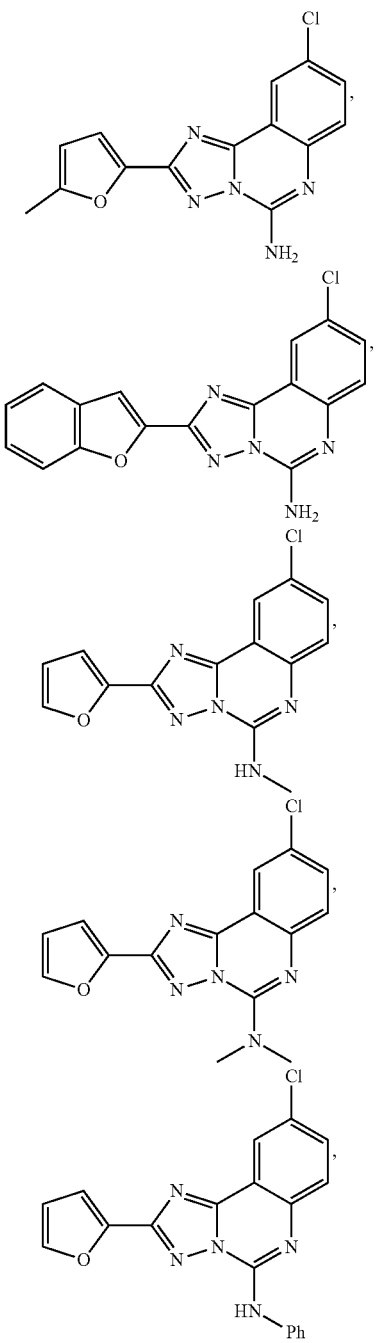

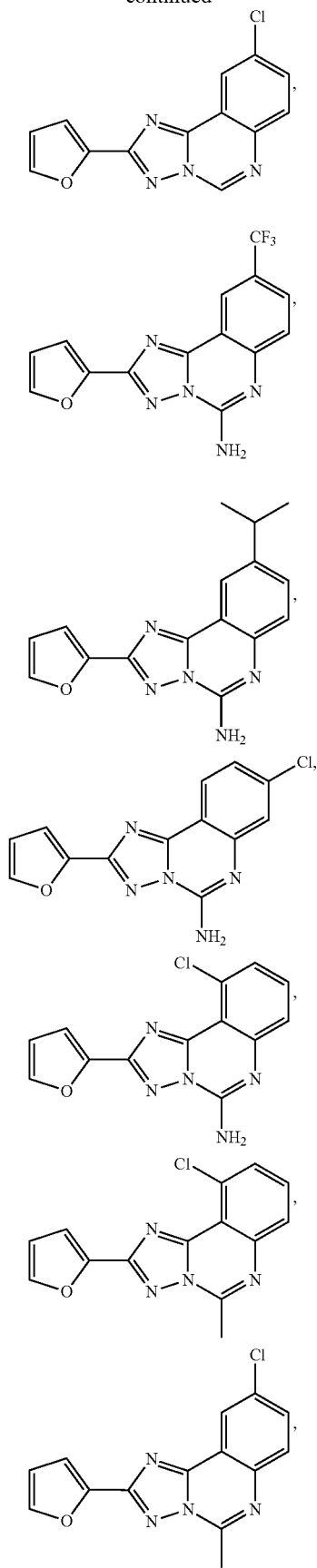
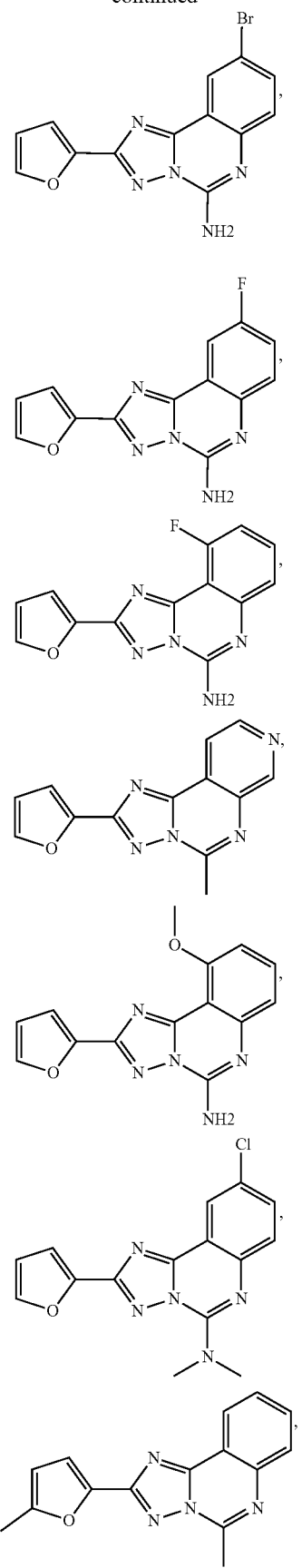

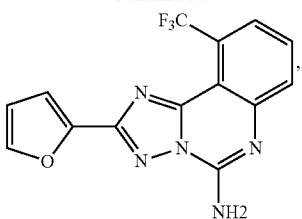
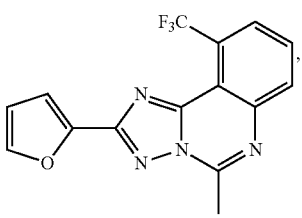
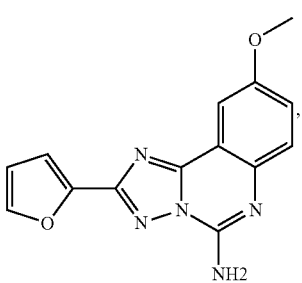
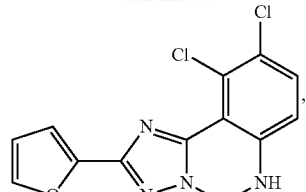
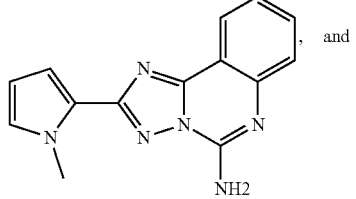
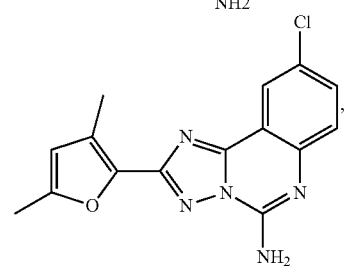
or a pharmaceutically acceptable salt, ester, amide, prodrug or stereoisomer thereof.
* * * * *